(12) United States Patent
Qian et al.

(10) Patent No.: US 8,895,582 B2
(45) Date of Patent: *Nov. 25, 2014

(54) CERTAIN CHEMICAL ENTITIES, COMPOSITIONS, AND METHODS

(75) Inventors: Xiangping Qian, Foster City, CA (US); Chihyuan (Grace) Chuang, San Mateo, CA (US); Pu-Ping Lu, Foster City, CA (US); Bing Yao, Millbrae, CA (US); Qing (Kevin) Lu, Fremont, CA (US); Hong Jiang, Palo Alto, CA (US); Wenyue Wang, Sunnyvale, CA (US); Bradley P. Morgan, Moraga, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 13/612,713

(22) Filed: Sep. 12, 2012

(65) Prior Publication Data

US 2013/0053348 A1 Feb. 28, 2013

Related U.S. Application Data

(63) Continuation of application No. 13/308,287, filed on Nov. 30, 2011, now Pat. No. 8,759,374, which is a continuation of application No. 12/228,421, filed on Aug. 11, 2008, now Pat. No. 8,088,793.

(60) Provisional application No. 60/965,020, filed on Aug. 15, 2007.

(51) Int. Cl.

| C07D 217/22 | (2006.01) |
| A61K 31/472 | (2006.01) |
| C07H 21/04 | (2006.01) |
| C07D 401/12 | (2006.01) |
| C07D 487/04 | (2006.01) |
| C07D 213/75 | (2006.01) |
| C07D 261/14 | (2006.01) |
| C07D 277/82 | (2006.01) |
| C07D 471/04 | (2006.01) |

(52) U.S. Cl.
CPC .............. *C07H 21/04* (2013.01); *C07D 217/22* (2013.01); *C07D 401/12* (2013.01); *C07D 487/04* (2013.01); *C07D 213/75* (2013.01); *C07D 261/14* (2013.01); *C07D 277/82* (2013.01); *C07D 471/04* (2013.01)
USPC .......................................... 514/310; 546/143

(58) Field of Classification Search
None
See application file for complete search history.

(56) References Cited

U.S. PATENT DOCUMENTS

| 3,227,709 A | 1/1966 | Patchett et al. |
| 3,907,782 A | 9/1975 | Edwards |
| 5,328,819 A | 7/1994 | Ohno et al. |
| 5,602,161 A | 2/1997 | Naito et al. |
| 5,958,944 A | 9/1999 | Arita et al. |
| 6,107,291 A | 8/2000 | Russo-Rodriguez et al. |
| 6,362,177 B1 | 3/2002 | Shiota et al. |
| 6,451,842 B1 | 9/2002 | Shiota et al. |
| 6,528,655 B1 | 3/2003 | N'Zemba et al. |
| 7,268,125 B2 | 9/2007 | Bruns, Jr. et al. |
| 7,294,642 B2 | 11/2007 | Fobian et al. |
| 7,759,357 B2 | 7/2010 | Bulusu et al. |
| 8,063,082 B2 | 11/2011 | Qian et al. |
| 8,071,625 B2 | 12/2011 | Qian et al. |
| 8,088,793 B2 * | 1/2012 | Qian et al. ................ 514/310 |
| 2003/0232826 A1 | 12/2003 | Bekkali et al. |
| 2005/0137230 A1 | 6/2005 | Dorsch et al. |
| 2007/0135435 A1 | 6/2007 | Qian et al. |
| 2007/0207991 A1 | 9/2007 | Schwink et al. |
| 2007/0293530 A1 | 12/2007 | Smil et al. |
| 2009/0275537 A1 | 11/2009 | Qian et al. |
| 2012/0135964 A1 | 5/2012 | Qian et al. |

FOREIGN PATENT DOCUMENTS

| DE | 28 51 953 A1 | 6/1980 |
| JP | 2005-179351 | 7/2005 |
| WO | WO-98/41510 A1 | 9/1998 |
| WO | WO-03/031407 A2 | 4/2003 |
| WO | WO-2004/022523 A2 | 3/2004 |
| WO | WO-2004/064730 A2 | 8/2004 |
| WO | WO-2004/081005 A1 | 9/2004 |
| WO | WO-2005/016870 | 2/2005 |
| WO | WO 2005/019177 | 3/2005 |
| WO | WO-2005/074919 | 8/2005 |
| WO | WO-2006/102283 A2 | 9/2006 |
| WO | WO-2006/137350 A1 | 12/2006 |
| WO | WO-2007/109615 A2 | 9/2007 |
| WO | WO-2007/117465 A2 | 10/2007 |
| WO | WO-2007/119889 A1 | 10/2007 |
| WO | WO-2008/016676 A2 | 2/2008 |

OTHER PUBLICATIONS

Charitos et al., Journal of Peptide Research (2000) 56(6), pp. 373-381.
Database CAPLUS on STN (Columbus, OH, USA) No. 177:58747, 'silver halide color photographic material containing gcyan coupler' abstract, Tsukahara et al (1992) RN 142050-83-7.
Database CAS on STN (Columbus, OH, USA) No. 119:82805, Silver halide color reversal image formation method abstract, Oono et al (1993) RN 149125-96-2.
Database CAS on STN (Columbus, OH, USA) No. 139:369336, Cosmetic compositions containing tetrzoles for increasing hair growth abstract, (2003) See RN 337503-04-5, 337503-17-0, 618453-22-8.
Database CAS on STN (Columbus, OH, USA) No. 143:7654, 'Acylation of amines with 5-phenyltetrao1-2-ylacetyl chloride' abstract, Putis et al, (2004) see RN 329933-13-3, 329933-14-4, 337498-87-0, 337503-04-5, 694500-81-7, 852312-44-8.

(Continued)

*Primary Examiner* — Zinna Northington Davis

(57) ABSTRACT

Chemical entities that modulate smooth muscle myosin and/or non-muscle myosin, pharmaceutical compositions and methods of treatment of diseases and conditions associated with smooth muscle myosin and/or non-muscle myosin are described.

45 Claims, No Drawings

(56) References Cited

OTHER PUBLICATIONS

Hiratani et al., "N,N019-Di (8-quinolyl)glutaramide exhibiting highly selective and efficient uphill transport of Cu(II) through liquid membranes," Bulletin of the Chemical Society of Japan (1992) 65(9): 2381-2387.

Jarvest et al., "Potent selective thienoxazinone inhibitors of herpes proteases," Bioorganic & Medicinal Chemistry Letters (1997) 7(13): 1733-1738.

Kaufmann et al., "Antibody interference with N-Acyl homoserine lactone-mediated bacterial quorum sensing," Journal of the American Chemical Society (2006) 128(9): 2802-2803.

Nguyen et al., "Slow-binding inhibition of peptide deformylase by cyclic peptidomimetics as revealed by a new spectrophotometric assay," Bioorganic Chemistry (2004) 32(3): 178-191.

Shepel et al., "Chemical transformations of amino alcohols and their derivatives: II. Reaction of amino alcohols with some carboxylic acis azides," Journal of Orbganic Chemistry of the USSR (1986) 22: 174-177.

Shi et al., "Solid-phase synthesis and anti-infective activity of a combinatorial library based on the natural product anisomycin," Bioorganic & Medicinal Chemistry Letters (2005) 15(18): 4151-4154.

Weiss et al., "High-resolution reversed-phase high-performance liquid chromatography analysis of polyamines and their monoacetyl conjugates by fluorescence detection after derivatization with N-hydroxysuccinimidyl 6-quinolinyl carbamate," Analytical Biochemistry (1997) 247(2): 294-304.

International Search Report dated Nov. 5, 2008 in PCT application PCT/US2008/09636.

International Search Report dated Jun. 3, 2008 in PCT application PCT/US2007/017231.

International Search Report dated Sep. 23, 2008 in PCT application PCT/US2007/071246.

US Office Action dated Mar. 24, 2011 in U.S. Appl. No. 11/888,892.
US Office Action dated Mar. 24, 2011 in U.S. Appl. No. 11/888,903.
US Office Action dated Oct. 22, 2010 in U.S. Appl. No. 11/888, 892.
US Office Action dated Oct. 22, 2010 in U.S. Appl. No. 11/888,903.
US Office Action dated Jul. 13, 2010 in U.S. Appl. No. 11/888,903.
US Office Action dated Jul. 14, 2010 in U.S. Appl. No. 11/888,892.
US Office Action dated Mar. 24, 2011 in U.S. Appl. No. 12/228,421.
Notice of Allowance dated Aug. 1, 2011 in U.S. Appl. No. 11/888,892.
Notice of Allowance dated Jul. 11, 2011 in U.S. Appl. No. 11/888,903.
Extended European Search Report for Application No. 08795242.0 dated May 18, 2011.

* cited by examiner

CERTAIN CHEMICAL ENTITIES, COMPOSITIONS, AND METHODS

This application is a continuation of U.S. patent application Ser. No. 13/308,287, filed Nov. 30, 2011 now U.S. Pat. No. 8,759,374, which is a continuation of U.S. patent application Ser. No. 12/228,421, filed Aug. 11, 2008, now U.S. Pat. No. 8,088,793, and claims the benefit of U.S. Provisional Patent Application No. 60/965,020, filed Aug. 15, 2007, each of which is hereby incorporated by reference for all purposes.

Provided are certain chemical entities that modulate smooth muscle myosin and/or non-muscle myosin, pharmaceutical compositions and methods of treatment of diseases and conditions associated with smooth muscle myosin and/or non-muscle myosin.

Myosin is present in all muscle and muscle cells. Of the ten distinct classes of myosin in human cells, myosin-II is thought to be the form responsible for contraction of skeletal, cardiac, and smooth muscle. Myosin-II is also the isoform present in non-muscle myosins, also known as cytoplasmic myosins. The non-muscle myosins are ubiquitously present in eukaryotic cells, where the smooth muscle myosins are generally present in smooth muscle cells.

Myosin-II is significantly different in amino acid composition and in overall structure from myosins in the other nine distinct classes. Myosin-II consists of two globular head domains, called Subfragment-1 or S1, linked together by a long alpha-helical coiled-coiled tail. Proteolysis of myosin generates either S1 or heavy meromyosin (HMM, a two-headed form with a truncated tail), depending on the proteolysis conditions. Si contains the ATPase and actin-binding properties of the molecule. S1 has been shown to be sufficient to move actin filaments in vitro, and is therefore likely to be the motor domain of the molecule.

Although myosin-II isoforms from various tissues differ in a number of biological properties, they share the same basic molecular structure as a dimer of two heavy chains (approximately 200 kDa) which are noncovalently associated with two pairs of light chains (approximately 20 and 17 kDa). The two globular amino-terminal heads are tethered together by the carboxy-terminal alpha-helical coiled-coil that forms a tail. The tails are believed to be involved in the assembly of myosin molecules into filaments, whereas the heads are thought to have an actin-activated $Mg^{2+}$-ATPase activity. Each myosin head can be divided by three protease-sensitive regions into peptides of approximately 25, 50, and 20 kDa. The more amino-terminal 25 kDa-50 kDa junction is close to the ATP binding region, whereas the actin-binding domain is near the 50 kDa-20 kDa junction.

S1 consists of a globular actin binding and nucleotide binding region known as the catalytic domain. This domain is attached at its carboxy-terminus to an alpha-helix that has two light chains of about 20 kDa each wrapped around it. This light-chain binding domain of S1 is known as the lever arm. Upon transitioning from the pre-stroke to the post-stroke state, the lever arm is believed to swing through an angle of about 90 degrees about a fulcrum point in the catalytic domain near the nucleotide-binding site. The "power stroke" is driven by the hydrolysis of ATP.

The other end of the myosin molecule is an alpha-helical coiled-coiled tail involved in self assembly of myosin molecules into bipolar thick filaments. These thick filaments interdigitate between thinner actin filaments, and the two filament systems slide past one another during contraction of the muscle. This filament sliding mechanism is thought to involve conformational changes in the myosin heads causing them to walk along the thin actin filaments at the expense of ATP hydrolysis. While non-muscle myosins act in a similar manner, they are understood to slide at a slower velocity than the smooth muscle myosins.

The complete cDNA of the human smooth muscle myosin has been described. The sequence of human smooth muscle myosin is 52% identical to human cardiac myosin in the catalytic S1 region. See, for example, PCT publication No. WO 03/14323.

Provided is at least one chemical entity selected from compounds of Formula I

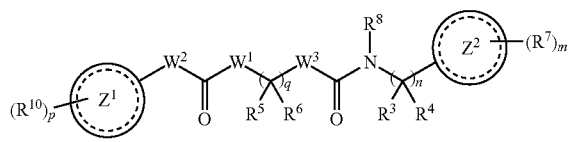

Formula I and pharmaceutically acceptable salts thereof, wherein $W^1$ and $W^2$ are independently selected from $CR^{11}R^{12}$, $NR^{13}$, and O; provided at least one of $W^1$ and $W^2$ is $NR^{13}$;

$W^3$ is selected from $CR^1R^2$, $NR^{14}$, and O;

$Z^1$ is selected from heteroaryl and heterocycloalkyl;

$Z^2$ is selected from aryl, heteroaryl, and heterocycloalkyl;

$R^8$ is selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl;

$R^1$, $R^2$, $R^{11}$, and $R^{12}$ are independently selected from hydrogen, hydroxy, carboxy, sulfonyl, sulfinyl, sulfanyl, optionally substituted alkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted alkoxycarbonyl, optionally substituted amino, optionally substituted aryl, optionally substituted heteroaryl, optionally substituted cycloalkyl, optionally substituted heterocycloalkyl, optionally substituted aminocarbonyl, and optionally substituted aminosulfonyl; or $R^1$ and $R^2$ may optionally be joined together with any intervening atoms to form a group selected from optionally substituted cycloalkyl and optionally substituted heterocycloalkyl;

$R^{13}$ and $R^{14}$ are independently selected from hydrogen, optionally substituted alkyl, optionally substituted alkenyl, optionally substituted alkynyl, optionally substituted aryl, optionally substituted heteroaryl, optionally substituted cycloalkyl, and optionally substituted heterocycloalkyl;

for each occurrence, $R^3$, $R^4$, $R^5$, and $R^6$ are independently selected from hydrogen, hydroxy, carboxy, sulfonyl, sulfinyl, sulfanyl, optionally substituted alkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted cycloalkyl, optionally substituted heterocycloalkyl, optionally substituted aminocarbonyl, and optionally substituted aminosulfonyl; or $R^5$ and $R^6$ taken together form an optionally substituted ring selected from optionally substituted cycloalkyl and optionally substituted heterocycloalkyl.

or $R^1$ and one occurrence of $R^5$ may optionally be joined together with any intervening atoms to form a group selected from optionally substituted cycloalkyl and optionally substituted heterocycloalkyl;

or $R^{14}$ and one occurrence of $R^5$ may optionally be joined together with any intervening atoms to form an optionally substituted heterocycloalkyl ring;

or if $W^1$ is $NR^{13}$, then $R^{13}$ and $R^1$ may optionally be joined together with any intervening atoms to form an optionally substituted heterocycloalkyl ring;

or if $W^1$ is $NR^{13}$, then $R^{13}$ and one occurrence of $R^5$ may optionally be joined together with any intervening atoms to form an optionally substituted heterocycloalkyl ring;

$R^7$ and $R^{10}$ are independently selected from hydrogen, cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;

m is selected from 0, 1, 2, and 3;

n is selected from 0, 1, 2, 3, and 4;

p is selected from 0, 1, 2, and 3; and q is selected from 1, 2, 3, and 4.

Also provided is a pharmaceutical composition comprising at least one chemical entity described herein, together with at least one pharmaceutically acceptable vehicle selected from carriers, adjuvants, and excipients.

Also provided are methods of treatment of one or more diseases associated with smooth muscle myosin or non-muscle myosin. The methods of treatment comprise administering a therapeutically effective amount of at least one chemical entity provided herein or a pharmaceutical composition comprising at least one chemical entity described herein, together with at least one pharmaceutically acceptable vehicle selected from carriers, adjuvants, and excipients.

Also provided are methods of treating or ameliorating a disease associated with airway wall remodeling in a mammal which method comprises administering to a mammal in need thereof a therapeutically effective amount of at least one chemical entity described herein.

Other aspects and embodiments will be apparent to those skilled in the art from the following detailed description.

As used in the present specification, the following words and phrases are generally intended to have the meanings as set forth below, except to the extent that the context in which they are used indicates otherwise.

The following abbreviations and terms have the indicated meanings throughout:

PIPES=1,4-piperazinediethanesulfonic acid
ATP=adenosine 5'-triphosphate
DTT=DL-dithiothreitol
BSA=bovine serum albumin
NADH=nicotinamide adenine dinucleotide
PEP=phosphoenolpyruvic acid
EGTA=ethylene glycol-bis(2-aminoethylether)-N,N,N',N'-tetraacetic acid
Ac=acetyl
APCI=atmospheric pressure chemical ionization
atm=atmosphere
Boc=tert-butoxycarbonyl
c-=cyclo
CBZ or Cbz=carbobenzyloxy=benzyloxycarbonyl
CDI=carbonyldiimidazole
DCM=dichloromethane=methylene chloride=$CH_2Cl_2$
DIAD=diisopropyl azodicarboxylate
DIEA=DIPEA=N,N-diisopropylethylamine
DMAP=4-(dimethylamino)pyridine
DMF=N,N-dimethylformamide
DMSO=dimethyl sulfoxide
$(DPPF)PdCl_2$=[1,1'-bis(diphenylphosphino)ferrocene]dichloropalladium(II)
Et=ethyl
EtOAc=ethyl acetate
EtOH=ethanol
G or g=gram
GC=gas chromatograghy
h or hr=hour
HATU=O-(7-azabenzotriazol-1-yl)-N,N,N',N'-tetramethyluronium hexafluorophosphate
HBTU=O-(benzotriazol-1-yl)-N,N,N',N'-tetramethyluronium hexafluorophosphate
HOBT=1-hydroxybenzotriazole
HPLC=high pressure liquid chromatography
i-=iso
kg or Kg=kilogram
L or l=liter
LC/MS=LCMS=liquid chromatography-mass spectrometry
LDA=lithium diisopropylamide
LRMS=low resolution mass spectrometry
m/z=mass-to-charge ratio
Me=methyl
NMP=N-Methyl-2-pyrrolidone
NMR=nuclear magnetic resonance
MPLC=medium pressure liquid chromatography
min=minute
mL=milliliter
mol=mole
mmol=milimole
MW=microwave
n-=normal
Ph=phenyl
$(Ph_3P)_4Pd$=tetrakis(triphenylphosphine)palladium(0)
$(Ph_3P)_2PdCl_2$=dichlorobis(triphenylphosphine)palladium(II)
RP-HPLC=reverse phase-high pressure liquid chromatography
rt or RT=room temperature
s-=sec-=secondary
t-=tert-=tertiary
TBAF=tetrabutylammonium fluoride
TBS=TBDMS=tert-butyldimethylsilyl
TES=triethylsilyl or triethylsilane
TMS=trimethylsilyl or trimethylsilane
TFA=trifluoroacetic acid
THF=tetrahydrofuran
TLC=thin layer chromatography
UV=ultraviolet
vol=volume equivalent in mL/g or L/Kg or the limiting reagent unless otherwise specified As used herein, when any variable occurs more than one time in a chemical formula, its definition on each occurrence is independent of its definition at every other occurrence.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "ATPase," as used herein, refers to an enzyme that is capable of hydrolyzing ATP. ATPases include proteins comprising molecular motors such as myosins.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

"Alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

"Alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

"Mono- and di-alkylcarboxamide" encompasses a group of the formula —(C=O)NR$_a$R$_b$ where R$_a$ and R$_b$ are independently selected from hydrogen and alkyl groups of the indicated number of carbon atoms, provided that R$_a$ and R$_b$ are not both hydrogen.

"Acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

"Formyl" refers to the group —C(O)H.

"Carboxy" and/or "carboxyl" refer to the group —C(O)OH.

By "alkoxycarbonyl" is meant a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

By "azido" is meant the group —$N_3$.

By "amino" is meant the group —$NH_2$.

"Mono- and di-(alkyl)amino" encompasses secondary and tertiary alkylamino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino.

The term "aminocarbonyl" refers to the group —CONR$^b$R$^c$, where

R$^b$ is selected from H, optionally substituted $C_1$-$C_6$ alkyl, optionally substituted cycloalkyl, optionally substituted heterocycloalkyl, optionally substituted aryl, and optionally substituted heteroaryl, optionally substituted alkoxy; and R$^c$ is independently selected from hydrogen and optionally substituted $C_1$-$C_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms selected from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "aralkyl" refers to the group -alkyl-aryl.

"Carbamimidoyl" refers to the group —C(=NH)—NH2.

"Substituted carbamimidoyl" refers to the group —C(=$NR^e$)—$NR^fR^g$ where $R^e$ is selected from hydrogen, cyano, optionally substituted alkyl, optionally substituted cycloalkyl, optionally substituted aryl, optionally substituted heteroaryl, and optionally substituted heterocycloalkyl; and $R^f$ and $R^g$ are independently selected from hydrogen optionally substituted alkyl, optionally substituted cycloalkyl, optionally substituted aryl, optionally substituted heteroaryl, and optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted C1-C6 alkyl, optionally substituted aryl, and optionally substituted heteroaryl;

$R^b$ is selected from H, optionally substituted C1-C6 alkyl, optionally substituted aryl, and optionally substituted heteroaryl; and $R^c$ is independently selected from hydrogen and optionally substituted C1-C4 alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_3$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:

5- to 7-membered aromatic, monocyclic rings containing one or more, for example, from 1 to 4, or in certain embodiments, from 1 to 3, heteroatoms selected from N, O, and S, with the remaining ring atoms being carbon;

bicyclic heterocycloalkyl rings containing one or more, for example, from 1 to 4, or in certain embodiments, from 1 to 3, heteroatoms selected from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms selected from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Other examples of heteroaryl groups include, but are not limited to, isoquinolinyl, isoxazol-3-yl, and isoxazol-5-yl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteratoms independently selected from oxygen, sulfur, and nitrogen and is not aromatic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)-(optionally substituted ($C_1$-$C_6$)alkyl), —S(O$_2$)-optionally substituted aryl), —S(O$_2$)-optionally substituted heteroaryl), —S(O$_2$)-(optionally substituted heterocycloalkyl), and —S(O$_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently selected from —R$^a$, —OR$^b$, optionally substituted amino (including —NR$^c$OR$^b$, —NR$^c$CO$_2$R$^a$, —NR$^c$CONR$^b$R$^c$, NR$^b$C(NR$^c$)NR$^b$R$^c$, NR$^b$C(NCN)NR$^b$R$^c$, —NR$^b$C(NH$_2$)NC(O)NH$_2$, —NR$^b$C(NH$_2$)N(CN), and —NR$^c$SO$_2$R$^a$), halo, cyano, azido, nitro, oxo (as a substitutent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is selected from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

R$^b$ is selected from hydrogen, optionally substituted $C_1$-$C_6$ alkyl, optionally substituted cycloalkyl, optionally substituted heterocycloalkyl, optionally substituted aryl, and optionally substituted heteroaryl; and R$^c$ is independently selected from hydrogen and optionally substituted $C_1$-$C_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl or heterocycloalkyl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

In some embodiments, a substituted alkoxy group is "polyalkoxy" or —O-(optionally substituted alkylene)-(optionally substituted alkoxy), and includes groups such as —OCH2CH2OCH3, and residues of glycol ethers such as polyethyleneglycol, and —O(CH2CH2O)xCH3, where x is an integer of 2-20, such as 2-10, and for example, 2-5. Another substituted alkoxy group is hydroxyalkoxy or —OCH2(CH2)yOH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bc(NCN)NR^bR^c$, and —$NR^cSO_2R^a$), halo, cyano, nitro, oxo (as a substitutent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_4$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "substituted amino" refers to the group —$NHR^d$ or —$NR^dR^e$ wherein $R^d$ is selected from hydroxy, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein $R^e$ is selected from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, $NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^d$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_4$-$C_4$ alkylphenyl), —$NH(C_1$-$C_4$ alkylphenyl), cyano, nitro, oxo (as a substitutent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "phosphato" refers to —$OP(O)(OR^b)OR^c$ where $R^b$ is selected from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl. In some embodiments, $R^b$ and $R^c$ are hydrogen.

Compounds of Formula I include, but are not limited to, optical isomers of compounds of Formula I, racemates, and other mixtures thereof. In those situations, the single enantiomers or diastereomers, i.e. optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities described herein include all tautomeric forms of the compound.

Chemical entities described herein include, but are not limited to compounds of Formula I and all pharmaceutically acceptable forms thereof. Pharmaceutically acceptable forms of the chemical entities recited herein include pharmaceutically acceptable salts, solvates, crystal forms (including polymorphs and clathrates), chelates, non-covalent complexes, prodrugs, and mixtures thereof. In certain embodiments, the chemical entities described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any chemical entities that become compounds of Formula I when administered to a patient, e.g. upon metabolic processing of the prodrug. Examples of prodrugs include, but are not limited to, acetate, formate, phosphate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

By "significant" is meant any detectable change that is statistically significant in a standard parametric test of statistical significance such as Student's T-test, where p<0.05.

The term "therapeutically effective amount" of a chemical entity described herein means an amount effective, when administered to a human or non-human patient, to provide a therapeutic benefit such as amelioration of symptoms, slowing of disease progression, or prevention of disease.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods described herein can be useful in both human therapy and veterinary applications. In some embodiments, the patient is a mammal; in some embodiments the patient is human; and in some embodiments the patient is selected from cats and dogs.

Provided is at least one chemical entity selected from compounds of Formula I

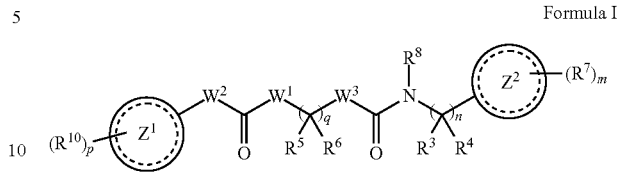

Formula I and pharmaceutically acceptable salts thereof, wherein
$W^1$ and $W^2$ are independently selected from $CR^{11}R^{12}$, $NR^{13}$, and O; provided at least one of $W^1$ and $W^2$ is $NR^{13}$;
$W^3$ is selected from $CR^1R^2$, $NR^{14}$, and O;
$Z^1$ is selected from heteroaryl and heterocycloalkyl;
$Z^2$ is selected from aryl, heteroaryl, and heterocycloalkyl;
$R^8$ is selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl;
$R^1$, $R^2$, $R^{11}$, and $R^{12}$ are independently selected from hydrogen, hydroxy, carboxy, sulfonyl, sulfinyl, sulfanyl, optionally substituted alkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted alkoxycarbonyl, optionally substituted amino, optionally substituted aryl, optionally substituted heteroaryl, optionally substituted cycloalkyl, optionally substituted heterocycloalkyl, optionally substituted aminocarbonyl, and optionally substituted aminosulfonyl; or $R^1$ and $R^2$ may optionally be joined together with any intervening atoms to form a group selected from optionally substituted cycloalkyl and optionally substituted heterocycloalkyl;
$R^{13}$ and $R^{14}$ are independently selected from hydrogen, optionally substituted alkyl, optionally substituted alkenyl, optionally substituted alkynyl, optionally substituted aryl, optionally substituted heteroaryl, optionally substituted cycloalkyl, and optionally substituted heterocycloalkyl;
for each occurrence, $R^3$, $R^4$, $R^5$, and $R^6$ are independently selected from hydrogen, hydroxy, carboxy, sulfonyl, sulfinyl, sulfanyl, optionally substituted alkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted cycloalkyl, optionally substituted heterocycloalkyl, optionally substituted aminocarbonyl, and optionally substituted aminosulfonyl; or $R^5$ and $R^6$ taken together form an optionally substituted ring selected from optionally substituted cycloalkyl and optionally substituted heterocycloalkyl.
or $R^1$ and one occurrence of $R^5$ may optionally be joined together with any intervening atoms to form a group selected from optionally substituted cycloalkyl and optionally substituted heterocycloalkyl;
or $R^{14}$ and one occurrence of $R^5$ may optionally be joined together with any intervening atoms to form an optionally substituted heterocycloalkyl ring;
or if $W^1$ is $NR^{13}$, then $R^{13}$ and $R^{14}$ may optionally be joined together with any intervening atoms to form an optionally substituted heterocycloalkyl ring;

or if $W^1$ is $NR^{13}$, then $R^{13}$ and one occurrence of $R^5$ may optionally be joined together with any intervening atoms to form an optionally substituted heterocycloalkyl ring;

$R^7$ and $R^{10}$ are independently selected from hydrogen, cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;

m is selected from 0, 1, 2, and 3;
n is selected from 0, 1, 2, 3, and 4;
p is selected from 0, 1, 2, and 3; and
q is selected from 1, 2, 3, and 4.

In some embodiments, $Z^1$ is selected from heteroaryl and heterocycloalkyl. In some embodiments, $Z^1$ is selected from quinolinyl, isoquinolinyl, pyridino[4,3-d]pyridinyl, benzothiazolyl, thiadiazolyl, pyridino[3,4-d]pyridinyl, pyridinyl, pyridino[3,2-d]pyridinyl, 8-hydropyrrolo[1,2-e]pyrimidinyl, isoxazolyl, 8-hydropyrazolo[1,5-a]pyridinyl, pyridino[2,3-d]pyridinyl, benzo[d]isozaolyl, pyrazinyl, thiazolyl, 4-oxo-3-hydroquinazolinyl, 4-hydroimidazo[1,2-a]pyridinyl, 1,3-thiazolo[5,4-b]pyridinyl, oxadiazolyl, benzoxazolyl, quinoxalinyl, thienyl, pyrimidinyl, benzimidazoll, piperidinyl, and pyrazolyl. In some embodiments, $Z^1$ is selected from isoquinolin-3-yl, benzo[d]thiazol-2-yl, benzo[d]oxazol-2-yl, 1,3,4-thiadiazol-2-yl, pyridin-2-yl, quinolin-2-yl, quinolin-3-yl, thiazol-5-yl, thien-2-yl, and pyrrolo[1,2-c]pyrimidin-3-yl.

In some embodiments, $Z^2$ is selected from aryl, heteroaryl, and heterocycloalkyl. In some embodiments, $Z^2$ is selected from phenyl, naphthyl, and indanyl. In some embodiments, $Z^2$ is phenyl.

In some embodiments, $W^1$ is $CR^{11}R^{12}$.

In some embodiments, $R^{11}$ and $R^{12}$ are each independently selected from hydrogen and optionally substituted lower alkyl.

In some embodiments, $R^{11}$ and $R^{12}$ are each independently selected from hydrogen and lower alkyl.

In some embodiments, $R^{11}$ and $R^{12}$ are both hydrogen.

In some embodiments, $W^1$ is $NR^{13}$.

In some embodiments, $R^{13}$ is selected from hydrogen and optionally substituted lower alkyl.

In some embodiments, $R^{13}$ is selected from hydrogen and lower alkyl.

In some embodiments, $R^{13}$ is hydrogen.

In some embodiments, $W^1$ is O.

In some embodiments, $W^2$ is $CR^{11}R^{12}$.

In some embodiments, $R^{11}$ and $R^{12}$ are each independently selected from hydrogen and optionally substituted lower alkyl.

In some embodiments, $R^{11}$ and $R^{12}$ are each independently selected from hydrogen and lower alkyl.

In some embodiments, $R^{11}$ and $R^{12}$ are both hydrogen.

In some embodiments, $W^2$ is $NR^{13}$.

In some embodiments, $R^{13}$ is selected from hydrogen and optionally substituted lower alkyl.

In some embodiments, $R^{13}$ is selected from hydrogen and lower alkyl.

In some embodiments, $R^{13}$ is hydrogen.

In some embodiments, $W^2$ is O.

In some embodiments, $W^1$ is O and $W^2$ is $NR^{13}$. In some embodiments, $R^{13}$ is hydrogen.

In some embodiments, $W^3$ is $CR^1R^2$.

In some embodiments, $R^1$ and $R^2$ are independently selected from hydrogen and optionally substituted alkyl.

In some embodiments, $R^1$ and $R^2$ are independently selected from hydrogen and optionally substituted lower alkyl.

In some embodiments, $R^1$ and $R^2$ are independently selected from hydrogen and lower alkyl.

In some embodiments, $R^1$ and $R^2$ are independently selected from hydrogen and methyl.

In some embodiments, $R^1$ and $R^2$, together with the carbon to which they are attached, form a group selected from optionally substituted cycloalkyl and optionally substituted heterocycloalkyl.

In some embodiments, $R^1$ and $R^2$, together with the carbon to which they are attached, form a group selected from cyclopropyl, cyclobutyl, cyclopentyl, cyclohexyl, piperidinyl, and tetrahydropyranyl, any of which is optionally substituted.

In some embodiments, $R^1$ and $R^2$, together with the carbon to which they are attached, form a group selected from piperidine and tetrahydropyran, either of which is optionally substituted with 2-aminoacetyl or 2-(tert-butoxycarbonylamino)acetyl.

In some embodiments, $R^1$ and $R^2$, together with the carbon to which they are attached, form a group selected from tetrahydropyran, 1-(2-(tert-butoxycarbonylamino)acetyl)piperidin-4-yl, and 1-(2-aminoacetyl)piperidin-4-yl.

In some embodiments, $W^3$ is $NR^{14}$.

In some embodiments, $R^{14}$ is selected from hydrogen and optionally substituted lower alkyl.

In some embodiments, $R^{14}$ is selected from hydrogen, lower alkyl, and lower alkyl substituted with one or two groups selected from hydroxy, halo, optionally substituted amino, and optionally substituted alkoxy.

In some embodiments, $R^{14}$ is selected from hydrogen, lower alkyl, and lower alkyl substituted with one or two groups selected from hydroxy, optionally substituted amino, and optionally substituted alkoxy.

In some embodiments, $R^{14}$ is selected from hydrogen, methyl, ethyl, propyl, and isopropyl, wherein methyl, ethyl, propyl, and isopropyl are optionally substituted with one or two groups selected from hydroxy, optionally substituted amino, and optionally substituted alkoxy.

In some embodiments, $R^{14}$ is selected from hydrogen, methyl, ethyl, propyl, and isopropyl, wherein methyl, ethyl, propyl, and isopropyl are optionally substituted with one or two hydroxy groups.

In some embodiments, $R^{14}$ is selected from methyl, ethyl, hydroxymethyl, 2-hydroxyethyl, 2,2-difluoroethyl, and isopropyl.

In some embodiments, $R^{14}$ is selected from methyl, ethyl, hydroxymethyl, 2-hydroxyethyl, and isopropyl.

In some embodiments, $R^{14}$ is selected from methyl and ethyl. In some embodiments, $R^{14}$ is methyl.

In some embodiments, $R^8$ is selected from hydrogen and optionally substituted lower alkyl.

In some embodiments, $R^8$ is selected from hydrogen and lower alkyl.

In some embodiments, $R^8$ is selected from hydrogen and methyl.

In some embodiments, $R^8$ is hydrogen.

In some embodiments, q is 3.
In some embodiments, q is 2.
In some embodiments, q is 1.

In some embodiments, for each occurrence, each $R^5$ is independently selected from hydrogen, optionally substituted lower alkyl, and optionally substituted alkenyl.

In some embodiments, for each occurrence, each $R^5$ is independently selected from hydrogen and optionally substituted lower alkyl.

In some embodiments, for each occurrence, each $R^5$ is independently selected from hydrogen, lower alkyl, and lower alkyl substituted with one, two, or three groups selected from optionally substituted heterocycloalkyl, optionally substituted heteroaryl, optionally substituted alkoxy, optionally substituted alkoxycarbonyl, hydroxy, optionally substituted amino, optionally substituted aminocarbonyl, acyl, halo, and azido.

In some embodiments, for each occurrence, each $R^5$ is independently selected from hydrogen, lower alkyl, and lower alkyl substituted with one, two, or three groups selected from optionally substituted heterocycloalkyl, optionally substituted alkoxy, optionally substituted alkoxycarbonyl, hydroxy, optionally substituted amino, optionally substituted aminocarbonyl, acyl, and azido.

In some embodiments, for each occurrence, each $R^5$ is independently selected from hydrogen, lower alkyl, and lower alkyl substituted with one, two, or three groups selected from 4-(lower alkyl)piperazin-1-yl, oxopiperazin-1-yl, morpholino, benzyloxy, benzyloxycarbonyl, methoxycarbonyl, hydroxy, amino, dimethylamino, methoxy(methyl)carbamoyl, acetamido, acetyl, and azido.

In some embodiments, for each occurrence, each $R^5$ is independently selected from hydrogen, methyl, ethyl, isopropyl, isobutyl, n-propyl, n-butyl, n-pentyl, isopentyl, and 4-methylpentyl, wherein each of methyl, ethyl, isopropyl, isobutyl, n-propyl, n-butyl, n-pentyl, isopentyl, and 4-methylpentyl is optionally substituted with one, two, or three groups selected from 4-methylpiperazin-1-yl, 3-oxopiperazin-1-yl, morpholino, benzyloxy, benzyloxycarbonyl, methoxycarbonyl, hydroxy, amino, dimethylamino, methoxy(methyl)carbamoyl, acetamido, acetyl, and azido.

In some embodiments, for each occurrence, each $R^5$ is independently selected from hydrogen, ethyl, 2-(benzyloxy)-2-oxoethyl, benzyloxymethyl, isobutyl, isopropyl, methyl, 2-hydroxyethyl, 2-methoxy-2-oxoethyl, 3-(benzyloxy)-3-oxopropyl, 3-hydroxypropyl, 3-methoxy-3-oxopropyl, 4-aminobutyl, 4-azidobutyl, 4-hydroxybutyl, 4-methoxy-4-oxobutyl, hydroxymethyl, 2-hydroxy-2-methylpropyl, 4-hydroxy-4-methylpentyl, 3-aminopropyl, (4-methylpiperazin-1-yl)methyl, 2-(3-oxopiperazin-1-yl)ethyl, morpholinoethyl, morpholinomethyl, (3-oxopiperazin-1-yl)methyl, (4-methylpiperazin-1-yl)ethyl, (dimethylamino)methyl, (R)-2-hydroxypropyl, (S)-2-hydroxypropyl, 2-(methoxy(methyl)amino)-2-oxoethyl, 3-(methoxy(methyl)amino)-3-oxopropyl, 3-hydroxy-3-methylbutyl, 3-hydroxybutyl, 4-acetamidobutyl, 4-hydroxypentyl, and 4-oxopentyl.

In some embodiments, for each occurrence, each $R^6$ is independently selected from hydrogen and optionally substituted lower alkyl.

In some embodiments, for each occurrence, each $R^6$ is independently selected from hydrogen and lower alkyl.

In some embodiments, for each occurrence, $R^6$ is hydrogen.

In some embodiments, $-(CR^5R^6)_q-$ is $-CH_2CH(R^5)-$ wherein $R^5$ is selected from hydrogen, lower alkyl, and lower alkyl substituted with one, two or three groups selected from 4-(lower alkyl)piperazin-1-yl, oxopiperazin-1-yl, morpholino, benzyloxy, benzyloxycarbonyl, methoxycarbonyl, hydroxy, amino, dimethylamino, methoxy(methyl)carbamoyl, acetamido, acetyl, azido, phosphato (such as $-OP(O)(OH)_2$), and halo.

In some embodiments, $-(CR^5R^6)_q-$ is $-CH_2CH(R^5)-$ wherein $R^5$ is lower alkyl substituted with one, two, or three groups selected from hydroxy and phosphato (such as $-OP(O)(OH)_2$). In some embodiments, $-(CR^5R^6)_q-$ is $-CH_2CH(R^5)-$ wherein $R^5$ is lower alkyl substituted with $-OP(O)(OH)_2$ and optionally further substituted with one or two hydroxy groups.

In some embodiments, $-(CR^5R^6)_q-$ is $-CH_2CH(R^5)-$ wherein $R^5$ is lower alkyl substituted with optionally substituted heteroaryl. In some embodiments, $R^5$ is lower alkyl substituted with imidazol-4-yl, imidazol-2-yl, pyridin-2-yl, 1,2,4-oxadiazol-5-yl, isoxazol-5-yl, imidazo[1,5-a]piperazin-3-yl, or 4-hydroimidazo[1,5-a]pyrazin-3-yl, each of which is optionally substituted. In some embodiments, $R^5$ is lower alkyl substituted with imidazol-4-yl, imidazol-2-yl, pyridin-2-yl, 1,2,4-oxadiazol-5-yl, isoxazol-5-yl, imidazo[1,5-a]piperazin-3-yl, or 4-hydroimidazo[1,5-a]pyrazin-3-yl, each of which is optionally substituted with a lower alkyl group.

In some embodiments, $-(CR^5R^6)_q-$ is $-CH_2CH(R^5)-$ wherein $R^5$ is lower alkyl substituted with optionally substitute aminocarbonyl. In some embodiments, $R^5$ is lower alkyl substituted with $-C(O)NR^{11}R^{12}$ wherein $R^{11}$ and $R^{12}$, together with the nitrogen to which they are bound, form an optionally substituted 5- to 7-membered heterocycloalkyl ring or optionally substituted 8- to 12-membered bicyclic heterocycloalkyl ring, each of which optionally includes an additional heteroatom chosen from oxygen, sulfur, and nitrogen. In some embodiments, $R^5$ is lower alkyl substituted with $-C(O)NR^{11}$ wherein $R^{11}$ and $R^{12}$, together with the nitrogen to which they are bound, form a ring chosen from 4-piperazinyl, 1,4-diazaperhydroepinyl, and 4,5,6,7-tetrahydroimidazo[5,4-c]pyridin-5-yl, each of which is optionally substituted. In some embodiments, $R^5$ is lower alkyl substituted with $-C(O)NR^{11}R^{12}$ wherein $R^{11}$ and $R^{12}$, together with the nitrogen to which they are bound, form a 4-piperazinyl ring which is optionally substituted. In some embodiments, $R^5$ is lower alkyl substituted with $-C(O)NR^{11}R^{12}$ wherein $R^{11}$ and $R^{12}$, together with the nitrogen to which they are bound, form a 4-piperazinyl ring which is optionally substituted with one or two groups chosen from lower alkyl, hydroxy substituted lower alkyl, and halo substituted lower alkyl.

In some embodiments, $W^2$ is NH, $W^1$ is O, and $W^3$ is $CR^1R^2$.

In some embodiments, $W^2$ is NH, $W^1$ is $CH_2$, and $W^3$ is $NR^{14}$.

In some embodiments, $W^2$ is NH, $W^1$ is O, and $W^3$ is $NR^{14}$.

In some embodiments, m is 0.

In some embodiments, m is selected from 1 and 2, and each $R^7$ is selected from halo and optionally substituted alkyl.

In some embodiments, $R^7$ is selected from halo and optionally substituted lower alkyl.

In some embodiments, $R^7$ is selected from halo and lower alkyl.

In some embodiments, each $R^7$ is selected from chloro, fluoro, and methyl.

In some embodiments, $-(R^7)_m$, together with $Z^2$ to which it is attached, forms a group selected from 2-chlorophenyl, 2-methylphenyl, 2-chloro-4-fluorophenyl, 2-chloro-3-fluorophenyl, 2,3-dichlorophenyl, 2,3-difluorophenyl, 2,4-dichlorophenyl, 2,4-difluorophenyl, and 3-chloro-2-fluorophenyl.

In some embodiments, n is selected from 1 and 2.

In some embodiments, n is 1.

In some embodiments, each $R^3$ and $R^4$ is independently selected from hydrogen and optionally substituted lower alkyl.

In some embodiments, each $R^3$ and $R^4$ is independently selected from hydrogen, methyl, ethyl, isopropyl, and hydroxymethyl.

In some embodiments, $R^3$ and $R^4$ is hydrogen.

In some embodiments, $Z^1$ is heteroaryl, p is selected from 0, 1, and 2, and $R^{10}$ is selected from halo, optionally substituted alkyl, optionally substituted alkenyl, optionally substituted heterocycloalkyl, and optionally substituted aryl.

In some embodiments, $Z^1$ is heteroaryl, p is selected from 0, 1, and 2, and $R^{10}$ is selected from halo, optionally substituted alkyl, optionally substituted alkenyl, and optionally substituted aryl.

In some embodiments, $Z^1$ is isoquinolinyl, p is 1, and $R^{10}$ is halo. In some embodiments, $Z^1$ is 6-fluoroisoquinolin-3-yl.

In some embodiments, $Z^1$ is pyridin-2-yl, p is 1, and $R^{10}$ is chosen from halo and optionally substituted lower alkyl. In some embodiments, $Z^1$ is pyridin-2-yl, p is 1, and $R^{10}$ is chosen from halo and trifluoromethyl.

In some embodiments, $Z^1$ is isoxazol-3-yl, p is 1, and $R^{10}$ is chosen from optionally substituted phenyl. In some embodiments, $Z^1$ is isoxazol-3-yl, p is 1, and $R^{10}$ is chosen from phenyl and halophenyl.

In some embodiments, $Z^1$ is isoxazol-5-yl, p is 1, and $R^{10}$ is chosen from optionally substituted phenyl. In some embodiments, $Z^1$ is isoxazol-5-yl, p is 1, and $R^{10}$ is chosen from phenyl and halophenyl.

In some embodiments, p is 0 and $Z^1$ is selected from 2,7-naphthyridinyl, isoquinolinyl, benzo[d]thiazolyl, benzo[d]oxazolyl, 1,3,4-thiadiazolyl, pyridinyl, quinolinyl, thiazolyl, thienyl, and pyrrolo[1,2-c]pyrimidinyl.

In some embodiments, p is 0 and $Z^1$ is selected from isoquinolinyl, benzo[d]thiazolyl, benzo[d]oxazolyl, 1,3,4-thiadiazolyl, pyridinyl, quinolinyl, thiazolyl, thienyl, and pyrrolo[1,2-c]pyrimidinyl.

In some embodiments, p is 0 and $Z^1$ is isoquinolin-3-yl. In some embodiments, p is 0 and $Z^1$ is benzo[d]thiazolyl.

In some embodiments, p is 0 and $Z^1$ is 2,7-naphthyridin-3-yl.

In some embodiments, $Z^1$ is selected from isoquinolin-3-yl, isoxazol-3-yl, benzo[d]thiazol-2-yl, benzo[d]oxazol-2-yl, 1,3,4-thiadiazol-2-yl, pyridin-2-yl, quinolin-2-yl, quinolin-3-yl, thiazol-5-yl, thien-2-yl, and pyrrolo[1,2-c]pyrimidin-3-yl, p is selected from 1 and 2, and each $R^{10}$ is independently selected from halo, optionally substituted alkyl, optionally substituted alkenyl, and optionally substituted aryl.

In some embodiments, $Z^1$ is selected from isoquinolin-3-yl, benzo[d]thiazol-2-yl, benzo[d]oxazol-2-yl, 1,3,4-thiadiazol-2-yl, pyridin-2-yl, quinolin-2-yl, quinolin-3-yl, thiazol-5-yl, thien-2-yl, and pyrrolo[1,2-c]pyrimidin-3-yl. p is selected from 1 and 2, and each $R^{10}$ is independently selected from halo, optionally substituted alkyl, optionally substituted alkenyl, and optionally substituted aryl.

In some embodiments, $R^{10}$ is independently selected from halo, optionally substituted lower alkyl, optionally substituted lower alkenyl, and optionally substituted phenyl.

In some embodiments, $R^{10}$ is independently selected from chloro, fluoro, bromo, trifluoromethyl, methyl, ethyl, vinyl, and phenyl.

In some embodiments, $Z^1$ is isoquinolin-3-yl, p is selected from 1 and 2, and each $R^{10}$ is independently selected from halo. In some embodiments, $Z^1$ is isoquinolin-3-yl, p is selected from 1 and 2, and each $R^{10}$ is fluoro. In some embodiments, $Z^1$ is isoquinolin-3-yl, p is 1, and $R^{10}$ is fluoro.

In some embodiments, $Z^1$ is isoxazol-5-yl, p is 1, and $R^{10}$ is selected from optionally substituted phenyl. In some embodiments, $Z^1$ is isoxazol-5-yl, p is 1, and $R^{10}$ is selected from phenyl optionally substituted with one or two halo groups.

In some embodiments, $Z^1$ is isoxazol-3-yl, p is 1, and $R^{10}$ is selected from optionally substituted phenyl. In some embodiments, $Z^1$ is isoxazol-3-yl, p is 1, and $R^{10}$ is selected from phenyl optionally substituted with one or two halo groups.

In some embodiments, $Z^1$ is 1,3,4-thiadiazol-2-yl, p is 1, and $R^{10}$ is selected from optionally substituted phenyl. In some embodiments, $Z^1$ is isoxazol-3-yl, p is 1, and $R^{10}$ is selected from phenyl optionally substituted with one or two halo groups.

In some embodiments, $-(R^{10})_p$, together with $Z^1$, forms a group selected from 3-phenylisoxazol-5-yl, 5-phenylisoxazol-3-yl, 6-methylbenzo[d]thiazol-2-yl, 5-ethylpyridin-2-yl, 4-methylbenzo[d]thiazol-2-yl, 5,6-dichlorobenzo[d]thiazol-2-yl, 5,6-difluorobenzo[d]thiazol-2-yl, 5,6-dimethylbenzo[d]thiazol-2-yl, 5-bromopyridin-2-yl, 5-phenyl-1,3,4-thiadiazol-2-yl, 5-vinylpyridin-2-yl, 6-fluoroisoquinolin-3-yl, 5-fluoroisoquinolin-3-yl, 7-fluoroisoquinolin-3-yl, 6-(trifluoromethyl)benzo[d]thiazol-2-yl, 5-phenylpyridin-2-yl, 4-methyl-2-phenylthiazol-5-yl, 5-methylpyridin-2-yl, 5-bromopyridin-2-yl, and 4-methylthiophen-2-yl.

In some embodiments, $-(R^{10})_p$, together with $Z^1$, forms a group selected from 6-methylbenzo[d]thiazol-2-yl, 5-ethylpyridin-2-yl, 4-methylbenzo[d]thiazol-2-yl, 5,6-dichlorobenzo[d]thiazol-2-yl, 5,6-difluorobenzo[d]thiazol-2-yl, 5,6-dimethylbenzo[d]thiazol-2-yl, 5-bromopyridin-2-yl, 5-phenyl-1,3,4-thiadiazol-2-yl, 5-vinylpyridin-2-yl, 6-fluoroisoquinolin-3-yl, 5-fluoroisoquinolin-3-yl, 7-fluoroisoquinolin-3-yl, 6-(trifluoromethyl)benzo[d]thiazol-2-yl, 5-phenylpyridin-2-yl, 4-methyl-2-phenylthiazol-5-yl, 5-methylpyridin-2-yl, 5-bromopyridin-2-yl, and 4-methylthiophen-2-yl.

Also provided is at least one chemical entity selected from compounds of Formula II

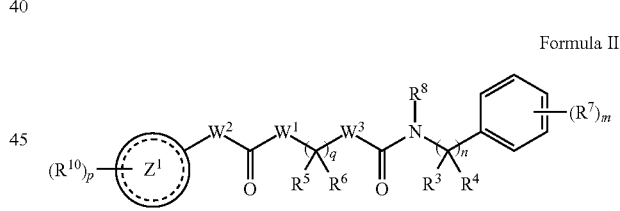

Formula II and pharmaceutically acceptable salts thereof wherein $W^1$, $W^2$, $W^3$, $Z^1$, $R^3$, $R^4$, $R^5$, $R^6$, $R^7$, $R^8$, $R^{10}$, m, n, p, and q are as described for compounds of Formula I.

Also provided is at least one chemical entity selected from compounds of Formula III Formula III and pharmaceutically acceptable salts thereof wherein $Z^1$, $R^3$, $R^4$, $R^5$, $R^6$, $R^7$, $R^8$, $R^{10}$, m, and p are as described for compounds of Formula I.

Also provided is at least one chemical entity selected from selected from

| Structure | Chemical Name |
|---|---|
| 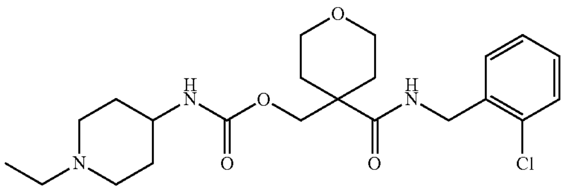 [SMILES: CCN1CCC(NC(=O)OCC2(C(=O)NCc3ccccc3Cl)CCOCC2)CC1] | N-[(2-chlorophenyl)methyl](4-{[N-(1-ethyl(4-piperidyl))carbamoyloxy]methyl}(2H-3,4,5,6-tetrahydropyran-4-yl))carboxamide |
| 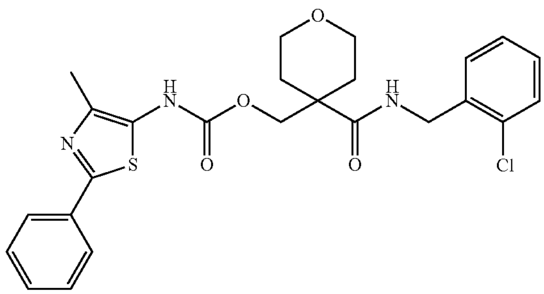 [SMILES: Cc1nc(-c2ccccc2)sc1NC(=O)OCC1(C(=O)NCc2ccccc2Cl)CCOCC1] | N-[(2-chlorophenyl)methyl](4-{[N-(4-methyl-2-phenyl(1,3-thiazol-5-yl))carbamoyloxy]methyl}(2H-3,4,5,6-tetrahydropyran-4-yl))carboxamide |
| 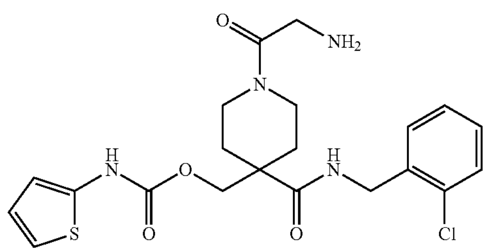 [SMILES: NCC(=O)N1CCC(COC(=O)Nc2cccs2)(C(=O)NCc2ccccc2Cl)CC1] | {1-(2-aminoacetyl)-4-[(N-(2-thienyl)carbamoyloxy)methyl](4-piperidyl)}-N-[(2-chlorophenyl)methyl]carboxamide |
| 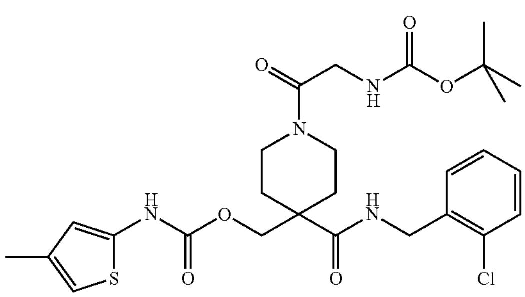 [SMILES: Cc1csc(NC(=O)OCC2(C(=O)NCc3ccccc3Cl)CCN(C(=O)CNC(=O)OC(C)(C)C)CC2)c1] | (tert-butoxy)-N-[2-(4-{N-[(2-chlorophenyl)methyl]carbamoyl}-4-{[N-(4-methyl(2-thienyl))carbamoyloxy]methyl}piperidyl)-2-oxoethyl]carboxamide |
| 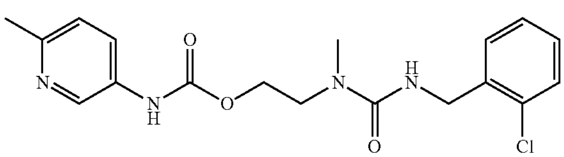 [SMILES: Cc1ccc(NC(=O)OCCN(C)C(=O)NCc2ccccc2Cl)cn1] | {[(2-chlorophenyl)methyl]amino}-N-methyl-N-{2-[N-(6-methyl(3-pyridyl))carbamoyloxy]ethyl}carboxamide |
| 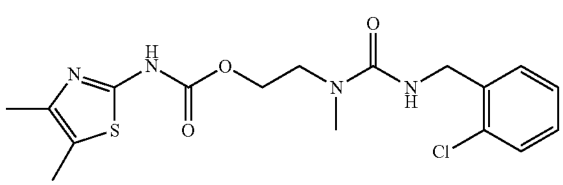 [SMILES: Cc1nc(NC(=O)OCCN(C)C(=O)NCc2ccccc2Cl)sc1C] | N-(4,5-dimethyl(1,3-thiazol-2-yl))[2-({[(2-chlorophenyl)methyl]amino}-N-methylcarbonylamino)ethoxy]carboxamide |
| 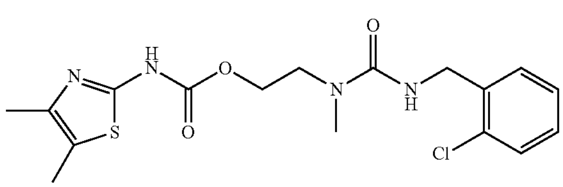 [SMILES: Cc1nc(NC(=O)OCCN(C)C(=O)NCc2ccccc2Cl)sc1C] | [2-({[(2-chlorophenyl)methyl]amino}-N-methylcarbonylamino)ethoxy]-N-(5-methyl(1,3-thiazol-2-yl))carboxamide |

-continued

| Structure | Chemical Name |
|---|---|
| 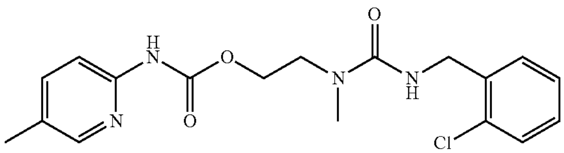 [SMILES: Cc1ccc(NC(=O)OCCN(C)C(=O)NCc2ccccc2Cl)nc1] | [2-({[(2-chlorophenyl)methyl]amino}-N-methylcarbonylamino)ethoxy]-N-(5-methyl(2-pyridyl))carboxamide |
| 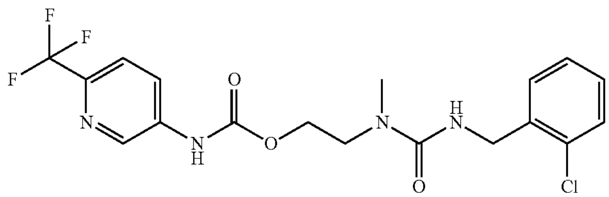 [SMILES: CN(CCOC(=O)Nc1ccc(C(F)(F)F)nc1)C(=O)NCc1ccccc1Cl] | {[(2-chlorophenyl)methyl]amino}-N-methyl-N-(2-{N-[6-(trifluoromethyl)(3-pyridyl)]carbamoyloxy}ethyl)carboxamide |
| 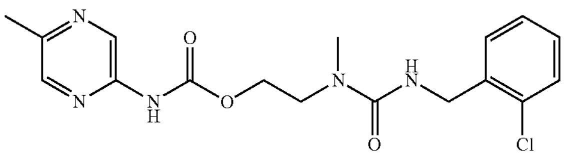 [SMILES: Cc1cnc(NC(=O)OCCN(C)C(=O)NCc2ccccc2Cl)cn1] | {[(2-chlorophenyl)methyl]amino}-N-methyl-N-{2-[N-(5-methylpyrazin-2-yl)carbamoyloxy]ethyl}carboxamide |
| 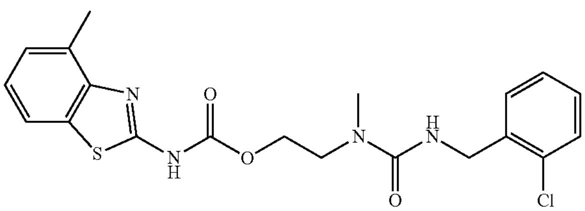 [SMILES: Cc1cccc2sc(NC(=O)OCCN(C)C(=O)NCc3ccccc3Cl)nc12] | {[(2-chlorophenyl)methyl]amino}-N-methyl-N-{2-[N-(4-methylbenzothiazol-2-yl)carbamoyloxy]ethyl}carboxamide |
| 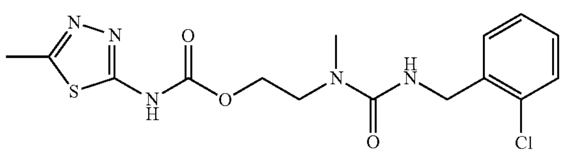 [SMILES: Cc1nnc(NC(=O)OCCN(C)C(=O)NCc2ccccc2Cl)s1] | {[(2-chlorophenyl)methyl]amino}-N-methyl-N-{2-[N-(5-methyl(1,3,4-thiadiazol-2-yl))carbamoyloxy]ethyl}carboxamide |
| 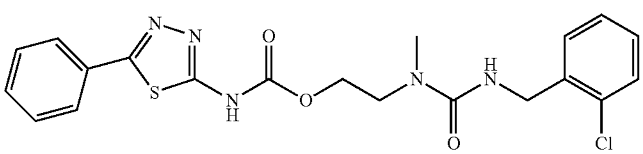 [SMILES: CN(CCOC(=O)Nc1nnc(-c2ccccc2)s1)C(=O)NCc1ccccc1Cl] | {[(2-chlorophenyl)methyl]amino}-N-methyl-N-{2-[N-(5-phenyl(1,3,4-thiadiazol-2-yl))carbamoyloxy]ethyl}carboxamide |
| 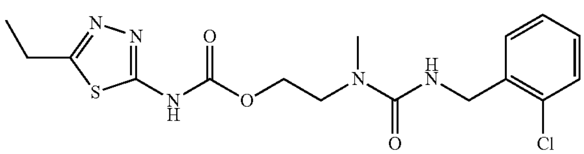 [SMILES: CCc1nnc(NC(=O)OCCN(C)C(=O)NCc2ccccc2Cl)s1] | {[(2-chlorophenyl)methyl]amino}-N-{2-[N-(5-ethyl(1,3,4-thiadiazol-2-yl))carbamoyloxy]ethyl}-N-methylcarboxamide |
| 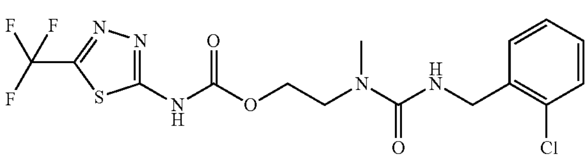 [SMILES: CN(CCOC(=O)Nc1nnc(C(F)(F)F)s1)C(=O)NCc1ccccc1Cl] | {[(2-chlorophenyl)methyl]amino}-N-methyl-N-(2-{N-[5-(trifluoromethyl)(1,3,4-thiadiazol-2-yl)]carbamoyloxy}ethyl)carboxamide |
| 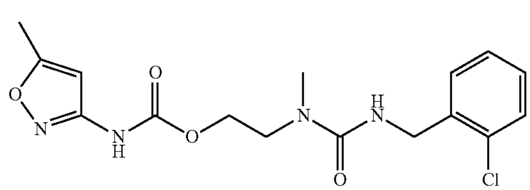 [SMILES: Cc1cc(NC(=O)OCCN(C)C(=O)NCc2ccccc2Cl)no1] | {[(2-chlorophenyl)methyl]amino}-N-methyl-N-{2-[N-(5-methylisoxazol-3-yl)carbamoyloxy]ethyl}carboxamide |

| Structure | Chemical Name |
|---|---|
| 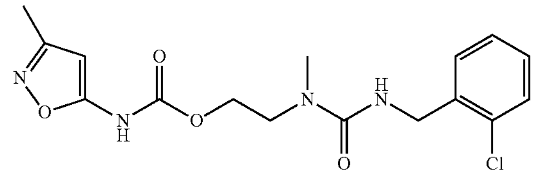 [SMILES: Cc1cc(NC(=O)OCCN(C)C(=O)NCc2ccccc2Cl)on1] | {[(2-chlorophenyl)methyl]amino}-N-methyl-N-{2-[N-(3-methylisoxazol-5-yl)carbamoyloxy]ethyl}carboxamide |
| 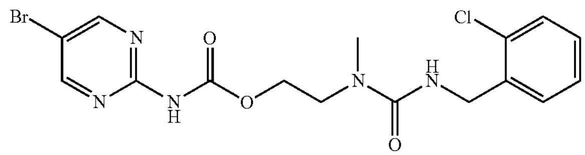 [SMILES: CN(CCOC(=O)Nc1ncc(Br)cn1)C(=O)NCc1ccccc1Cl] | N-{2-[N-(5-bromopyrimidin-2-yl)carbamoyloxy]ethyl}{[(2-chlorophenyl)methyl]amino}-N-methylcarboxamide |
| 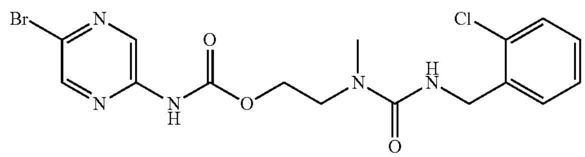 [SMILES: CN(CCOC(=O)Nc1cnc(Br)cn1)C(=O)NCc1ccccc1Cl] | N-{2-[N-(5-bromopyrazin-2-yl)carbamoyloxy]ethyl}{[(2-chlorophenyl)methyl]amino}-N-methylcarboxamide |
| 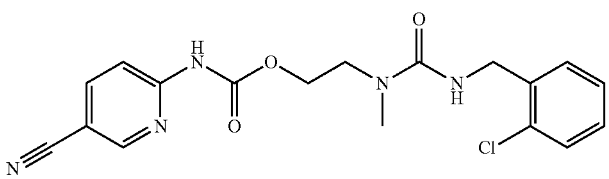 [SMILES: CN(CCOC(=O)Nc1ccc(C#N)cn1)C(=O)NCc1ccccc1Cl] | [2-({[(2-chlorophenyl)methyl]amino}-N-methylcarbonylamino)ethoxy]-N-(5-cyano(2-pyridyl))carboxamide |
| 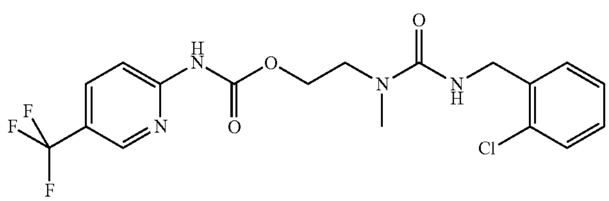 [SMILES: CN(CCOC(=O)Nc1ccc(C(F)(F)F)cn1)C(=O)NCc1ccccc1Cl] | [2-({[(2-chlorophenyl)methyl]amino}-N-methylcarbonylamino)ethoxy]-N-[5-(trifluoromethyl)(2-pyridyl)]carboxamide |
| 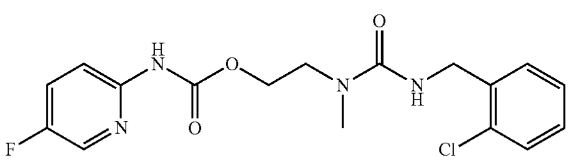 [SMILES: CN(CCOC(=O)Nc1ccc(F)cn1)C(=O)NCc1ccccc1Cl] | [2-({[(2-chlorophenyl)methyl]amino}-N-methylcarbonylamino)ethoxy]-N-(5-fluoro(2-pyridyl))carboxamide |
| 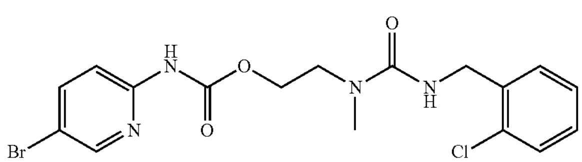 [SMILES: CN(CCOC(=O)Nc1ccc(Br)cn1)C(=O)NCc1ccccc1Cl] | N-(5-bromo(2-pyridyl))[2-({[(2-chlorophenyl)methyl]amino}-N-methylcarbonylamino)ethoxy]carboxamide |
| 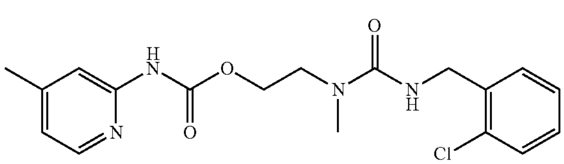 [SMILES: Cc1ccnc(NC(=O)OCCN(C)C(=O)NCc2ccccc2Cl)c1] | [2-({[(2-chlorophenyl)methyl]amino}-N-methylcarbonylamino)ethoxy]-N-(4-methyl(2-pyridyl))carboxamide |
| 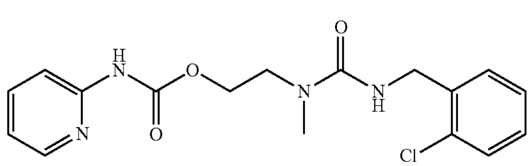 [SMILES: CN(CCOC(=O)Nc1ccccn1)C(=O)NCc1ccccc1Cl] | [2-({[(2-chlorophenyl)methyl]amino}-N-methylcarbonylamino)ethoxy]-N-(2-pyridyl)carboxamide |

| Structure | Chemical Name |
|---|---|
| 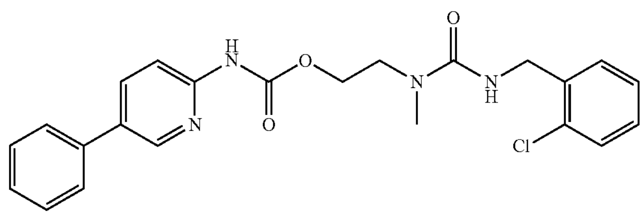 [SMILES: CN(CCOC(=O)Nc1ccc(-c2ccccc2)cn1)C(=O)NCc1ccccc1Cl] | [2-({[(2-chlorophenyl)methyl]amino}-N-methylcarbonylamino)ethoxy]-N-(5-phenyl(2-pyridyl))carboxamide |
| 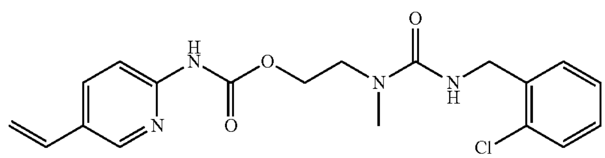 [SMILES: C=Cc1ccc(NC(=O)OCCN(C)C(=O)NCc2ccccc2Cl)nc1] | [2-({[(2-chlorophenyl)methyl]amino}-N-methylcarbonylamino)ethoxy]-N-(5-vinyl(2-pyridyl))carboxamide |
| 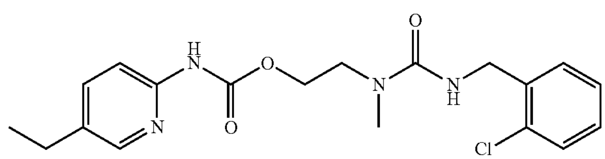 [SMILES: CCc1ccc(NC(=O)OCCN(C)C(=O)NCc2ccccc2Cl)nc1] | [2-({[(2-chlorophenyl)methyl]amino}-N-methylcarbonylamino)ethoxy]-N-(5-ethyl(2-pyridyl))carboxamide |
| 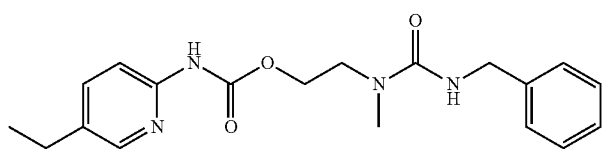 [SMILES: CCc1ccc(NC(=O)OCCN(C)C(=O)NCc2ccccc2)nc1] | N-(5-ethyl(2-pyridyl))2-{N-methyl[benzylamino]carbonylamino}ethoxy)carboxamide |
| 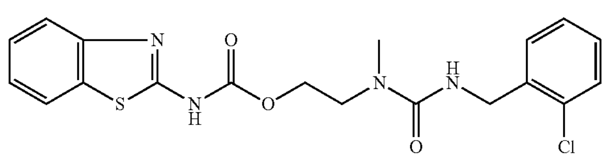 [SMILES: CN(CCOC(=O)Nc1nc2ccccc2s1)C(=O)NCc1ccccc1Cl] | N-[2-(N-benzothiazol-2-ylcarbamoyloxy)ethyl]{[(2-chlorophenyl)methyl]amino}-N-methylcarboxamide |
| 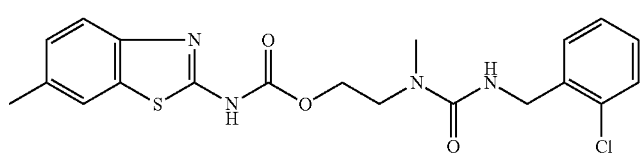 | {[(2-chlorophenyl)methyl]amino}-N-methyl-N-{2-[N-(6-methylbenzothiazol-2-yl)carbamoyloxy]ethyl}carboxamide |
| 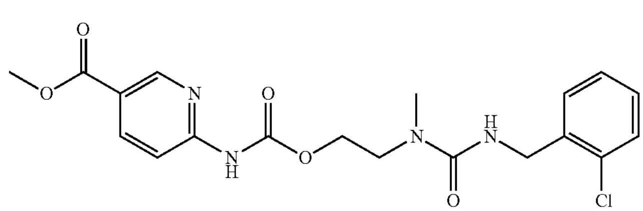 [SMILES: COC(=O)c1ccc(NC(=O)OCCN(C)C(=O)NCc2ccccc2Cl)nc1] | methyl 6-{[2-({[(2-chlorophenyl)methyl]amino}-N-methylcarbonylamino)ethoxy]carbonylamino}pyridine-3-carboxylate |
| 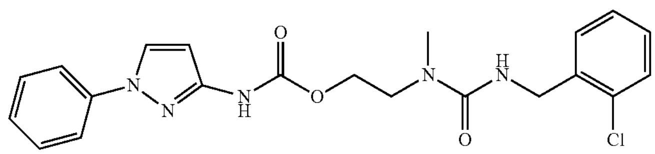 [SMILES: CN(CCOC(=O)Nc1ccn(-c2ccccc2)n1)C(=O)NCc1ccccc1Cl] | {[(2-chlorophenyl)methyl]amino}-N-methyl-N-{2-[N-(1-phenylpyrazol-3-yl)carbamoyloxy]ethyl}carboxamide |

-continued

| Structure | Chemical Name |
|---|---|
| 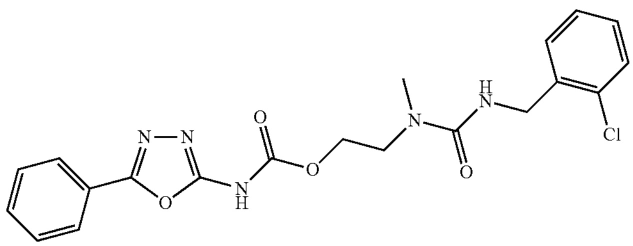 [SMILES: CN(CCOC(=O)Nc1nnc(-c2ccccc2)o1)C(=O)NCc1ccccc1Cl] | [2-({[(2-chlorophenyl)methyl]amino}-N-methylcarbonylamino)ethoxy]-N-(5-phenyl(1,3,4-oxadiazol-2-yl))carboxamide |
| 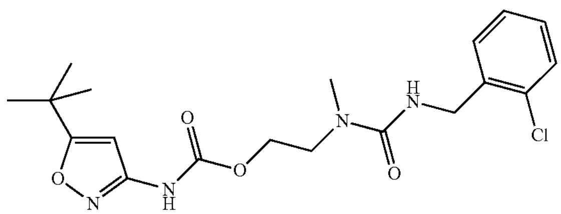 [SMILES: CN(CCOC(=O)Nc1cc(C(C)(C)C)on1)C(=O)NCc1ccccc1Cl] | N-[5-(tert-butyl)isoxazol-3-yl][2-({[(2-chlorophenyl)methyl]amino}-N-methylcarbonylamino)ethoxy]carboxamide |
| 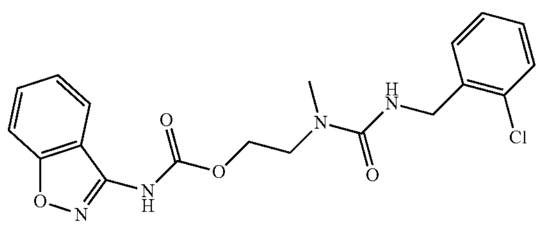 [SMILES: CN(CCOC(=O)Nc1noc2ccccc12)C(=O)NCc1ccccc1Cl] | N-benzo[d]isoxazol-3-yl[2-({[(2-chlorophenyl)methyl]amino}-N-methylcarbonylamino)ethoxy]carboxamide |
| 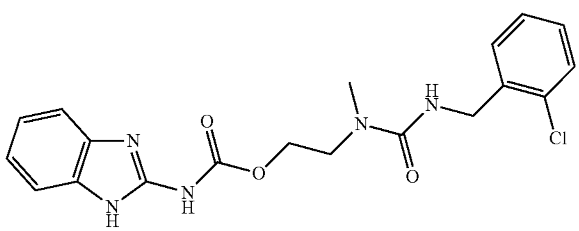 [SMILES: CN(CCOC(=O)Nc1nc2ccccc2[nH]1)C(=O)NCc1ccccc1Cl] | N-benzimidazol-2-yl[2-({[(2-chlorophenyl)methyl]amino}-N-methylcarbonylamino)ethoxy]carboxamide |
| 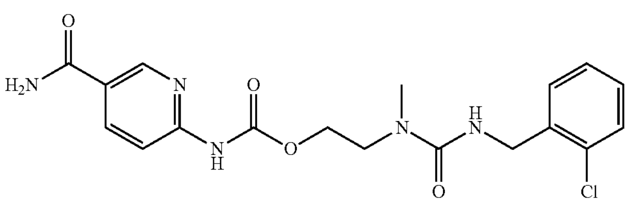 [SMILES: CN(CCOC(=O)Nc1ccc(C(N)=O)cn1)C(=O)NCc1ccccc1Cl] | 6-{[2-({[(2-chlorophenyl)methyl]amino}-N-methylcarbonylamino)ethoxy]carbonylamino}pyridine-3-carboxamide |
| 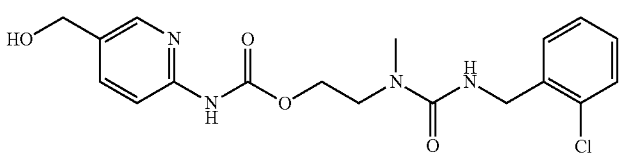 [SMILES: CN(CCOC(=O)Nc1ccc(CO)cn1)C(=O)NCc1ccccc1Cl] | {[(2-chlorophenyl)methyl]amino}-N-(2-{N-[5-(hydroxymethyl)(2-pyridyl)]carbamoyloxy}ethyl)-N-methylcarboxamide |
| 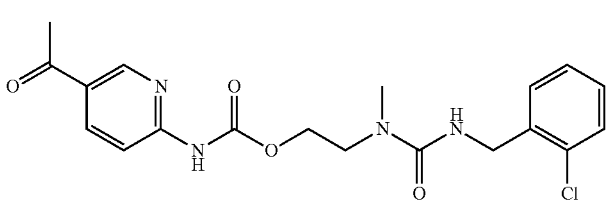 [SMILES: CC(=O)c1ccc(NC(=O)OCCN(C)C(=O)NCc2ccccc2Cl)nc1] | N-{2-[N-(5-acetyl(2-pyridyl))carbamoyloxy]ethyl}{[(2-chlorophenyl)methyl]amino}-N-methylcarboxamide |

| Structure | Chemical Name |
|---|---|
| 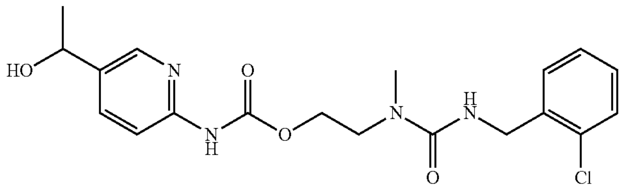 [SMILES: CC(O)c1ccc(NC(=O)OCCN(C)C(=O)NCc2ccccc2Cl)nc1] | {[(2-chlorophenyl)methyl]amino}-N-(2-{N-[5-(hydroxyethyl)(2-pyridyl)]carbamoyloxy}ethyl)-N-methylcarboxamide |
| 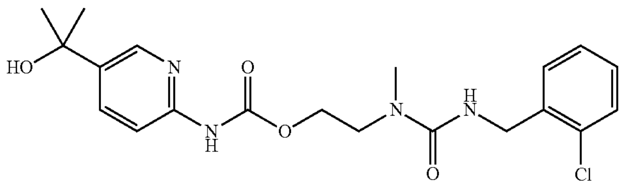 [SMILES: CN(CCOC(=O)Nc1ccc(C(C)(C)O)cn1)C(=O)NCc1ccccc1Cl] | {[(2-chlorophenyl)methyl]amino}-N-(2-{N-[5-(1-hydroxy-isopropyl)(2-pyridyl)]carbamoyloxy}ethyl)-N-methylcarboxamide |
| 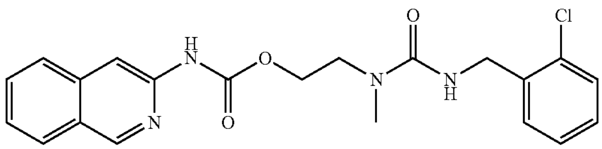 [SMILES: CN(CCOC(=O)Nc1cc2ccccc2cn1)C(=O)NCc1ccccc1Cl] | [2-({[(2-chlorophenyl)methyl]amino}-N-methylcarbonylamino)ethoxy]-N-(3-isoquinolyl)carboxamide |
| 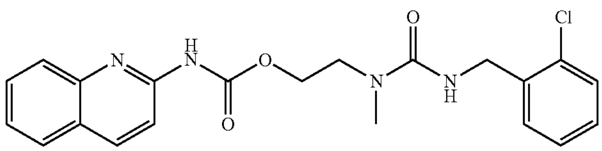 [SMILES: CN(CCOC(=O)Nc1ccc2ccccc2n1)C(=O)NCc1ccccc1Cl] | [2-({[(2-chlorophenyl)methyl]amino}-N-methylcarbonylamino)ethoxy]-N-(2-quinolyl)carboxamide |
| 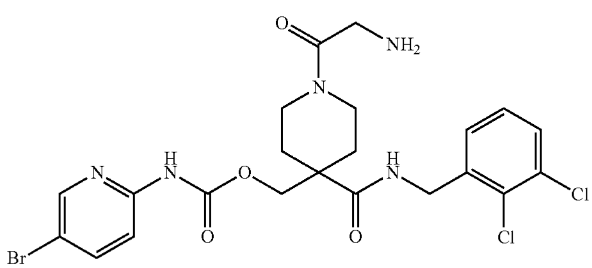 [SMILES: NCC(=O)N1CCC(COC(=O)Nc2ccc(Br)cn2)(C(=O)NCc2cccc(Cl)c2Cl)CC1] | (1-(2-aminoacetyl)-4-{[N-(5-bromo(2-pyridyl))carbamoyloxy]methyl}(4-piperidyl))-N-[(2,3-dichlorophenyl)methyl]carboxamide |
| 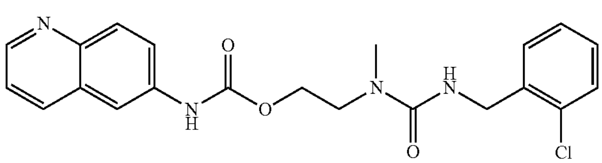 [SMILES: CN(CCOC(=O)Nc1ccc2ncccc2c1)C(=O)NCc1ccccc1Cl] | {[(2-chlorophenyl)methyl]amino}-N-methyl-N-[2-(N-(6-quinolyl)carbamoyloxy)ethyl]carboxamide |
| 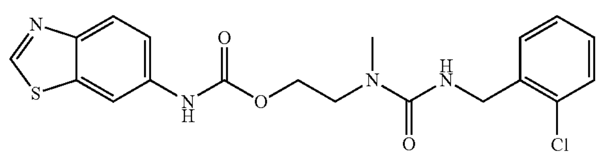 [SMILES: CN(CCOC(=O)Nc1ccc2ncsc2c1)C(=O)NCc1ccccc1Cl] | N-[2-(N-benzothiazol-6-ylcarbamoyloxy)ethyl]{[(2-chlorophenyl)methyl]amino}-N-methylcarboxamide |
| 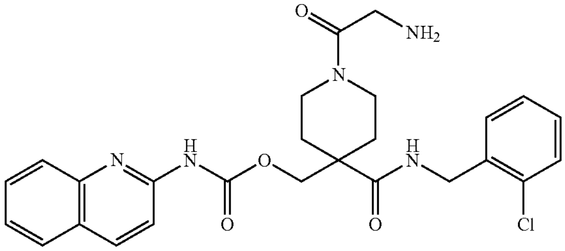 [SMILES: NCC(=O)N1CCC(COC(=O)Nc2ccc3ccccc3n2)(C(=O)NCc2ccccc2Cl)CC1] | {1-(2-aminoacetyl)-4-[(N-(2-quinolyl)carbamoyloxy)methyl](4-piperidyl)}-N-[(2-chlorophenyl)methyl]carboxamide |

-continued

| Structure | Chemical Name |
|---|---|
| 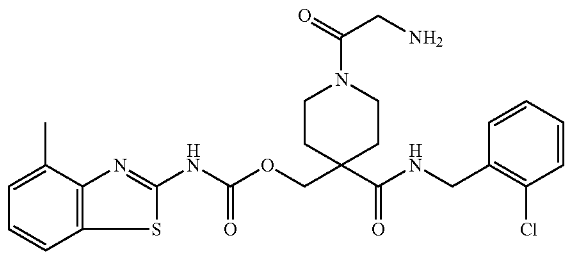 [SMILES: Cc1cccc2sc(NC(=O)OCC3(C(=O)NCc4ccccc4Cl)CCN(C(=O)CN)CC3)nc12] | (1-(2-aminoacetyl)-4-{[N-(4-methylbenzothiazol-2-yl)carbamoyloxy]methyl}(4-piperidyl))-N-[(2-chlorophenyl)methyl]carboxamide |
| 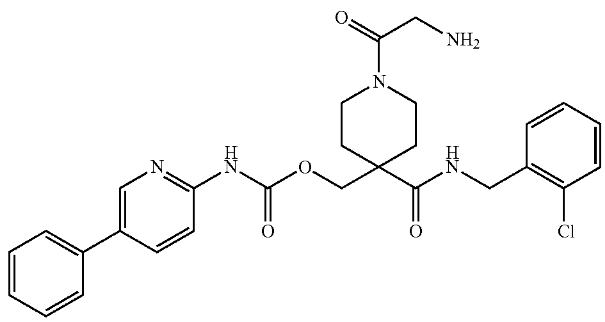 [SMILES: NCC(=O)N1CCC(COC(=O)Nc2ccc(-c3ccccc3)cn2)(C(=O)NCc2ccccc2Cl)CC1] | (1-(2-aminoacetyl)-4-{[N-(5-phenyl(2-pyridyl))carbamoyloxy]methyl}(4-piperidyl))-N-[(2-chlorophenyl)methyl]carboxamide |
| 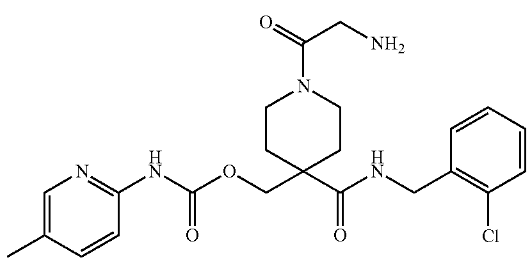 [SMILES: Cc1ccc(NC(=O)OCC2(C(=O)NCc3ccccc3Cl)CCN(C(=O)CN)CC2)nc1] | (1-(2-aminoacetyl)-4-{[N-(5-methyl(2-pyridyl))carbamoyloxy]methyl}(4-piperidyl))-N-[(2-chlorophenyl)methyl]carboxamide |
| 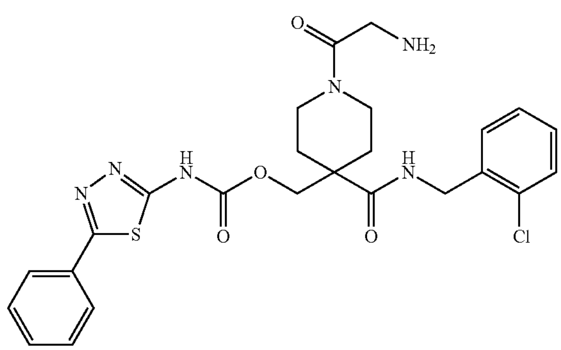 [SMILES: NCC(=O)N1CCC(COC(=O)Nc2nnc(-c3ccccc3)s2)(C(=O)NCc2ccccc2Cl)CC1] | (1-(2-aminoacetyl)-4-{[N-(5-phenyl(1,3,4-thiadiazol-2-yl))carbamoyloxy]methyl}(4-piperidyl))-N-[(2-chlorophenyl)methyl]carboxamide |
| 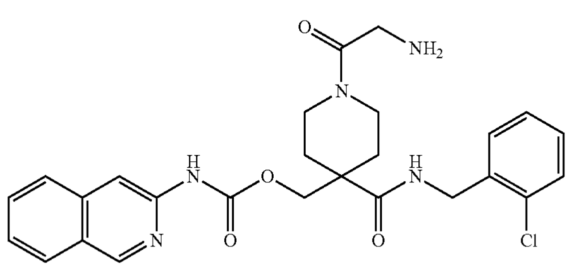 [SMILES: NCC(=O)N1CCC(COC(=O)Nc2cc3ccccc3cn2)(C(=O)NCc2ccccc2Cl)CC1] | {1-(2-aminoacetyl)-4-[(N-(3-isoquinolyl)carbamoyloxy)methyl](4-piperidyl)}-N-[(2-chlorophenyl)methyl]carboxamide |

-continued

| Structure | Chemical Name |
|---|---|
| 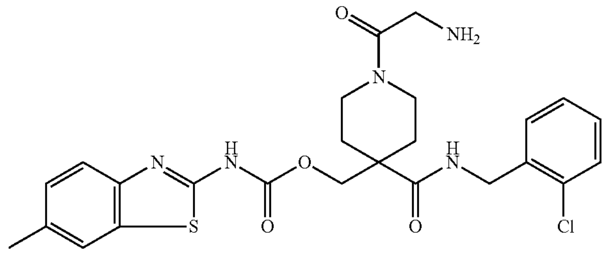 [SMILES: Cc1ccc2nc(NC(=O)OCC3(C(=O)NCc4ccccc4Cl)CCN(C(=O)CN)CC3)sc2c1] | (1-(2-aminoacetyl)-4-{[N-(6-methylbenzothiazol-2-yl)carbamoyloxy]methyl}(4-piperidyl))-N-[(2-chlorophenyl)methyl]carboxamide |
| 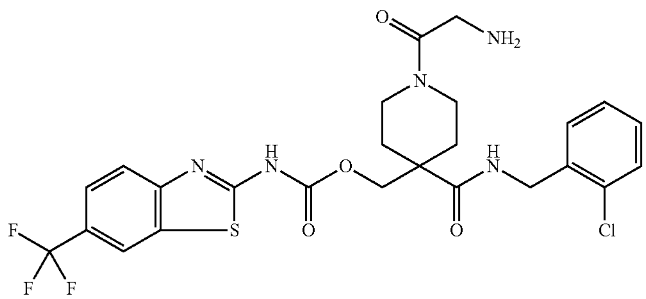 [SMILES: NCC(=O)N1CCC(COC(=O)Nc2nc3ccc(C(F)(F)F)cc3s2)(C(=O)NCc2ccccc2Cl)CC1] | [1-(2-aminoacetyl)-4-({N-[6-(trifluoromethyl)benzothiazol-2-yl]carbamoyloxy}methyl)(4-piperidyl)]-N-[(2-chlorophenyl)methyl]carboxamide |
| 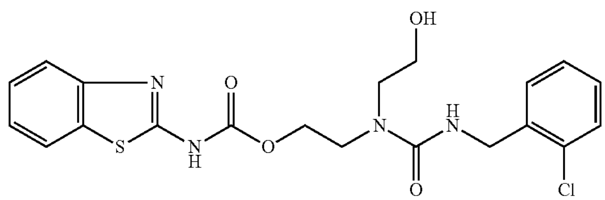 [SMILES: O=C(Nc1nc2ccccc2s1)OCCN(CCO)C(=O)NCc1ccccc1Cl] | N-[2-(N-benzothiazol-2-ylcarbamoyloxy)ethyl]{[(2-chlorophenyl)methyl]amino}-N-(2-hydroxyethyl)carboxamide |
| 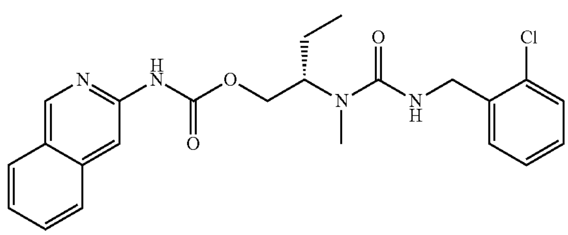 [SMILES: CC[C@@H](COC(=O)Nc1cc2ccccc2cn1)N(C)C(=O)NCc1ccccc1Cl] | [(2S)-2-({[(2-chlorophenyl)methyl]amino}-N-methylcarbonylamino)butoxy]-N-(3-isoquinolyl)carboxamide |
| 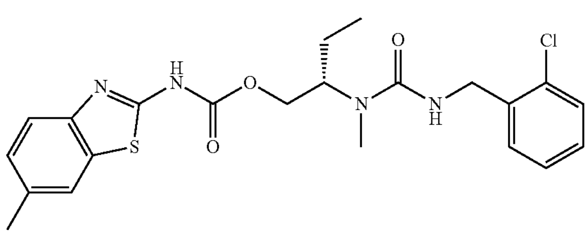 [SMILES: CC[C@@H](COC(=O)Nc1nc2ccc(C)cc2s1)N(C)C(=O)NCc1ccccc1Cl] | [(2S)-2-({[(2-chlorophenyl)methyl]amino}-N-methylcarbonylamino)butoxy]-N-(6-methylbenzothiazol-2-yl)carboxamide |
| 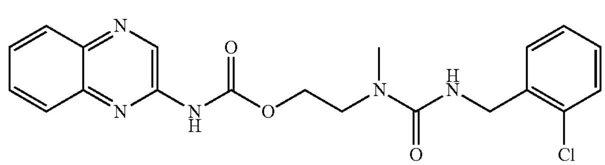 [SMILES: CN(CCOC(=O)Nc1cnc2ccccc2n1)C(=O)NCc1ccccc1Cl] | [2-({[(2-chlorophenyl)methyl]amino}-N-methylcarbonylamino)ethoxy]-N-quinoxalin-2-ylcarboxamide |
| 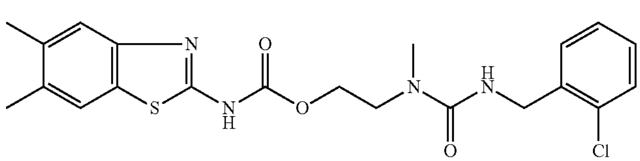 [SMILES: Cc1cc2nc(NC(=O)OCCN(C)C(=O)NCc3ccccc3Cl)sc2cc1C] | N-(5,6-dimethylbenzothiazol-2-yl)[2-({[(2-chlorophenyl)methyl]amino}-N-methylcarbonylamino)ethoxy]carboxamide |

| Structure | Chemical Name |
|---|---|
| 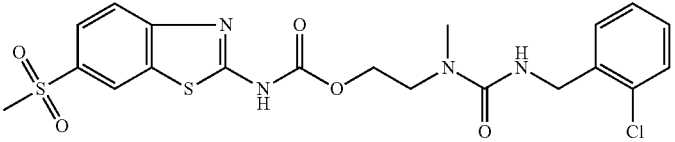 [SMILES: CN(CCOC(=O)Nc1nc2ccc(S(C)(=O)=O)cc2s1)C(=O)NCc1ccccc1Cl] | [2-({[(2-chlorophenyl)methyl]amino}-N-methylcarbonylamino)ethoxy]-N-[6-(methylsulfonyl)benzothiazol-2-yl]carboxamide |
| 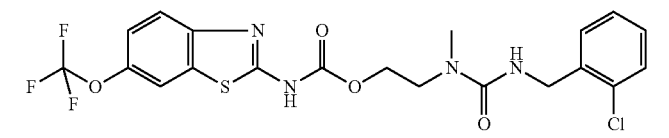 [SMILES: CN(CCOC(=O)Nc1nc2ccc(OC(F)(F)F)cc2s1)C(=O)NCc1ccccc1Cl] | [2-({[(2-chlorophenyl)methyl]amino}-N-methylcarbonylamino)ethoxy]-N-[6-(trifluoromethoxy)benzothiazol-2-yl]carboxamide |
| 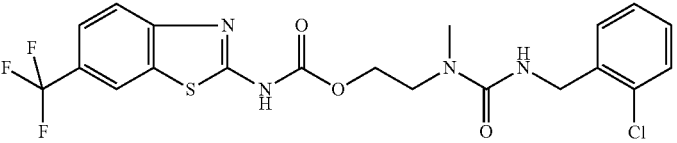 [SMILES: CN(CCOC(=O)Nc1nc2ccc(C(F)(F)F)cc2s1)C(=O)NCc1ccccc1Cl] | [2-({[(2-chlorophenyl)methyl]amino}-N-methylcarbonylamino)ethoxy]-N-[6-(trifluoromethyl)benzothiazol-2-yl]carboxamide |
| 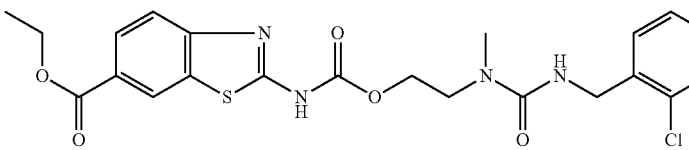 | ethyl 2-{[2-({[(2-chlorophenyl)methyl]amino}-N-methylcarbonylamino)ethoxy]carbonylamino}benzothiazole-6-carboxylate |
| 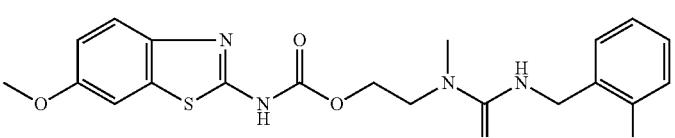 | [2-({[(2-chlorophenyl)methyl]amino}-N-methylcarbonylamino)ethoxy]-N-(6-methoxybenzothiazol-2-yl)carboxamide |
| 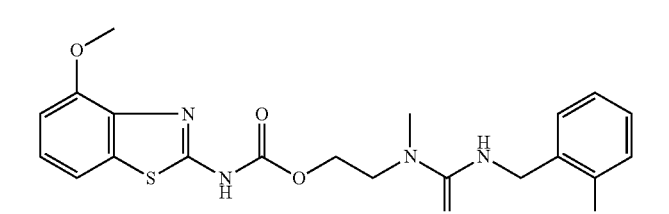 | [2-({[(2-chlorophenyl)methyl]amino}-N-methylcarbonylamino)ethoxy]-N-(4-methoxybenzothiazol-2-yl)carboxamide |
| 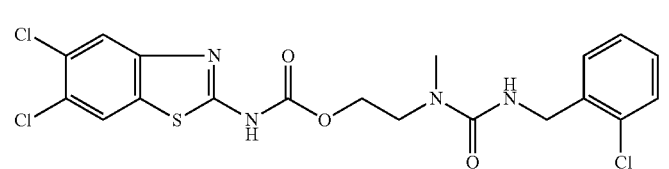 [SMILES: CN(CCOC(=O)Nc1nc2cc(Cl)c(Cl)cc2s1)C(=O)NCc1ccccc1Cl] | N-(5,6-dichlorobenzothiazol-2-yl)[2-({[(2-chlorophenyl)methyl]amino}-N-methylcarbonylamino)ethoxy]carboxamide |
| 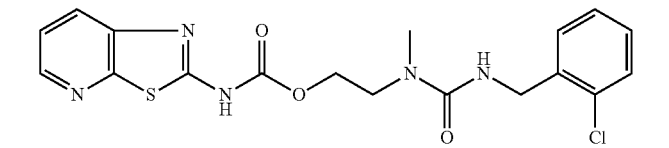 | [(2-({[(2-chlorophenyl)methyl]amino}-N-methylcarbonylamino)ethoxy]-N-(1,3-thiazolo[5,4-b]pyridin-2-yl)carboxamide |
| 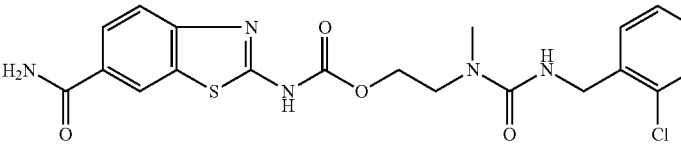 | 2-{[2-({[(2-chlorophenyl)methyl]amino}-N-methylcarbonylamino)ethoxy]carbonylamino}benzothiazole-6-carboxamide |

-continued

| Structure | Chemical Name |
|---|---|
| 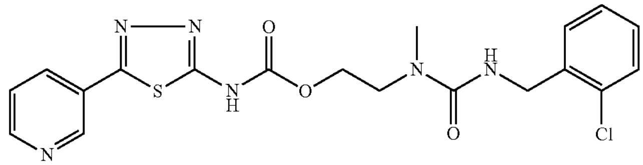 [SMILES: CN(CCOC(=O)Nc1nnc(-c2cccnc2)s1)C(=O)NCc1ccccc1Cl] | [2-({[(2-chlorophenyl)methyl]amino}-N-methylcarbonylamino)ethoxy]-N-(5-(3-pyridyl)(1,3,4-thiadiazol-2-yl))carboxamide |
| 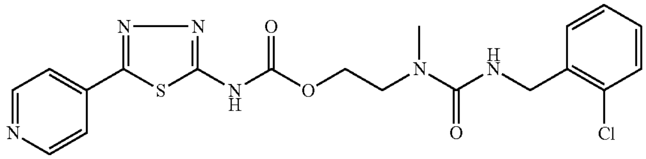 [SMILES: CN(CCOC(=O)Nc1nnc(-c2ccncc2)s1)C(=O)NCc1ccccc1Cl] | [2-({[(2-chlorophenyl)methyl]amino}-N-methylcarbonylamino)ethoxy]-N-(5-(4-pyridyl)(1,3,4-thiadiazol-2-yl))carboxamide |
| 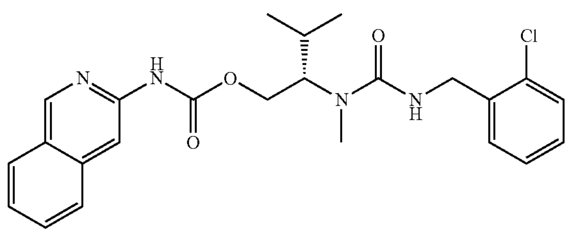 [SMILES: CC(C)[C@@H](COC(=O)Nc1cc2ccccc2cn1)N(C)C(=O)NCc1ccccc1Cl] | [(2S)-2-({[(2-chlorophenyl)methyl]amino}-N-methylcarbonylamino)-3-methylbutoxy]-N-(3-isoquinolyl)carboxamide |
| 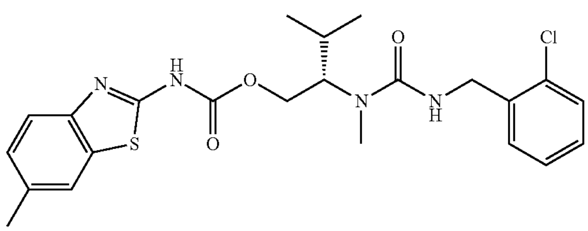 [SMILES: Cc1ccc2nc(NC(=O)OC[C@H](C(C)C)N(C)C(=O)NCc3ccccc3Cl)sc2c1] | [(2S)-2-({[(2-chlorophenyl)methyl]amino}-N-methylcarbonylamino)-3-methylbutoxy]-N-(6-methylbenzothiazol-2-yl)carboxamide |
| 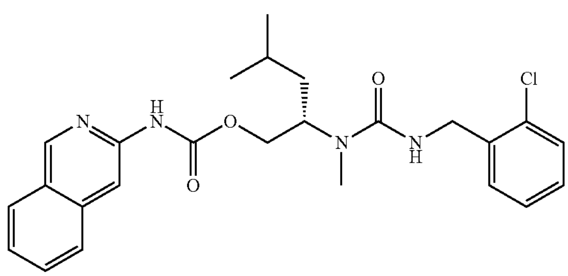 [SMILES: CC(C)C[C@@H](COC(=O)Nc1cc2ccccc2cn1)N(C)C(=O)NCc1ccccc1Cl] | [(2S)-2-({[(2-chlorophenyl)methyl]amino}-N-methylcarbonylamino)-4-methylpentyloxy]-N-(3-isoquinolyl)carboxamide |
| 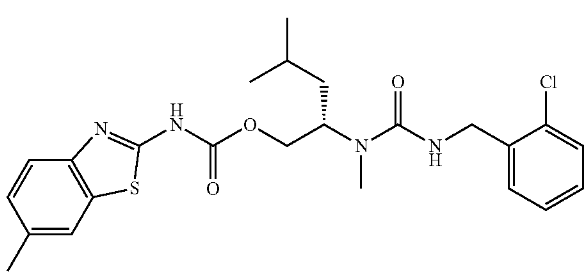 [SMILES: Cc1ccc2nc(NC(=O)OC[C@H](CC(C)C)N(C)C(=O)NCc3ccccc3Cl)sc2c1] | [(2S)-2-({[(2-chlorophenyl)methyl]amino}-N-methylcarbonylamino)-4-methylpentyloxy]-N-(6-methylbenzothiazol-2-yl)carboxamide |
| 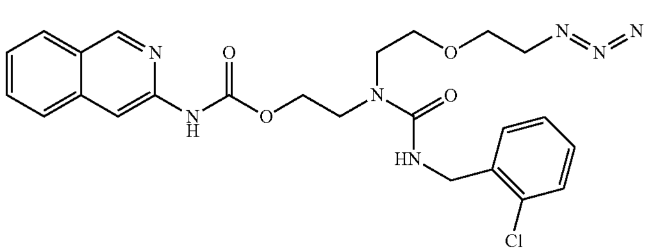 | {[(2-chlorophenyl)methyl]amino}-N-[2-(3-diazo-3-azaprop-3-enyloxy)ethyl]-N-[2-(N-(3-isoquinolyl)carbamoyloxy)ethyl]carboxamide |

-continued

| Structure | Chemical Name |
|---|---|
| 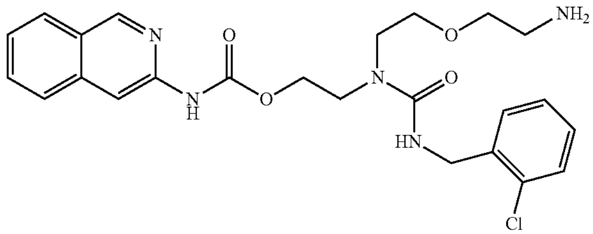 [SMILES: NCCOCCN(CCOC(=O)Nc1cc2ccccc2cn1)C(=O)NCc1ccccc1Cl] | N-[2-(2-aminoethoxy)ethyl]{[(2-chlorophenyl)methyl]amino}-N-[2-(N-(3-isoquinolyl)carbamoyloxy)ethyl]carboxamide |
| 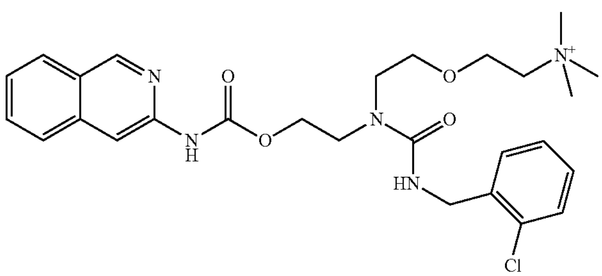 [SMILES: C[N+](C)(C)CCOCCN(CCOC(=O)Nc1cc2ccccc2cn1)C(=O)NCc1ccccc1Cl] | {[(2-chlorophenyl)methyl]amino}-N-[2-(N-(3-isoquinolyl)carbamoyloxy)ethyl]-N-{2-[2-(trimethylamino)ethoxy]ethyl}carboxamide |
| 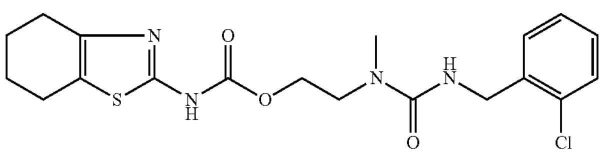 [SMILES: CN(CCOC(=O)Nc1nc2c(s1)CCCC2)C(=O)NCc1ccccc1Cl] | [2-({[(2-chlorophenyl)methyl]amino}-N-methylcarbonylamino)ethoxy]-N-(4,5,6,7-tetrahydrobenzothiazol-2-yl)carboxamide |
| 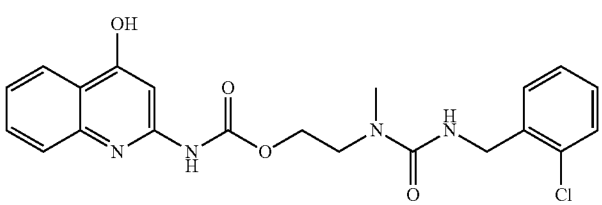 [SMILES: CN(CCOC(=O)Nc1cc(O)c2ccccc2n1)C(=O)NCc1ccccc1Cl] | [2-({[(2-chlorophenyl)methyl]amino}-N-methylcarbonylamino)ethoxy]-N-(4-hydroxy(2-quinolyl))carboxamide |
| 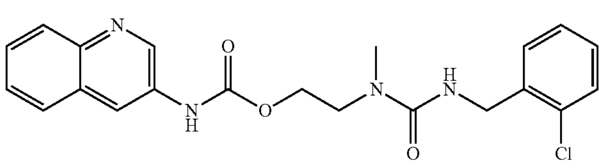 [SMILES: CN(CCOC(=O)Nc1cnc2ccccc2c1)C(=O)NCc1ccccc1Cl] | [2-({[(2-chlorophenyl)methyl]amino}-N-methylcarbonylamino)ethoxy]-N-(3-quinolyl)carboxamide |
| 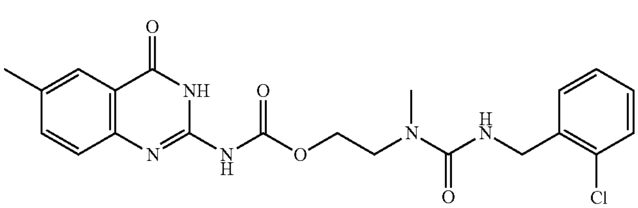 [SMILES: Cc1ccc2nc(NC(=O)OCCN(C)C(=O)NCc3ccccc3Cl)[nH]c(=O)c2c1] | [2-({[(2-chlorophenyl)methyl]amino}-N-methylcarbonylamino)ethoxy]-N-(6-methyl-4-oxo(3-hydroquinazolin-2-yl))carboxamide |

-continued

| Structure | Chemical Name |
|---|---|
| 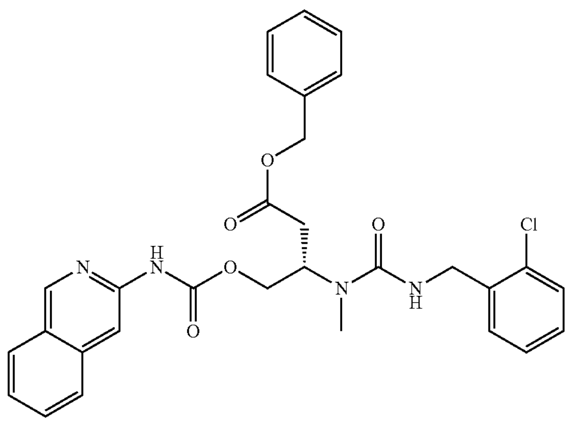 [SMILES: CN(C(=O)NCc1ccccc1Cl)[C@H](COC(=O)Nc1cc2ccccc2cn1)CC(=O)OCc1ccccc1] | phenylmethyl (3S)-3-({[(2-chlorophenyl)methyl]amino}-N-methylcarbonylamino)-4-(N-(3-isoquinolyl)carbamoyloxy)butanoate |
| 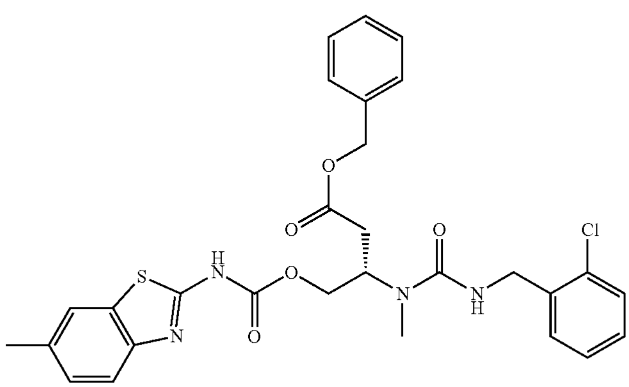 [SMILES: Cc1ccc2nc(NC(=O)OC[C@H](CC(=O)OCc3ccccc3)N(C)C(=O)NCc3ccccc3Cl)sc2c1] | phenylmethyl (3S)-3-({[(2-chlorophenyl)methyl]amino}-N-methylcarbonylamino)-4-[N-(6-methylbenzothiazol-2-yl)carbamoyloxy]butanoate |
| 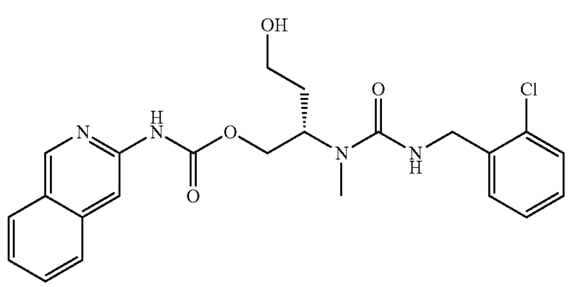 [SMILES: CN(C(=O)NCc1ccccc1Cl)[C@@H](CCO)COC(=O)Nc1cc2ccccc2cn1] | [(2S)-2-({[(2-chlorophenyl)methyl]amino}-N-methylcarbonylamino)-4-hydroxybutoxy]-N-(3-isoquinolyl)carboxamide |
| 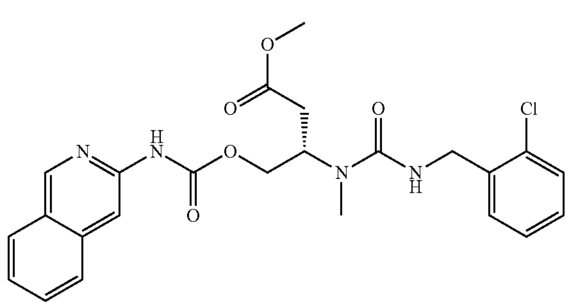 [SMILES: COC(=O)C[C@@H](COC(=O)Nc1cc2ccccc2cn1)N(C)C(=O)NCc1ccccc1Cl] | methyl (3S)-3-({[(2-chlorophenyl)methyl]amino}-N-methylcarbonylamino)-4-(N-(3-isoquinolyl)carbamoyloxy)butanoate |

-continued

| Structure | Chemical Name |
|---|---|
| 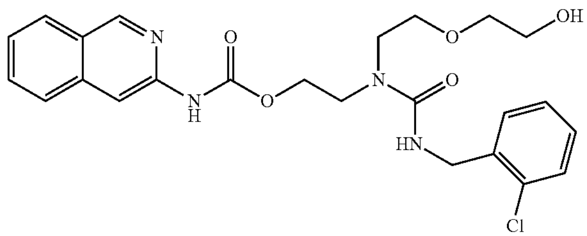 [SMILES: O=C(Nc1cc2ccccc2cn1)OCCN(CCOCCO)C(=O)NCc1ccccc1Cl] | {[(2-chlorophenyl)methyl]amino}-N-[2-(2-hydroxyethoxy)ethyl]-N-[2-(N-(3-isoquinolyl)carbamoyloxy)ethyl] carboxamide |
| 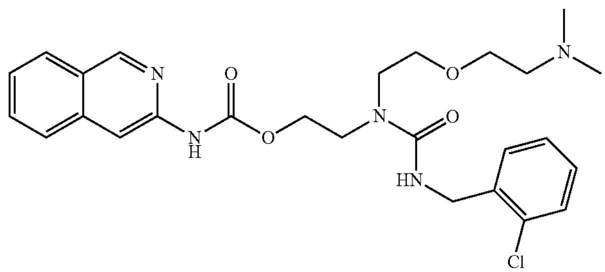 [SMILES: CN(C)CCOCCN(CCOC(=O)Nc1cc2ccccc2cn1)C(=O)NCc1ccccc1Cl] | N-{2-[2-(dimethylamino)ethoxy]ethyl}{[(2-chlorophenyl)methyl]amino}-N-[2-(N-(3-isoquinolyl)carbamoyloxy)ethyl] carboxamide |
| 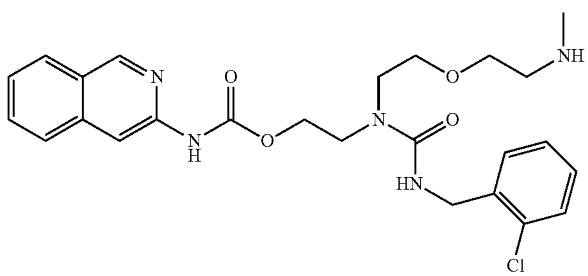 [SMILES: CNCCOCCN(CCOC(=O)Nc1cc2ccccc2cn1)C(=O)NCc1ccccc1Cl] | {[(2-chlorophenyl)methyl]amino}-N-[2-(N-(3-isoquinolyl)carbamoyloxy)ethyl]-N-{2-[2-(methylamino)ethoxy]ethyl} carboxamide |
| 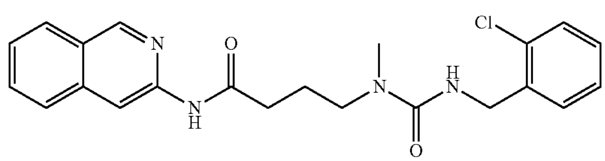 [SMILES: CN(CCCC(=O)Nc1cc2ccccc2cn1)C(=O)NCc1ccccc1Cl] | 4-({[(2-chlorophenyl)methyl]amino}-N-methylcarbonylamino)-N-(3-isoquinolyl)butanamide |
| 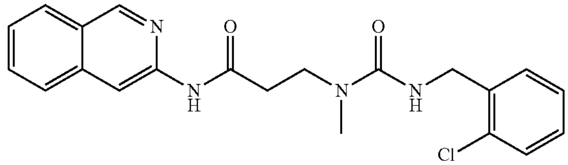 [SMILES: CN(CCC(=O)Nc1cc2ccccc2cn1)C(=O)NCc1ccccc1Cl] | 3-({[(2-chlorophenyl)methyl]amino}-N-methylcarbonylamino)-N-(3-isoquinolyl)propanamide |
| 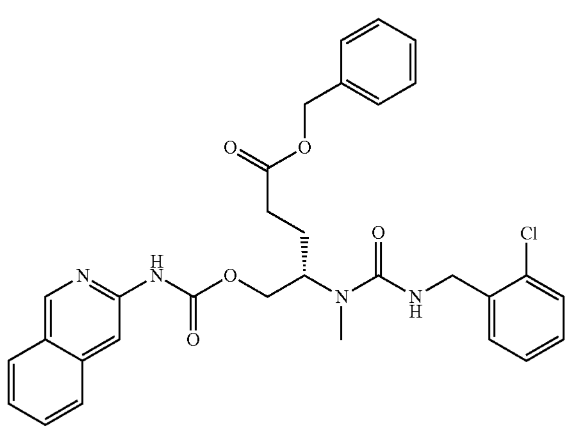 [SMILES: CN(C(=O)NCc1ccccc1Cl)[C@@H](CCC(=O)OCc1ccccc1)COC(=O)Nc1cc2ccccc2cn1] | phenylmethyl (4S)-4-({[(2-chlorophenyl)methyl]amino}-N-methylcarbonylamino)-5-(N-(3-isoquinolyl)carbamoyloxy)pentanoate |

| Structure | Chemical Name |
|---|---|
| 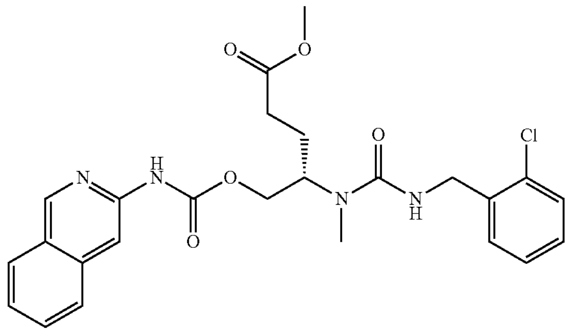 [SMILES: COC(=O)CC[C@@H](COC(=O)Nc1cc2ccccc2cn1)N(C)C(=O)NCc1ccccc1Cl] | methyl (4S)-4-({[(2-chlorophenyl)methyl]amino}-N-methylcarbonylamino)-5-(N-(3-isoquinolyl)carbamoyloxy)pentanoate |
| 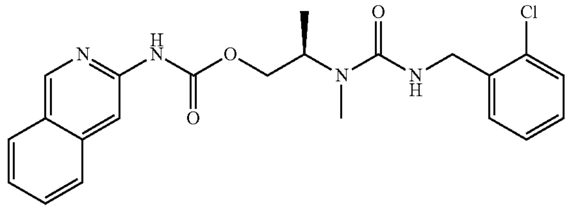 [SMILES: C[C@H](COC(=O)Nc1cc2ccccc2cn1)N(C)C(=O)NCc1ccccc1Cl] | [(2R)-2-({[(2-chlorophenyl)methyl]amino}-N-methylcarbonylamino)propoxy]-N-(3-isoquinolyl)carboxamide |
| 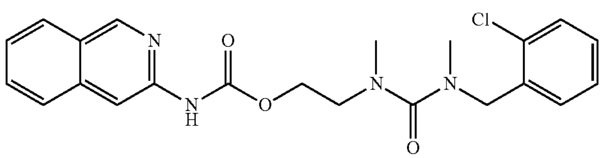 [SMILES: CN(CCOC(=O)Nc1cc2ccccc2cn1)C(=O)N(C)Cc1ccccc1Cl] | {[(2-chlorophenyl)methyl]methylamino}-N-[2-(N-(3-isoquinolyl)carbamoyloxy)ethyl]-N-methylcarboxamide |
| 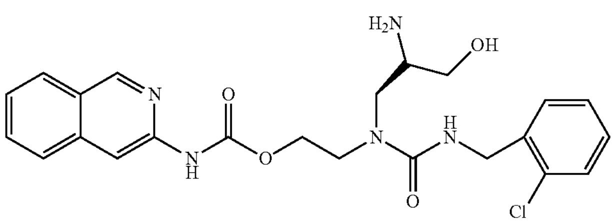 | [2-(N-((2R)-2-amino-3-hydroxypropyl){[(2-chlorophenyl)methyl]amino}carbonylamino)ethoxy]-N-(3-isoquinolyl)carboxamide |
| 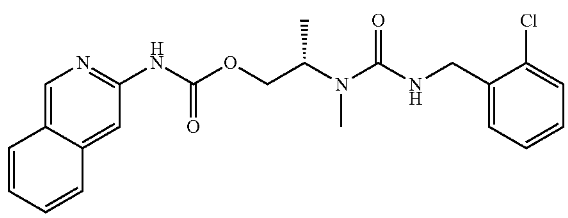 [SMILES: C[C@@H](COC(=O)Nc1cc2ccccc2cn1)N(C)C(=O)NCc1ccccc1Cl] | [(2S)-2-({[(2-chlorophenyl)methyl]amino}-N-methylcarbonylamino)propoxy]-N-(3-isoquinolyl)carboxamide |
| 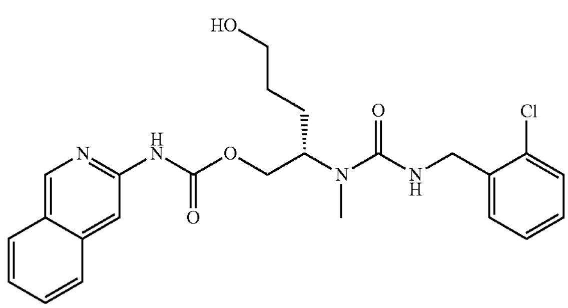 [SMILES: CN(C(=O)NCc1ccccc1Cl)[C@@H](CCCO)COC(=O)Nc1cc2ccccc2cn1] | [(2S)-2-({[(2-chlorophenyl)methyl]amino}-N-methylcarbonylamino)-5-hydroxypentyloxy]-N-(3-isoquinolyl)carboxamide |

-continued

| Structure | Chemical Name |
|---|---|
| 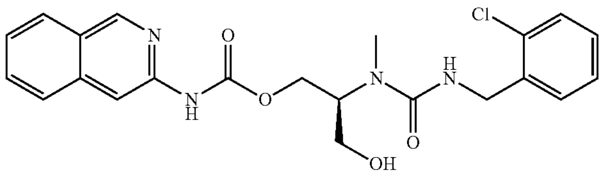 [SMILES: CN(C(=O)NCc1ccccc1Cl)[C@@H](CO)COC(=O)Nc1cc2ccccc2cn1] | N-{(1S)-2-hydroxy-1-[(N-(3-isoquinolyl)carbamoyloxy)methyl]ethyl}{[(2-chlorophenyl)methyl]amino}-N-methylcarboxamide |
| 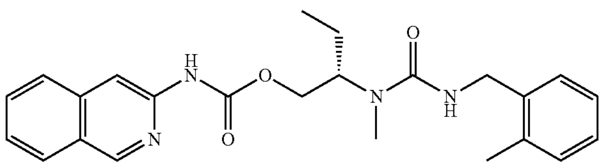 [SMILES: CC[C@@H](COC(=O)Nc1cc2ccccc2cn1)N(C)C(=O)NCc1ccccc1C] | N-{(1S)-1-[(N-(3-isoquinolyl)carbamoyloxy)methyl]propyl}-N-methyl{[(2-methylphenyl)methyl]amino}carboxamide |
| 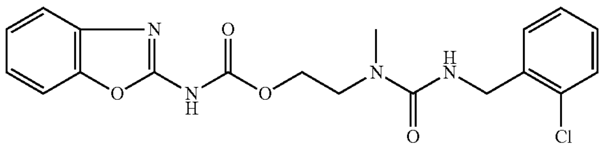 | N-benzoxazol-2-yl[2-({[(2-chlorophenyl)methyl]amino}-N-methylcarbonylamino)ethoxy]carboxamide |
| 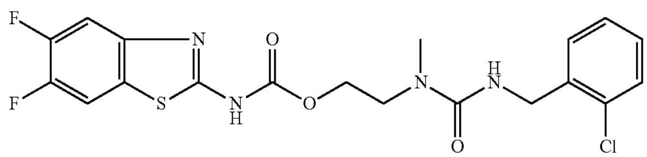 [SMILES: CN(CCOC(=O)Nc1nc2cc(F)c(F)cc2s1)C(=O)NCc1ccccc1Cl] | N-(5,6-difluorobenzothiazol-2-yl)[2-({[(2-chlorophenyl)methyl]amino}-N-methylcarbonylamino)ethoxy]carboxamide |
| 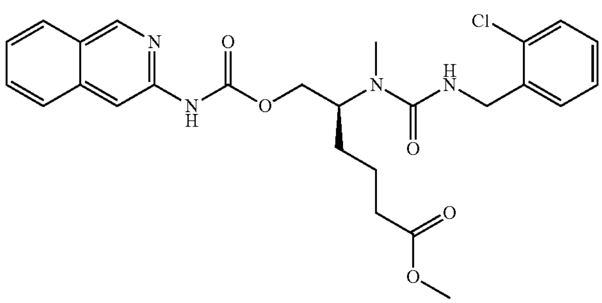 [SMILES: COC(=O)CCC[C@@H](COC(=O)Nc1cc2ccccc2cn1)N(C)C(=O)NCc1ccccc1Cl] | methyl (5S)-5-({[(2-chlorophenyl)methyl]amino}-N-methylcarbonylamino)-6-(N-(3-isoquinolyl)carbamoyloxy)hexanoate |
| 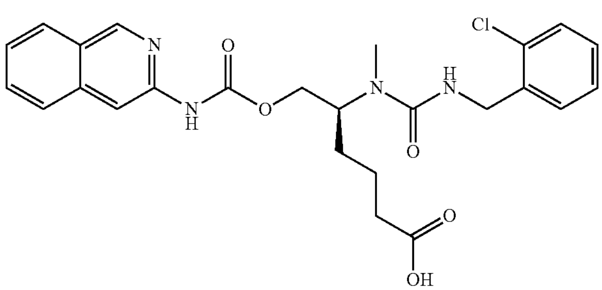 [SMILES: CN(C(=O)NCc1ccccc1Cl)[C@@H](CCCC(=O)O)COC(=O)Nc1cc2ccccc2cn1] | (5S)-5-({[(2-chlorophenyl)methyl]amino}-N-methylcarbonylamino)-6-(N-(3-isoquinolyl)carbamoyloxy)hexanoic acid |
| 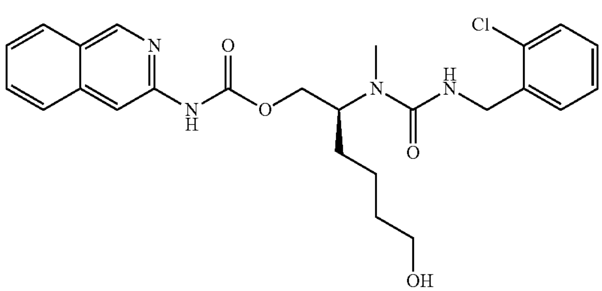 [SMILES: CN(C(=O)NCc1ccccc1Cl)[C@@H](CCCCO)COC(=O)Nc1cc2ccccc2cn1] | N-{(1S)-5-hydroxy-1-[(N-(3-isoquinolyl)carbamoyloxy)methyl]pentyl}{[(2-chlorophenyl)methyl]amino}-N-methylcarboxamide |

-continued

| Structure | Chemical Name |
|---|---|
| 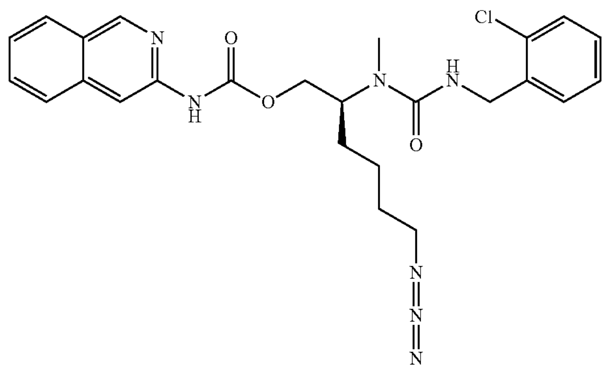 | N-{(1S)-6-diazo-1-[(N-(3-isoquinolyl)carbamoyloxy)methyl]-6-azahex-6-enyl}{[(2-chlorophenyl)methyl]amino}-N-methylcarboxamide |
| 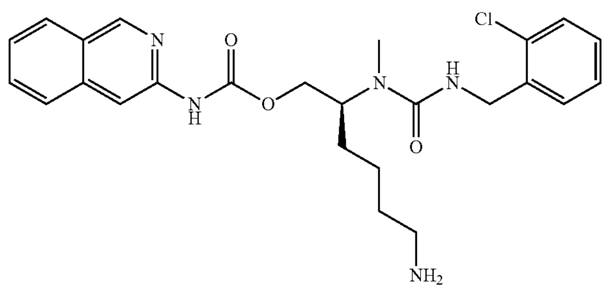 [SMILES: CN(C(=O)NCc1ccccc1Cl)[C@@H](CCCCN)COC(=O)Nc1cc2ccccc2cn1] | N-{(1S)-5-amino-1-[(N-(3-isoquinolyl)carbamoyloxy)methyl]pentyl}{[(2-chlorophenyl)methyl]amino}-N-methylcarboxamide |
| 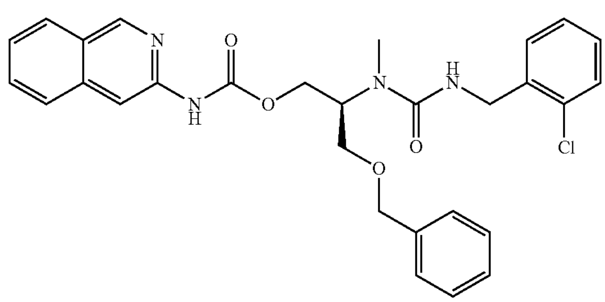 [SMILES: CN(C(=O)NCc1ccccc1Cl)[C@@H](COCc1ccccc1)COC(=O)Nc1cc2ccccc2cn1] | N-{(1S)-2-(N-(3-isoquinolyl)carbamoyloxy)-1-[(phenylmethoxy)methyl]ethyl}{[(2-chlorophenyl)methyl]amino}-N-methylcarboxamide |
| 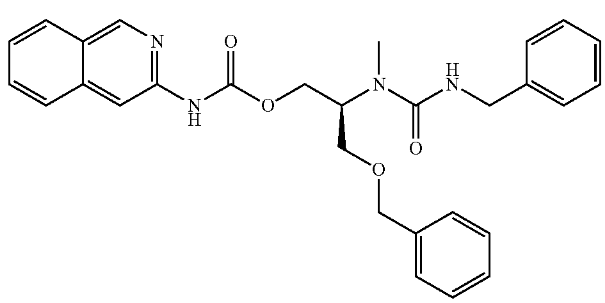 [SMILES: CN(C(=O)NCc1ccccc1)[C@@H](COCc1ccccc1)COC(=O)Nc1cc2ccccc2cn1] | N-{(1S)-2-(N-(3-isoquinolyl)carbamoyloxy)-1-[(phenylmethoxy)methyl]ethyl}-N-methyl[benzylamino]carboxamide |
| 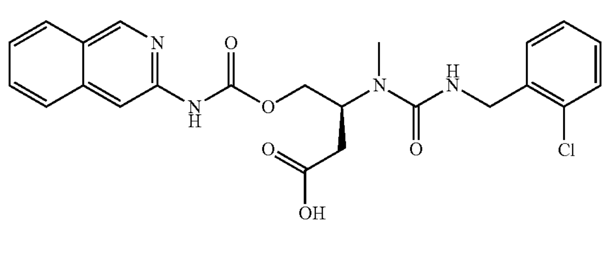 [SMILES: CN(C(=O)NCc1ccccc1Cl)[C@H](COC(=O)Nc1cc2ccccc2cn1)CC(=O)O] | (3S)-3-({[(2-chlorophenyl)methyl]amino}-N-methylcarbonylamino)-4-(N-(3-isoquinolyl)carbamoyloxy)butanoic acid |

-continued

| Structure | Chemical Name |
|---|---|
| 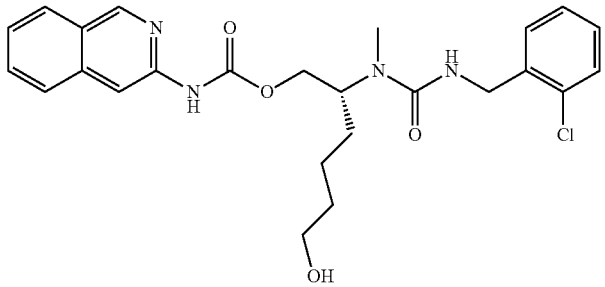 [SMILES: CN(C(=O)NCc1ccccc1Cl)[C@H](CCCCO)COC(=O)Nc1cc2ccccc2cn1] | [(2R)-2-({[(2-chlorophenyl)methyl]amino}-N-methylcarbonylamino)-6-hydroxyhexyloxy]-N-(3-isoquinolyl)carboxamide |
| 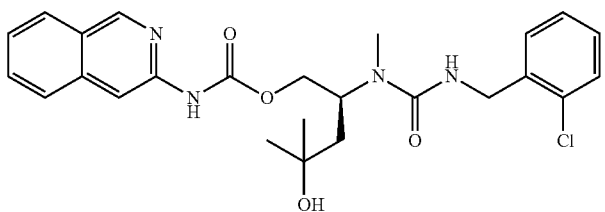 [SMILES: CN(C(=O)NCc1ccccc1Cl)[C@H](COC(=O)Nc1cc2ccccc2cn1)CC(C)(C)O] | N-{(1S)-3-hydroxy-1-[(N-(3-isoquinolyl)carbamoyloxy)methyl]-3-methylbutyl}{[(2-chlorophenyl)methyl]amino}-N-methylcarboxamide |
| 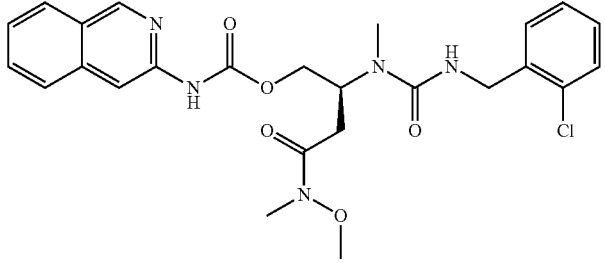 [SMILES: CON(C)C(=O)C[C@@H](COC(=O)Nc1cc2ccccc2cn1)N(C)C(=O)NCc1ccccc1Cl] | (3S)-3-({[(2-chlorophenyl)methyl]amino}-N-methylcarbonylamino)-4-(N-(3-isoquinolyl)carbamoyloxy)-N-methoxy-N-methylbutanamide |
| 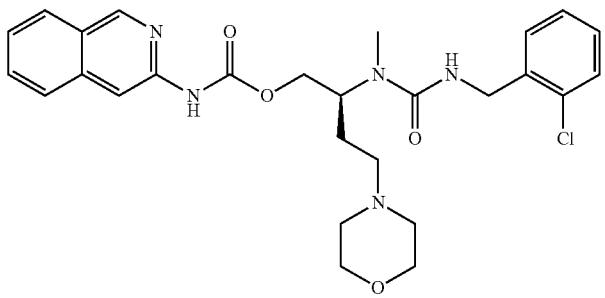 [SMILES: CN(C(=O)NCc1ccccc1Cl)[C@@H](CCN1CCOCC1)COC(=O)Nc1cc2ccccc2cn1] | N-{(1S)-1-[(N-(3-isoquinolyl)carbamoyloxy)methyl]-3-morpholin-4-ylpropyl}{[(2-chlorophenyl)methyl]amino}-N-methylcarboxamide |
| 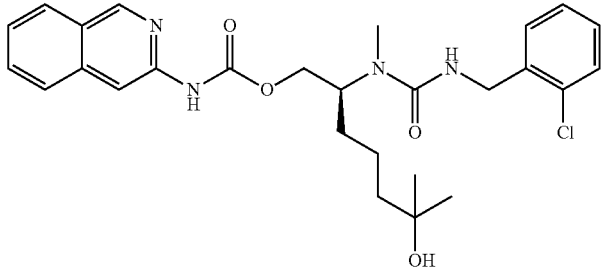 [SMILES: CN(C(=O)NCc1ccccc1F)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2-chlorophenyl)methyl]amino}-N-methylcarboxamide |

-continued

| Structure | Chemical Name |
|---|---|
| 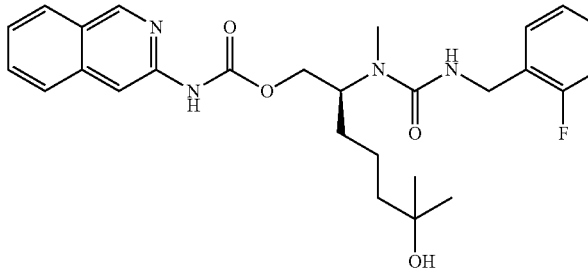 | N-{(1S)-5-hydroxy-1-[(N-(3-isoquinolyl)carbamoyloxy)methyl]-5-methylhexyl}{[(2-fluorophenyl)methyl]amino}-N-methylcarboxamide |
| 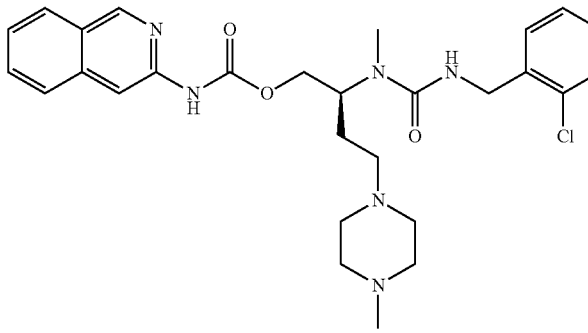 | N-{(1S)-1-[(N-(3-isoquinolyl)carbamoyloxy)methyl]-3-(4-methylpiperazinyl)propyl}{[(2-chlorophenyl)methyl]amino}-N-methylcarboxamide |
| 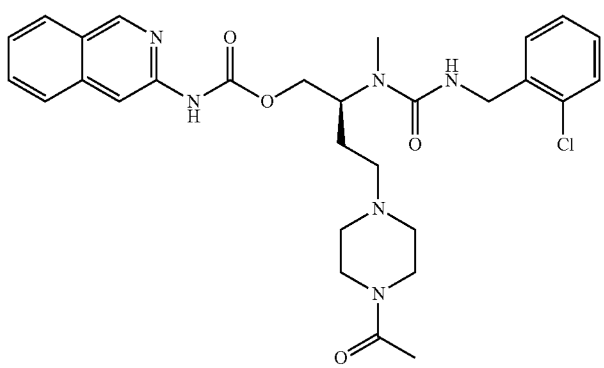 [SMILES: CC(=O)N1CCN(CC[C@@H](COC(=O)Nc2cc3ccccc3cn2)N(C)C(=O)NCc2ccccc2Cl)CC1] | N-{(1S)-3-(4-acetylpiperazinyl)-1-[(N-(3-isoquinolyl)carbamoyloxy)methyl]propyl}{[(2-chlorophenyl)methyl]amino}-N-methylcarboxamide |
| 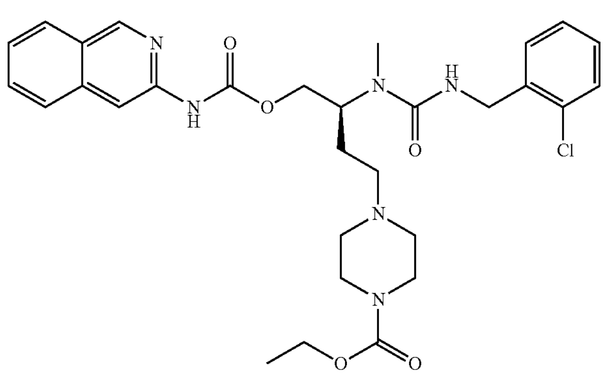 [SMILES: CCOC(=O)N1CCN(CC[C@@H](COC(=O)Nc2cc3ccccc3cn2)N(C)C(=O)NCc2ccccc2Cl)CC1] | ethyl 4-[(3S)-3-({[(2-chlorophenyl)methyl]amino}-N-methylcarbonyl-amino)-4-(N-(3-isoquinolyl)carbamoyloxy)butyl]piperazinecarboxylate |

-continued

| Structure | Chemical Name |
|---|---|
| 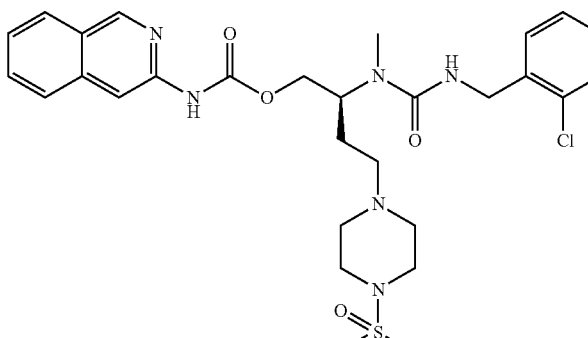 | N-{(1S)-1-[(N-(3-isoquinolyl)carbamoyloxy)methyl]-3-[4-(methylsulfonyl)piperazinyl]propyl}{[(2-chlorophenyl)methyl]amino}-N-methylcarboxamide |
| 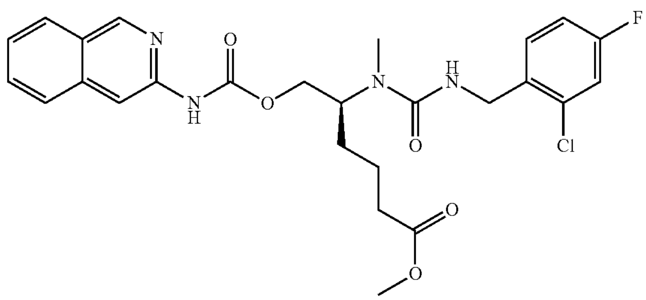 [SMILES: COC(=O)CCC[C@@H](COC(=O)Nc1cc2ccccc2cn1)N(C)C(=O)NCc1ccc(F)cc1Cl] | methyl (5S)-5-({[(2-chloro-4-fluorophenyl)methyl]amino}-N-methylcarbonylamino)-6-(N-(3-isoquinolyl)carbamoyloxy)hexanoate |
| 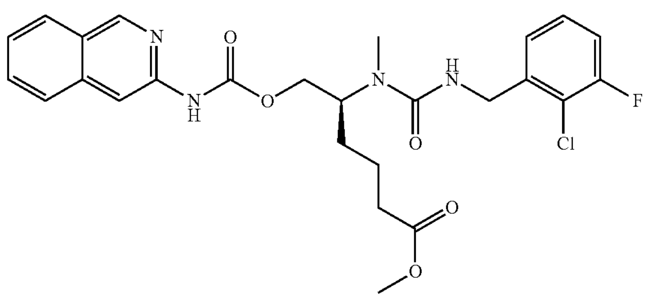 [SMILES: COC(=O)CCC[C@@H](COC(=O)Nc1cc2ccccc2cn1)N(C)C(=O)NCc1cccc(F)c1Cl] | methyl (5S)-5-({[(2-chloro-3-fluorophenyl)methyl]amino}-N-methylcarbonylamino)-6-(N-(3-isoquinolyl)carbamoyloxy)hexanoate |
| 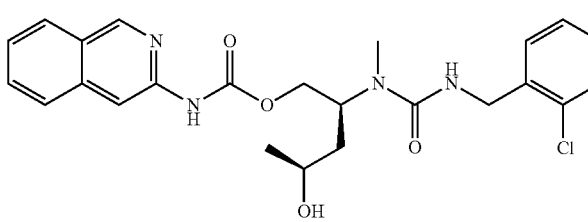 | N-{(1S,3S)-3-hydroxy-1-[(N-(3-isoquinolyl)carbamoyloxy)methyl]butyl}{[(2-chlorophenyl)methyl]amino}-N-methylcarboxamide |
| 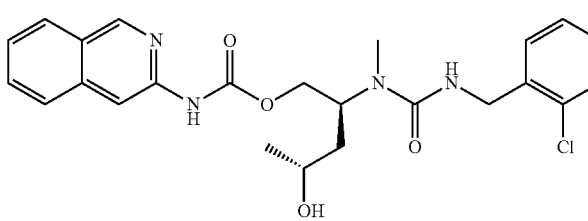 | N-{(1S,3R)-3-hydroxy-1-[(N-(3-isoquinolyl)carbamoyloxy)methyl]butyl}{[(2-chlorophenyl)methyl]amino}-N-methylcarboxamide |

-continued

| Structure | Chemical Name |
|---|---|
| 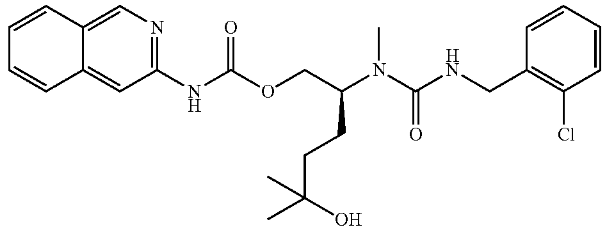 [SMILES: CN(C(=O)NCc1ccccc1Cl)[C@@H](CCC(C)(C)O)COC(=O)Nc1cc2ccccc2cn1] | N-{(1S)-4-hydroxy-1-[(N-(3-isoquinolyl)carbamoyloxy)methyl]-4-methylpentyl}{[(2-chlorophenyl)methyl]amino}-N-methylcarboxamide |
| 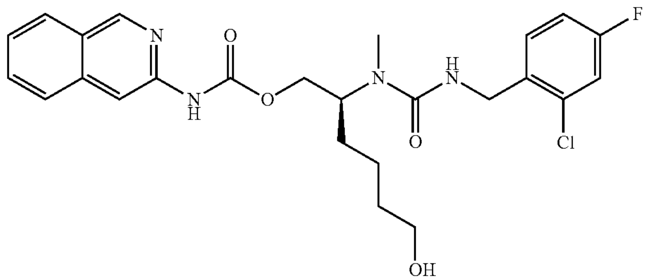 [SMILES: CN(C(=O)NCc1ccc(F)cc1Cl)[C@@H](CCCCO)COC(=O)Nc1cc2ccccc2cn1] | N-{(1S)-5-hydroxy-1-[(N-(3-isoquinolyl)carbamoyloxy)methyl]pentyl}{[(2-chloro-4-fluorophenyl)methyl]amino}-N-methylcarboxamide |
| 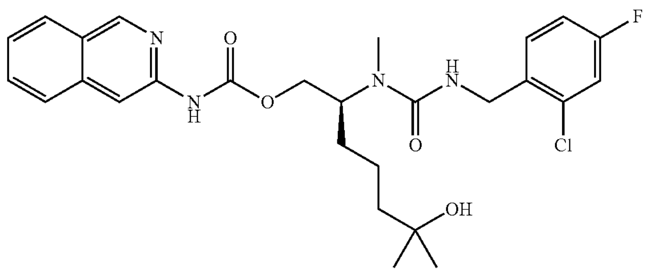 [SMILES: CN(C(=O)NCc1ccc(F)cc1Cl)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2-chloro-4-fluorophenyl)methyl]amino}-N-methylcarboxamide |
| 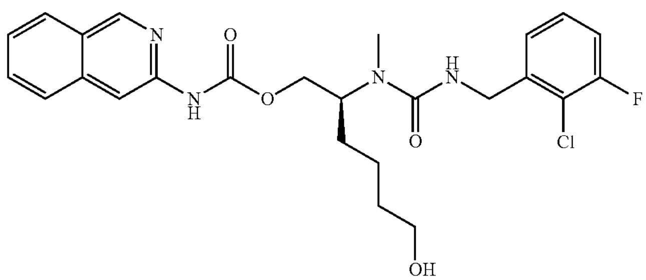 [SMILES: CN(C(=O)NCc1cccc(F)c1Cl)[C@@H](CCCCO)COC(=O)Nc1cc2ccccc2cn1] | N-{(1S)-5-hydroxy-1-[(N-(3-isoquinolyl)carbamoyloxy)methyl]pentyl}{[(2-chloro-3-fluorophenyl)methyl]amino}-N-methylcarboxamide |
| 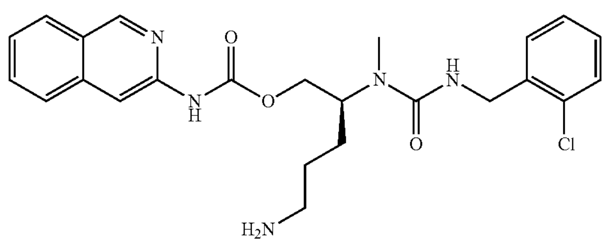 [SMILES: CN(C(=O)NCc1ccccc1Cl)[C@@H](CCCN)COC(=O)Nc1cc2ccccc2cn1] | [(2S)-5-amino-2-({[(2-chlorophenyl)methyl]amino}-N-methylcarbonylamino)pentyloxy]-N-(3-isoquinolyl)carboxamide |
| 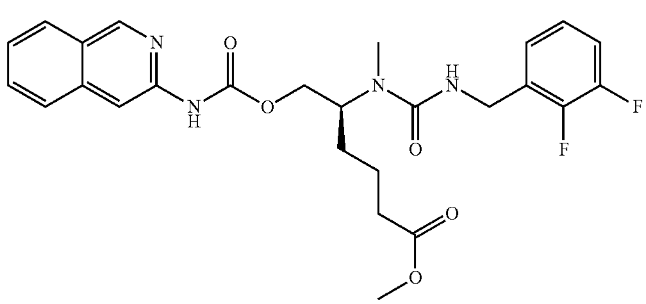 [SMILES: COC(=O)CCC[C@@H](COC(=O)Nc1cc2ccccc2cn1)N(C)C(=O)NCc1cccc(F)c1F] | methyl (5S)-5-({[(2,3-difluorophenyl)methyl]amino}-N-methylcarbonylamino)-6-(N-(3-isoquinolyl)carbamoyloxy)hexanoate |

-continued

| Structure | Chemical Name |
|---|---|
| 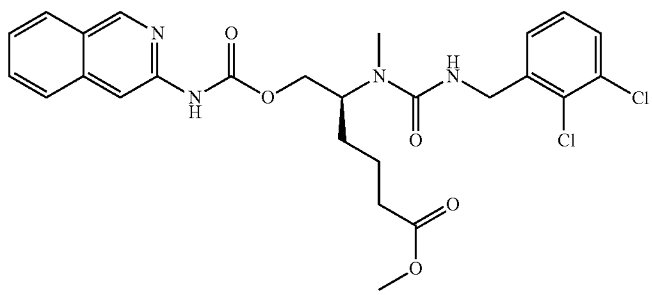 [SMILES: COC(=O)CCC[C@@H](COC(=O)Nc1cc2ccccc2cn1)N(C)C(=O)NCc1cccc(Cl)c1F] | methyl (5S)-5-({[(2,3-dichlorophenyl)methyl]amino}-N-methylcarbonylamino)-6-(N-(3-isoquinolyl)carbamoyloxy)hexanoate |
| 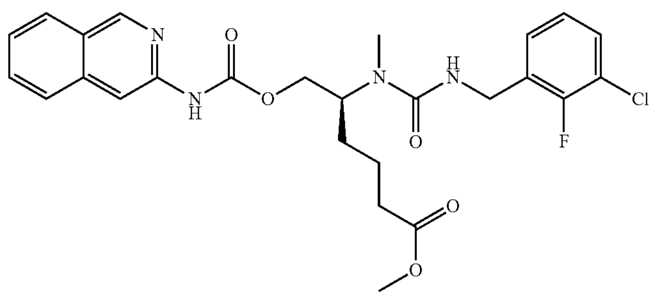 | methyl (5S)-5-({[(3-chloro-2-fluorophenyl)methyl]amino}-N-methylcarbonylamino)-6-(N-(3-isoquinolyl)carbamoyloxy)hexanoate |
| 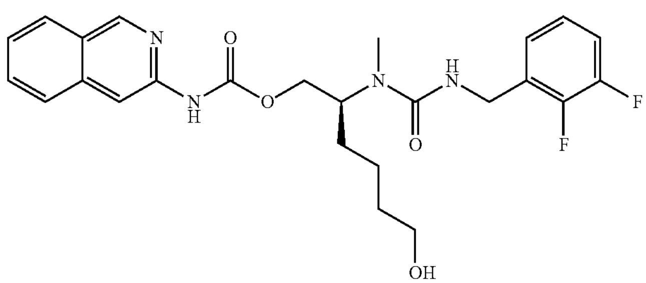 [SMILES: CN(C(=O)NCc1cccc(F)c1F)[C@@H](CCCCO)COC(=O)Nc1cc2ccccc2cn1] | N-{(1S)-5-hydroxy-1-[(N-(3-isoquinolyl)carbamoyloxy)methyl]pentyl}{[(2,3-difluorophenyl)methyl]amino}-N-methylcarboxamide |
| 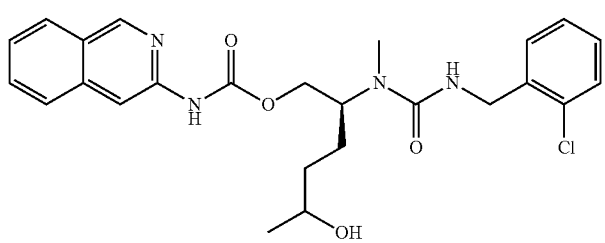 [SMILES: CC(O)CC[C@@H](COC(=O)Nc1cc2ccccc2cn1)N(C)C(=O)NCc1ccccc1Cl] | N-{(1S)-4-hydroxy-1-[(N-(3-isoquinolyl)carbamoyloxy)methyl]pentyl}{[(2-chlorophenyl)methyl]amino}-N-methylcarboxamide |
| 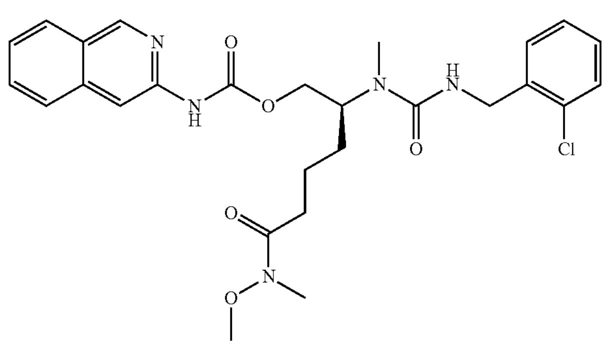 [SMILES: CON(C)C(=O)CCC[C@@H](COC(=O)Nc1cc2ccccc2cn1)N(C)C(=O)NCc1ccccc1Cl] | (5S)-5-({[(2-chlorophenyl)methyl]amino}-N-methylcarbonylamino)-6-(N-(3-isoquinolyl)carbamoyloxy)-N-methoxy-N-methylhexanamide |

-continued

| Structure | Chemical Name |
|---|---|
| 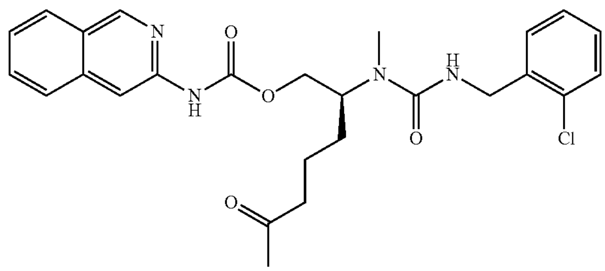 [SMILES: CC(=O)CCC[C@@H](COC(=O)Nc1cc2ccccc2cn1)N(C)C(=O)NCc1ccccc1Cl] | N-{(1S)-1-[(N-3-isoquinolyl)carbamoyloxy)methyl]-5-oxohexyl}{[(2-chlorophenyl)methyl]amino}-N-methylcarboxamide |
| 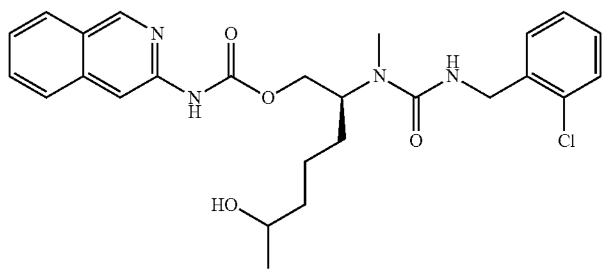 [SMILES: CC(O)CCC[C@@H](COC(=O)Nc1cc2ccccc2cn1)N(C)C(=O)NCc1ccccc1Cl] | N-{(1S)-5-hydroxy-1-[(N-(3-isoquinolyl)carbamoyloxy)methyl]hexyl}{[(2-chlorophenyl)methyl]amino}-N-methylcarboxamide |
| 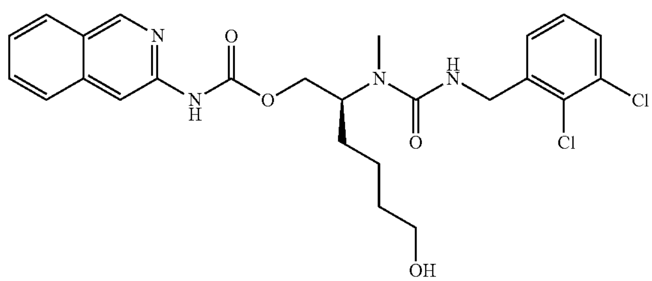 [SMILES: CN(C(=O)NCc1cccc(Cl)c1Cl)[C@@H](CCCCO)COC(=O)Nc1cc2ccccc2cn1] | N-{(1S)-5-hydroxy-1-[(N-(3-isoquinolyl)carbamoyloxy)methyl]pentyl}{[(2,3-dichlorophenyl)methyl]amino}-N-methylcarboxamide |
| 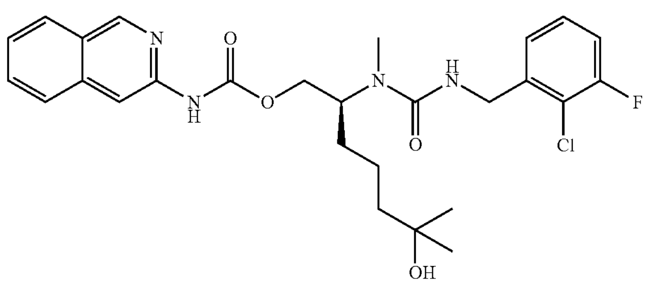 [SMILES: CN(C(=O)NCc1cccc(F)c1Cl)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2-chloro-3-fluorophenyl)methyl]amino}-N-methylcarboxamide |
| 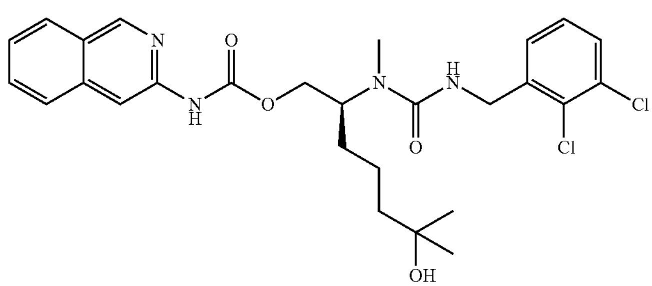 [SMILES: CN(C(=O)NCc1cccc(Cl)c1Cl)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2,3-dichlorophenyl)methyl]amino}-N-methylcarboxamide |

| Structure | Chemical Name |
|---|---|
| 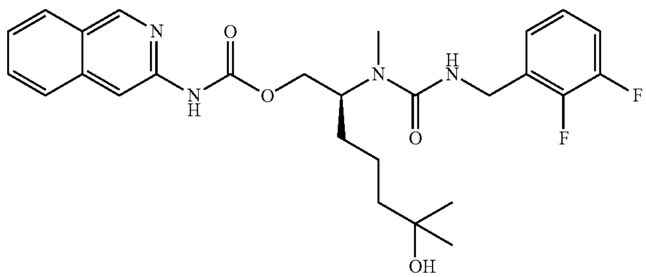 [SMILES: CN(C(=O)NCc1cccc(F)c1F)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2,3-difluorophenyl)methyl]amino}-N-methylcarboxamide |
| 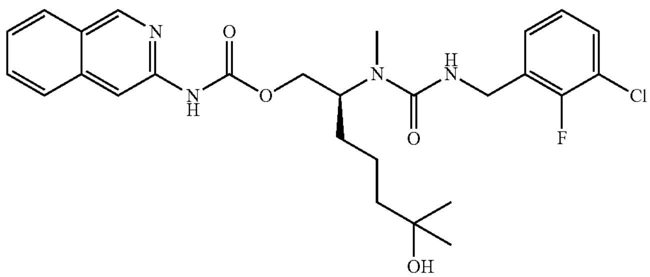 [SMILES: CN(C(=O)NCc1cccc(Cl)c1F)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(3-chloro-2-fluorophenyl)methyl]amino}-N-methylcarboxamide |
| 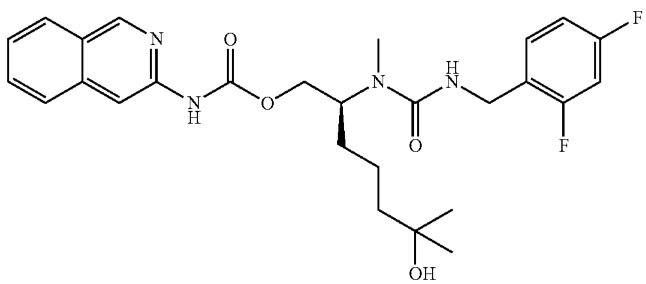 [SMILES: CN(C(=O)NCc1ccc(F)cc1F)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2,4-difluorophenyl)methyl]amino}-N-methylcarboxamide |
| 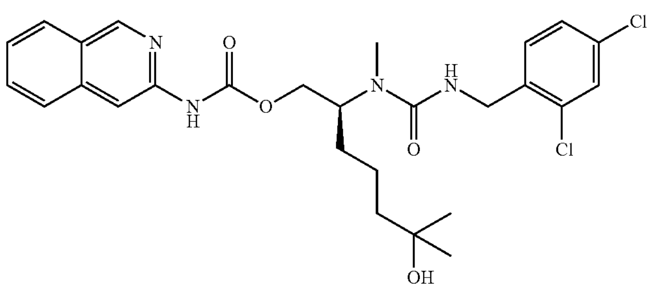 [SMILES: CN(C(=O)NCc1ccc(Cl)cc1Cl)[C@@H](CCCC(C)(C)O)COC(=O)Nc1cc2ccccc2cn1] | N-{(1S)-5-hydroxy-1-[(N-(3-isoquinolyl)carbamoyloxy)methyl]-5-methylhexyl}{[(2,4-dichlorophenyl)methyl]amino}-N-methylcarboxamide |
| 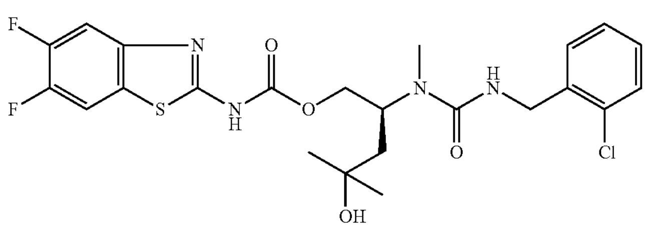 [SMILES: CN(C(=O)NCc1ccccc1Cl)[C@H](COC(=O)Nc1nc2cc(F)c(F)cc2s1)CC(C)(C)O] | [(2S)-2-({[(2-chlorophenyl)methyl]amino}-N-methylcarbonylamino)-4-hydroxy-4-methylpentyloxy]-N-(5,6-difluorobenzothiazol-2-yl)carboxamide |
| 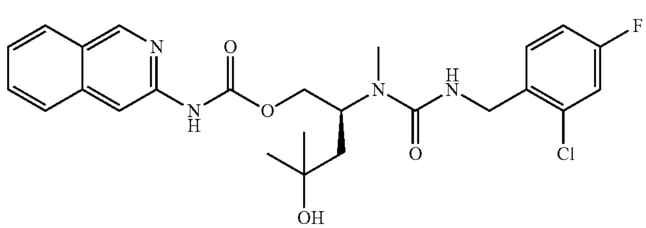 [SMILES: CN(C(=O)NCc1ccc(F)cc1Cl)[C@H](COC(=O)Nc1cc2ccccc2cn1)CC(C)(C)O] | N-{(1S)-3-hydroxy-1-[(N-(3-isoquinolyl)carbamoyloxy)methyl]-3-methylbutyl}{[(2-chloro-4-fluorophenyl)methyl]amino}-N-methylcarboxamide |

-continued

| Structure | Chemical Name |
|---|---|
| 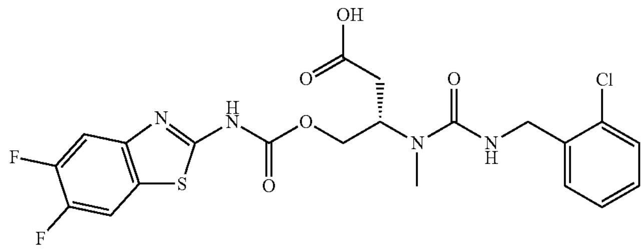 [SMILES: CN(C(=O)NCc1ccccc1Cl)[C@H](COC(=O)Nc1nc2cc(F)c(F)cc2s1)CC(=O)O] | (3S)-4-[N-(5,6-difluorobenzothiazol-2-yl)carbamoyloxy]-3-({[(2-chlorophenyl)methyl]amino}-N-methylcarbonylamino)butanoic acid |
| 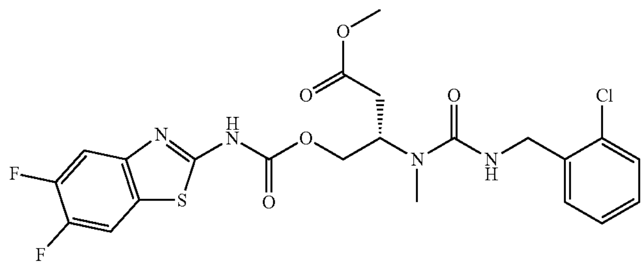 [SMILES: COC(=O)C[C@@H](COC(=O)Nc1nc2cc(F)c(F)cc2s1)N(C)C(=O)NCc1ccccc1Cl] | methyl (3S)-4-[N-(5,6-difluorobenzothiazol-2-yl)carbamoyloxy]-3-({[(2-chlorophenyl)methyl]amino}-N-methylcarbonylamino)butanoate |
| 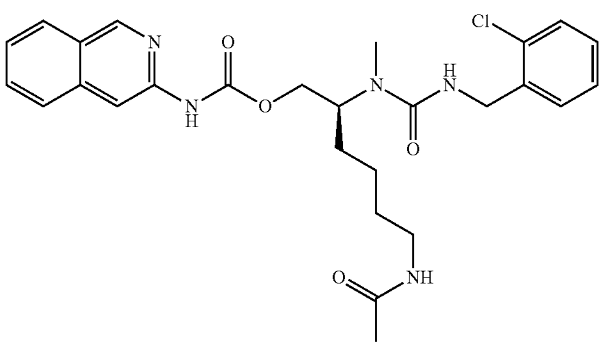 [SMILES: CC(=O)NCCCC[C@@H](COC(=O)Nc1cc2ccccc2cn1)N(C)C(=O)NCc1ccccc1Cl] | N-[(5S)-5-({[(2-chlorophenyl)methyl]amino}-N-methylcarbonylamino)-6-(N-(3-isoquinolyl)carbamoyloxy)hexyl]acetamide |
| 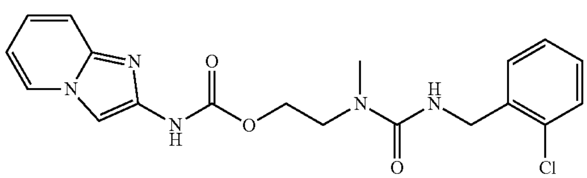 [SMILES: CN(CCOC(=O)Nc1cn2ccccc2n1)C(=O)NCc1ccccc1Cl] | {[(2-chlorophenyl)methyl]amino}-N-[2-(N-(4-hydroimidazo[1,2-a]pyridin-2-yl)carbamoyloxy)ethyl]-N-methylcarboxamide |
| 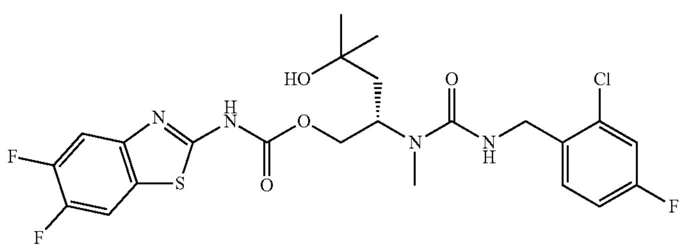 [SMILES: CN(C(=O)NCc1ccc(F)cc1Cl)[C@H](COC(=O)Nc1nc2cc(F)c(F)cc2s1)CC(C)(C)O] | N-((1S)-1-{[N-(5,6-difluorobenzothiazol-2-yl)carbamoyloxy]methyl}-3-hydroxy-3-methylbutyl){[(2-chloro-4-fluorophenyl)methyl]amino}-N-methylcarboxamide |
| 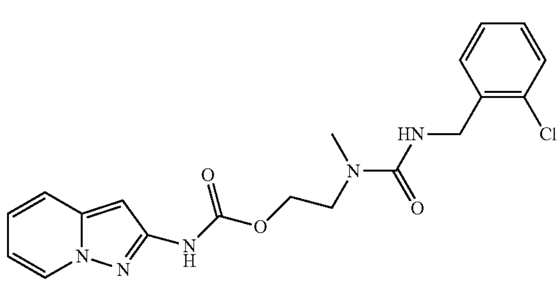 [SMILES: CN(CCOC(=O)Nc1cc2ccccn2n1)C(=O)NCc1ccccc1Cl] | [2-({[(2-chlorophenyl)methyl]amino}-N-methylcarbonylamino)ethoxy]-N-(8-hydropyrazolo[1,5-a]pyridin-2-yl)carboxamide |

| Structure | Chemical Name |
|---|---|
| 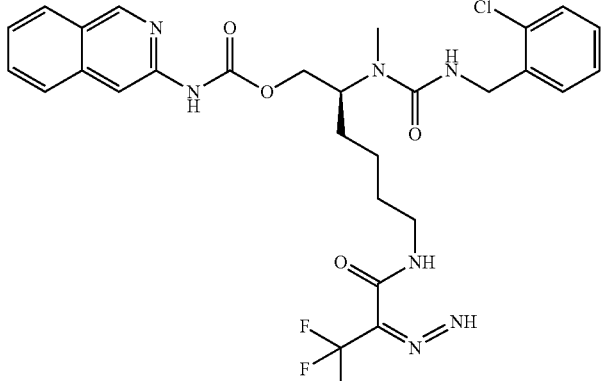 | N-[(5S)-5-({[(2-chlorophenyl)methyl]amino}-N-methylcarbonylamino)-6-(N-(3-isoquinolyl)carbamoyloxy)hexyl]-2-diazo-3,3,3-trifluoropropanamide |
| 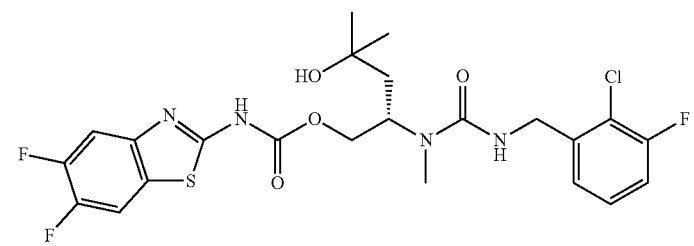 [SMILES: CN(C(=O)NCc1cccc(F)c1Cl)[C@H](COC(=O)Nc1nc2cc(F)c(F)cc2s1)CC(C)(C)O] | N-((1S)-1-{[N-(5,6-difluorobenzothiazol-2-yl)carbamoyloxy]methyl}-3-hydroxy-3-methylbutyl){[(2-chloro-3-fluorophenyl)methyl]amino}-N-methylcarboxamide |
| 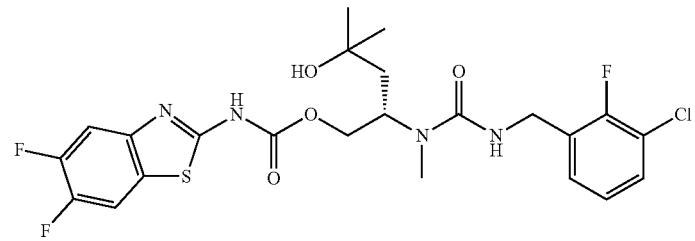 [SMILES: CN(C(=O)NCc1cccc(Cl)c1F)[C@H](COC(=O)Nc1nc2cc(F)c(F)cc2s1)CC(C)(C)O] | N-((1S)-1-{[N-(5,6-difluorobenzothiazol-2-yl)carbamoyloxy]methyl}-3-hydroxy-3-methylbutyl){[(3-chloro-2-fluorophenyl)methyl]amino}-N-methylcarboxamide |
| 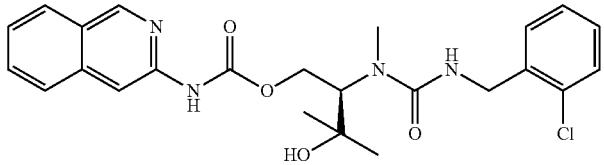 [SMILES: CN(C(=O)NCc1ccccc1Cl)[C@H](COC(=O)Nc1cc2ccccc2cn1)C(C)(C)O] | N-{(1R)-2-hydroxy-1-[(N-(3-isoquinolyl)carbamoyloxy)methyl]-2-methylpropyl}{[(2-chlorophenyl)methyl]amino}-N-methylcarboxamide |
| 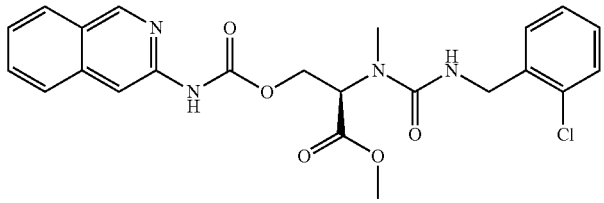 [SMILES: COC(=O)[C@@H](COC(=O)Nc1cc2ccccc2cn1)N(C)C(=O)NCc1ccccc1Cl] | methyl (2R)-2-({[(2-chlorophenyl)methyl]amino}-N-methylcarbonylamino)-3-(N-(3-isoquinolyl)carbamoyloxy)propanoate |
| 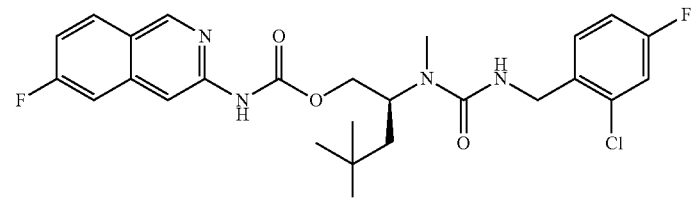 | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-methylcarboxamide |

-continued

| Structure | Chemical Name |
|---|---|
| 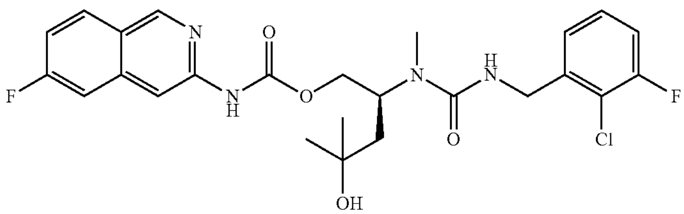 [SMILES: CN(C(=O)NCc1cccc(F)c1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chloro-3-fluorophenyl)methyl]amino}-N-methylcarboxamide |
| 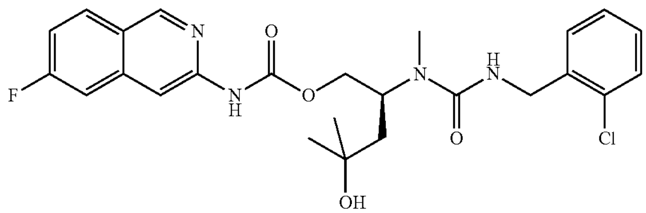 [SMILES: CN(C(=O)NCc1ccccc1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chlorophenyl)methyl]amino}-N-methylcarboxamide |
| 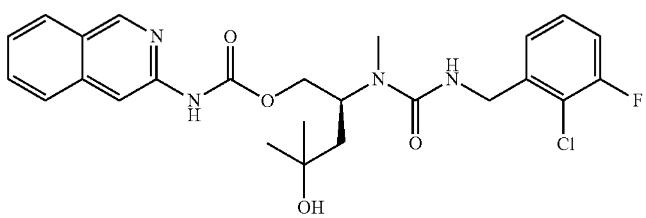 [SMILES: CN(C(=O)NCc1cccc(F)c1Cl)[C@H](COC(=O)Nc1cc2ccccc2cn1)CC(C)(C)O] | N-{(1S)-3-hydroxy-1-[(N-(3-isoquinolyl)carbamoyloxy)methyl]-3-methylbutyl}{[(2-chloro-3-fluorophenyl)methyl]amino}-N-methylcarboxamide |
| 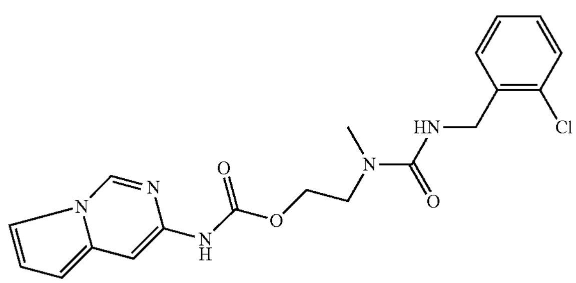 [SMILES: CN(CCOC(=O)Nc1cc2cccn2cn1)C(=O)NCc1ccccc1Cl] | [2-({[(2-chlorophenyl)methyl]amino}-N-methylcarbonylamino)ethoxy]-N-(8-hydropyrrolo[1,2-e]pyrimidin-3-yl)carboxamide |
| 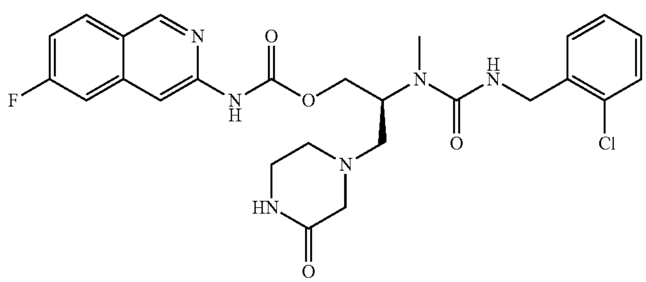 [SMILES: CN(C(=O)NCc1ccccc1Cl)[C@H](COC(=O)Nc1cc2cc(F)ccc2cn1)CN1CCNC(=O)C1] | N-{(1S)-2-[N-(6-fluoro(3-isoquinolyl))carbamoyloxy]-1-[(3-oxopiperazinyl)methyl]ethyl}{[(2-chlorophenyl)methyl]amino}-N-methylcarboxamide |
| 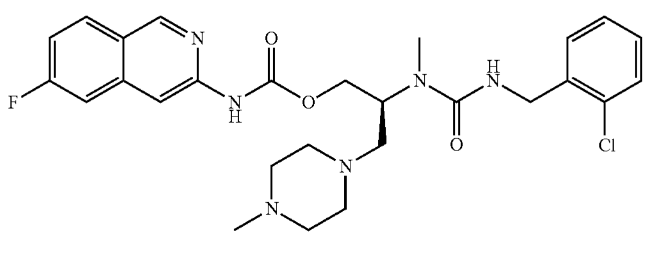 [SMILES: CN1CCN(C[C@@H](COC(=O)Nc2cc3cc(F)ccc3cn2)N(C)C(=O)NCc2ccccc2Cl)CC1] | N-{(1S)-2-[N-(6-fluoro(3-isoquinolyl))carbamoyloxy]-1-[(4-methylpiperazinyl)methyl]ethyl}{[(2-chlorophenyl)methyl]amino}-N-methylcarboxamide |

-continued

| Structure | Chemical Name |
|---|---|
| 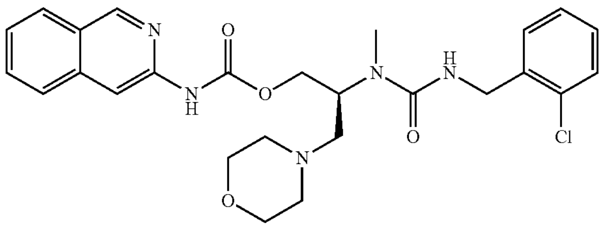 [SMILES: CN(C(=O)NCc1ccccc1Cl)[C@H](COC(=O)Nc1cc2ccccc2cn1)CN1CCOCC1] | N-[(1S)-2-(N-(3-isoquinolyl) carbamoyloxy)-1-(morpholin-4-ylmethyl)ethyl]{[(2-chlorophenyl)methyl]amino}-N-methylcarboxamide |
| 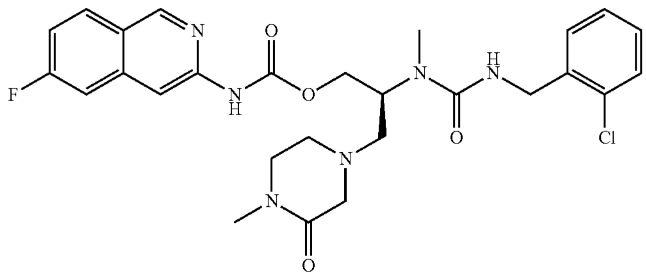 [SMILES: CN1CCN(C[C@@H](COC(=O)Nc2cc3cc(F)ccc3cn2)N(C)C(=O)NCc2ccccc2Cl)CC1=O] | [(2S)-2-({[(2-chlorophenyl) methyl]amino}-N-methylcarbonylamino)-3-(4-methyl-3-oxopiperazinyl)propoxy]-N-(6-fluoro(3-isoquinolyl))carboxamide |
| | [(2S)-2-({[(2-chlorophenyl)methyl]amino}-N-methylcarbonylamino)-4-hydroxy-3,4-dimethylpentyloxy]-N-(6-fluoro(3-isoquinolyl))carboxamide |
| | [(2S)-2-({[(2-chlorophenyl)methyl]amino}-N-methylcarbonylamino)-4-hydroxy-3,4-dimethylpentyloxy]-N-(6-fluoro(3-isoquinolyl))carboxamide |
| 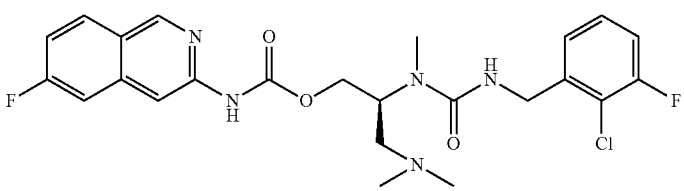 [SMILES: CN(C)C[C@@H](COC(=O)Nc1cc2cc(F)ccc2cn1)N(C)C(=O)NCc1cccc(F)c1Cl] | N-{(1S)-1-[(dimethylamino)methyl]-2-[N-(6-fluoro(3-isoquinolyl))carbamoyloxy]ethyl}{[(2-chloro-3-fluorophenyl)methyl]amino}-N-methylcarboxamide |
| 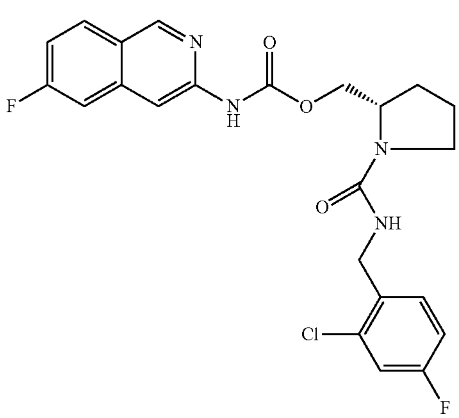 [SMILES: O=C(Nc1cc2cc(F)ccc2cn1)OC[C@@H]1CCCN1C(=O)NCc1ccc(F)cc1Cl] | [((2S)-1-{N-[(2-chloro-4-fluorophenyl)methyl]carbamoyl}pyrrolidin-2-yl)methoxy]-N-(6-fluoro(3-isoquinolyl))carboxamide |

-continued

| Structure | Chemical Name |
| --- | --- |
| 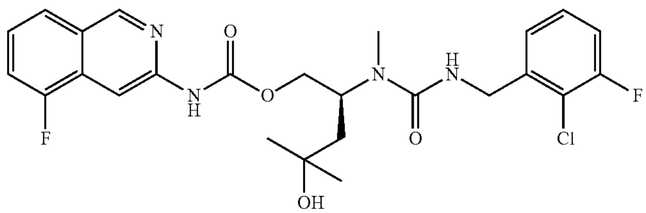 [SMILES: CN(C(=O)NCc1cccc(F)c1Cl)[C@H](COC(=O)Nc1cc2c(F)cccc2cn1)CC(C)(C)O] | [(2S)-2-({[(2-chloro-3-fluorophenyl)methyl]amino}-N-methylcarbonylamino)-4-hydroxy-4-methylpentyloxy]-N-(5-fluoro(3-isoquinolyl))carboxamide |
| 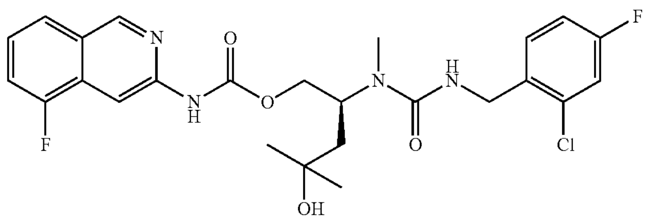 [SMILES: CN(C(=O)NCc1ccc(F)cc1Cl)[C@H](COC(=O)Nc1cc2c(F)cccc2cn1)CC(C)(C)O] | [(2S)-2-({[(2-chloro-4-fluorophenyl)methyl]amino}-N-methylcarbonylamino)-4-hydroxy-4-methylpentyloxy]-N-(5-fluoro(3-isoquinolyl))carboxamide |
| 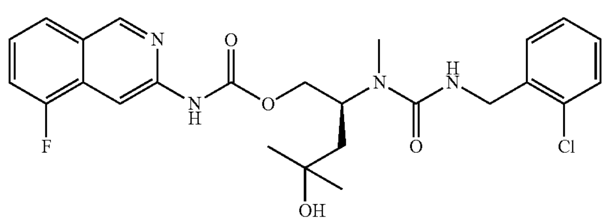 [SMILES: CN(C(=O)NCc1ccccc1Cl)[C@H](COC(=O)Nc1cc2c(F)cccc2cn1)CC(C)(C)O] | [(2S)-2-({[(2-chlorophenyl)methyl]amino}-N-methylcarbonylamino)-4-hydroxy-4-methylpentyloxy]-N-(5-fluoro(3-isoquinolyl))carboxamide |
| 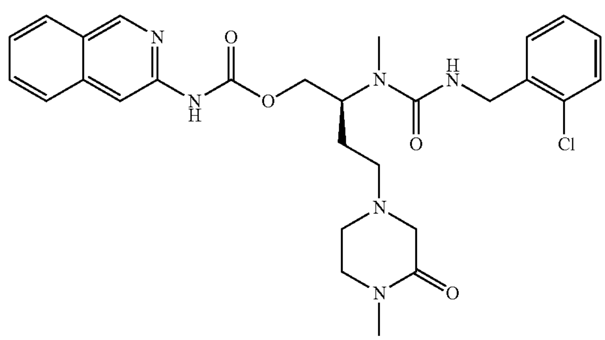 [SMILES: CN1CCN(CC[C@@H](COC(=O)Nc2cc3ccccc3cn2)N(C)C(=O)NCc2ccccc2Cl)CC1=O] | N-{(1S)-1-[(N-(3-isoquinolyl)carbamoyloxy)methyl]-3-(4-methyl-3-oxopiperazinyl)propyl}{[(2-chlorophenyl)methyl]amino}-N-methylcarboxamide |
| 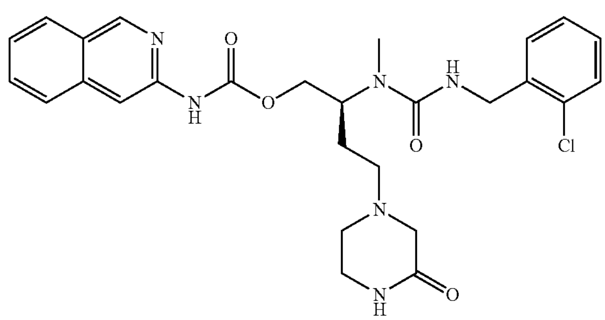 [SMILES: CN(C(=O)NCc1ccccc1Cl)[C@@H](CCN1CCNC(=O)C1)COC(=O)Nc1cc2ccccc2cn1] | N-{(1S)-1-[(N-(3-isoquinolyl)carbamoyloxy)methyl]-3-(3-oxopiperazinyl)propyl}{[(2-chlorophenyl)methyl]amino}-N-methylcarboxamide |
| 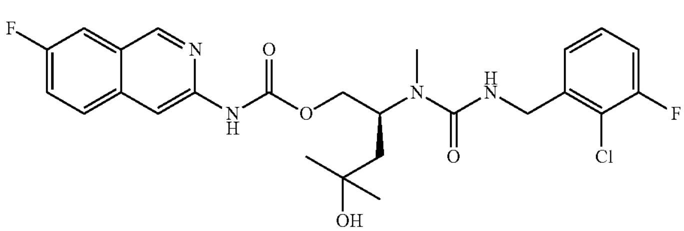 [SMILES: CN(C(=O)NCc1cccc(F)c1Cl)[C@H](COC(=O)Nc1cc2ccc(F)cc2cn1)CC(C)(C)O] | [(2S)-2-({[(2-chloro-3-fluorophenyl)methyl]amino}-N-methylcarbonylamino)-4-hydroxy-4-methylpentyloxy]-N-(7-fluoro(3-isoquinolyl))carboxamide |

| Structure | Chemical Name |
|---|---|
|  | [(2S)-2-({[[(2-chloro-4-fluorophenyl)methyl]amino}-N-methylcarbonylamino)-4-hydroxy-4-methylpentyloxy]-N-(7-fluoro(3-isoquinolyl))carboxamide |
|  | [(2S)-2-({[[(2-chlorophenyl)methyl]amino}-N-methylcarbonylamino)-4-hydroxy-4-methylpentyloxy}-N-(7-fluoro(3-isoquinolyl))carboxamide |
| 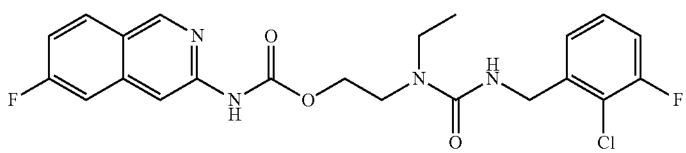 [SMILES: CCN(CCOC(=O)Nc1cc2cc(F)ccc2cn1)C(=O)NCc1cccc(F)c1Cl] | {[(2-chloro-3-fluorophenyl)methyl]amino}-N-ethyl-N-{2-[N-(6-fluoro(3-isoquinolyl))carbamoyloxy]ethyl}carboxamide |
| 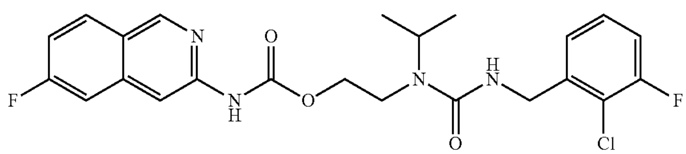 [SMILES: CC(C)N(CCOC(=O)Nc1cc2cc(F)ccc2cn1)C(=O)NCc1cccc(F)c1Cl] | {[(2-chloro-3-fluorophenyl)methyl]amino}-N-{2-[N-(6-fluoro(3-isoquinolyl))carbamoyloxy]ethyl}-N-(methylethyl)carboxamide |
| 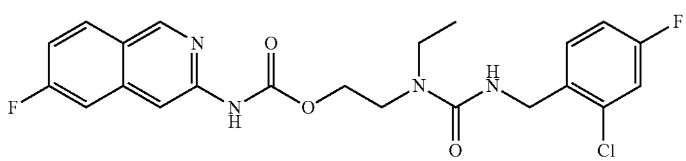 [SMILES: CCN(CCOC(=O)Nc1cc2cc(F)ccc2cn1)C(=O)NCc1ccc(F)cc1Cl] | {[(2-chloro-4-fluorophenyl)methyl]amino}-N-ethyl-N-{2-[N-(6-fluoro(3-isoquinolyl))carbamoyloxy]ethyl}carboxamide |
| 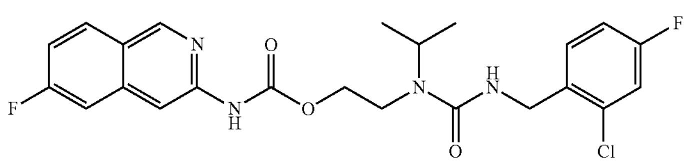 [SMILES: CC(C)N(CCOC(=O)Nc1cc2cc(F)ccc2cn1)C(=O)NCc1ccc(F)cc1Cl] | {[(2-chloro-4-fluorophenyl)methyl]amino}-N-{2-[N-(6-fluoro(3-isoquinolyl))carbamoyloxy]ethyl}-N-(methylethyl)carboxamide |
| 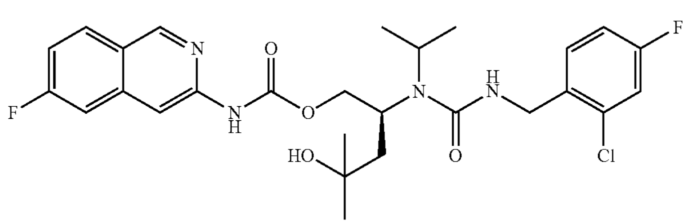 [SMILES: CC(C)N(C(=O)NCc1ccc(F)cc1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-(methylethyl)carboxamide |
| 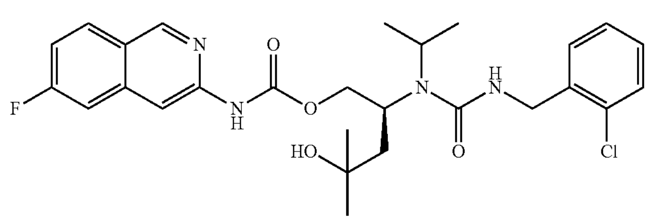 [SMILES: CC(C)N(C(=O)NCc1ccccc1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chlorophenyl)methyl]amino}-N-(methylethyl)carboxamide |

| Structure | Chemical Name |
|---|---|
| 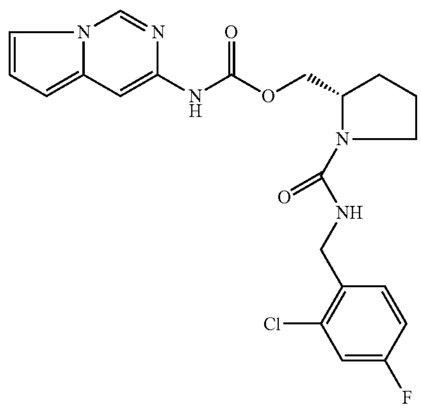 [SMILES: O=C(Nc1cc2cccn2cn1)OC[C@@H]1CCCN1C(=O)NCc1ccc(F)cc1Cl] | [((2S)-1-{N-[(2-chloro-4-fluorophenyl)methyl]carbamoyl}pyrrolidin-2-yl)methoxy]-N-(8-hydropyrrolo[1,2-e]pyrimidin-3-yl)carboxamide |
| 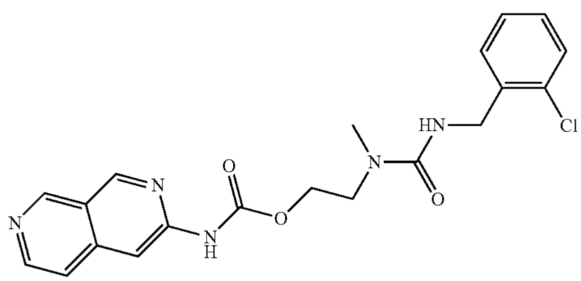 [SMILES: CN(CCOC(=O)Nc1cc2ccncc2cn1)C(=O)NCc1ccccc1Cl] | [2-({[(2-chlorophenyl)methyl]amino}-N-methylcarbonylamino)ethoxy]-N-pyridino[4,3-d]pyridin-3-ylcarboxamide |
| 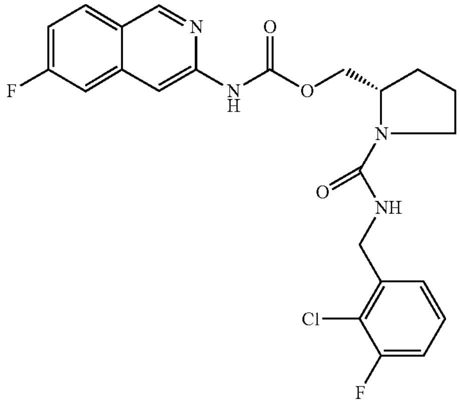 [SMILES: O=C(Nc1cc2cc(F)ccc2cn1)OC[C@@H]1CCCN1C(=O)NCc1cccc(F)c1Cl] | [((2S)-1-{N-[(2-chloro-3-fluorophenyl)methyl]carbamoyl}pyrrolidin-2-yl)methoxy]-N-(6-fluoro(3-isoquinolyl))carboxamide |
| 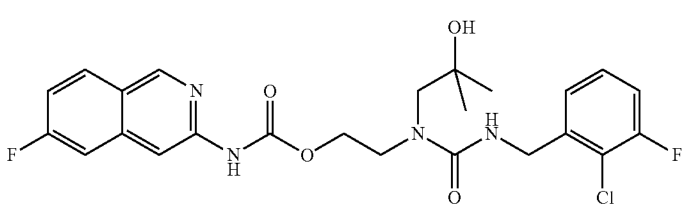 [SMILES: CC(C)(O)CN(CCOC(=O)Nc1cc2cc(F)ccc2cn1)C(=O)NCc1cccc(F)c1Cl] | {[(2-chloro-3-fluorophenyl)methyl]amino}-N-{2-[N-(6-fluoro(3-isoquinolyl))carbamoyloxy]ethyl}-N-(2-hydroxy-2-methylpropyl)carboxamide |
| 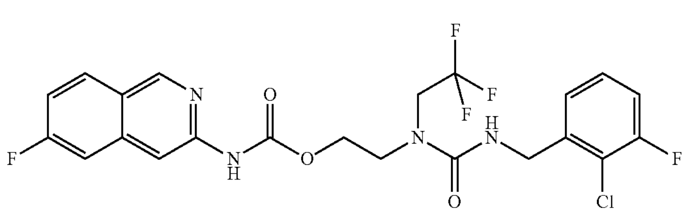 [SMILES: O=C(Nc1cc2cc(F)ccc2cn1)OCCN(CC(F)(F)F)C(=O)NCc1cccc(F)c1Cl] | {[(2-chloro-3-fluorophenyl)methyl]amino}-N-{2-[N-(6-fluoro(3-isoquinolyl))carbamoyloxy]ethyl}-N-(2,2,2-trifluoroethyl)carboxamide |

| Structure | Chemical Name |
| --- | --- |
| 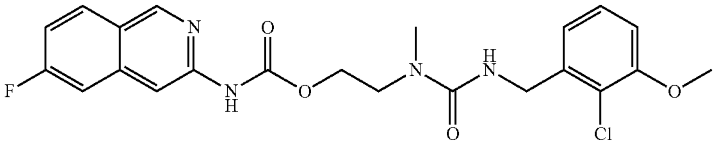 [SMILES: COc1cccc(CNC(=O)N(C)CCOC(=O)Nc2cc3cc(F)ccc3cn2)c1Cl] | {[(2-chloro-3-methoxyphenyl)methyl]amino}-N-{2-[N-(6-fluoro(3-isoquinolyl))carbamoyloxy]ethyl}-N-methylcarboxamide |
| 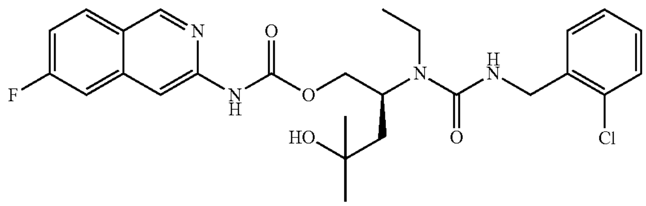 [SMILES: CCN(C(=O)NCc1ccccc1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chlorophenyl)methyl]amino}-N-ethylcarboxamide |
| 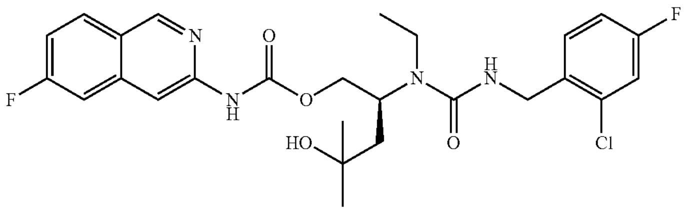 [SMILES: CCN(C(=O)NCc1ccc(F)cc1Cl)[C@H](COC(=O)Nc1cc2cc(F)ccc2cn1)CC(C)(C)O] | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-ethylcarboxamide |
| 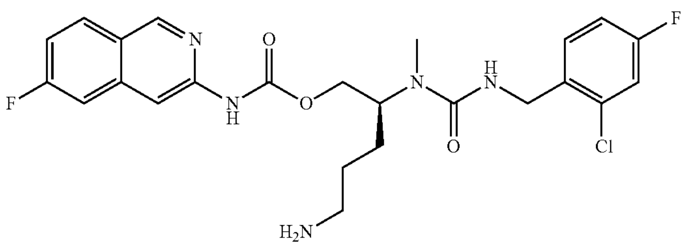 [SMILES: CN(C(=O)NCc1ccc(F)cc1Cl)[C@@H](CCCN)COC(=O)Nc1cc2cc(F)ccc2cn1] | N-((1S)-4-amino-1-{[N-(6-fluoro(3-isoquinolyl))carbamoyloxy]methyl}butyl){[(2-chloro-4-fluorophenyl)methyl]amino}-N-methylcarboxamide |
| 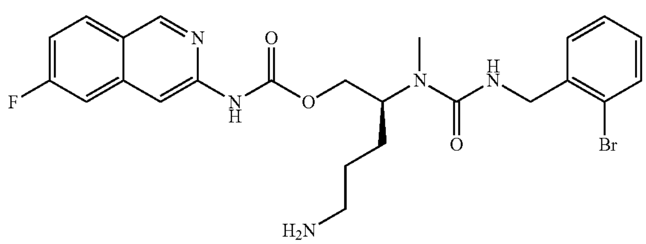 [SMILES: CN(C(=O)NCc1ccccc1Br)[C@@H](CCCN)COC(=O)Nc1cc2cc(F)ccc2cn1] | N-((1S)-4-amino-1-{[N-(6-fluoro(3-isoquinolyl))carbamoyloxy]methyl}butyl){[(2-bromophenyl)methyl]amino}-N-methylcarboxamide |
| 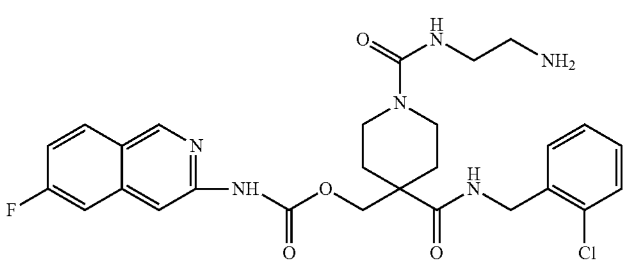 [SMILES: NCCNC(=O)N1CCC(COC(=O)Nc2cc3cc(F)ccc3cn2)(C(=O)NCc2ccccc2Cl)CC1] | N-(2-aminoethyl)(4-{N-[(2-chlorophenyl)methyl]carbamoyl}-4-{[N-(6-fluoro(3-isoquinolyl))carbamoyloxy]methyl}piperidyl)carboxamide |

| Structure | Chemical Name |
|---|---|
| | (tert-butoxy)-N-[2-(4-{N-[(2-bromophenyl)methyl]carbamoyl}-4-{[N-(4-ethylphenyl)carbamoyloxy]methyl}piperidyl)-2-oxoethyl]-N-methylcarboxamide |
| 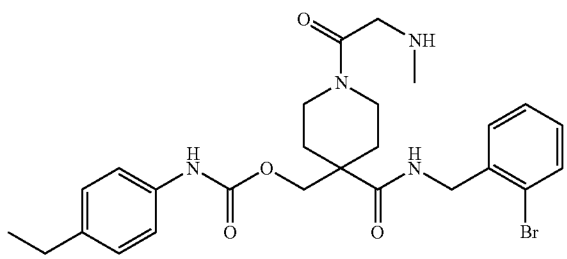 [SMILES: CCc1ccc(NC(=O)OCC2(C(=O)NCc3ccccc3Br)CCN(C(=O)CNC)CC2)cc1] | [(4-{N-[(2-bromophenyl)methyl]carbamoyl}-1-[2-(methylamino)acetyl](4-piperidyl))methoxy]-N-(4-ethylphenyl)carboxamide |
| 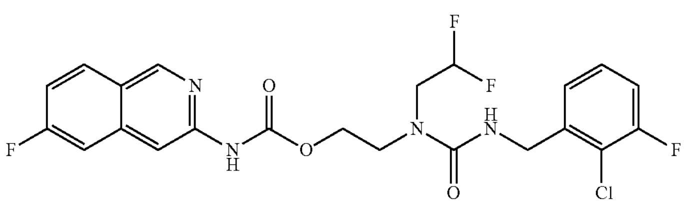 [SMILES: O=C(Nc1cc2cc(F)ccc2cn1)OCCN(CC(F)F)C(=O)NCc1cccc(F)c1Cl] | N-(2,2-difluoroethyl){[(2-chloro-3-fluorophenyl)methyl]amino}-N-{2-[N-(6-fluoro(3-isoquinolyl))carbamoyloxy]ethyl}carboxamide |
| 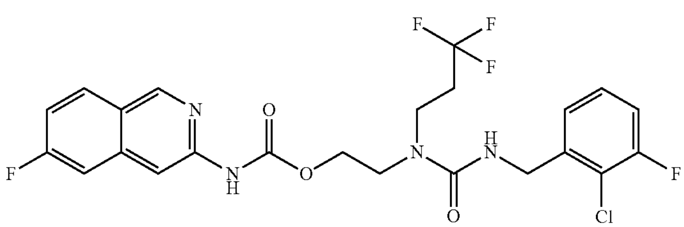 [SMILES: O=C(Nc1cc2cc(F)ccc2cn1)OCCN(CCC(F)(F)F)C(=O)NCc1cccc(F)c1Cl] | {[(2-chloro-3-fluorophenyl)methyl]amino}-N-{2-[N-(6-fluoro(3-isoquinolyl))carbamoyloxy]ethyl}-N-(3,3,3-trifluoropropyl)carboxamide |
| 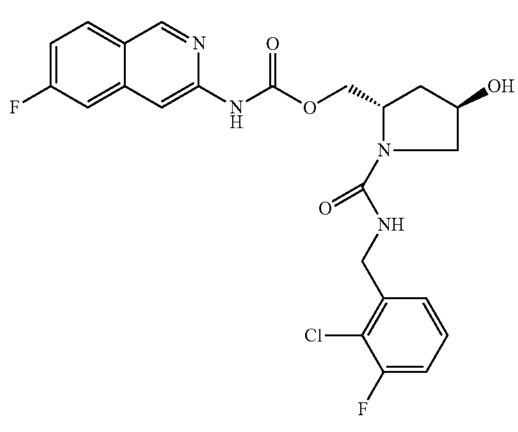 [SMILES: O=C(Nc1cc2cc(F)ccc2cn1)OC[C@@H]1C[C@@H](O)CN1C(=O)NCc1cccc(F)c1Cl] | [((2S,4R)-1-{N-[(2-chloro-3-fluorophenyl)methyl]carbamoyl}-4-hydroxypyrrolidin-2-yl)methoxy]-N-(6-fluoro(3-isoquinolyl))carboxamide |

-continued

| Structure | Chemical Name |
|---|---|
| 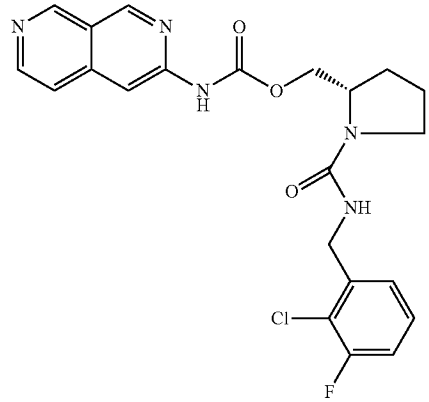 [SMILES: O=C(Nc1cc2ccncc2cn1)OC[C@@H]1CCCN1C(=O)NCc1cccc(F)c1Cl] | [((2S)-1-{N-[(2-chloro-3-fluorophenyl)methyl]carbamoyl}pyrrolidin-2-yl)methoxy]-N-pyridino[4,3-d]pyridin-3-ylcarboxamide |
| 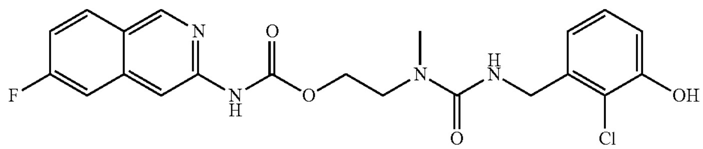 [SMILES: CN(CCOC(=O)Nc1cc2cc(F)ccc2cn1)C(=O)NCc1cccc(O)c1Cl] | {[(2-chloro-3-hydroxyphenyl)methyl]amino}-N-{2-[N-(6-fluoro(3-isoquinolyl))carbamoyloxy]ethyl}-N-methylcarboxamide |
| 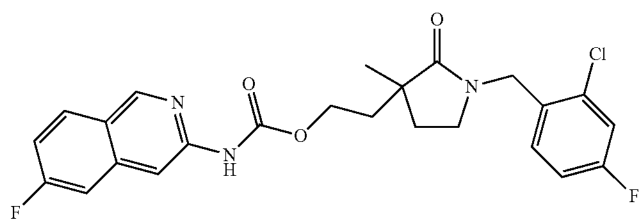 [SMILES: CC1(CCOC(=O)Nc2cc3cc(F)ccc3cn2)CCN(Cc2ccc(F)cc2Cl)C1=O] | (2-{1-[(2-chloro-4-fluorophenyl)methyl]-3-methyl-2-oxopyrrolidin-3-yl}ethoxy)-N-(6-fluoro(3-isoquinolyl))carboxamide |
| 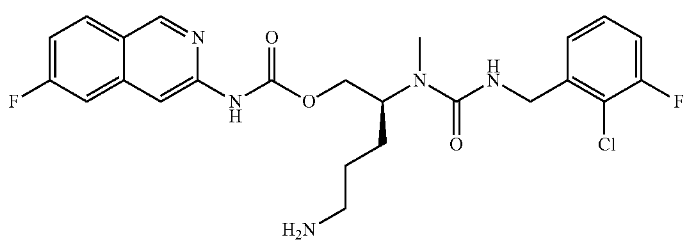 | N-((1S)-4-amino-1-{[N-(6-fluoro(3-isoquinolyl))carbamoyloxy]methyl}butyl){[(2-chloro-3-fluorophenyl)methyl]amino}-N-methylcarboxamide |
| 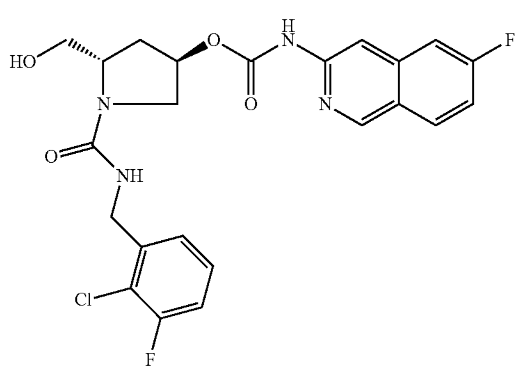 [SMILES: O=C(Nc1cc2cc(F)ccc2cn1)O[C@@H]1C[C@@H](CO)N(C(=O)NCc2cccc(F)c2Cl)C1] | ((5S,3R)-1-{N-[(2-chloro-3-fluorophenyl)methyl]carbamoyl}-5-(hydroxymethyl)pyrrolidin-3-yloxy)-N-(6-fluoro(3-isoquinolyl))carboxamide |

| Structure | Chemical Name |
|---|---|
| 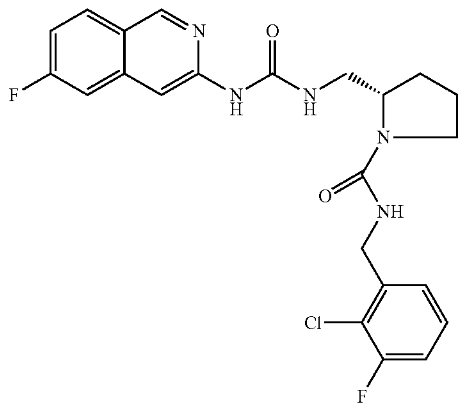 [SMILES: O=C(NC[C@@H]1CCCN1C(=O)NCc1cccc(F)c1Cl)Nc1cc2cc(F)ccc2cn1] | {[((2S)-1-{N-[(2-chloro-3-fluorophenyl)methyl]carbamoyl}pyrrolidin-2-yl)methyl]amino}-N-(6-fluoro(3-isoquinolyl))carboxamide |
| 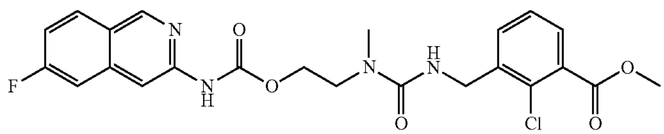 [SMILES: COC(=O)c1cccc(CNC(=O)N(C)CCOC(=O)Nc2cc3cc(F)ccc3cn2)c1Cl] | methyl 2-chloro-3-{[(N-{2-[N-(6-fluoro(3-isoquinolyl))carbamoyloxy]ethyl}-N-methylcarbamoyl)amino]methyl}benzoate |
| 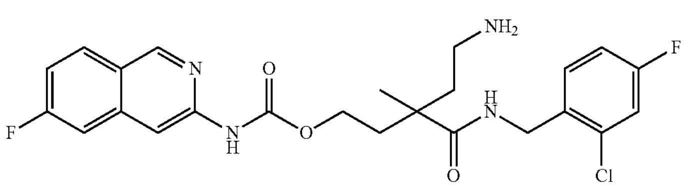 [SMILES: CC(CCN)(CCOC(=O)Nc1cc2cc(F)ccc2cn1)C(=O)NCc1ccc(F)cc1Cl] | 4-amino-N-[(2-chloro-4-fluorophenyl)methyl]-2-{2-[N-(6-fluoro(3-isoquinolyl))carbamoyloxy]ethyl}-2-methylbutanamide |
| 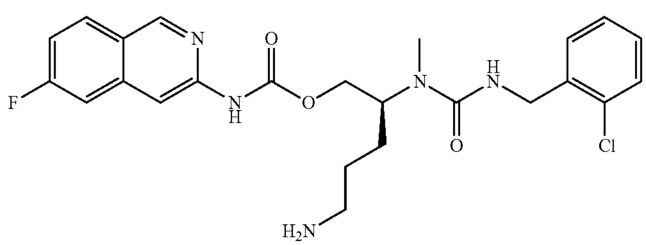 [SMILES: CN(C(=O)NCc1ccccc1Cl)[C@@H](CCCN)COC(=O)Nc1cc2cc(F)ccc2cn1] | N-((1S)-4-amino-1-{[N-(6-fluoro(3-isoquinolyl))carbamoyloxy]methyl}butyl){[(2-chlorophenyl)methyl]amino}-N-methylcarboxamide |
| 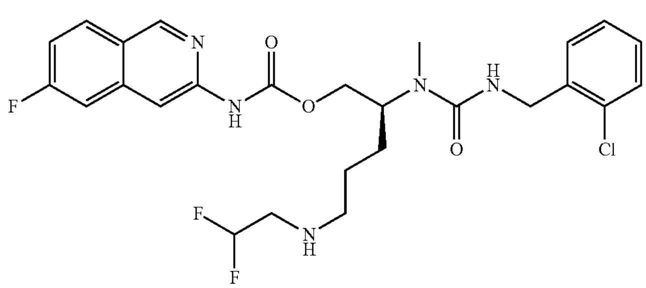 [SMILES: CN(C(=O)NCc1ccccc1Cl)[C@@H](CCCNCC(F)F)COC(=O)Nc1cc2cc(F)ccc2cn1] | N-((1S)-4-[(2,2-difluoroethyl)amino]-1-{[N-(6-fluoro(3-isoquinolyl))carbamoyloxy]methyl}butyl){[(2-chlorophenyl)methyl]amino}-N-methylcarboxamide |

| Structure | Chemical Name |
|---|---|
| 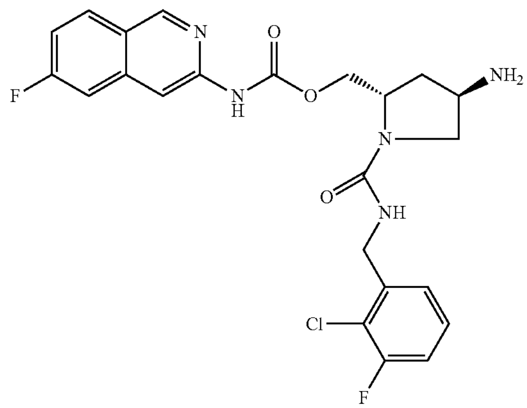 [SMILES: N[C@@H]1C[C@@H](COC(=O)Nc2cc3cc(F)ccc3cn2)N(C(=O)NCc2cccc(F)c2Cl)C1] | [((2S,4R)-4-amino-1-{N-[(2-chloro-3-fluorophenyl)methyl]carbamoyl}pyrrolidin-2-yl)methoxy]-N-(6-fluoro(3-isoquinolyl))carboxamide |
| | N-((5S,3R)-1-{N-[(2-chloro-3-fluorophenyl)methyl]carbamoyl}-5-{[N-(6-fluoro(3-isoquinolyl))carbamoyloxy]methyl}pyrrolidin-3-yl)-2-[(tert-butoxy)carbonylamino]acetamide |
| 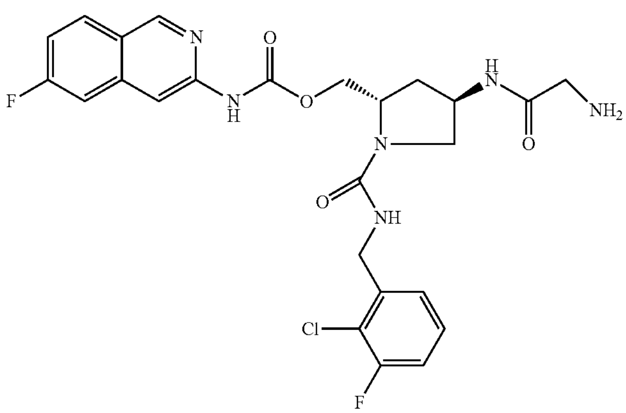 [SMILES: NCC(=O)N[C@@H]1C[C@@H](COC(=O)Nc2cc3cc(F)ccc3cn2)N(C(=O)NCc2cccc(F)c2Cl)C1] | N-((5S,3R)-1-{N-[(2-chloro-3-fluorophenyl)methyl]carbamoyl}-5-{[N-(6-fluoro(3-isoquinolyl))carbamoyloxy]methyl}pyrrolidin-3-yl)-2-aminoacetamide |
| 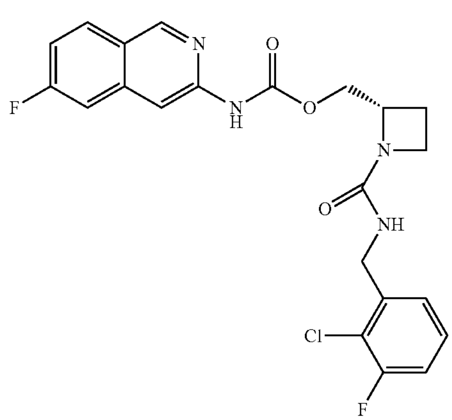 [SMILES: O=C(Nc1cc2cc(F)ccc2cn1)OC[C@@H]1CCN1C(=O)NCc1cccc(F)c1Cl] | [((2S)-1-{N-[(2-chloro-3-fluorophenyl)methyl]carbamoyl}azetidin-2-yl)methoxy]-N-(6-fluoro(3-isoquinolyl))carboxamide |

| Structure | Chemical Name |
|---|---|
| | N-((1S)-1-{[N-(6-fluoro-3-isoquinolyl))carbamoyloxy]methyl}but-3-enyl){[(2-chloro-3-fluorophenyl)methyl]amino}-N-methylcarboxamide |
| | N-((1S)-1-{[N-(6-fluoro-3-isoquinolyl))carbamoyloxy]methyl}-3,4-dihydroxybutyl){[(2-chloro-3-fluorophenyl)methyl]amino}-N-methylcarboxamide |
| 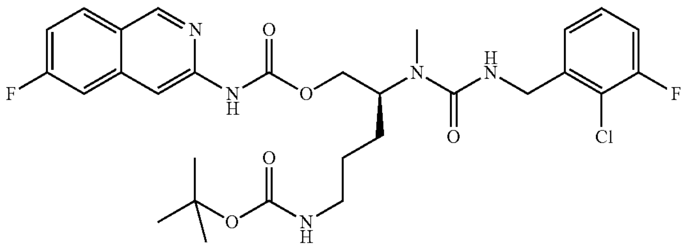 [SMILES: CN(C(=O)NCc1cccc(F)c1Cl)[C@@H](CCCNC(=O)OC(C)(C)C)COC(=O)Nc1cc2cc(F)ccc2cn1] | N-((1S)-4-[(tert-butoxy)carbonylamino]-1-{[N-(6-fluoro(3-isoquinolyl))carbamoyloxy]methyl}butyl){[(2-chloro-3-fluorophenyl)methyl]amino}-N-methylcarboxamide |
| 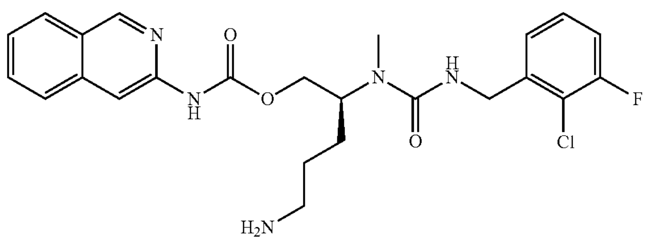 | N-{(1S)-4-amino-1-[(N-(3-isoquinolyl)carbamoyloxy)methyl]butyl}{[(2-chloro-3-fluorophenyl)methyl]amino}-N-methylcarboxamide |
| 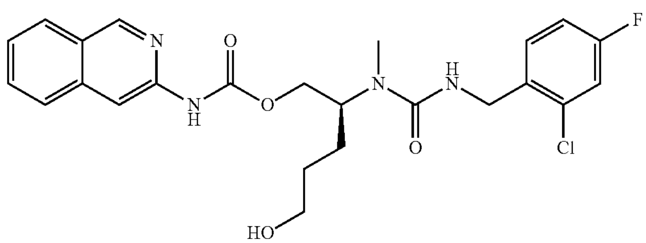 [SMILES: CN(C(=O)NCc1ccc(F)cc1Cl)[C@@H](CCCO)COC(=O)Nc1cc2ccccc2cn1] | N-{(1S)-4-amino-1-[(N-(3-isoquinolyl)carbamoyloxy)methyl]butyl}{[(2-chloro-4-fluorophenyl)methyl]amino}-N-methylcarboxamide |
| 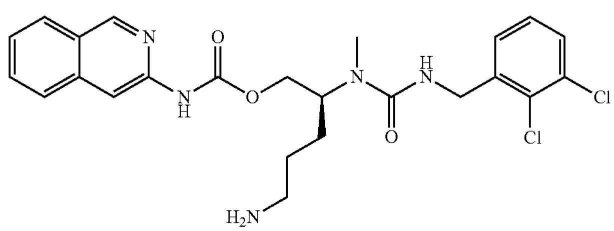 [SMILES: CN(C(=O)NCc1cccc(Cl)c1Cl)[C@@H](CCCN)COC(=O)Nc1cc2ccccc2cn1] | N-{(1S)-4-amino-1-[(N-(3-isoquinolyl)carbamoyloxy)methyl]butyl}{[(2,3-dichlorophenyl)methyl]amino}-N-methylcarboxamide |
| 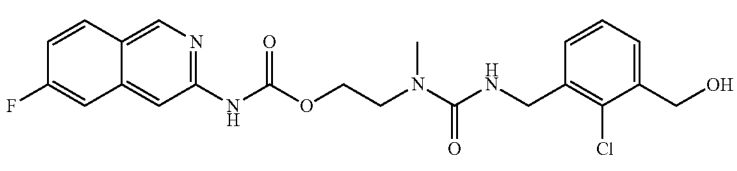 [SMILES: CN(CCOC(=O)Nc1cc2cc(F)ccc2cn1)C(=O)NCc1cccc(CO)c1Cl] | ({[2-chloro-3-(hydroxymethyl)phenyl]methyl}amino)-N-{2-[N-(6-fluoro(3-isoquinolyl))carbamoyloxy]ethyl}-N-methylcarboxamide |

| Structure | Chemical Name |
|---|---|
| 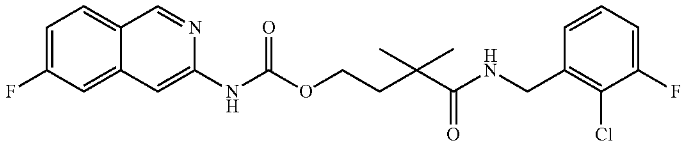 [SMILES: CC(C)(CCOC(=O)Nc1cc2cc(F)ccc2cn1)C(=O)NCc1cccc(F)c1Cl] | N-[(2-chloro-3-fluorophenyl)methyl]-4-[N-(6-fluoro(3-isoquinolyl))carbamoyloxy]-2,2-dimethylbutanamide |
| 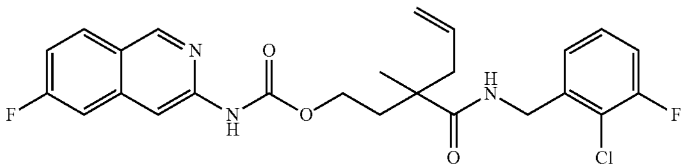 [SMILES: C=CCC(C)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-2-methylpent-4-enamide |
| 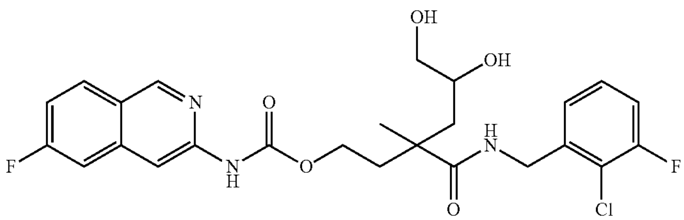 [SMILES: CC(CCOC(=O)Nc1cc2cc(F)ccc2cn1)(CC(O)CO)C(=O)NCc1cccc(F)c1Cl] | N-[(2-chloro-3-fluorophenyl)methyl]-2-{2-[N-(6-fluoro(3-isoquinolyl))carbamoyloxy]ethyl}-4,5-dihydroxy-2-methylpentanamide |
| 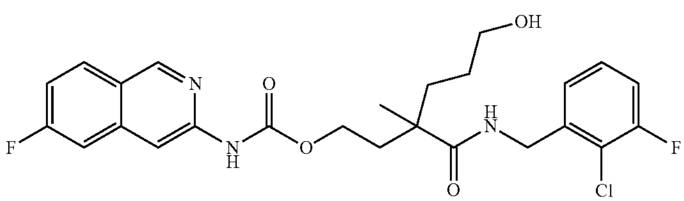 [SMILES: CC(CCCO)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-5-hydroxy-2-methylpentanamide |
| 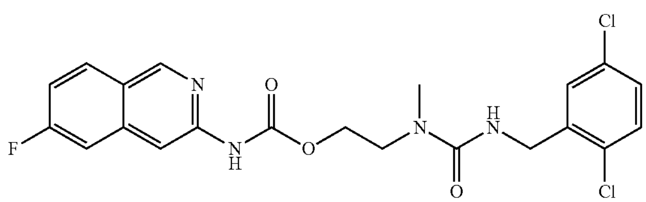 [SMILES: CN(CCOC(=O)Nc1cc2cc(F)ccc2cn1)C(=O)NCc1cc(Cl)ccc1Cl] | {[(2,5-dichlorophenyl)methyl]amino}-N-{2-[N-(6-fluoro(3-isoquinolyl))carbamoyloxy]ethyl}-N-methylcarboxamide |
| 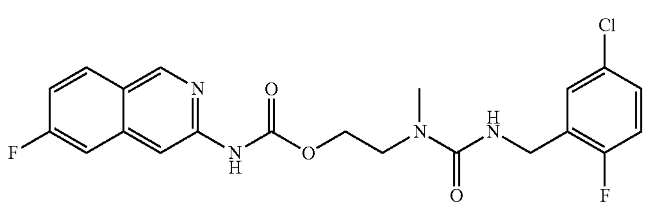 [SMILES: CN(CCOC(=O)Nc1cc2cc(F)ccc2cn1)C(=O)NCc1cc(Cl)ccc1F] | {[(5-chloro-2-fluorophenyl)methyl]amino}-N-{2-[N-(6-fluoro(3-isoquinolyl))carbamoyloxy]ethyl}-N-methylcarboxamide |
| 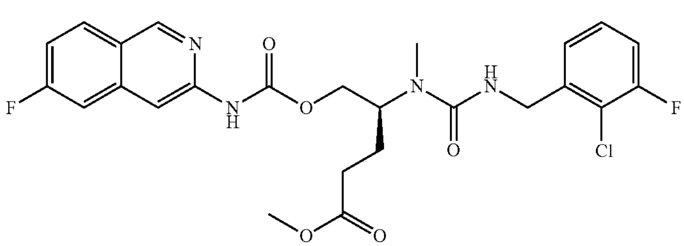 [SMILES: COC(=O)CC[C@@H](COC(=O)Nc1cc2cc(F)ccc2cn1)N(C)C(=O)NCc1cccc(F)c1Cl] | methyl (4S)-4-({[(2-chloro-3-fluorophenyl)methyl]amino}-N-methylcarbonylamino)-5-[N-(6-fluoro(3-isoquinolyl))carbamoyloxy]pentanoate |

-continued

| Structure | Chemical Name |
|---|---|
| 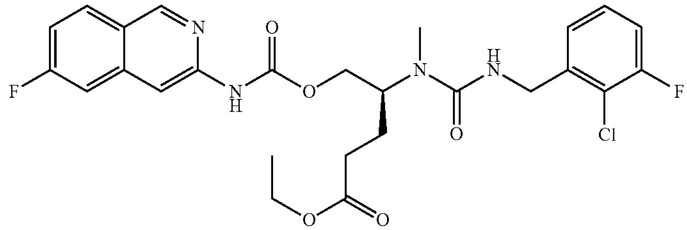 [SMILES: CCOC(=O)CC[C@@H](COC(=O)Nc1cc2cc(F)ccc2cn1)N(C)C(=O)NCc1cccc(F)c1Cl] | ethyl (4S)-4-({[(2-chloro-3-fluorophenyl)methyl]amino}-N-methylcarbonylamino)-5-[N-(6-fluoro(3-isoquinolyl))carbamoyloxy]pentanoate |
| 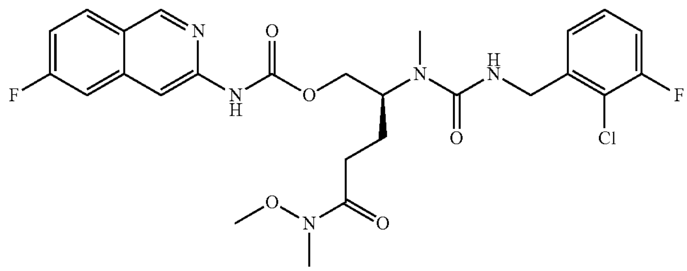 [SMILES: CON(C)C(=O)CC[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]-N-methoxy-N-methylpentanamide |
| 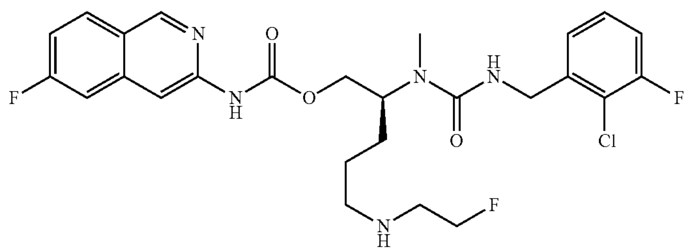 [SMILES: CN(C(=O)NCc1cccc(F)c1Cl)[C@@H](CCCNCCF)COC(=O)Nc1cc2cc(F)ccc2cn1] | N-((1S)-1-{[N-(6-fluoro(3-isoquinolyl))carbamoyloxy]methyl}-4-[(2-fluoroethyl)amino]butyl){[(2-chloro-3-fluorophenyl)methyl]amino}-N-methylcarboxamide |
| 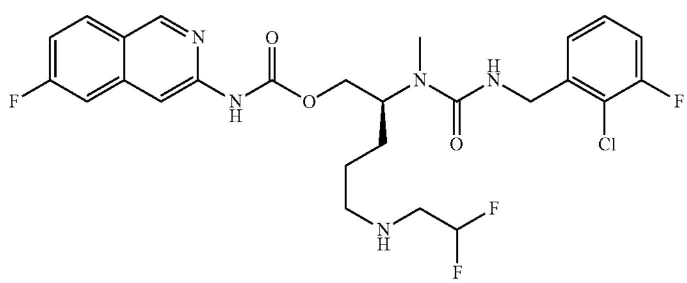 [SMILES: CN(C(=O)NCc1cccc(F)c1Cl)[C@@H](CCCNCC(F)F)COC(=O)Nc1cc2cc(F)ccc2cn1] | N-((1S)-4-[(2,2-difluoroethyl)amino]-1-{[N-(6-fluoro(3-isoquinolyl))carbamoyloxy]methyl}butyl){[(2-chloro-3-fluorophenyl)methyl]amino}-N-methylcarboxamide |
| 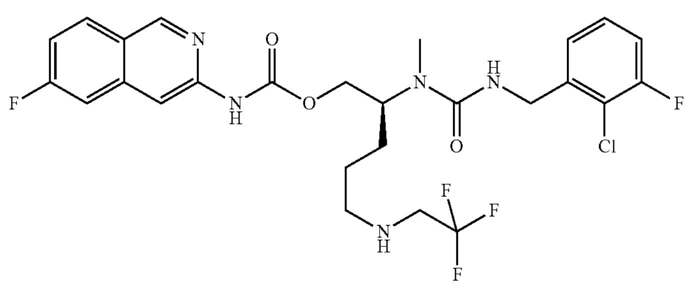 [SMILES: CN(C(=O)NCc1cccc(F)c1Cl)[C@@H](CCCNCC(F)(F)F)COC(=O)Nc1cc2cc(F)ccc2cn1] | N-((1S)-1-{[N-(6-fluoro(3-isoquinolyl))carbamoyloxy]methyl}-4-[(2,2,2-trifluoroethyl)amino]butyl){[(2-chloro-3-fluorophenyl)methyl]amino}-N-methylcarboxamide |

-continued

| Structure | Chemical Name |
|---|---|
| 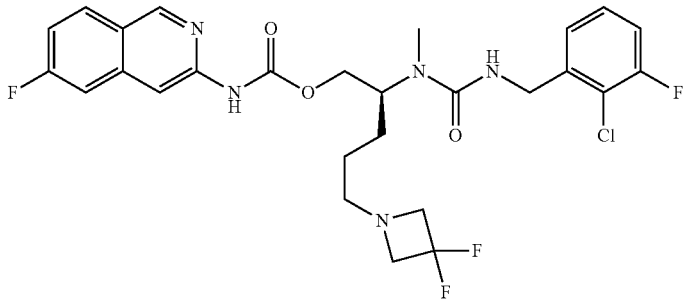 [SMILES: CN(C(=O)NCc1cccc(F)c1Cl)[C@@H](CCCN1CC(F)(F)C1)COC(=O)Nc1cc2cc(F)ccc2cn1] | N-((1S)-4-(3,3-difluoroazetidinyl)-1-{[N-(6-fluoro(3-isoquinolyl))carbamoyloxy]methyl}butyl){[(2-chloro-3-fluorophenyl)methyl]amino}-N-methylcarboxamide |
| 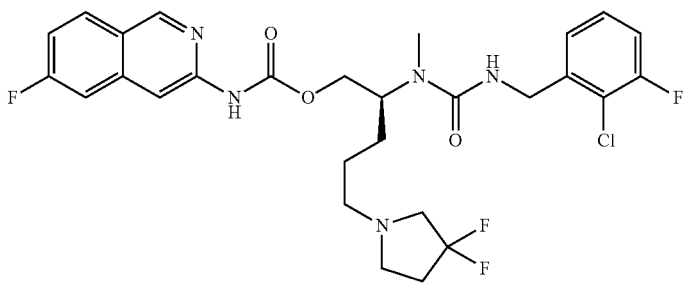 [SMILES: CN(C(=O)NCc1cccc(F)c1Cl)[C@@H](CCCN1CCC(F)(F)C1)COC(=O)Nc1cc2cc(F)ccc2cn1] | N-((1S)-4-(3,3-difluoropyrrolidinyl)-1-{[N-(6-fluoro(3-isoquinolyl))carbamoyloxy]methyl}butyl){[(2-chloro-3-fluorophenyl)methyl]amino}-N-methylcarboxamide |
| 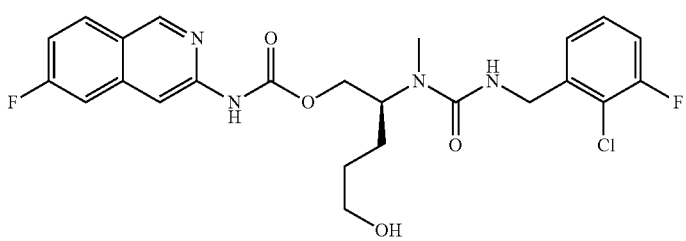 [SMILES: CN(C(=O)NCc1cccc(F)c1Cl)[C@@H](CCCO)COC(=O)Nc1cc2cc(F)ccc2cn1] | N-((1S)-1-{[N-(6-fluoro(3-isoquinolyl))carbamoyloxy]methyl}-4-hydroxybutyl){[(2-chloro-3-fluorophenyl)methyl]amino}-N-methylcarboxamide |
| 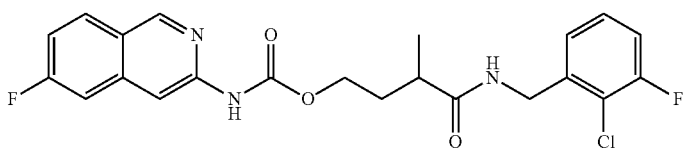 [SMILES: CC(CCOC(=O)Nc1cc2cc(F)ccc2cn1)C(=O)NCc1cccc(F)c1Cl] | N-[(2-chloro-3-fluorophenyl)methyl]-4-[N-(6-fluoro(3-isoquinolyl))carbamoyloxy]-2-methylbutanamide |
| 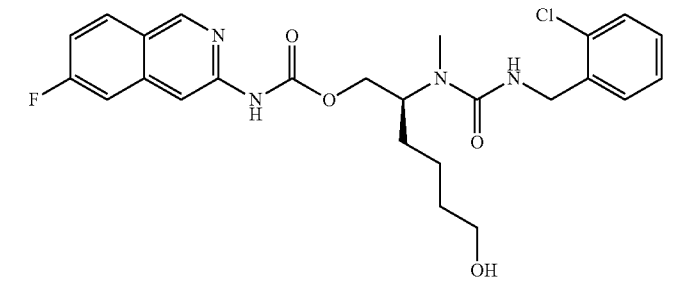 [SMILES: CN(C(=O)NCc1ccccc1Cl)[C@@H](CCCCO)COC(=O)Nc1cc2cc(F)ccc2cn1] | N-((1S)-1-{[N-(6-fluoro(3-isoquinolyl))carbamoyloxy]methyl}-5-hydroxypentyl){[(2-chlorophenyl)methyl]amino}-N-methylcarboxamide |
| 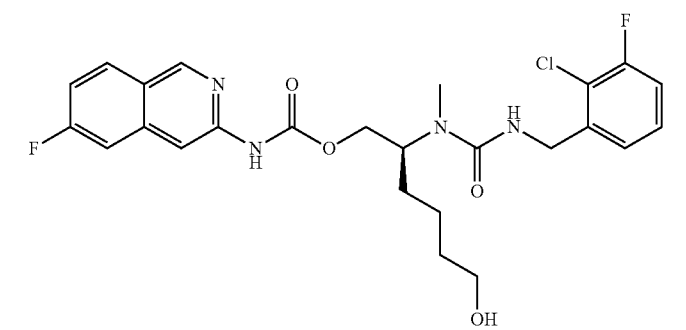 [SMILES: CN(C(=O)NCc1cccc(F)c1Cl)[C@@H](CCCCO)COC(=O)Nc1cc2cc(F)ccc2cn1] | N-((1S)-1-{[N-(6-fluoro(3-isoquinolyl))carbamoyloxy]methyl}-5-hydroxypentyl){[(2-chloro-3-fluorophenyl)methyl]amino}-N-methylcarboxamide |

-continued

| Structure | Chemical Name |
|---|---|
| 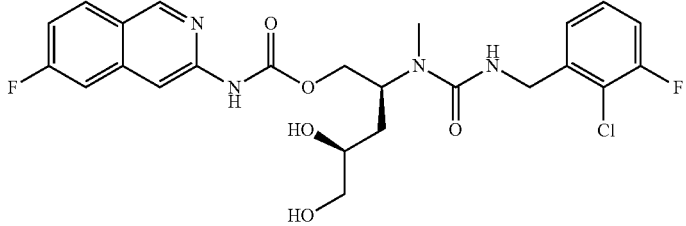 | N-((1S,3S)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 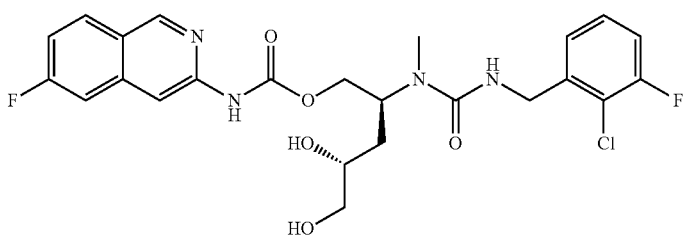 [SMILES: CN(C(=O)NCc1cccc(F)c1Cl)[C@H](COC(=O)Nc1cc2cc(F)ccc2cn1)C[C@@H](O)CO] | N-((1S,3R)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 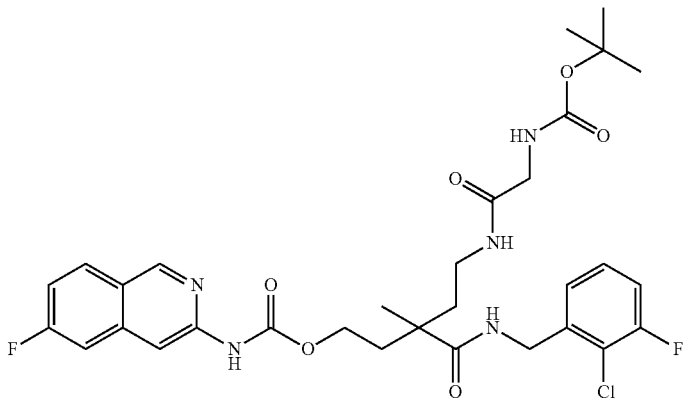 [SMILES: CC(C)(C)OC(=O)NCC(=O)NCCC(C)(CCOC(=O)Nc1cc2cc(F)ccc2cn1)C(=O)NCc1cccc(F)c1Cl] | 4-{2-[(tert-butoxy)carbonylamino]acetylamino}-N-[(2-chloro-3-fluorophenyl)methyl]-2-{2-[N-(6-fluoro(3-isoquinolyl))carbamoyloxy]ethyl}-2-methylbutanamide |
| 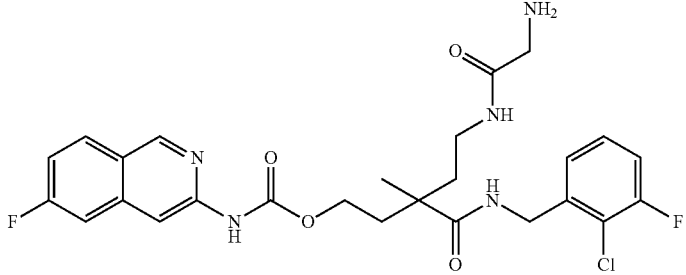 [SMILES: CC(CCNC(=O)CN)(CCOC(=O)Nc1cc2cc(F)ccc2cn1)C(=O)NCc1cccc(F)c1Cl] | 4-(2-aminoacetylamino)-N-[(2-chloro-3-fluorophenyl)methyl]-2-{2-[N-(6-fluoro(3-isoquinolyl))carbamoyloxy]ethyl}-2-methylbutanamide |
| 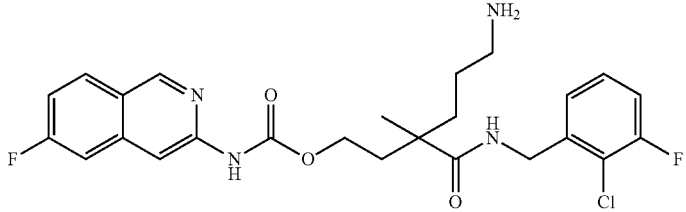 [SMILES: CC(CCCN)(CCOC(=O)Nc1cc2cc(F)ccc2cn1)C(=O)NCc1cccc(F)c1Cl] | 5-amino-N-[(2-chloro-3-fluorophenyl)methyl]-2-{2-[N-(6-fluoro(3-isoquinolyl))carbamoyloxy]ethyl}-2-methylpentanamide |

-continued

| Structure | Chemical Name |
|---|---|
| 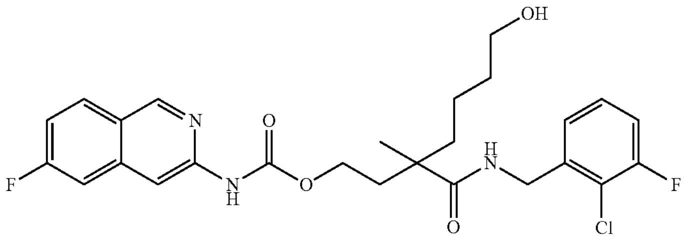 [SMILES: CC(CCCCO)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-6-hydroxy-2-methylhexanamide |
| 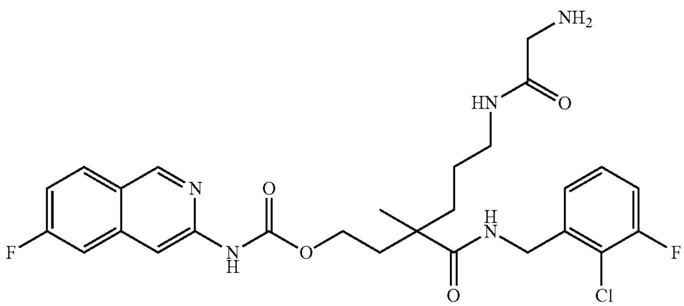 [SMILES: CC(CCCNC(=O)CN)(CCOC(=O)Nc1cc2cc(F)ccc2cn1)C(=O)NCc1cccc(F)c1Cl] | 5-(2-aminoacetylamino)-N-[(2-chloro-3-fluorophenyl)methyl]-2-{2-[N-(6-fluoro(3-isoquinolyl))carbamoyloxy]ethyl}-2-methylpentanamide |
| 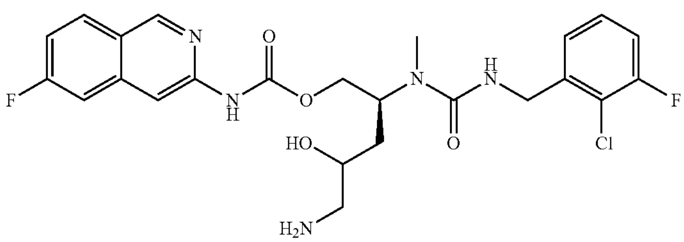 | N-((1S)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 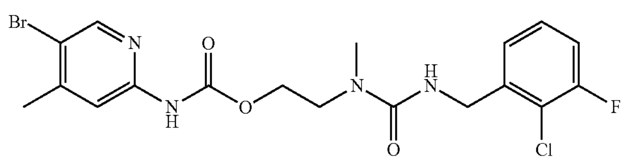 [SMILES: Cc1cc(NC(=O)OCCN(C)C(=O)NCc2cccc(F)c2Cl)ncc1Br] | N-{2-[N-(5-bromo-4-methyl(2-pyridyl))carbamoyloxy]ethyl}{[(2-chloro-3-fluorophenyl)methyl]amino}-N-methylcarboxamide |
| 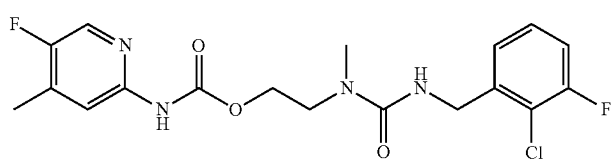 [SMILES: Cc1cc(NC(=O)OCCN(C)C(=O)NCc2cccc(F)c2Cl)ncc1F] | {[(2-chloro-3-fluorophenyl)methyl]amino}-N-{2-[N-(5-fluoro-4-methyl(2-pyridyl))carbamoyloxy]ethyl}-N-methylcarboxamide |
| 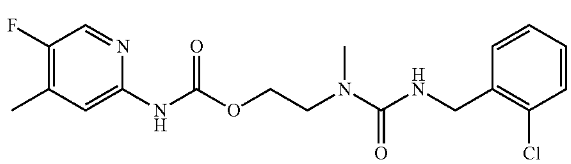 [SMILES: Cc1cc(NC(=O)OCCN(C)C(=O)NCc2ccccc2Cl)ncc1F] | {[(2-chlorophenyl)methyl]amino}-N-{2-[N-(5-fluoro-4-methyl(2-pyridyl))carbamoyloxy]ethyl}-N-methylcarboxamide |
| 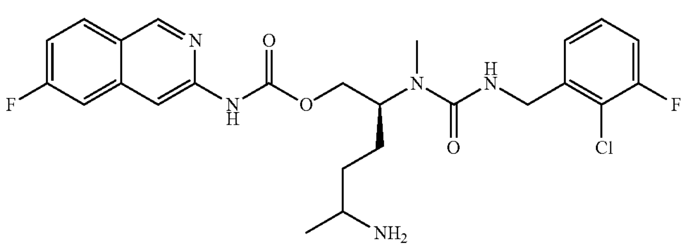 [SMILES: CC(N)CC[C@@H](COC(=O)Nc1cc2cc(F)ccc2cn1)N(C)C(=O)NCc1cccc(F)c1Cl] | N-((1S)-4-amino-1-{[N-(6-fluoro(3-isoquinolyl))carbamoyloxy]methyl}pentyl){[(2-chloro-3-fluorophenyl)methyl]amino}-N-methylcarboxamide |

-continued

| Structure | Chemical Name |
|---|---|
| 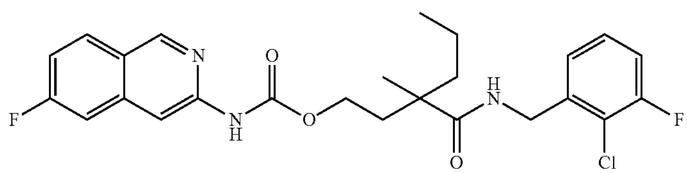 [SMILES: CCCC(C)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-2-methylpentanamide |
| 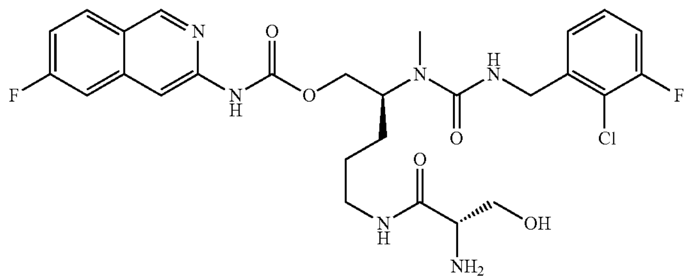 [SMILES: CN(C(=O)NCc1cccc(F)c1Cl)[C@@H](CCCNC(=O)[C@@H](N)CO)COC(=O)Nc1cc2cc(F)ccc2cn1] | (2S)-N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-amino-3-hydroxypropanamide |
| 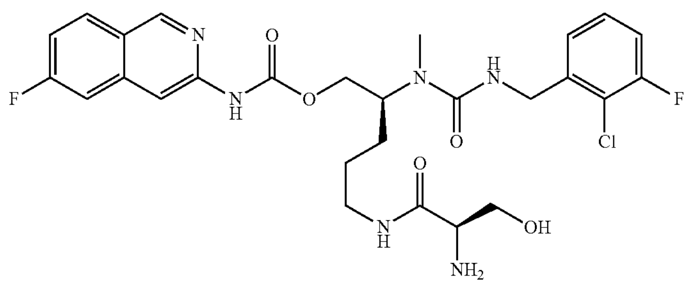 [SMILES: CN(C(=O)NCc1cccc(F)c1Cl)[C@@H](CCCNC(=O)[C@H](N)CO)COC(=O)Nc1cc2cc(F)ccc2cn1] | (2R)-N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-amino-3-hydroxypropanamide |
| 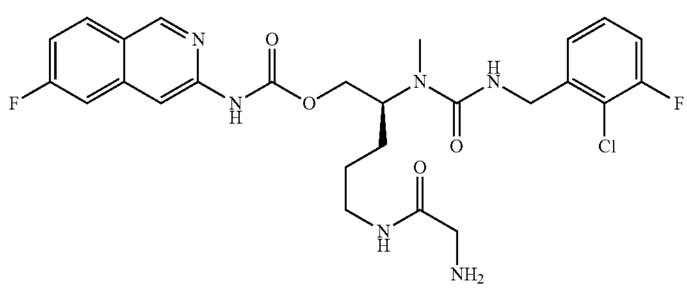 [SMILES: CN(C(=O)NCc1cccc(F)c1Cl)[C@@H](CCCNC(=O)CN)COC(=O)Nc1cc2cc(F)ccc2cn1] | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-aminoacetamide |
| 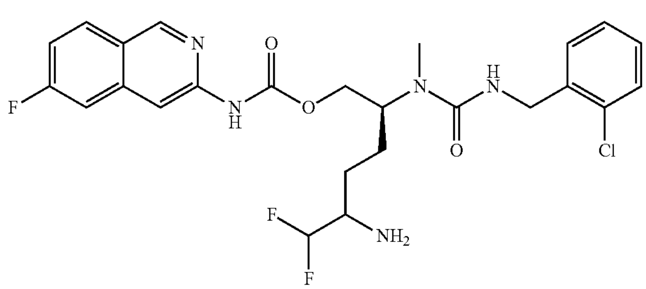 [SMILES: CN(C(=O)NCc1ccccc1Cl)[C@@H](CCC(N)C(F)F)COC(=O)Nc1cc2cc(F)ccc2cn1] | N-((1S)-4-amino-5,5-difluoro-1-{[N-(6-fluoro(3-isoquinolyl))carbamoyloxy]methyl}pentyl){[(2-chlorophenyl)methyl]amino}-N-methylcarboxamide |
| 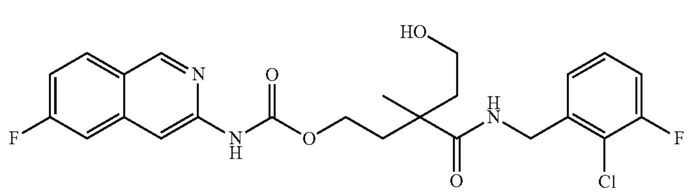 [SMILES: CC(CCO)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-4-hydroxy-2-methylbutanamide |

| Structure | Chemical Name |
|---|---|
| 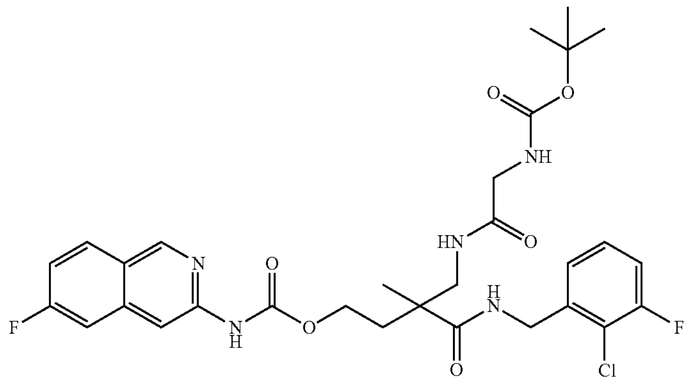 [SMILES: CC(C)(C)OC(=O)NCC(=O)NCC(C)(CCOC(=O)Nc1cc2cc(F)ccc2cn1)C(=O)NCc1cccc(F)c1Cl] | 2-({2-[(tert-butoxy)carbonylamino]acetylamino}methyl)-N-[(2-chloro-3-fluorophenyl)methyl]-4-[N-(6-fluoro(3-isoquinolyl))carbamoyloxy]-2-methylbutanamide |
| 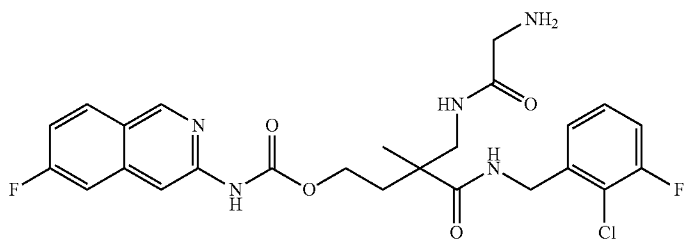 [SMILES: CC(CCOC(=O)Nc1cc2cc(F)ccc2cn1)(CNC(=O)CN)C(=O)NCc1cccc(F)c1Cl] | 2-[(2-aminoacetylamino)methyl]-N-[(2-chloro-3-fluorophenyl)methyl]-4-[N-(6-fluoro(3-isoquinolyl))carbamoyloxy]-2-methylbutanamide |
| 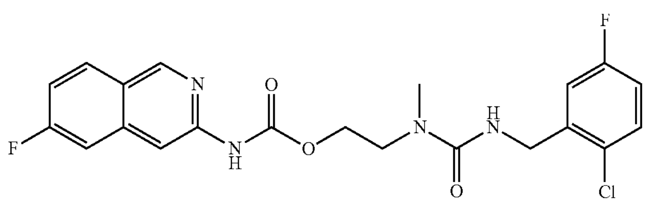 [SMILES: CN(CCOC(=O)Nc1cc2cc(F)ccc2cn1)C(=O)NCc1cc(F)ccc1Cl] | {[(2-chloro-5-fluorophenyl)methyl]amino}-N-{2-[N-(6-fluoro(3-isoquinolyl))carbamoyloxy]ethyl}-N-methylcarboxamide |
| 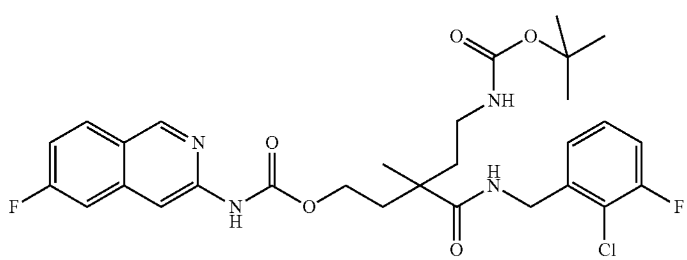 [SMILES: CC(C)(C)OC(=O)NCCC(C)(CCOC(=O)Nc1cc2cc(F)ccc2cn1)C(=O)NCc1cccc(F)c1Cl] | 2-{2-[(tert-butoxy)carbonylamino]ethyl}-N-[(2-chloro-3-fluorophenyl)methyl]-4-[N-(6-fluoro(3-isoquinolyl))carbamoyloxy]-2-methylbutanamide |
| 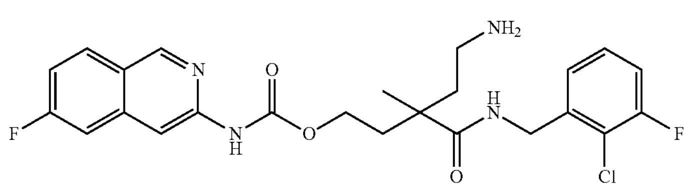 [SMILES: CC(CCN)(CCOC(=O)Nc1cc2cc(F)ccc2cn1)C(=O)NCc1cccc(F)c1Cl] | 4-amino-N-[(2-chloro-3-fluorophenyl)methyl]-2-{2-[N-(6-fluoro(3-isoquinolyl))carbamoyloxy]ethyl}-2-methylbutanamide |
| 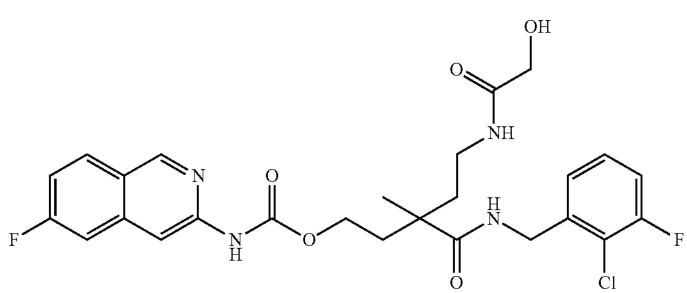 [SMILES: CC(CCNC(=O)CO)(CCOC(=O)Nc1cc2cc(F)ccc2cn1)C(=O)NCc1cccc(F)c1Cl] | N-[(2-chloro-3-fluorophenyl)methyl]-2-{2-[N-(6-fluoro(3-isoquinolyl))carbamoyloxy]ethyl}-4-(2-hydroxyacetylamino)-2-methylbutanamide |

-continued

| Structure | Chemical Name |
|---|---|
| 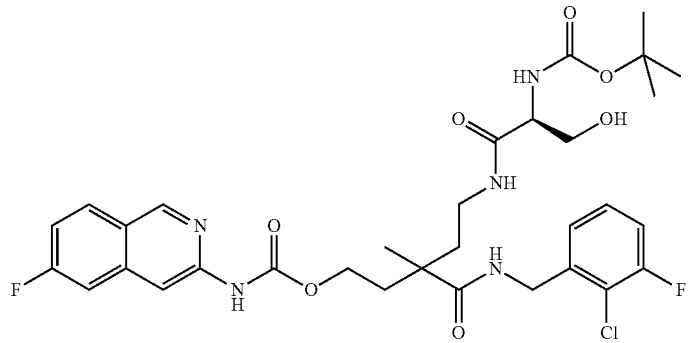 [SMILES: CC(C)(C)OC(=O)N[C@@H](CO)C(=O)NCCC(C)(CCOC(=O)Nc1cc2cc(F)ccc2cn1)C(=O)NCc1cccc(F)c1Cl] | 4-{(2S)-2-[(tert-butoxy)carbonylamino]-3-hydroxypropanoylamino}-N-[(2-chloro-3-fluorophenyl)methyl]-2-{2-[N-(6-fluoro(3-isoquinolyl))carbamoyloxy]ethyl}-2-methylbutanamide |
| 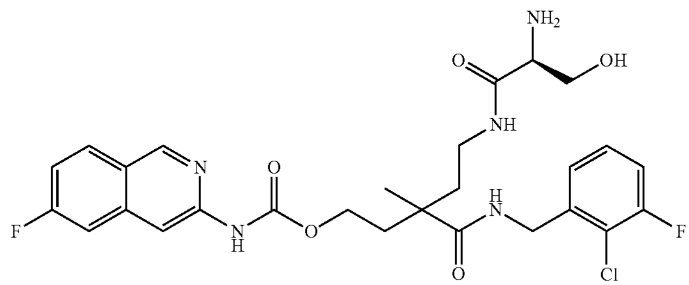 [SMILES: CC(CCNC(=O)[C@@H](N)CO)(CCOC(=O)Nc1cc2cc(F)ccc2cn1)C(=O)NCc1cccc(F)c1Cl] | 4-((2S)-2-amino-3-hydroxypropanoylamino)-N-[(2-chloro-3-fluorophenyl)methyl]-2-{2-[N-(6-fluoro(3-isoquinolyl))carbamoyloxy]ethyl}-2-methylbutanamide |
| 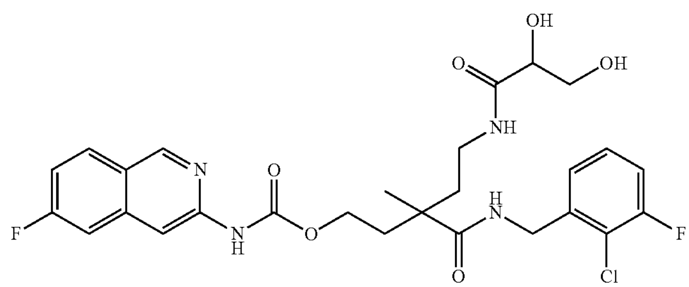 [SMILES: CC(CCNC(=O)C(O)CO)(CCOC(=O)Nc1cc2cc(F)ccc2cn1)C(=O)NCc1cccc(F)c1Cl] | 4-(2,3-dihydroxypropanoylamino)-N-[(2-chloro-3-fluorophenyl)methyl]-2-{2-[N-(6-fluoro(3-isoquinolyl))carbamoyloxy]ethyl}-2-methylbutanamide |
| 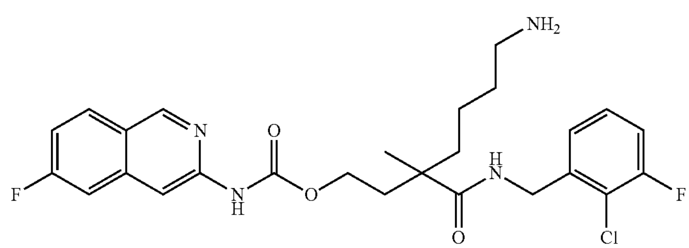 [SMILES: CC(CCCCN)(CCOC(=O)Nc1cc2cc(F)ccc2cn1)C(=O)NCc1cccc(F)c1Cl] | 6-amino-N-[(2-chloro-3-fluorophenyl)methyl]-2-{2-[N-(6-fluoro(3-isoquinolyl))carbamoyloxy]ethyl}-2-methylhexanamide |
| 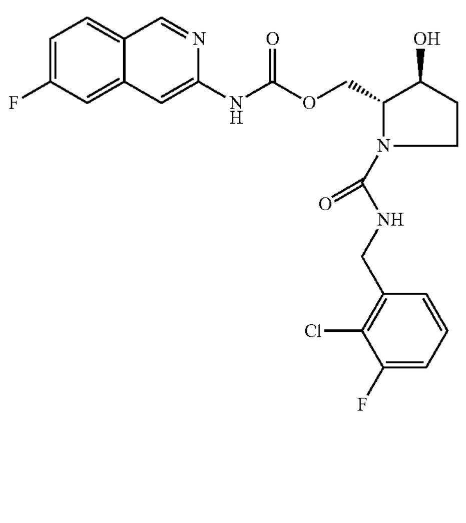 [SMILES: O=C(Nc1cc2cc(F)ccc2cn1)OC[C@@H]1[C@@H](O)CCN1C(=O)NCc1cccc(F)c1Cl] | [((2R,3R)-1-{N-[(2-chloro-3-fluorophenyl)methyl]carbamoyl}-3-hydroxypyrrolidin-2-yl)methoxy]-N-(6-fluoro(3-isoquinolyl))carboxamide |

-continued

| Structure | Chemical Name |
|---|---|
| 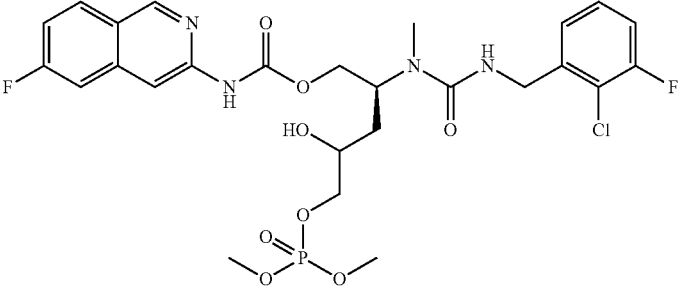 [SMILES: COP(=O)(OC)OCC(O)C[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dimethyl phosphate |
| 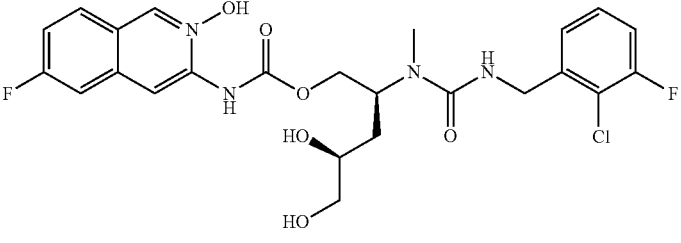 | N-((1S,3S)-1-{[N-(6-fluoro-2-hydroxy(3-isoquinolyl))carbamoyloxy]methyl}-3,4-dihydroxybutyl){[(2-chloro-3-fluorophenyl)methyl]amino}-N-methylcarboxamide |
| 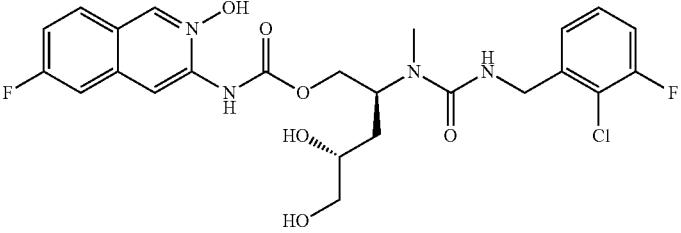 | N-((1S,3R)-1-[N-(6-fluoro-2-hydroxy(3-isoquinolyl))carbamoyloxy]methyl}-3,4-dihydroxybutyl){[(2-chloro-3-fluorophenyl)methyl]amino}-N-methylcarboxamide |
| 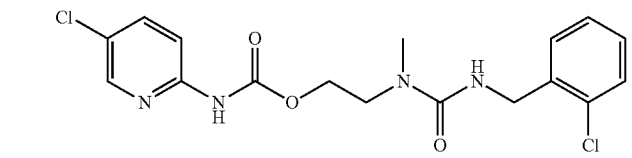 [SMILES: CN(CCOC(=O)Nc1ccc(Cl)cn1)C(=O)NCc1ccccc1Cl] | N-[2-[N-(5-chloro(2-pyridyl))carbamoyloxy]ethyl]{[(2-chlorophenyl)methyl]amino}-N-methylcarboxamide |
| 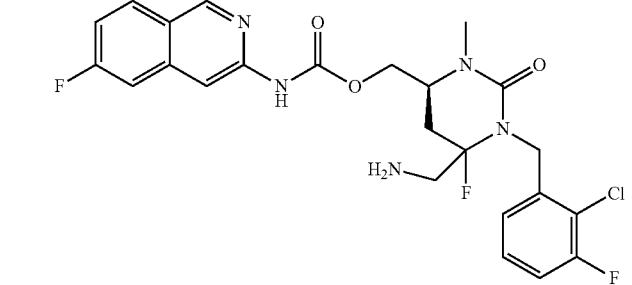 | ({(4S)-6-(aminomethyl)-1-[(2-chloro-3-fluorophenyl)methyl]-6-fluoro-3-methyl-2-oxo(1,3-diazaperhydroin-4-yl)}methoxy)-N-(6-fluoro(3-isoquinolyl))carboxamide |
| 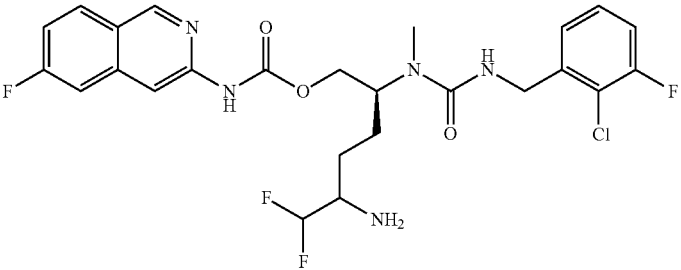 [SMILES: CN(C(=O)NCc1cccc(F)c1Cl)[C@@H](CCC(N)C(F)F)COC(=O)Nc1cc2cc(F)ccc2cn1] | N-((1S)-4-amino-5,5-difluoro-1-{[N-(6-fluoro(3-isoquinolyl))carbamoyloxy]methyl}pentyl){[(2-chloro-3-fluorophenyl)methyl]amino}-N-methylcarboxamide |

-continued

| Structure | Chemical Name |
|---|---|
| 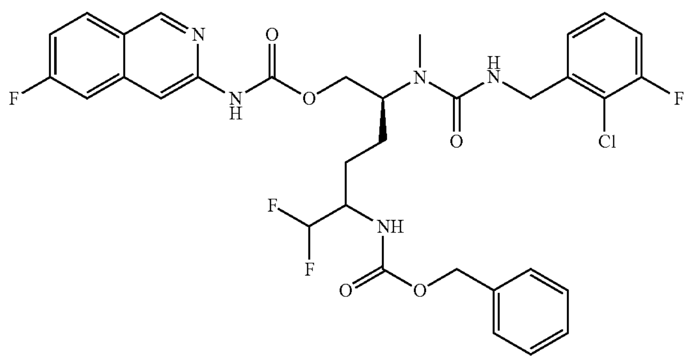 [SMILES: CN(C(=O)NCc1cccc(F)c1Cl)[C@@H](CCC(NC(=O)OCc1ccccc1)C(F)F)COC(=O)Nc1cc2cc(F)ccc2cn1] | N-((1S)-5,5-difluoro-1-{[N-(6-fluoro(3-isoquinolyl))carbamoyloxy]methyl}-4-[(phenylmethoxy)carbonylamino]pentyl){[(2-chloro-3-fluorophenyl)methyl]amino}-N-methylcarboxamide |
| 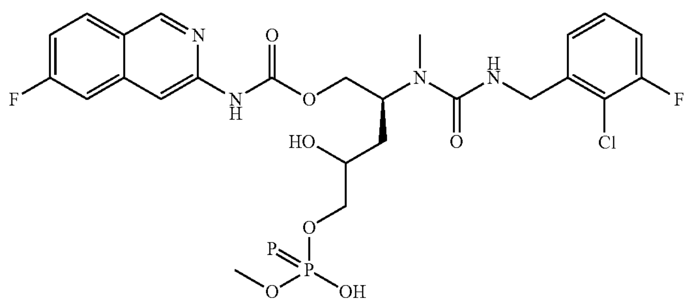 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl hydrogen methyl phosphate |
| 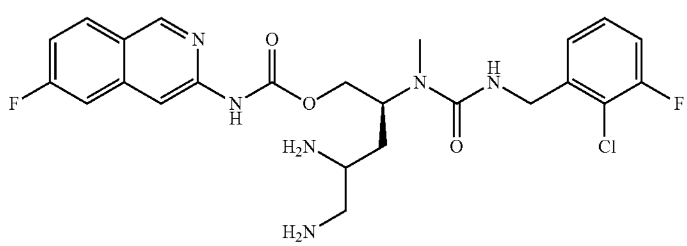 [SMILES: CN(C(=O)NCc1cccc(F)c1Cl)[C@H](COC(=O)Nc1cc2cc(F)ccc2cn1)CC(N)CN] | N-((1S)-3,4-diamino-1-{[N-(6-fluoro(3-isoquinolyl))carbamoyloxy]methyl}butyl){[(2-chloro-3-fluorophenyl)methyl]amino}-N-methylcarboxamide |
| 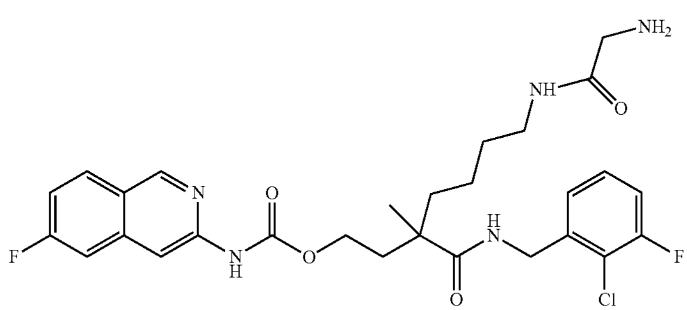 [SMILES: CC(CCCCNC(=O)CN)(CCOC(=O)Nc1cc2cc(F)ccc2cn1)C(=O)NCc1cccc(F)c1Cl] | 6-(2-aminoacetylamino)-N-[(2-chloro-3-fluorophenyl)methyl]-2-{2-[N-(6-fluoro(3-isoquinolyl))carbamoyloxy]ethyl}-2-methylhexanamide |
| 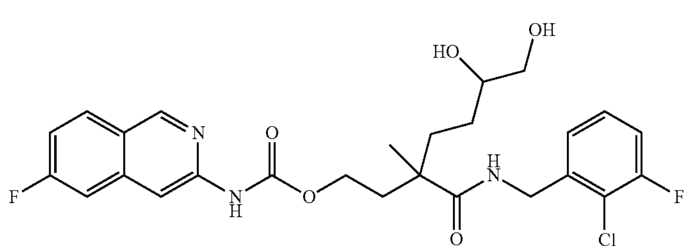 [SMILES: CC(CCOC(=O)Nc1cc2cc(F)ccc2cn1)(CCC(O)CO)C(=O)NCc1cccc(F)c1Cl] | N-[(2-chloro-3-fluorophenyl)methyl]-2-{2-[N-(6-fluoro(3-isoquinolyl))carbamoyloxy]ethyl}-5,6-dihydroxy-2-methylhexanamide |

-continued

| Structure | Chemical Name |
|---|---|
| 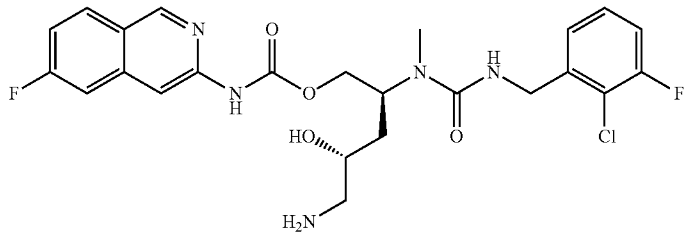 [SMILES: CN(C(=O)NCc1cccc(F)c1Cl)[C@H](COC(=O)Nc1cc2cc(F)ccc2cn1)C[C@@H](O)CN] | N-((1S,3R)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 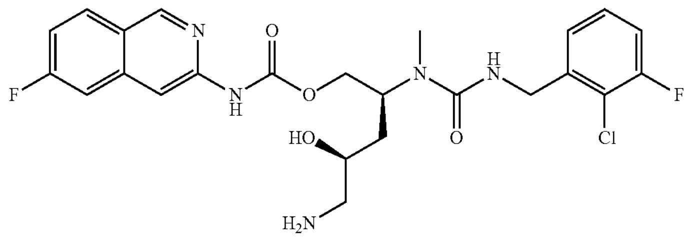 [SMILES: CN(C(=O)NCc1cccc(F)c1Cl)[C@H](COC(=O)Nc1cc2cc(F)ccc2cn1)C[C@H](O)CN] | N-((1S,3S)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 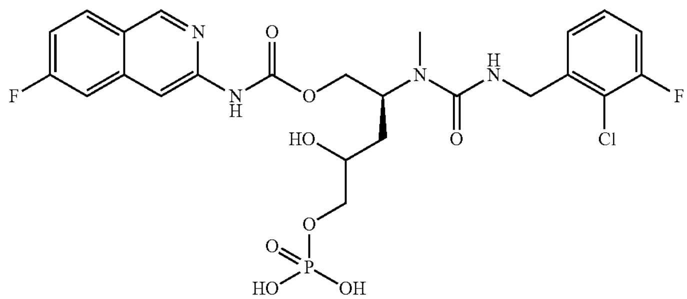 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 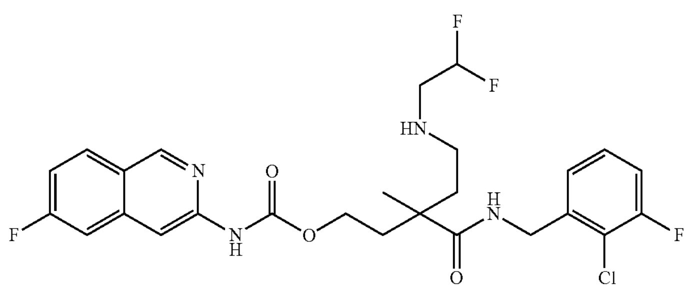 [SMILES: CC(CCNCC(F)F)(CCOC(=O)Nc1cc2cc(F)ccc2cn1)C(=O)NCc1cccc(F)c1Cl] | 2-{2-[(2,2-difluoroethyl)amino]ethyl}-N-[(2-chloro-3-fluorophenyl)methyl]-4-[N-(6-fluoro(3-isoquinolyl))carbamoyloxy]-2-methylbutanamide |
| 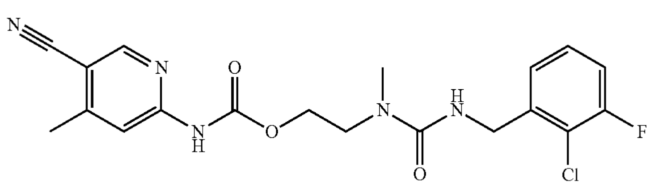 [SMILES: Cc1cc(NC(=O)OCCN(C)C(=O)NCc2cccc(F)c2Cl)ncc1C#N] | {[(2-chloro-3-fluorophenyl)methyl]amino}-N-{2-[N-(5-cyano-4-methyl(2-pyridyl))carbamoyloxy]ethyl}-N-methylcarboxamide |
| 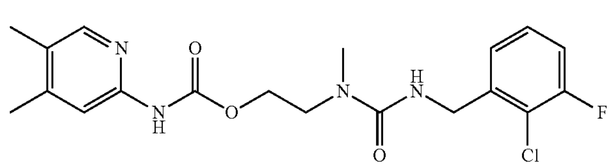 [SMILES: Cc1cnc(NC(=O)OCCN(C)C(=O)NCc2cccc(F)c2Cl)cc1C] | N-{2-[N-(4,5-dimethy(2-pyridyl))carbamoyloxy]ethyl}{[(2-chloro-3-fluorophenyl)methyl]amino}-N-methylcarboxamide |
| 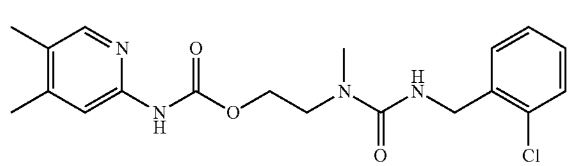 [SMILES: Cc1cnc(NC(=O)OCCN(C)C(=O)NCc2ccccc2Cl)cc1C] | N-{2-[N-(4,5-dimethyl(2-pyridyl))carbamoyloxy]ethyl}{[(2-chlorophenyl)methyl]amino}-N-methylcarboxamide |

| Structure | Chemical Name |
|---|---|
| 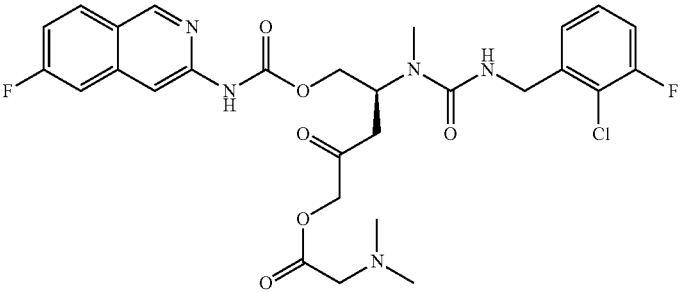 [SMILES: CN(C)CC(=O)OCC(=O)C[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl 2-(dimethylamino)acetate |
| 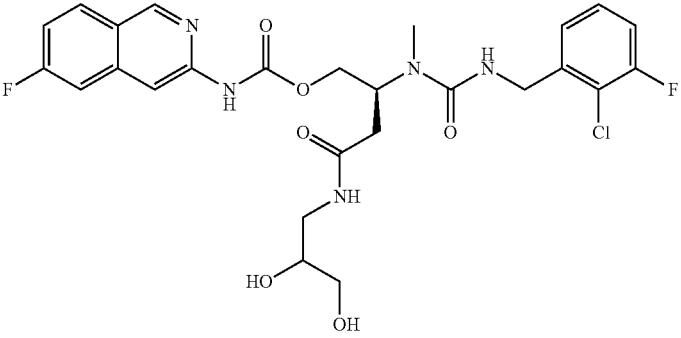 [SMILES: CN(C(=O)NCc1cccc(F)c1Cl)[C@H](COC(=O)Nc1cc2cc(F)ccc2cn1)CC(=O)NCC(O)CO] | (3S)-N-(2,3-dihydroxypropyl)-3-({[(2-chloro-3-fluorophenyl)methyl]amino}-N-methylcarbonylamino)-4-[N-(6-fluoro(3-isoquinolyl))carbamoyloxy]butanamide |
| 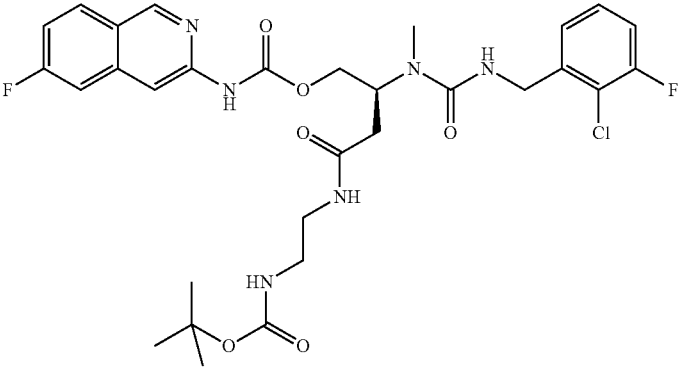 [SMILES: CN(C(=O)NCc1cccc(F)c1Cl)[C@H](COC(=O)Nc1cc2cc(F)ccc2cn1)CC(=O)NCCNC(=O)OC(C)(C)C] | (3S)-N-{2-[(tert-butoxy)carbonylamino]ethyl}-3-({[(2-chloro-3-fluorophenyl)methyl]amino}-N-methylcarbonylamino)-4-[N-(6-fluoro(3-isoquinolyl))carbamoyloxy]butanamide |
| 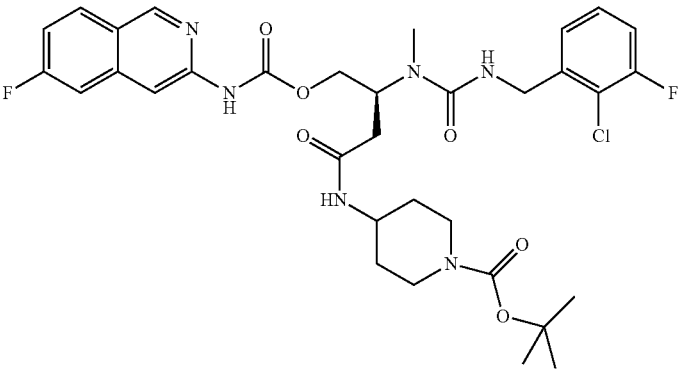 [SMILES: CN(C(=O)NCc1cccc(F)c1Cl)[C@H](COC(=O)Nc1cc2cc(F)ccc2cn1)CC(=O)NC1CCN(C(=O)OC(C)(C)C)CC1] | tert-butyl 4-[(3S)-3-({[(2-chloro-3-fluorophenyl)methyl]amino}-N-methylcarbonylamino)-4-[N-(6-fluoro(3-isoquinolyl))carbamoyloxy]butanoylamino]piperidinecarboxylate |

-continued

| Structure | Chemical Name |
|---|---|
| 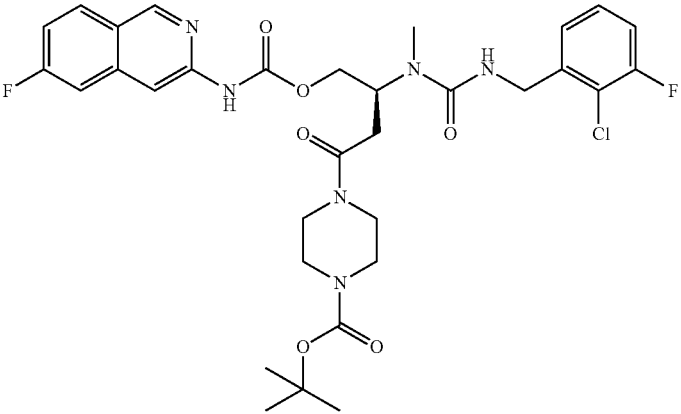 [SMILES: CN(C(=O)NCc1cccc(F)c1Cl)[C@H](COC(=O)Nc1cc2cc(F)ccc2cn1)CC(=O)N1CCN(C(=O)OC(C)(C)C)CC1] | tert-butyl 4-[(3S)-3-({[(2-chloro-3-fluorophenyl)methyl]amino}-N-methylcarbonylamino)-4-[N-(6-fluoro(3-isoquinolyl))carbamoyloxy]butanoyl]piperazinecarboxylate |
| 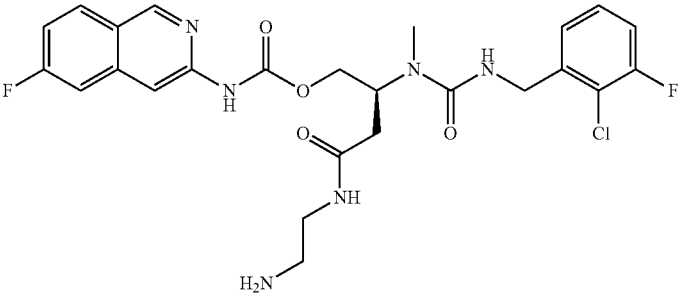 [SMILES: CN(C(=O)NCc1cccc(F)c1Cl)[C@H](COC(=O)Nc1cc2cc(F)ccc2cn1)CC(=O)NCCN] | (3S)-N-(2-aminoethyl)-3-({[(2-chloro-3-fluorophenyl)methyl]amino}-N-methylcarbonylamino)-4-[N-(6-fluoro(3-isoquinolyl))carbamoyloxy]butanamide |
| 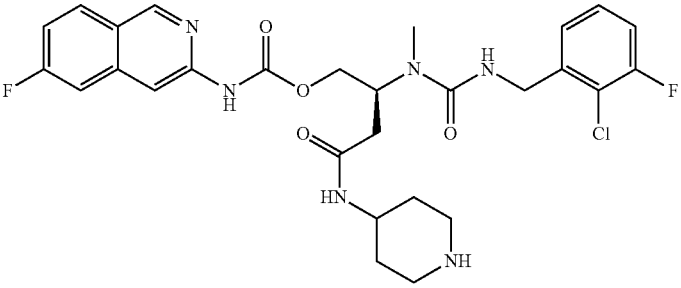 [SMILES: CN(C(=O)NCc1cccc(F)c1Cl)[C@H](COC(=O)Nc1cc2cc(F)ccc2cn1)CC(=O)NC1CCNCC1] | (3S)-3-({[(2-chloro-3-fluorophenyl)methyl]amino}-N-methylcarbonylamino)-4-[N-(6-fluoro(3-isoquinolyl))carbamoyloxy]-N-(4-piperidyl)butanamide |
| 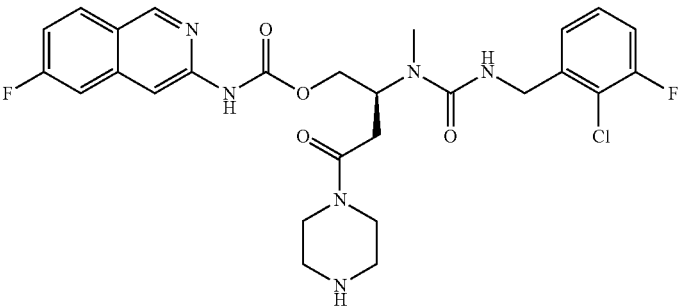 [SMILES: CN(C(=O)NCc1cccc(F)c1Cl)[C@H](COC(=O)Nc1cc2cc(F)ccc2cn1)CC(=O)N1CCNCC1] | [(2S)-2-({[(2-chloro-3-fluorophenyl)methyl]amino}-N-methylcarbonylamino)-4-oxo-4-piperazinylbutoxy]-N-(6-fluoro(3-isoquinolyl))carboxamide |

-continued

| Structure | Chemical Name |
|---|---|
| 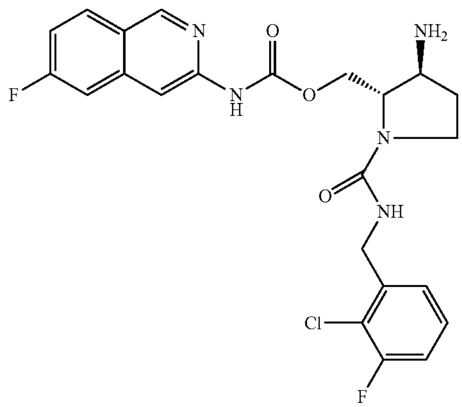 [SMILES: N[C@H]1CCN(C(=O)NCc2cccc(F)c2Cl)[C@@H]1COC(=O)Nc1cc2cc(F)ccc2cn1] | [((2S,3S)-3-amino-1-{N-[(2-chloro-3-fluorophenyl)methyl]carbamoyl}pyrrolidin-2-yl)methoxy]-N-(6-fluoro(3-isoquinolyl))carboxamide |
| 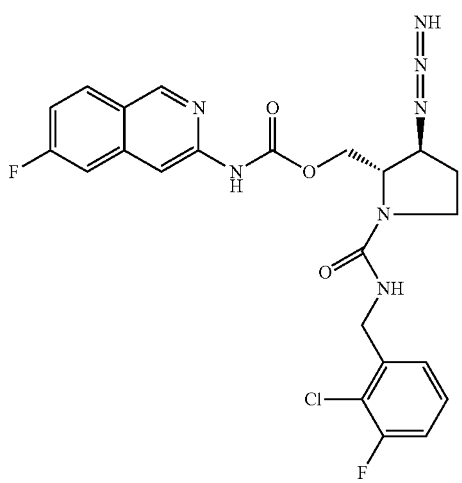 | [((2S,3S)-1-{N-[(2-chloro-3-fluorophenyl)methyl]carbamoyl}-3-(diazoazamvinyl)pyrrolidin-2-yl)methoxy]-N-(6-fluoro(3-isoquinolyl))carboxamide |
| 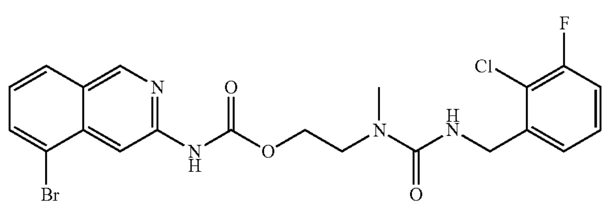 [SMILES: CN(CCOC(=O)Nc1cc2c(Br)cccc2cn1)C(=O)NCc1cccc(F)c1Cl] | N-{2-[N-(5-bromo(3-isoquinolyl))carbamoyloxy]ethyl}{[(2-chloro-3-fluorophenyl)methyl]amino}-N-methylcarboxamide |
| 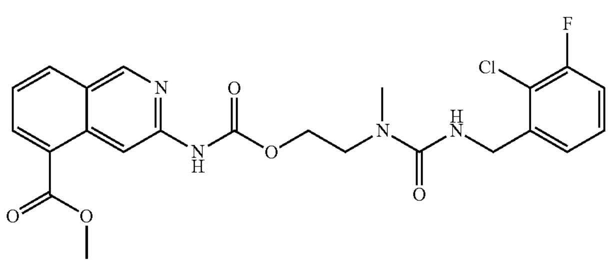 [SMILES: COC(=O)c1cccc2cnc(NC(=O)OCCN(C)C(=O)NCc3cccc(F)c3Cl)cc12] | methyl 3-{[2-({[(2-chloro-3-fluorophenyl)methyl]amino}-N-methylcarbonylamino)ethoxy]carbonylamino}isoquinoline-5-carboxylate |
| 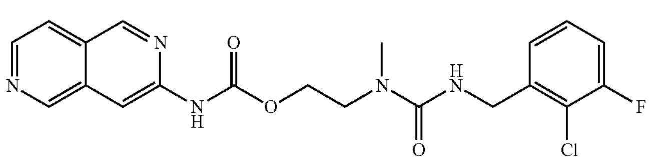 [SMILES: CN(CCOC(=O)Nc1cc2cnccc2cn1)C(=O)NCc1cccc(F)c1Cl] | {[(2-chloro-3-fluorophenyl)methyl]amino}-N-methyl-N-[2-(N-pyridino[3,4-d]pyridin-3-ylcarbamoyloxy)ethyl]carboxamide |

-continued

| Structure | Chemical Name |
|---|---|
| 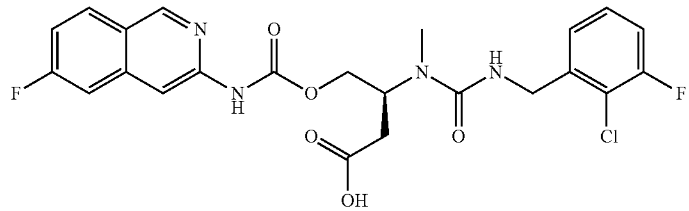 [SMILES: CN(C(=O)NCc1cccc(F)c1Cl)[C@H](COC(=O)Nc1cc2cc(F)ccc2cn1)CC(=O)O] | (3S)-3-({[(2-chloro-3-fluorophenyl)methyl]amino}-N-methylcarbonylamino)-4-[N-(6-fluoro(3-isoquinolyl))carbamoyloxy]butanoic acid |
| 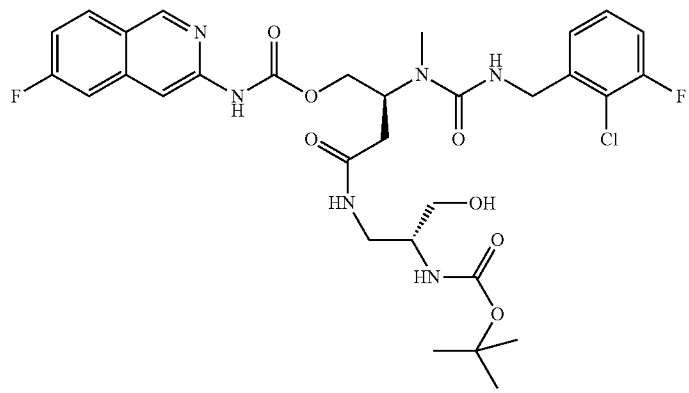 [SMILES: CN(C(=O)NCc1cccc(F)c1Cl)[C@H](COC(=O)Nc1cc2cc(F)ccc2cn1)CC(=O)NC[C@H](CO)NC(=O)OC(C)(C)C] | N-{(2R)-2-[(tert-butoxy)carbonylamino]-3-hydroxypropyl}(3S)-3-({[(2-chloro-3-fluorophenyl)methyl]amino}-N-methylcarbonylamino)-4-[N-(6-fluoro(3-isoquinolyl))carbamoyloxy]butanamide |
| 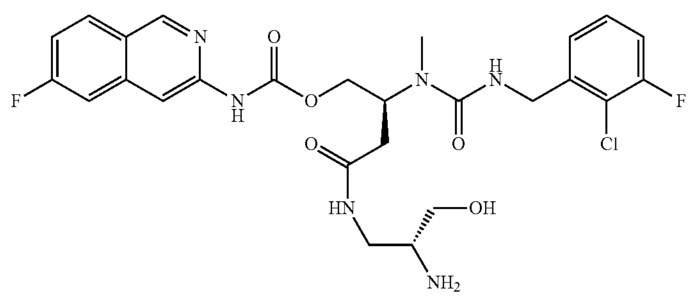 [SMILES: CN(C(=O)NCc1cccc(F)c1Cl)[C@H](COC(=O)Nc1cc2cc(F)ccc2cn1)CC(=O)NC[C@@H](N)CO] | N-((2R)-2-amino-3-hydroxypropyl)(3S)-3-({[(2-chloro-3-fluorophenyl)methyl]amino}-N-methylcarbonylamino)-4-[N-(6-fluoro(3-isoquinolyl))carbamoyloxy]butanamide |
| 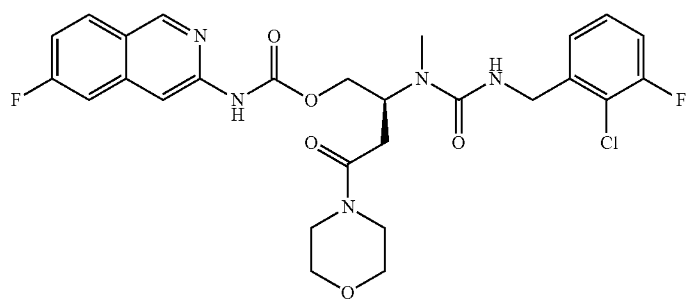 [SMILES: CN(C(=O)NCc1cccc(F)c1Cl)[C@H](COC(=O)Nc1cc2cc(F)ccc2cn1)CC(=O)N1CCOCC1] | [(2S)-2-({[(2-chloro-3-fluorophenyl)methyl]amino}-N-methylcarbonylamino)-4-morpholin-4-yl-4-oxobutoxy]-N-(6-fluoro(3-isoquinolyl))carboxamide |
| 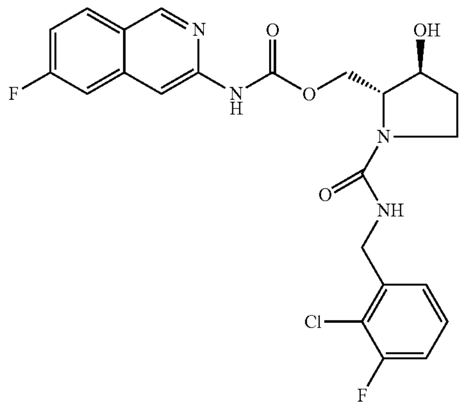 [SMILES: O=C(Nc1cc2cc(F)ccc2cn1)OC[C@@H]1[C@@H](O)CCN1C(=O)NCc1cccc(F)c1Cl] | [((3S,2R)-1-{N-[(2-chloro-3-fluorophenyl)methyl]carbamoyl}-3-hydroxypyrrolidin-2-yl)methoxy]-N-(6-fluoro(3-isoquinolyl))carboxamide |

-continued

| Structure | Chemical Name |
|---|---|
| 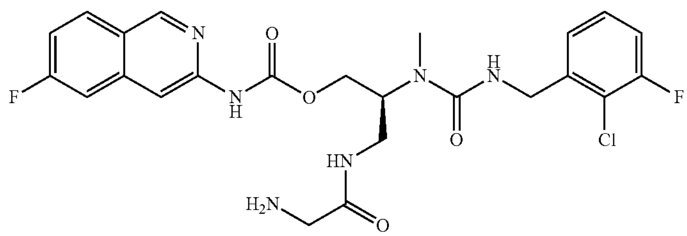 [SMILES: CN(C(=O)NCc1cccc(F)c1Cl)[C@@H](CNC(=O)CN)COC(=O)Nc1cc2cc(F)ccc2cn1] | N-[(2S)-2-({[(2-chloro-3-fluorophenyl)methyl]amino}-N-methylcarbonylamino)-3-[N-(6-fluoro(3-isoquinolyl))carbamoyloxy]propyl]-2-aminoacetamide |
| 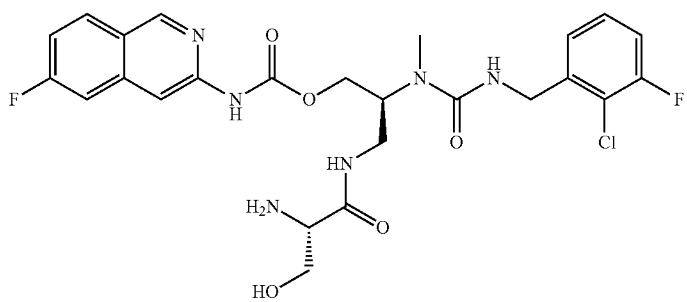 [SMILES: CN(C(=O)NCc1cccc(F)c1Cl)[C@@H](CNC(=O)[C@@H](N)CO)COC(=O)Nc1cc2cc(F)ccc2cn1] | (2S)-N-[(2S)-2-({[(2-chloro-3-fluorophenyl)methyl]amino}-N-methylcarbonylamino)-3-[N-(6-fluoro(3-isoquinolyl))carbamoyloxy]propyl]-2-amino-3-hydroxypropanamide |
| 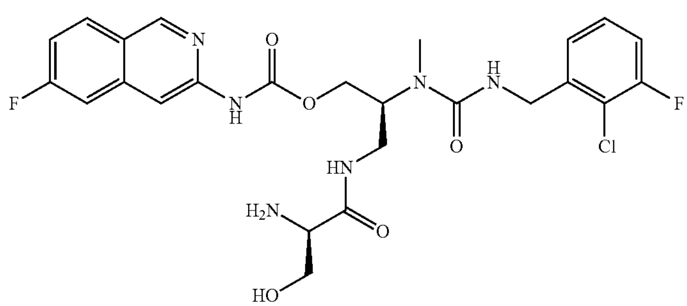 [SMILES: CN(C(=O)NCc1cccc(F)c1Cl)[C@@H](CNC(=O)[C@H](N)CO)COC(=O)Nc1cc2cc(F)ccc2cn1] | (2R)-N-[(2S)-2-({[(2-chloro-3-fluorophenyl)methyl]amino}-N-methylcarbonylamino)-3-[N-(6-fluoro(3-isoquinolyl))carbamoyloxy]propyl]-2-amino-3-hydroxypropanamide |
| 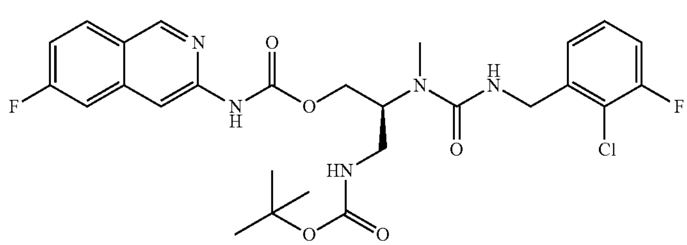 [SMILES: CN(C(=O)NCc1cccc(F)c1Cl)[C@@H](CNC(=O)OC(C)(C)C)COC(=O)Nc1cc2cc(F)ccc2cn1] | [(2S)-3-[(tert-butoxy)carbonylamino]-2-({[(2-chloro-3-fluorophenyl)methyl]amino}-N-methylcarbonylamino)propoxy]-N-(6-fluoro(3-isoquinolyl))carboxamide |
| 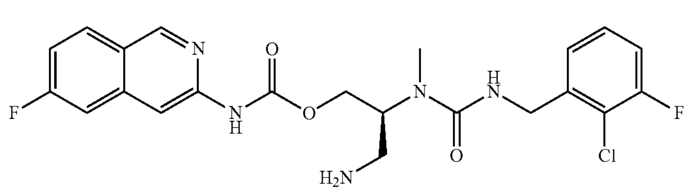 [SMILES: CN(C(=O)NCc1cccc(F)c1Cl)[C@@H](CN)COC(=O)Nc1cc2cc(F)ccc2cn1] | [(2S)-3-amino-2-({[(2-chloro-3-fluorophenyl)methyl]amino}-N-methylcarbonylamino)propoxy]-N-(6-fluoro(3-isoquinolyl))carboxamide |

| Structure | Chemical Name |
|---|---|
| 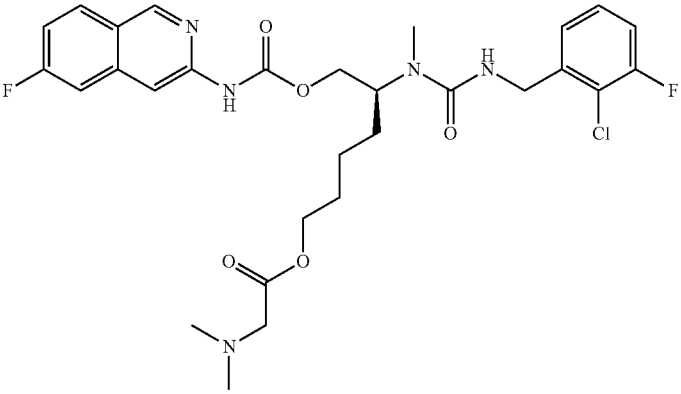 [SMILES: CN(C)CC(=O)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl 2-(dimethylamino)acetate |
| 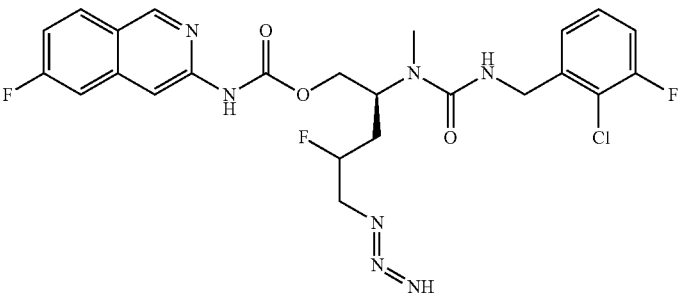 | N-((1S)-5-diazo-3-fluoro-1-{[N-(6-fluoro(3-isoquinolyl))carbamoyloxy]methyl}-5-azapent-5-enyl){[(2-chloro-3-fluorophenyl)methyl]amino}-N-methylcarboxamide |
| 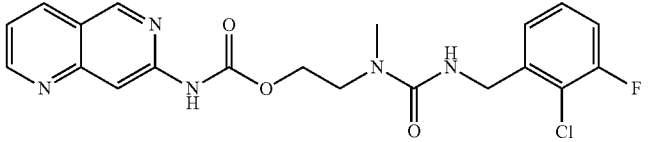 [SMILES: CN(CCOC(=O)Nc1cc2ncccc2cn1)C(=O)NCc1cccc(F)c1Cl] | {[(2-chloro-3-fluorophenyl)methyl]amino}-N-methyl-N-[2-(N-pyridino[2,3-d]pyridin-7-ylcarbamoyloxy)ethyl]carboxamide |
| 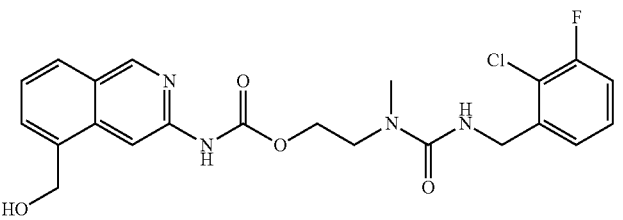 [SMILES: CN(CCOC(=O)Nc1cc2c(CO)cccc2cn1)C(=O)NCc1cccc(F)c1Cl] | {[(2-chloro-3-fluorophenyl)methyl]amino}-N-(2-{N-[5-(hydroxymethyl)(3-isoquinolyl)]carbamoyloxy}ethyl)-N-methylcarboxamide |
| 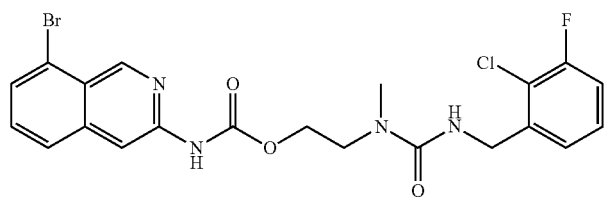 [SMILES: CN(CCOC(=O)Nc1cc2cccc(Br)c2cn1)C(=O)NCc1cccc(F)c1Cl] | N-{2-[N-(8-bromo(3-isoquinolyl))carbamoyloxylethyl]}{[(2-chloro-3-fluorophenyl)methyl]amino}-N-methylcarboxamide |
| 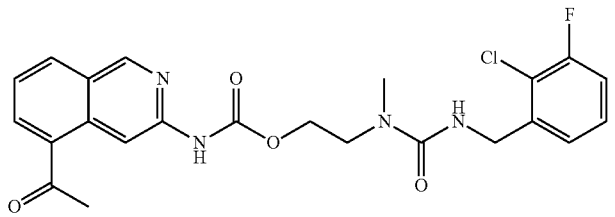 [SMILES: CC(=O)c1cccc2cnc(NC(=O)OCCN(C)C(=O)NCc3cccc(F)c3Cl)cc12] | N-{2-[N-(5-acetyl(3-isoquinolyl))carbamoyloxy]ethyl}{[(2-chloro-3-fluorophenyl)methyl]amino}-N-methylcarboxamide |

-continued

| Structure | Chemical Name |
|---|---|
| 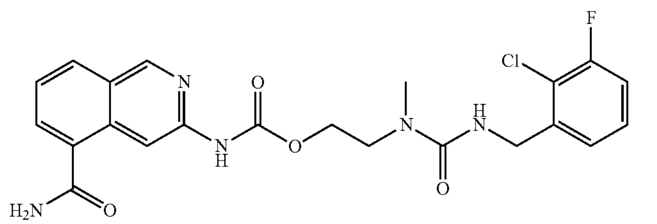 [SMILES: CN(CCOC(=O)Nc1cc2c(C(N)=O)cccc2cn1)C(=O)NCc1cccc(F)c1Cl] | 3-{[2-({[(2-chloro-3-fluorophenyl)methyl]amino}-N-methylcarbonylamino)ethoxy]carbonylamino}isoquinoline-5-carboxamide |
| 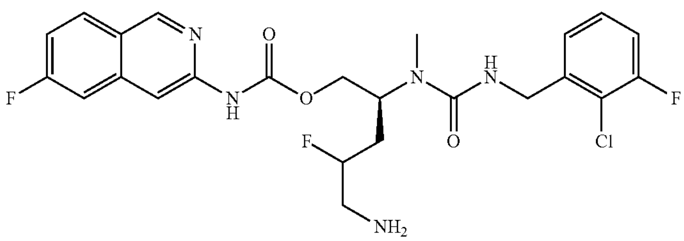 [SMILES: CN(C(=O)NCc1cccc(F)c1Cl)[C@H](COC(=O)Nc1cc2cc(F)ccc2cn1)CC(F)CN] | N-((1S)-4-amino-3-fluoro-1-{[N-(6-fluoro(3-isoquinolyl))carbamoyloxy]methyl}butyl){[(2-chloro-3-fluorophenyl)methyl]amino}-N-methylcarboxamide |
| 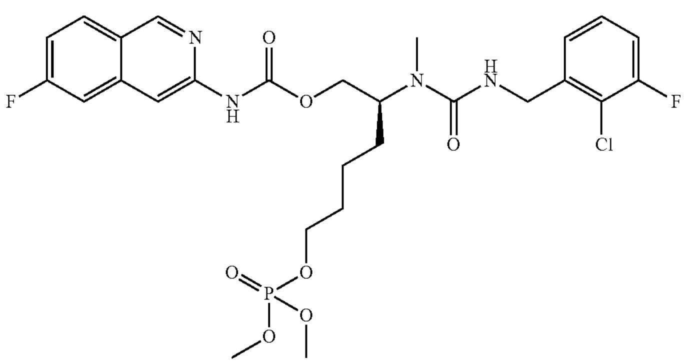 [SMILES: COP(=O)(OC)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl dimethyl phosphate |
| 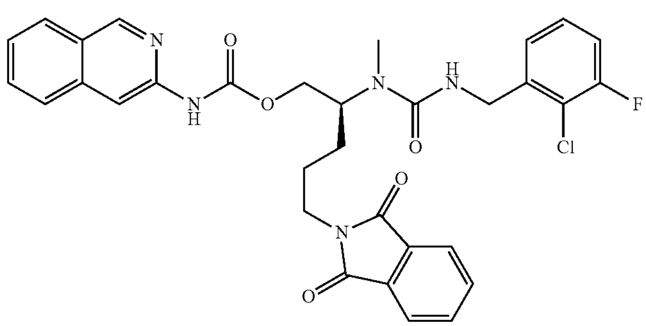 [SMILES: CN(C(=O)NCc1cccc(F)c1Cl)[C@@H](CCCN1C(=O)c2ccccc2C1=O)COC(=O)Nc1cc2ccccc2cn1] | N-{(1S)-4-(1,3-dioxobenzo[c]azolin-2-yl)-1-[(N-(3-isoquinolyl)carbamoyloxy)methyl]butyl}{[(2-chloro-3-fluorophenyl)methyl]amino}-N-methylcarboxamide |
| 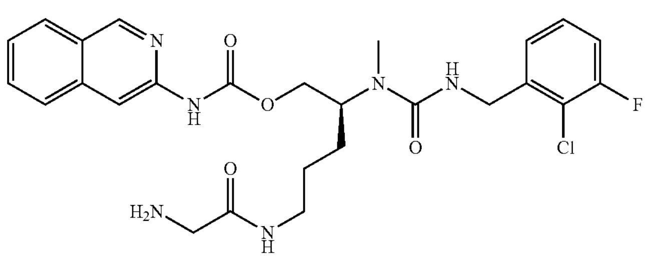 [SMILES: CN(C(=O)NCc1cccc(F)c1Cl)[C@@H](CCCNC(=O)CN)COC(=O)Nc1cc2ccccc2cn1] | N-[(4S)-4-({[(2-chloro-3-fluorophenyl)methyl]amino}-N-methylcarbonylamino)-5-(N-(3-isoquinolyl)carbamoyloxy)pentyl]-2-aminoacetamide |

-continued

| Structure | Chemical Name |
|---|---|
| 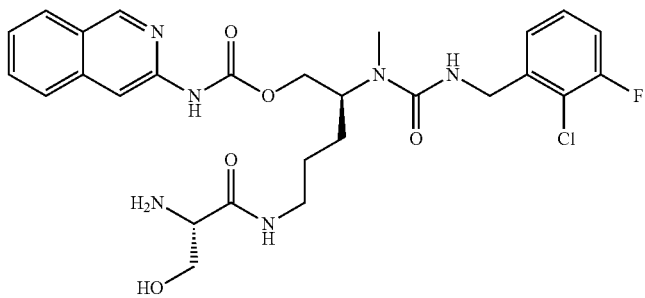 [SMILES: CN(C(=O)NCc1cccc(F)c1Cl)[C@@H](CCCNC(=O)[C@@H](N)CO)COC(=O)Nc1cc2ccccc2cn1] | (2S)-N-[(4S)-4-({[(2-chloro-3-fluorophenyl)methyl]amino}-N-methylcarbonylamino)-5-(N-(3-isoquinolyl)carbamoyloxy)pentyl]-2-amino-3-hydroxypropanamide |
| 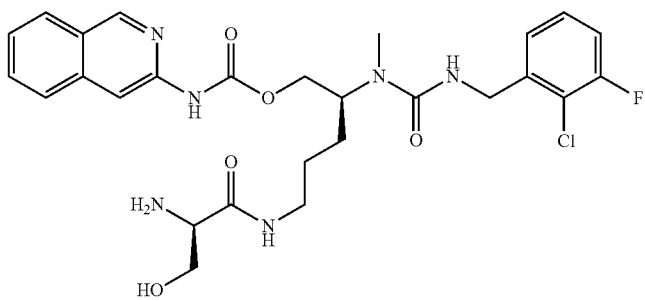 [SMILES: CN(C(=O)NCc1cccc(F)c1Cl)[C@@H](CCCNC(=O)[C@H](N)CO)COC(=O)Nc1cc2ccccc2cn1] | (2R)-N-[(4S)-4-({[(2-chloro-3-fluorophenyl)methyl]amino}-N-methylcarbonylamino)-5-(N-(3-isoquinolyl)carbamoyloxy)pentyl]-2-amino-3-hydroxypropanamide |
| 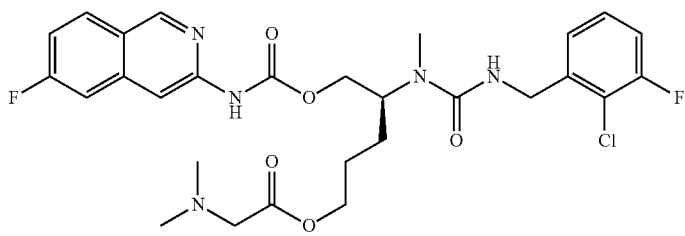 [SMILES: CN(C)CC(=O)OCCC[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]pentyl 2-(dimethylamino)acetate |
| 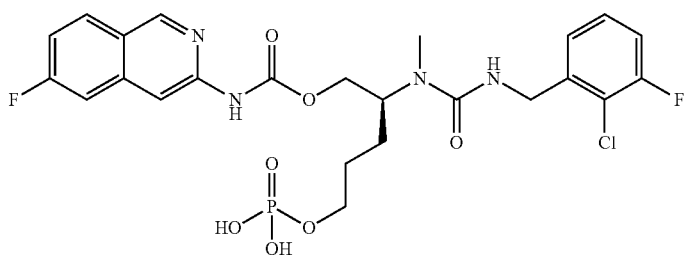 [SMILES: CN(C(=O)NCc1cccc(F)c1Cl)[C@@H](CCCOP(=O)(O)O)COC(=O)Nc1cc2cc(F)ccc2cn1] | (4S)-4-({[(2-chloro-3-fluorophenyl)methyl]amino}-N-methylcarbonylamino)-5-[N-(6-fluoro(3-isoquinolyl))carbamoyloxy]pentyl dihydrogen phosphate |
| 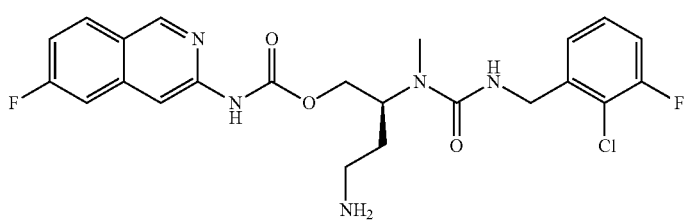 [SMILES: CN(C(=O)NCc1cccc(F)c1Cl)[C@@H](CCN)COC(=O)Nc1cc2cc(F)ccc2cn1] | [(2S)-4-amino-2-({[(2-chloro-3-fluorophenyl)methyl]amino}-N-methylcarbonylamino)butoxy]-N-(6-fluoro(3-isoquinolyl))carboxamide |

| Structure | Chemical Name |
|---|---|
| 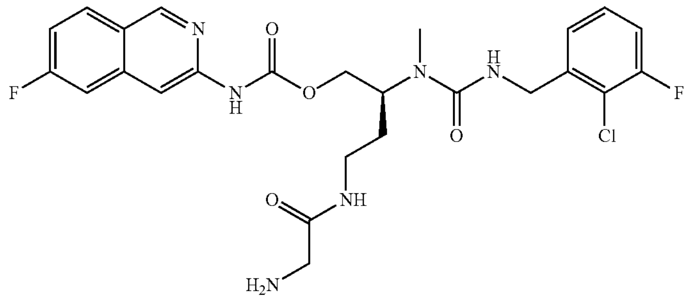 [SMILES: CN(C(=O)NCc1cccc(F)c1Cl)[C@@H](CCNC(=O)CN)COC(=O)Nc1cc2cc(F)ccc2cn1] | N-[(3S)-3-({[(2-chloro-3-fluorophenyl)methyl]amino}-N-methylcarbonylamino)-4-[N-(6-fluoro(3-isoquinolyl))carbamoyloxy]butyl]-2-aminoacetamide |
| 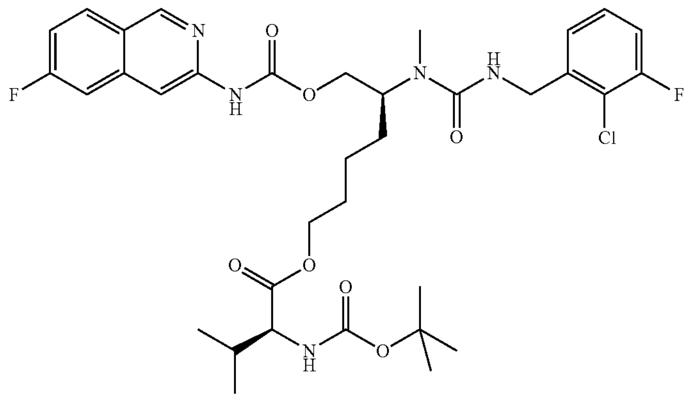 [SMILES: CC(C)[C@H](NC(=O)OC(C)(C)C)C(=O)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-[(tert-butoxy)carbonylamino]-3-methylbutanoate |
| 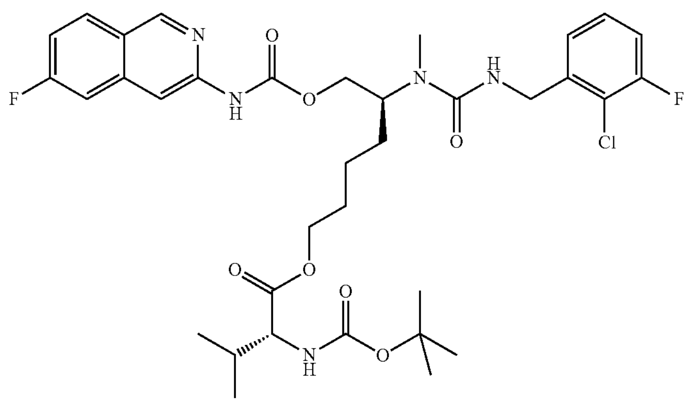 [SMILES: CC(C)[C@@H](NC(=O)OC(C)(C)C)C(=O)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-[(tert-butoxy)carbonylamino]-3-methylbutanoate |
| 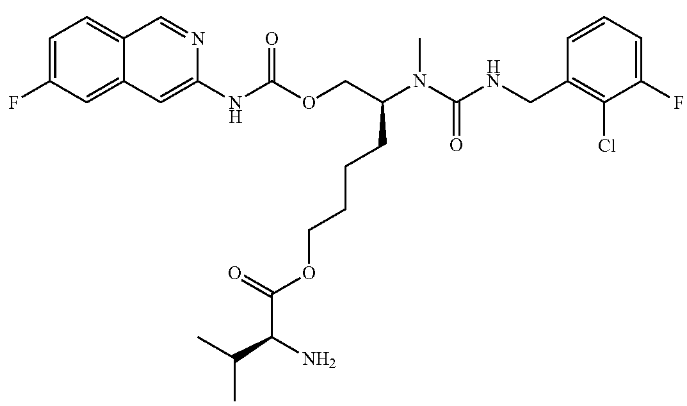 [SMILES: CC(C)[C@H](N)C(=O)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-amino-3-methylbutanoate |

-continued

| Structure | Chemical Name |
|---|---|
| 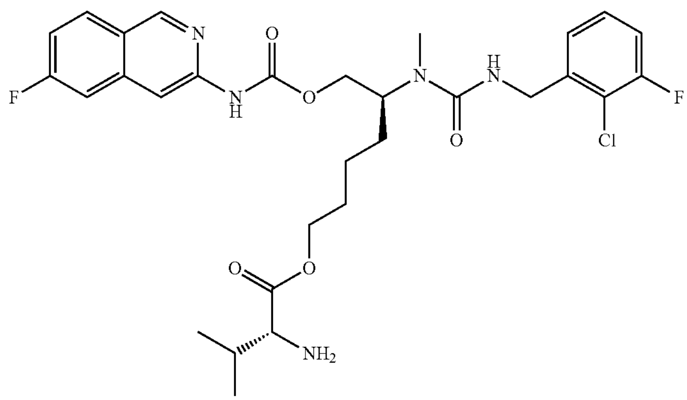 [SMILES: CC(C)[C@@H](N)C(=O)OCCCC[C@@H](COC(=O)Nc1cc2cc(F)ccc2cn1)N(C)C(=O)NCc1cccc(F)c1Cl] | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-amino-3-methylbutanoate |
| 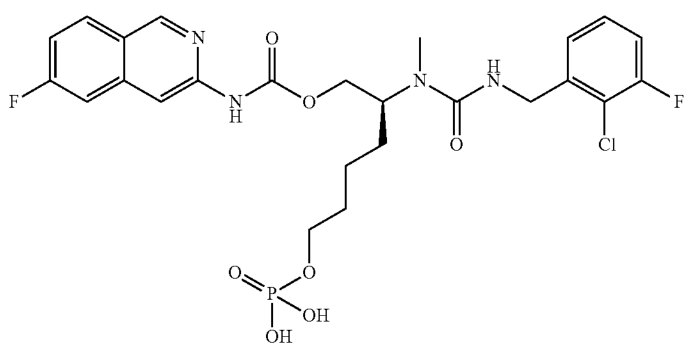 [SMILES: CN(C(=O)NCc1cccc(F)c1Cl)[C@@H](CCCCOP(=O)(O)O)COC(=O)Nc1cc2cc(F)ccc2cn1] | (5S)-5-({[(2-chloro-3-fluorophenyl)methyl]amino}-N-methylcarbonylamino)-6-[N-(6-fluoro(3-isoquinolyl))carbamoyloxy]hexyl dihydrogen phosphate |
| 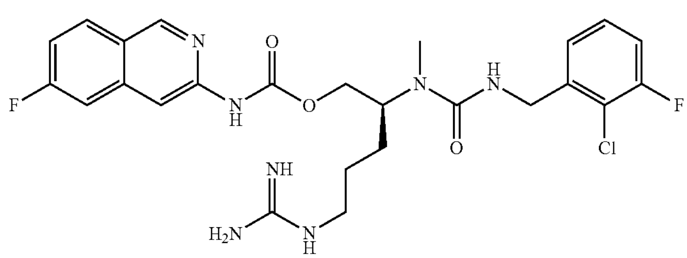 [SMILES: CN(C(=O)NCc1cccc(F)c1Cl)[C@@H](CCCNC(=N)N)COC(=O)Nc1cc2cc(F)ccc2cn1] | N-((1S)-4-(amidinoamino)-1-{[N-(6-fluoro(3-isoquinolyl))carbamoyloxy]methyl}butyl){[(2-chloro-3-fluorophenyl)methyl]amino}-N-methylcarboxamide |
| 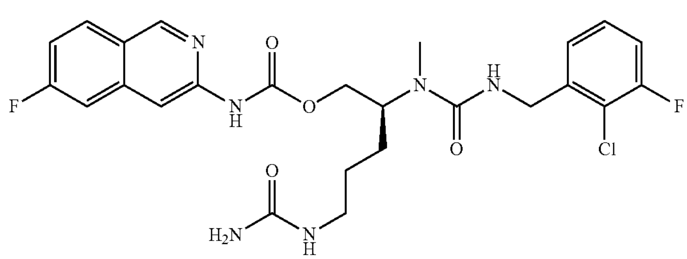 [SMILES: CN(C(=O)NCc1cccc(F)c1Cl)[C@@H](CCCNC(N)=O)COC(=O)Nc1cc2cc(F)ccc2cn1] | N-[(4S)-4-({[(2-chloro-3-fluorophenyl)methyl]amino}-N-methylcarbonylamino)-5-[N-(6-fluoro(3-isoquinolyl))carbamoyloxy]pentyl]aminoamide |
| 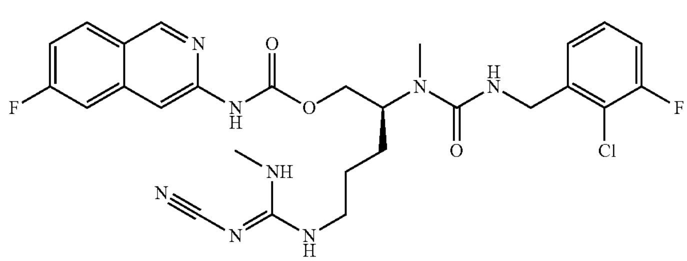 [SMILES: CN/C(=N\C#N)NCCC[C@@H](COC(=O)Nc1cc2cc(F)ccc2cn1)N(C)C(=O)NCc1cccc(F)c1Cl] | N-(4-{[(1E)-2-cyano-1-(methylamino)-2-azavinyl]amino}(1S)-1-{[N-(6-fluoro(3-isoquinolyl))carbamoyloxy]methyl}butyl){[(2-chloro-3-fluorophenyl)methyl]amino}-N-methylcarboxamide |

-continued

| Structure | Chemical Name |
|---|---|
| 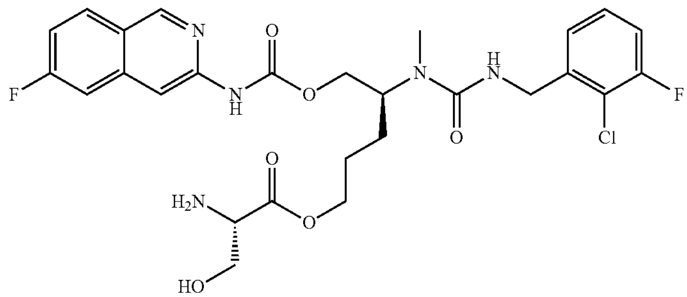 [SMILES: CN(C(=O)NCc1cccc(F)c1Cl)[C@@H](CCCOC(=O)[C@@H](N)CO)COC(=O)Nc1cc2cc(F)ccc2cn1] | (4S)-4-({[(2-chloro-3-fluorophenyl)methyl]amino}-N-methylcarbonylamino)-5-[N-(6-fluoro(3-isoquinolyl))carbamoyloxy]pentyl (2S)-2-amino-3-hydroxypropanoate |
| 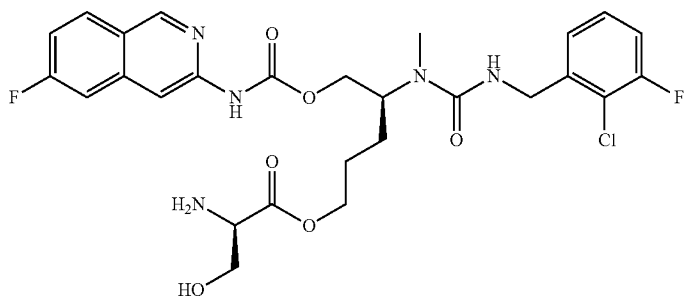 [SMILES: CN(C(=O)NCc1cccc(F)c1Cl)[C@@H](CCCOC(=O)[C@H](N)CO)COC(=O)Nc1cc2cc(F)ccc2cn1] | (4S)-4-({[(2-chloro-3-fluorophenyl)methyl]amino}-N-methylcarbonylamino)-5-[N-(6-fluoro(3-isoquinolyl))carbamoyloxy]pentyl (2R)-2-amino-3-hydroxypropanoate |
| 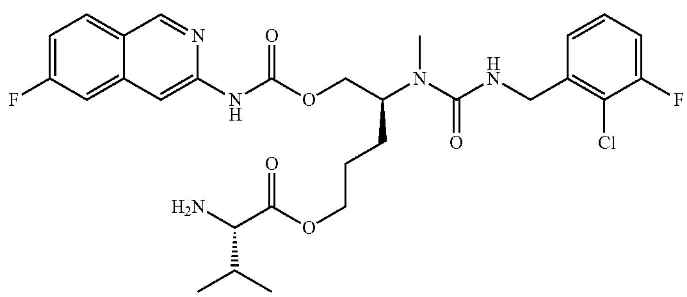 [SMILES: CC(C)[C@H](N)C(=O)OCCC[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]pentyl (2S)-2-amino-3-methylbutanoate |
| 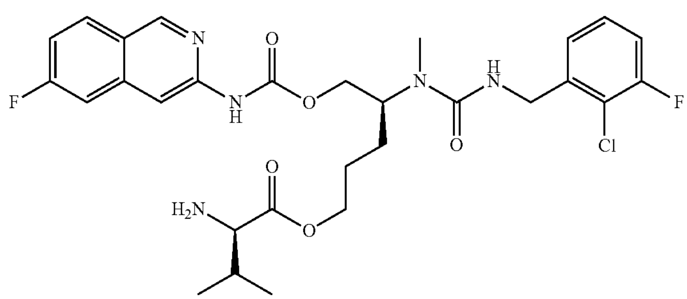 [SMILES: CC(C)[C@@H](N)C(=O)OCCC[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]pentyl (2R)-2-amino-3-methylbutanoate |
| 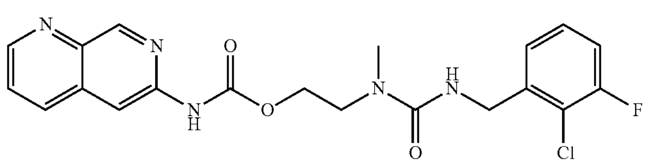 [SMILES: CN(CCOC(=O)Nc1cc2cccnc2cn1)C(=O)NCc1cccc(F)c1Cl] | {[(2-chloro-3-fluorophenyl)methyl]amino}-N-methyl-N-[2-(N-pyridino[3,2-d]pyridin-6-ylcarbamoyloxy)ethyl]carboxamide |
| 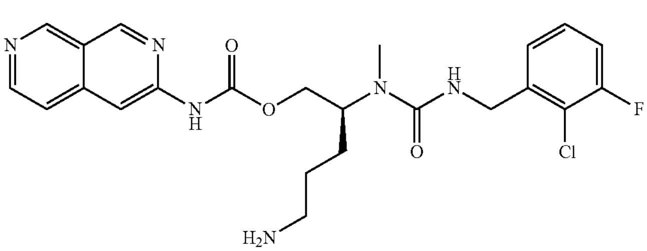 [SMILES: CN(C(=O)NCc1cccc(F)c1Cl)[C@@H](CCCN)COC(=O)Nc1cc2ccncc2cn1] | N-{(1S)-4-amino-1-[(N-pyridino[4,3-d]pyridin-3-ylcarbamoyloxy)methyl]butyl}{[(2-chloro-3-fluorophenyl)methyl]amino}-N-methylcarboxamide |

| Structure | Chemical Name |
|---|---|
| 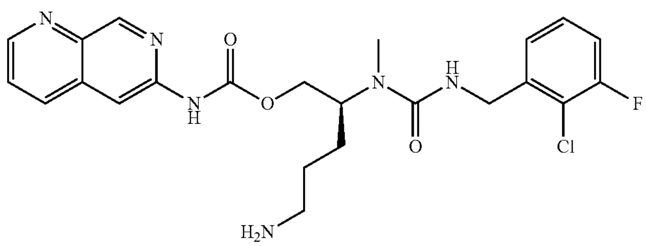 [SMILES: CN(C(=O)NCc1cccc(F)c1Cl)[C@@H](CCCN)COC(=O)Nc1cc2cccnc2cn1] | N-{(1S)-4-amino-1-[(N-pyridino[3,2-d]pyridin-6-ylcarbamoyloxy)methyl]butyl}{[(2-chloro-3-fluorophenyl)methyl]amino}-N-methylcarboxamide |
| 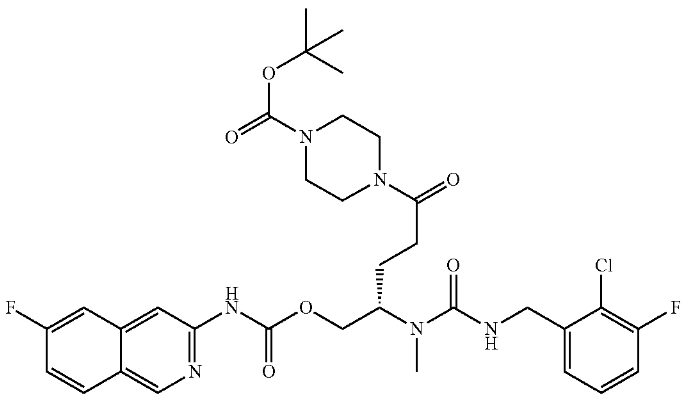 [SMILES: CN(C(=O)NCc1cccc(F)c1Cl)[C@@H](CCC(=O)N1CCN(C(=O)OC(C)(C)C)CC1)COC(=O)Nc1cc2cc(F)ccc2cn1] | tert-butyl 4-[(4S)-4-({[(2-chloro-3-fluorophenyl)methyl]amino}-N-methylcarbonylamino)-5-[N-(6-fluoro(3-isoquinolyl))carbamoyloxy]pentanoyl]piperazinecarboxylate |
| 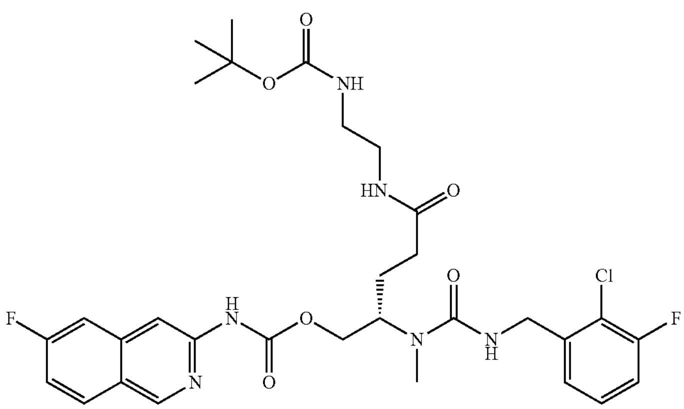 [SMILES: CN(C(=O)NCc1cccc(F)c1Cl)[C@@H](CCC(=O)NCCNC(=O)OC(C)(C)C)COC(=O)Nc1cc2cc(F)ccc2cn1] | (4S)-N-{2-[(tert-butoxy)carbonylamino]ethyl}-4-({[(2-chloro-3-fluorophenyl)methyl]amino}-N-methylcarbonylamino)-5-[N-(6-fluoro(3-isoquinolyl))carbamoyloxy]pentanamide |
| 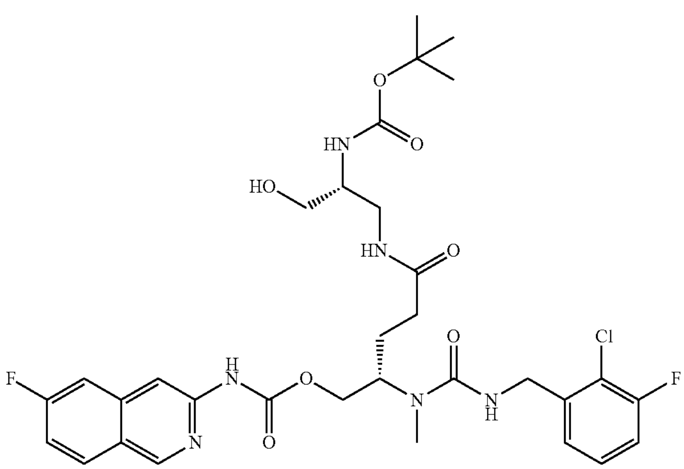 [SMILES: CN(C(=O)NCc1cccc(F)c1Cl)[C@@H](CCC(=O)NC[C@H](CO)NC(=O)OC(C)(C)C)COC(=O)Nc1cc2cc(F)ccc2cn1] | N-{(2R)-2-[(tert-butoxy)carbonylamino]-3-hydroxypropyl}(4S)-4-({[(2-chloro-3-fluorophenyl)methyl]amino}-N-methylcarbonylamino)-5-[N-(6-fluoro(3-isoquinolyl))carbamoyloxy]pentanamide |

| Structure | Chemical Name |
|---|---|
| 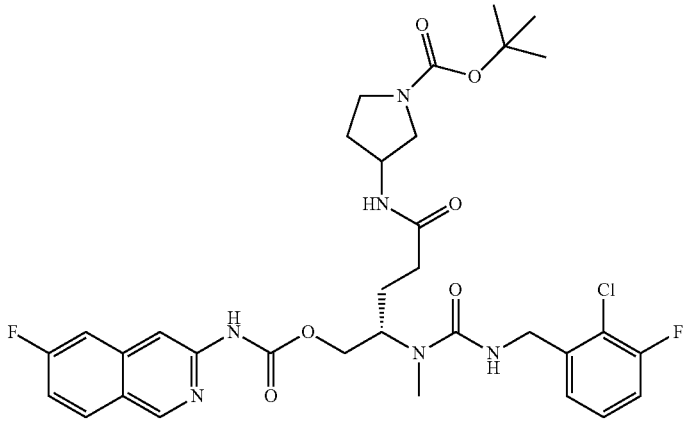 [SMILES: CN(C(=O)NCc1cccc(F)c1Cl)[C@@H](CCC(=O)NC1CCN(C(=O)OC(C)(C)C)C1)COC(=O)Nc1cc2cc(F)ccc2cn1] | tert-butyl 3-[(4S)-4-({[(2-chloro-3-fluorophenyl)methyl]amino}-N-methylcarbonylamino)-5-[N-(6-fluoro(3-isoquinolyl))carbamoyloxy]pentanoylamino]pyrrolidinecarboxylate |
| 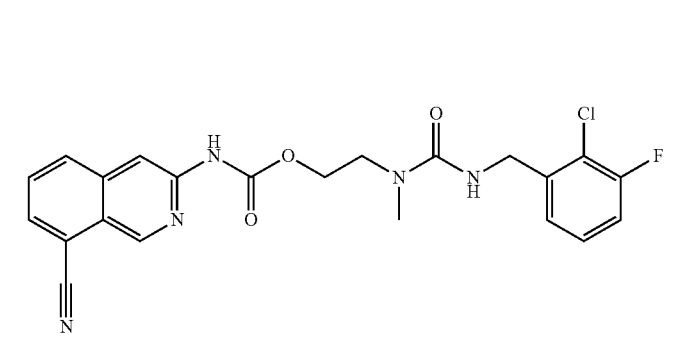 [SMILES: CN(CCOC(=O)Nc1cc2cccc(C#N)c2cn1)C(=O)NCc1cccc(F)c1Cl] | {[(2-chloro-3-fluorophenyl)methyl]amino}-N-{2-[N-(8-cyano(3-isoquinolyl))carbamoyloxy]ethyl}-N-methylcarboxamide |
| 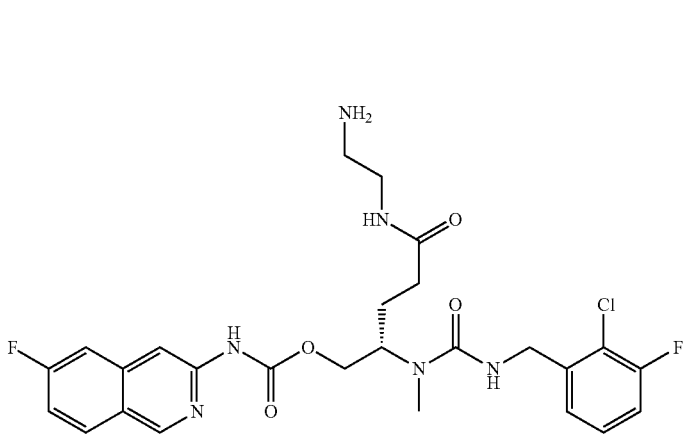 [SMILES: CN(C(=O)NCc1cccc(F)c1Cl)[C@@H](CCC(=O)NCCN)COC(=O)Nc1cc2cc(F)ccc2cn1] | (4S)-N-(2-aminoethyl)-4-({[(2-chloro-3-fluorophenyl)methyl]amino}-N-methylcarbonylamino)-5-[N-(6-fluoro(3-isoquinolyl))carbamoyloxy]pentanamide |
| 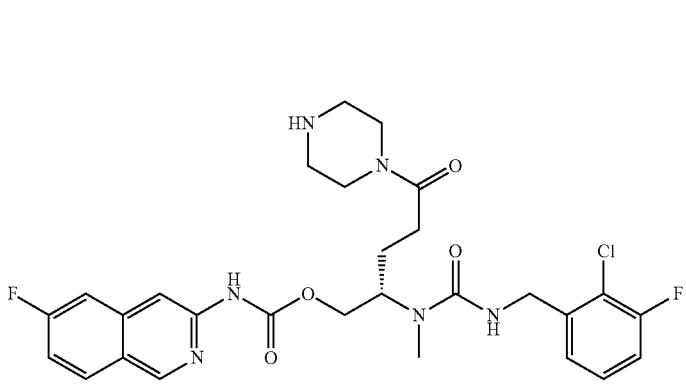 [SMILES: CN(C(=O)NCc1cccc(F)c1Cl)[C@@H](CCC(=O)N1CCNCC1)COC(=O)Nc1cc2cc(F)ccc2cn1] | N-((1S)-1-{[N-(6-fluoro(3-isoquinolyl))carbamoyloxy]methyl}-4-oxo-4-piperazinylbutyl){[(2-chloro-3-fluorophenyl)methyl]amino}-N-methylcarboxamide |

| Structure | Chemical Name |
|---|---|
| 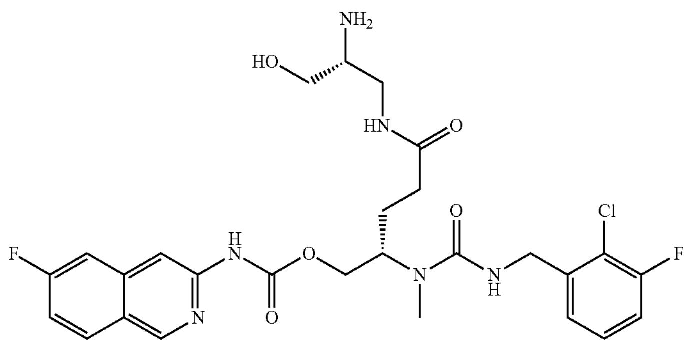 [SMILES: CN(C(=O)NCc1cccc(F)c1Cl)[C@@H](CCC(=O)NC[C@@H](N)CO)COC(=O)Nc1cc2cc(F)ccc2cn1] | N-((2R)-2-amino-3-hydroxypropyl)(4S)-4-({[(2-chloro-3-fluorophenyl)methyl]amino}-N-methylcarbonylamino)-5-[N-(6-fluoro(3-isoquinolyl))carbamoyloxy]pentanamide |
| 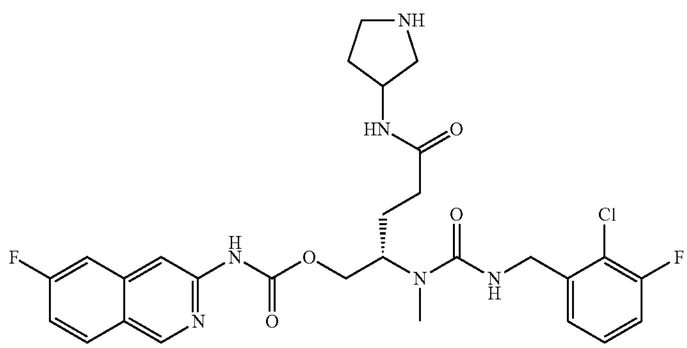 [SMILES: CN(C(=O)NCc1cccc(F)c1Cl)[C@@H](CCC(=O)NC1CCNC1)COC(=O)Nc1cc2cc(F)ccc2cn1] | (4S)-4-({[(2-chloro-3-fluorophenyl)methyl]amino}-N-methylcarbonylamino)-5-[N-(6-fluoro(3-isoquinolyl))carbamoyloxy]-N-pyrrolidin-3-ylpentanamide |
| 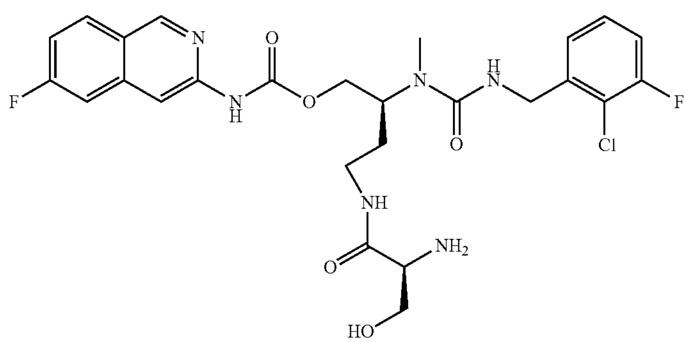 [SMILES: CN(C(=O)NCc1cccc(F)c1Cl)[C@@H](CCNC(=O)[C@@H](N)CO)COC(=O)Nc1cc2cc(F)ccc2cn1] | (2S)-N-[(3S)-3-({[(2-chloro-3-fluorophenyl)methyl]amino}-N-methylcarbonylamino)-4-[N-(6-fluoro(3-isoquinolyl))carbamoyloxy]butyl]-2-amino-3-hydroxypropanamide |
| 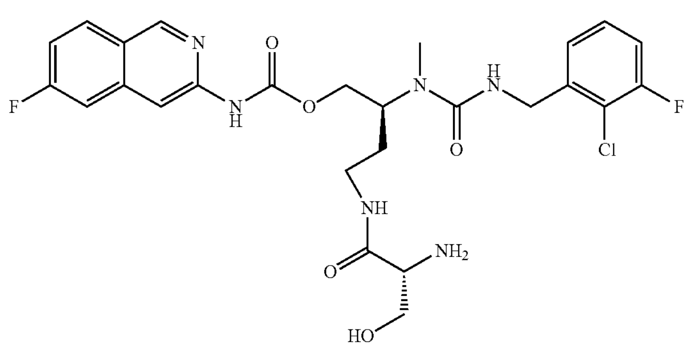 [SMILES: CN(C(=O)NCc1cccc(F)c1Cl)[C@@H](CCNC(=O)[C@H](N)CO)COC(=O)Nc1cc2cc(F)ccc2cn1] | (2R)-N-[(3S)-3-({[(2-chloro-3-fluorophenyl)methyl]amino}-N-methylcarbonylamino)-4-[N-(6-fluoro(3-isoquinolyl))carbamoyloxy]butyl]-2-amino-3-hydroxypropanamide |

-continued

| Structure | Chemical Name |
|---|---|
| 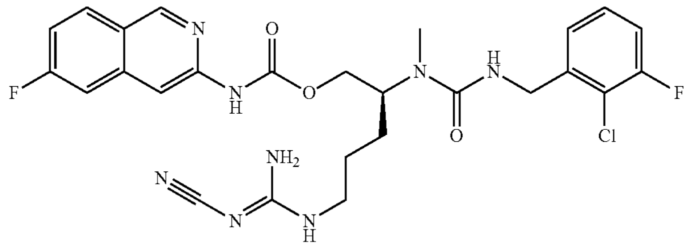 [SMILES: CN(C(=O)NCc1cccc(F)c1Cl)[C@@H](CCCN/C(N)=N/C#N)COC(=O)Nc1cc2cc(F)ccc2cn1] | N-(4-[((1E)-1-amino-2-cyano-2-azavinyl)amino](1S)-1-{[N-(6-fluoro(3-isoquinolyl))carbamoyloxy]methyl}butyl){[(2-chloro-3-fluorophenyl)methyl]amino}-N-methylcarboxamide |
| | N-(4-[((1E)-1-amino-2-carbamoyl-2-azavinyl)amino](1S)-1-{[N-(6-fluoro-3-isoquinolyl))carbamoyloxy]methyl}butyl){[(2-chloro-3-fluorophenyl)methyl]amino}-N-methylcarboxamide |
| 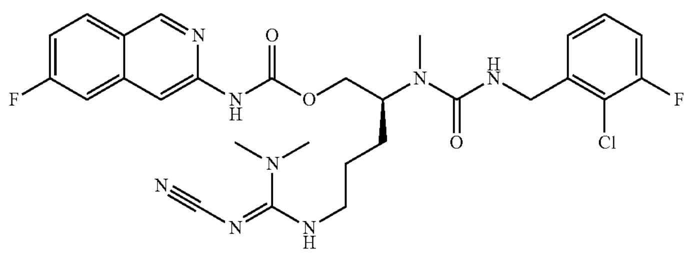 [SMILES: CN(C)/C(=N\C#N)NCCC[C@@H](COC(=O)Nc1cc2cc(F)ccc2cn1)N(C)C(=O)NCc1cccc(F)c1Cl] | N-((1S)-4-{[(1Z)-1-(dimethylamino)-2-cyano-2-azavinyl]amino}-1-{[N-(6-fluoro(3-isoquinolyl))carbamoyloxy]methyl}butyl){[(2-chloro-3-fluorophenyl)methyl]amino}-N-methylcarboxamide |
| 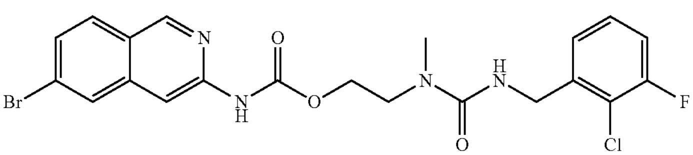 [SMILES: CN(CCOC(=O)Nc1cc2cc(Br)ccc2cn1)C(=O)NCc1cccc(F)c1Cl] | N-(6-bromo(3-isoquinolyl))[2-({[(2-chloro-3-fluorophenyl)methyl]amino}-N-methylcarbonylamino)ethoxy]carboxamide |
| 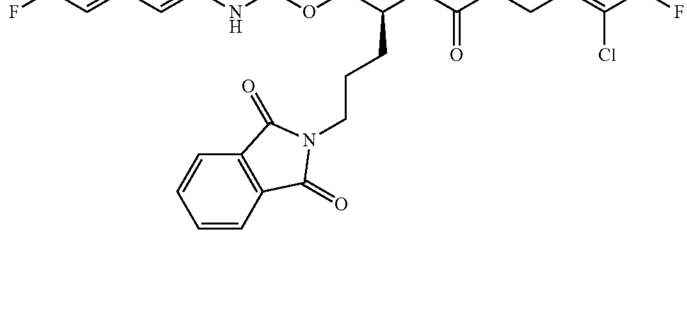 | N-((1S)-4-(1,3-dioxobenzo[c]azolin-2-yl)-1-{[N-(6-fluoro(3-isoquinolyl))carbamoyloxy]methyl}butyl){[(2-chloro-3-fluorophenyl)methyl]amino}-N-methylcarboxamide |

| Structure | Chemical Name |
|---|---|
| 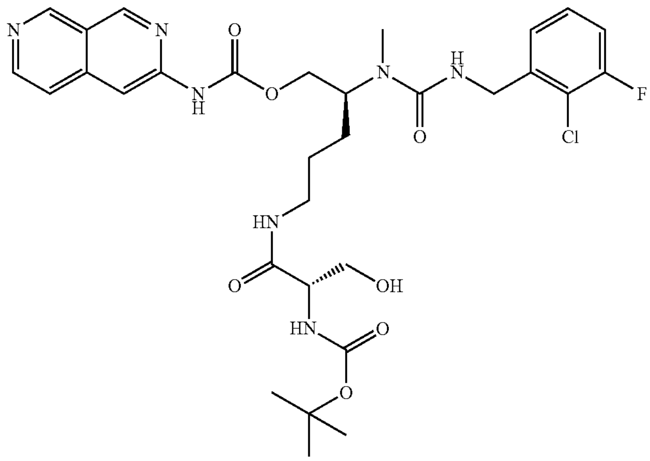 [SMILES: CN(C(=O)NCc1cccc(F)c1Cl)[C@@H](CCCNC(=O)[C@H](CO)NC(=O)OC(C)(C)C)COC(=O)Nc1cc2ccncc2cn1] | (2S)-N-[(4S)-4-({[(2-chloro-3-fluorophenyl)methyl]amino}-N-methylcarbonylamino)-5-(N-pyridino[4,3-d]pyridin-3-ylcarbamoyloxy)pentyl]-2-[(tert-butoxy)carbonylamino]-3-hydroxypropanamide |
| 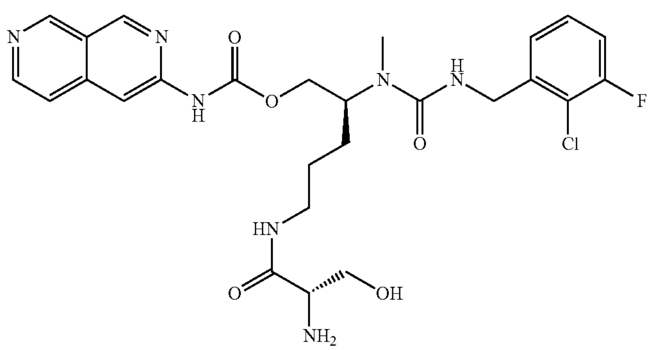 [SMILES: CN(C(=O)NCc1cccc(F)c1Cl)[C@@H](CCCNC(=O)[C@@H](N)CO)COC(=O)Nc1cc2ccncc2cn1] | (2S)-N-[(4S)-4-({[(2-chloro-3-fluorophenyl)methyl]amino}-N-methylcarbonylamino)-5-(N-pyridino[4,3-d]pyridin-3-ylcarbamoyloxy)pentyl]-2-amino-3-hydroxypropanamide |
| 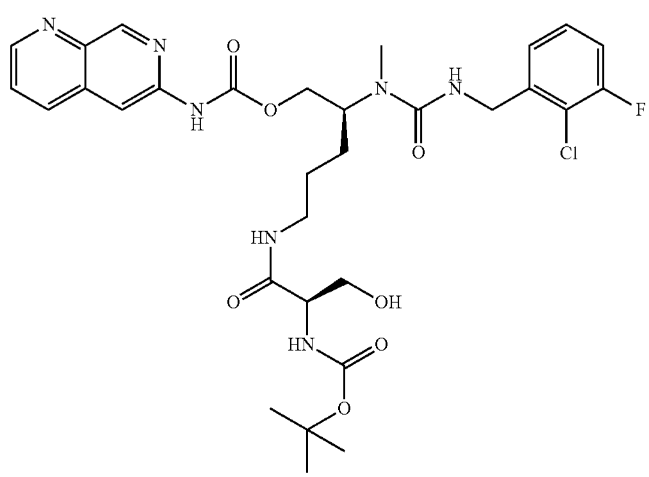 [SMILES: CN(C(=O)NCc1cccc(F)c1Cl)[C@@H](CCCNC(=O)[C@@H](CO)NC(=O)OC(C)(C)C)COC(=O)Nc1cc2cccnc2cn1] | (2S)-N-[(4S)-4-({[(2-chloro-3-fluorophenyl)methyl]amino}-N-methylcarbonylamino)-5-(N-pyridino[3,2-d]pyridin-6-ylcarbamoyloxy)pentyl]-2-[(tert-butoxy)carbonylamino]-3-hydroxypropanamide |

| Structure | Chemical Name |
|---|---|
| 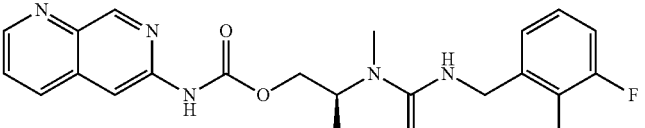 | (2S)-N-[(4S)-4-({[(2-chloro-3-fluorophenyl)methyl]amino}-N-methylcarbonylamino)-5-(N-pyridino[3,2-d]pyridin-6-ylcarbamoyloxy)pentyl]-2-amino-3-hydroxypropanamide |
| 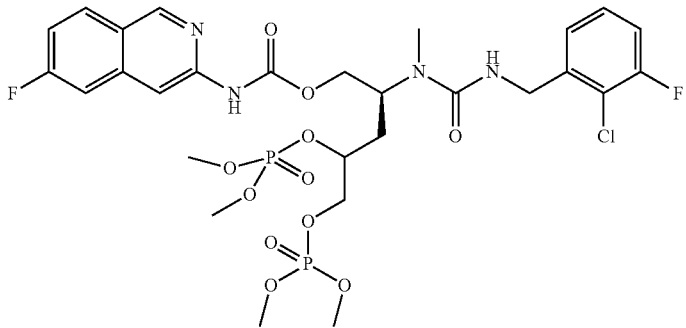 [SMILES: COP(=O)(OC)OCC(C[C@@H](COC(=O)Nc1cc2cc(F)ccc2cn1)N(C)C(=O)NCc1cccc(F)c1Cl)OP(=O)(OC)OC] | (3S)-3-({[(2-chloro-3-fluorophenyl)methyl]amino}-N-methylcarbonylamino)-4-[N-(6-fluoro(3-isoquinolyl))carbamoyloxy]-1-[(methoxyphosphinyl)methyl]butyl dimethyl phosphate |
| 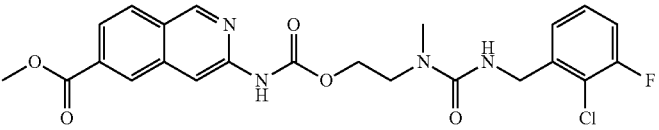 [SMILES: COC(=O)c1ccc2cnc(NC(=O)OCCN(C)C(=O)NCc3cccc(F)c3Cl)cc2c1] | methyl 3-{[2-({[(2-chloro-3-fluorophenyl)methyl]amino}-N-methylcarbonylamino)ethoxy]carbonylamino}isoquinoline-6-carboxylate |
| 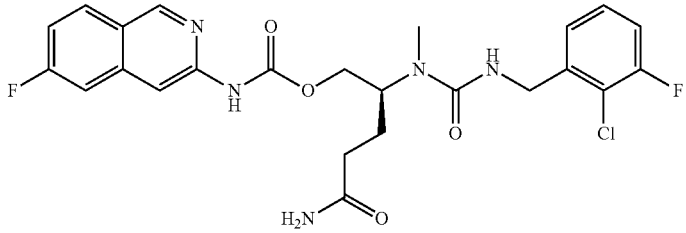 [SMILES: CN(C(=O)NCc1cccc(F)c1Cl)[C@@H](CCC(N)=O)COC(=O)Nc1cc2cc(F)ccc2cn1] | N-((1S)-3-carbamoyl-1-{[N-(6-fluoro(3-isoquinolyl))carbamoyloxy]methyl}propyl){[(2-chloro-3-fluorophenyl)methyl]amino}-N-methylcarboxamide |
| 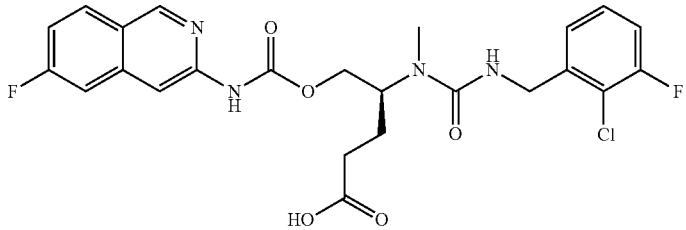 | (4S)-4-({[(2-chloro-3-fluorophenyl)methyl]amino}-N-methylcarbonylamino)-5-[N-(6-fluoro(3-isoquinolyl))carbamoyloxy]pentanoic acid |
| 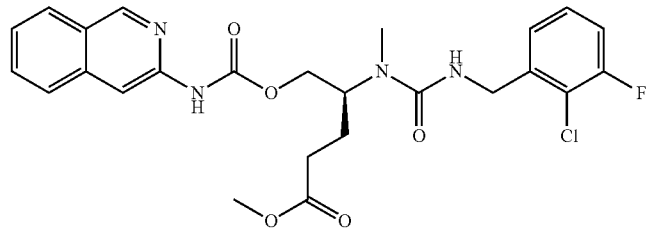 [SMILES: COC(=O)CC[C@@H](COC(=O)Nc1cc2ccccc2cn1)N(C)C(=O)NCc1cccc(F)c1Cl] | methyl (4S)-4-({[(2-chloro-3-fluorophenyl)methyl]amino}-N-methylcarbonylamino)-5-(N-(3-isoquinolyl)carbamoyloxy)pentanoate |

-continued

| Structure | Chemical Name |
|---|---|
| 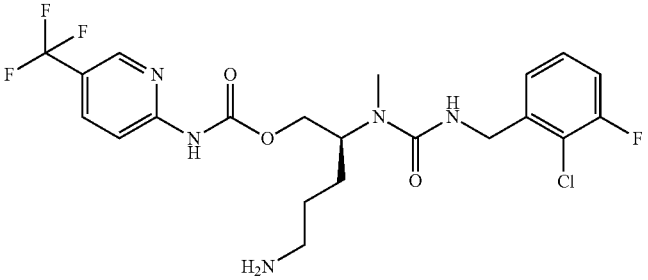 [SMILES: CN(C(=O)NCc1cccc(F)c1Cl)[C@@H](CCCN)COC(=O)Nc1ccc(C(F)(F)F)cn1] | N-[(1S)-4-amino-1-({N-[5-(trifluoromethyl)(2-pyridyl)]carbamoyloxy}methyl)butyl]{[(2-chloro-3-fluorophenyl)methyl]amino}-N-methylcarboxamide |
| 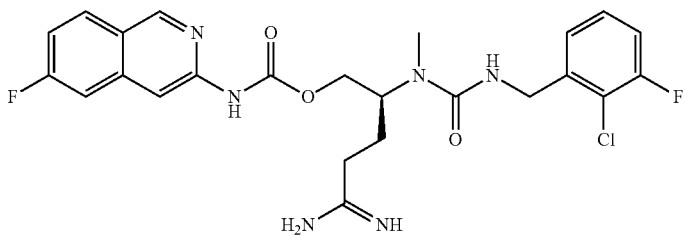 [SMILES: CN(C(=O)NCc1cccc(F)c1Cl)[C@@H](CCC(=N)N)COC(=O)Nc1cc2cc(F)ccc2cn1] | N-((1S)-3-amidino-1-{[N-(6-fluoro(3-isoquinolyl))carbamoyloxy]methyl}propyl){[(2-chloro-3-fluorophenyl)methyl]amino}-N-methylcarboxamide |
| 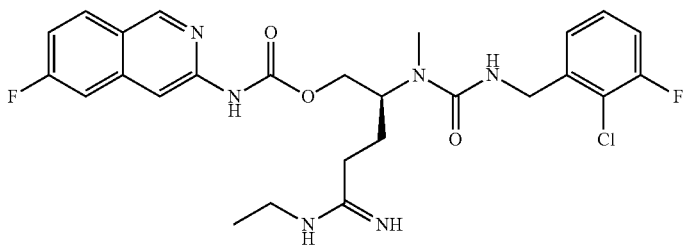 [SMILES: CCNC(=N)CC[C@@H](COC(=O)Nc1cc2cc(F)ccc2cn1)N(C)C(=O)NCc1cccc(F)c1Cl] | N-((1S)-4-(ethylamino)-1-{[N-(6-fluoro(3-isoquinolyl))carbamoyloxy]methyl}-4-iminobutyl){[(2-chloro-3-fluorophenyl)methyl]amino}-N-methylcarboxamide |
| 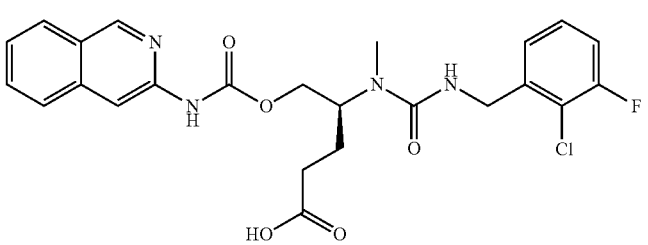 [SMILES: CN(C(=O)NCc1cccc(F)c1Cl)[C@@H](CCC(=O)O)COC(=O)Nc1cc2ccccc2cn1] | (4S)-4-({[(2-chloro-3-fluorophenyl)methyl]amino}-N-methylcarbonylamino)-5-(N-(3-isoquinolyl)carbamoyloxy)pentanoic acid |
| 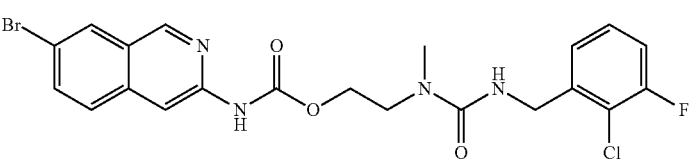 [SMILES: CN(CCOC(=O)Nc1cc2ccc(Br)cc2cn1)C(=O)NCc1cccc(F)c1Cl] | N-(7-bromo(3-isoquinolyl))[2-({[(2-chloro-3-fluorophenyl)methyl]amino}-N-methylcarbonylamino)ethoxy]carboxamide |
| 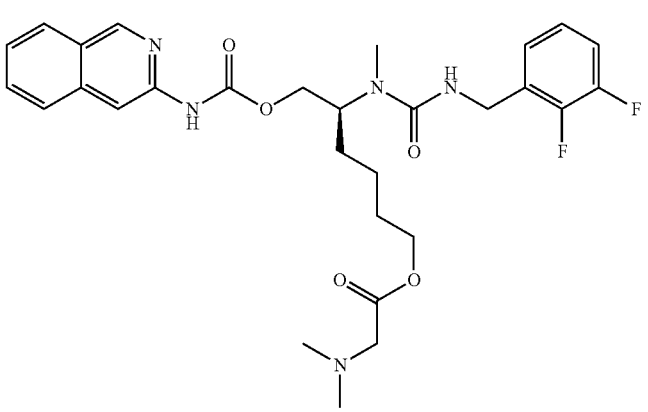 | (5S)-5-({[(2,3-difluorophenyl)methyl]amino}-N-methylcarbonylamino)-6-(N-(3-isoquinolyl)carbamoyloxy)hexyl 2-(dimethylamino)acetate |

-continued

| Structure | Chemical Name |
|---|---|
| 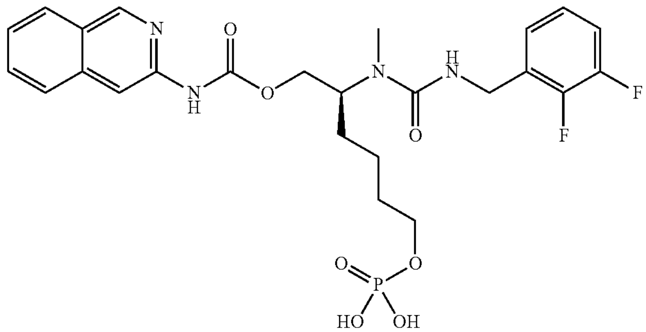 | (5S)-5-({[(2,3-difluorophenyl) methyl]amino}-N-methylcarbonylamino)-6-(N-(3-isoquinolyl)carbamoyloxy) hexyl dihydrogen phosphate |
| 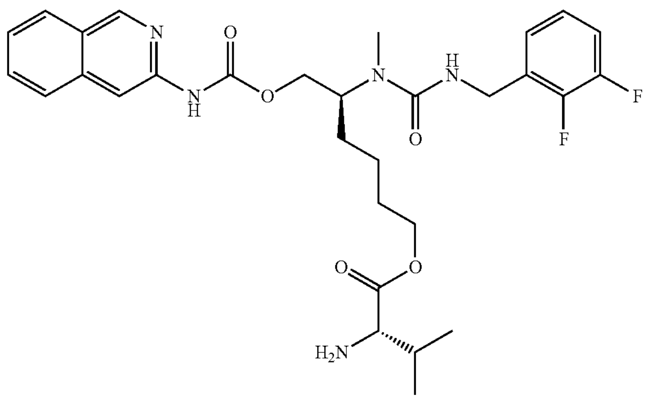 | (5S)-5-({[(2,3-difluorophenyl) methyl]amino}-N-methylcarbonylamino)-6-(N-(3-isoquinolyl)carbamoyloxy) hexyl (2S)-2-amino-3-methylbutanoate |
| 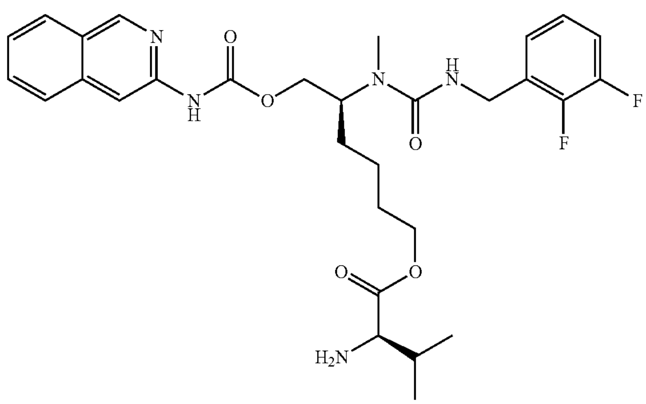 | (5S)-5-({[(2,3-difluorophenyl) methyl]amino}-N-methylcarbonylamino)-6-(N-(3-isoquinolyl)carbamoyloxy) hexyl (2R)-2-amino-3-methylbutanoate |
| 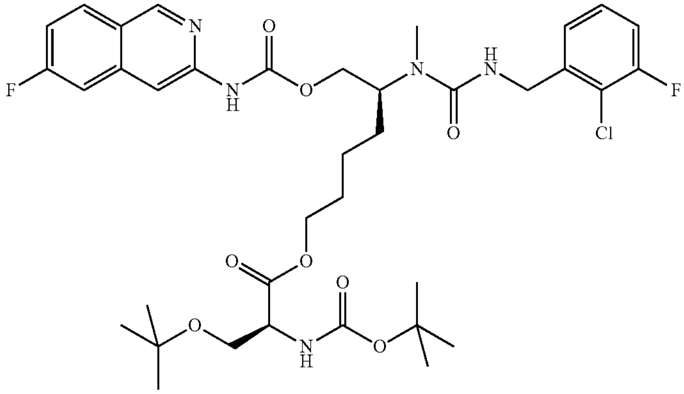 [SMILES: CN(C(=O)NCc1cccc(F)c1Cl)[C@@H](CCCCOC(=O)[C@H](COC(C)(C)C)NC(=O)OC(C)(C)C)COC(=O)Nc1cc2cc(F)ccc2cn1] | (5S)-5-({[(2-chloro-3-fluorophenyl)methyl]amino}-N-methylcarbonylamino)-6-[N-(6-fluoro(3-isoquinolyl))carbamoyloxy]hexyl (2S)-3-(tert-butoxy)-2-[(tert-butoxy)carbonylamino]propanoate |

| Structure | Chemical Name |
|---|---|
| 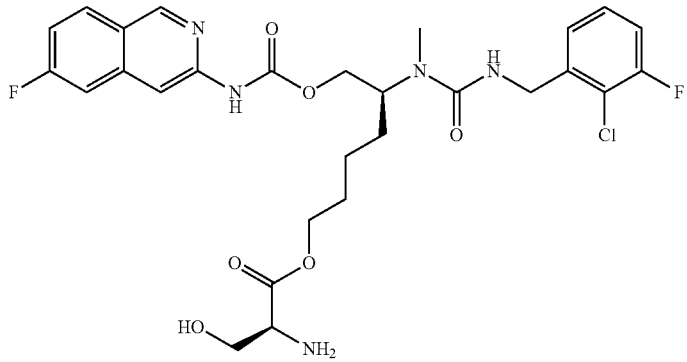 [SMILES: CN(C(=O)NCc1cccc(F)c1Cl)[C@@H](CCCCOC(=O)[C@@H](N)CO)COC(=O)Nc1cc2cc(F)ccc2cn1] | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-amino-3-hydroxypropanoate |
| 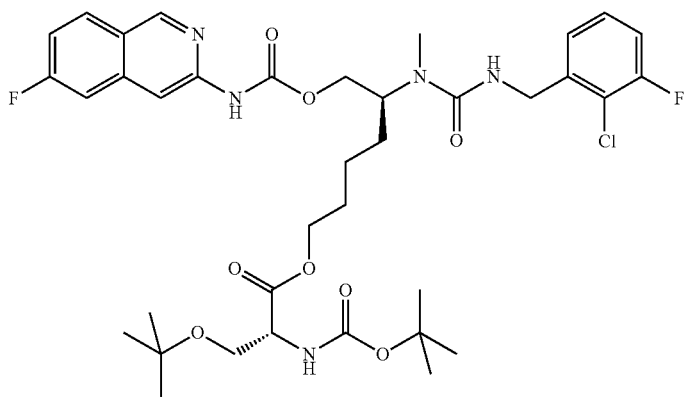 [SMILES: CN(C(=O)NCc1cccc(F)c1Cl)[C@@H](CCCCOC(=O)[C@@H](COC(C)(C)C)NC(=O)OC(C)(C)C)COC(=O)Nc1cc2cc(F)ccc2cn1] | (5S)-5-({[(2-chloro-3-fluorophenyl)methyl]amino}-N-methylcarbonylamino)-6-[N-(6-fluoro(3-isoquinolyl))carbamoyloxy]hexyl (2R)-3-(tert-butoxy)-2-[(tert-butoxy)carbonylamino]propanoate |
| 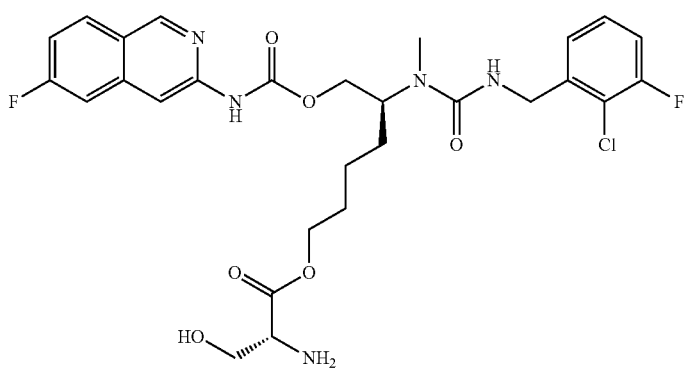 [SMILES: CN(C(=O)NCc1cccc(F)c1Cl)[C@@H](CCCCOC(=O)[C@H](N)CO)COC(=O)Nc1cc2cc(F)ccc2cn1] | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-amino-3-hydroxypropanoate |
| 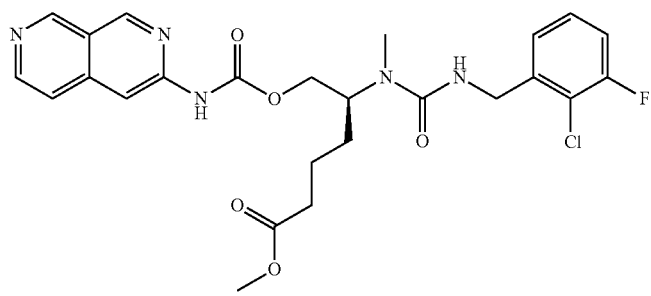 [SMILES: COC(=O)CCC[C@@H](COC(=O)Nc1cc2ccncc2cn1)N(C)C(=O)NCc1cccc(F)c1Cl] | methyl (5S)-5-({[(2-chloro-3-fluorophenyl)methyl]amino}-N-methylcarbonylamino)-6-(N-pyridino[4,3-d]pyridin-3-ylcarbamoyloxy)hexanoate |

-continued

| Structure | Chemical Name |
|---|---|
| 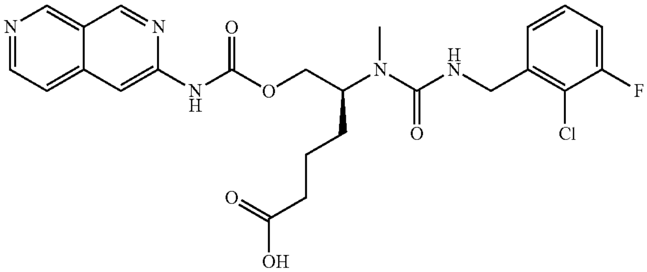 [SMILES: CN(C(=O)NCc1cccc(F)c1Cl)[C@@H](CCCC(=O)O)COC(=O)Nc1cc2ccncc2cn1] | (5S)-5-({[(2-chloro-3-fluorophenyl)methyl]amino}-N-methylcarbonylamino)-6-(N-pyridino[4,3-d]pyridin-3-ylcarbamoyloxy)hexanoic acid |
| 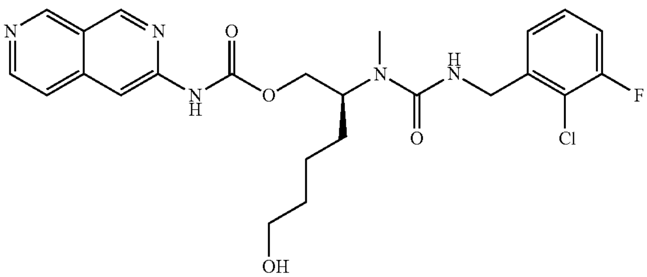 [SMILES: CN(C(=O)NCc1cccc(F)c1Cl)[C@@H](CCCCO)COC(=O)Nc1cc2ccncc2cn1] | N-{(1S)-5-hydroxy-1-[(N-pyridino[4,3-d]pyridin-3-ylcarbamoyloxy)methyl]pentyl}{[(2-chloro-3-fluorophenyl)methyl]amino}-N-methylcarboxamide |
| 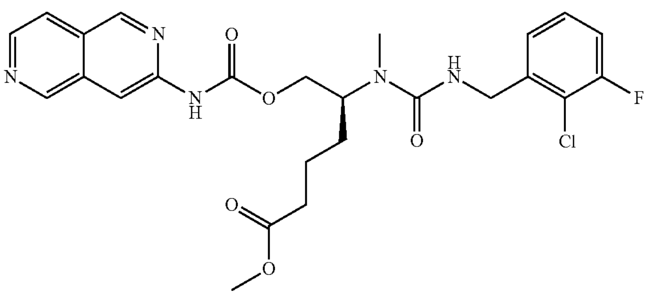 [SMILES: COC(=O)CCC[C@@H](COC(=O)Nc1cc2cnccc2cn1)N(C)C(=O)NCc1cccc(F)c1Cl] | methyl (5S)-5-({[(2-chloro-3-fluorophenyl)methyl]amino}-N-methylcarbonylamino)-6-(N-pyridino[3,4-d]pyridin-3-ylcarbamoyloxy)hexanoate |
| 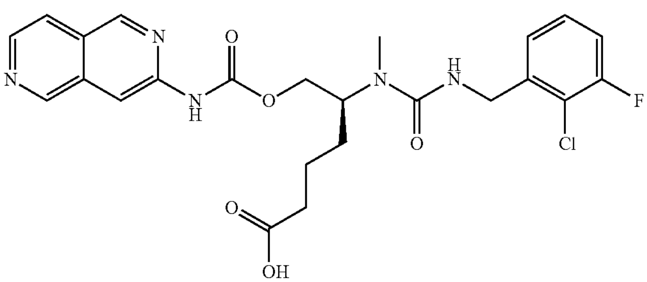 [SMILES: CN(C(=O)NCc1cccc(F)c1Cl)[C@@H](CCCC(=O)O)COC(=O)Nc1cc2cnccc2cn1] | (5S)-5-({[(2-chloro-3-fluorophenyl)methyl]amino}-N-methylcarbonylamino)-6-(N-pyridino[3,4-d]pyridin-3-ylcarbamoyloxy)hexanoic acid |
| 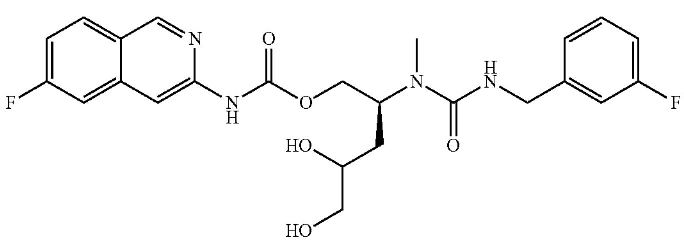 [SMILES: CN(C(=O)NCc1cccc(F)c1)[C@H](COC(=O)Nc1cc2cc(F)ccc2cn1)CC(O)CO] | N-((1S)-1-{[N-(6-fluoro(3-isoquinolyl))carbamoyloxy]methyl}-3,4-dihydroxybutyl){[(3-fluorophenyl)methyl]amino}-N-methylcarboxamide |
| 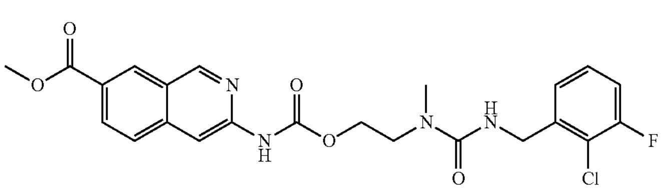 [SMILES: COC(=O)c1ccc2cc(NC(=O)OCCN(C)C(=O)NCc3cccc(F)c3Cl)ncc2c1] | methyl 3-{[2-({[(2-chloro-3-fluorophenyl)methyl]amino}-N-methylcarbonylamino)ethoxy]carbonylamino}isoquinoline-7-carboxylate |

-continued

| Structure | Chemical Name |
|---|---|
| 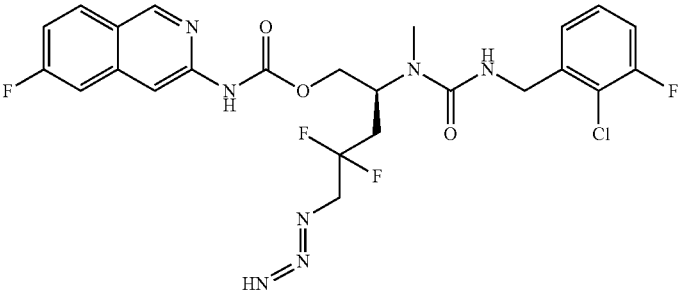 | N-((1S)-5-diazo-3,3-difluoro-1-{[N-(6-fluoro(3-isoquinolyl))carbamoyloxy]methyl}-5-azapent-5-enyl){[(2-chloro-3-fluorophenyl)methyl]amino}-N-methylcarboxamide |
| 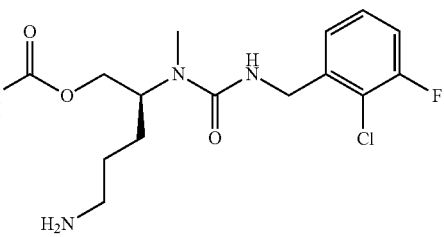 | [(2S)-5-amino-2-({[(2-chloro-3-fluorophenyl)methyl]amino}-N-methylcarbonylamino)pentyloxy]-N-(5-chloro(2-pyridyl))carboxamide |
| 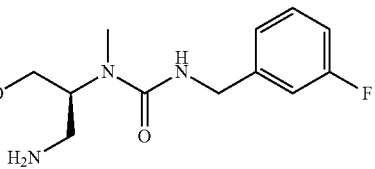 | [(2S)-3-amino-2-({[(3-fluorophenyl)methyl]amino}-N-methylcarbonylamino)propoxy]-N-(6-fluoro(3-isoquinolyl))carboxamide |
| 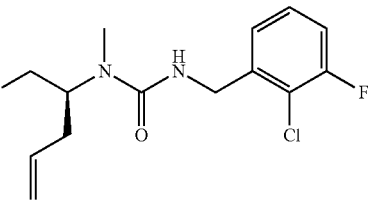 | N-{(1S)-1-[(N-pyridino[3,4-d]pyridin-3-ylcarbamoyloxy)methyl]but-3-enyl}{[(2-chloro-3-fluorophenyl)methyl]amino}-N-methylcarboxamide |
| 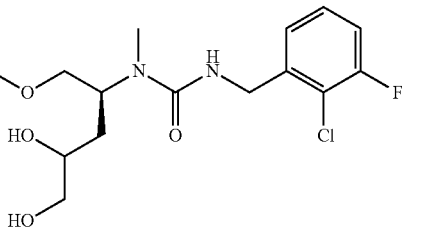 | N-{(1S)-3,4-dihydroxy-1-[(N-pyridino[3,4-d]pyridin-3-ylcarbamoyloxy)methyl]butyl}{[(2-chloro-3-fluorophenyl)methyl]amino}-N-methylcarboxamide |
| 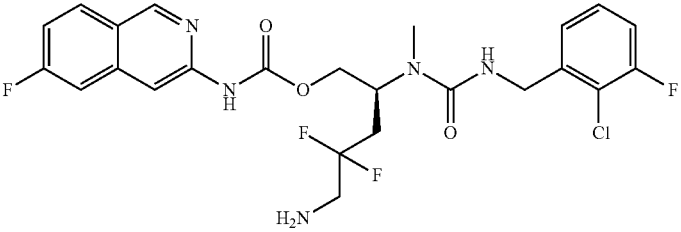 [SMILES: CN(C(=O)NCc1cccc(F)c1Cl)[C@H](COC(=O)Nc1cc2cc(F)ccc2cn1)CC(F)(F)CN] | N-((1S)-4-amino-3,3-difluoro-1-{[N-(6-fluoro(3-isoquinolyl))carbamoyloxy]methyl}butyl){[(2-chloro-3-fluorophenyl)methyl]amino}-N-methylcarboxamide |

| Structure | Chemical Name |
|---|---|
| 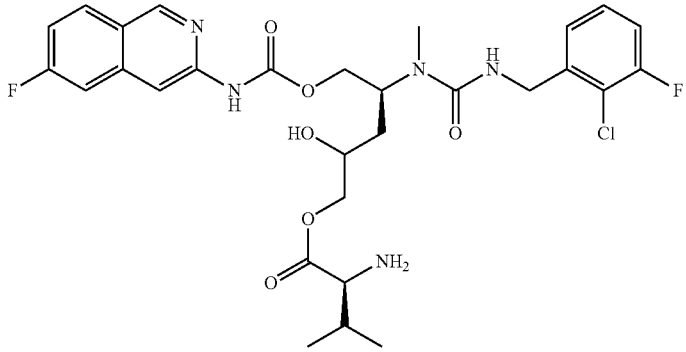 [SMILES: CC(C)[C@H](N)C(=O)OCC(O)C[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2S)-2-amino-3-methylbutanoate |
| 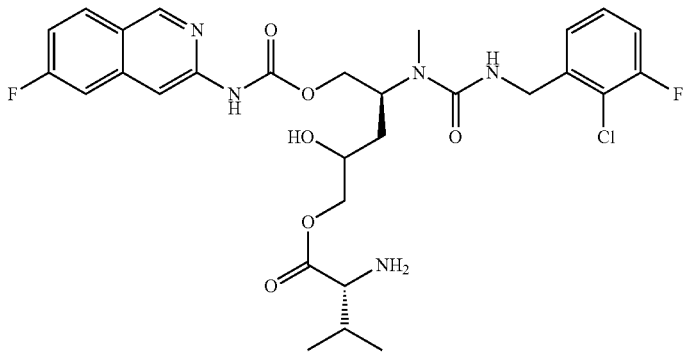 [SMILES: CC(C)[C@@H](N)C(=O)OCC(O)C[C@@H](COC(=O)Nc1cc2cc(F)ccc2cn1)N(C)C(=O)NCc1cccc(F)c1Cl] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2R)-2-amino-3-methylbutanoate |
| 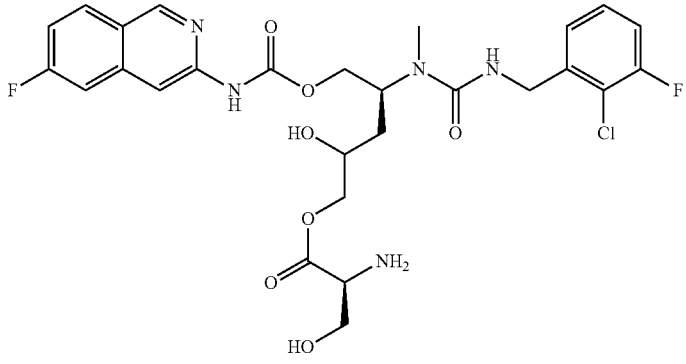 [SMILES: CN(C(=O)NCc1cccc(F)c1Cl)[C@H](COC(=O)Nc1cc2cc(F)ccc2cn1)CC(O)COC(=O)[C@@H](N)CO] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2S)-2-amino-3-hydroxypropanoate |
| 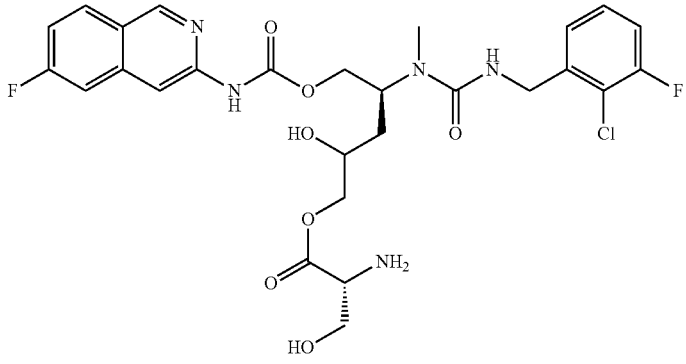 [SMILES: CN(C(=O)NCc1cccc(F)c1Cl)[C@H](COC(=O)Nc1cc2cc(F)ccc2cn1)CC(O)COC(=O)[C@H](N)CO] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2R)-2-amino-3-hydroxypropanoate |

-continued

| Structure | Chemical Name |
|---|---|
| 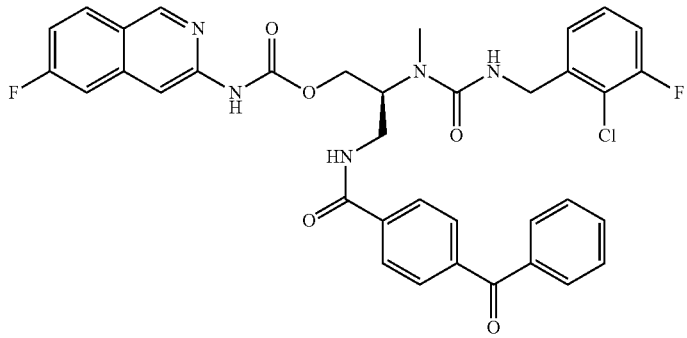 [SMILES: CN(C(=O)NCc1cccc(F)c1Cl)[C@@H](CNC(=O)c1ccc(C(=O)c2ccccc2)cc1)COC(=O)Nc1cc2cc(F)ccc2cn1] | N-[(2S)-2-({[(2-chloro-3-fluorophenyl)methyl]amino}-N-methylcarbonylamino)-3-[N-(6-fluoro(3-isoquinolyl))carbamoyloxy]propyl][4-(phenylcarbonyl)phenyl]carboxamide |
| 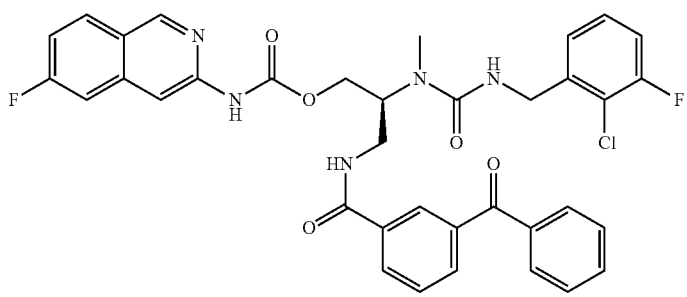 [SMILES: CN(C(=O)NCc1cccc(F)c1Cl)[C@@H](CNC(=O)c1cccc(C(=O)c2ccccc2)c1)COC(=O)Nc1cc2cc(F)ccc2cn1] | N-[(2S)-2-({[(2-chloro-3-fluorophenyl)methyl]amino}-N-methylcarbonylamino)-3-[N-(6-fluoro(3-isoquinolyl))carbamoyloxy]propyl][3-(phenylcarbonyl)phenyl]carboxamide |
| 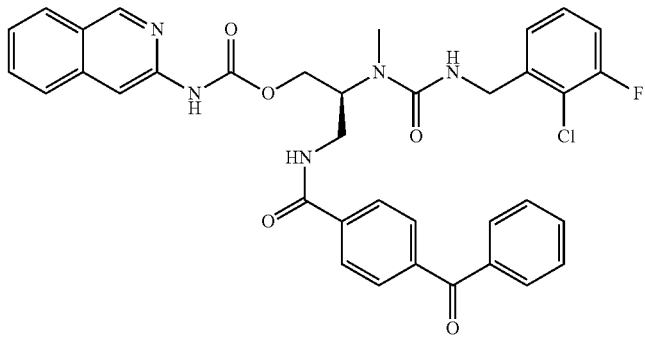 [SMILES: CN(C(=O)NCc1cccc(F)c1Cl)[C@@H](CNC(=O)c1ccc(C(=O)c2ccccc2)cc1)COC(=O)Nc1cc2ccccc2cn1] | N-[(4S)-4-({[(2-chloro-3-fluorophenyl)methyl]amino}-N-methylcarbonylamino)-5-(N-(3-isoquinolyl)carbamoyloxy)pentyl][4-(phenylcarbonyl)phenyl]carboxamide |
| 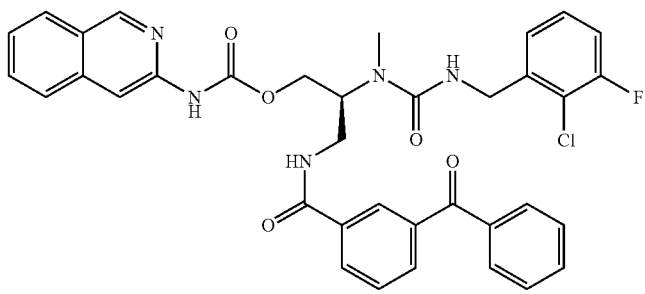 [SMILES: CN(C(=O)NCc1cccc(F)c1Cl)[C@@H](CNC(=O)c1cccc(C(=O)c2ccccc2)c1)COC(=O)Nc1cc2ccccc2cn1] | N-[(4S)-4-({[(2-chloro-3-fluorophenyl)methyl]amino}-N-methylcarbonylamino)-5-(N-(3-isoquinolyl)carbamoyloxy)pentyl][3-(phenylcarbonyl)phenyl]carboxamide |
| 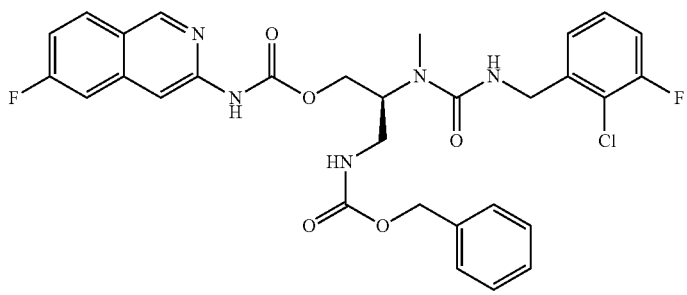 [SMILES: CN(C(=O)NCc1cccc(F)c1Cl)[C@@H](CNC(=O)OCc1ccccc1)COC(=O)Nc1cc2cc(F)ccc2cn1] | [(2S)-2-({[(2-chloro-3-fluorophenyl)methyl]amino}-N-methylcarbonylamino)-3-[(phenylmethoxy)carbonylamino]propoxy]-N-(6-fluoro(3-isoquinolyl))carboxamide |

-continued

| Structure | Chemical Name |
|---|---|
| 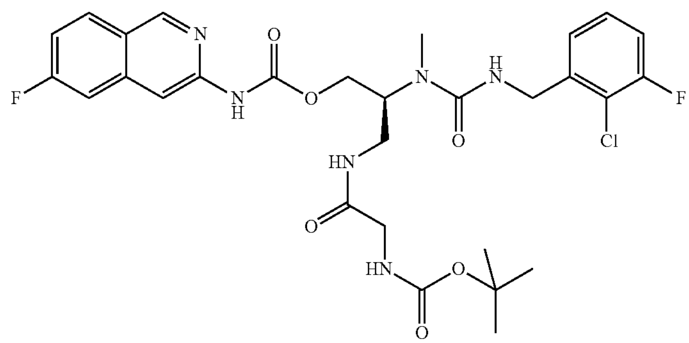 [SMILES: CN(C(=O)NCc1cccc(F)c1Cl)[C@@H](CNC(=O)CNC(=O)OC(C)(C)C)COC(=O)Nc1cc2cc(F)ccc2cn1] | N-[(2S)-2-({[(2-chloro-3-fluorophenyl)methyl]amino}-N-methylcarbonylamino)-3-[N-(6-fluoro(3-isoquinolyl))carbamoyloxy]propyl]-2-[(tert-butoxy)carbonylamino]acetamide |
| 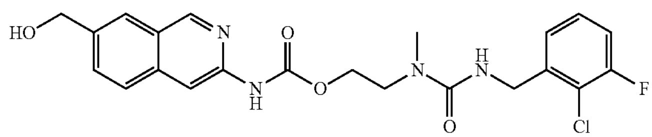 [SMILES: CN(CCOC(=O)Nc1cc2ccc(CO)cc2cn1)C(=O)NCc1cccc(F)c1Cl] | {[(2-chloro-3-fluorophenyl)methyl]amino}-N-(2-{N-[7-(hydroxymethyl)(3-isoquinolyl)]carbamoyloxy}ethyl)-N-methylcarboxamide |
| 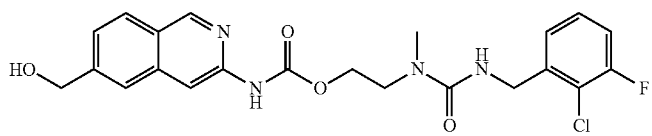 [SMILES: CN(CCOC(=O)Nc1cc2cc(CO)ccc2cn1)C(=O)NCc1cccc(F)c1Cl] | {[(2-chloro-3-fluorophenyl)methyl]amino}-N-(2-{N-[6-(hydroxymethyl)(3-isoquinolyl)]carbamoyloxy}ethyl)-N-methylcarboxamide |
| 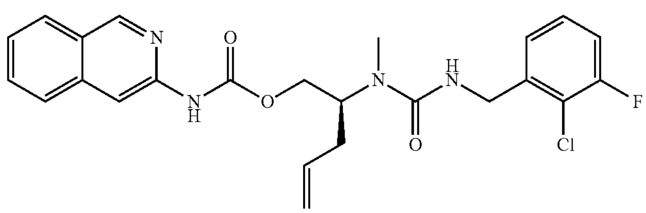 [SMILES: C=CC[C@@H](COC(=O)Nc1cc2ccccc2cn1)N(C)C(=O)NCc1cccc(F)c1Cl] | [(2S)-2-({[(2-chloro-3-fluorophenyl)methyl]amino}-N-methylcarbonylamino)pent-4-enyloxy]-N-(3-isoquinolyl)carboxamide |
| 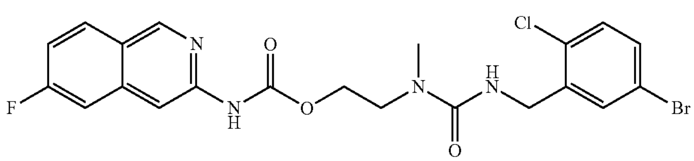 [SMILES: CN(CCOC(=O)Nc1cc2cc(F)ccc2cn1)C(=O)NCc1cc(Br)ccc1Cl] | {[(5-bromo-2-chlorophenyl)methyl]amino}-N-(2-[N-(6-fluoro(3-isoquinolyl))carbamoyloxy]ethyl}-N-methylcarboxamide |
| 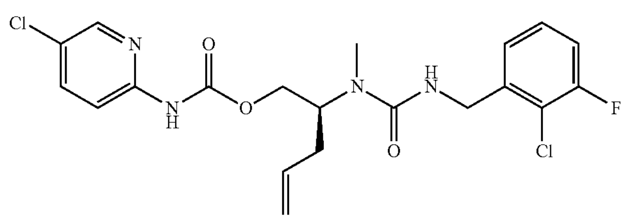 [SMILES: C=CC[C@@H](COC(=O)Nc1ccc(Cl)cn1)N(C)C(=O)NCc1cccc(F)c1Cl] | [(2S)-2-({[(2-chloro-3-fluorophenyl)methyl]amino}-N-methylcarbonylamino)pent-4-enyloxy]-N-(5-chloro(2-pyridyl))carboxamide |
| 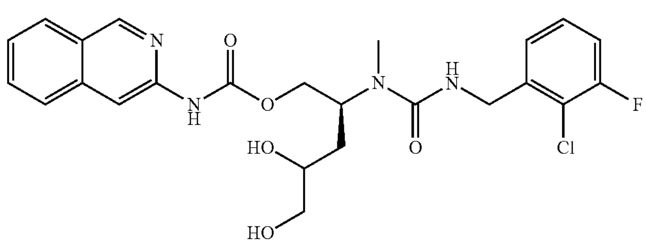 [SMILES: CN(C(=O)NCc1cccc(F)c1Cl)[C@H](COC(=O)Nc1cc2ccccc2cn1)CC(O)CO] | [(2S)-2-({[(2-chloro-3-fluorophenyl)methyl]amino}-N-methylcarbonylamino)-4,5-dihydroxypentyloxy]-N-(3-isoquinolyl)carboxamide |

| Structure | Chemical Name |
|---|---|
| 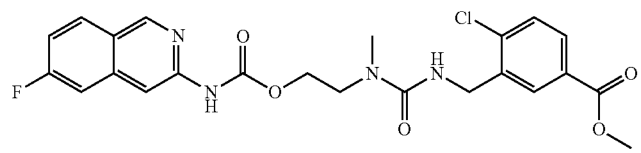 [SMILES: COC(=O)c1ccc(Cl)c(CNC(=O)N(C)CCOC(=O)Nc2cc3cc(F)ccc3cn2)c1] | methyl 4-chloro-3-{[(N-{2-[N-(6-fluoro(3-isoquinolyl))carbamoyloxy]ethyl}-N-methylcarbamoyl)amino]methyl}benzoate |
| 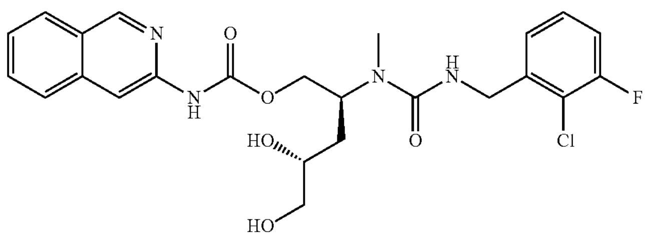 [SMILES: CN(C(=O)NCc1cccc(F)c1Cl)[C@H](COC(=O)Nc1cc2ccccc2cn1)C[C@@H](O)CO] | [(2S,4R)-2-({[(2-chloro-3-fluorophenyl)methyl]amino}-N-methylcarbonylamino)-4,5-dihydroxypentyloxy]-N-(3-isoquinolyl)carboxamide |
| 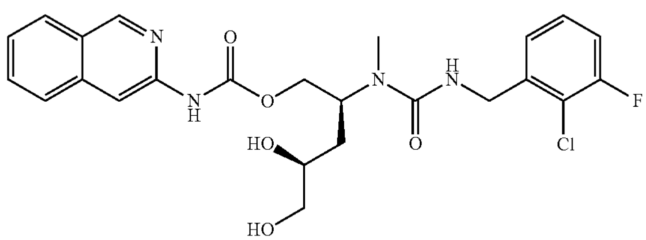 [SMILES: CN(C(=O)NCc1cccc(F)c1Cl)[C@H](COC(=O)Nc1cc2ccccc2cn1)C[C@H](O)CO] | [(2S,4S)-2-(({[(2-chloro-3-fluorophenyl)methyl]amino}-N-methylcarbonylamino)-4,5-dihydroxypentyloxy]-N-(3-isoquinolyl)carboxamide |
| 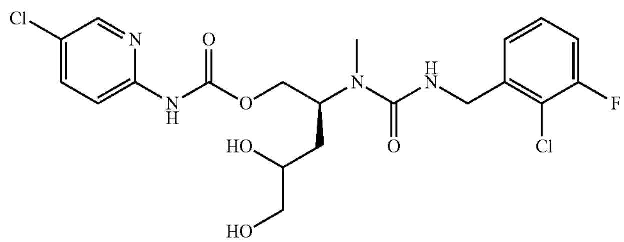 [SMILES: CN(C(=O)NCc1cccc(F)c1Cl)[C@H](COC(=O)Nc1ccc(Cl)cn1)CC(O)CO] | [(2S)-2-({[(2-chloro-3-fluorophenyl)methyl]amino}-N-methylcarbonylamino)-4,5-dihydroxypentyloxy]-N-(5-chloro(2-pyridyl))carboxamide |
| 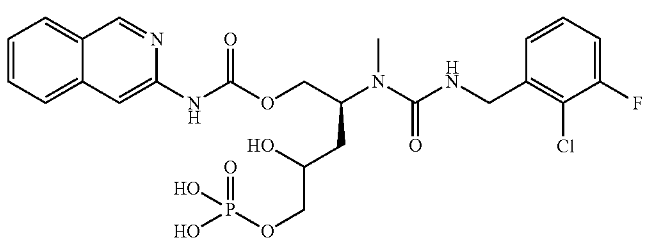 | (4S)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate |
| 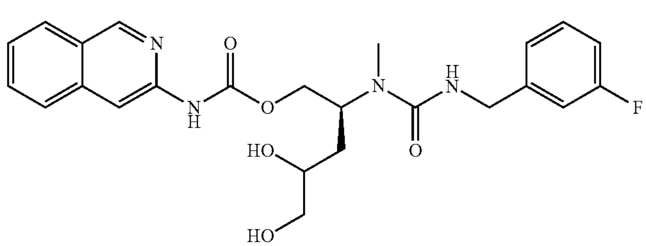 [SMILES: CN(C(=O)NCc1cccc(F)c1)[C@H](COC(=O)Nc1cc2ccccc2cn1)CC(O)CO] | [(2S)-2-({[(3-fluorophenyl)methyl]amino}-N-methylcarbonylamino)-4,5-dihydroxypentyloxy]-N-(3-isoquinolyl)carboxamide |

-continued

| Structure | Chemical Name |
|---|---|
| 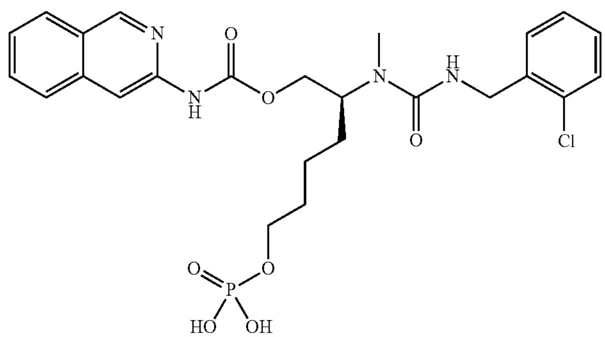 [SMILES: CN(C(=O)NCc1ccccc1Cl)[C@@H](CCCCOP(=O)(O)O)COC(=O)Nc1cc2ccccc2cn1] | (5S)-5-({[(2-chlorophenyl)methyl]amino}-N-methylcarbonylamino)-6-(N-(3-isoquinolyl)carbamoyloxy)hexyl dihydrogen phosphate |
| 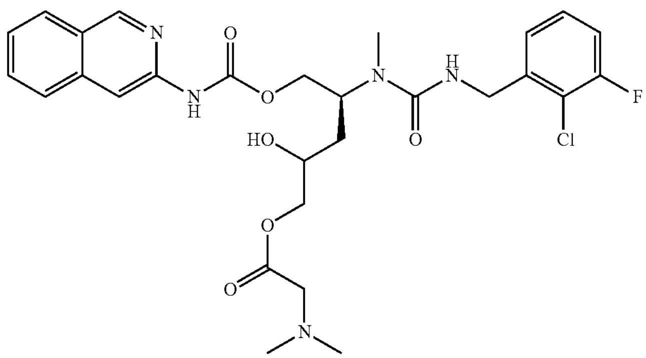 [SMILES: CN(C)CC(=O)OCC(O)C[C@@H](COC(=O)Nc1cc2ccccc2cn1)N(C)C(=O)NCc1cccc(F)c1Cl] | (4S)-4-({[(2-chloro-3-fluorophenyl)methyl]amino}-N-methylcarbonylamino)-2-hydroxy-5-(N-(3-isoquinolyl)carbamoyloxy)pentyl 2-(dimethylamino)acetate |
| 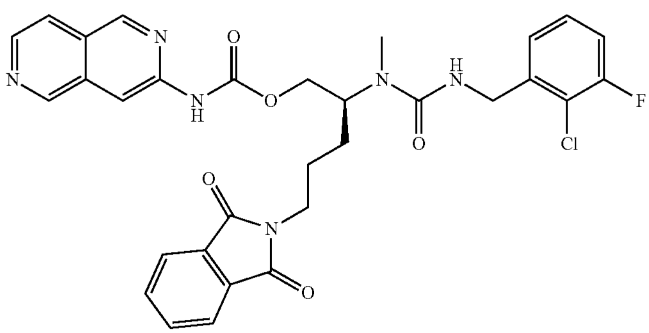 [SMILES: CN(C(=O)NCc1cccc(F)c1Cl)[C@@H](CCCN1C(=O)c2ccccc2C1=O)COC(=O)Nc1cc2cnccc2cn1] | N-{(1S)-4-(1,3-dioxobenzo[c]azolin-2-yl)-1-[(N-pyridino[3,4-d]pyridin-3-ylcarbamoyloxy)methyl]butyl}{[(2-chloro-3-fluorophenyl)methyl]amino}-N-methylcarboxamide |
| | N-{(1S)-4-amino-1-[(N-pyridino[3,4-d]pyridin-3-ylcarbamoyloxy)methyl]butyl}{[(2-chloro-3-fluorophenyl)methyl]amino}-N-methylcarboxamide |
| 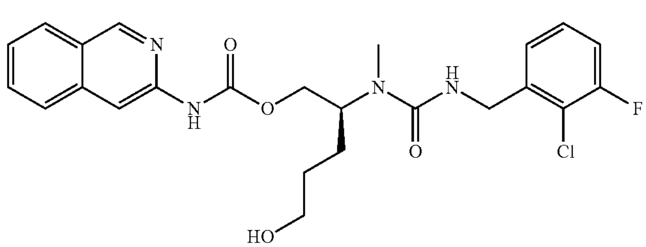 [SMILES: CN(C(=O)NCc1cccc(F)c1Cl)[C@@H](CCCO)COC(=O)Nc1cc2ccccc2cn1] | [(2S)-2-({[(2-chloro-3-fluorophenyl)methyl]amino}-N-methylcarbonylamino)-5-hydroxypentyloxy]-N-(3-isoquinolyl)carboxamide |

-continued

| Structure | Chemical Name |
|---|---|
| 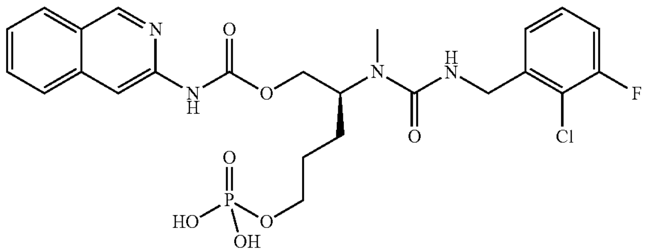 [SMILES: CN(C(=O)NCc1cccc(F)c1Cl)[C@@H](CCCOP(=O)(O)O)COC(=O)Nc1cc2ccccc2cn1] | (4S)-4-({[(2-chloro-3-fluorophenyl)methyl]amino}-N-methylcarbonylamino)-5-(N-(3-isoquinolyl)carbamoyloxy) pentyl dihydrogen phosphate |
| 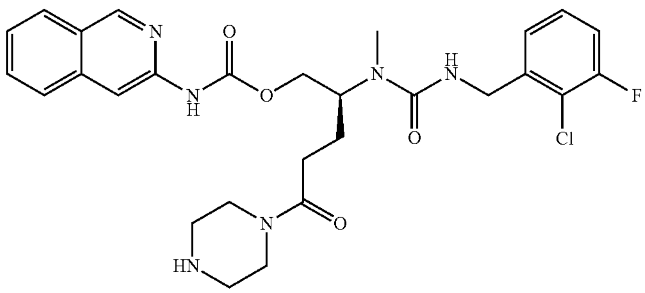 | [(2S)-2-({[(2-chloro-3-fluorophenyl)methyl]amino}-N-methylcarbonylamino)-5-oxo-5-piperazinylpentyloxy]-N-(3-isoquinolyl)carboxamide |
| 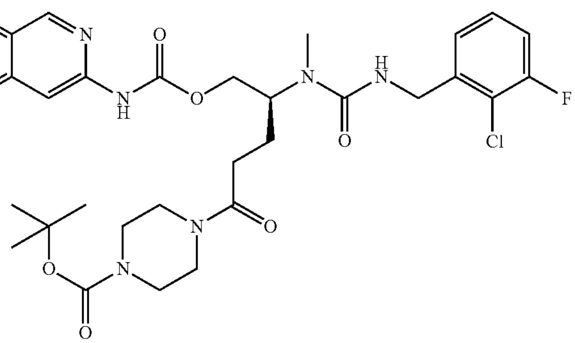 | tert-butyl 4-[(4S)-4-({[(2-chloro-3-fluorophenyl)methyl]amino}-N-methylcarbonylamino)-5-(N-(3-isoquinolyl)carbamoyloxy)pentanoyl] piperazinecarboxylate |
| 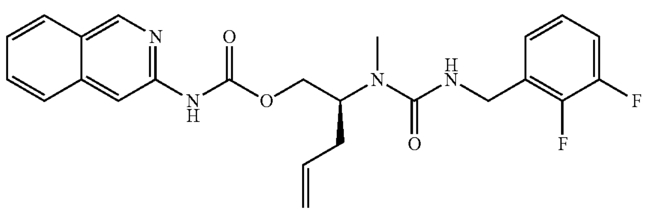 [SMILES: C=CC[C@@H](COC(=O)Nc1cc2ccccc2cn1)N(C)C(=O)NCc1cccc(F)c1F] | N-{(1S)-1-[(N-(3-isoquinolyl)carbamoyloxy)methyl]but-3-enyl}{[(2,3-difluorophenyl)methyl]amino}-N-methylcarboxamide |
| 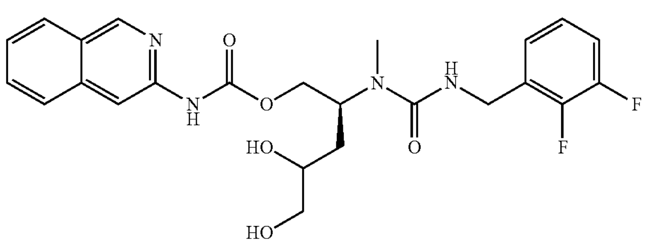 | N-{(1S)-3,4-dihydroxy-1-[(N-(3-isoquinolyl)carbamoyloxy)methyl]butyl}{[(2,3-difluorophenyl)methyl]amino}-N-methylcarboxamide |
| 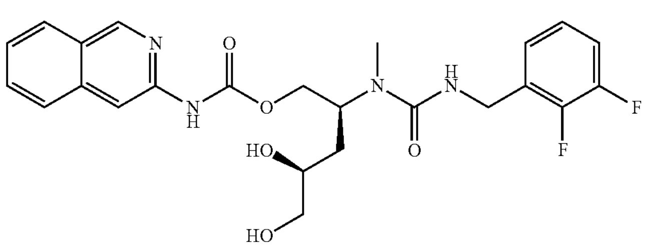 | N-{(1S,3S)-3,4-dihydroxy-1-[(N-(3-isoquinolyl)carbamoyloxy)methyl]butyl}{[(2,3-difluorophenyl)methyl]amino}-N-methylcarboxamide |

-continued

| Structure | Chemical Name |
|---|---|
| 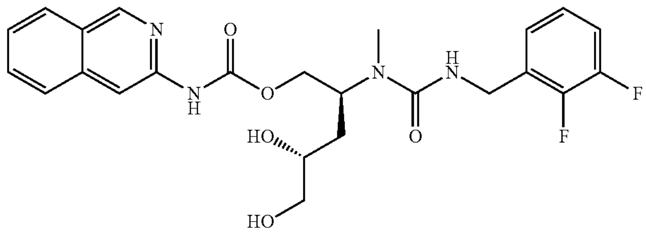 | N-{(1S,3R)-3,4-dihydroxy-1-[(N-(3-isoquinolyl)carbamoyloxy)methyl]butyl}{[(2,3-difluorophenyl)methyl]amino}-N-methylcarboxamide |
| 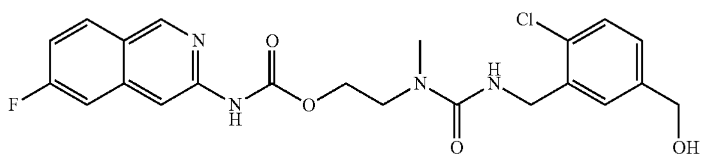 | ({[2-chloro-5-(hydroxymethyl)phenyl]methyl}amino)-N-{2-[N-(6-fluoro(3-isoquinolyl))carbamoyloxy]ethyl}-N-methylcarboxamide |
| 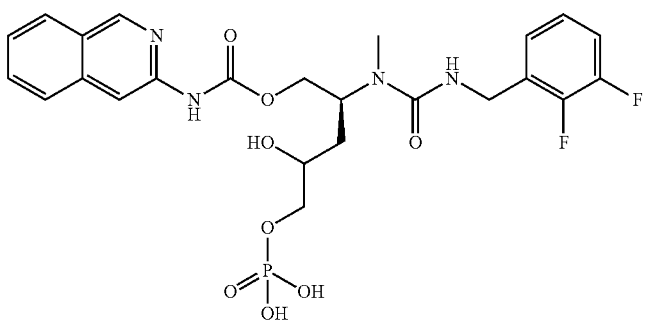 | (4S)-4-({[(2,3-difluorophenyl)methyl]amino}-N-methylcarbonylamino)-2-hydroxy-5-(N-(3-isoquinolyl)carbamoyloxy) pentyl dihydrogen phosphate |
| 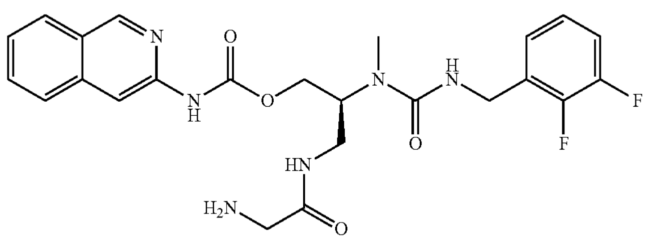 [SMILES: CN(C(=O)NCc1cccc(F)c1F)[C@@H](CNC(=O)CN)COC(=O)Nc1cc2ccccc2cn1] | N-[(2S)-2-({[(2,3-difluorophenyl)methyl]amino}-N-methylcarbonylamino)-3-(N-(3-isoquinolyl)carbamoyloxy)propyl]-2-aminoacetamide |
| 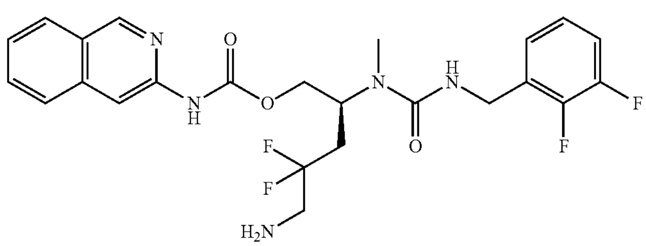 | N-{(1S)-4-amino-3,3-difluoro-1-[(N-(3-isoquinolyl)carbamoyloxy)methyl]butyl}{[(2,3-difluorophenyl)methyl]amino}-N-methylcarboxamide |
| 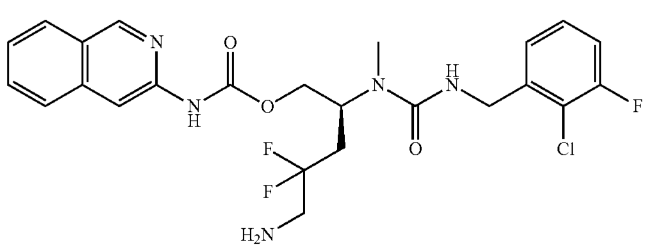 [SMILES: CN(C(=O)NCc1cccc(F)c1F)[C@H](COC(=O)Nc1cc2ccccc2cn1)CC(F)(F)CN] | N-{(1S)-4-amino-3,3-difluoro-1-[(N-(3-isoquinolyl)carbamoyloxy)methyl]butyl}{[(2-chloro-3-fluorophenyl)methyl]amino}-N-methylcarboxamide |

-continued

| Structure | Chemical Name |
|---|---|
| 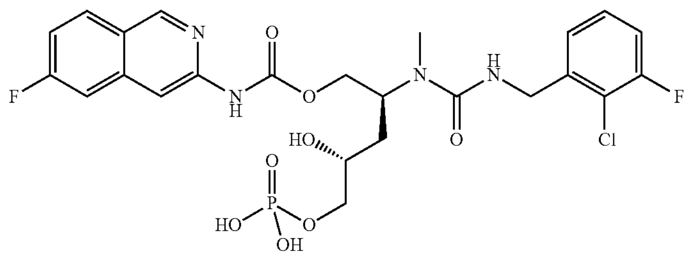 [SMILES: CN(C(=O)NCc1cccc(F)c1Cl)[C@H](COC(=O)Nc1cc2cc(F)ccc2cn1)C[C@@H](O)COP(=O)(O)O] | (4S,2R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 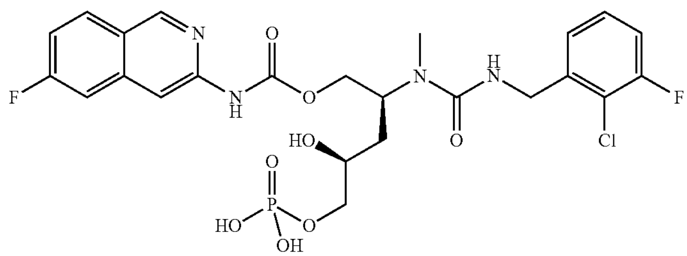 [SMILES: CN(C(=O)NCc1cccc(F)c1Cl)[C@H](COC(=O)Nc1cc2cc(F)ccc2cn1)C[C@H](O)COP(=O)(O)O] | (2S,4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 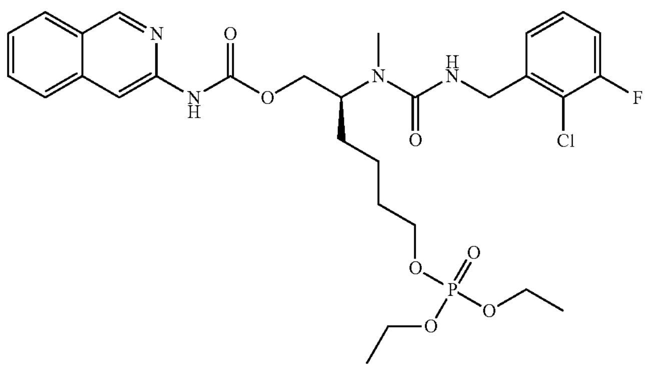 [SMILES: CCOP(=O)(OCC)OCCCC[C@@H](COC(=O)Nc1cc2ccccc2cn1)N(C)C(=O)NCc1cccc(F)c1Cl] | (5S)-5-({[(2-chloro-3-fluorophenyl)methyl]amino}-N-methylcarbonylamino)-6-(N-(3-isoquinolyl)carbamoyloxy)hexyl diethyl phosphate |
| 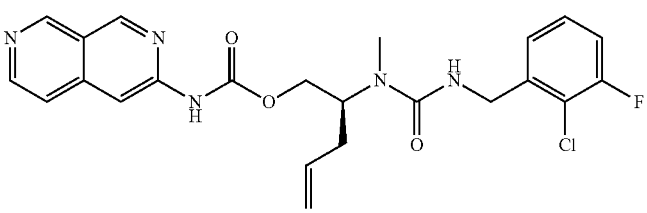 [SMILES: C=CC[C@@H](COC(=O)Nc1cc2ccncc2cn1)N(C)C(=O)NCc1cccc(F)c1Cl] | N-{(1S)-1-[(N-pyridino[4,3-d]pyridin-3-ylcarbamoyloxy)methyl]but-3-enyl}{[(2-chloro-3-fluorophenyl)methyl]amino}-N-methylcarboxamide |
| 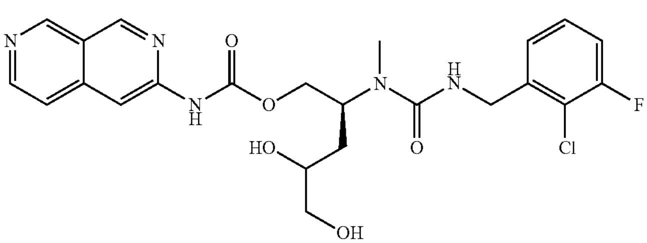 [SMILES: CN(C(=O)NCc1cccc(F)c1Cl)[C@H](COC(=O)Nc1cc2ccncc2cn1)CC(O)CO] | N-{(1S)-3,4-dihydroxy-1-[(N-pyridino[4,3-d]pyridin-3-ylcarbamoyloxy)methyl]butyl}{[(2-chloro-3-fluorophenyl)methyl]amino}-N-methylcarboxamide |
| 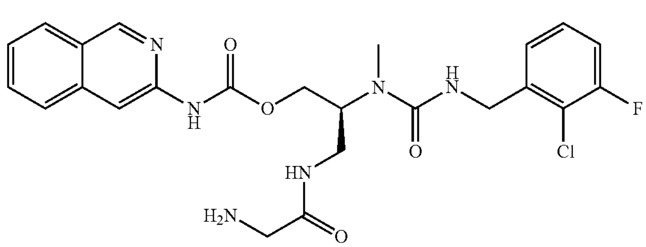 | N-[(2S)-2-({[(2-chloro-3-fluorophenyl)methyl]amino}-N-methylcarbonylamino)-3-(N-(3-isoquinolyl)carbamoyloxy)propyl]-2-aminoacetamide |

| Structure | Chemical Name |
|---|---|
| 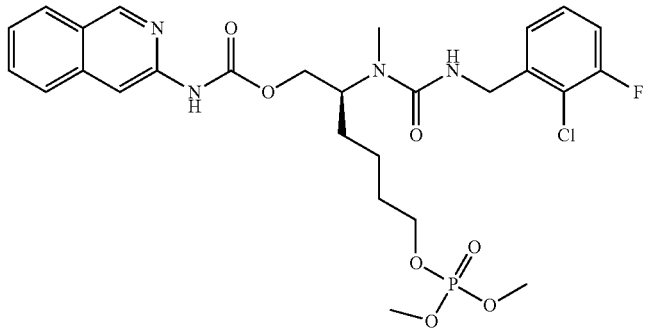 [SMILES: COP(=O)(OC)OCCCC[C@@H](COC(=O)Nc1cc2ccccc2cn1)N(C)C(=O)NCc1cccc(F)c1Cl] | (5S)-5-({[(2-chloro-3-fluorophenyl)methyl]amino}-N-methylcarbonylamino)-6-(N-(3-isoquinolyl)carbamoyloxy) hexyl dimethyl phosphate |
| 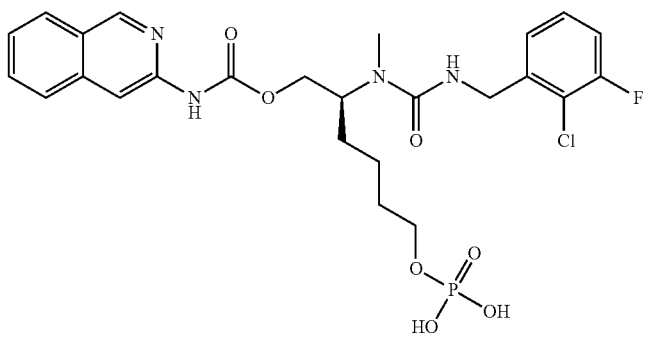 [SMILES: CN(C(=O)NCc1cccc(F)c1Cl)[C@@H](CCCCOP(=O)(O)O)COC(=O)Nc1cc2ccccc2cn1] | (5S)-5-({[(2-chloro-3-fluorophenyl)methyl]amino}-N-methylcarbonylamino)-6-(N-(3-isoquinolyl)carbamoyloxy)hexyl dihydrogen phosphate |
| 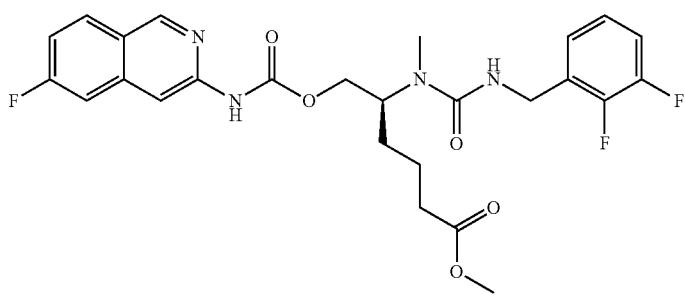 [SMILES: COC(=O)CCC[C@@H](COC(=O)Nc1cc2cc(F)ccc2cn1)N(C)C(=O)NCc1cccc(F)c1F] | methyl (5S)-5-({[(2,3-difluorophenyl)methyl]amino}-N-methylcarbonylamino)-6-[N-(6-fluoro(3-isoquinolyl))carbamoyloxy] hexanoate |
| 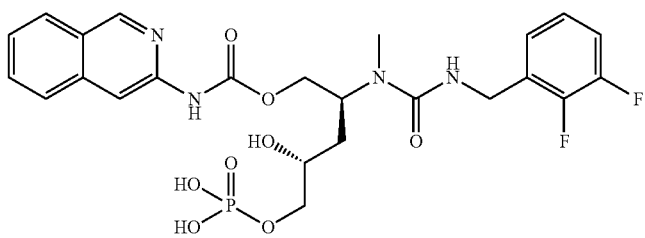 | (4S,2R)-4-({[(2,3-difluorophenyl)methyl]amino}-N-methylcarbonylamino)-2-hydroxy-5-(N-(3-isoquinolyl)carbamoyloxy) pentyl dihydrogen phosphate |
| 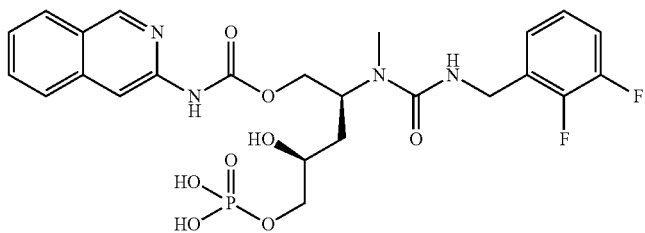 [SMILES: CN(C(=O)NCc1cccc(F)c1F)[C@H](COC(=O)Nc1cc2ccccc2cn1)C[C@H](O)COP(=O)(O)O] | (2S,4S)-4-({[(2,3-difluorophenyl)methyl]amino}-N-methylcarbonylamino)-2-hydroxy-5-(N-(3-isoquinolyl)carbamoyloxy) pentyl dihydrogen phosphate |

| Structure | Chemical Name |
|---|---|
| 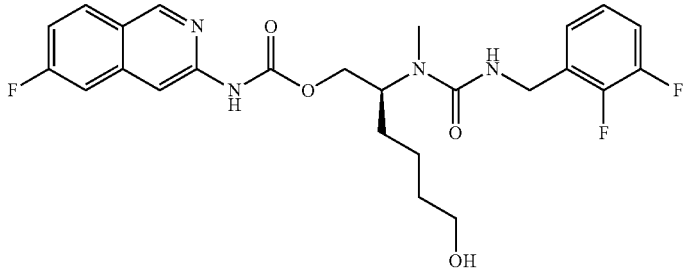 [SMILES: CN(C(=O)NCc1cccc(F)c1F)[C@@H](CCCCO)COC(=O)Nc1cc2cc(F)ccc2cn1] | [(2S)-2-({[(2,3-difluorophenyl)methyl]amino}-N-methylcarbonylamino)-6-hydroxyhexyloxy]-N-(6-fluoro(3-isoquinolyl))carboxamide |
| 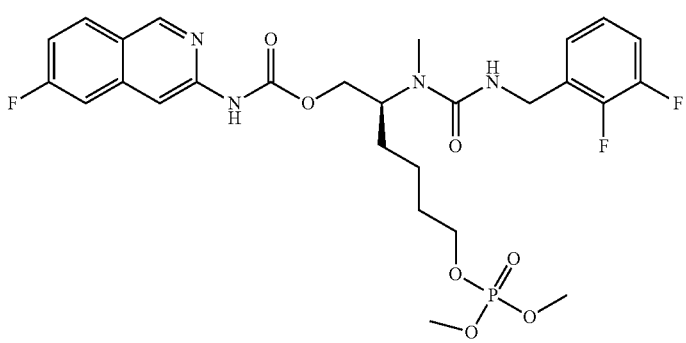 [SMILES: COP(=O)(OC)OCCCC[C@@H](COC(=O)Nc1cc2cc(F)ccc2cn1)N(C)C(=O)NCc1cccc(F)c1F] | (5S)-5-({[(2,3-difluorophenyl)methyl]amino}-N-methylcarbonylamino)-6-[N-(6-fluoro(3-isoquinolyl))carbamoyloxy]hexyl dimethyl phosphate |
| 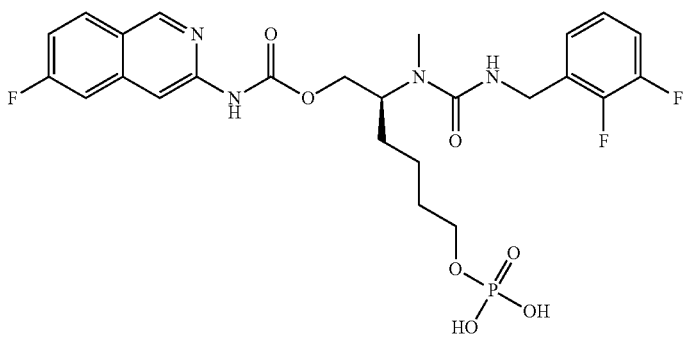 [SMILES: CN(C(=O)NCc1cccc(F)c1F)[C@@H](CCCCOP(=O)(O)O)COC(=O)Nc1cc2cc(F)ccc2cn1] | (5S)-5-({[(2,3-difluorophenyl)methyl]amino}-N-methylcarbonylamino)-6-(N-(6-fluoro(3-isoquinolyl))carbamoyloxy]hexyl dihydrogen phosphate |
| 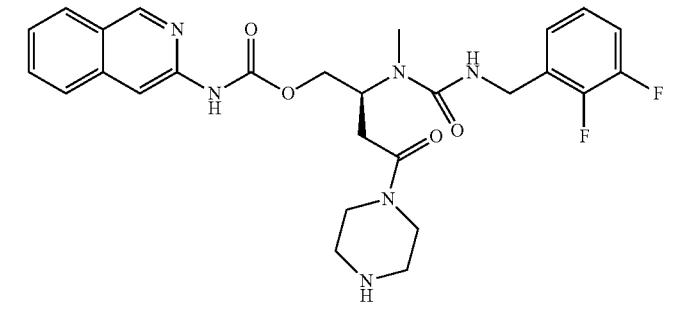 [SMILES: CN(C(=O)NCc1cccc(F)c1F)[C@H](COC(=O)Nc1cc2ccccc2cn1)CC(=O)N1CCNCC1] | [(2S)-2-({[(2,3-difluorophenyl)methyl]amino}-N-methyl-carbonylamino)-4-oxo-4-piperazinylbutoxy]-N-(3-isoquinolyl)carboxamide |
| 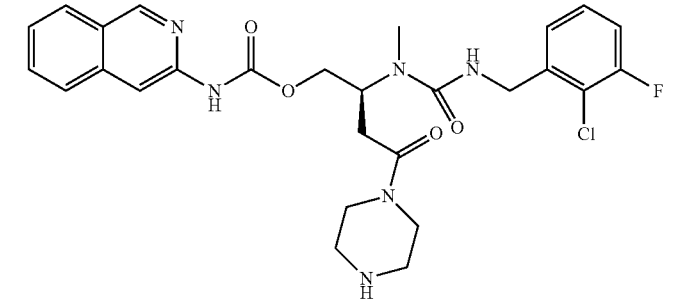 [SMILES: CN(C(=O)NCc1cccc(F)c1Cl)[C@H](COC(=O)Nc1cc2ccccc2cn1)CC(=O)N1CCNCC1] | [(2S)-2-({[(2-chloro-3-fluorophenyl)methyl]amino)-N-methylcarbonylamino)-4-oxo-4-piperazinylbutoxy]-N-(3-isoquinolyl)carboxamide |

| Structure | Chemical Name |
|---|---|
| 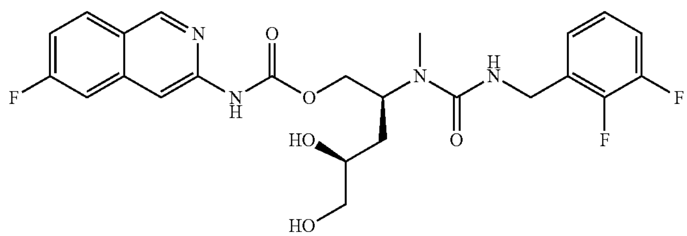 [SMILES: CN(C(=O)NCc1cccc(F)c1F)[C@H](COC(=O)Nc1cc2cc(F)ccc2cn1)C[C@H](O)CO] | [(2S,4S)-2-({[(2,3-difluorophenyl)methyl]amino}-N-methylcarbonylamino)-4,5-dihydroxypentyloxy]-N-(6-fluoro(3-isoquinolyl))carboxamide |
| 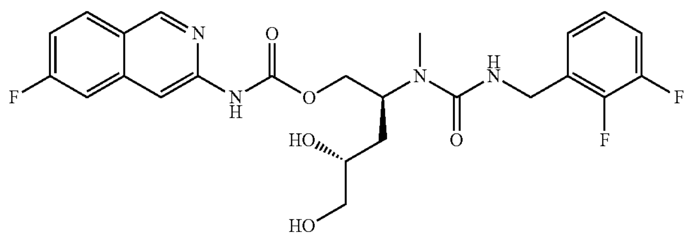 [SMILES: CN(C(=O)NCc1cccc(F)c1F)[C@H](COC(=O)Nc1cc2cc(F)ccc2cn1)C[C@@H](O)CO] | [(2S,4R)-2-({[(2,3-difluorophenyl)methyl]amino}-N-methylcarbonylamino)-4,5-dihydroxypentyloxy]-N-(6-fluoro(3-isoquinolyl))carboxamide |
| 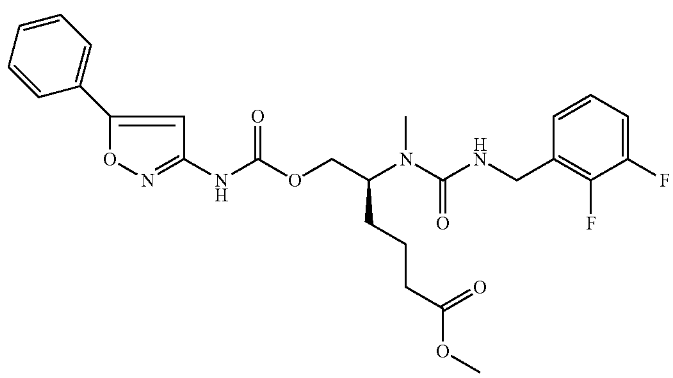 [SMILES: COC(=O)CCC[C@@H](COC(=O)Nc1cc(-c2ccccc2)on1)N(C)C(=O)NCc1cccc(F)c1F] | methyl (5S)-5-({[(2,3-difluorophenyl)methyl]amino}-N-methylcarbonylamino)-6-[N-(5-phenylisoxazol-3-yl)carbamoyloxy]hexanoate |
| 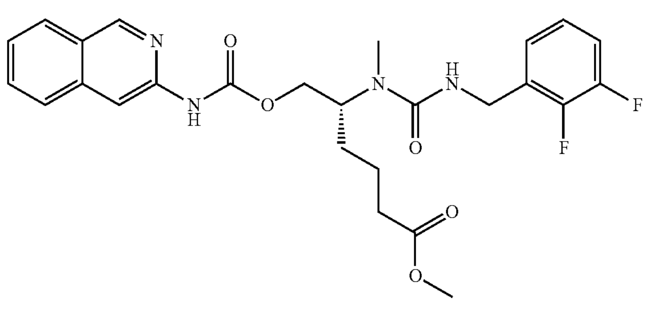 [SMILES: COC(=O)CCC[C@H](COC(=O)Nc1cc2ccccc2cn1)N(C)C(=O)NCc1cccc(F)c1F] | methyl (5R)-5-({[(2,3-difluorophenyl)methyl]amino}-N-methylcarbonylamino)-6-(N-(3-isoquinolyl)carbamoyloxy)hexanoate |
| 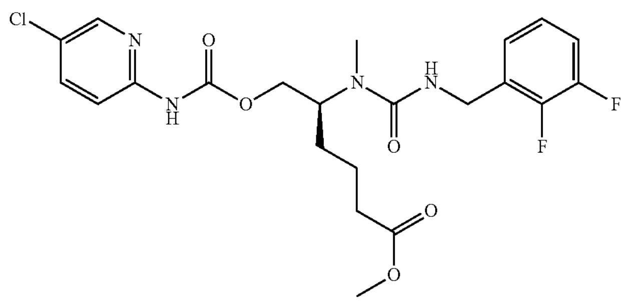 [SMILES: COC(=O)CCC[C@@H](COC(=O)Nc1ccc(Cl)cn1)N(C)C(=O)NCc1cccc(F)c1F] | methyl (5S)-5-({[(2,3-difluorophenyl)methyl]amino}-N-methylcarbonylamino)-6-[N-(5-chloro(2-pyridyl))carbamoyloxy]hexanoate |

| Structure | Chemical Name |
|---|---|
| 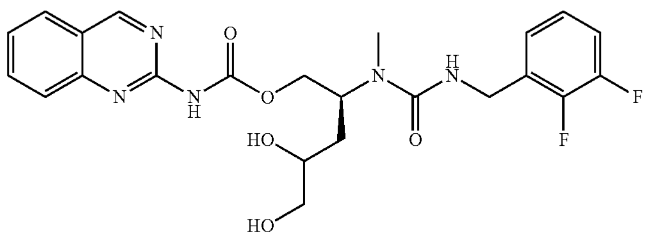 [SMILES: CN(C(=O)NCc1cccc(F)c1F)[C@H](COC(=O)Nc1ncc2ccccc2n1)CC(O)CO] | N-{(1S)-3,4-dihydroxy-1-[(N-quinazolin-2-ylcarbamoyloxy)methyl]butyl}{[(2,3-difluorophenyl)methyl]amino}-N-methylcarboxamide |
| 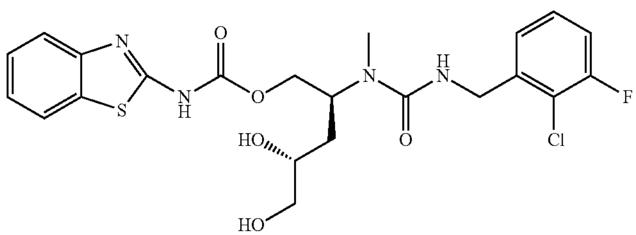 [SMILES: CN(C(=O)NCc1cccc(F)c1Cl)[C@H](COC(=O)Nc1nc2ccccc2s1)C[C@@H](O)CO] | [(2S,4R)-2-({[(2-chloro-3-fluorophenyl)methyl]amino}-N-methylcarbonylamino)-4,5-dihydroxypentyloxy]-N-benzothiazol-2-ylcarboxamide |
| 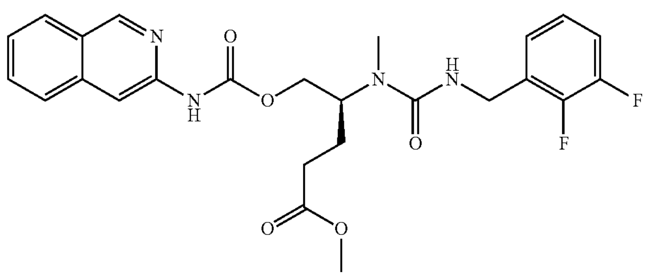 [SMILES: COC(=O)CC[C@@H](COC(=O)Nc1cc2ccccc2cn1)N(C)C(=O)NCc1cccc(F)c1F] | methyl (4S)-4-({[(2,3-difluorophenyl)methyl]amino}-N-methylcarbonylamino)-5-(N-(3-isoquinolyl)carbamoyloxy)pentanoate |
| 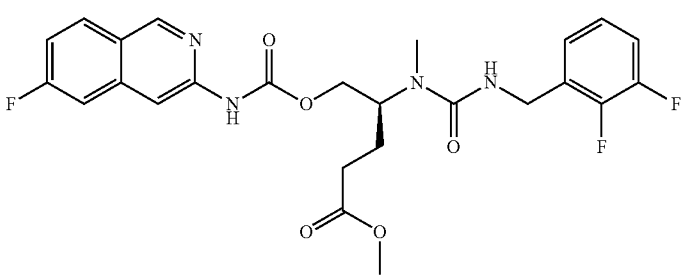 [SMILES: COC(=O)CC[C@@H](COC(=O)Nc1cc2cc(F)ccc2cn1)N(C)C(=O)NCc1cccc(F)c1F] | methyl (4S)-4-({[(2,3-difluorophenyl)methyl]amino}-N-methylcarbonylamino)-5-[N-(6-fluoro(3-isoquinolyl))carbamoyloxy]pentanoate |
| 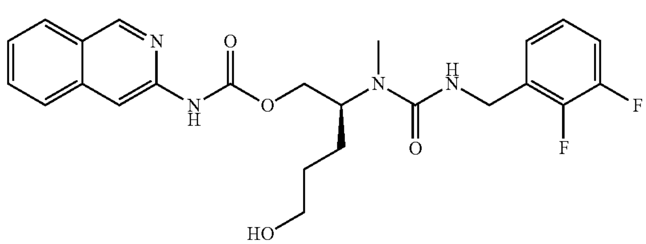 [SMILES: CN(C(=O)NCc1cccc(F)c1F)[C@@H](CCCO)COC(=O)Nc1cc2ccccc2cn1] | N-{(1S)-4-hydroxy-1-[(N-(3-isoquinolyl)carbamoyloxy)methyl]butyl}{[(2,3-difluorophenyl)methyl]amino}-N-methylcarboxamide |
| 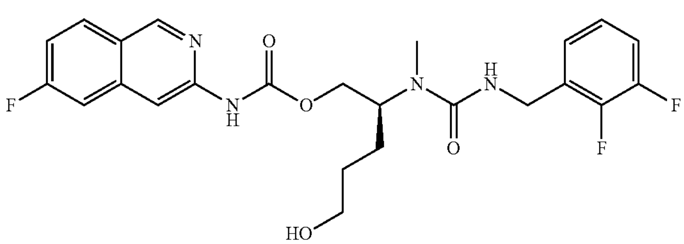 [SMILES: CN(C(=O)NCc1cccc(F)c1F)[C@@H](CCCO)COC(=O)Nc1cc2cc(F)ccc2cn1] | N-((1S)-1-{[N-(6-fluoro(3-isoquinolyl))carbamoyloxy]methyl}-4-hydroxybutyl){[(2,3-difluorophenyl)methyl]amino}-N-methylcarboxamide |

| Structure | Chemical Name |
|---|---|
| 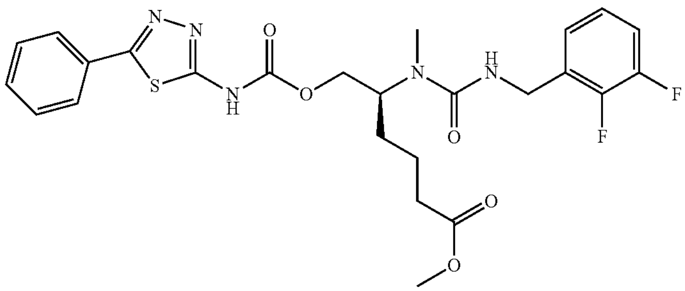 [SMILES: COC(=O)CCC[C@@H](COC(=O)Nc1nnc(-c2ccccc2)s1)N(C)C(=O)NCc1cccc(F)c1F] | methyl (5S)-5-({[(2,3-difluorophenyl)methyl]amino}-N-methylcarbonylamino)-6-[N-(5-phenyl(1,3,4-thiadiazol-2-yl))carbamoyloxy]hexanoate |
| 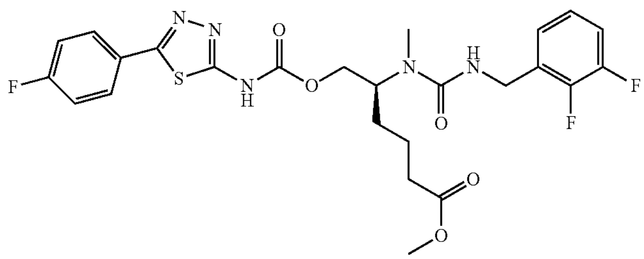 [SMILES: COC(=O)CCC[C@@H](COC(=O)Nc1nnc(-c2ccc(F)cc2)s1)N(C)C(=O)NCc1cccc(F)c1F] | methyl (5S)-5-({[(2,3-difluorophenyl)methyl]amino}-N-methylcarbonylamino)-6-{N-[5-(4-fluorophenyl)(1,3,4-thiadiazol-2-yl)]carbamoyloxy}hexanoate |
| 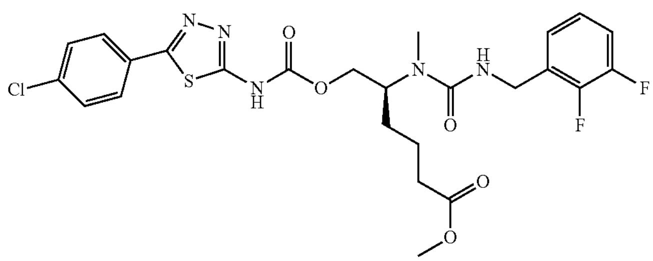 [SMILES: COC(=O)CCC[C@@H](COC(=O)Nc1nnc(-c2ccc(Cl)cc2)s1)N(C)C(=O)NCc1cccc(F)c1F] | methyl (5S)-5-({[(2,3-difluorophenyl)methyl]amino}-N-methylcarbonylamino)-6-{N-[5-(4-chlorophenyl)(1,3,4-thiadiazol-2-yl)]carbamoyloxy}hexanoate |
| 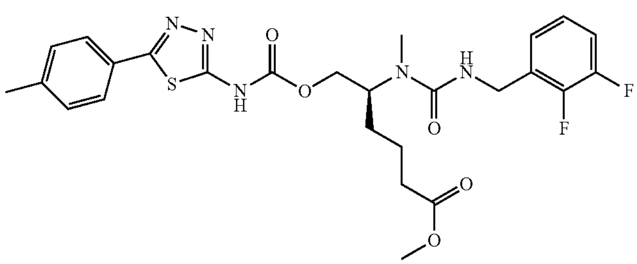 [SMILES: COC(=O)CCC[C@@H](COC(=O)Nc1nnc(-c2ccc(C)cc2)s1)N(C)C(=O)NCc1cccc(F)c1F] | methyl (5S)-5-({[(2,3-difluorophenyl)methyl]amino}-N-methylcarbonylamino)-6-{N-[5-(4-methylphenyl)(1,3,4-thiadiazol-2-yl)]carbamoyloxy}hexanoate |
| 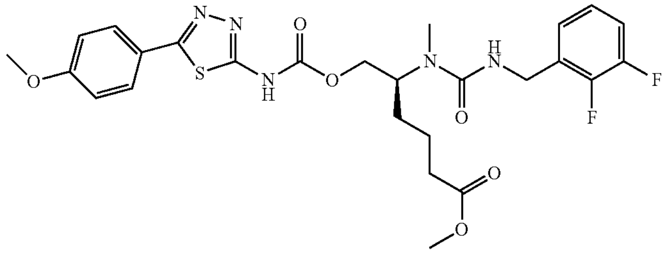 [SMILES: COC(=O)CCC[C@@H](COC(=O)Nc1nnc(-c2ccc(OC)cc2)s1)N(C)C(=O)NCc1cccc(F)c1F] | methyl (5S)-5-({[(2,3-difluorophenyl)methyl]amino}-N-methylcarbonylamino)-6-{N-[5-(4-methoxyphenyl)(1,3,4-thiadiazol-2-yl)]carbamoyloxy}hexanoate |

| Structure | Chemical Name |
|---|---|
| 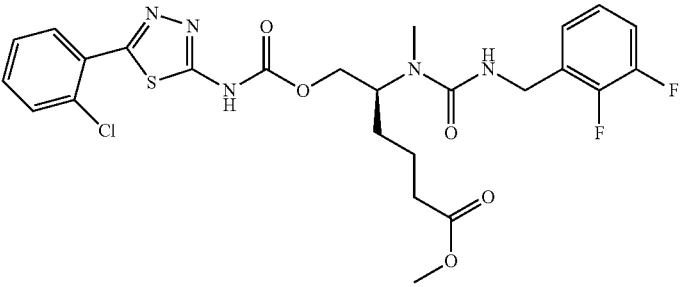 [SMILES: COC(=O)CCC[C@@H](COC(=O)Nc1nnc(-c2ccccc2Cl)s1)N(C)C(=O)NCc1cccc(F)c1F] | methyl (5S)-5-({[(2,3-difluorophenyl)methyl]amino}-N-methylcarbonylamino)-6-{N-[5-(2-chlorophenyl)(1,3,4-thiadiazol-2-yl)]carbamoyloxy}hexanoate |
| 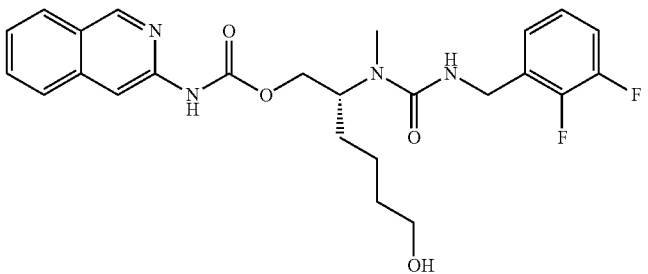 [SMILES: CN(C(=O)NCc1cccc(F)c1F)[C@H](CCCCO)COC(=O)Nc1cc2ccccc2cn1] | [(2R)-2-({[(2,3-difluorophenyl)methyl]amino}-N-methylcarbonylamino)-6-hydroxyhexyloxy]-N-(3-isoquinolyl)carboxamide |
| 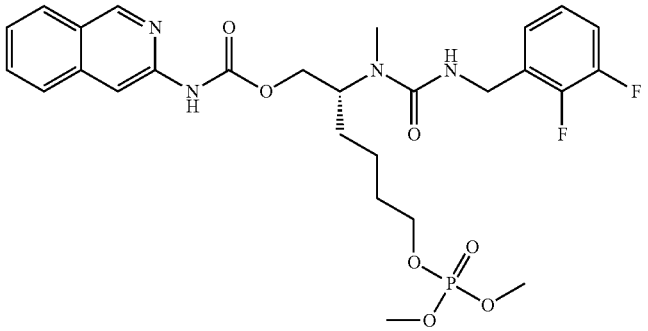 [SMILES: COP(=O)(OC)OCCCC[C@H](COC(=O)Nc1cc2ccccc2cn1)N(C)C(=O)NCc1cccc(F)c1F] | (5R)-5-({[(2,3-difluorophenyl)methyl]amino}-N-methylcarbonylamino)-6-(N-(3-isoquinolyl)carbamoyloxy)hexyl dimethyl phosphate |
| 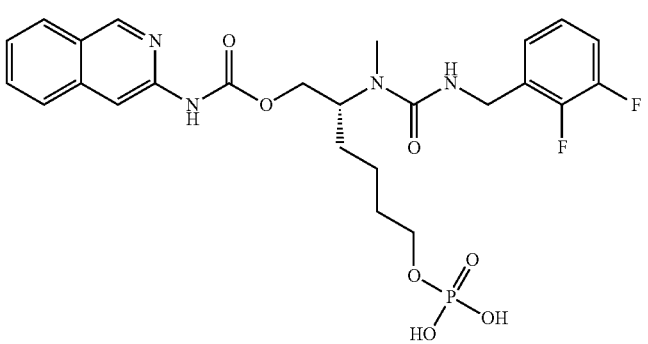 [SMILES: CN(C(=O)NCc1cccc(F)c1F)[C@H](CCCCOP(=O)(O)O)COC(=O)Nc1cc2ccccc2cn1] | (5R)-5-({[(2,3-difluorophenyl)methyl]amino}-N-methylcarbonylamino)-6-(N-(3-isoquinolyl)carbamoyloxy)hexyl dihydrogen phosphate |
| 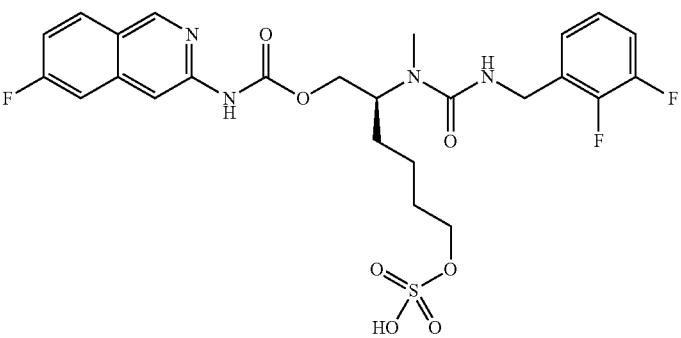 [SMILES: CN(C(=O)NCc1cccc(F)c1F)[C@@H](CCCCOS(=O)(=O)O)COC(=O)Nc1cc2cc(F)ccc2cn1] | (5S)-5-({[(2,3-difluorophenyl)methyl]amino}-N-methylcarbonylamino)-6-[N-(6-fluoro(3-isoquinolyl))carbamoyloxy]hexyl hydroxysulfonate |

| Structure | Chemical Name |
|---|---|
| 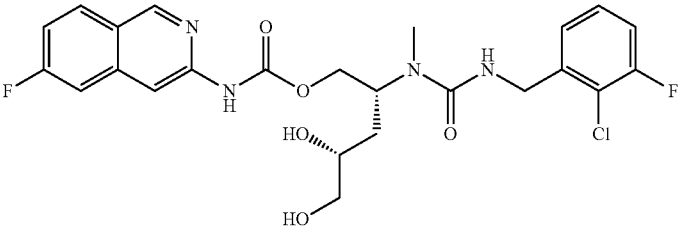 [SMILES: CN(C(=O)NCc1cccc(F)c1Cl)[C@@H](COC(=O)Nc1cc2cc(F)ccc2cn1)C[C@@H](O)CO] | [(2R,4R)-2-({[(2-chloro-3-fluorophenyl)methyl]amino}-N-methylcarbonylamino)-4,5-dihydroxypentyloxy]-N-(6-fluoro(3-isoquinolyl))carboxamide |
| 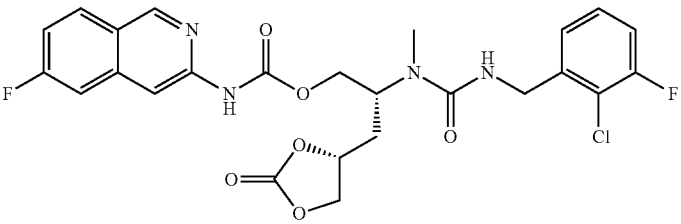 [SMILES: CN(C(=O)NCc1cccc(F)c1Cl)[C@@H](COC(=O)Nc1cc2cc(F)ccc2cn1)C[C@@H]1COC(=O)O1] | [(2R)-3-((4R)-2-oxo(1,3-dioxolan-4-yl))-2-({[(2-chloro-3-fluorophenyl)methyl]amino}-N-methylcarbonylamino)propoxy]-N-(6-fluoro(3-isoquinolyl))carboxamide |
| 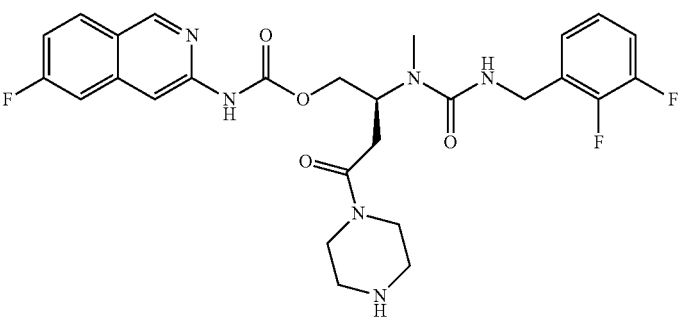 [SMILES: CN(C(=O)NCc1cccc(F)c1F)[C@H](COC(=O)Nc1cc2cc(F)ccc2cn1)CC(=O)N1CCNCC1] | [(2S)-2-({[(2,3-difluorophenyl)methyl]amino}-N-methylcarbonylamino)-4-oxo-4-piperazinylbutoxy]-N-(6-fluoro(3-isoquinolyl))carboxamide |
| 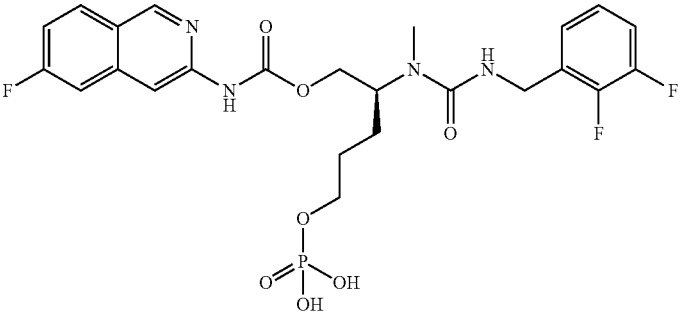 [SMILES: CN(C(=O)NCc1cccc(F)c1F)[C@@H](CCCOP(=O)(O)O)COC(=O)Nc1cc2cc(F)ccc2cn1] | (4S)-4-({[(2,3-difluorophenyl)methyl]amino}-N-methylcarbonylamino)-5-[N-(6-fluoro(3-isoquinolyl))carbamoyloxy]pentyl dihydrogen phosphate |
| 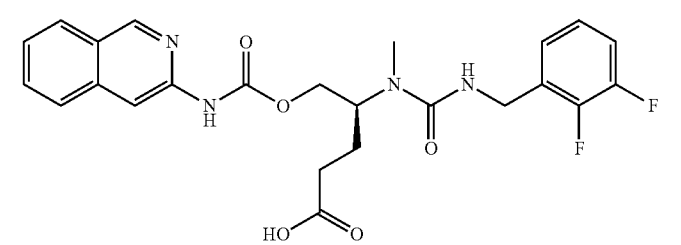 | (4S)-4-({[(2,3-difluorophenyl)methyl]amino}-N-methylcarbonylamino)-5-(N-(3-isoquinolyl)carbamoyloxy)pentanoic acid |
| 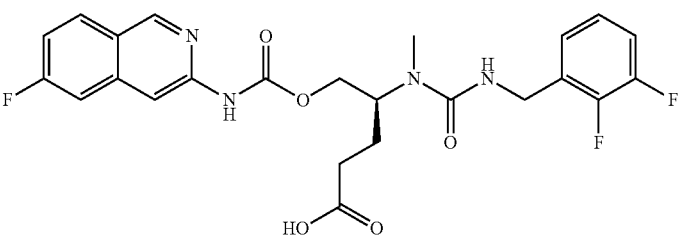 [SMILES: CN(C(=O)NCc1cccc(F)c1F)[C@@H](CCC(=O)O)COC(=O)Nc1cc2cc(F)ccc2cn1] | (4S)-4-({[(2,3-difluorophenyl)methyl]amino}-N-methylcarbonylamino)-5-[N-(6-fluoro(3-isoquinolyl))carbamoyloxy]pentanoic acid |

| Structure | Chemical Name |
|---|---|
| 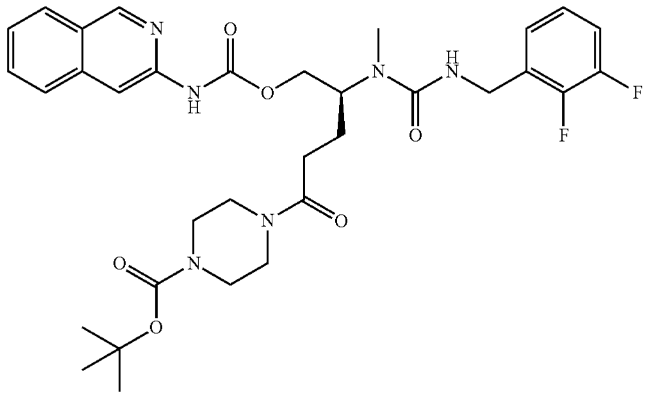 [SMILES: CN(C(=O)NCc1cccc(F)c1F)[C@@H](CCC(=O)N1CCN(C(=O)OC(C)(C)C)CC1)COC(=O)Nc1cc2ccccc2cn1] | tert-butyl 4-[(4S)-4-({[(2,3-difluorophenyl)methyl]amino}-N-methylcarbonylamino)-5-(N-(3-isoquinolyl)carbamoyloxy)pentanoyl]piperazinecarboxylate |
| 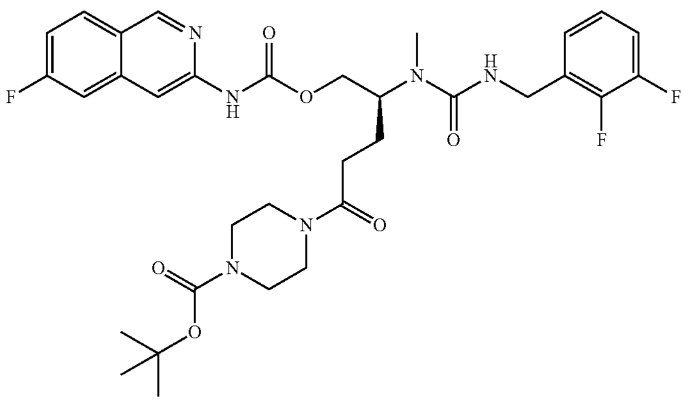 [SMILES: CN(C(=O)NCc1cccc(F)c1F)[C@@H](CCC(=O)N1CCN(C(=O)OC(C)(C)C)CC1)COC(=O)Nc1cc2cc(F)ccc2cn1] | tert-butyl 4-[(4S)-4-({[(2,3-difluorophenyl)methyl]amino}-N-methylcarbonylamino)-5-[N-(6-fluoro(3-isoquinolyl))carbamoyloxy]pentanoyl]piperazinecarboxylate |
| 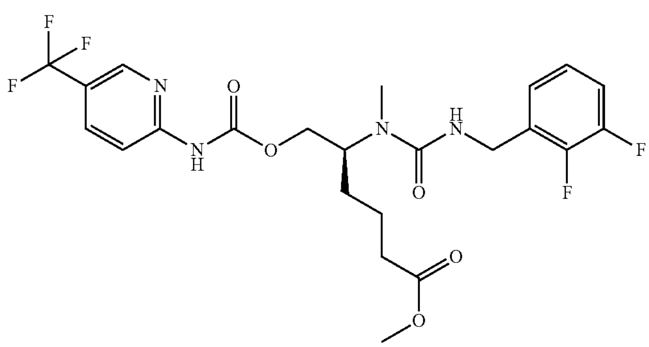 [SMILES: COC(=O)CCC[C@@H](COC(=O)Nc1ccc(C(F)(F)F)cn1)N(C)C(=O)NCc1cccc(F)c1F] | methyl (5S)-5-({[(2,3-difluorophenyl)methyl]amino}-N-methylcarbonylamino)-6-{N-[5-(trifluoromethyl)(2-pyridyl)]carbamoyloxy}hexanoate |
| 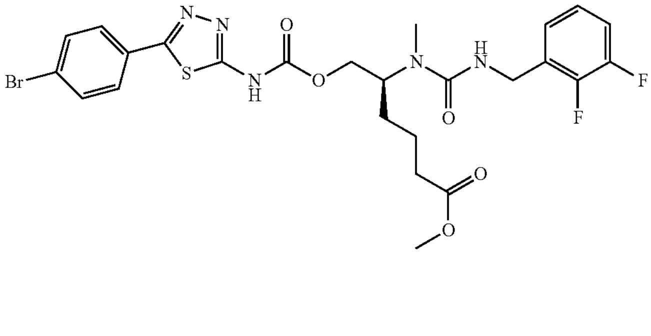 | methyl (5S)-5-({[(2,3-difluorophenyl)methyl]amino}-N-methylcarbonylamino)-6-{N-[5-(4-bromophenyl)(1,3,4-thiadiazol-2-yl)]carbamoyloxy}hexanoate |

| Structure | Chemical Name |
|---|---|
| 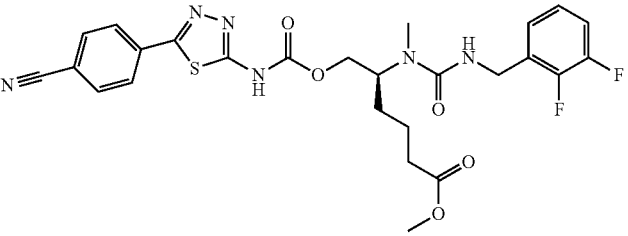 [SMILES: COC(=O)CCC[C@@H](COC(=O)Nc1nnc(-c2ccc(C#N)cc2)s1)N(C)C(=O)NCc1cccc(F)c1F] | methyl (5S)-5-({[(2,3-difluorophenyl)methyl]amino}-N-methylcarbonylamino)-6-{N-[5-(4-cyanophenyl)(1,3,4-thiadiazol-2-yl)]carbamoyloxy}hexanoate |
| 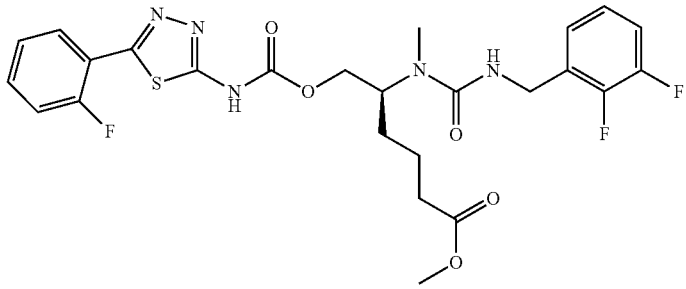 | methyl (5S)-5-({[(2,3-difluorophenyl)methyl]amino}-N-methylcarbonylamino)-6-{N-[5-(2-fluorophenyl)(1,3,4-thiadiazol-2-yl)]carbamoyloxy}hexanoate |
| 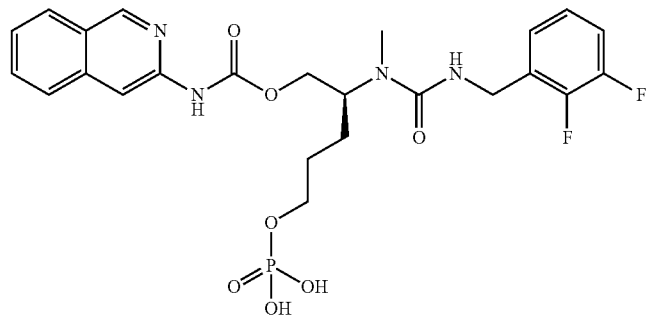 | (4S)-4-({[(2,3-difluorophenyl)methyl]amino}-N-methylcarbonylamino)-5-(N-(3-isoquinolyl)carbamoyloxy)pentyl dihydrogen phosphate |
| 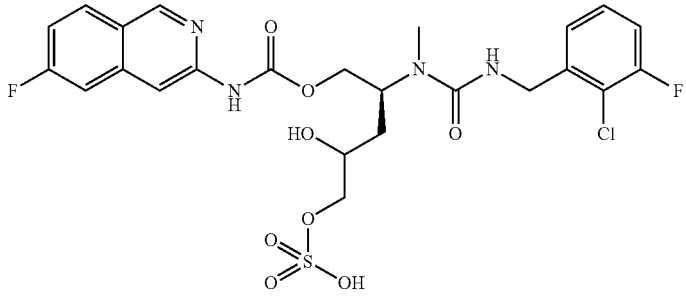 [SMILES: CN(C(=O)NCc1cccc(F)c1Cl)[C@H](COC(=O)Nc1cc2cc(F)ccc2cn1)CC(O)COS(=O)(=O)O] | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl hydroxysulfonate |
| 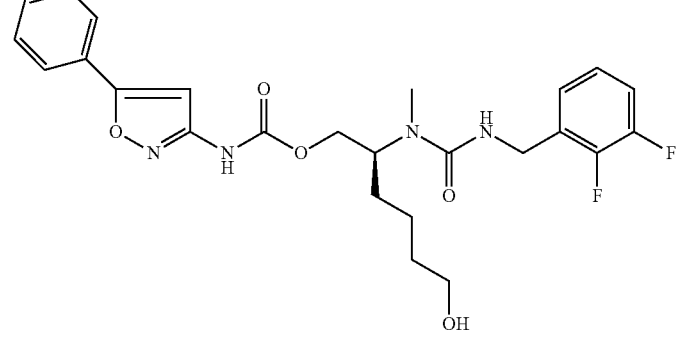 | N-((1S)-5-hydroxy-1-{[N-(5-phenylisoxazol-3-yl)carbamoyloxy]methyl}pentyl){[(2,3-difluorophenyl)methyl]amino}-N-methylcarboxamide |

| Structure | Chemical Name |
|---|---|
| 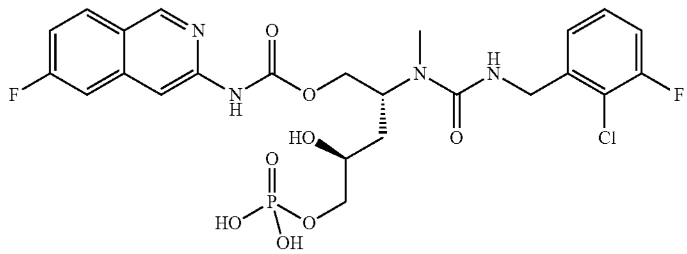 [SMILES: CN(C(=O)NCc1cccc(F)c1Cl)[C@@H](COC(=O)Nc1cc2cc(F)ccc2cn1)C[C@H](O)COP(=O)(O)O] | (2S,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| | (2R,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 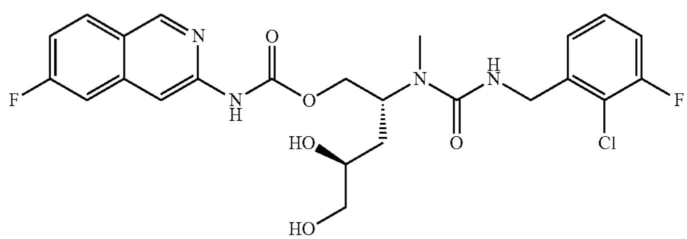 [SMILES: CN(C(=O)NCc1cccc(F)c1Cl)[C@@H](COC(=O)Nc1cc2cc(F)ccc2cn1)C[C@H](O)CO] | N-((3S,1R)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| | N-{(1R)-1-[((4S)-2-oxo(1,3-dioxolan-4-yl))methyl]-2-[N-(6-fluoro(3-isoquinolyl))carbamoyloxyethyl}{[(2-chloro-3-fluorophenyl)methyl]amino}-N-methylcarboxamide |
| 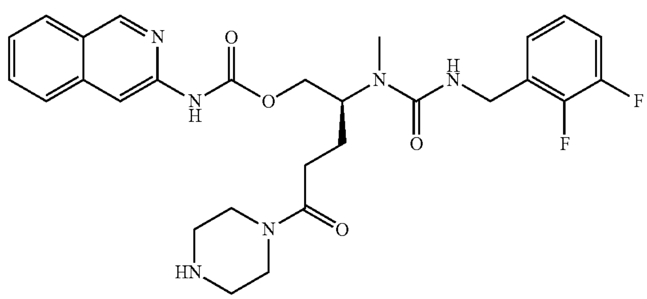 [SMILES: CN(C(=O)NCc1cccc(F)c1F)[C@@H](CCC(=O)N1CCNCC1)COC(=O)Nc1cc2ccccc2cn1] | N-{(1S)-1-[(N-(3-isoquinolyl)carbamoyloxy)methyl]-4-oxo-4-piperazinylbutyl}{[(2,3-difluorophenyl)methyl]amino}-N-methylcarboxamide |
| 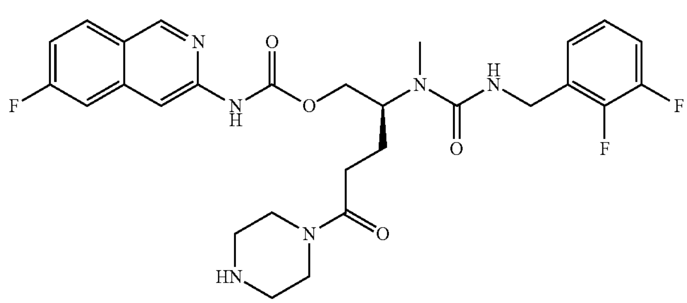 [SMILES: CN(C(=O)NCc1cccc(F)c1F)[C@@H](CCC(=O)N1CCNCC1)COC(=O)Nc1cc2cc(F)ccc2cn1] | N-((1S)-1-{[N-(6-fluoro(3-isoquinolyl))carbamoyloxy]methyl}-4-oxo-4-piperazinylbutyl){[(2,3-difluorophenyl)methyl]amino}-N-methylcarboxamide |

| Structure | Chemical Name |
|---|---|
| 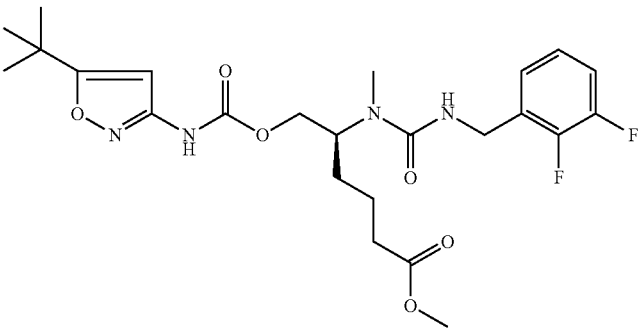 [SMILES: COC(=O)CCC[C@@H](COC(=O)Nc1cc(C(C)(C)C)on1)N(C)C(=O)NCc1cccc(F)c1F] | methyl (5S)-5-({[[(2,3-difluorophenyl)methyl]amino}-N-methylcarbonylamino)-6-{N-[5-(tert-butyl)isoxazol-3-yl]carbamoyloxy}hexanoate |
| 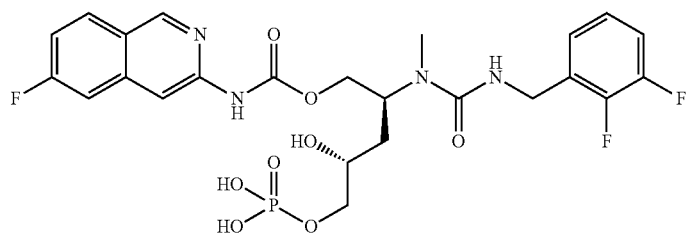 [SMILES: CN(C(=O)NCc1cccc(F)c1F)[C@H](COC(=O)Nc1cc2cc(F)ccc2cn1)C[C@@H](O)COP(=O)(O)O] | (4S,2R)-4-({[[(2,3-difluorophenyl)methyl]amino}-N-methylcarbonylamino)-5-[N-(6-fluoro(3-isoquinolyl))carbamoyloxy]-2-hydroxypentyl dihydrogen phosphate |
| 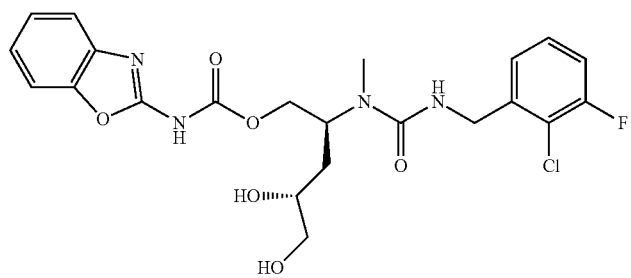 [SMILES: CN(C(=O)NCc1cccc(F)c1Cl)[C@H](COC(=O)Nc1nc2ccccc2o1)C[C@@H](O)CO] | ({(1S,3R)-1-[(N-benzoxazol-2-ylcarbamoyloxy)methyl]-3,4-dihydroxybutyl}methylamino)-N-[(2-chloro-3-fluorophenyl)methyl]carboxamide |
| 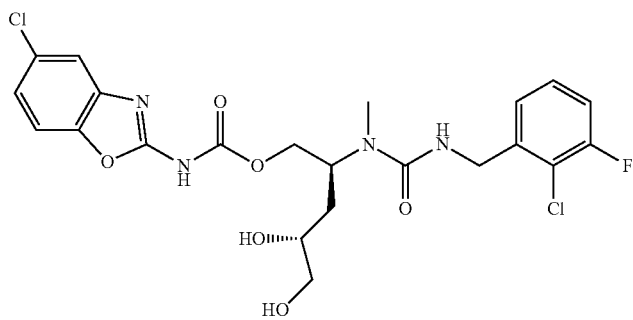 [SMILES: CN(C(=O)NCc1cccc(F)c1Cl)[C@H](COC(=O)Nc1nc2cc(Cl)ccc2o1)C[C@@H](O)CO] | [((1S,3R)-1-{[N-(5-chlorobenzoxazol-2-yl)carbamoyloxy]methyl}-3,4-dihydroxybutyl)methylamino]-N-[(2-chloro-3-fluorophenyl)methyl]carboxamide |
| 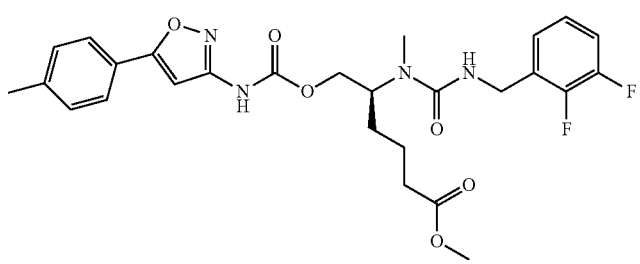 [SMILES: COC(=O)CCC[C@@H](COC(=O)Nc1cc(-c2ccc(C)cc2)on1)N(C)C(=O)NCc1cccc(F)c1F] | methyl (5S)-5-({N-[(2,3-difluorophenyl)methyl]carbamoyl}methylamino)-6-{N-[5-(4-methylphenyl)isoxazol-3-yl]carbamoyloxy}hexanoate |

-continued

| Structure | Chemical Name |
|---|---|
| 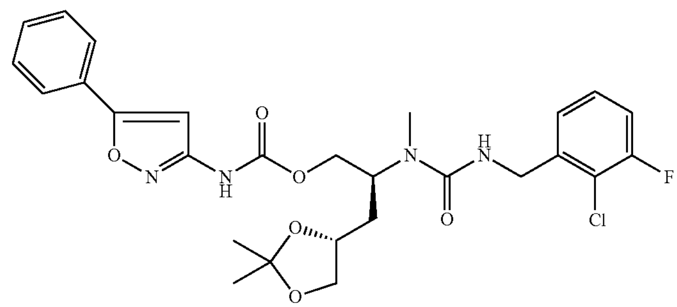 [SMILES: CN(C(=O)NCc1cccc(F)c1Cl)[C@H](COC(=O)Nc1cc(-c2ccccc2)on1)C[C@@H]1COC(C)(C)O1] | N-{1-[((4R)-2,2-dimethyl(1,3-dioxolan-4-yl))methyl](1S)-2-[N-(5-phenylisoxazol-3-yl)carbamoyloxy]ethy}{[(2-chloro-3-fluorophenyl)methyl]amino}-N-methylcarboxamide |
| 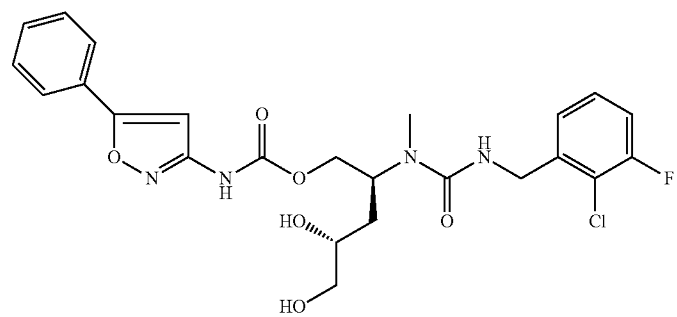 [SMILES: CN(C(=O)NCc1cccc(F)c1Cl)[C@H](COC(=O)Nc1cc(-c2ccccc2)on1)C[C@@H](O)CO] | N-((1S,3R)-3,4-dihydroxy-1-{[N-(5-phenylisoxazol-3-yl)carbamoyloxy]methyl}butyl){[(2-chloro-3-fluorophenyl)methyl]amino}-N-methylcarboxamide |
| 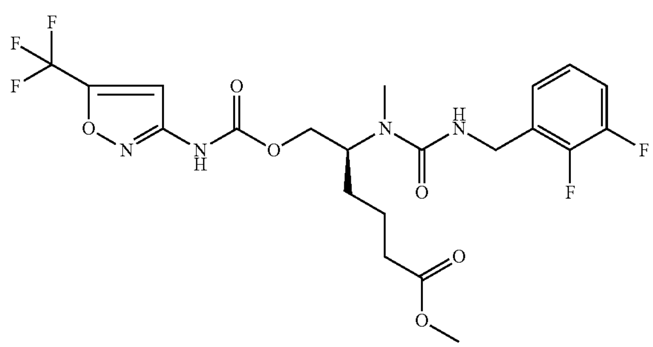 [SMILES: COC(=O)CCC[C@@H](COC(=O)Nc1cc(C(F)(F)F)on1)N(C)C(=O)NCc1cccc(F)c1F] | methyl (5S)-5-({[(2,3-difluorophenyl)methyl]amino}-N-methylcarbonylamino)-6-{N-[5-(trifluoromethyl)isoxazol-3-yl]carbamoyloxy}hexanoate |
| 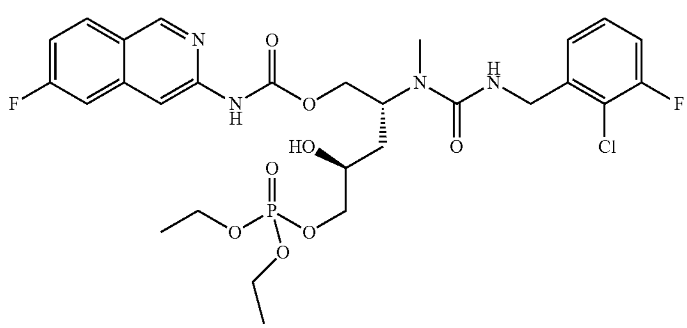 [SMILES: CCOP(=O)(OCC)OC[C@@H](O)C[C@H](COC(=O)Nc1cc2cc(F)ccc2cn1)N(C)C(=O)NCc1cccc(F)c1Cl] | (2S,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl diethyl phosphate |
| 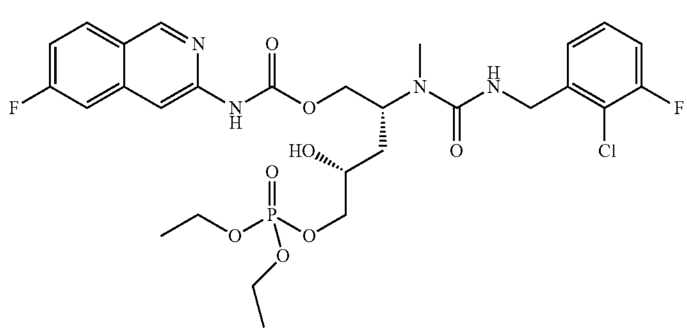 [SMILES: CCOP(=O)(OCC)OC[C@H](O)C[C@H](COC(=O)Nc1cc2cc(F)ccc2cn1)N(C)C(=O)NCc1cccc(F)c1Cl] | (2R,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl diethyl phosphate |

| Structure | Chemical Name |
|---|---|
| 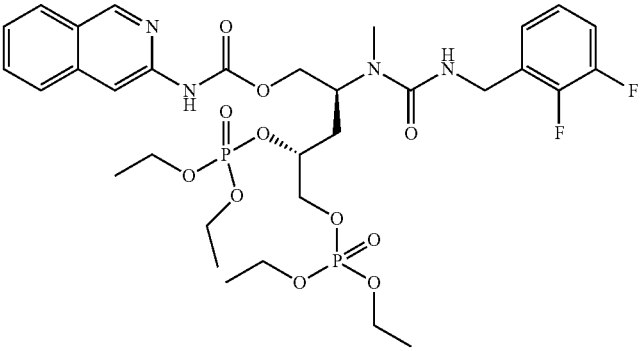 [SMILES: CCOP(=O)(OCC)OC[C@@H](C[C@@H](COC(=O)Nc1cc2ccccc2cn1)N(C)C(=O)NCc1cccc(F)c1F)OP(=O)(OCC)OCC] | (3S,1R)-3-({[(2,3-difluorophenyl)methyl]amino}-N-methylcarbonylamino)-1-[(ethoxyphosphinyl)methyl]-4-(N-(3-isoquinolyl)carbamoyloxy) butyl diethyl phosphate |
| 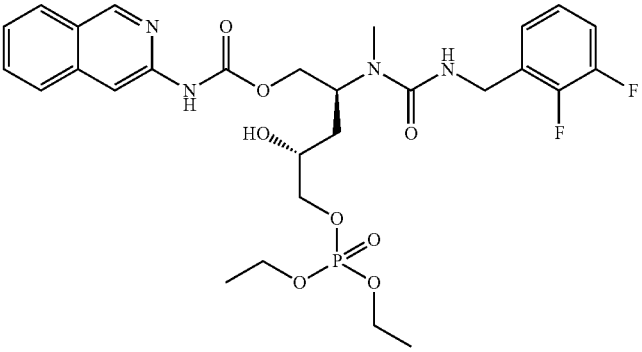 [SMILES: CCOP(=O)(OCC)OC[C@H](O)C[C@@H](COC(=O)Nc1cc2ccccc2cn1)N(C)C(=O)NCc1cccc(F)c1F] | (4S,2R)-4-({[(2,3-difluorophenyl)methyl]amino}-N-methylcarbonylamino)-2-hydroxy-5-(N-(3-isoquinolyl)carbamoyloxy) pentyl diethyl phosphate |
| 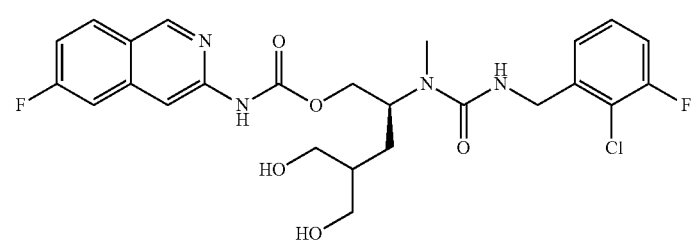 [SMILES: CN(C(=O)NCc1cccc(F)c1Cl)[C@H](COC(=O)Nc1cc2cc(F)ccc2cn1)CC(CO)CO] | N-((1S)-1-{[N-(6-fluoro(3-isoquinolyl))carbamoyloxy] methyl}-4-hydroxy-3-(hydroxymethyl)butyl){[(2-chloro-3-fluorophenyl)methyl]amino}-N-methylcarboxamide |
| 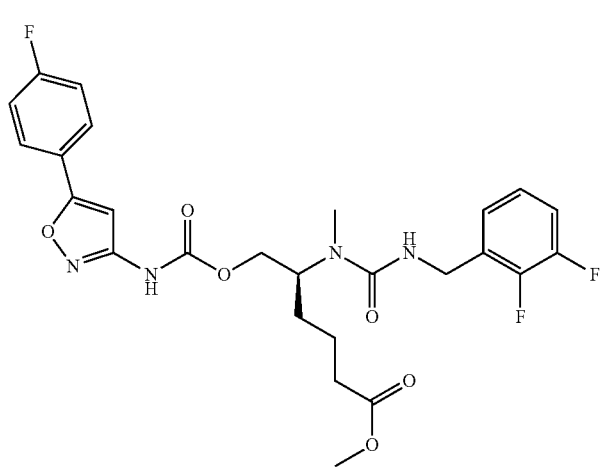 [SMILES: COC(=O)CCC[C@@H](COC(=O)Nc1cc(-c2ccc(F)cc2)on1)N(C)C(=O)NCc1cccc(F)c1F] | methyl (5S)-5-({[(2,3-difluorophenyl)methyl]amino}-N-methylcarbonylamino)-6-{N-[5-(4-fluorophenyl)isoxazol-3-yl]carbamoyloxy}hexanoate |

-continued

| Structure | Chemical Name |
|---|---|
| 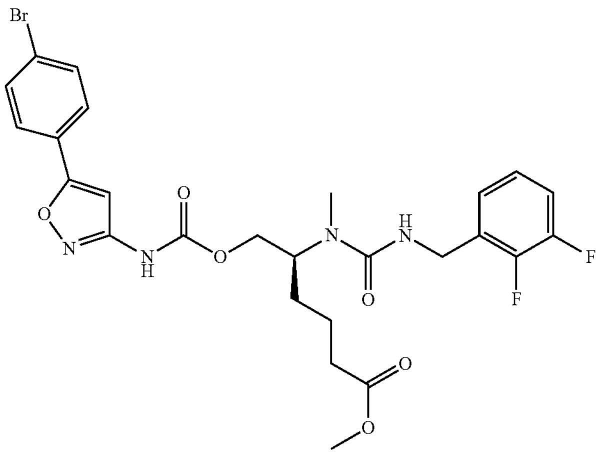 [SMILES: COC(=O)CCC[C@@H](COC(=O)Nc1cc(-c2ccc(Br)cc2)on1)N(C)C(=O)NCc1cccc(F)c1F] | methyl (5S)-5-({[(2,3-difluorophenyl)methyl]amino}-N-methylcarbonylamino)-6-{N-[5-(4-bromophenyl)isoxazol-3-yl]carbamoyloxy}hexanoate |
| 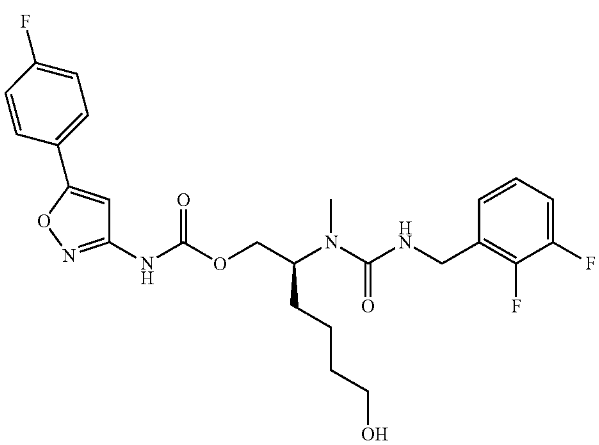 [SMILES: CN(C(=O)NCc1cccc(F)c1F)[C@@H](CCCCO)COC(=O)Nc1cc(-c2ccc(F)cc2)on1] | N-[(1S)-1-({N-[5-(4-fluorophenyl)isoxazol-3-yl]carbamoyloxy}methyl)-5-hydroxypentyl]{[(2,3-difluorophenyl)methyl]amino}-N-methylcarboxamide |
| 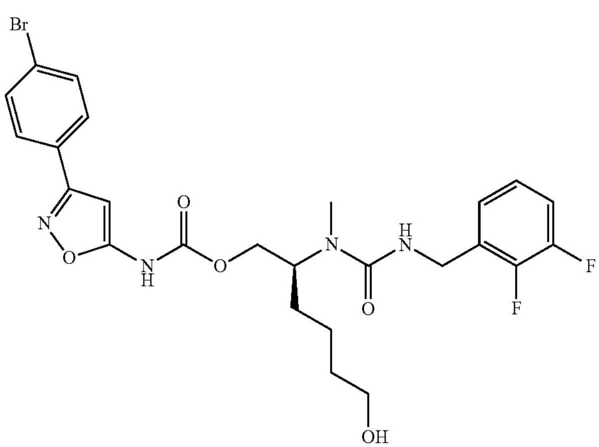 [SMILES: CN(C(=O)NCc1cccc(F)c1F)[C@@H](CCCCO)COC(=O)Nc1cc(-c2ccc(Br)cc2)no1] | N-[(1S)-1-({N-[3-(4-bromophenyl)isoxazol-5-yl]carbamoyloxy}methyl)-5-hydroxypentyl]{[(2,3-difluorophenyl)methyl]amino}-N-methylcarboxamide |

| Structure | Chemical Name |
|---|---|
| 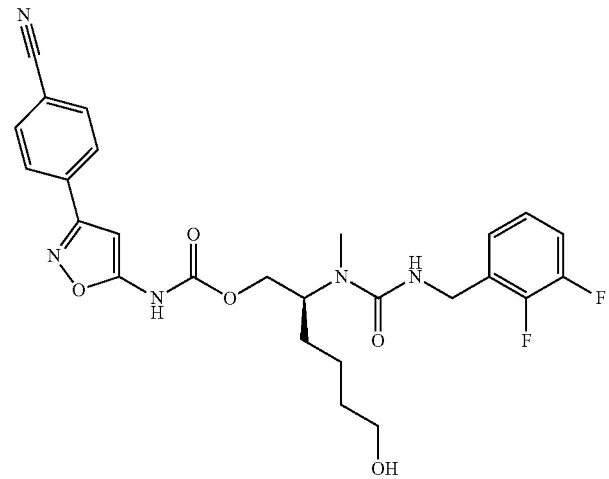 [SMILES: CN(C(=O)NCc1cccc(F)c1F)[C@@H](CCCCO)COC(=O)Nc1cc(-c2ccc(C#N)cc2)no1] | N-[(1S)-1-({N-[3-(4-cyanophenyl)isoxazol-5-yl]carbamoyloxy}methyl)-5-hydroxypentyl]{[(2,3-difluorophenyl)methyl]amino}-N-methylcarboxamide |
| 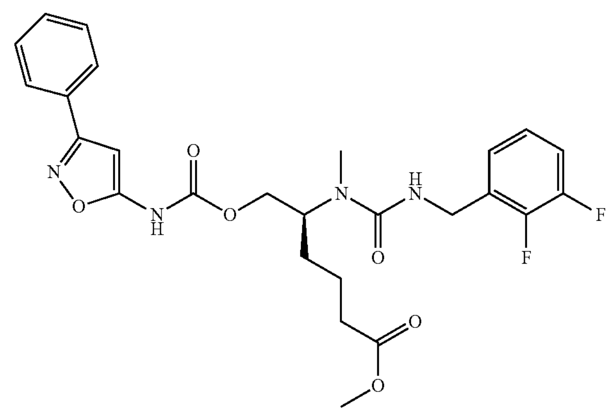 [SMILES: COC(=O)CCC[C@@H](COC(=O)Nc1cc(-c2ccccc2)no1)N(C)C(=O)NCc1cccc(F)c1F] | methyl (5S)-5-({[(2,3-difluorophenyl)methyl]amino}-N-methylcarbonylamino)-6-[N-(3-phenylisoxazol-5-yl)carbamoyloxy]hexanoate |
| 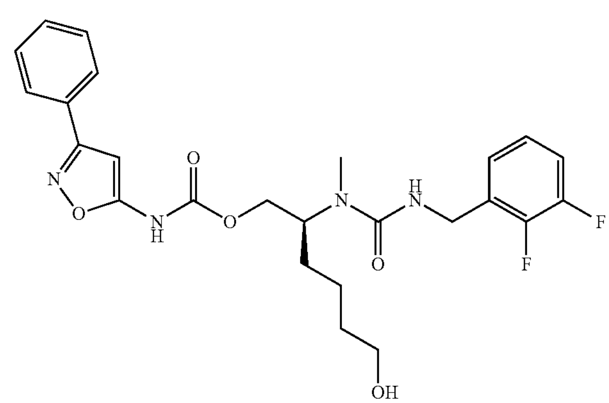 [SMILES: CN(C(=O)NCc1cccc(F)c1F)[C@@H](CCCCO)COC(=O)Nc1cc(-c2ccccc2)no1] | N-((1S)-5-hydroxy-1-{[N-(3-phenylisoxazol-5-yl)carbamoyloxy]methyl}pentyl){[(2,3-difluorophenyl)methyl]amino}-N-methylcarboxamide |

| Structure | Chemical Name |
|---|---|
| 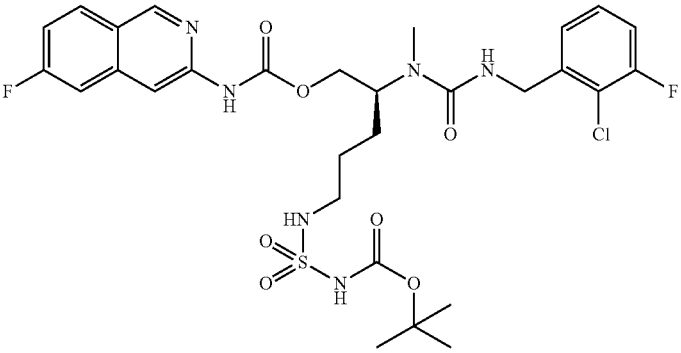 [SMILES: CN(C(=O)NCc1cccc(F)c1Cl)[C@@H](CCCNS(=O)(=O)NC(=O)OC(C)(C)C)COC(=O)Nc1cc2cc(F)ccc2cn1] | [(2S)-5-({[(tert-butoxy)carbonylamino]sulfonyl}amino)-2-({[(2-chloro-3-fluorophenyl)methyl]amino}-N-methylcarbonylamino)pentyloxy]-N-(6-fluoro(3-isoquinolyl))carboxamide |
| 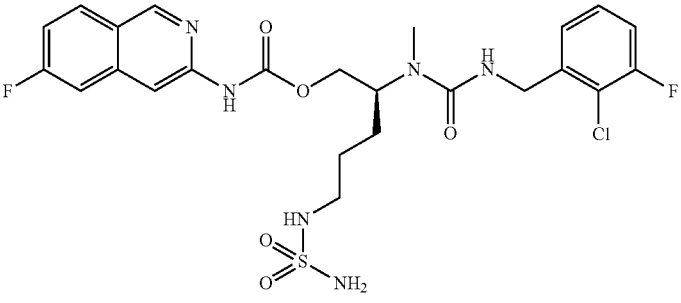 [SMILES: CN(C(=O)NCc1cccc(F)c1Cl)[C@@H](CCCNS(N)(=O)=O)COC(=O)Nc1cc2cc(F)ccc2cn1] | N-((1S)-1-{[N-(6-fluoro(3-isoquinolyl))carbamoyloxy]methyl}-4-(sulfamoylamino)butyl){[(2-chloro-3-fluorophenyl)methyl]amino}-N-methylcarboxamide |
| 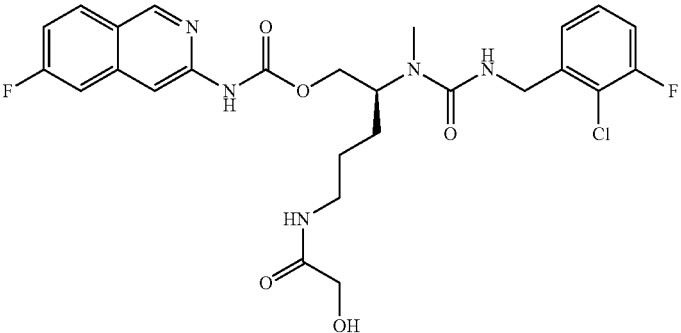 [SMILES: CN(C(=O)NCc1cccc(F)c1Cl)[C@@H](CCCNC(=O)CO)COC(=O)Nc1cc2cc(F)ccc2cn1] | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-hydroxyacetamide |
| 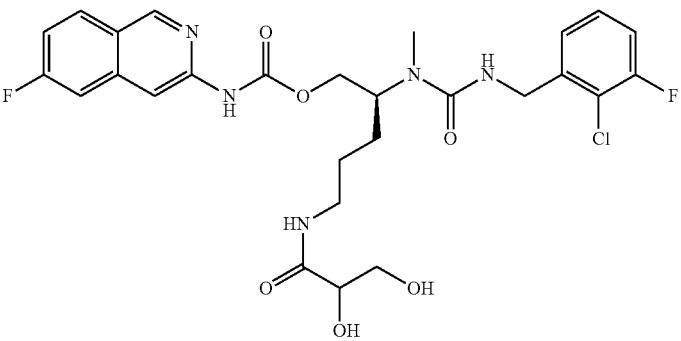 [SMILES: CN(C(=O)NCc1cccc(F)c1Cl)[C@@H](CCCNC(=O)C(O)CO)COC(=O)Nc1cc2cc(F)ccc2cn1] | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2,3-dihydroxypropanamide |

-continued

| Structure | Chemical Name |
|---|---|
| 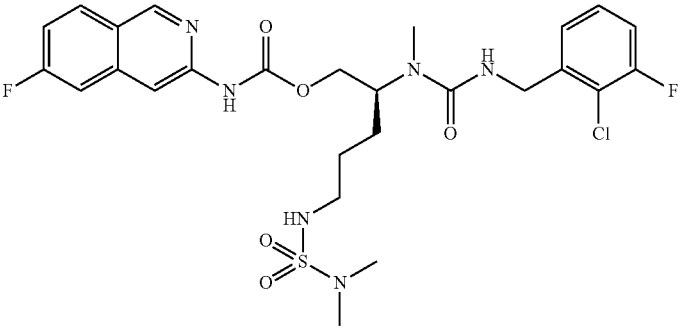 [SMILES: CN(C(=O)NCc1cccc(F)c1Cl)[C@@H](CCCNS(=O)(=O)N(C)C)COC(=O)Nc1cc2cc(F)ccc2cn1] | N-((1S)-4-{[(dimethylamino) sulfonyl]amino}-1-{[N-(6-fluoro(3-isoquinolyl))carbamoyloxy]methyl}butyl){[(2-chloro-3-fluorophenyl)methyl]amino}-N-methylcarboxamide |
| 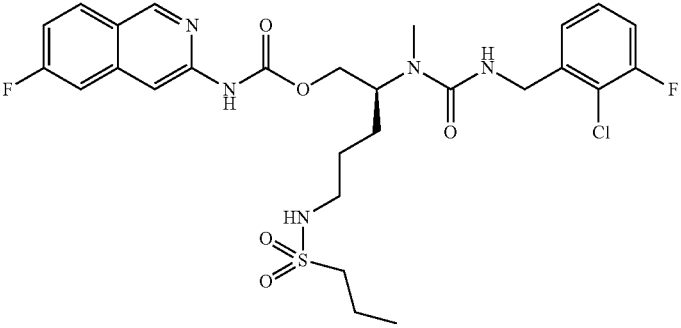 [SMILES: CCCS(=O)(=O)NCCC[C@@H](COC(=O)Nc1cc2cc(F)ccc2cn1)N(C)C(=O)NCc1cccc(F)c1Cl] | N-((1S)-1-{[N-(6-fluoro(3-isoquinolyl))carbamoyloxy]methyl}-4-[(propylsulfonyl)amino]butyl){[(2-chloro-3-fluorophenyl)methyl]amino}-N-methylcarboxamide |
| 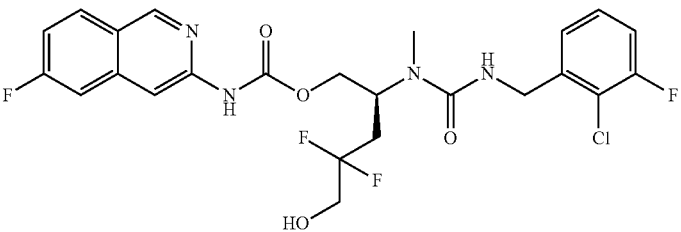 [SMILES: CN(C(=O)NCc1cccc(F)c1Cl)[C@H](COC(=O)Nc1cc2cc(F)ccc2cn1)CC(F)(F)CO] | N-((1S)-3,3-difluoro-1-{[N-(6-fluoro(3-isoquinolyl))carbamoyloxy]methyl}-4-hydroxybutyl)({[(2-chloro-3-fluorophenyl)methyl]amino}-N-methylcarboxamide |
| 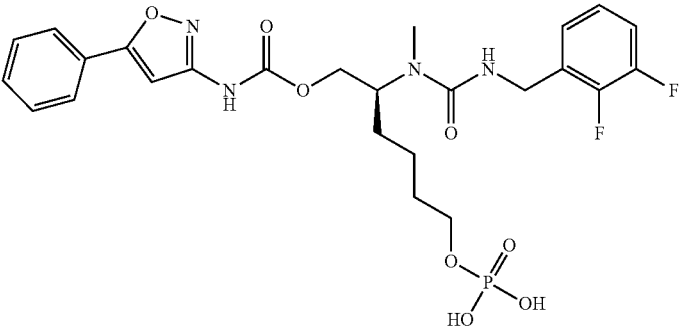 [SMILES: CN(C(=O)NCc1cccc(F)c1F)[C@@H](CCCCOP(=O)(O)O)COC(=O)Nc1cc(-c2ccccc2)on1] | (5S)-5-({[[(2,3-difluorophenyl)methyl]amino}-N-methylcarbonylamino)-6-[N-(5-phenylisoxazol-3-yl)carbamoyloxy] hexyl dihydrogen phosphate |
| 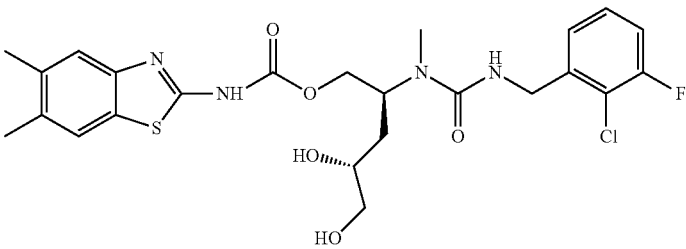 [SMILES: Cc1cc2nc(NC(=O)OC[C@H](C[C@@H](O)CO)N(C)C(=O)NCc3cccc(F)c3Cl)sc2cc1C] | [(2S,4R)-2-({[(2-chloro-3-fluorophenyl)methyl]amino}-N-methylcarbonylamino)-4,5-dihydroxypentyloxy]-N-(5,6-dimethylbenzothiazol-2-yl)carboxamide |

| Structure | Chemical Name |
|---|---|
| 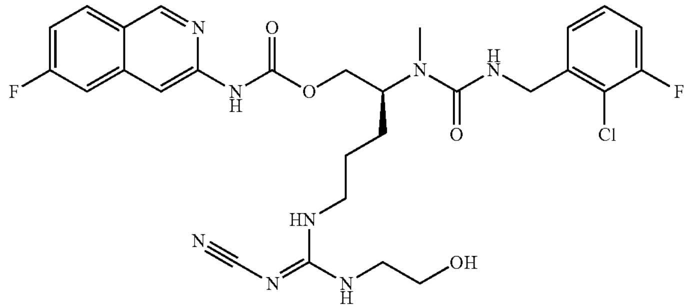 [SMILES: CN(C(=O)NCc1cccc(F)c1Cl)[C@@H](CCCN/C(=N\C#N)NCCO)COC(=O)Nc1cc2cc(F)ccc2cn1] | N-[4-({(1E)-2-cyano-1-[(2-hydroxyethyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 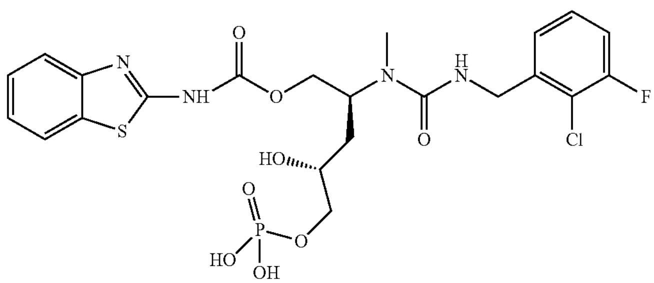 [SMILES: CN(C(=O)NCc1cccc(F)c1Cl)[C@H](COC(=O)Nc1nc2ccccc2s1)C[C@@H](O)COP(=O)(O)O] | (4S,2R)-5-(N-benzothiazol-2-ylcarbamoyloxy)-4-({[(2-chloro-3-fluorophenyl)methyl]amino}-N-methylcarbonylamino)-2-hydroxypentyl dihydrogen phosphate |
| 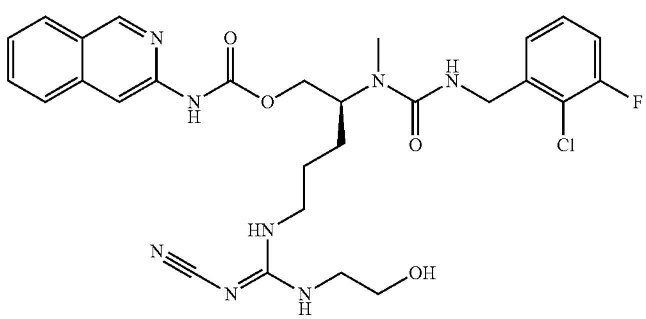 [SMILES: CN(C(=O)NCc1cccc(F)c1Cl)[C@@H](CCCN/C(=N\C#N)NCCO)COC(=O)Nc1cc2ccccc2cn1] | N-[4-({(1E)-2-cyano-1-[(2-hydroxyethyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| 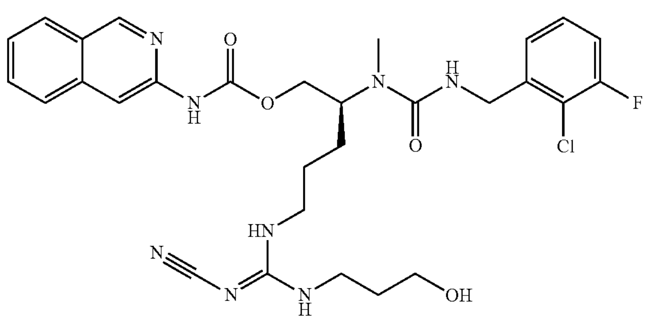 [SMILES: CN(C(=O)NCc1cccc(F)c1Cl)[C@@H](CCCN/C(=N\C#N)NCCCO)COC(=O)Nc1cc2ccccc2cn1] | N-[4-({(1E)-2-cyano-1-[(3-hydroxypropyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| | [(2S,4R)-2-({[[(2-chloro-3-fluorophenyl)methyl]amino}-N-methylcarbonylamino)-4,5-dihydroxypentyloxy]-N-(6-methylbenzothiazol-2-yl)carboxamide |

-continued

| Structure | Chemical Name |
|---|---|
| 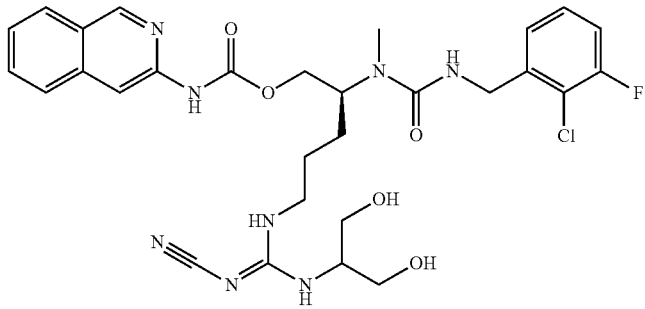 [SMILES: CN(C(=O)NCc1cccc(F)c1Cl)[C@@H](CCCN/C(=N\C#N)NC(CO)CO)COC(=O)Nc1cc2ccccc2cn1] | N-{4-[((1E)-2-cyano-1-{[2-hydroxy-1-(hydroxymethyl)ethyl]amino}-2-azavinyl)amino](1S)-1-[(N-(3-isoquinolyl)carbamoyloxy)methyl]butyl}{[(2-chloro-3-fluorophenyl)methyl]amino}-N-methylcarboxamide |
| 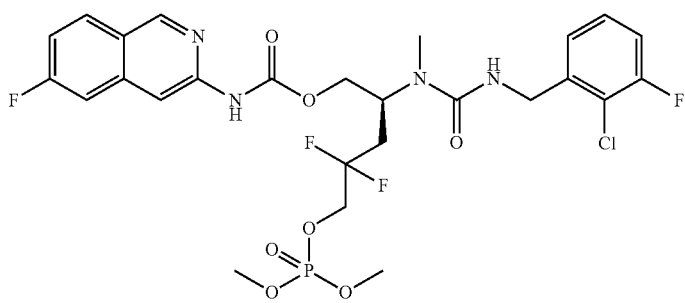 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl dimethyl phosphate |
| 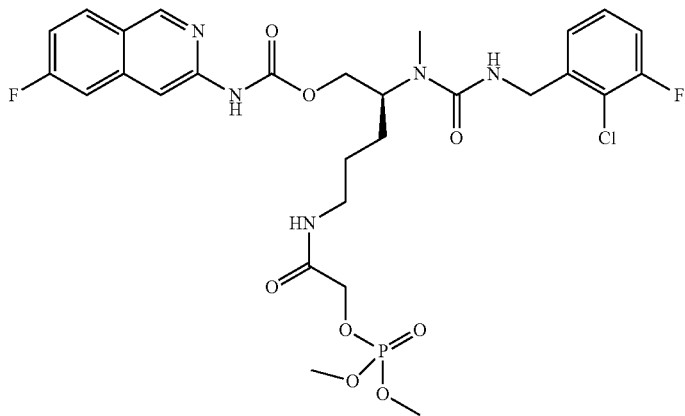 | {N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}methyl dimethyl phosphate |
| 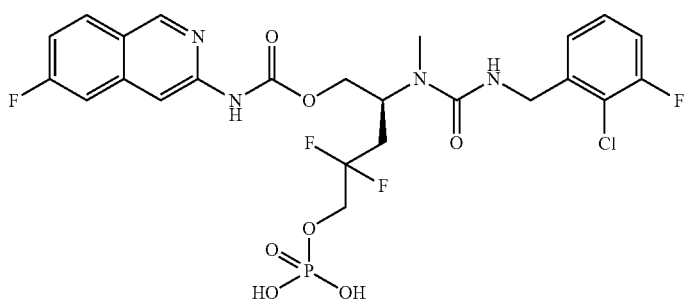 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl dihydrogen phosphate |

-continued

| Structure | Chemical Name |
|---|---|
| 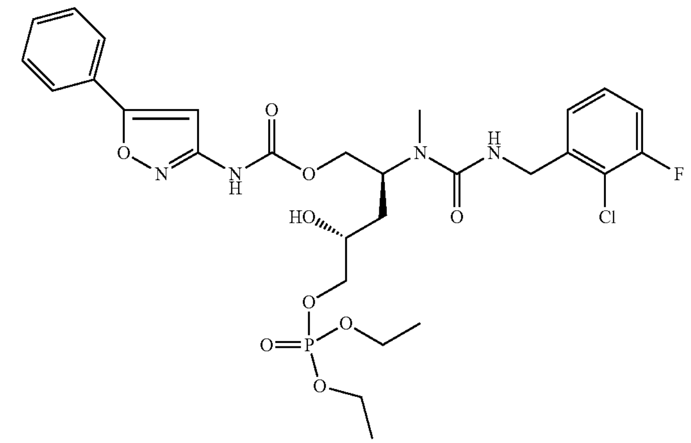 [SMILES: CCOP(=O)(OCC)OC[C@H](O)C[C@@H](COC(=O)Nc1cc(-c2ccccc2)on1)N(C)C(=O)NCc1cccc(F)c1Cl] | (4S,2R)-4-({[(2-chloro-3-fluorophenyl)methyl]amino}-N-methylcarbonylamino)-2-hydroxy-5-[N-(5-phenylisoxazol-3-yl)carbamoyloxy]pentyl diethyl phosphate |
| 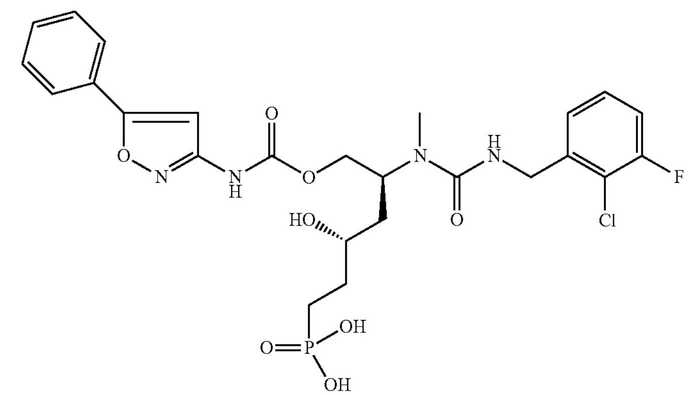 [SMILES: CN(C(=O)NCc1cccc(F)c1Cl)[C@H](COC(=O)Nc1cc(-c2ccccc2)on1)C[C@@H](O)CCP(=O)(O)O] | (4S,2R)-4-({[(2-chloro-3-fluorophenyl)methyl]amino}-N-methylcarbonylamino)-2-hydroxy-5-[N-(5-phenylisoxazol-3-yl)carbamoyloxy]pentyl dihydrogen phosphate |
| 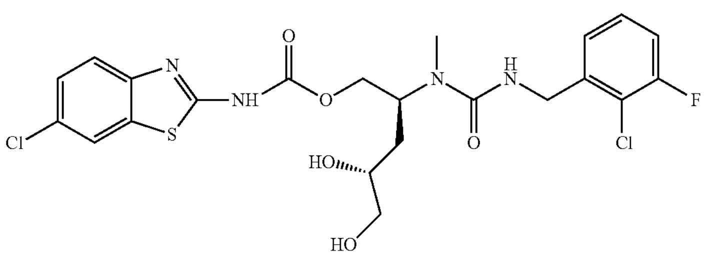 [SMILES: CN(C(=O)NCc1cccc(F)c1Cl)[C@H](COC(=O)Nc1nc2ccc(Cl)cc2s1)C[C@@H](O)CO] | [(2S,4R)-2-({[(2-chloro-3-fluorophenyl)methyl]amino}-N-methylcarbonylamino)-4,5-dihydroxypentyloxy]-N-(6-chlorobenzothiazol-2-yl)carboxamide |
| 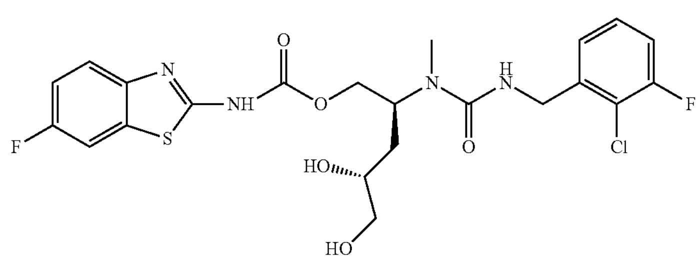 [SMILES: CN(C(=O)NCc1cccc(F)c1Cl)[C@H](COC(=O)Nc1nc2ccc(F)cc2s1)C[C@@H](O)CO] | [(2S,4R)-2-({[(2-chloro-3-fluorophenyl)methyl]amino}-N-methylcarbonylamino)-4,5-dihydroxypentyloxy]-N-(6-fluorobenzothiazol-2-yl)carboxamide |
| 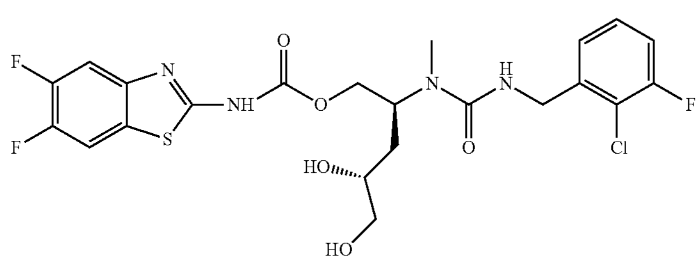 [SMILES: CN(C(=O)NCc1cccc(F)c1Cl)[C@H](COC(=O)Nc1nc2cc(F)c(F)cc2s1)C[C@@H](O)CO] | [(2S,4R)-2-({[(2-chloro-3-fluorophenyl)methyl]amino}-N-methylcarbonylamino)-4,5-dihydroxypentyloxy]-N-(5,6-difluorobenzothiazol-2-yl)carboxamide |

| Structure | Chemical Name |
|---|---|
| 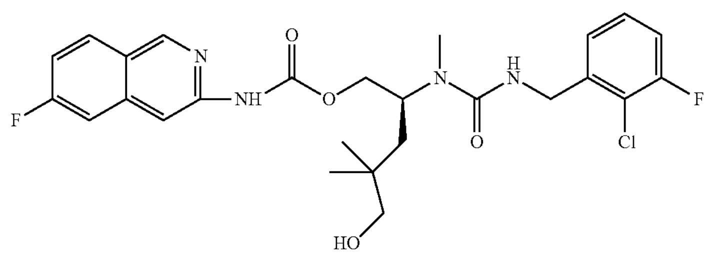 [SMILES: CN(C(=O)NCc1cccc(F)c1Cl)[C@H](COC(=O)Nc1cc2cc(F)ccc2cn1)CC(C)(C)CO] | [(2S)-2-({[(2-chloro-3-fluorophenyl)methyl]amino}-N-methylcarbonylamino)-5-hydroxy-4,4-dimethylpentyloxy]-N-(6-fluoro(3-isoquinolyl))carboxamide |
| 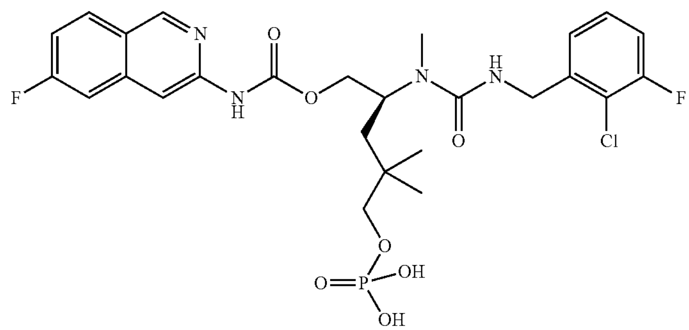 | (4S)-4-({[(2-chloro-3-fluorophenyl)methyl]amino}-N-methylcarbonylamino)-5-[N-(6-fluoro(3-isoquinolyl))carbamoyloxy]-2,2-dimethylpentyl dihydrogen phosphate |
| 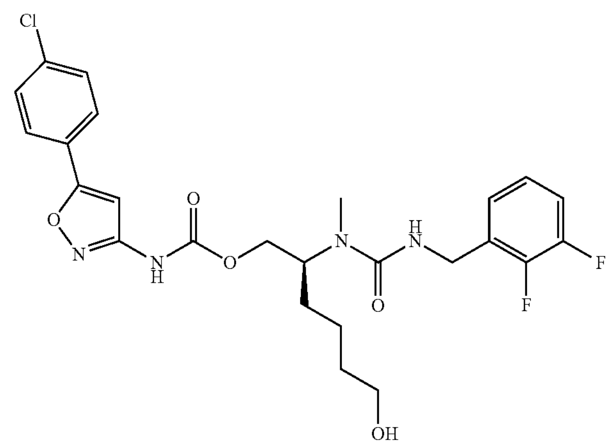 | N-[(1S)-1-({N-[5-(4-chlorophenyl)isoxazol-3-yl]carbamoyloxy}methyl)-5-hydroxypentyl]{[(2,3-difluorophenyl)methyl]amino}-N-methylcarboxamide |
| 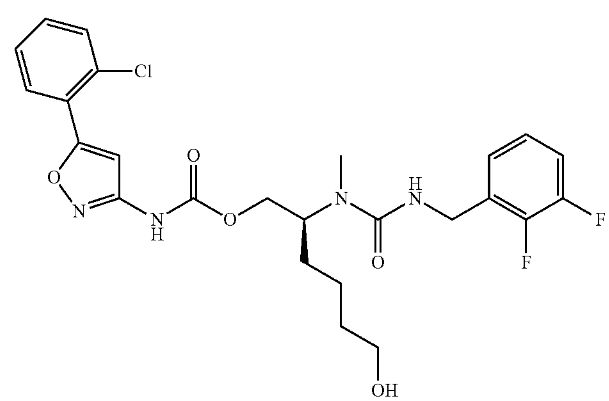 [SMILES: CN(C(=O)NCc1cccc(F)c1F)[C@@H](CCCCO)COC(=O)Nc1cc(-c2ccccc2Cl)on1] | N-[(1S)-1-({N-[5-(2-chlorophenyl)isoxazol-3-yl]carbamoyloxy}methyl)-5-hydroxypentyl]{[(2,3-difluorophenyl)methyl]amino}-N-methylcarboxamide |

-continued

| Structure | Chemical Name |
| --- | --- |
| 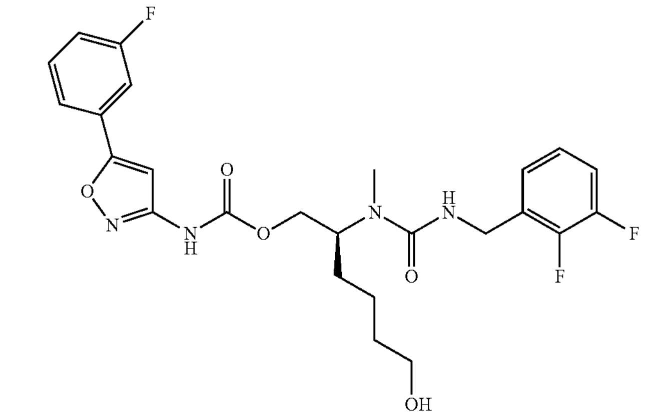 [SMILES: CN(C(=O)NCc1cccc(F)c1F)[C@@H](CCCCO)COC(=O)Nc1cc(-c2cccc(F)c2)on1] | N-[(1S)-1-({N-[5-(3-fluorophenyl)isoxazol-3-yl]carbamoyloxy}methyl)-5-hydroxypentyl]{[(2,3-difluorophenyl)methyl]amino}-N-methylcarboxamide |
| 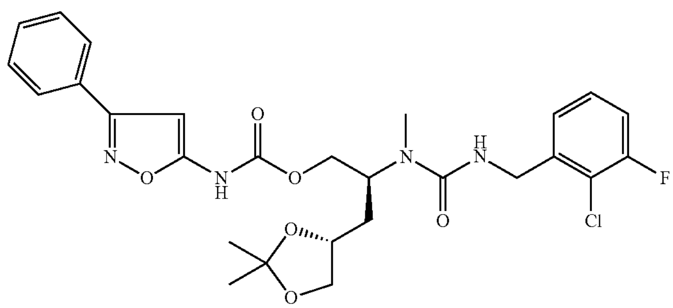 [SMILES: CN(C(=O)NCc1cccc(F)c1Cl)[C@H](COC(=O)Nc1cc(-c2ccccc2)no1)C[C@@H]1COC(C)(C)O1] | N-{1-[((4R)-2,2-dimethyl(1,3-dioxolan-4-yl))methyl](1S)-2-[N-(3-phenylisoxazol-5-yl)carbamoyloxy]ethyl}{[(2-chloro-3-fluorophenyl)methyl]amino}-N-methylcarboxamide |
| 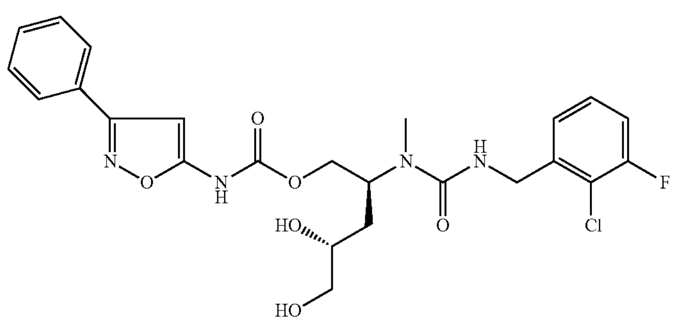 [SMILES: CN(C(=O)NCc1cccc(F)c1Cl)[C@H](COC(=O)Nc1cc(-c2ccccc2)no1)C[C@@H](O)CO] | N-((1S,3R)-3,4-dihydroxy-1-{[N-(3-phenylisoxazol-5-yl)carbamoyloxy]methyl}butyl){[(2-chloro-3-fluorophenyl)methyl]amino}-N-methylcarboxamide |
| 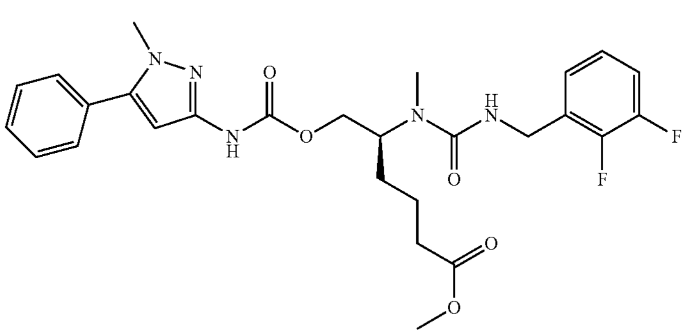 [SMILES: COC(=O)CCC[C@@H](COC(=O)Nc1cc(-c2ccccc2)n(C)n1)N(C)C(=O)NCc1cccc(F)c1F] | methyl (5S)-5-({[(2,3-difluorophenyl)methyl]amino}-N-methylcarbonylamino)-6-[N-(1-methyl-5-phenylpyrazol-3-yl)carbamoyloxy]hexanoate |

-continued

| Structure | Chemical Name |
|---|---|
| 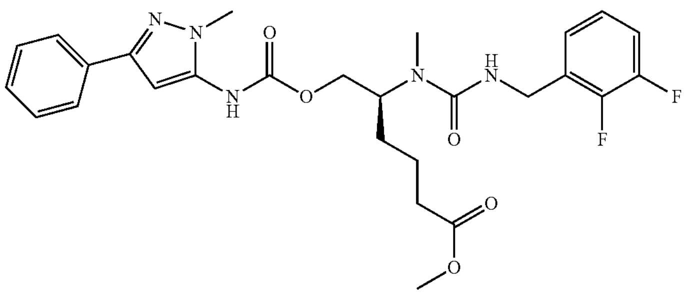 [SMILES: COC(=O)CCC[C@@H](COC(=O)Nc1cc(-c2ccccc2)nn1C)N(C)C(=O)NCc1cccc(F)c1F] | methyl (5S)-5-({[(2,3-difluorophenyl)methyl]amino}-N-methylcarbonylamino)-6-[N-(1-methyl-3-phenylpyrazol-5-yl)carbamoyloxy]hexanoate |
| 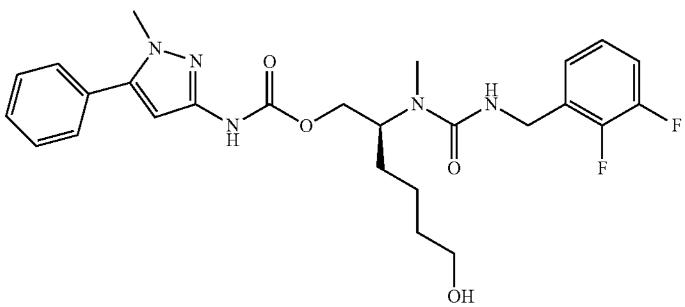 [SMILES: CN(C(=O)NCc1cccc(F)c1F)[C@@H](CCCCO)COC(=O)Nc1cc(-c2ccccc2)n(C)n1] | N-((1S)-5-hydroxy-1-{[N-(1-methyl-5-phenylpyrazol-3-yl)carbamoyloxy]methyl}pentyl){[(2,3-difluorophenyl)methyl]amino}-N-methylcarboxamide |
| 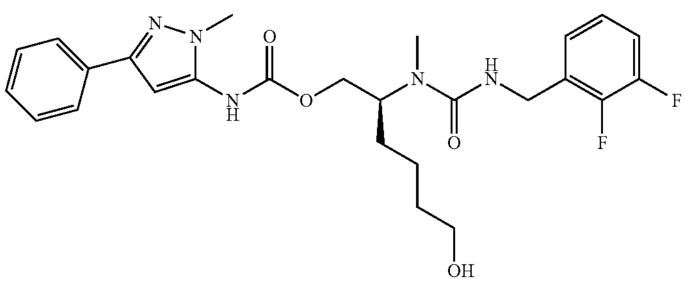 [SMILES: CN(C(=O)NCc1cccc(F)c1F)[C@@H](CCCCO)COC(=O)Nc1cc(-c2ccccc2)nn1C] | N-((1S)-5-hydroxy-1-{[N-(1-methyl-3-phenylpyrazol-5-yl)carbamoyloxy]methyl}pentyl){[(2,3-difluorophenyl)methyl]amino}-N-methylcarboxamide |
| 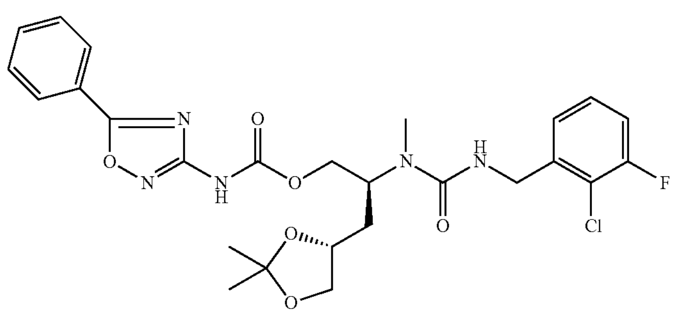 [SMILES: CN(C(=O)NCc1cccc(F)c1Cl)[C@H](COC(=O)Nc1noc(-c2ccccc2)n1)C[C@@H]1COC(C)(C)O1] | N-{1-[((4R)-2,2-dimethyl(1,3-dioxolan-4-yl))methyl](1S)-2-[N-(5-phenyl(1,2,4-oxadiazol-3-yl))carbamoyloxy]ethyl}{[(2-chloro-3-fluorophenyl)methyl]amino}-N-methylcarboxamide |
| 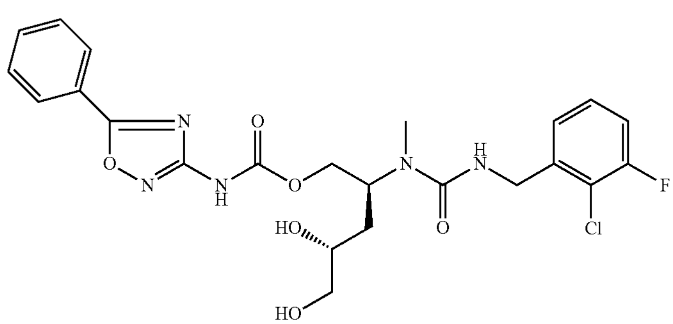 [SMILES: CN(C(=O)NCc1cccc(F)c1Cl)[C@H](COC(=O)Nc1noc(-c2ccccc2)n1)C[C@@H](O)CO] | N-((1S,3R)-3,4-dihydroxy-1-{[N-(5-phenyl(1,2,4-oxadiazol-3-yl))carbamoyloxy]methyl}butyl){[(2-chloro-3-fluorophenyl)methyl]amino}-N-methylcarboxamide |

| Structure | Chemical Name |
|---|---|
| 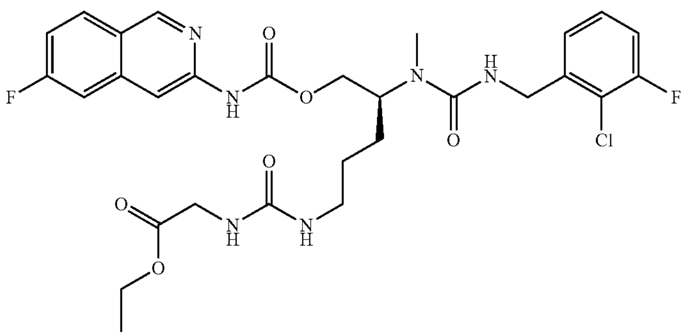 [SMILES: CCOC(=O)CNC(=O)NCCC[C@@H](COC(=O)Nc1cc2cc(F)ccc2cn1)N(C)C(=O)NCc1cccc(F)c1Cl] | ethyl 2-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)acetate |
| 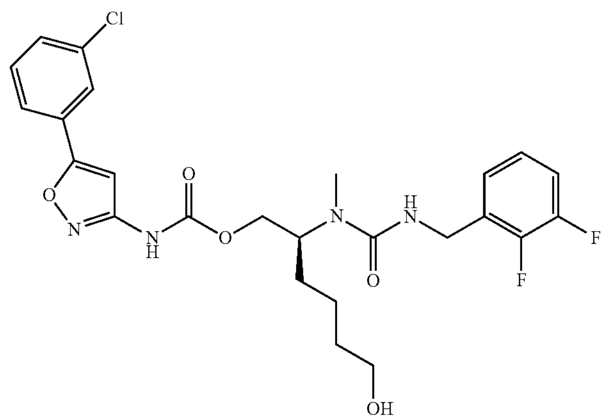 | N-[(1S)-1-({N-[5-(3-chlorophenyl)isoxazol-3-yl]carbamoyloxy}methyl)-5-hydroxypentyl]{[(2,3-difluorophenyl)methyl]amino}-N-methylcarboxamide |
| | methyl (5S)-5-({[[(2,3-difluorophenyl)methyl]amino}-N-methylcarbonylamino)-6-[N-(4-methyl-3-phenylisoxazol-5-yl)carbamoyloxy]hexanoate |
| 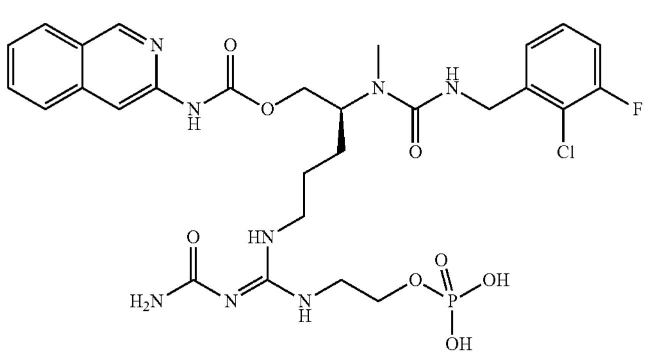 | 2-[((1E)-1-{[(4S)-4-({[(2-chloro-3-fluorophenyl)methyl]amino}-N-methylcarbonylamino)-5-(N-(3-isoquinolyl)carbamoyloxy)pentyl]amino}-2-carbamoyl-2-azavinyl)amino]ethyl dihydrogen phosphate |

| Structure | Chemical Name |
|---|---|
| 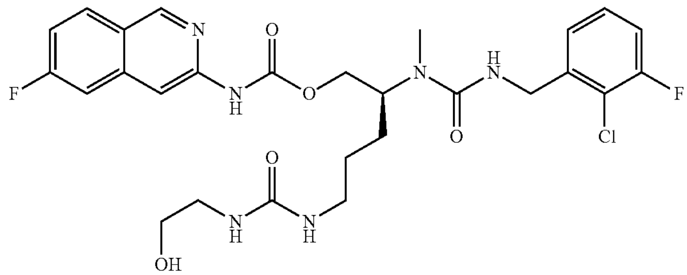 | [(2S)-2-({[(2-chloro-3-fluorophenyl)methyl]amino}-N-methylcarbonylamino)-5-{[(2-hydroxyethyl)amino]carbonylamino}pentyloxy]-N-(6-fluoro(3-isoquinolyl))carboxamide |
| 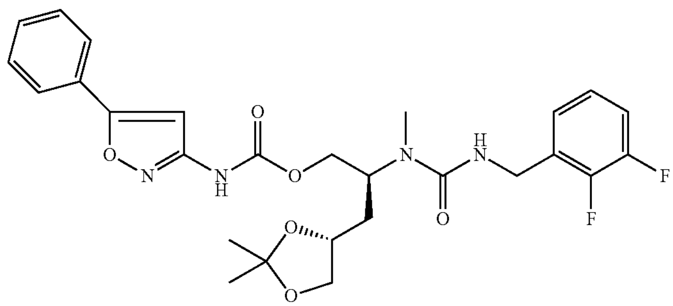 [SMILES: CN(C(=O)NCc1cccc(F)c1F)[C@H](COC(=O)Nc1cc(-c2ccccc2)on1)C[C@@H]1COC(C)(C)O1] | N-{1-[((4R)-2,2-dimethyl(1,3-dioxolan-4-yl))methyl](1S)-2-[N-(5-phenylisoxazol-3-yl)carbamoyloxy]ethyl}{[(2,3-difluorophenyl)methyl]amino}-N-methylcarboxamide |
| 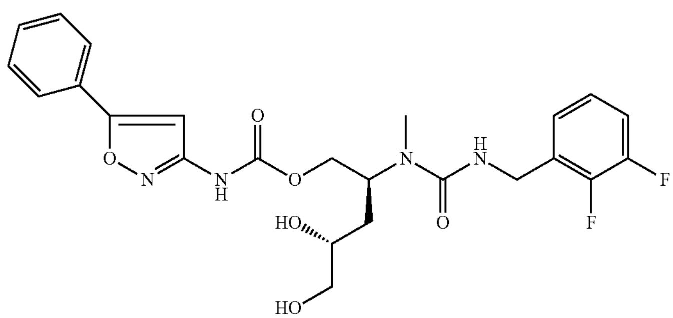 [SMILES: CN(C(=O)NCc1cccc(F)c1F)[C@H](COC(=O)Nc1cc(-c2ccccc2)on1)C[C@@H](O)CO] | N-((1S,3R)-3,4-dihydroxy-1-{[N-(5-phenylisoxazol-3-yl)carbamoyloxy]methyl}butyl){[(2,3-difluorophenyl)methyl]amino}-N-methylcarboxamide |
| 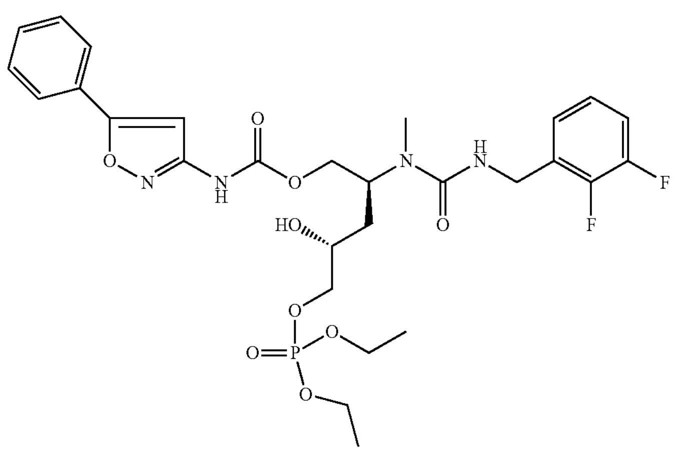 | (4S,2R)-4-({[(2,3-difluorophenyl)methyl]amino}-N-methylcarbonylamino)-2-hydroxy-5-[N-(5-phenylisoxazol-3-yl)carbamoyloxy]pentyl diethyl phosphate |

| Structure | Chemical Name |
|---|---|
| | (3S,1R)-3-({[[(2,3-difluorophenyl)methyl]amino}-N-methylcarbonylamino)-1-[(ethoxyphosphinyl)methyl]-4-[N-(5-phenylisoxazol-3-yl)carbamoyloxy]butyl diethyl phosphate |
| | (4S,2R)-4-({[[(2-chloro-3-fluorophenyl)methyl]amino}-N-methylcarbonylamino)-2-hydroxy-5-(N-(3-isoquinolyl)carbamoyloxy) pentyl dihydrogen phosphate |
| | (4S,2R)-4-({[[(2,3-difluorophenyl)methyl]amino}-N-methylcarbonylamino)-2-hydroxy-5-[N-(5-phenylisoxazol-3-yl)carbamoyloxy]pentyl dihydrogen phosphate |
| | 2-({N-[(4S)-4-({[[(2-chloro-3-fluorophenyl)methyl]amino}-N-methylcarbonylamino)-5-[N-(6-fluoro(3-isoquinolyl))carbamoyloxy]pentyl]carbamoyl}amino)ethyl dihydrogen phosphate |

| Structure | Chemical Name |
|---|---|
| 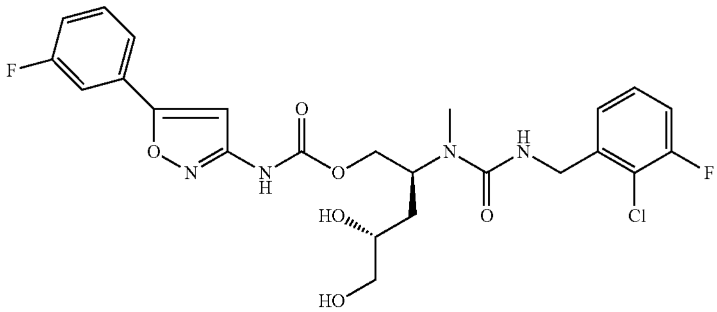 [SMILES: CN(C(=O)NCc1cccc(F)c1Cl)[C@H](COC(=O)Nc1cc(-c2cccc(F)c2)on1)C[C@@H](O)CO] | N-[(1S,3R)-1-({N-[5-(3-fluorophenyl)isoxazol-3-yl]carbamoyloxy}methyl)-3,4-dihydroxybutyl]{[(2-chloro-3-fluorophenyl)methyl]amino}-N-methylcarboxamide |
| 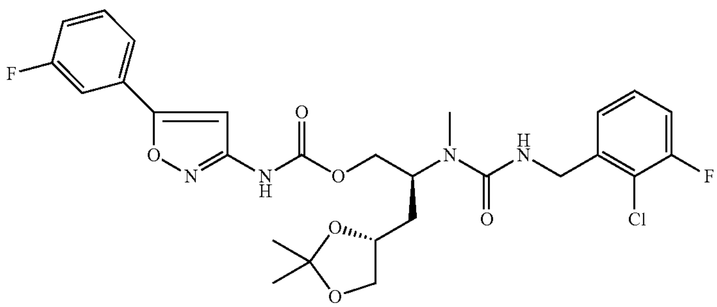 [SMILES: CN(C(=O)NCc1cccc(F)c1Cl)[C@H](COC(=O)Nc1cc(-c2cccc(F)c2)on1)C[C@@H]1COC(C)(C)O1] | N-(1-[((4R)-2,2-dimethyl(1,3-dioxolan-4-yl))methyl](1S)-2-{N-[5-(3-fluorophenyl)isoxazol-3-yl]carbamoyloxy}ethyl){[(2-chloro-3-fluorophenyl)methyl]amino}-N-methylcarboxamide |
| 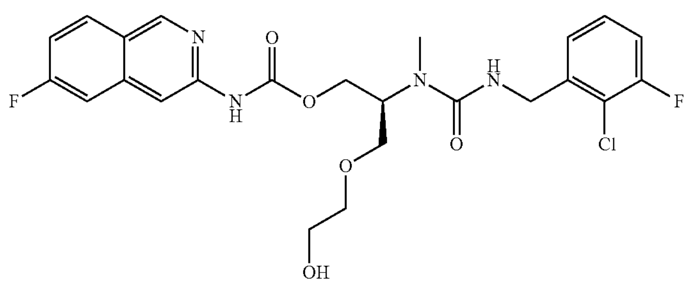 | N-{(1S)-2-[N-(6-fluoro(3-isoquinolyl))carbamoyloxy]-1-[(2-hydroxyethoxy)methyl]ethyl}{[(2-chloro-3-fluorophenyl)methyl]amino}-N-methylcarboxamide |
| 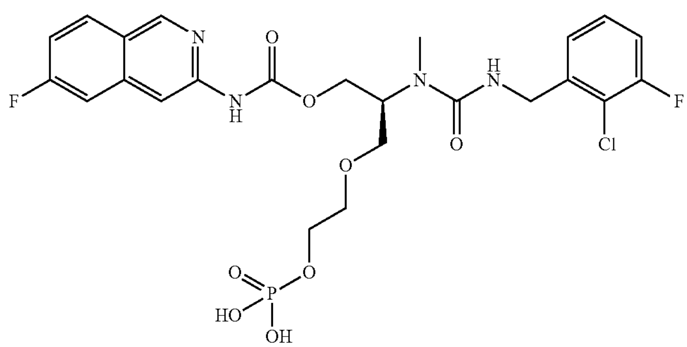 | 2-[(2S)-2-({[(2-chloro-3-fluorophenyl)methyl]amino}-N-methylcarbonylamino)-3-[N-(6-fluoro(3-isoquinolyl))carbamoyloxy]propoxy]ethyl dihydrogen phosphate |
| 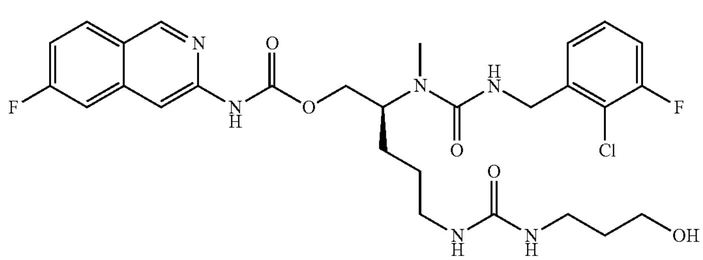 | N-[(4S)-4-({[(2-chloro-3-fluorophenyl)methyl]amino}-N-methylcarbonylamino)-5-[N-(6-fluoro(3-isoquinolyl))carbamoyloxy]pentyl][(3-hydroxypropyl)amino]carboxamide |

-continued

| Structure | Chemical Name |
|---|---|
| 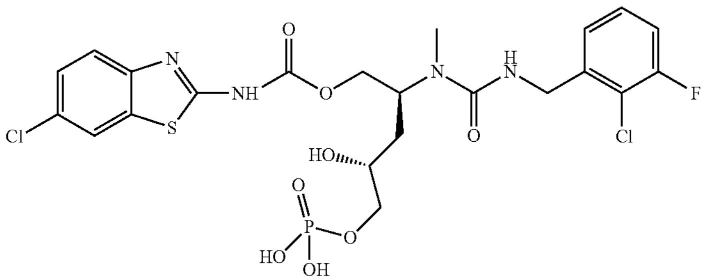 [SMILES: CN(C(=O)NCc1cccc(F)c1Cl)[C@H](COC(=O)Nc1nc2ccc(Cl)cc2s1)C[C@@H](O)COP(=O)(O)O] | (4S,2R)-5-[N-(6-chlorobenzothiazol-2-yl)carbamoyloxy]-4-({[(2-chloro-3-fluorophenyl)methyl]amino}-N-methylcarbonylamino)-2-hydroxypentyl dihydrogen phosphate |
| 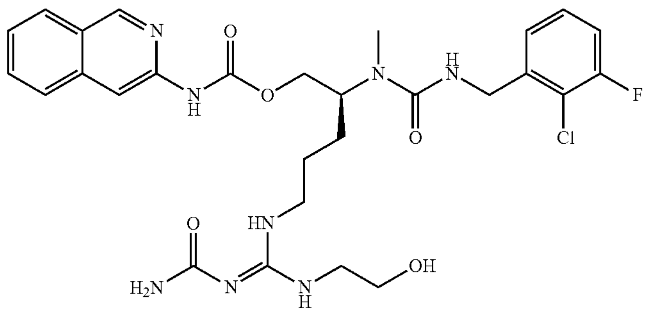 | N-[4-({(1E)-2-carbamoyl-1-[(2-hydroxyethyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| 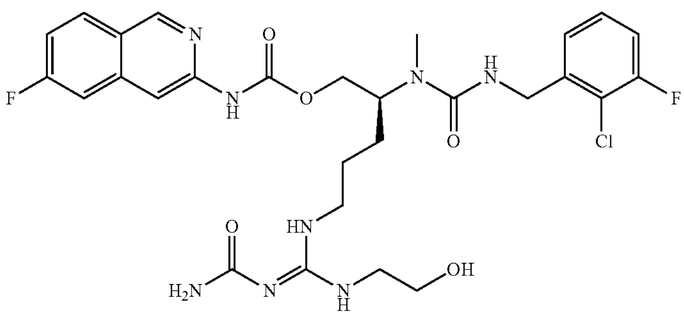 | N-[4-({(1E)-2-carbamoyl-1-[(2-hydroxyethyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 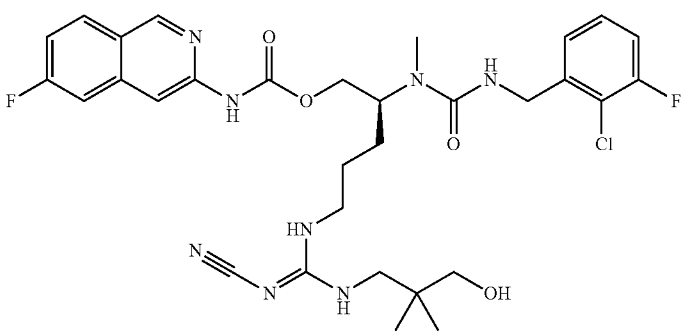 | N-[4-({(1E)-2-cyano-1-[(3-hydroxy-2,2-dimethylpropyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 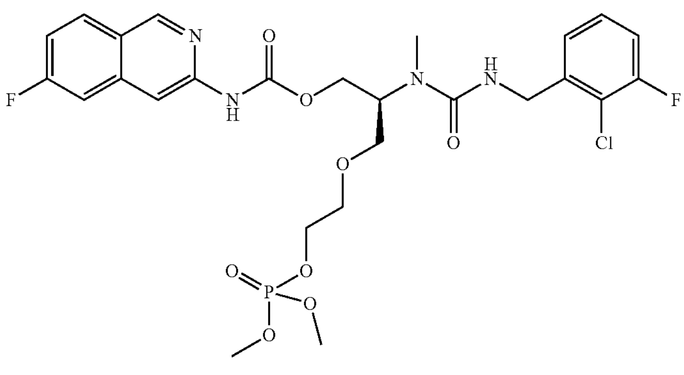 | 2-[(2S)-2-({[(2-chloro-3-fluorophenyl)methyl]amino}-N-methylcarbonylamino)-3-[N-(6-fluoro(3-isoquinolyl))carbamoyloxy]propoxy]ethyl dimethyl phosphate |

-continued

| Structure | Chemical Name |
|---|---|
| 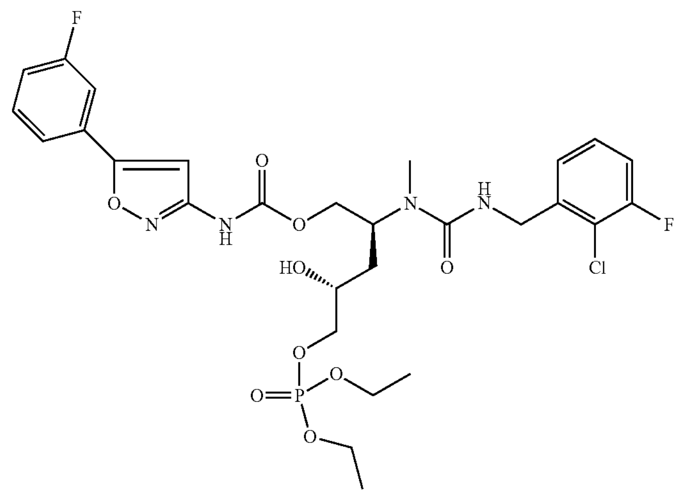 [SMILES: CCOP(=O)(OCC)OC[C@H](O)C[C@@H](COC(=O)Nc1cc(-c2cccc(F)c2)on1)N(C)C(=O)NCc1cccc(F)c1Cl] | (4S,2R)-4-({[(2-chloro-3-fluorophenyl)methyl]amino}-N-methylcarbonylamino)-5-{N-[5-(3-fluorophenyl)isoxazol-3-yl]carbamoyloxy}-2-hydroxypentyl diethyl phosphate |
| 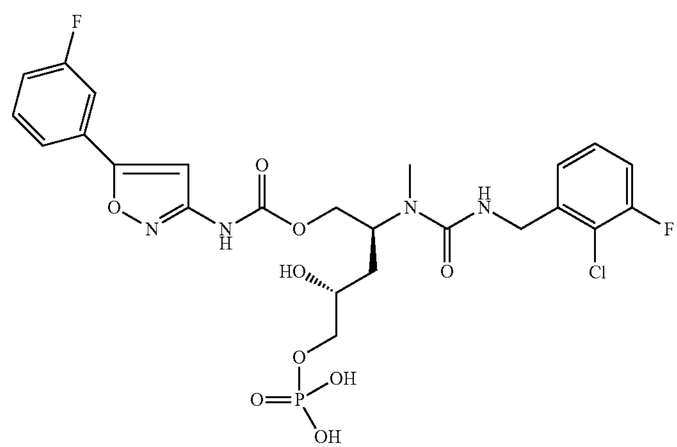 [SMILES: CN(C(=O)NCc1cccc(F)c1Cl)[C@H](COC(=O)Nc1cc(-c2cccc(F)c2)on1)C[C@@H](O)COP(=O)(O)O] | (4S,2R)-4-({[(2-chloro-3-fluorophenyl)methyl]amino}-N-methylcarbonylamino)-5-{N-[5-(3-fluorophenyl)isoxazol-3-yl]carbamoyloxy}-2-hydroxypentyl dihydrogen phosphate |
| 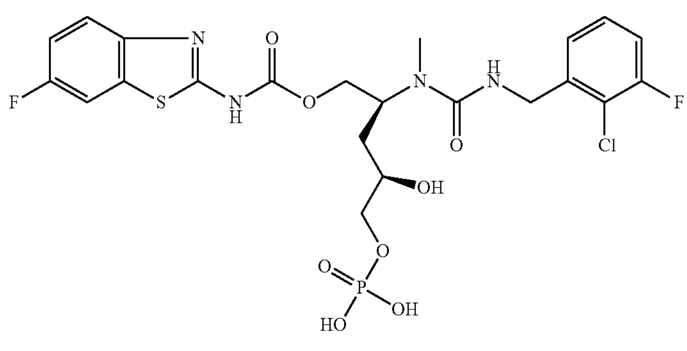 [SMILES: CN(C(=O)NCc1cccc(F)c1Cl)[C@H](COC(=O)Nc1nc2ccc(F)cc2s1)C[C@@H](O)COP(=O)(O)O] | (4S,2R)-4-({[(2-chloro-3-fluorophenyl)methyl]amino}-N-methylcarbonylamino)-5-[N-(6-fluorobenzothiazol-2-yl)carbamoyloxy]-2-hydroxypentyl dihydrogen phosphate |
| 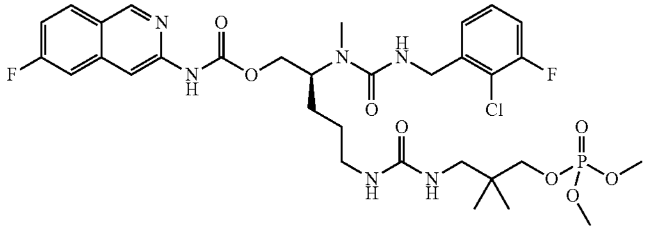 | 3-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)-2,2-dimethylpropyl dimethyl phosphate |

-continued

| Structure | Chemical Name |
|---|---|
| 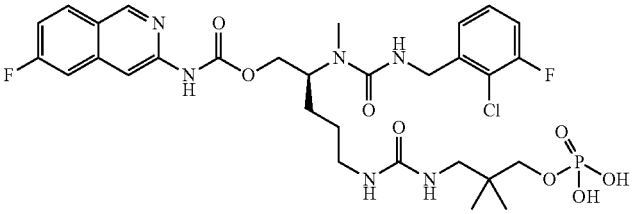 | 3-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)-2,2-dimethylpropyl dihydrogen phosphate |
| 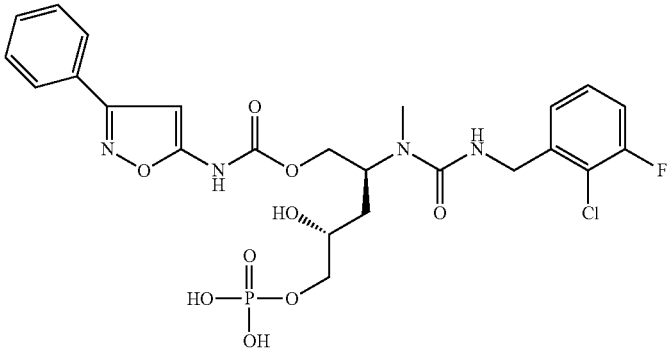 [SMILES: CN(C(=O)NCc1cccc(F)c1Cl)[C@H](COC(=O)Nc1cc(-c2ccccc2)no1)C[C@@H](O)COP(=O)(O)O] | (4S,2R)-4-({[(2-chloro-3-fluorophenyl)methyl]amino}-N-methylcarbonylamino)-2-hydroxy-5-[N-(3-phenylisoxazol-5-yl)carbamoyloxy]pentyl dihydrogen phosphate |
| 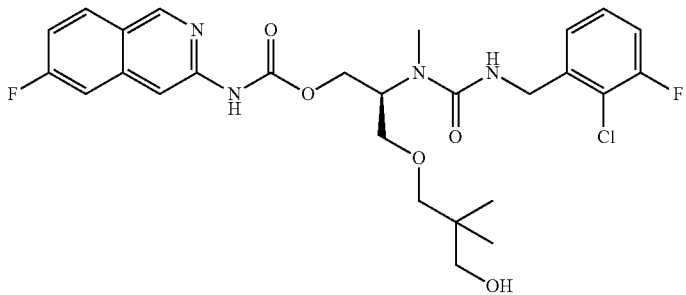 | N-{(1S)-2-[N-(6-fluoro(3-isoquinolyl))carbamoyloxy]-1-[(3-hydroxy-2,2-dimethylpropoxy)methyl]ethyl}{[(2-chloro-3-fluorophenyl)methyl]amino}-N-methylcarboxamide |
| 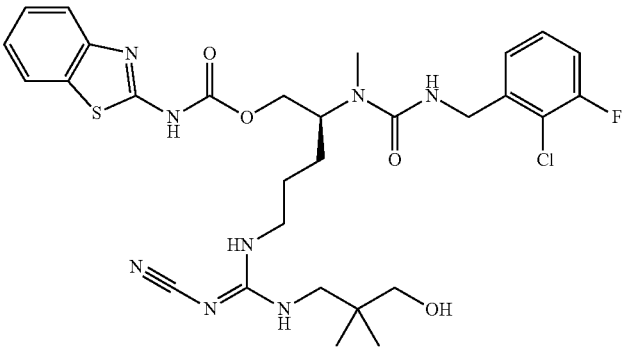 [SMILES: CN(C(=O)NCc1cccc(F)c1Cl)[C@@H](CCCN/C(=N\C#N)NCC(C)(C)CO)COC(=O)Nc1nc2ccccc2s1] | N-[4-({(1E)-2-cyano-1-[(3-hydroxy-2,2-dimethylpropyl)amino]-2-azavinyl}amino)(1S)-1-[(N-benzothiazol-2-ylcarbamoyloxy)methyl]butyl]{[(2-chloro-3-fluorophenyl)methyl]amino}-N-methylcarboxamide |
| 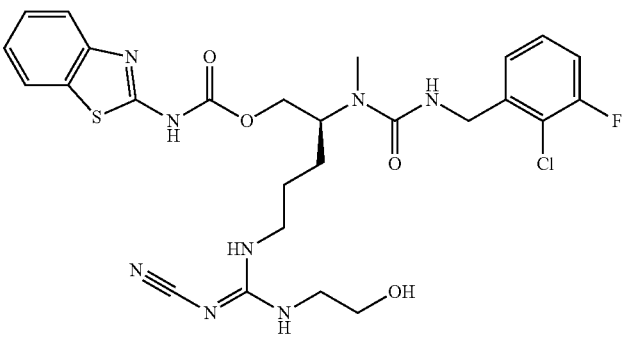 [SMILES: CN(C(=O)NCc1cccc(F)c1Cl)[C@@H](CCCN/C(=N\C#N)NCCO)COC(=O)Nc1nc2ccccc2s1] | N-[4-({(1E)-2-cyano-1-[(2-hydroxyethyl)amino]-2-azavinyl}amino)(1S)-1-[(N-benzothiazol-2-ylcarbamoyloxy)methyl]butyl]{[(2-chloro-3-fluorophenyl)methyl]amino}-N-methylcarboxamide |

-continued

| Structure | Chemical Name |
|---|---|
| 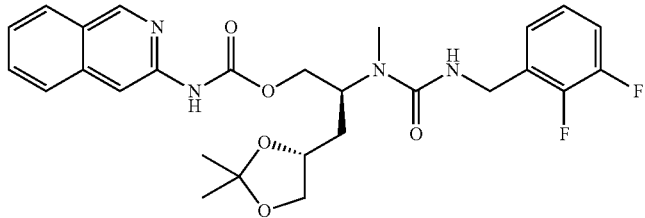 | N-{1-[((4R)-2,2-dimethyl(1,3-dioxolan-4-yl))methyl](1S)-2-(N-(3-isoquinolyl)carbamoyloxy)ethyl}{[(2,3-difluorophenyl)methyl]amino}-N-methylcarboxamide |
| 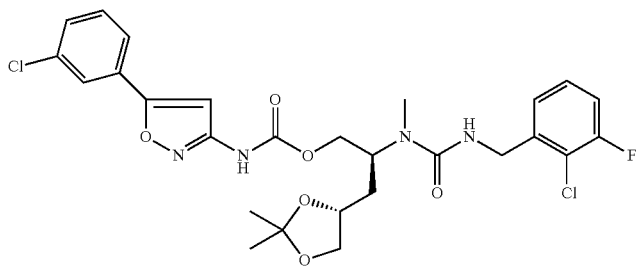 [SMILES: CN(C(=O)NCc1cccc(F)c1Cl)[C@H](COC(=O)Nc1cc(-c2cccc(Cl)c2)on1)C[C@@H]1COC(C)(C)O1] | N-(1-[((4R)-2,2-dimethyl(1,3-dioxolan-4-yl))methyl](1S)-2-{N-[5-(3-chlorophenyl)isoxazol-3-yl]carbamoyloxy}ethyl){[(2-chloro-3-fluorophenyl)methyl]amino}-N-methylcarboxamide |
| 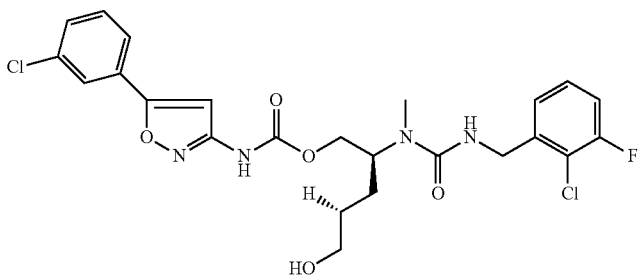 | N-[(1S,3R)-1-({N-[5-(3-chlorophenyl)isoxazol-3-yl]carbamoyloxy}methyl)-3,4-dihydroxybutyl]{[(2-chloro-3-fluorophenyl)methyl]amino}-N-methylcarboxamide |
| 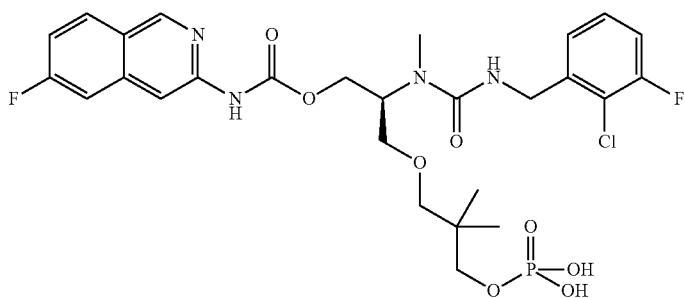 | 3-[(2S)-2-({[(2-chloro-3-fluorophenyl)methyl]amino}-N-methylcarbonylamino)-3-[N-(6-fluoro(3-isoquinolyl))carbamoyloxy]propoxy]-2,2-dimethylpropyl dihydrogen phosphate |
| 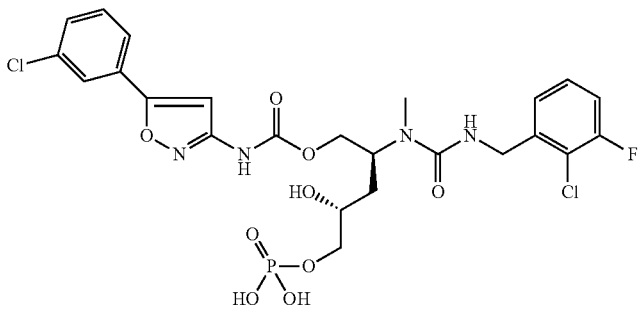 [SMILES: CN(C(=O)NCc1cccc(F)c1Cl)[C@H](COC(=O)Nc1cc(-c2cccc(Cl)c2)on1)C[C@@H](O)COP(=O)(O)O] | (4S,2R)-4-({[(2-chloro-3-fluorophenyl)methyl]amino}-N-methylcarbonylamino)-5-{N-[5-(3-chlorophenyl)isoxazol-3-yl]carbamoyloxy}-2-hydroxypentyl dihydrogen phosphate |

| Structure | Chemical Name |
|---|---|
| 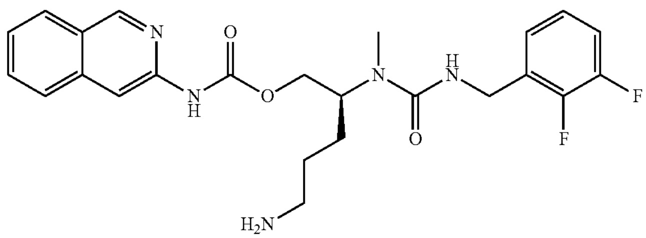 | N-{(1S)-4-amino-1-[(N-(3-isoquinolyl)carbamoyloxy)methyl]butyl}{[(2,3-difluorophenyl)methyl]amino}-N-methylcarboxamide |
| 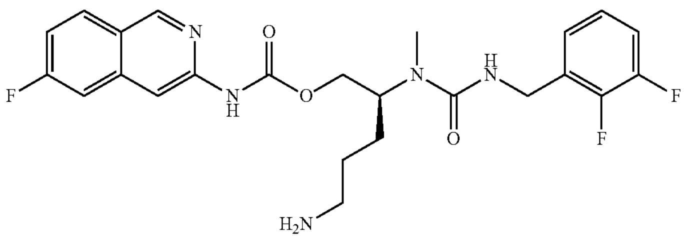 | N-((1S)-4-amino-1-{[N-(6-fluoro(3-isoquinolyl))carbamoyloxy]methyl}butyl){[(2,3-difluorophenyl)methyl]amino}-N-methylcarboxamide |
| 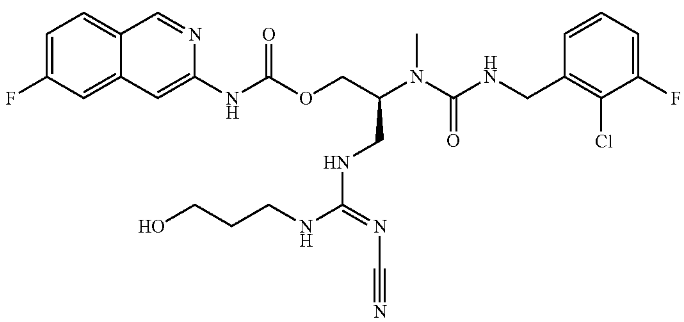 | N-{1-[({(1E)-2-cyano-1-[(3-hydroxypropyl)amino]-2-azavinyl}amino)methyl](1S)-2-[N-(6-fluoro(3-isoquinolyl))carbamoyloxy]ethyl}{[(2-chloro-3-fluorophenyl)methyl]amino}-N-methylcarboxamide |
| 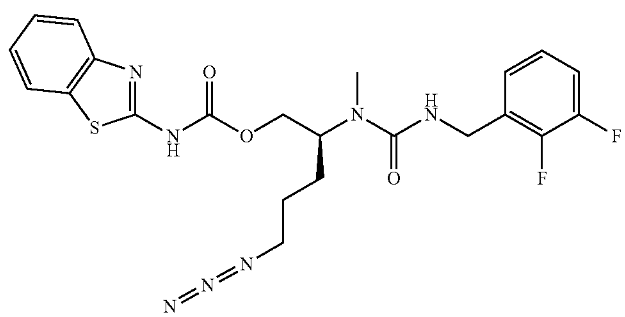 | N-{(1S)-1-[(N-benzothiazol-2-ylcarbamoyloxy)methyl]-5-diazo-5-azapent-5-enyl}{[(2,3-difluorophenyl)methyl]amino}-N-methylcarboxamide |
| 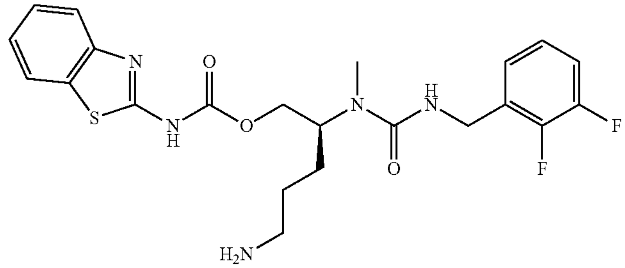 [SMILES: CN(C(=O)NCc1cccc(F)c1F)[C@@H](CCCN)COC(=O)Nc1nc2ccccc2s1] | N-{(1S)-4-amino-1-[(N-benzothiazol-2-ylcarbamoyloxy)methyl]butyl}{[(2,3-difluorophenyl)methyl]amino}-N-methylcarboxamide |

-continued

| Structure | Chemical Name |
|---|---|
| 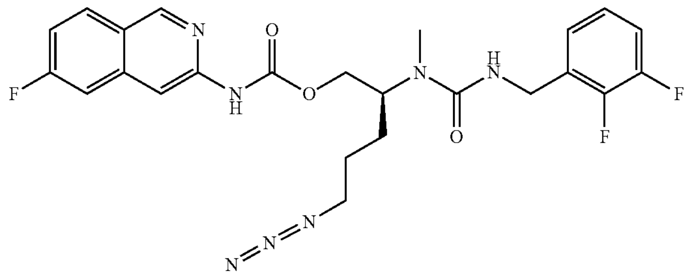 | N-((1S)-5-diazo-1-{[N-(6-fluoro(3-isoquinolyl))carbamoyloxy]methyl}-5-azapent-5-enyl){[(2,3-difluorophenyl)methyl]amino}-N-methylcarboxamide |
| 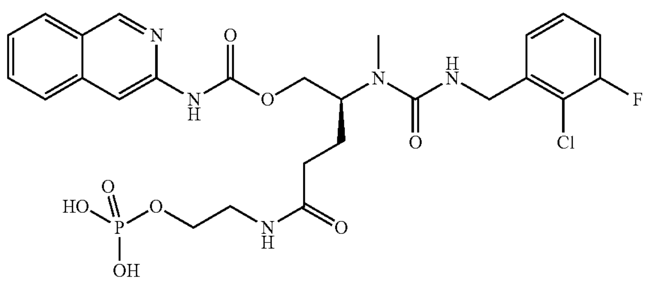 | 2-[(4S)-4-({[(2-chloro-3-fluorophenyl)methyl]amino}-N-methylcarbonylamino)-5-(N-(3-isoquinolyl)carbamoyloxy)pentanoyl-amino]ethyl dihydrogen phosphate |
| 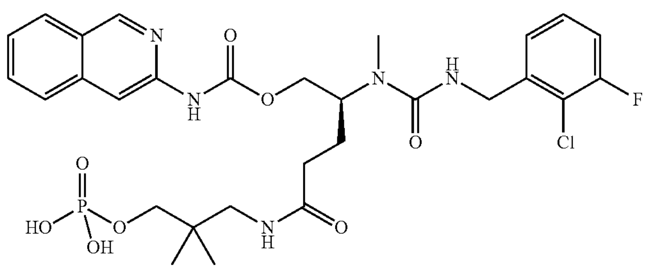 | 3-[(4S)-4-({[(2-chloro-3-fluorophenyl)methyl]amino}-N-methylcarbonylamino)-5-(N-(3-isoquinolyl)carbamoyloxy)pentanoylamino]-2,2-dimethylpropyl dihydrogen phosphate |
| 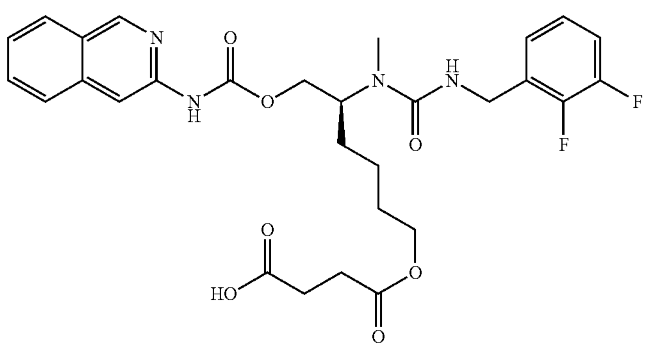 | 3-{[(5S)-5-({[(2,3-difluorophenyl)methyl]amino}-N-methylcarbonylamino)-6-(N-(3-isoquinolyl)carbamoyloxy)hexyl]oxycarbonyl}propanoic acid |
| 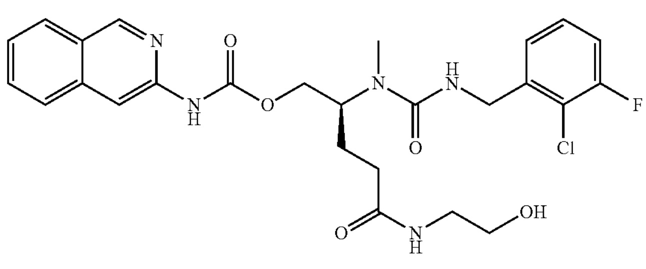 | (4S)-4-({[(2-chloro-3-fluorophenyl)methyl]amino}-N-methylcarbonylamino)-N-(2-hydroxyethyl)-5-(N-(3-isoquinolyl)carbamoyloxy)pentanamide |

| Structure | Chemical Name |
|---|---|
| 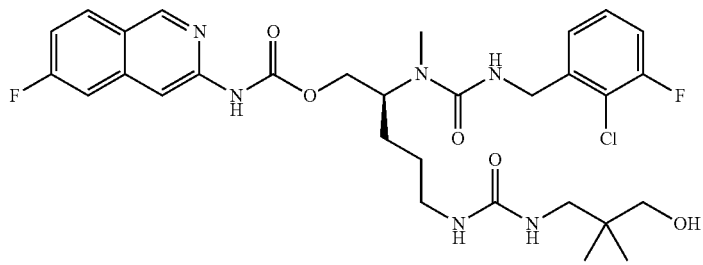 | N-[(4S)-4-({[(2-chloro-3-fluorophenyl)methyl]amino}-N-methylcarbonylamino)-5-[N-(6-fluoro(3-isoquinolyl))carbamoyloxy]pentyl][(3-hydroxy-2,2-dimethylpropyl)amino]carboxamide |
| 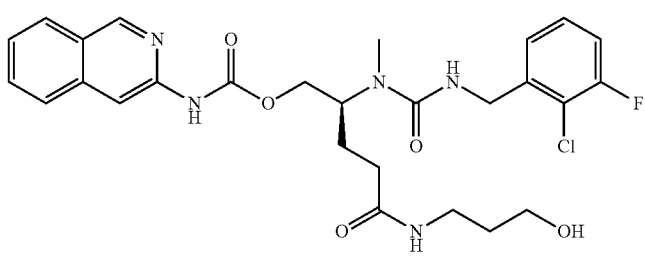 | (4S)-4-({[(2-chloro-3-fluorophenyl)methyl]amino}-N-methylcarbonylamino)-N-(3-hydroxypropyl)-5-(N-(3-isoquinolyl)carbamoyloxy)pentanamide |
| 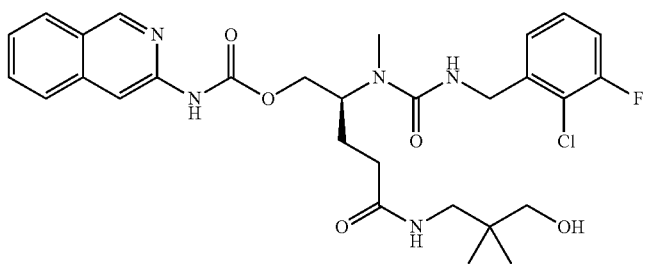 | (4S)-4-({[(2-chloro-3-fluorophenyl)methyl]amino}-N-methylcarbonylamino)-N-(3-hydroxy-2,2-dimethylpropyl)-5-(N-(3-isoquinolyl)carbamoyloxy)pentanamide |
| 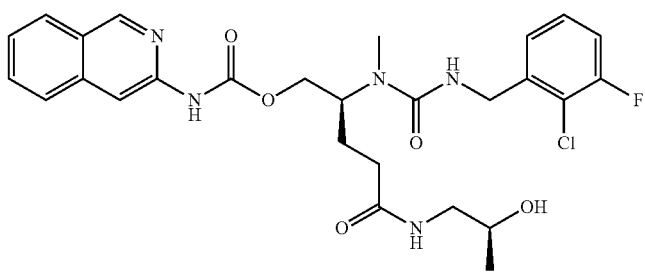 | (4S)-N-((2S)-2-hydroxypropyl)-4-({[(2-chloro-3-fluorophenyl)methyl]amino}-N-methylcarbonylamino)-5-(N-(3-isoquinolyl)carbamoyloxy)pentanamide |
| 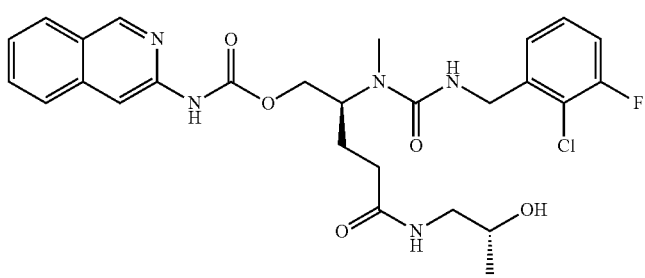 | N-((2R)-2-hydroxypropyl)(4S)-4-({[(2-chloro-3-fluorophenyl)methyl]amino}-N-methylcarbonylamino)-5-(N-(3-isoquinolyl)carbamoyloxy)pentanamide |

-continued

| Structure | Chemical Name |
|---|---|
| 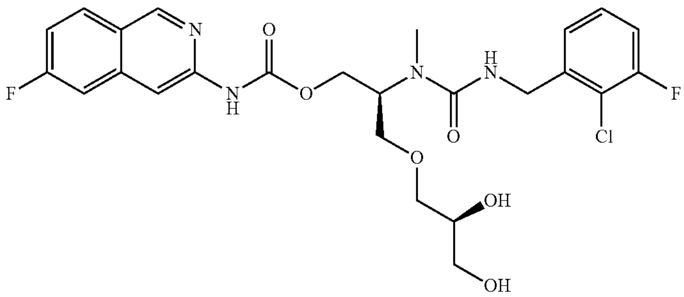 | N-{(1S)-1-[((2S)-2,3-dihydroxypropoxy)methyl]-2-[N-(6-fluoro(3-isoquinolyl))carbamoyloxy]ethyl}{[(2-chloro-3-fluorophenyl)methyl]amino}-N-methylcarboxamide |
| | 2-[(4S)-4-({[(2-chloro-3-fluorophenyl)methyl]amino}-N-methylcarbonylamino)-5-(N-(3-isoquinolyl)carbamoyloxy)pentanoylamino] ethyl ditert-butyl phosphate |
| 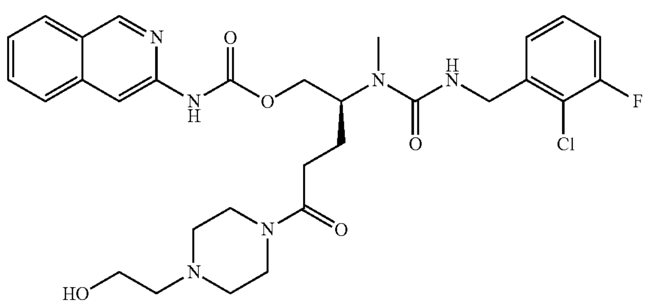 | [(2S)-2-({[(2-chloro-3-fluorophenyl)methyl]amino}-N-methylcarbonylamino)-5-[4-(2-hydroxyethyl)piperazinyl]-5-oxopentyloxy]-N-(3-isoquinolyl)carboxamide |
| 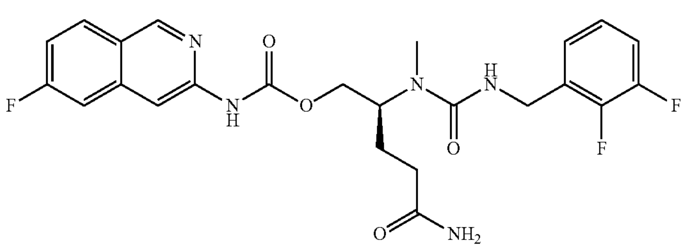 | N-((1S)-3-carbamoyl-1-{[N-(6-fluoro(3-isoquinolyl))carbamoyloxy]methyl}propyl){[(2,3-difluorophenyl)methyl]amino}-N-methylcarboxamide |
| 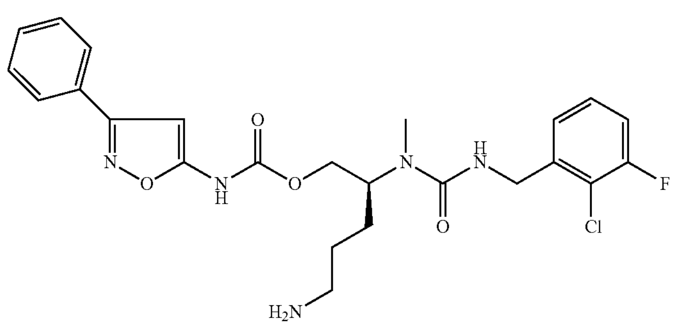 [SMILES: CN(C(=O)NCc1cccc(F)c1Cl)[C@@H](CCCN)COC(=O)Nc1cc(-c2ccccc2)no1] | N-((1S)-4-amino-1-{[N-(3-phenylisoxazol-5-yl)carbamoyloxy]methyl}butyl){[(2-chloro-3-fluorophenyl)methyl]amino}-N-methylcarboxamide |

-continued

| Structure | Chemical Name |
|---|---|
| 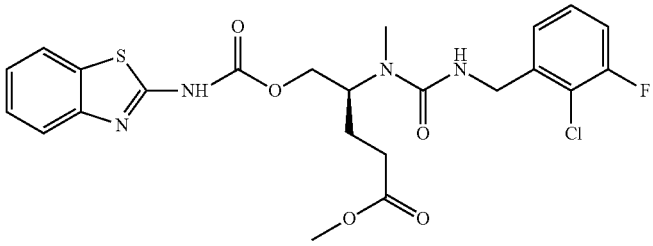 [SMILES: COC(=O)CC[C@@H](COC(=O)Nc1nc2ccccc2s1)N(C)C(=O)NCc1cccc(F)c1Cl] | methyl (4S)-5-(N-benzothiazol-2-ylcarbamoyloxy)-4-({[(2-chloro-3-fluorophenyl)methyl]amino}-N-methylcarbonylamino)pentanoate |
| 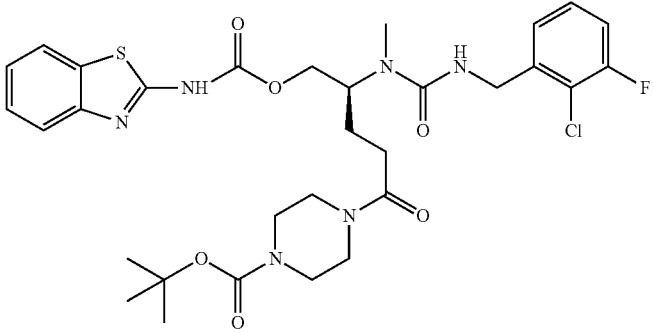 [SMILES: CN(C(=O)NCc1cccc(F)c1Cl)[C@@H](CCC(=O)N1CCN(C(=O)OC(C)(C)C)CC1)COC(=O)Nc1nc2ccccc2s1] | tert-butyl 4-[(4S)-5-(N-benzothiazol-2-ylcarbamoyloxy)-4-({[(2-chloro-3-fluorophenyl)methyl]amino}-N-methylcarbonylamino)pentanoyl]piperazinecarboxylate |
| 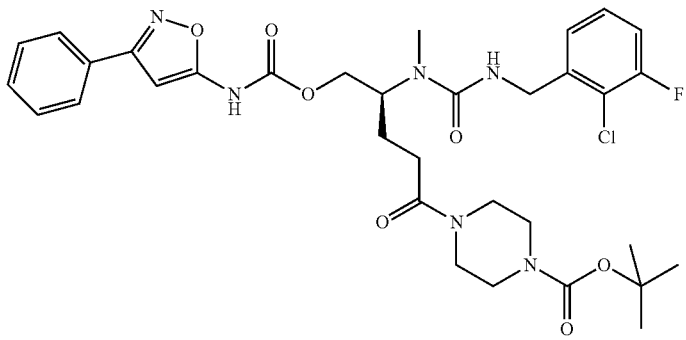 | tert-butyl 4-[(4S)-4-({[(2-chloro-3-fluorophenyl)methyl]amino}-N-methylcarbonylamino)-5-[N-(3-phenylisoxazol-5-yl)carbamoyloxy]pentanoyl]piperazinecarboxylate |
| 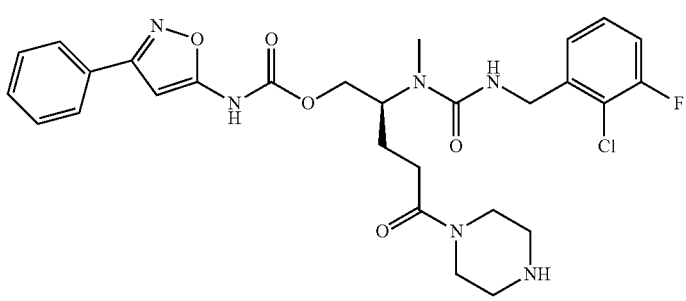 | N-((1S)-4-oxo-1-{[N-(3-phenylisoxazol-5-yl)carbamoyloxy]methyl}-4-piperazinylbutyl){[(2-chloro-3-fluorophenyl)methyl]amino}-N-methylcarboxamide |
| 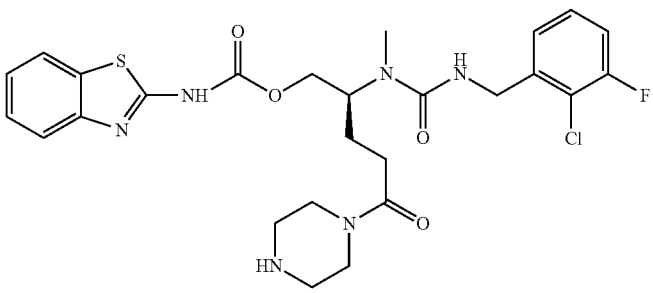 [SMILES: CN(C(=O)NCc1cccc(F)c1Cl)[C@@H](CCC(=O)N1CCNCC1)COC(=O)Nc1nc2ccccc2s1] | N-{(1S)-1-[(N-benzothiazol-2-ylcarbamoyloxy)methyl]-4-oxo-4-piperazinylbutyl}{[(2-chloro-3-fluorophenyl)methyl]amino}-N-methylcarboxamide |

-continued

| Structure | Chemical Name |
|---|---|
| 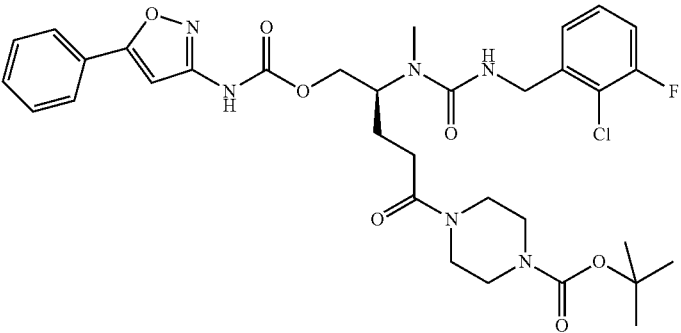 | tert-butyl 4-[(4S)-4-({[(2-chloro-3-fluorophenyl)methyl]amino}-N-methylcarbonylamino)-5-[N-(5-phenylisoxazol-3-yl)carbamoyloxy]pentanoyl]piperazinecarboxylate |
| 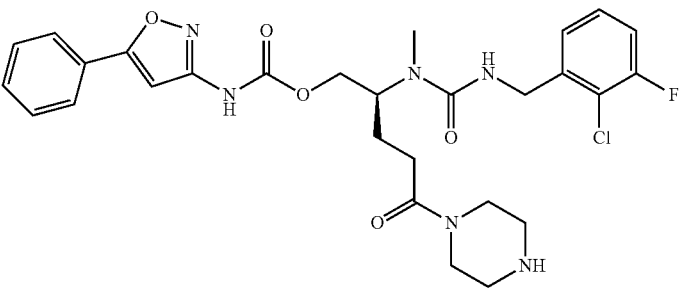 | N-((1S)-4-oxo-1-{[N-(5-phenylisoxazol-3-yl)carbamoyloxy]methyl}-4-piperazinylbutyl){[(2-chloro-3-fluorophenyl)methyl]amino}-N-methylcarboxamide |
| 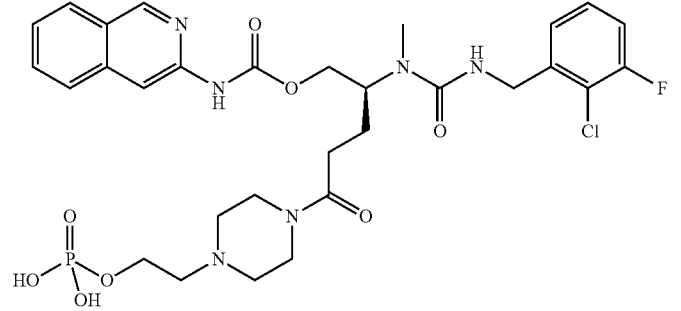 | 2-{4-[(4S)-4-({[(2-chloro-3-fluorophenyl)methyl]amino}-N-methylcarbonylamino)-5-(N-(3-isoquinolyl)carbamoyloxy)pentanoyl]piperazinyl} ethyl dihydrogen phosphate |
| 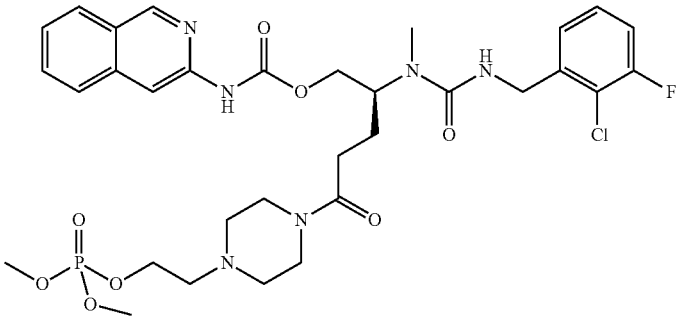 | 2-{4-[(4S)-4-({[(2-chloro-3-fluorophenyl)methyl]amino}-N-methylcarbonylamino)-5-(N-(3-isoquinolyl)carbamoyloxy)pentanoyl]piperazinyl}ethyl dimethyl phosphate |

-continued

| Structure | Chemical Name |
|---|---|
| 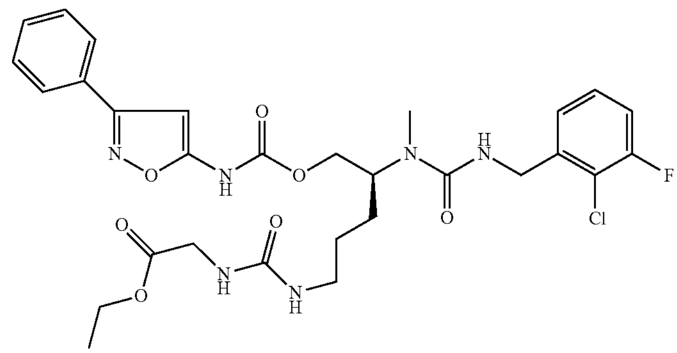 [SMILES: CCOC(=O)CNC(=O)NCCC[C@@H](COC(=O)Nc1cc(-c2ccccc2)no1)N(C)C(=O)NCc1cccc(F)c1Cl] | ethyl 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)acetate |
| 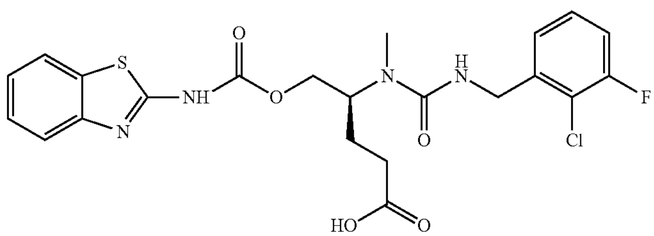 [SMILES: CN(C(=O)NCc1cccc(F)c1Cl)[C@@H](CCC(=O)O)COC(=O)Nc1nc2ccccc2s1] | (4S)-5-(N-benzothiazol-2-ylcarbamoyloxy)-4-({[(2-chloro-3-fluorophenyl)methyl]amino}-N-methylcarbonylamino)pentanoic acid |
| 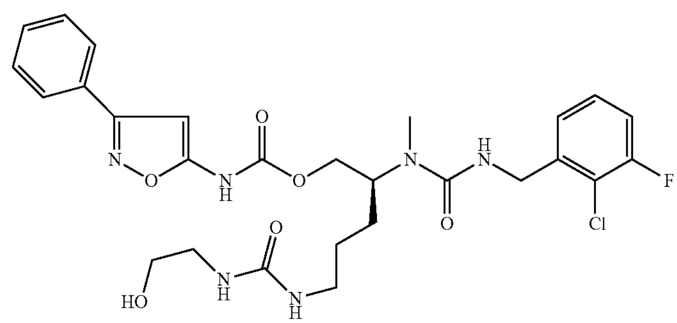 [SMILES: CN(C(=O)NCc1cccc(F)c1Cl)[C@@H](CCCNC(=O)NCCO)COC(=O)Nc1cc(-c2ccccc2)no1] | N-[(4S)-4-({[(2-chloro-3-fluorophenyl)methyl]amino}-N-methylcarbonylamino)-5-[N-(3-phenylisoxazol-5-yl)carbamoyloxy]pentyl][(2-hydroxyethyl)amino]carboxamide |
| 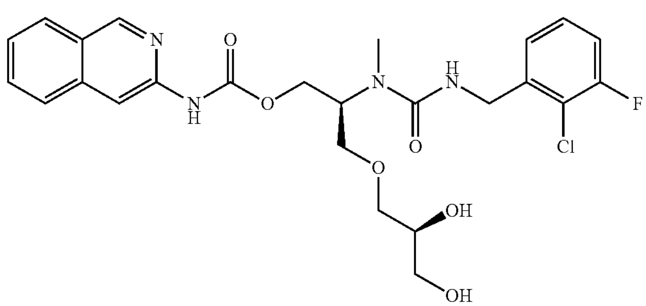 | N-{(1S)-1-[((2S)-2,3-dihydroxypropoxy)methyl]-2-(N-(3-isoquinolyl)carbamoyloxy)ethyl}{[(2-chloro-3-fluorophenyl)methyl]amino}-N-methylcarboxamide |
| 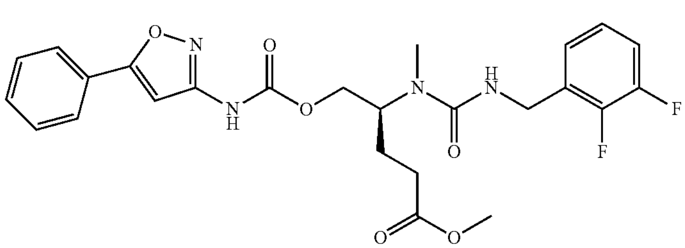 | methyl (4S)-4-({[(2,3-difluorophenyl)methyl]amino}-N-methylcarbonylamino)-5-[N-(5-phenylisoxazol-3-yl)carbamoyloxy]pentanoate |

-continued

| Structure | Chemical Name |
|---|---|
| 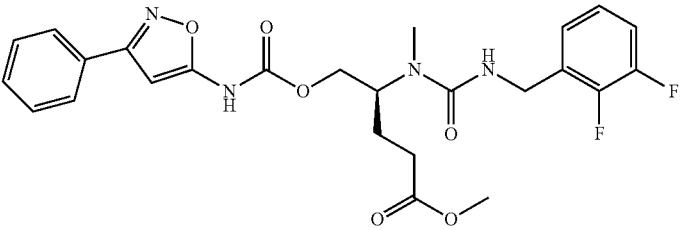 | methyl (4S)-4-({[(2,3-difluorophenyl)methyl]amino}-N-methylcarbonylamino)-5-[N-(3-phenylisoxazol-5-yl)carbamoyloxy]pentanoate |
| 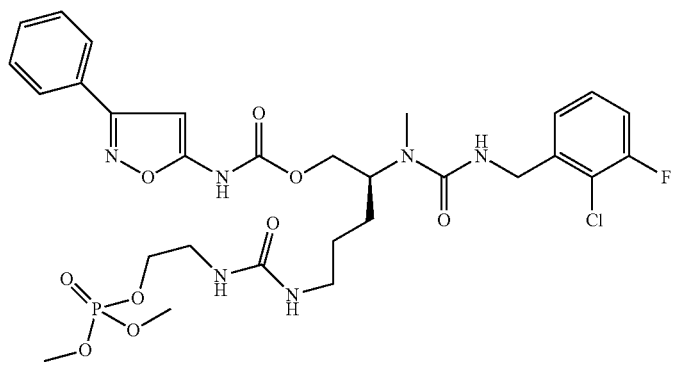 | 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)ethyl dimethyl phosphate |
| 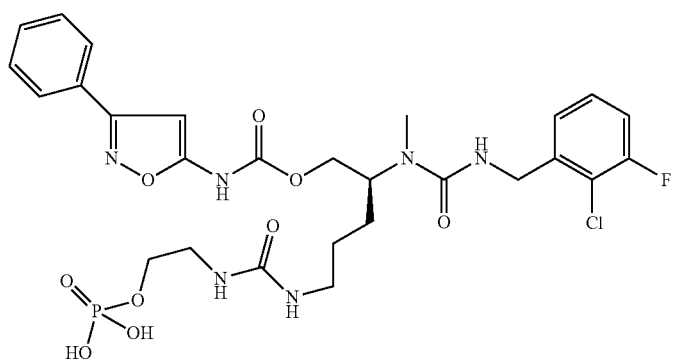 [SMILES: CN(C(=O)NCc1cccc(F)c1Cl)[C@@H](CCCNC(=O)NCCOP(=O)(O)O)COC(=O)Nc1cc(-c2ccccc2)no1] | 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)ethyl dihydrogen phosphate |
| 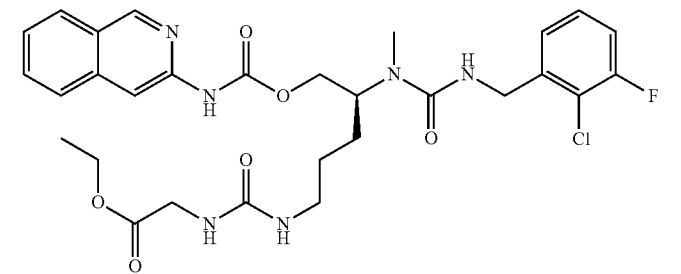 | ethyl 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino) acetate |
| 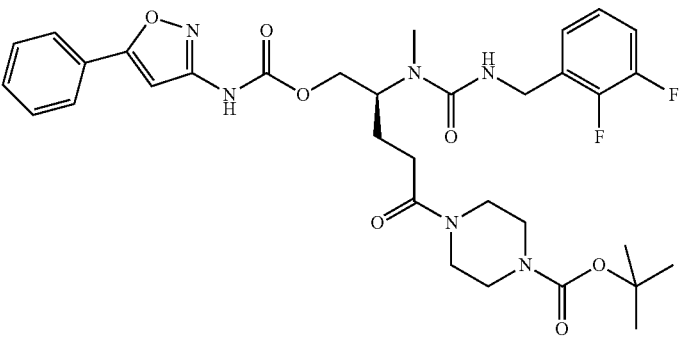 | tert-butyl 4-[(4S)-4-({[(2,3-difluorophenyl)methyl]amino}-N-methylcarbonylamino)-5-[N-(5-phenylisoxazol-3-yl)carbamoyloxy]pentanoyl]piperazinecarboxylate |

| Structure | Chemical Name |
|---|---|
| 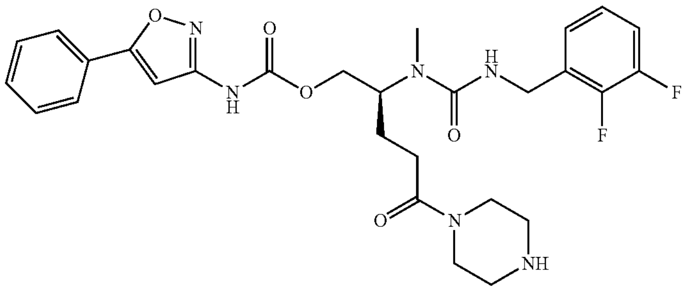 | [(2S)-2-({[(2,3-difluorophenyl)methyl]amino}-N-methylcarbonylamino)-5-oxo-5-piperazinylpentyloxy]-N-(5-phenylisoxazol-3-yl)carboxamide |
| 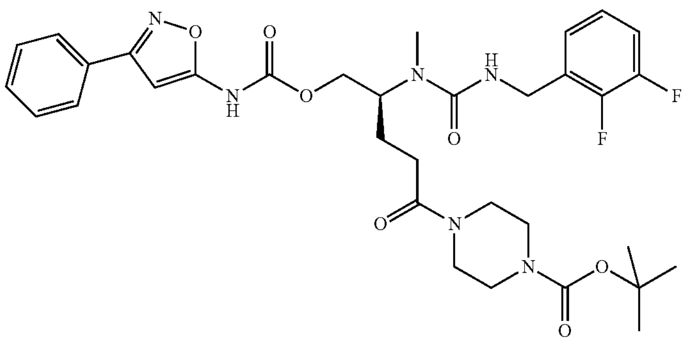 | tert-butyl 4-[(4S)-4-({[(2,3-difluorophenyl)methyl]amino}-N-methylcarbonylamino)-5-[N-(3-phenylisoxazol-5-yl)carbamoyloxy]pentanoyl]piperazinecarboxylate |
| 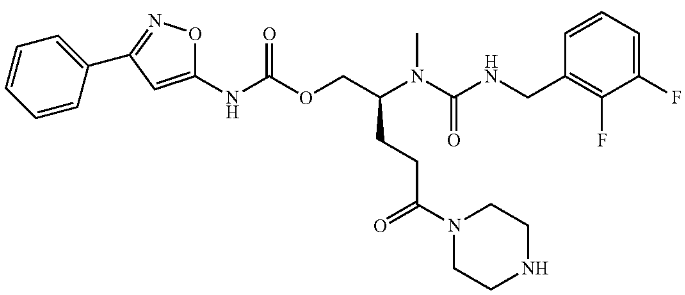 | [(2S)-2-({[(2,3-difluorophenyl)methyl]amino}-N-methylcarbonylamino)-5-oxo-5-piperazinylpentyloxy]-N-(3-phenylisoxazol-5-yl)carboxamide |
| 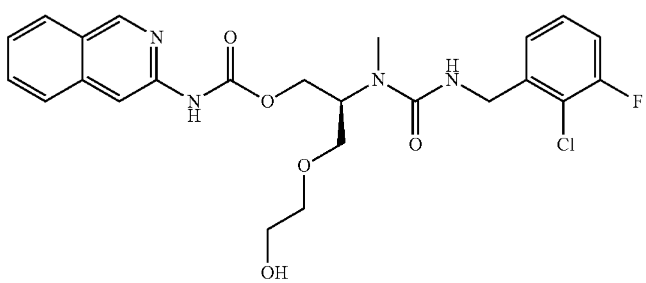 | N-{(1S)-1-[(2-hydroxyethoxy)methyl]-2-(N-(3-isoquinolyl)carbamoyloxy)ethyl}{[(2-chloro-3-fluorophenyl)methyl]amino}-N-methylcarboxamide |
| 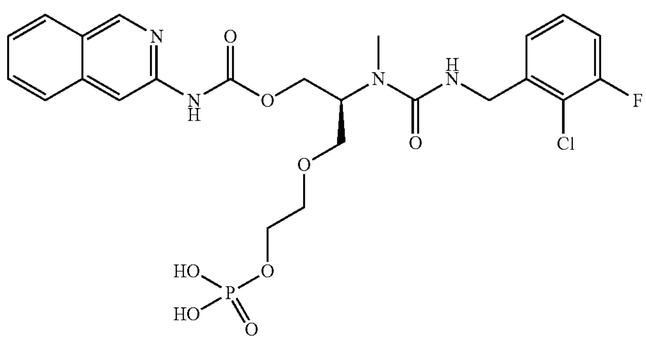 | 2-[(2S)-2-({[(2-chloro-3-fluorophenyl)methyl]amino}-N-methylcarbonylamino)-3-(N-(3-isoquinolyl)carbamoyloxy)propoxy]ethyl dihydrogen phosphate |

-continued

| Structure | Chemical Name |
|---|---|
| 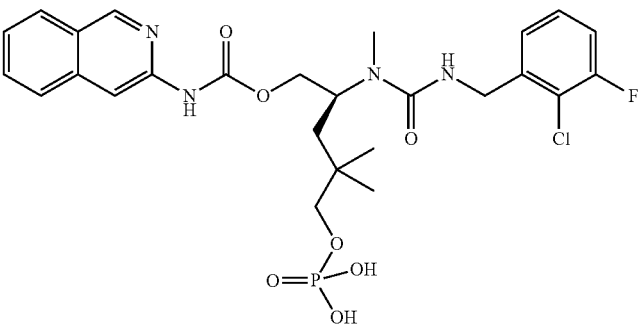 | (4S)-4-({[(2-chloro-3-fluorophenyl)methyl]amino}-N-methylcarbonylamino)-5-(N-(3-isoquinolyl)carbamoyloxy)-2,2-dimethylpentyl dihydrogen phosphate |
| 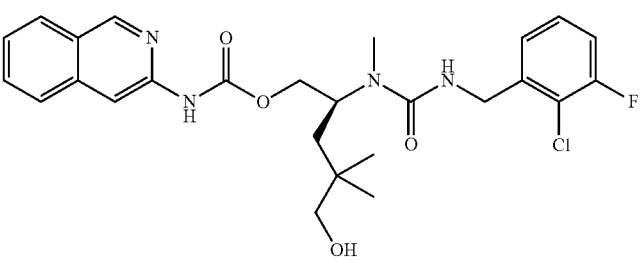 | [(2S)-2-({[(2-chloro-3-fluorophenyl)methyl]amino}-N-methylcarbonylamino)-5-hydroxy-4,4-dimethylpentyloxy]-N-(3-isoquinolyl)carboxamide |
| 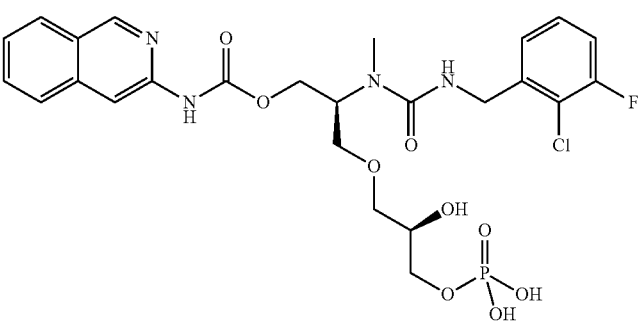 | (2R)-3-[(2S)-2-({[(2-chloro-3-fluorophenyl)methyl]amino}-N-methylcarbonylamino)-3-(N-(3-isoquinolyl)carbamoyloxy)propoxy]-2-hydroxypropyl dihydrogen phosphate |
| 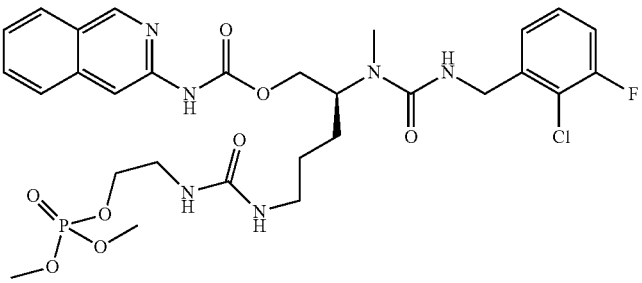 | 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino)ethyl dimethyl phosphate |
| 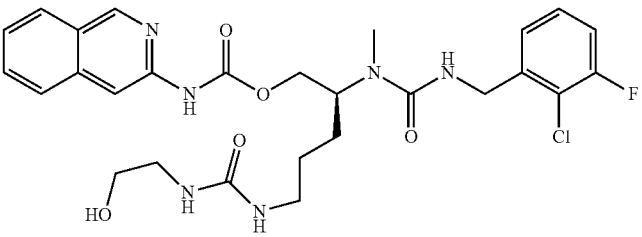 | N-[(4S)-4-({[(2-chloro-3-fluorophenyl)methyl]amino}-N-methylcarbonylamino)-5-(N-(3-isoquinolyl)carbamoyloxy)pentyl][(2-hydroxyethyl)amino]carboxamide |

-continued

| Structure | Chemical Name |
|---|---|
| 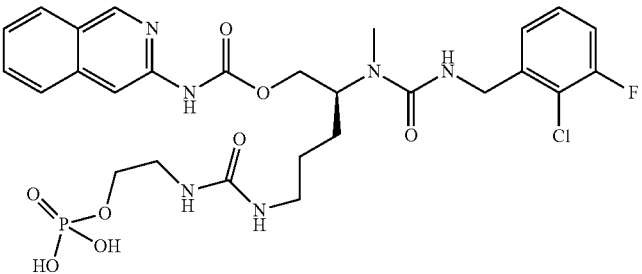 | 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino)ethyl dihydrogen phosphate |
| 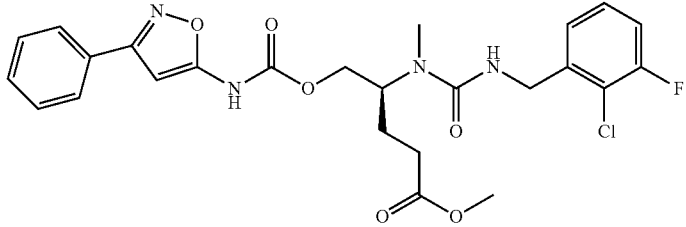 | methyl (4S)-4-({[(2-chloro-3-fluorophenyl)methyl]amino}-N-methylcarbonylamino)-5-[N-(3-phenylisoxazol-5-yl)carbamoyloxy]pentanoate |
| 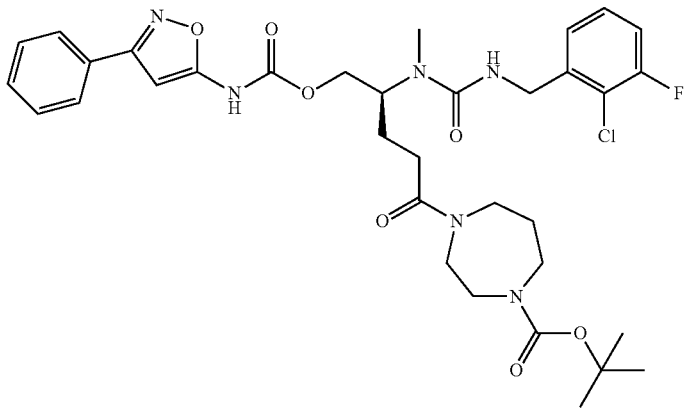 | tert-butyl 4-[(4S)-4-({[(2-chloro-3-fluorophenyl)methyl]amino}-N-methylcarbonylamino)-5-[N-(3-phenylisoxazol-5-yl)carbamoyloxy]pentanoyl]-1,4-diazaperhydroepinecarboxylate |
| 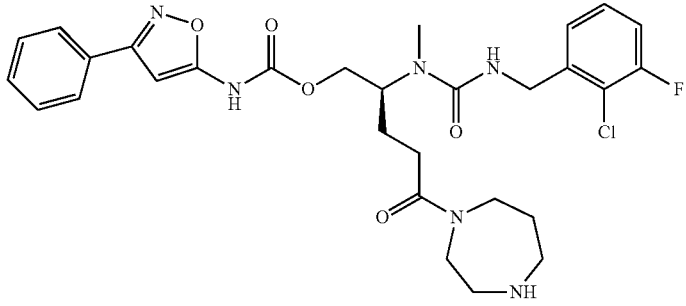 | [(2S)-2-({[(2-chloro-3-fluorophenyl)methyl]amino}-N-methylcarbonylamino)-5-(1,4-diazaperhydroepinyl)-5-oxopentyloxy]-N-(3-phenylisoxazol-5-yl)carboxamide |
| 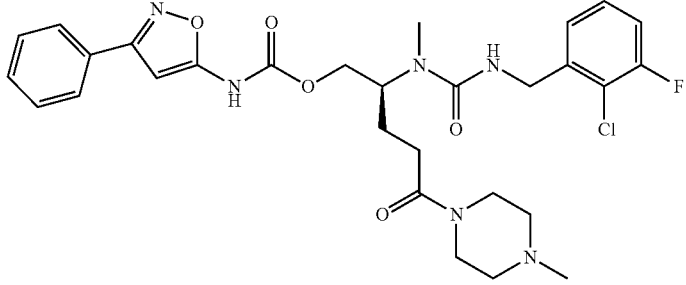 | [(2S)-2-({[(2-chloro-3-fluorophenyl)methyl]amino}-N-methylcarbonylamino)-5-(4-methylpiperazinyl)-5-oxopentyloxy]-N-(3-phenyl-isoxazol-5-yl)carboxamide |

-continued

| Structure | Chemical Name |
|---|---|
| 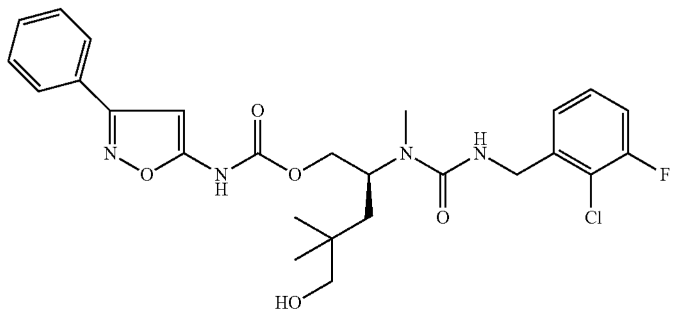 [SMILES: CN(C(=O)NCc1cccc(F)c1Cl)[C@H](COC(=O)Nc1cc(-c2ccccc2)no1)CC(C)(C)CO] | N-((1S)-4-hydroxy-3,3-dimethyl-1-{[N-(3-phenylisoxazol-5-yl)carbamoyloxy]methyl}butyl){[(2-chloro-3-fluorophenyl)methyl]amino}-N-methylcarboxamide |
| 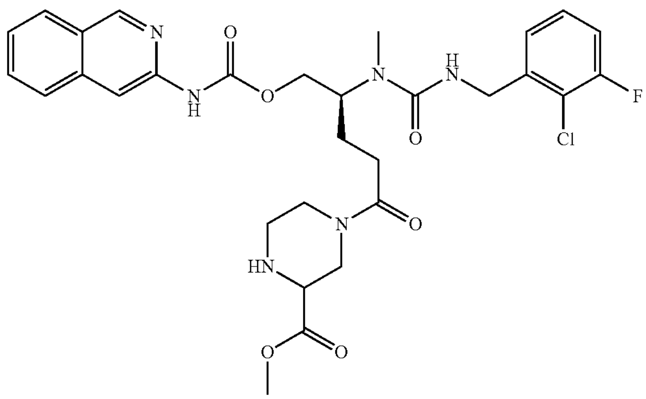 | methyl 4-[(4S)-4-({[(2-chloro-3-fluorophenyl)methyl]amino}-N-methylcarbonylamino)-5-(N-(3-isoquinolyl)carbamoyloxy)pentanoyl]piperazine-2-carboxylate |
| 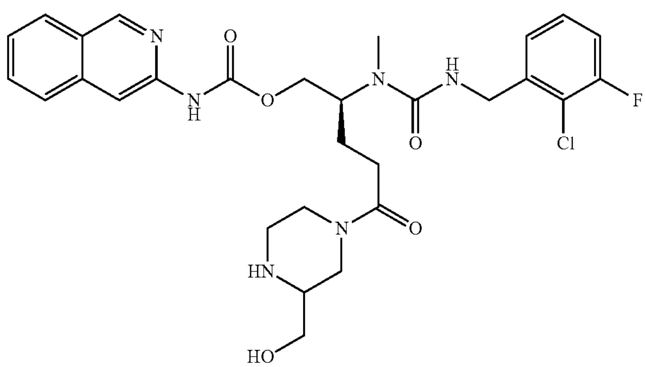 | N-{(1S)-4-[3-(hydroxymethyl)piperazinyl]-1-[(N-(3-isoquinolyl)carbamoyloxy)methyl]-4-oxobutyl}{[(2-chloro-3-fluorophenyl)methyl]amino}-N-methylcarboxamide |
| 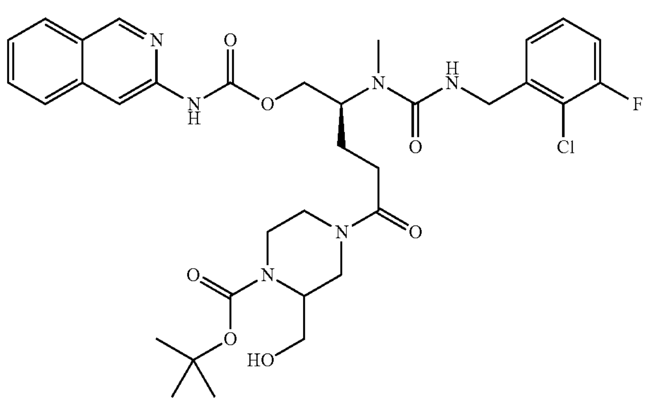 | tert-butyl 4-[(4S)-4-({[(2-chloro-3-fluorophenyl)methyl]amino}-N-methylcarbonylamino)-5-(N-(3-isoquinolyl)carbamoyloxy)pentanoyl]-2-(hydroxymethyl)piperazinecarboxylate |

-continued

| Structure | Chemical Name |
|---|---|
| 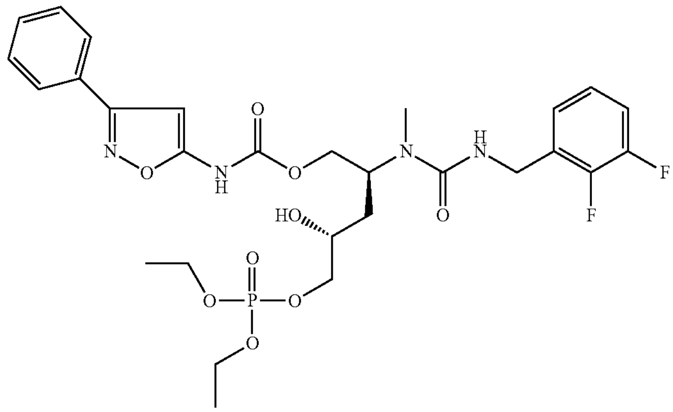 [SMILES: CCOP(=O)(OCC)OC[C@H](O)C[C@@H](COC(=O)Nc1cc(-c2ccccc2)no1)N(C)C(=O)NCc1cccc(F)c1F] | (4S,2R)-4-({[(2,3-difluorophenyl)methyl]amino}-N-methylcarbonylamino)-2-hydroxy-5-[N-(3-phenylisoxazol-5-yl)carbamoyloxy]pentyl diethyl phosphate |
| 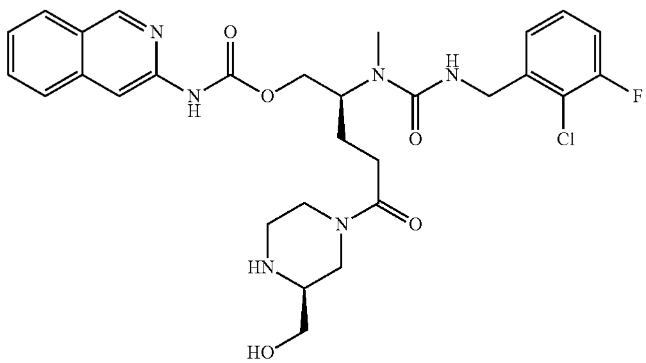 | N-{(1S)-4-[(3S)-3-(hydroxymethyl)piperazinyl]-1-[(N-(3-isoquinolyl)carbamoyloxy)methyl]-4-oxobutyl}{[(2-chloro-3-fluorophenyl)methyl]amino}-N-methylcarboxamide |
| 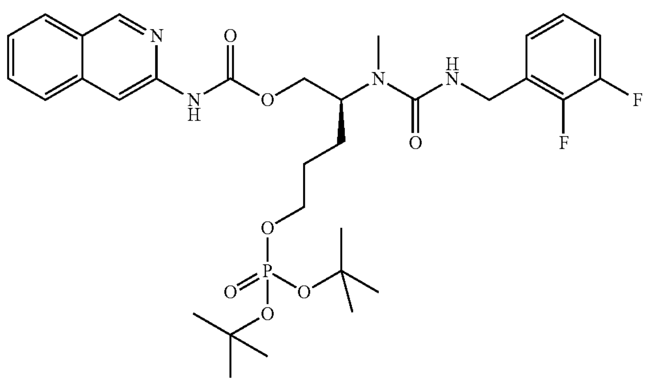 | (4S)-4-({[(2,3-difluorophenyl)methyl]amino}-N-methylcarbonylamino)-5-(N-(3-isoquinolyl)carbamoyloxy)pentyl ditert-butyl phosphate |
| | N-((1S)-4-hydroxy-4-methyl-1-{[[N-(3-phenylisoxazol-5-yl)carbamoyloxy]methyl}pentyl){[(2-chloro-3-fluorophenyl)methyl]amino}-N-methylcarboxamide |

-continued

| Structure | Chemical Name |
|---|---|
| 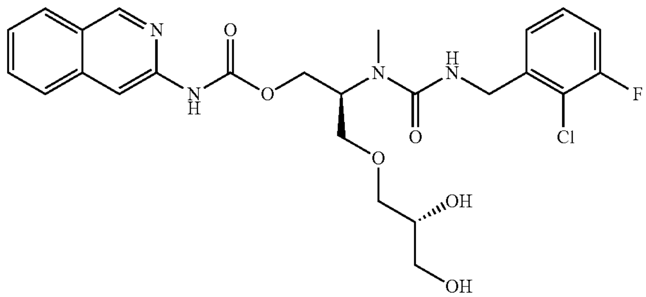 | N-{1-[((2R)-2,3-dihydroxypropoxy)methyl](1S)-2-(N-(3-isoquinolyl)carbamoyloxy)ethyl}{[(2-chloro-3-fluorophenyl)methyl]amino}-N-methylcarboxamide |
| 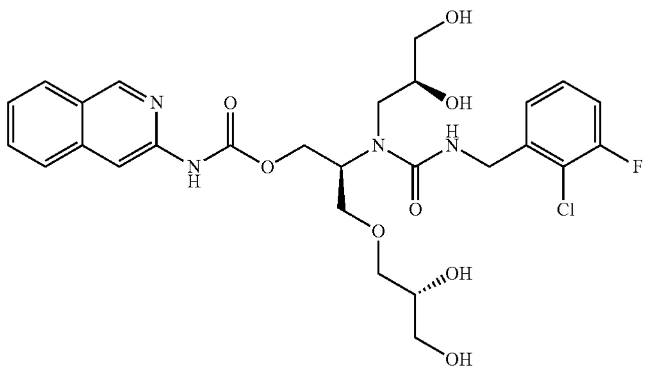 | N-{1-[((2R)-2,3-dihydroxypropoxy)methyl](1S)-2-(N-(3-isoquinolyl)carbamoyloxy)ethyl}-N-((2S)-2,3-dihydroxypropyl){[(2-chloro-3-fluorophenyl)methyl]amino}carboxamide |
| 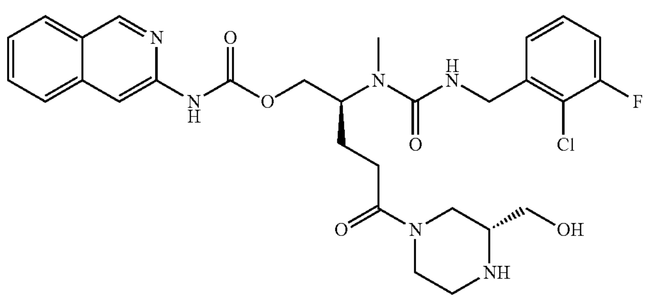 | N-{4-[(3R)-3-(hydroxymethyl)piperazinyl](1S)-1-[(N-(3-isoquinolyl)carbamoyloxy)methyl]-4-oxobutyl}{[(2-chloro-3-fluorophenyl)methyl]amino}-N-methylcarboxamide |
| 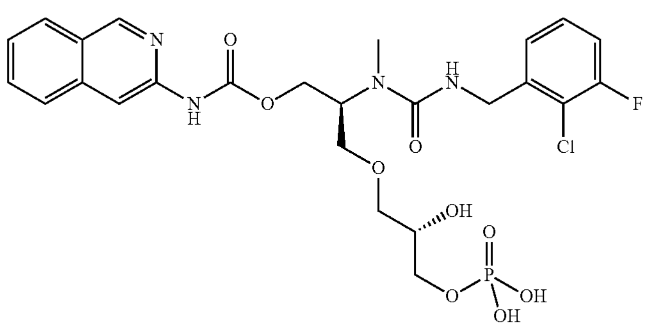 | (2S)-3-[(2S)-2-({[(2-chloro-3-fluorophenyl)methyl]amino}-N-methylcarbonylamino)-3-(N-(3-isoquinolyl)carbamoyloxy)propoxy]-2-hydroxypropyl dihydrogen phosphate |
| 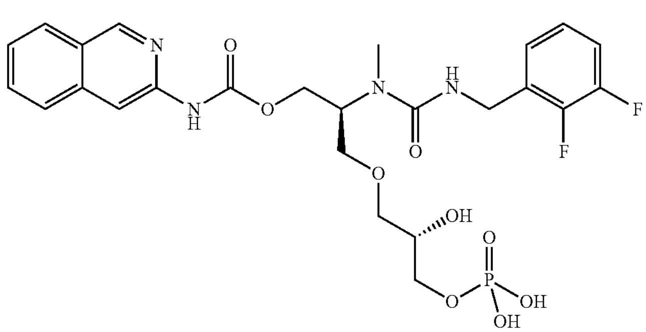 | (2S)-3-[(2S)-2-({[(2,3-difluorophenyl)methyl]amino}-N-methylcarbonylamino)-3-(N-(3-isoquinolyl)carbamoyloxy)propoxy]-2-hydroxypropyl dihydrogen phosphate |

-continued

| Structure | Chemical Name |
|---|---|
| 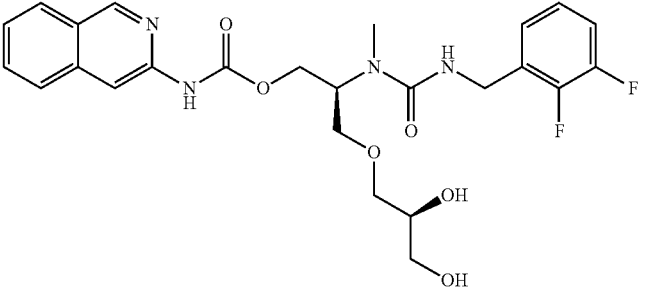 | N-{(1S)-1-[((2S)-2,3-dihydroxypropoxy)methyl]-2-(N-(3-isoquinolyl)carbamoyloxy)ethyl}{[(2,3-difluorophenyl)methyl]amino}-N-methylcarboxamide |
| 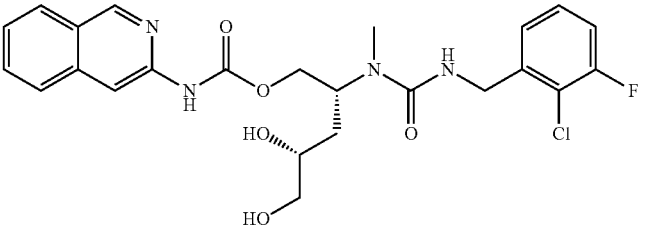 | [(2R,4R)-2-({[(2-chloro-3-fluorophenyl)methyl]amino}-N-methylcarbonylamino)-4,5-dihydroxypentyloxy]-N-(3-isoquinolyl)carboxamide |
| 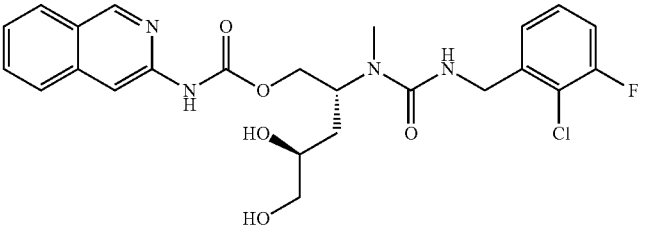 | [(4S,2R)-2-({[(2-chloro-3-fluorophenyl)methyl]amino}-N-methylcarbonylamino)-4,5-dihydroxypentyloxy]-N-(3-isoquinolyl)carboxamide |
| 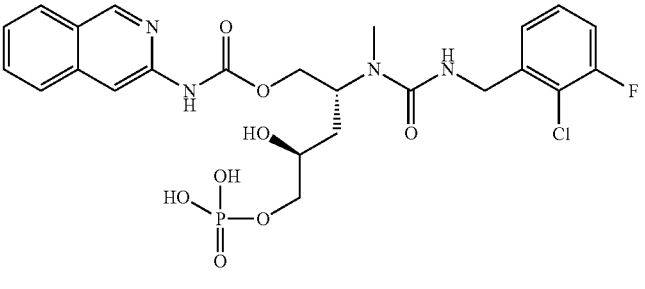 | (2S,4R)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate |
| 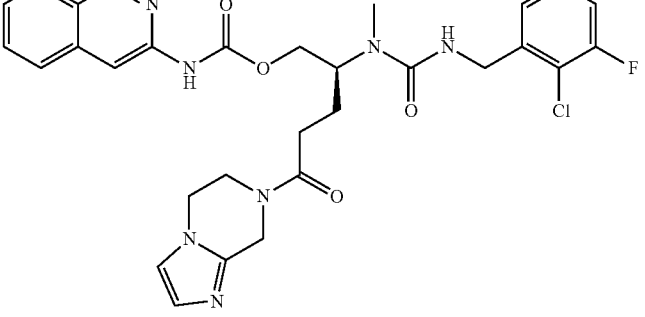 | [(2S)-2-({[(2-chloro-3-fluorophenyl)methyl]amino}-N-methylcarbonylamino)-5-imidazo[2,1-c]piperazin-7-yl-5-oxopentyloxy]-N-(3-isoquinolyl)carboxamide |

-continued

| Structure | Chemical Name |
|---|---|
| 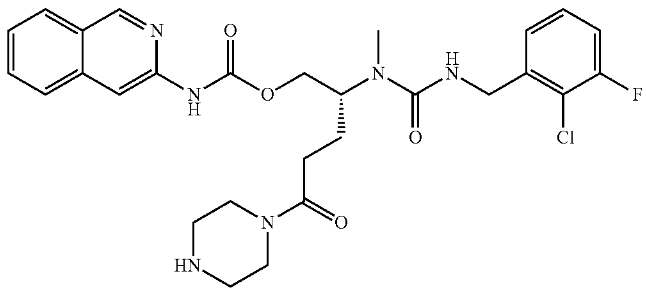 | [(2R)-2-({[(2-chloro-3-fluorophenyl)methyl]amino}-N-methylcarbonylamino)-5-oxo-5-piperazinylpentyloxy]-N-(3-isoquinolyl)carboxamide |
| 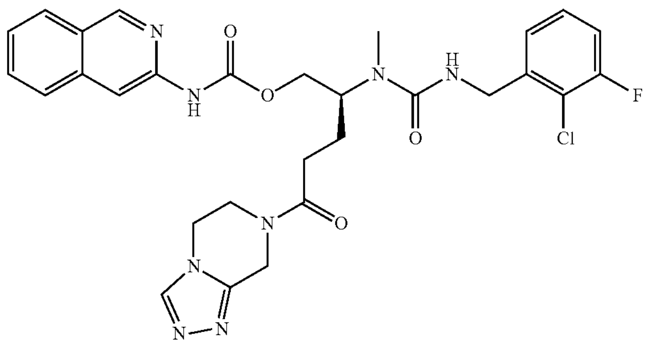 | [(2S)-2-({[(2-chloro-3-fluorophenyl)methyl]amino}-N-methylcarbonylamino)-5-oxo-5-(1,2,4-triazolo[3,4-c]piperazin-7-yl)pentyloxy]-N-(3-isoquinolyl)carboxamide |
| 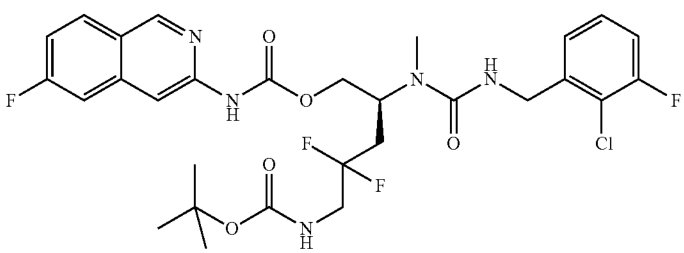 | N-((1S)-4-[(tert-butoxy)carbonylamino]-3,3-difluoro-1-{[N-(6-fluoro(3-isoquinolyl))carbamoyloxy]methyl}butyl){[(2-chloro-3-fluorophenyl)methyl]amino}-N-methylcarboxamide |
| 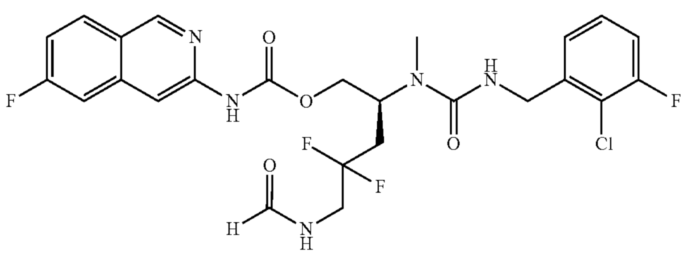 | N-((1S)-4-carbonylamino-3,3-difluoro-1-{[N-(6-fluoro(3-isoquinolyl))carbamoyloxy]methyl}butyl){[(2-chloro-3-fluorophenyl)methyl]amino}-N-methylcarboxamide |
| 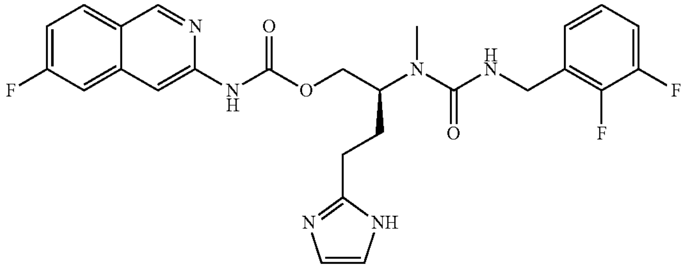 | [(2S)-2-({[(2,3-difluorophenyl)methyl]amino}-N-methylcarbonylamino)-4-imidazol-2-ylbutoxy]-N-(6-fluoro(3-isoquinolyl))carboxamide |

-continued

| Structure | Chemical Name |
|---|---|
| 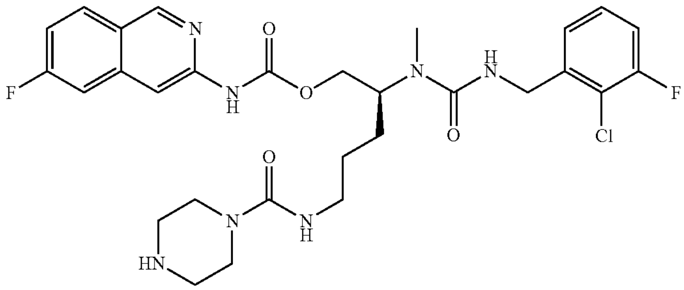 | N-((1S)-1-{[N-(6-fluoro(3-isoquinolyl))carbamoyloxy]methyl}-4-(piperazinylcarbonylamino)butyl){[(2-chloro-3-fluorophenyl)methyl]amino}-N-methylcarboxamide |
| 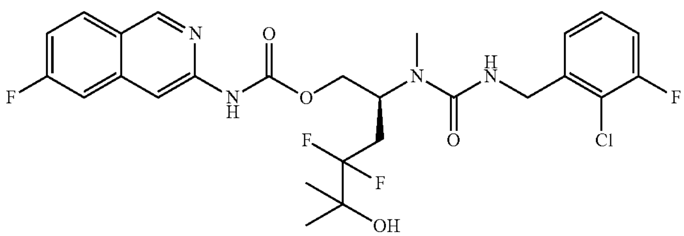 | [(2S)-2-({[(2-chloro-3-fluorophenyl)methyl]amino}-N-methylcarbonylamino)-4,4-difluoro-5-hydroxy-5-methylhexyloxy]-N-(6-fluoro(3-isoquinolyl))carboxamide |
| 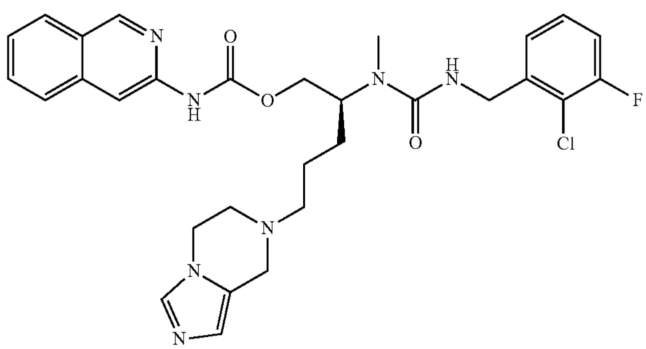 | N-{(1S)-4-imidazo[5,1-c]piperazin-7-yl-1-[(N-(3-isoquinolyl)carbamoyloxy)methyl]butyl}{[(2-chloro-3-fluorophenyl)methyl]amino}-N-methylcarboxamide |
| 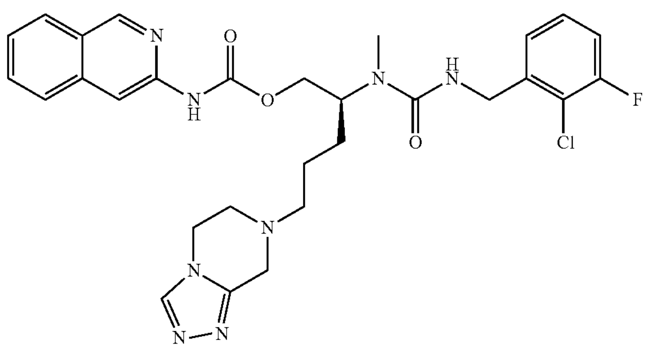 | N-{(1S)-1-[(N-(3-isoquinolyl)carbamoyloxy)methyl]-4-(1,2,4-triazolo[3,4-c]piperazin-7-yl)butyl}{[(2-chloro-3-fluorophenyl)methyl]amino}-N-methylcarboxamide |
| 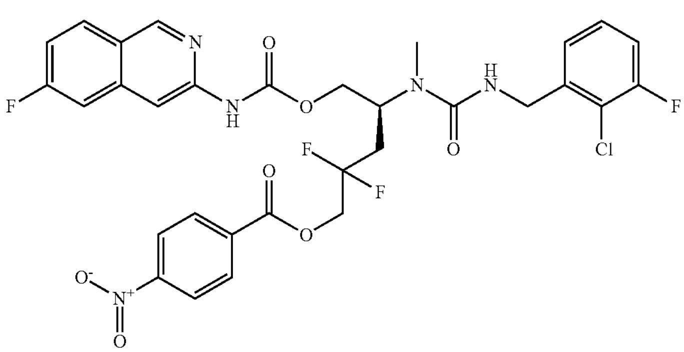 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl 4-nitrobenzoate |

-continued

| Structure | Chemical Name |
|---|---|
| 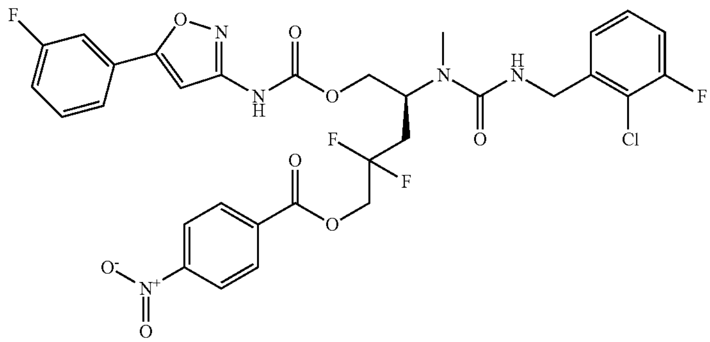 | (4S)-4-({[(2-chloro-3-fluorophenyl)methyl]amino}-N-methylcarbonylamino)-2,2-difluoro-5-{N-[5-(3-fluorophenyl)isoxazol-3-yl]carbamoyloxy}pentyl 4-nitrobenzoate |
| 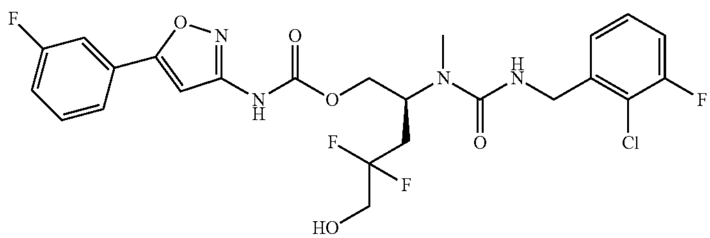 | N-[(1S)-3,3-difluoro-1-({N-[5-(3-fluorophenyl)isoxazol-3-yl]carbamoyloxy}methyl)-4-hydroxybutyl]{[(2-chloro-3-fluorophenyl)methyl]amino}-N-methylcarboxamide |
| 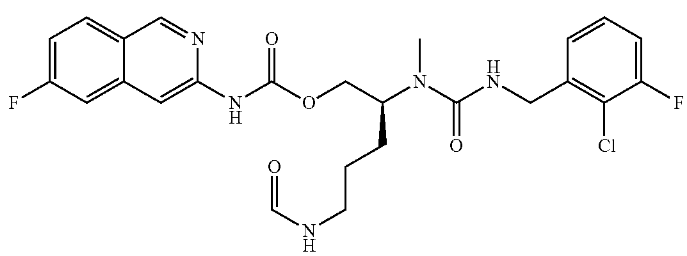 | N-((1S)-4-carbonylamino-1-{[N-(6-fluoro(3-isoquinolyl))carbamoyloxy]methyl}butyl){[(2-chloro-3-fluorophenyl)methyl]amino}-N-methylcarboxamide |
| 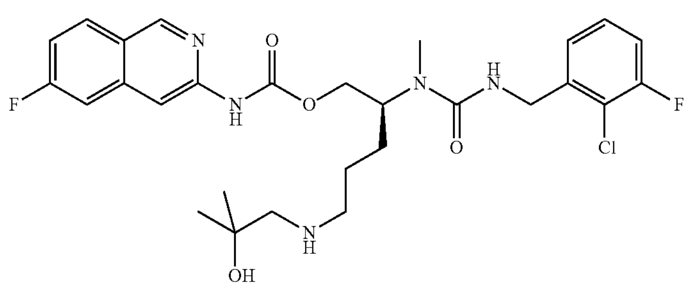 | N-((1S)-1-{[N-(6-fluoro(3-isoquinolyl))carbamoyloxy]methyl}-4-[(2-hydroxy-2-methylpropyl)amino]butyl){[(2-chloro-3-fluorophenyl)methyl]amino}-N-methylcarboxamide |
| 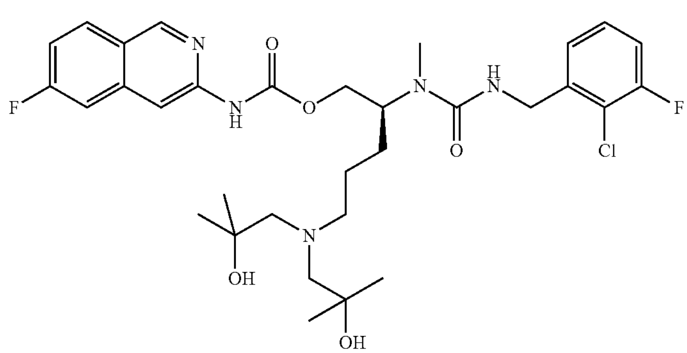 | N-((1S)-4-[bis(2-hydroxy-2-methylpropyl)amino]-1-{[N-(6-fluoro(3-isoquinolyl))carbamoyloxy]methyl}butyl){[(2-chloro-3-fluorophenyl)methyl]amino}-N-methylcarboxamide |

-continued

| Structure | Chemical Name |
|---|---|
| 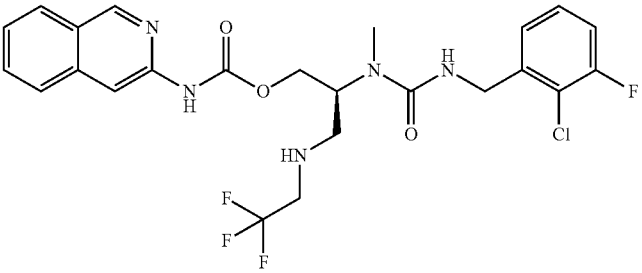 | [(2S)-2-({[(2-chloro-3-fluorophenyl)methyl]amino}-N-methylcarbonylamino)-3-[(2,2,2-trifluoroethyl)amino]propoxy]-N-(3-isoquinolyl)carboxamide |
| 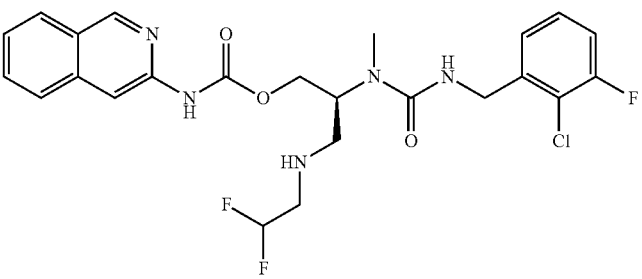 | [(2S)-3-[(2,2-difluoroethyl)amino]-2-({[(2-chloro-3-fluorophenyl)methyl]amino}-N-methylcarbonylamino)propoxy]-N-(3-isoquinolyl)carboxamide |
| 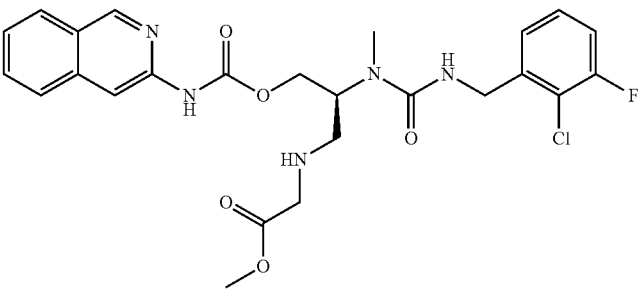 | methyl 2-{[(2S)-2-({[(2-chloro-3-fluorophenyl)methyl]amino}-N-methylcarbonylamino)-3-(N-(3-isoquinolyl)carbamoyloxy)propyl]amino}acetate |
| 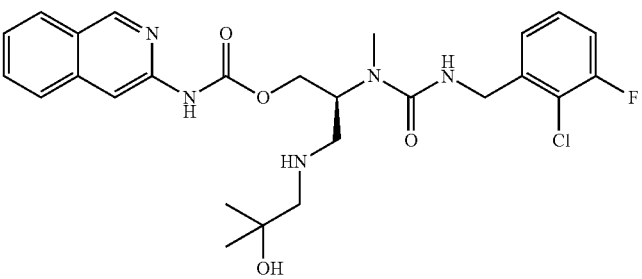 | [(2S)-2-({[(2-chloro-3-fluorophenyl)methyl]amino}-N-methylcarbonylamino)-3-[(2-hydroxy-2-methylpropyl)amino]propoxy]-N-(3-isoquinolyl)carboxamide |
| 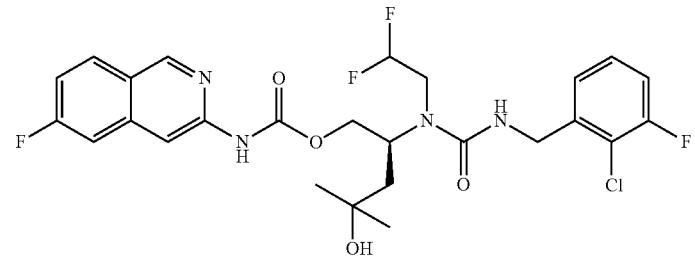 | N-((1S)-1-{[N-(6-fluoro(3-isoquinolyl))carbamoyloxy]methyl}-3-hydroxy-3-methylbutyl)-N-(2,2-difluoroethyl){[(2-chloro-3-fluorophenyl)methyl]amino}carboxamide |

-continued

| Structure | Chemical Name |
|---|---|
| 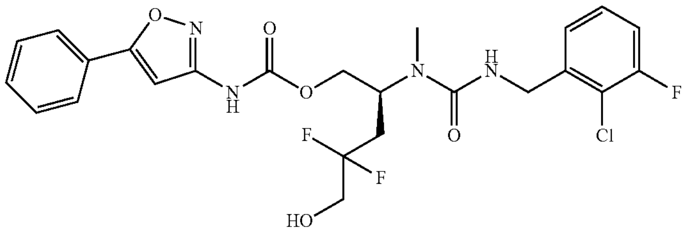 | N-((1S)-3,3-difluoro-4-hydroxy-1-{[N-(5-phenylisoxazol-3-yl)carbamoyloxy]methyl}butyl){[(2-chloro-3-fluorophenyl)methyl]amino}-N-methylcarboxamide |
| 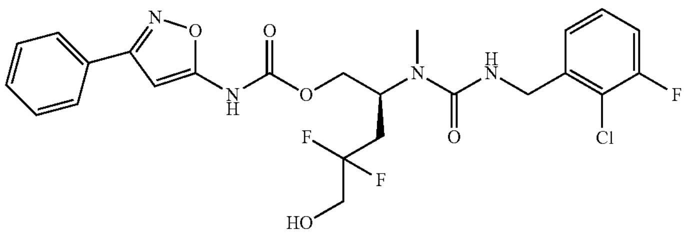 | N-((1S)-3,3-difluoro-4-hydroxy-1-{[N-(3-phenylisoxazol-5-yl)carbamoyloxy]methyl}butyl){[(2-chloro-3-fluorophenyl)methyl]amino}-N-methylcarboxamide |
| 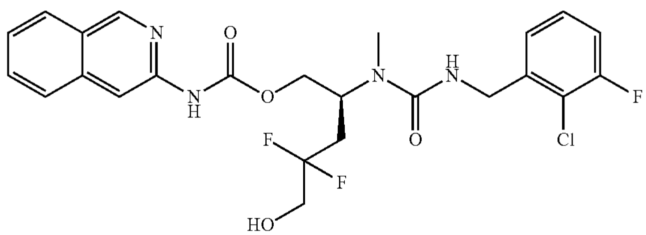 | N-{(1S)-3,3-difluoro-4-hydroxy-1-[(N-(3-isoquinolyl)carbamoyloxy)methyl]butyl}{[(2-chloro-3-fluorophenyl)methyl]amino}-N-methylcarboxamide |
| 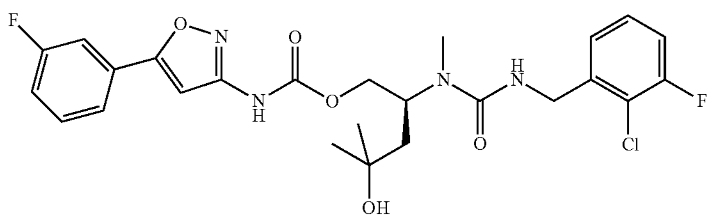 | N-[(1S)-1-({N-[5-(3-fluorophenyl)isoxazol-3-yl]carbamoyloxy}methyl)-3-hydroxy-3-methylbutyl]{[(2-chloro-3-fluorophenyl)methyl]amino}-N-methylcarboxamide |
| 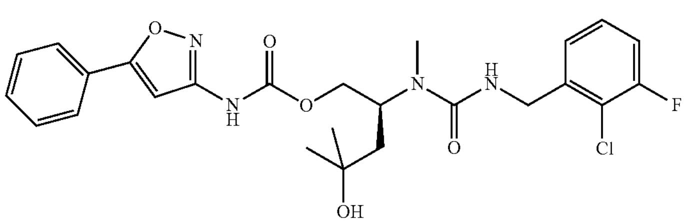 | N-((1S)-3-hydroxy-3-methyl-1-{[N-(5-phenylisoxazol-3-yl)carbamoyloxy]methyl}butyl){[(2-chloro-3-fluorophenyl)methyl]amino}-N-methylcarboxamide |
| 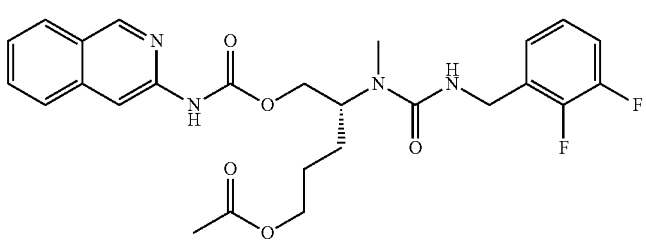 | (4R)-4-({[(2,3-difluorophenyl)methyl]amino}-N-methylcarbonylamino)-5-(N-(3-isoquinolyl)carbamoyloxy)pentyl acetate |

| Structure | Chemical Name |
|---|---|
| 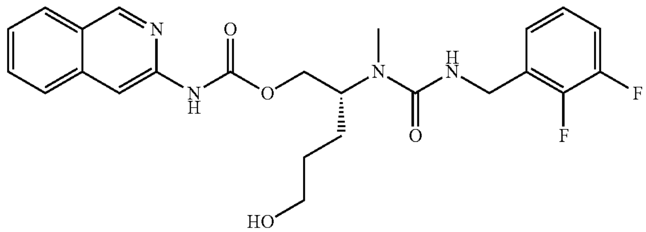 | N-{(1R)-4-hydroxy-1-[(N-(3-isoquinolyl)carbamoyloxy)methyl]butyl}{[(2,3-difluorophenyl)methyl}amino}-N-methylcarboxamide |
| 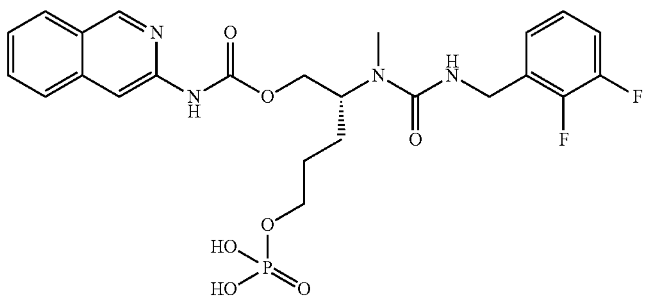 | (4R)-4-({[(2,3-difluorophenyl)methyl]amino}-N-methylcarbonylamino)-5-(N-(3-isoquinolyl)carbamoyloxy) pentyl dihydrogen phosphate |
| 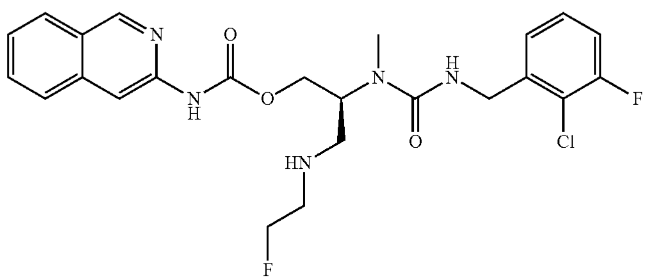 | [(2S)-2-({[(2-chloro-3-fluorophenyl)methyl]amino}-N-methylcarbonylamino)-3-[(2-fluoroethyl)amino]propoxy]-N-(3-isoquinolyl)carboxamide |
| 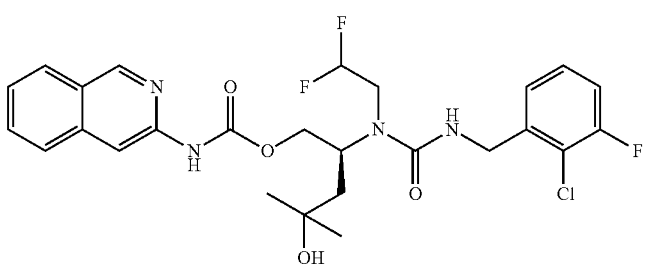 | N-{(1S)-3-hydroxy-1-[(N-(3-isoquinolyl)carbamoyloxy)methyl]-3-methylbutyl}-N-(2,2-difluoroethyl){[(2-chloro-3-fluorophenyl)methyl]amino}carboxamide |
| 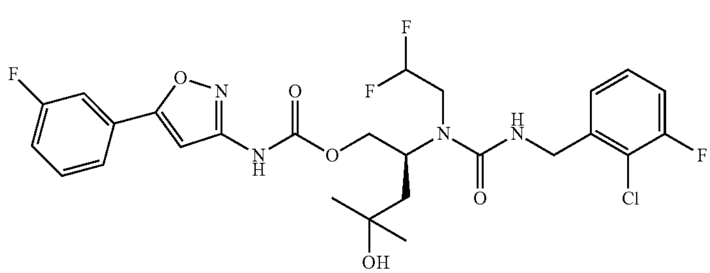 | N-[(1S)-1-({N-[5-(3-fluorophenyl)isoxazol-3-yl]carbamoyloxy}methyl)-3-hydroxy-3-methylbutyl]-N-(2,2-difluoroethyl){[(2-chloro-3-fluorophenyl)methyl]amino}carboxamide |
| 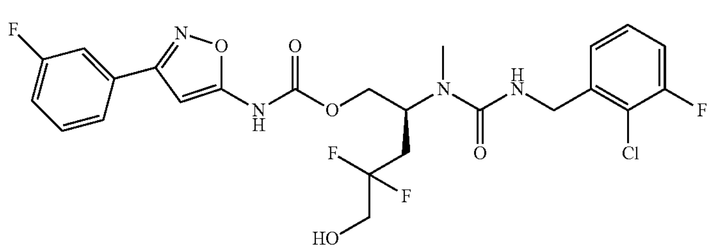 | N-[(1S)-3,3-difluoro-1-({N-[3-(3-fluorophenyl)isoxazol-5-yl]carbamoyloxy}methyl)-4-hydroxybutyl]{[(2-chloro-3-fluorophenyl)methyl]amino}-N-methylcarboxamide |

| Structure | Chemical Name |
|---|---|
| 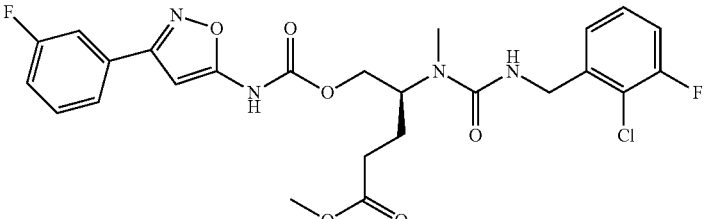 | methyl (4S)-4-({[(2-chloro-3-fluorophenyl)methyl]amino}-N-methylcarbonylamino)-5-{N-[3-(3-fluorophenyl)isoxazol-5-yl]carbamoyloxy}pentanoate |
| 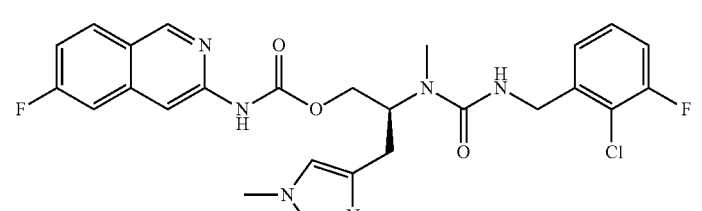 | [(2S)-2-({[(2-chloro-3-fluorophenyl)methyl]amino}-N-methylcarbonylamino)-3-(1-methylimidazol-4-yl)propoxy]-N-(6-fluoro(3-isoquinolyl))carboxamide |
| 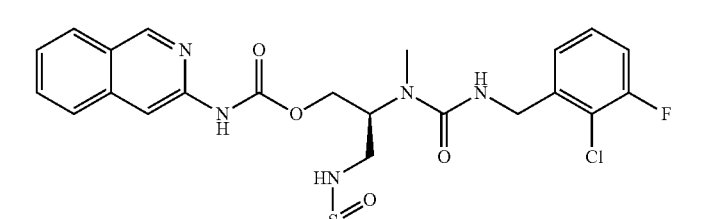 | [(2S)-2-({[(2-chloro-3-fluorophenyl)methyl]amino}-N-methylcarbonylamino)-3-[(methylsulfonyl)amino]propoxy]-N-(3-isoquinolyl)carboxamide |
| 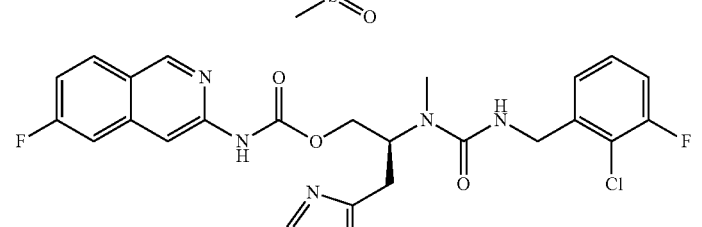 | [(2S)-2-({[(2-chloro-3-fluorophenyl)methyl]amino}-N-methylcarbonylamino)-3-imidazol-4-ylpropoxy]-N-(6-fluoro(3-isoquinolyl))carboxamide |
| 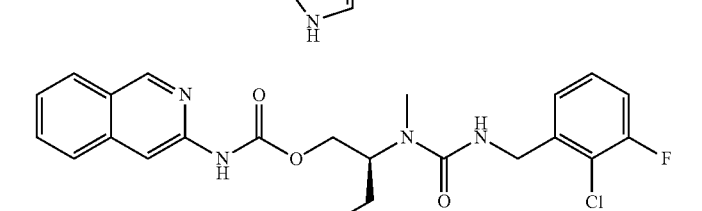 | N-{(1S)-1-[(N-(3-isoquinolyl)carbamoyloxy)methyl]-4-[2-(trifluoromethyl)(1,2,4-triazolo[5,1-c]piperazin-7-yl)]butyl}{[(2-chloro-3-fluorophenyl)methyl]amino}-N-methylcarboxamide |
| 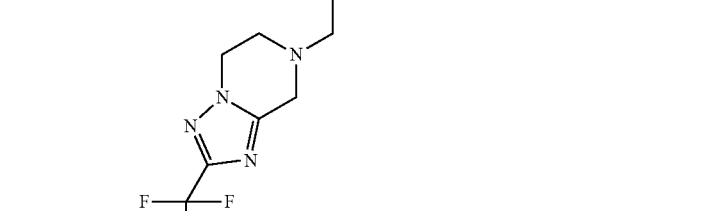 | [(2S)-2-({[(2-chloro-3-fluorophenyl)methyl]amino}-N-methylcarbonylamino)-3-(2-pyridyl)propoxy]-N-(3-isoquinolyl)carboxamide |

-continued

| Structure | Chemical Name |
|---|---|
| 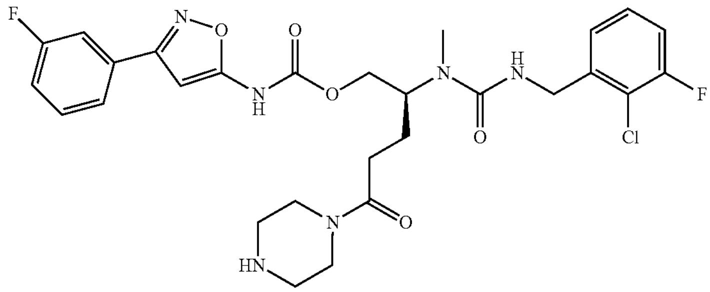 | [(2S)-2-({[(2-chloro-3-fluorophenyl)methyl]amino}-N-methylcarbonylamino)-5-oxo-5-piperazinylpentyloxy]-N-[3-(3-fluorophenyl)isoxazol-5-yl]carboxamide |
| 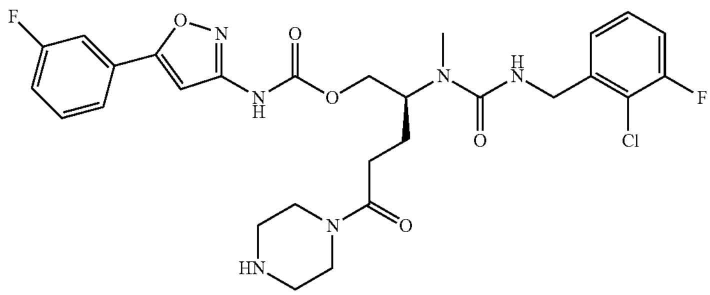 | [(2S)-2-({[(2-chloro-3-fluorophenyl)methyl]amino}-N-methylcarbonylamino)-5-oxo-5-piperazinylpentyloxy]-N-[5-(3-fluorophenyl)isoxazol-3-yl]carboxamide |
| 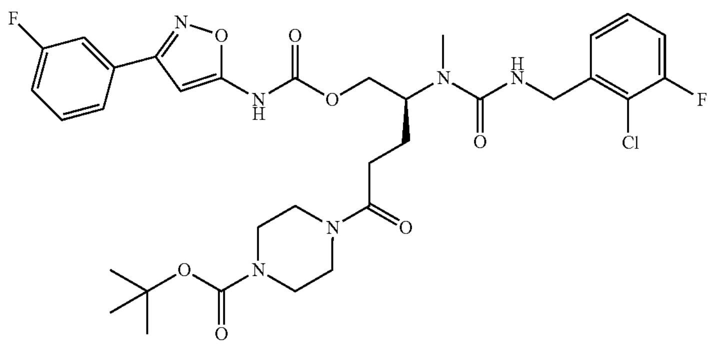 | tert-butyl 4-[(4S)-4-({[(2-chloro-3-fluorophenyl)methyl]amino}-N-methylcarbonylamino)-5-{N-[3-(3-fluorophenyl)isoxazol-5-yl]carbamoyloxy}pentanoyl]piperazinecarboxylate |
| 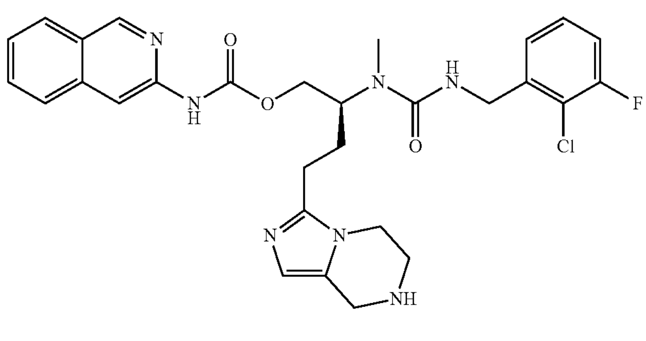 | N-{(1S)-3-imidazo[1,5-a]piperazin-3-yl-1-[(N-(3-isoquinolyl)carbamoyloxy)methyl]propyl}{[(2-chloro-3-fluorophenyl)methyl]amino}-N-methylcarboxamide |

| Structure | Chemical Name |
|---|---|
| 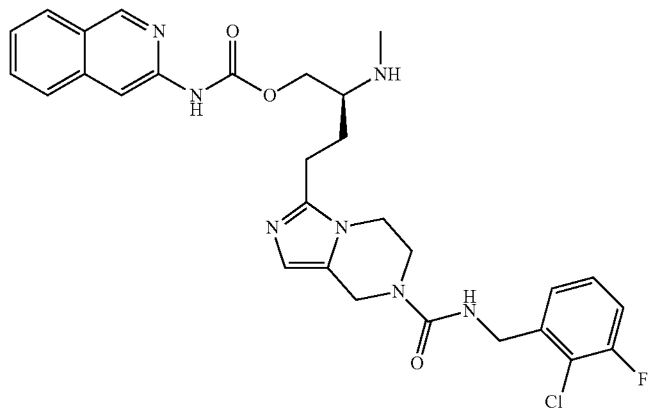 [SMILES: CN[C@@H](CCc1ncc2n1CCN(C(=O)NCc1cccc(F)c1Cl)C2)COC(=O)Nc1cc2ccccc2cn1] | [(2S)-4-(7-{N-[(2-chloro-3-fluorophenyl)methyl]carbamoyl}imidazo[1,5-a]piperazin-3-yl)-2-(methylamino)butoxy]-N-(3-isoquinolyl)carboxamide |
| 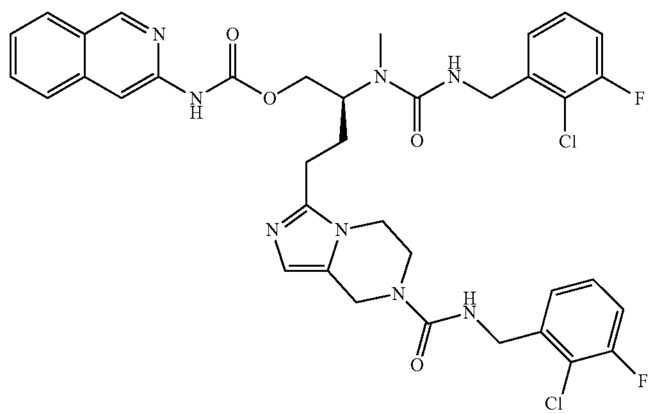 | N-[(1S)-3-(7-{N-[(2-chloro-3-fluorophenyl)methyl]carbamoyl}imidazo[1,5-a]piperazin-3-yl)-1-[(N-(3-isoquinolyl)carbamoyloxy)methyl]propyl]{[(2-chloro-3-fluorophenyl)methyl]amino}-N-methylcarboxamide |
| 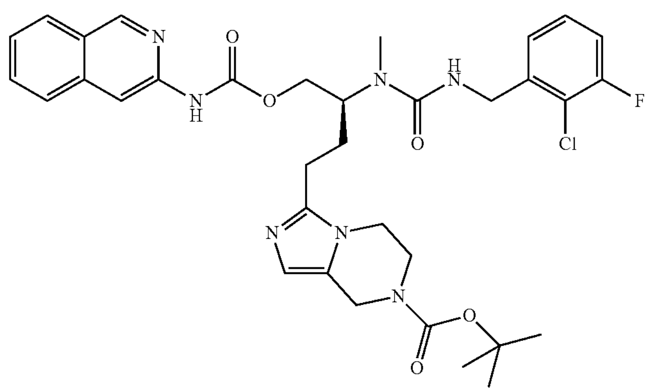 | tert-butyl 3-[(3S)-3-({[(2-chloro-3-fluorophenyl)methyl]amino}-N-methylcarbonylamino)-4-(N-(3-isoquinolyl)carbamoyloxy)butyl]imidazo[5,1-c]piperazine-7-carboxylate |
| 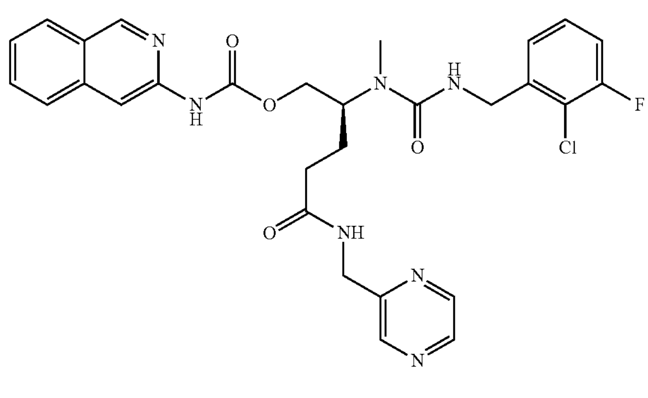 | (4S)-4-({[(2-chloro-3-fluorophenyl)methyl]amino}-N-methylcarbonylamino)-5-(N-(3-isoquinolyl)carbamoyloxy)-N-(pyrazin-2-ylmethyl)pentanamide |

-continued

| Structure | Chemical Name |
|---|---|
| 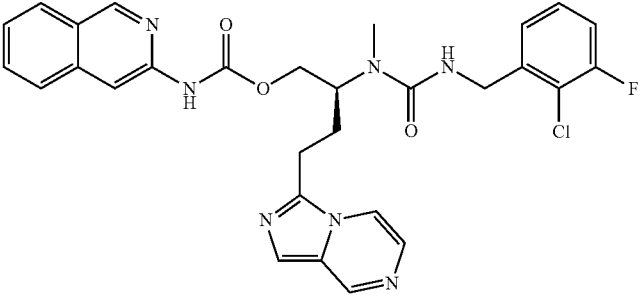 | N-{(1S)-3-(4-hydroimidazo[1,5-a]pyrazin-3-yl)-1-[(N-(3-isoquinolyl)carbamoyloxy)methyl]propyl}{[(2-chloro-3-fluorophenyl)methyl]amino}-N-methylcarboxamide |
| 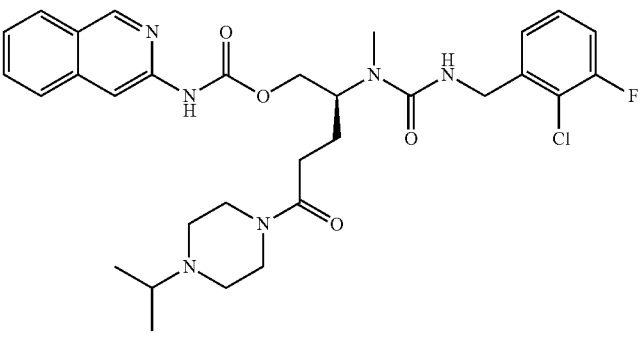 | [(2S)-2-({[(2-chloro-3-fluorophenyl)methyl]amino}-N-methylcarbonylamino)-5-[4-(methylethyl)piperazinyl]-5-oxopentyloxy]-N-(3-isoquinolyl)carboxamide |
| 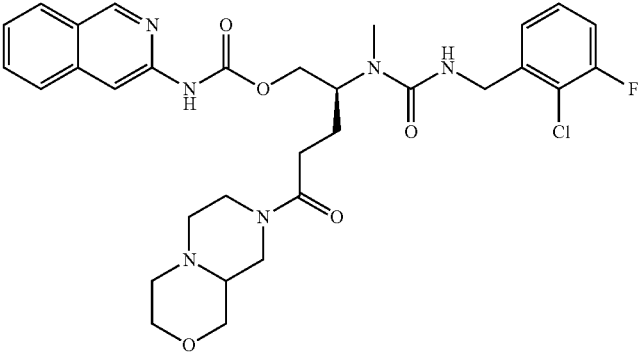 | [(2S)-2-({[(2-chloro-3-fluorophenyl)methyl]amino}-N-methylcarbonylamino)-5-(9-oxa-3,6-diazabicyclo[4.4.0]dec-3-yl)-5-oxopentyloxy]-N-(3-isoquinolyl)carboxamide |
| 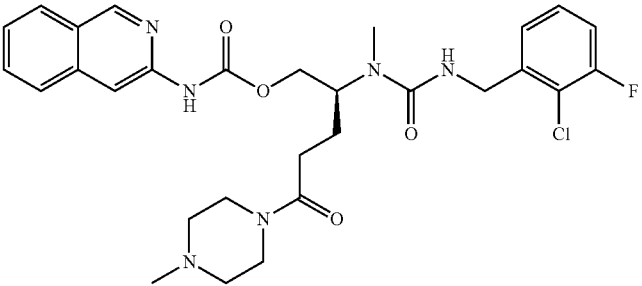 | [(2S)-2-({[(2-chloro-3-fluorophenyl)methyl]amino}-N-methylcarbonylamino)-5-(4-methylpiperazinyl)-5-oxopentyloxy]-N-(3-isoquinolyl)carboxamide |

| Structure | Chemical Name |
|---|---|
| 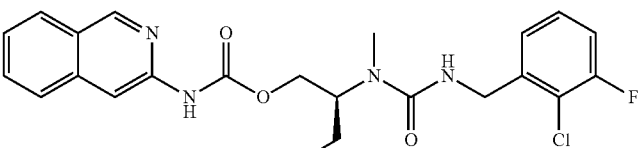 | N-{(1S)-1-[(N-(3-isoquinolyl)carbamoyloxy)methyl]-4-(1,2,4-triazolo[5,1-c]piperazin-7-yl)butyl}{[(2-chloro-3-fluorophenyl)methyl]amino}-N-methylcarboxamide |
| 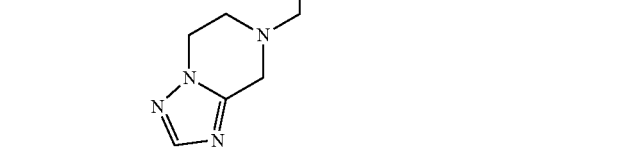 | N-{(1S)-1-[(N-(3-isoquinolyl)carbamoyloxy)methyl]-4-(3-methyl(1,2,4-triazolo[3,4-c]piperazin-7-yl))butyl}{[(2-chloro-3-fluorophenyl)methyl]amino}-N-methylcarboxamide |
| 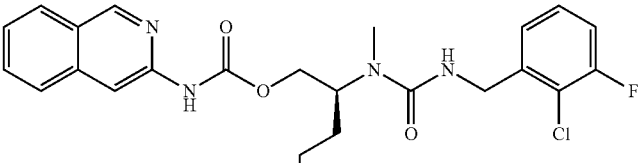 | N-{(1S)-4-(1,1-dioxo(1,4-thiazaperhydroin-4-yl))-1-[(N-(3-isoquinolyl)carbamoyloxy)methyl]butyl}{[(2-chloro-3-fluorophenyl)methyl]amino}-N-methylcarboxamide |
| 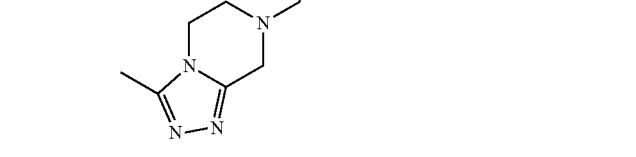 | N-{(1S)-1-[(N-(3-isoquinolyl)carbamoyloxy)methyl]-4-(4-methylpiperazinyl)butyl}{[(2-chloro-3-fluorophenyl)methyl]amino}-N-methylcarboxamide |
| 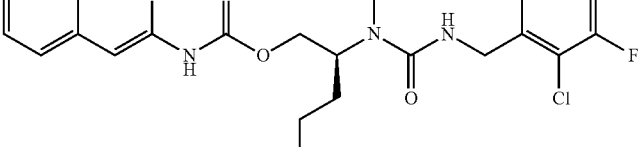 | N-{(1S)-1-[(N-(3-isoquinolyl)carbamoyloxy)methyl]-4-morpholin-4-ylbutyl}{[(2-chloro-3-fluorophenyl)methyl]amino}-N-methylcarboxamide |

| Structure | Chemical Name |
|---|---|
| 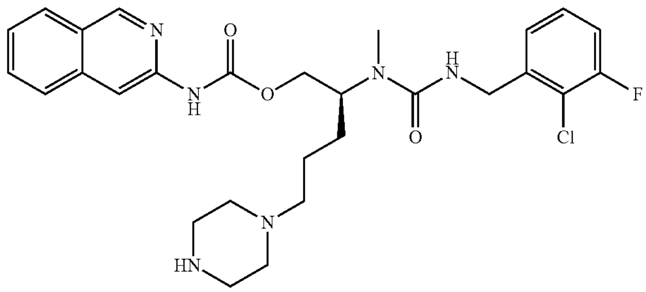 [SMILES: CN(C(=O)NCc1cccc(F)c1Cl)[C@@H](CCCN1CCNCC1)COC(=O)Nc1cc2ccccc2cn1] | N-{(1S)-1-[(N-(3-isoquinolyl)carbamoyloxy)methyl]-4-piperazinylbutyl}{[(2-chloro-3-fluorophenyl)methyl]amino}-N-methylcarboxamide |
| 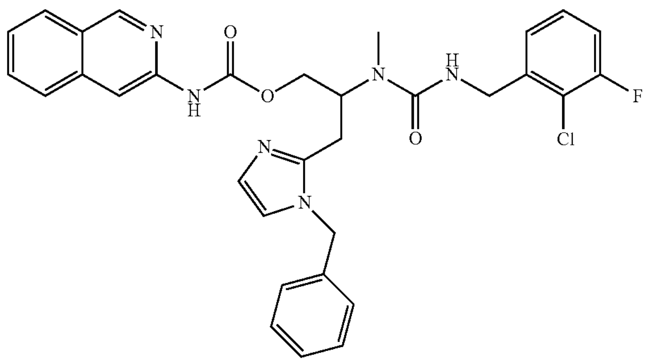 [SMILES: CN(C(=O)NCc1cccc(F)c1Cl)C(COC(=O)Nc1cc2ccccc2cn1)Cc1nccn1Cc1ccccc1] | {[(2-chloro-3-fluorophenyl)methyl]amino}-N-(2-(N-(3-isoquinolyl)carbamoyloxy)-1-{[1-benzylimidazol-2-yl]methyl}ethyl)-N-methylcarboxamide |
| 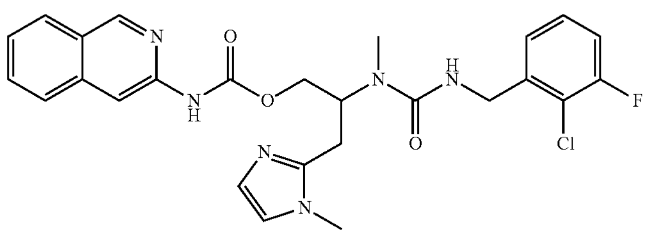 [SMILES: CN(C(=O)NCc1cccc(F)c1Cl)C(COC(=O)Nc1cc2ccccc2cn1)Cc1nccn1C] | {[(2-chloro-3-fluorophenyl)methyl]amino}-N-{2-(N-(3-isoquinolyl)carbamoyloxy)-1-[(1-methylimidazol-2-yl)methyl]ethyl}-N-methylcarboxamide |
| 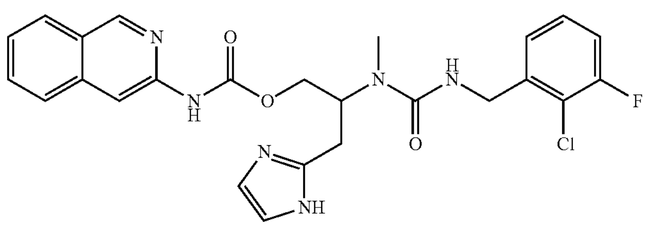 [SMILES: CN(C(=O)NCc1cccc(F)c1Cl)C(COC(=O)Nc1cc2ccccc2cn1)Cc1ncc[nH]1] | {[(2-chloro-3-fluorophenyl)methyl]amino}-N-[1-(imidazol-2-ylmethyl)-2-(N-(3-isoquinolyl)carbamoyloxy)ethyl]-N-methylcarboxamide |
| 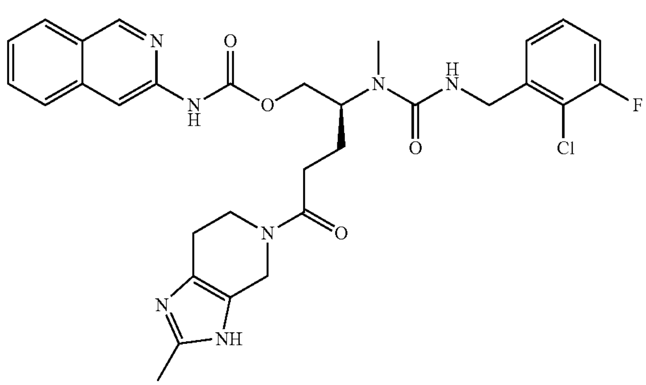 [SMILES: Cc1nc2c([nH]1)CN(C(=O)CC[C@@H](COC(=O)Nc1cc3ccccc3cn1)N(C)C(=O)NCc1cccc(F)c1Cl)CC2] | N-{(1S)-1-[(N-(3-isoquinolyl)carbamoyloxy)methyl]-4-(2-methyl(4,5,6,7-tetrahydroimidazo[5,4-c]pyridin-5-yl))-4-oxobutyl}{[(2-chloro-3-fluorophenyl)methyl]amino}-N-methylcarboxamide |

| Structure | Chemical Name |
|---|---|
| 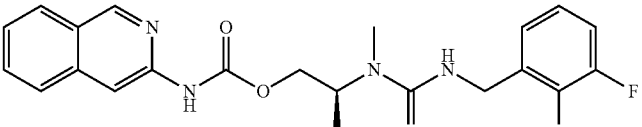 | N-{(1S)-1-[(N-(3-isoquinolyl)carbamoyloxy)methyl]-4-[4-(2,2,2-trifluoroethyl)piperazinyl]butyl}{[(2-chloro-3-fluorophenyl)methyl]amino}-N-methylcarboxamide |
| 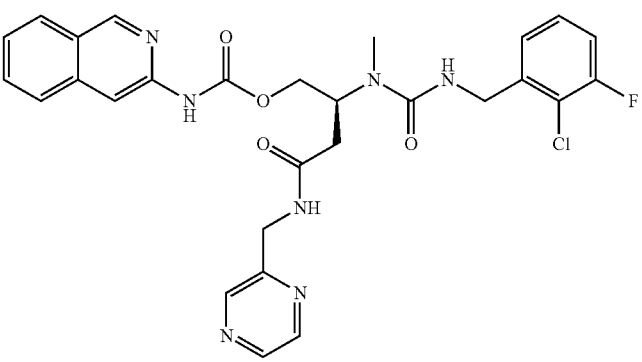 [SMILES: CN(C(=O)NCc1cccc(F)c1Cl)[C@H](COC(=O)Nc1cc2ccccc2cn1)CC(=O)NCc1cnccn1] | (3S)-3-({[(2-chloro-3-fluorophenyl)methyl]amino}-N-methylcarbonylamino)-4-(N-(3-isoquinolyl)carbamoyloxy)-N-(pyrazin-2-ylmethyl)butanamide |
| 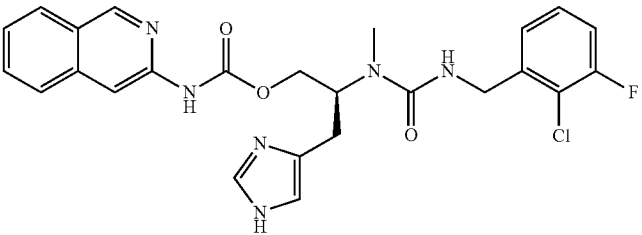 [SMILES: CN(C(=O)NCc1cccc(F)c1Cl)[C@H](COC(=O)Nc1cc2ccccc2cn1)Cc1c[nH]cn1] | [(2S)-2-({[(2-chloro-3-fluorophenyl)methyl]amino}-N-methylcarbonylamino)-3-imidazol-4-ylpropoxy]-N-(3-isoquinolyl)carboxamide |
| 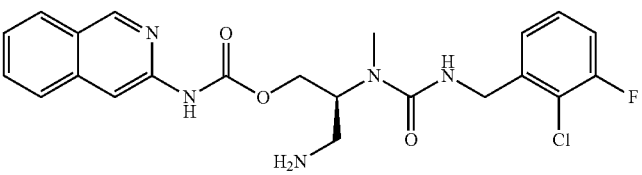 [SMILES: CN(C(=O)NCc1cccc(F)c1Cl)[C@@H](CN)COC(=O)Nc1cc2ccccc2cn1] | N-{(1S)-2-amino-1-[(N-(3-isoquinolyl)carbamoyloxy)methyl]ethyl}{[(2-chloro-3-fluorophenyl)methyl]amino}-N-methylcarboxamide |
| 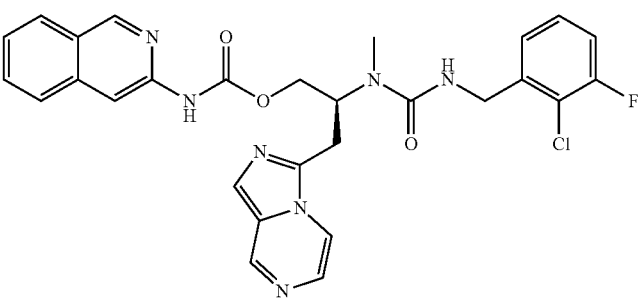 [SMILES: CN(C(=O)NCc1cccc(F)c1Cl)[C@H](COC(=O)Nc1cc2ccccc2cn1)Cc1ncc2cnccn12] | N-[(1S)-1-(4-hydroimidazo[1,5-a]pyrazin-3-ylmethyl)-2-(N-(3-isoquinolyl)carbamoyloxy)ethyl]{[(2-chloro-3-fluorophenyl)methyl]amino}-N-methylcarboxamide |

-continued

| Structure | Chemical Name |
|---|---|
| 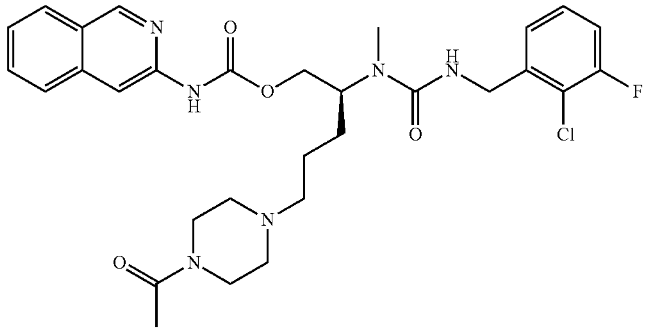 [SMILES: CC(=O)N1CCN(CCC[C@@H](COC(=O)Nc2cc3ccccc3cn2)N(C)C(=O)NCc2cccc(F)c2Cl)CC1] | N-{(1S)-4-(4-acetylpiperazinyl)-1-[(N-(3-isoquinolyl)carbamoyloxy)methyl]butyl}{[(2-chloro-3-fluorophenyl)methyl]amino}-N-methylcarboxamide |
| 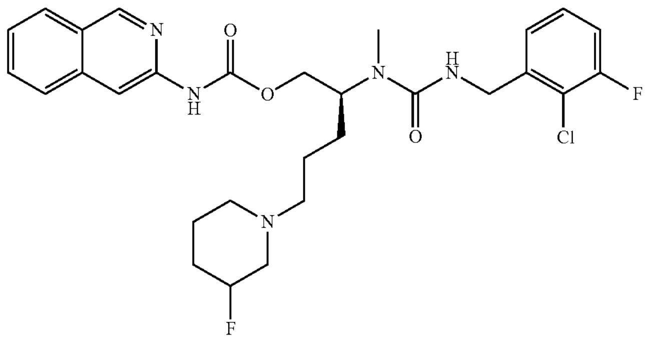 [SMILES: CN(C(=O)NCc1cccc(F)c1Cl)[C@@H](CCCN1CCCC(F)C1)COC(=O)Nc1cc2ccccc2cn1] | N-{(1S)-4-(3-fluoropiperidyl)-1-[(N-(3-isoquinolyl)carbamoyloxy)methyl]butyl}{[(2-chloro-3-fluorophenyl)methyl]amino}-N-methylcarboxamide |
| 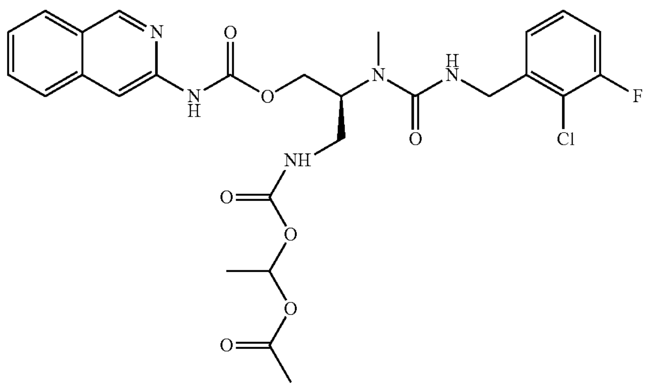 [SMILES: CC(=O)OC(C)OC(=O)NC[C@@H](COC(=O)Nc1cc2ccccc2cn1)N(C)C(=O)NCc1cccc(F)c1Cl] | {N-[(2S)-2-({[(2-chloro-3-fluorophenyl)methyl]amino}-N-methylcarbonylamino)-3-(N-(3-isoquinolyl)carbamoyloxy)propyl]carbamoyloxy}ethyl acetate |
| 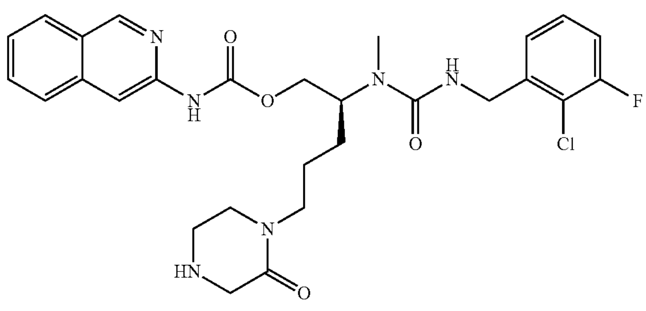 [SMILES: CN(C(=O)NCc1cccc(F)c1Cl)[C@@H](CCCN1CCNCC1=O)COC(=O)Nc1cc2ccccc2cn1] | N-{(1S)-1-[(N-(3-isoquinolyl)carbamoyloxy)methyl]-4-(2-oxopiperazinyl)butyl}{[(2-chloro-3-fluorophenyl)methyl]amino}-N-methylcarboxamide |
| 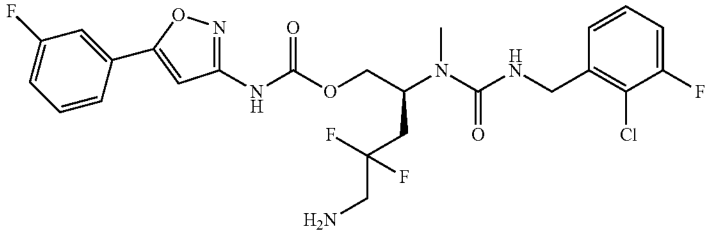 | N-[(1S)-4-amino-3,3-difluoro-1-({N-[5-(3-fluorophenyl)isoxazol-3-yl]carbamoyloxy}methyl)butyl]{[(2-chloro-3-fluorophenyl)methyl]amino}-N-methylcarboxamide |

| Structure | Chemical Name |
|---|---|
| 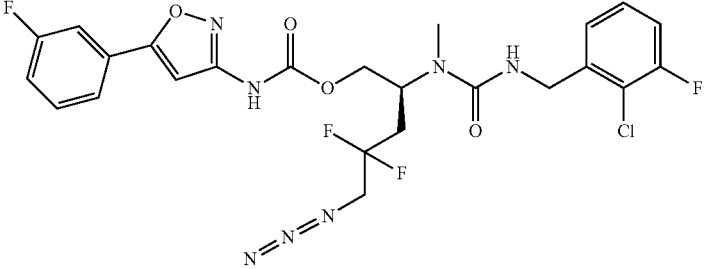 | N-[(1S)-5-diazo-3,3-difluoro-1-({N-[5-(3-fluorophenyl)isoxazol-3-yl]carbamoyloxy}methyl)-5-azapent-5-enyl]{[(2-chloro-3-fluorophenyl)methyl]amino}-N-methylcarboxamide |
| 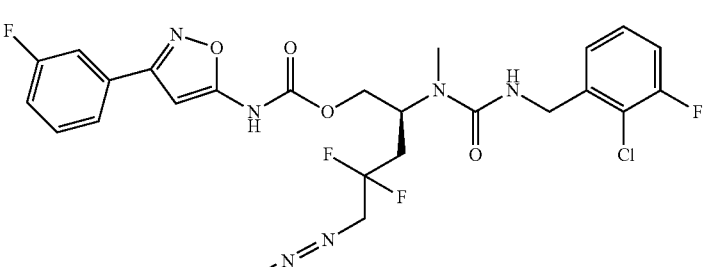 | N-[(1S)-5-diazo-3,3-difluoro-1-({N-[3-(3-fluorophenyl)isoxazol-5-yl]carbamoyloxy}methyl)-5-azapent-5-enyl]{[(2-chloro-3-fluorophenyl)methyl]amino}-N-methylcarboxamide |
| 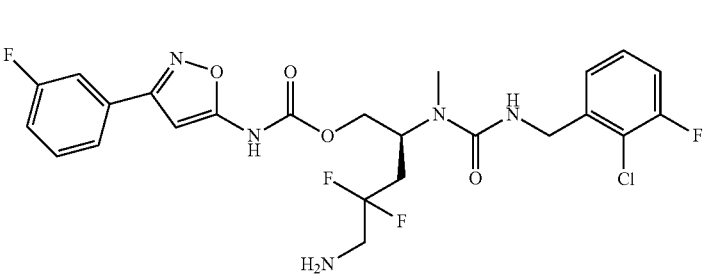 | N-[(1S)-4-amino-3,3-difluoro-1-({N-[3-(3-fluorophenyl)isoxazol-5-yl]carbamoyloxy}methyl)butyl]{[(2-chloro-3-fluorophenyl)methyl]amino}-N-methylcarboxamide |
| 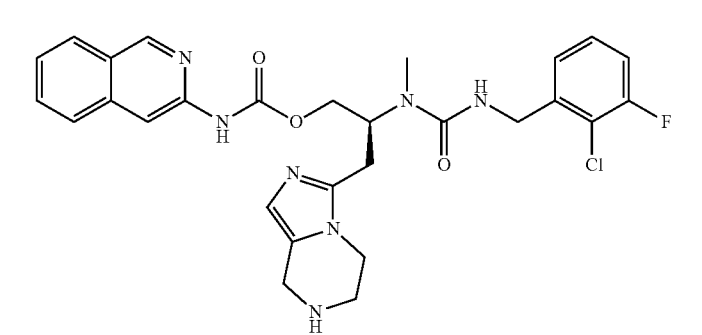 [SMILES: CN(C(=O)NCc1cccc(F)c1Cl)[C@H](COC(=O)Nc1cc2ccccc2cn1)Cc1ncc2n1CCNC2] | N-[(1S)-1-(imidazo[1,5-a]piperazin-3-ylmethyl)-2-(N-(3-isoquinolyl)carbamoyloxy)ethyl]{[(2-chloro-3-fluorophenyl)methyl]amino}-N-methylcarboxamide |
| 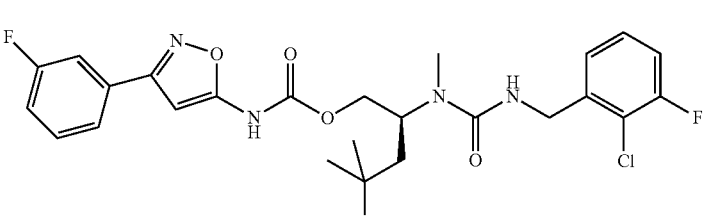 | N-[(1S)-1-({N-[3-(3-fluorophenyl)isoxazol-5-yl]carbamoyloxy}methyl)-3-hydroxy-3-methylbutyl]{[(2-chloro-3-fluorophenyl)methyl]amino}-N-methylcarboxamide |

-continued

| Structure | Chemical Name |
|---|---|
| 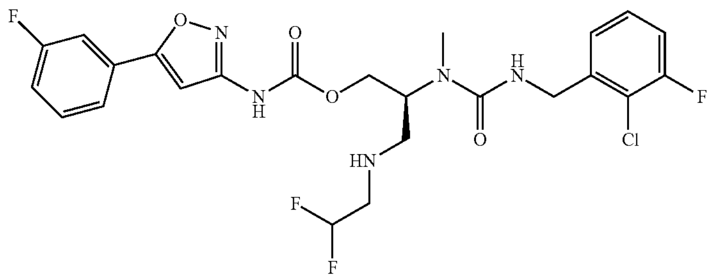 | [(2S)-3-[(2,2-difluoroethyl)amino]-2-({[(2-chloro-3-fluorophenyl)methyl]amino}-N-methylcarbonylamino)propoxy]-N-[5-(3-fluorophenyl)isoxazol-3-yl]carboxamide |
| 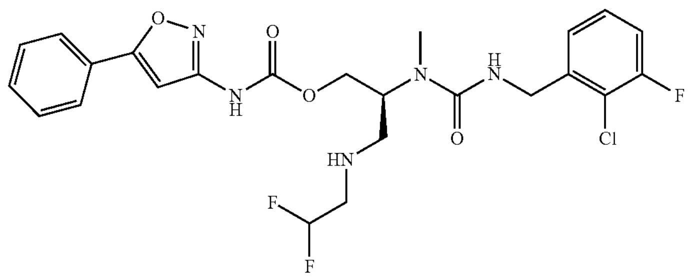 | [(2S)-3-[(2,2-difluoroethyl)amino]-2-({[(2-chloro-3-fluorophenyl)methyl]amino}-N-methylcarbonylamino)propoxy]-N-(5-phenylisoxazol-3-yl)carboxamide |
| 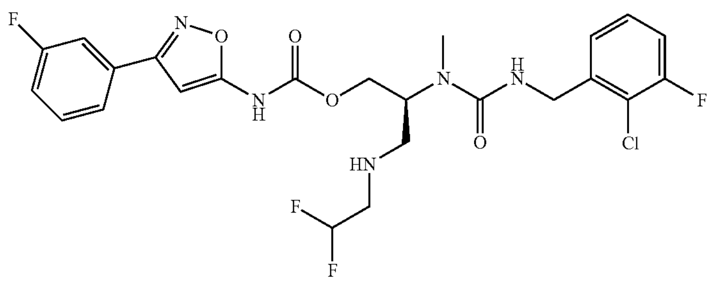 | [(2S)-3-[(2,2-difluoroethyl)amino]-2-({[(2-chloro-3-fluorophenyl)methyl]amino}-N-methylcarbonylamino)propoxy]-N-[3-(3-fluorophenyl)isoxazol-5-yl]carboxamide |
| 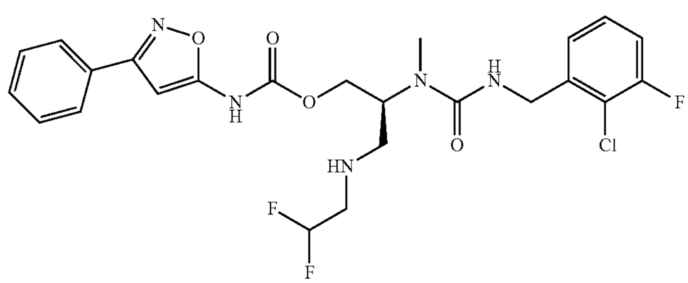 | [(2S)-3-[(2,2-difluoroethyl)amino]-2-({[(2-chloro-3-fluorophenyl)methyl]amino}-N-methylcarbonylamino)propoxy]-N-(3-phenylisoxazol-5-yl)carboxamide |
| 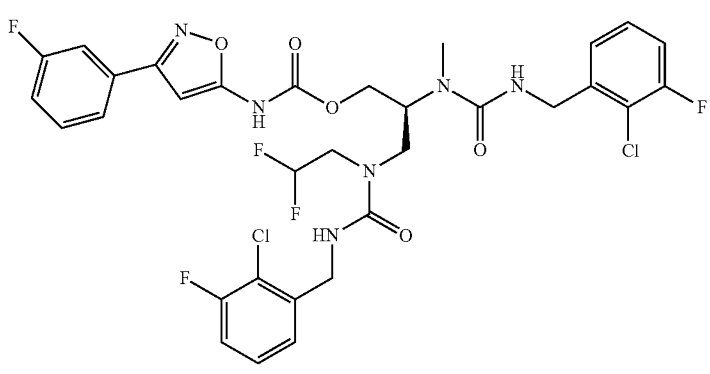 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-[3-(3-fluorophenyl)isoxazol-5-yl]carbo |

-continued

| Structure | Chemical Name |
|---|---|
| 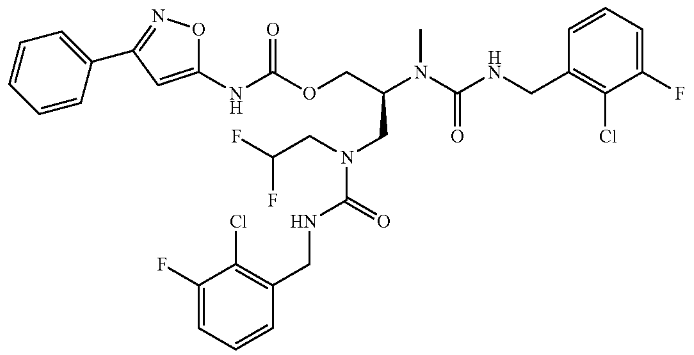 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-(3-phenylisoxazol-5-yl)carboxamide |
| 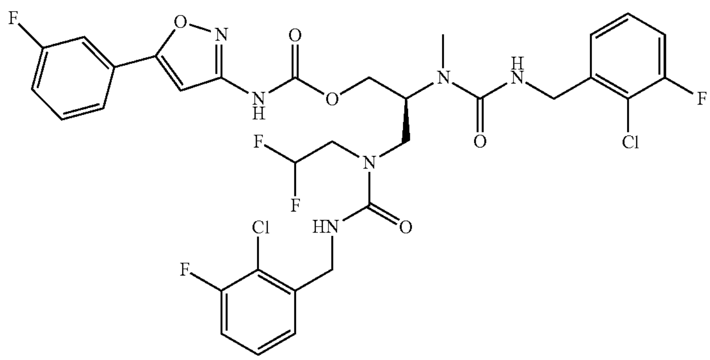 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-[5-(3-fluorophenyl)isoxazol-3-yl]carbo |
| 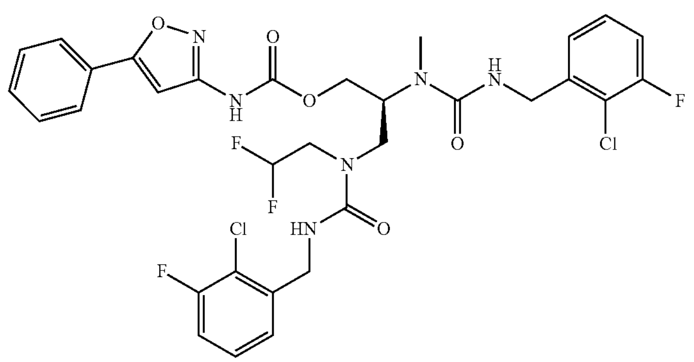 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-(5-phenylisoxazol-3-yl)carboxamide |
| 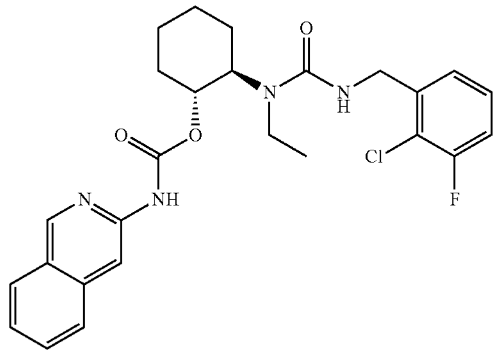 [SMILES: CCN(C(=O)NCc1cccc(F)c1Cl)[C@@H]1CCCC[C@H]1OC(=O)Nc1cc2ccccc2cn1] | N-[(1R,2R)-2-(N-(3-isoquinolyl)carbamoyloxy)cyclohexyl]{[(2-chloro-3-fluorophenyl)methyl]amino}-N-ethylcarboxamide |
| 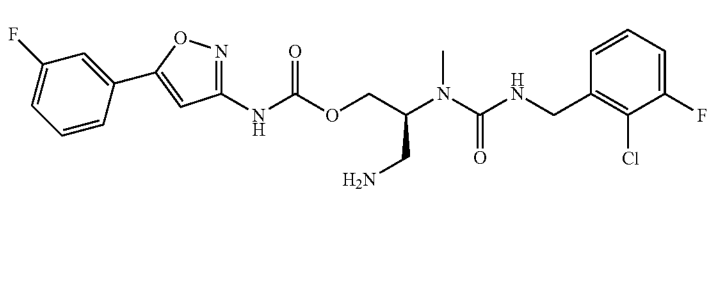 [SMILES: CN(C(=O)NCc1cccc(F)c1Cl)[C@@H](CN)COC(=O)Nc1cc(-c2cccc(F)c2)on1] | N-[(1S)-2-amino-1-({N-[5-(3-fluorophenyl)isoxazol-3-yl]carbamoyloxy}methyl)ethyl]{[(2-chloro-3-fluorophenyl)methyl]amino}-N-methylcarboxamide |

-continued

| Structure | Chemical Name |
|---|---|
| 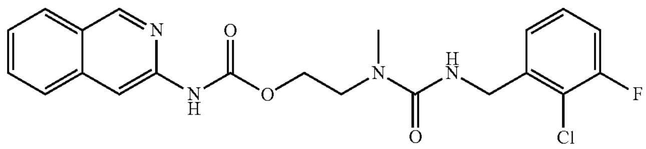 [SMILES: CN(CCOC(=O)Nc1cc2ccccc2cn1)C(=O)NCc1cccc(F)c1Cl] | {[(2-chloro-3-fluorophenyl)methyl]amino}-N-[2-(N-(3-isoquinolyl)carbamoyloxy)ethyl]-N-methylcarboxamide |
| 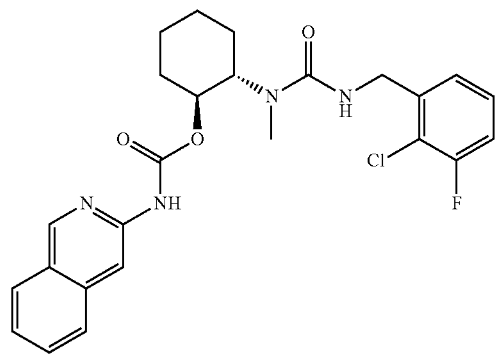 [SMILES: CN(C(=O)NCc1cccc(F)c1Cl)[C@H]1CCCC[C@@H]1OC(=O)Nc1cc2ccccc2cn1] | N-[(1S,2S)-2-(N-(3-isoquinolyl)carbamoyloxy)cyclohexyl]{[(2-chloro-3-fluorophenyl)methyl]amino}-N-methylcarboxamide |
| 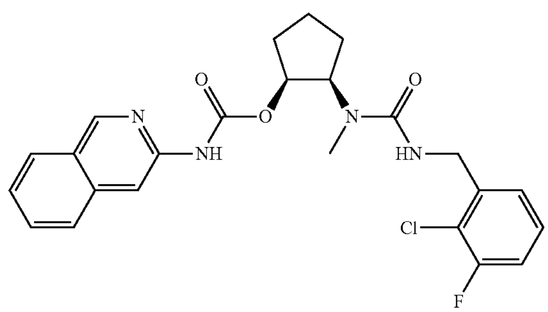 [SMILES: CN(C(=O)NCc1cccc(F)c1Cl)[C@@H]1CCC[C@@H]1OC(=O)Nc1cc2ccccc2cn1] | N-[(2S,1R)-2-(N-(3-isoquinolyl)carbamoyloxy)cyclopentyl]{[(2-chloro-3-fluorophenyl)methyl]amino}-N-methylcarboxamide |
| 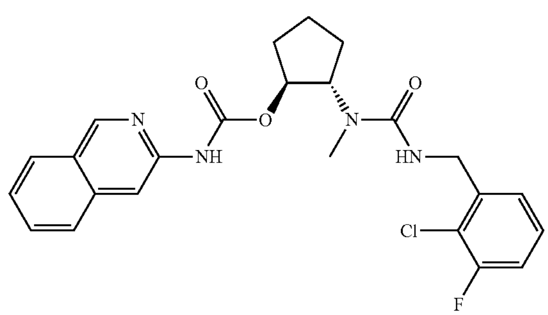 [SMILES: CN(C(=O)NCc1cccc(F)c1Cl)[C@H]1CCC[C@@H]1OC(=O)Nc1cc2ccccc2cn1] | N-[(1S,2S)-2-(N-(3-isoquinolyl)carbamoyloxy)cyclopentyl]{[(2-chloro-3-fluorophenyl)methyl]amino}-N-methylcarboxamide |
| 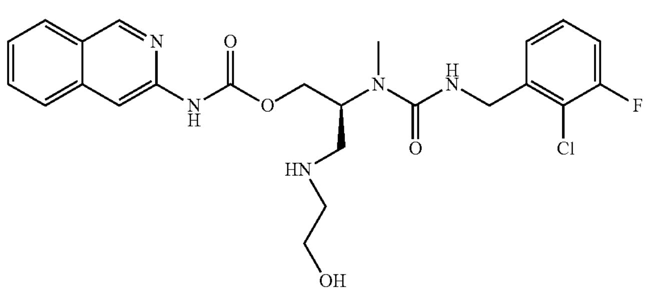 [SMILES: CN(C(=O)NCc1cccc(F)c1Cl)[C@@H](CNCCO)COC(=O)Nc1cc2ccccc2cn1] | [(2S)-2-({[(2-chloro-3-fluorophenyl)methyl]amino}-N-methylcarbonylamino)-3-[(2-hydroxyethyl)amino]propoxy]-N-(3-isoquinolyl)carboxamide |

-continued

| Structure | Chemical Name |
|---|---|
| 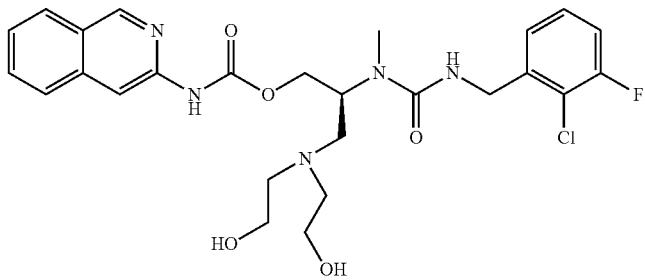 [SMILES: CN(C(=O)NCc1cccc(F)c1Cl)[C@H](COC(=O)Nc1cc2ccccc2cn1)CN(CCO)CCO] | [(2S)-3-[bis(2-hydroxyethyl)amino]-2-({[(2-chloro-3-fluorophenyl)methyl]amino}-N-methylcarbonylamino)propoxy]-N-(3-isoquinolyl)carboxamide |
| 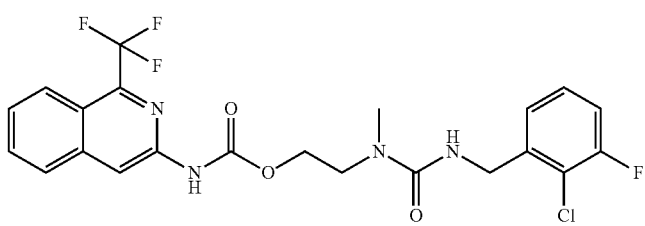 [SMILES: CN(CCOC(=O)Nc1cc2ccccc2c(C(F)(F)F)n1)C(=O)NCc1cccc(F)c1Cl] | [2-({[(2-chloro-3-fluorophenyl)methyl]amino}-N-methylcarbonylamino)ethoxy]-N-[1-(trifluoromethyl)(3-isoquinolyl)]carboxamide |
| 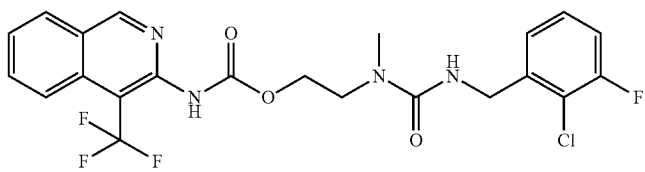 [SMILES: CN(CCOC(=O)Nc1ncc2ccccc2c1C(F)(F)F)C(=O)NCc1cccc(F)c1Cl] | [2-({[(2-chloro-3-fluorophenyl)methyl]amino}-N-methylcarbonylamino)ethoxy]-N-[4-(trifluoromethyl)(3-isoquinolyl)]carboxamide |
| 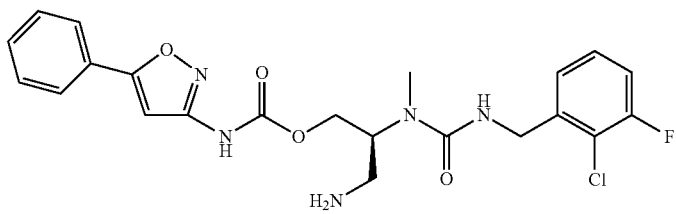 | [(2S)-3-amino-2-({[(2-chloro-3-fluorophenyl)methyl]amino}-N-methylcarbonylamino)propoxy]-N-(5-phenylisoxazol-3-yl)carboxamide |
| 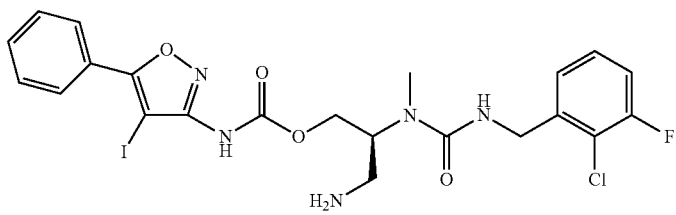 [SMILES: CN(C(=O)NCc1cccc(F)c1Cl)[C@@H](CN)COC(=O)Nc1noc(-c2ccccc2)c1I] | [(2S)-3-amino-2-({[(2-chloro-3-fluorophenyl)methyl]amino}-N-methylcarbonylamino)propoxy]-N-(4-iodo-5-phenylisoxazol-3-yl)carboxamide |
| 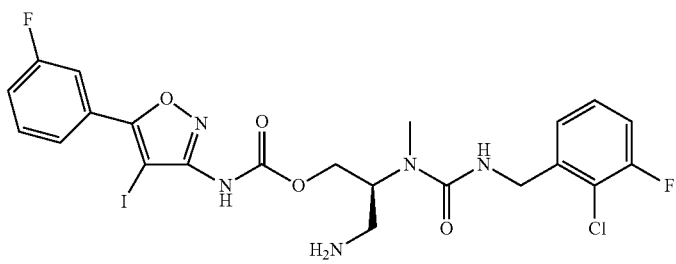 [SMILES: CN(C(=O)NCc1cccc(F)c1Cl)[C@@H](CN)COC(=O)Nc1noc(-c2cccc(F)c2)c1I] | [(2S)-3-amino-2-({[(2-chloro-3-fluorophenyl)methyl]amino}-N-methylcarbonylamino)propoxy]-N-[5-(3-fluorophenyl)-4-iodoisoxazol-3-yl]carboxamide |

| Structure | Chemical Name |
|---|---|
| 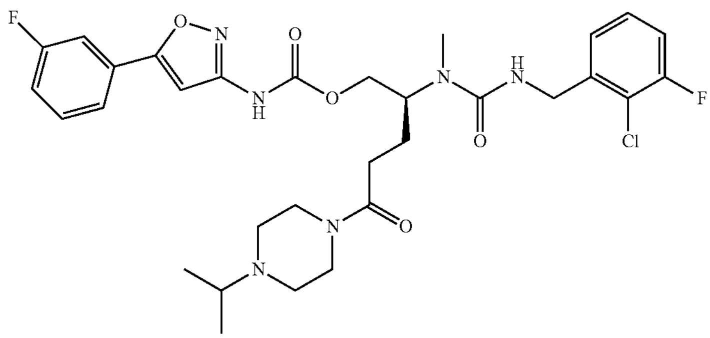 [SMILES: CC(C)N1CCN(C(=O)CC[C@@H](COC(=O)Nc2cc(-c3cccc(F)c3)on2)N(C)C(=O)NCc2cccc(F)c2Cl)CC1] | [(2S)-2-({[(2-chloro-3-fluorophenyl)methyl]amino}-N-methylcarbonylamino)-5-[4-(methylethyl)piperazinyl]-5-oxopentyloxy]-N-[5-(3-fluorophenyl)isoxazol-3-yl]carboxamide |
| 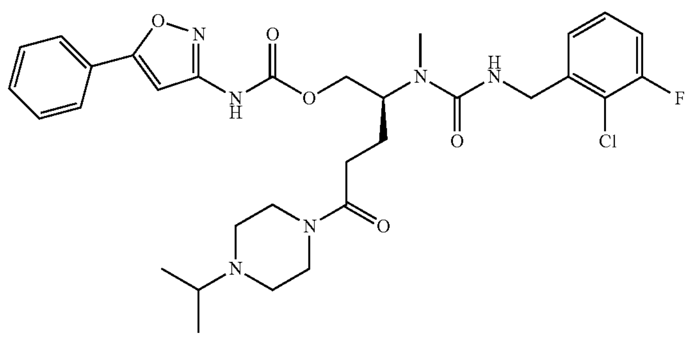 [SMILES: CC(C)N1CCN(C(=O)CC[C@@H](COC(=O)Nc2cc(-c3ccccc3)on2)N(C)C(=O)NCc2cccc(F)c2Cl)CC1] | [(2S)-2-({[(2-chloro-3-fluorophenyl)methyl]amino}-N-methylcarbonylamino)-5-[4-(methylethyl)piperazinyl]-5-oxopentyloxy]-N-(5-phenylisoxazol-3-yl)carboxamide |
| 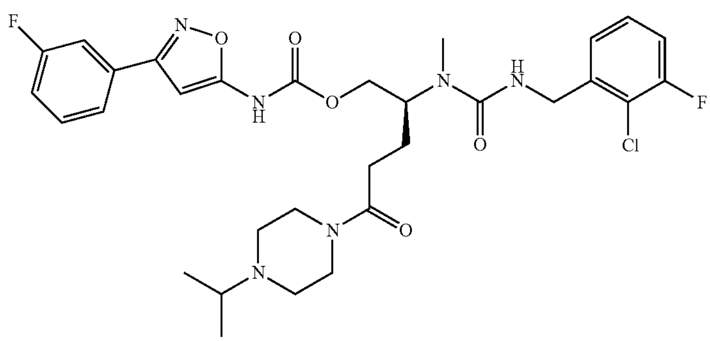 [SMILES: CC(C)N1CCN(C(=O)CC[C@@H](COC(=O)Nc2cc(-c3cccc(F)c3)no2)N(C)C(=O)NCc2cccc(F)c2Cl)CC1] | [(2S)-2-({[(2-chloro-3-fluorophenyl)methyl]amino}-N-methylcarbonylamino)-5-[4-(methylethyl)piperazinyl]-5-oxopentyloxy]-N-[3-(3-fluorophenyl)isoxazol-5-yl]carboxamide |
| 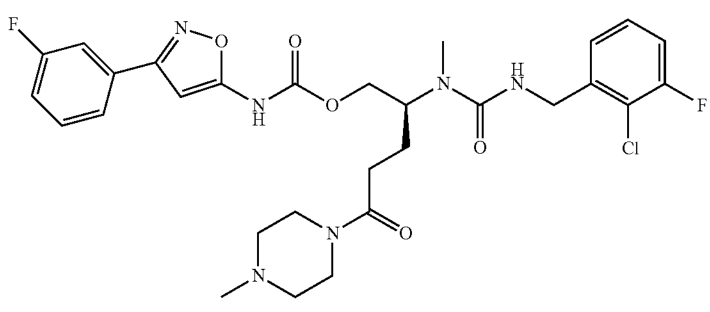 [SMILES: CN1CCN(C(=O)CC[C@@H](COC(=O)Nc2cc(-c3cccc(F)c3)no2)N(C)C(=O)NCc2cccc(F)c2Cl)CC1] | [(2S)-2-({[(2-chloro-3-fluorophenyl)methyl]amino}-N-methylcarbonylamino)-5-(4-methylpiperazinyl)-5-oxopentyloxy]-N-[3-(3-fluorophenyl)isoxazol-5-yl]carboxamide |
| 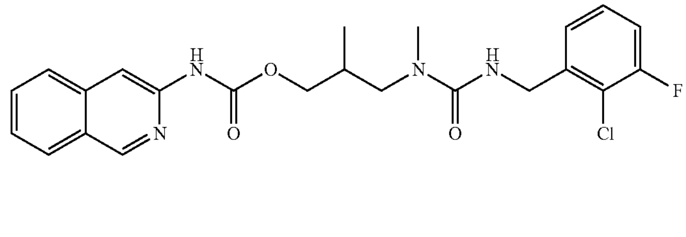 [SMILES: CC(COC(=O)Nc1cc2ccccc2cn1)CN(C)C(=O)NCc1cccc(F)c1Cl] | [3-({[(2-chloro-3-fluorophenyl)methyl]amino}-N-methylcarbonylamino)-2-methylpropoxy]-N-(3-isoquinolyl)carboxamide |

| Structure | Chemical Name |
|---|---|
| 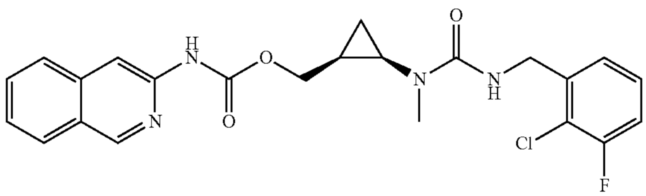 [SMILES: CN(C(=O)NCc1cccc(F)c1Cl)[C@@H]1C[C@@H]1COC(=O)Nc1cc2ccccc2cn1] | N-{(2S,1R)-2-[(N-(3-isoquinolyl)carbamoyloxy)methyl]cyclopropyl}{[(2-chloro-3-fluorophenyl)methyl]amino}-N-methylcarboxamide |
| 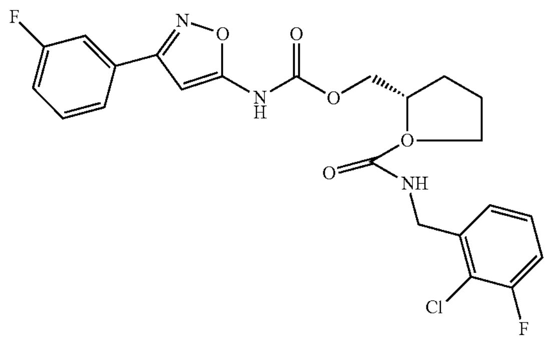 | [((2S)-1-{N-[(2-chloro-3-fluorophenyl)methyl]carbamoyl}pyrrolidin-2-yl)methoxy]-N-[3-(3-fluorophenyl)isoxazol-5-yl]carboxamide |
| 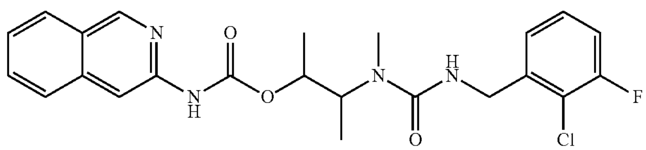 | {[(2-chloro-3-fluorophenyl)methyl]amino}-N-[2-(N-(3-isoquinolyl)carbamoyloxy)-1-methylpropyl]-N-methylcarboxamide |
| 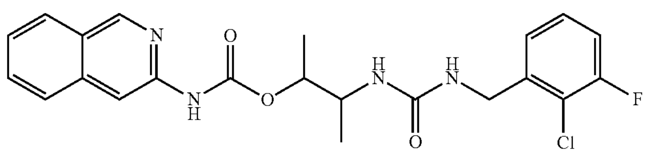 | {[(2-chloro-3-fluorophenyl)methyl]amino}-N-[2-(N-(3-isoquinolyl)carbamoyloxy)-1-methylpropyl]carboxamide |
| 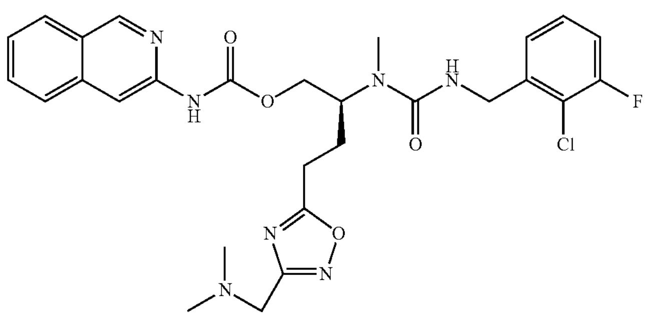 [SMILES: CN(C)Cc1noc(CC[C@@H](COC(=O)Nc2cc3ccccc3cn2)N(C)C(=O)NCc2cccc(F)c2Cl)n1] | N-((1S)-3-{3-[(dimethylamino)methyl](1,2,4-oxadiazol-5-yl)}-1-[(N-(3-isoquinolyl)carbamoyloxy)methyl]propyl){[(2-chloro-3-fluorophenyl)methyl]amino}-N-methylcarboxamide |
| 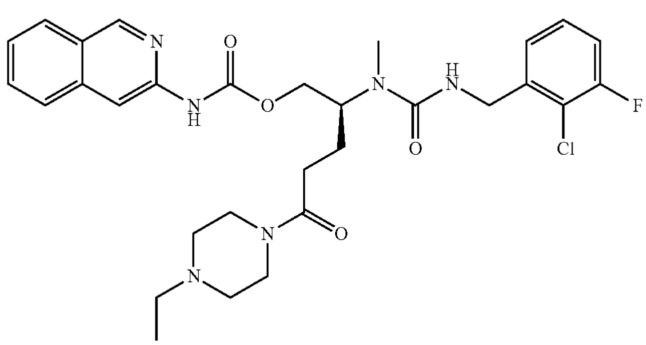 [SMILES: CCN1CCN(C(=O)CC[C@@H](COC(=O)Nc2cc3ccccc3cn2)N(C)C(=O)NCc2cccc(F)c2Cl)CC1] | N-{(1S)-4-(4-ethylpiperazinyl)-1-[(N-(3-isoquinolyl)carbamoyloxy)methyl]-4-oxobutyl}{[(2-chloro-3-fluorophenyl)methyl]amino}-N-methylcarboxamide |

-continued

| Structure | Chemical Name |
|---|---|
| 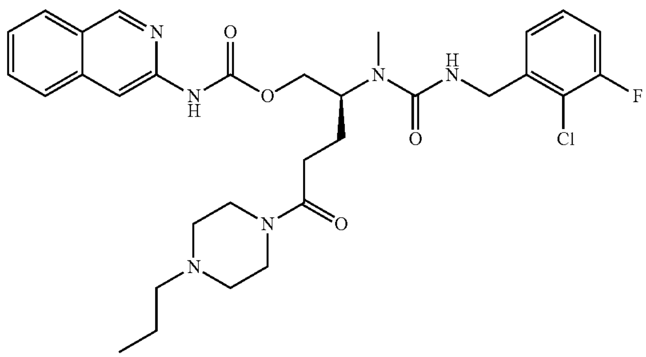 [SMILES: CCCN1CCN(C(=O)CC[C@@H](COC(=O)Nc2cc3ccccc3cn2)N(C)C(=O)NCc2cccc(F)c2Cl)CC1] | N-{(1S)-1-[(N-(3-isoquinolyl)carbamoyloxy)methyl]-4-oxo-4-(4-propylpiperazinyl)butyl}{[(2-chloro-3-fluorophenyl)methyl]amino}-N-methylcarboxamide |
| 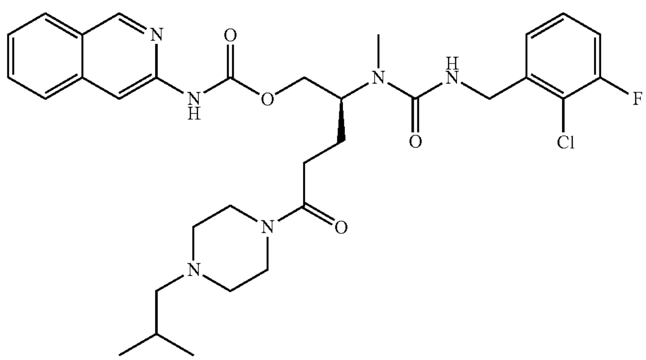 [SMILES: CC(C)CN1CCN(C(=O)CC[C@@H](COC(=O)Nc2cc3ccccc3cn2)N(C)C(=O)NCc2cccc(F)c2Cl)CC1] | N-{(1S)-1-[(N-(3-isoquinolyl)carbamoyloxy)methyl]-4-[4-(2-methylpropyl)piperazinyl]-4-oxobutyl}{[(2-chloro-3-fluorophenyl)methyl]amino}-N-methylcarboxamide |
| 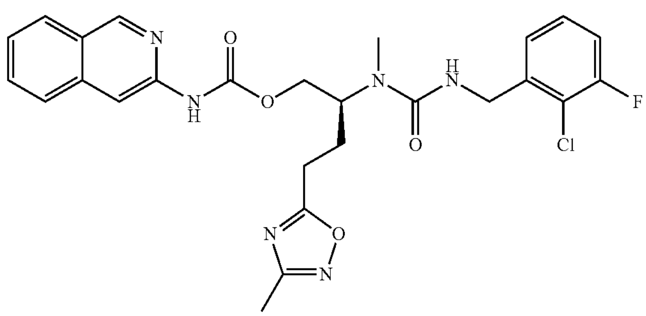 [SMILES: Cc1noc(CC[C@@H](COC(=O)Nc2cc3ccccc3cn2)N(C)C(=O)NCc2cccc(F)c2Cl)n1] | N-{(1S)-1-[(N-(3-isoquinolyl)carbamoyloxy)methyl]-3-(3-methyl(1,2,4-oxadiazol-5-yl))propyl}{[(2-chloro-3-fluorophenyl)methyl]amino}-N-methylcarboxamide |
| 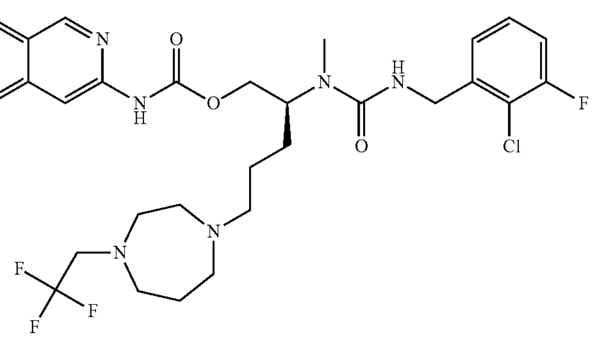 | N-{(1S)-1-[(N-(3-isoquinolyl)carbamoyloxy)methyl]-4-[4-(2,2,2-trifluoroethyl)(1,4-diazaperhydroepinyl)]butyl}{[(2-chloro-3-fluorophenyl)methyl]amino}-N-methylcarboxamide |

-continued

| Structure | Chemical Name |
|---|---|
| 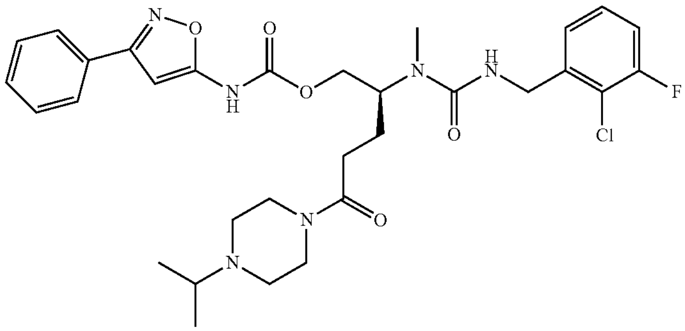 [SMILES: CC(C)N1CCN(C(=O)CC[C@@H](COC(=O)Nc2cc(-c3ccccc3)no2)N(C)C(=O)NCc2cccc(F)c2Cl)CC1] | [(2S)-2-({[(2-chloro-3-fluorophenyl)methyl]amino}-N-methylcarbonylamino)-5-[4-(methylethyl)piperazinyl]-5-oxopentyloxy]-N-(3-phenylisoxazol-5-yl)carboxamide |
| 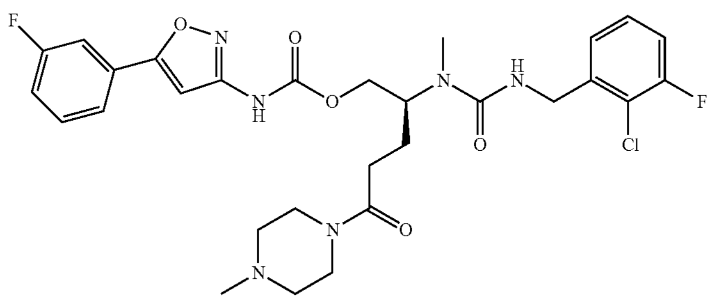 [SMILES: CN1CCN(C(=O)CC[C@@H](COC(=O)Nc2cc(-c3cccc(F)c3)on2)N(C)C(=O)NCc2cccc(F)c2Cl)CC1] | [(2S)-2-({[(2-chloro-3-fluorophenyl)methyl]amino}-N-methylcarbonylamino)-5-(4-methylpiperazinyl)-5-oxopentyloxy]-N-[5-(3-fluorophenyl)isoxazol-3-yl]carboxamide |
| 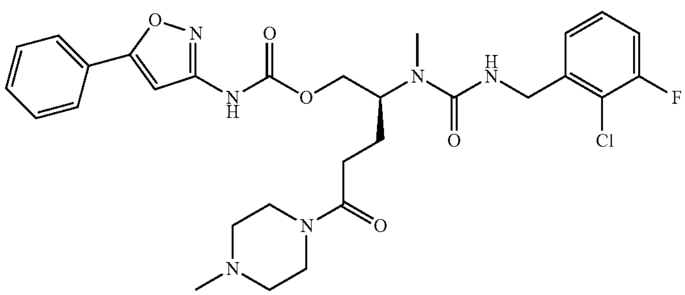 [SMILES: CN1CCN(C(=O)CC[C@@H](COC(=O)Nc2cc(-c3ccccc3)on2)N(C)C(=O)NCc2cccc(F)c2Cl)CC1] | [(2S)-2-({[(2-chloro-3-fluorophenyl)methyl]amino}-N-methylcarbonylamino)-5-(4-methylpiperazinyl)-5-oxopentyloxy]-N-(5-phenylisoxazol-3-yl)carboxamide |
| 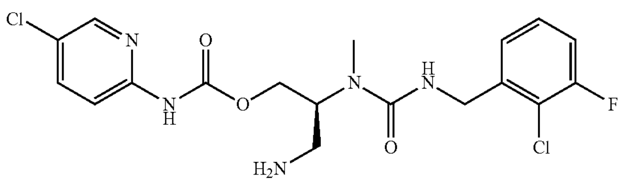 [SMILES: CN(C(=O)NCc1cccc(F)c1Cl)[C@@H](CN)COC(=O)Nc1ccc(Cl)cn1] | N-((1S)-2-amino-1-{[N-(5-chloro(2-pyridyl))carbamoyloxy]methyl}ethyl){[(2-chloro-3-fluorophenyl)methyl]amino}-N-methylcarboxamide |
| 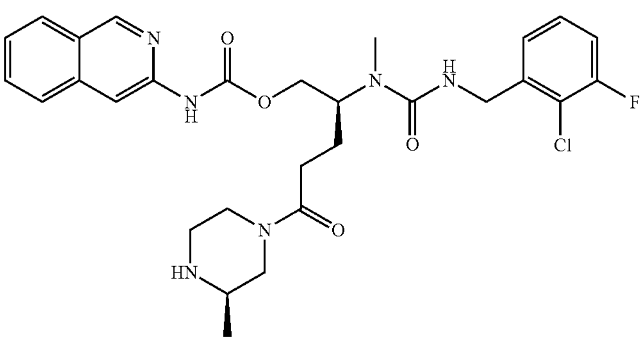 [SMILES: C[C@@H]1CN(C(=O)CC[C@@H](COC(=O)Nc2cc3ccccc3cn2)N(C)C(=O)NCc2cccc(F)c2Cl)CCN1] | [5-((3R)-3-methylpiperazinyl)(2S)-2-({[(2-chloro-3-fluorophenyl)methyl]amino}-N-methylcarbonylamino)-5-oxopentyloxy]-N-(3-isoquinolyl)carboxamide |

-continued

| Structure | Chemical Name |
|---|---|
| 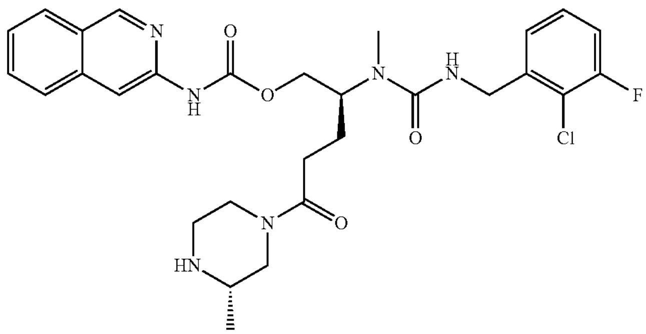 [SMILES: C[C@H]1CN(C(=O)CC[C@@H](COC(=O)Nc2cc3ccccc3cn2)N(C)C(=O)NCc2cccc(F)c2Cl)CCN1] | [(2S)-5-((3S)-3-methylpiperazinyl)-2-({[(2-chloro-3-fluorophenyl)methyl]amino}-N-methylcarbonylamino)-5-oxopentyloxy]-N-(3-isoquinolyl)carboxamide |
| 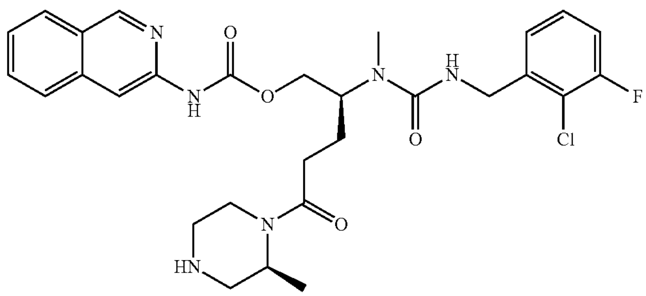 [SMILES: C[C@H]1CNCCN1C(=O)CC[C@@H](COC(=O)Nc1cc2ccccc2cn1)N(C)C(=O)NCc1cccc(F)c1Cl] | [(2S)-5-((2S)-2-methylpiperazinyl)-2-({[(2-chloro-3-fluorophenyl)methyl]amino}-N-methylcarbonylamino)-5-oxopentyloxy]-N-(3-isoquinolyl)carboxamide |
| 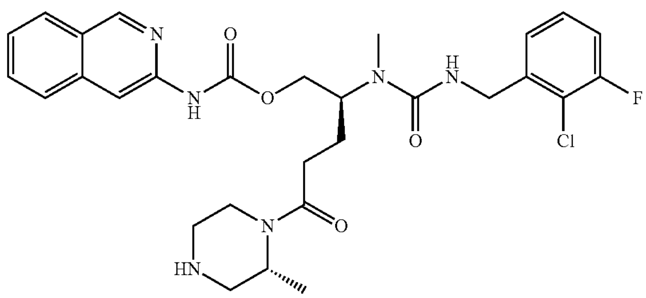 [SMILES: C[C@@H]1CNCCN1C(=O)CC[C@@H](COC(=O)Nc1cc2ccccc2cn1)N(C)C(=O)NCc1cccc(F)c1Cl] | [5-((2R)-2-methylpiperazinyl)(2S)-2-({[(2-chloro-3-fluorophenyl)methyl]amino}-N-methylcarbonylamino)-5-oxopentyloxy]-N-(3-isoquinolyl)carboxamide |
| 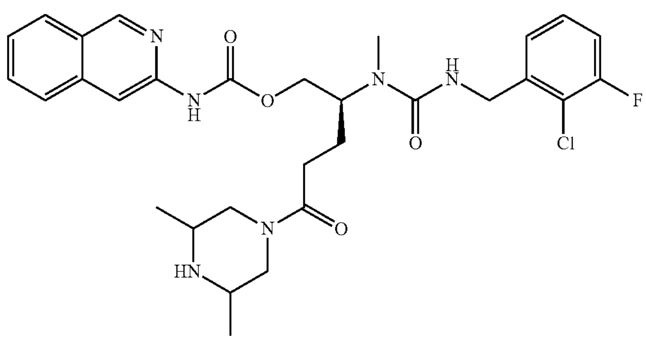 [SMILES: CC1CN(C(=O)CC[C@@H](COC(=O)Nc2cc3ccccc3cn2)N(C)C(=O)NCc2cccc(F)c2Cl)CC(C)N1] | [(2S)-5-(3,5-dimethylpiperazinyl)-2-({[(2-chloro-3-fluorophenyl)methyl]amino}-N-methylcarbonylamino)-5-oxopentyloxy]-N-(3-isoquinolyl)carboxamide |
| 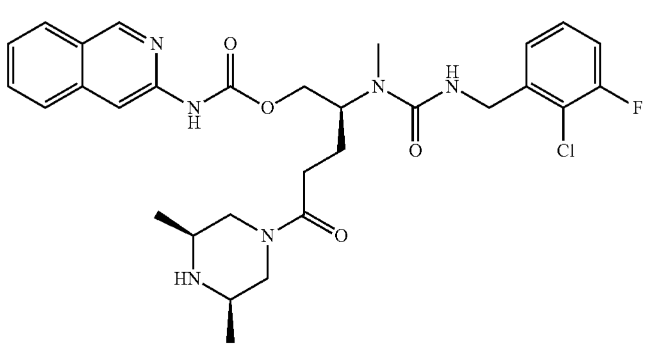 [SMILES: C[C@@H]1CN(C(=O)CC[C@@H](COC(=O)Nc2cc3ccccc3cn2)N(C)C(=O)NCc2cccc(F)c2Cl)C[C@H](C)N1] | [(2S)-5-((3S,5R)-3,5-dimethylpiperazinyl)-2-({[(2-chloro-3-fluorophenyl)methyl]amino}-N-methylcarbonylamino)-5-oxopentyloxy]-N-(3-isoquinolyl)carboxamide |

-continued

| Structure | Chemical Name |
|---|---|
| 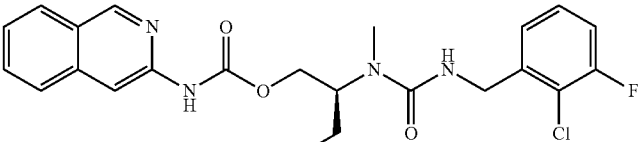 | [(2S)-2-({[(2-chloro-3-fluorophenyl)methyl]amino}-N-methylcarbonylamino)-5-(4-cyclopropylpiperazinyl)-5-oxopentyloxy]-N-(3-isoquinolyl)carboxamide |
| 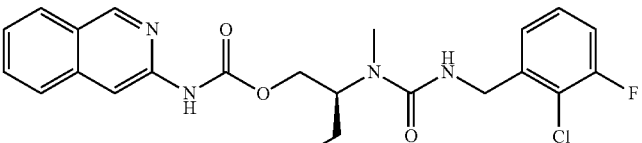 | [(2S)-2-({[(2-chloro-3-fluorophenyl)methyl]amino}-N-methylcarbonylamino)-5-(4-cyclobutylpiperazinyl)-5-oxopentyloxy]-N-(3-isoquinolyl)carboxamide |
| 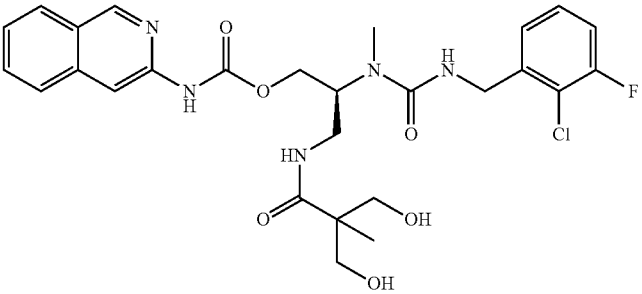 [SMILES: CN(C(=O)NCc1cccc(F)c1Cl)[C@@H](CNC(=O)C(C)(CO)CO)COC(=O)Nc1cc2ccccc2cn1] | N-[(2S)-2-({[(2-chloro-3-fluorophenyl)methyl]amino}-N-methylcarbonylamino)-3-(N-(3-isoquinolyl)carbamoyloxy)propyl]-3-hydroxy-2-(hydroxymethyl)-2-methylpropanamide |
| 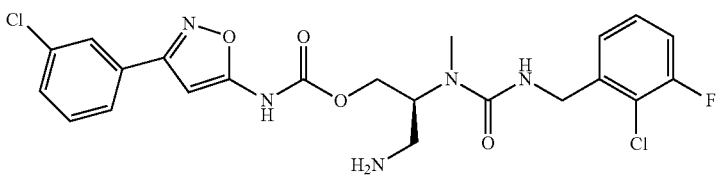 [SMILES: CN(C(=O)NCc1cccc(F)c1Cl)[C@@H](CN)COC(=O)Nc1cc(-c2cccc(Cl)c2)no1] | N-[(1S)-2-amino-1-({N-[3-(3-chlorophenyl)isoxazol-5-yl]carbamoyloxy}methyl)ethyl]{[(2-chloro-3-fluorophenyl)methyl]amino}-N-methylcarboxamide |
| 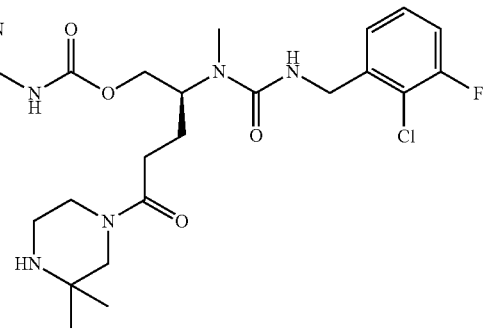 | [(2S)-5-(3,3-dimethylpiperazinyl)-2-({[(2-chloro-3-fluorophenyl)methyl]amino}-N-methylcarbonylamino)-5-oxopentyloxy]-N-(3-isoquinolyl)carboxamide |

| Structure | Chemical Name |
|---|---|
| 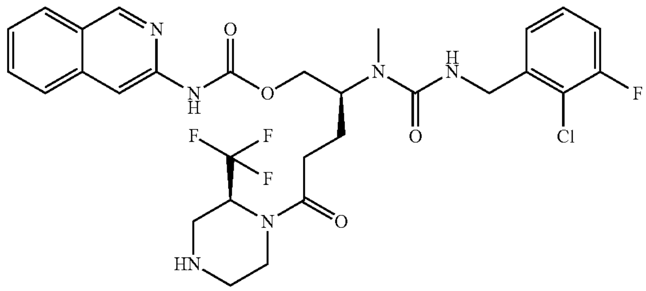 [SMILES: CN(C(=O)NCc1cccc(F)c1Cl)[C@@H](CCC(=O)N1CCNC[C@H]1C(F)(F)F)COC(=O)Nc1cc2ccccc2cn1] | [(2S)-5-[(2S)-2-(trifluoromethyl)piperazinyl]-2-({[(2-chloro-3-fluorophenyl)methyl]amino}-N-methylcarbonylamino)-5-oxopentyloxy]-N-(3-isoquinolyl)carboxamide |
| | N-((1S)-2-{N-[3-(3-chlorophenyl)isoxazol-5-yl]carbamoyloxy}-1-{[(phenylmethoxy)carbonylamino]methyl}ethyl){[(2-chloro-3-fluorophenyl)methyl]amino}-N-methylcarboxamide | and pharmaceutically acceptable salts thereof.

Also provided is at least one chemical entity selected from

N-{(1S)-5-hydroxy-1-[(N-(3-isoquinolyl)carbamoyloxy)methyl]pentyl}{[(2-chloro-4-fluorophenyl)methyl]amino}-N-methylcarboxamide;

N-((1S)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide;

N-((1S,3S)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide;

N-((1S,3R)-1-{[N-(6-fluoro(3-isoquinoly))carbamoyloxy]methyl}-3,4-dihydroxybutyl){[(2-chloro-3-fluorophenyl)methyl]amino}-N-methylcarboxamide;

N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-aminoacetamide;

(4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate;

N-[(2S)-2-({[(2-chloro-3-fluorophenyl)methyl]amino}-N-methylcarbonylamino)-3-[N-(6-fluoro(3-isoquinolyl))carbamoyloxy]propyl]-2-aminoacetamide;

N-{(1S)-4-amino-1-[(N-pyridino[4,3-d]pyridin-3-ylcarbamoyloxy)methyl]butyl}{[(2-chloro-3-fluorophenyl)methyl]amino}-N-methylcarboxamide;

N-((1S)-1-{[N-(6-fluoro(3-isoquinolyl))carbamoyloxy]methyl}-4-oxo-4-piperazinylbutyl){[(2-chloro-3-fluorophenyl)methyl]amino}-N-methylcarboxamide;

N-(4-[((1E)-1-amino-2-carbamoyl-2-azavinyl)amino](1S)-1-{[N-(6-fluoro(3-isoquinolyl))carbamoyloxy]methyl}butyl){[(2-chloro-3-fluorophenyl)methyl]amino}-N-methylcarboxamide;

N-[(1S)-4-amino-1-({N-[5-(trifluoromethyl)(2-pyridyl)]carbamoyloxy}methyl)butyl]{[(2-chloro-3-fluorophenyl)methyl]amino}-N-methylcarboxamide;

(5S)-5-({[(2,3-difluorophenyl)methyl]amino}-N-methylcarbonylamino)-6-(N-(3-isoquinolyl)carbamoyloxy)hexyl dihydrogen phosphate;

[(2S)-5-amino-2-({[(2-chloro-3-fluorophenyl)methyl]amino}-N-methylcarbonylamino)pentyloxy]-N-(5-chloro(2-pyridyl))carboxamide;

N-((1S)-4-amino-3,3-difluoro-1-{[N-(6-fluoro(3-isoquinolyl))carbamoyloxy]methyl}butyl){[(2-chloro-3-fluorophenyl)methyl]amino}-N-methylcarboxamide;

[(2S,4R)-2-({[(2-chloro-3-fluorophenyl)methyl]amino}-N-methylcarbonylamino)-4,5-dihydroxypentyloxy]-N-(3-isoquinolyl)carboxamide;

[(2S,4S)-2-({[(2-chloro-3-fluorophenyl)methyl]amino}-N-methylcarbonylamino)-4,5-dihydroxypentyloxy]-N-(3-isoquinolyl)carboxamide;

[(2S)-2-({[(2-chloro-3-fluorophenyl)methyl]amino}-N-methylcarbonylamino)-5-oxo-5-piperazinylpentyloxy]-N-(3-isoquinolyl)carboxamide;

N-{(1S,3S)-3,4-dihydroxy-1-[(N-(3-isoquinolyl)carbamoyloxy)methyl]butyl}{[(2,3-difluorophenyl)methyl]amino}-N-methylcarboxamide;

N-{(1S,3R)-3,4-dihydroxy-1-[(N-(3-isoquinolyl)carbamoyloxy)methyl]butyl}{[(2,3-difluorophenyl)methyl]amino}-N-methylcarboxamide;

(4S,2R)-4-({[(2,3-difluorophenyl)methyl]amino}-N-methylcarbonylamino)-2-hydroxy-5-(N-(3-isoquinolyl)carbamoyloxy)pentyl dihydrogen phosphate;

(2S,4S)-4-({[(2,3-difluorophenyl)methyl]amino}-N-methylcarbonylamino)-2-hydroxy-5-(N-(3-isoquinolyl)carbamoyloxy)pentyl dihydrogen phosphate;

N-{(1S)-4-hydroxy-1-[(N-(3-isoquinolyl)carbamoyloxy)methyl]butyl}{[(2,3-difluorophenyl)methyl]amino}-N-methylcarboxamide;

(4S)-4-({[(2,3-difluorophenyl)methyl]amino}-N-methylcarbonylamino)-5-(N-(3-isoquinolyl)carbamoyloxy)pentyl dihydrogen phosphate;

[(2S)-2-({[(2-chloro-3-fluorophenyl)methyl]amino}-N-methylcarbonylamino)-5-hydroxy-4,4-dimethylpentyloxy]-N-(6-fluoro(3-isoquinolyl))carboxamide;

(4S)-4-({[(2-chloro-3-fluorophenyl)methyl]amino}-N-methylcarbonylamino)-5-[N-(6-fluoro(3-isoquinolyl))carbamoyloxy]-2,2-dimethylpentyl dihydrogen phosphate;

N-((1S,3R)-3,4-dihydroxy-1-{[N-(3-phenylisoxazol-5-yl)carbamoyloxy]methyl}butyl){[(2-chloro-3-fluorophenyl)methyl]amino}-N-methylcarboxamide;

(4S,2R)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate;

(4S,2R)-4-({[(2-chloro-3-fluorophenyl)methyl]amino}-N-methylcarbonylamino)-2-hydroxy-5-[N-(3-phenylisoxazol-5-yl)carbamoyloxy]pentyl dihydrogen phosphate;

N-{(1S)-1-[(N-benzothiazol-2-ylcarbamoyloxy)methyl]-4-oxo-4-piperazinylbutyl}{[(2-chloro-3-fluorophenyl)methyl]amino}-N-methylcarboxamide;

N-{(1S)-1-[((2S)-2,3-dihydroxypropoxy)methyl]-2-(N-(3-isoquinolyl)carbamoyloxy)ethyl}{[(2-chloro-3-fluorophenyl)methyl]amino}-N-methylcarboxamide;

(2R)-3-[(2S)-2-({[(2-chloro-3-fluorophenyl)methyl]amino}-N-methylcarbonylamino)-3-(N-(3-isoquinolyl)carbamoyloxy)propoxy]-2-hydroxypropyl dihydrogen phosphate;

N-{(1S)-1-[(N-(3-isoquinolyl)carbamoyloxy)methyl]-4-(1,2,4-triazolo[3,4-c]piperazin-7-yl)butyl}{[(2-chloro-3-fluorophenyl)methyl]amino}-N-methylcarboxamide;

[(2S)-2-({[(2-chloro-3-fluorophenyl)methyl]amino}-N-methylcarbonylamino)-3-imidazol-4-ylpropoxy]-N-(6-fluoro(3-isoquinolyl))carboxamide;

[(2S)-2-({[(2-chloro-3-fluorophenyl)methyl]amino}-N-methylcarbonylamino)-3-(2-pyridyl)propoxy]-N-(3-isoquinolyl)carboxamide;

[(2S)-2-({[(2-chloro-3-fluorophenyl)methyl]amino}-N-methylcarbonylamino)-5-oxo-5-piperazinylpentyloxy]-N-[3-(3-fluorophenyl)isoxazol-5-yl]carboxamide;

[(2S)-2-({[(2-chloro-3-fluorophenyl)methyl]amino}-N-methylcarbonylamino)-5-oxo-5-piperazinylpentyloxy]-N-[5-(3-fluorophenyl)isoxazol-3-yl]carboxamide;

[(2S)-2-({[(2-chloro-3-fluorophenyl)methyl]amino}-N-methylcarbonylamino)-5-[4-(methylethyl)piperazinyl]-5-oxopentyloxy]-N-(3-isoquinolyl)carboxamide;

N-{(1S)-1-[(N-(3-isoquinolyl)carbamoyloxy)methyl]-4-(4-methylpiperazinyl)butyl}{[(2-chloro-3-fluorophenyl)methyl]amino}-N-methylcarboxamide;

N-{(1S)-1-[(N-(3-isoquinolyl)carbamoyloxy)methyl]-4-(2-methyl(4,5,6,7-tetrahydroimidazo[5,4-c]pyridin-5-yl))-4-oxobutyl}{[(2-chloro-3-fluorophenyl)methyl]amino}-N-methylcarboxamide;

N-{(1S)-1-[(N-(3-isoquinolyl)carbamoyloxy)methyl]-4-(2-oxopiperazinyl)butyl}{[(2-chloro-3-fluorophenyl)methyl]amino}-N-methylcarboxamide;

N-[(1S)-4-amino-3,3-difluoro-1-({N-[3-(3-fluorophenyl)isoxazol-5-yl]carbamoyloxy}methyl)butyl]{[(2-chloro-3-fluorophenyl)methyl]amino}-N-methylcarboxamide;

N-[(1S)-1-(imidazo[1,5-a]piperazin-3-ylmethyl)-2-(N-(3-isoquinolyl)carbamoyloxy)ethyl]{[(2-chloro-3-fluorophenyl)methyl]amino}-N-methylcarboxamide; and

[(2S)-3-[(2,2-difluoroethyl)amino]-2-({[(2-chloro-3-fluorophenyl)methyl]amino}-N-methylcarbonylamino)propoxy]-N-[3-(3-fluorophenyl)isoxazol-5-yl]carboxamide, and pharmaceutically acceptable salts thereof.

Many of the optionally substituted starting compounds and other reactants are commercially available, e.g. from Aldrich Chemical Company (Milwaukee, Wis.) or can be readily prepared by those skilled in the art using commonly employed synthetic methodology.

The chemical entities described herein can be synthesized utilizing techniques well known in the art from commercially available starting materials and reagents. For example, the chemical entities described herein can be prepared as illustrated below with reference to the examples and reaction schemes.

Unless specified to the contrary, the reactions described herein take place at atmospheric pressure, generally within a temperature range from −10° C. to 200° C. Further, except as employed in the examples or as otherwise specified, reaction times and conditions are intended to be approximate, e.g. taking place at about atmospheric pressure within a temperature range of about −10° C. to about 110° C. over a period of about 1 to about 24 hours; reactions left to run overnight average a period of about 16 hours. For each gram of the limiting reagent, one cc (or mL) of solvent constitutes a volume equivalent.

The terms "solvent," "organic solvent," and "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like]. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R) and (S) isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that when the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts and/or solvents, or by converting one enantiomer to the other by asymmetric transformation.

The chemical entities described herein may be useful in a variety of applications involving smooth muscle cells and/or non-muscle cells. In certain embodiments, the chemical entities may be used to inhibit smooth muscle myosin. The chemical entities may be useful to bind to, and/or inhibit the activity of, smooth muscle myosin. In certain embodiments, the smooth muscle myosin is human, although the chemical entities may be used to bind to or inhibit the activity of smooth muscle myosin from other organisms, such as other mammals.

In certain embodiments, the chemical entities may be used to inhibit non-muscle myosin. The chemical entities may be useful to bind to, and/or inhibit the activity of, non-muscle myosin. In certain embodiments, the non-muscle myosin is human, although the chemical entities may be used to bind to or inhibit the activity of non-muscle myosin from other organisms, such as other mammals.

The chemical entities described herein may be used to treat disease states associated with smooth muscle and/or non-muscle myosin. Such disease states which can be treated by the chemical entities described herein include, but are not limited to, hypertension, asthma, incontinence, chronic obstructive pulmonary disorder, pre-term labor, and the like. It is appreciated that in some cases the cells may not be in an abnormal state and still require treatment. Other disease states which may be treated by the chemical entities described herein include, but are not limited to, systemic hypertension, chronic heart failure, migraine and outpatient treatment of angina, pulmonary hypertension, perioperative hypertension, hypertensive emergency, cerebral vasospasm after cerebrovascular hemorrhage, in-hospital treatment of angina (including atypical angina) and/or acute heart failure. Additional disease states which may be treated include, but are not limited to, Also bronchospasm, asthma, cardiovascular, cerebrovascular and peripheral vascular diseases, vasospasm after cerebrovascular hemorrhage, erectile dysfunction, gastrointestinal motility dysfunction (e.g., irritable bowel syndrome), overactive bladder/stress urinary incontinence, and preterm labor.

Thus, in certain embodiments, the chemical entities described herein are applied to cells or administered to individuals afflicted or subject to impending affliction with any one of these disorders or states.

More specifically, the chemical entities described herein may be useful for the treatment of diseases or symptoms related to abnormal increased muscle tone or excessive contraction, or spasm of vascular smooth muscle in systemic, coronary, pulmonary circulation, and micro-circulatory smooth muscle as well, such as systemic hypertension, malignant hypertension, hypertension crisis, symptomatic hypertension, pulmonary hypertension, pulmonary infarction, angina pectoris, cardiac infarction, micro-circulation malfunction under shock condition, and infarction occurred in other location or organs of the human or animal body. Other diseases or symptoms that can be treated with the chemical entities described herein include:

spasm of gastro-intestine smooth muscle, including sphincters, such as gastric spasm, pylorospasm, and spasms of biliary tract, pancreatic tract, urinary tract, caused by inflammation, stimulation of stones or parasites;

spasm of other visceral organs such as uterus, Fallopian tube, and so on;

spasm of trachea-bronchial tree smooth muscle, diaphragm muscle, such as various asthma, breathlessness, dyspnea, diaphragmatic convulsion, and so on;

spasm of alimentary canal smooth muscle, including stomach, intestine and colons, biliary and pancreatic duct etc.; and spasm of urinary tract smooth muscle.

In addition, the chemical entities described herein can be used for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

Further, the chemical entities described herein can be used for the treatment of "airway wall remodeling", which is a condition associated with diseases or conditions characterized by airway wall thickening and air obstruction, which may, for example, occur in the small airways of patients with certain respiratory disease conditions, such as chronic obstructive pulmonary disease (COPD).

Such disease states which can be treated by the chemical entities, compositions and methods provided herein also include, but are not limited to glaucoma and other ocular indications. More specifically, chemical entities described herein may be useful for the treatment of diseases or symptoms related to glaucoma, including increased intraocular pressure, reduced flow of intraocular aqueous humor, and optical nerve damage. Other diseases or symptoms that can be treated with the chemical entities, compositions, and methods described herein including intraocular hypertenstion.

ATP hydrolysis is employed by myosin to produce force. An increase in ATP hydrolysis would correspond to an increase in the force or velocity of muscle contraction. In the presence of actin, myosin ATPase activity is stimulated more than 100-fold. Thus, the measurement of ATP hydrolysis not only measures myosin enzymatic activity but also its interaction with the actin filament. Assays for such activity may employ smooth muscle myosin from a human source, although myosin from other organisms can also be used. Systems that model the regulatory role of calcium in myosin binding may also be used.

The in vitro rate of ATP hydrolysis correlates to smooth muscle myosin potentiating activity, which can be determined by monitoring the production of either ADP or phosphate, for example as described in U.S. Pat. No. 6,410,254. ADP production can also be monitored by coupling the ADP production to NADH oxidation (using, for example, the enzymes pyruvate kinase and lactate dehydrogenase) and monitoring the NADH level, by example, either by absorbance or fluorescence (Greengard, P., *Nature* 178 (Part 4534): 632-634 (1956); *Mol Pharmacol* 1970 January; 6(1):31-40). Phosphate production can be monitored using purine nucleoside phosphorylase to couple phosphate production to the cleavage of a purine analog, which results in either a change in absorbance (*Proc Natl Acad Sci USA* 1992 Jun. 1; 89(11): 4884-7) or fluorescence (*Biochem J* 1990 Mar. 1; 266(2):611-4). While a single measurement is employed, multiple measurements of the same sample at different times in order may be used to determine the absolute rate of the protein activity; such measurements have higher specificity particularly in the presence of test compounds that have similar absorbance or fluorescence properties with those of the enzymatic readout.

Test compounds may be assayed in a highly parallel fashion using multiwell plates by placing the compounds either individually in wells or testing them in mixtures. Assay components including the target protein complex, coupling enzymes and substrates, and ATP may then be added to the wells and the absorbance or fluorescence of each well of the plate can be measured with a plate reader.

One method uses a 384 well plate format and a 25 µL reaction volume. A pyruvate kinase/lactate dehydrogenase coupled enzyme system (Huang T G and Hackney D D. (1994) J Biol Chem 269(23):16493-16501) is used to measure the rate of ATP hydrolysis in each well. As will be appreciated by those of skill in the art, the assay components are added in buffers and reagents. Since the methods outlined herein allow kinetic measurements, incubation periods may be optimized to give adequate detection signals over the background. The assay is performed in real time to give the kinetics of ATP hydrolysis to increase the signal-to-noise ratio of the assay.

Selectivity for smooth muscle myosin may be determined by substituting other myosins in one or more of the above-described assays and comparing the results obtained against those obtained using the cardiac equivalents.

Chemical entities identified by the methods described herein as smooth muscle myosin modulators may be further tested in an efficacy screen, such as a screen using strips of permeabilized smooth muscle from, e.g. chicken gizzard. Calcium-sensitive smooth muscle strips are prepared by dissecting chicken gizzard tissue, followed by treatment with 1% Triton X-100 to make the strips permeable to exogenous compounds (Barsotti, R J, et al., Am J. Physiol. 1987 May; 252(5 Pt 1):C543-54). These strips can be stored in 50% glycerol for several weeks at −20° C., allowing multiple experiments to be performed with each batch of muscle strips. Experiments are performed using a solution of 20 mM imidazole pH 7.0, 5.5 mM ATP, 7 mM $MgCl_2$, 55 mM KCl, 1 µM Calmodulin, and 10 mM EGTA. Free calcium will be controlled by addition of various amounts of $CaCl_2$, according to the calculations of MAXChelator (Patton, et al. Cell Calcium. 35/5 pp. 427-431, 2004). An isometric muscle fiber apparatus is used to measure isometric tension, for example using an Aurora Scientific 400A transducer with National Instruments PCI-MIO-16E-4, 16 channels, 12 bit A/D board for data acquisition. The chemically skinned gizzard fibers are relaxed when bathed in low calcium solutions (pCa 8), but develop isometric tension when the free calcium of the bathing solution is increased to pCa 5. These fibers can be repeatedly contracted and relaxed by switching between high and low calcium bathing solutions.

Compounds are first tested for their ability to prevent contraction of gizzard strips, by preincubating relaxed fibers with a compound, followed by transfer to high calcium solution containing the compound. Next, compounds are tested for their ability to cause relaxation of contracting fibers by adding the compound to fibers already incubating in high calcium solution. Washout experiments are performed to ensure that the inhibitory effects are reversible, so that the compounds do not cause denaturation or other irreparable damage to the smooth muscle myosin.

The chemical entities are administered at a therapeutically effective dosage, e.g. a dosage sufficient to provide treatment of the disease states previously described. Generally, a daily dose is from about 0.05 to about 100 mg/kg of body weight, such as from about 0.10 to about 10 mg/kg of body weight or from about 0.15 to about 1 mg/kg of body weight. Thus, for administration to a 70 kg person, the dosage range is from about 3.5 to about 7000 mg per day, such as from about 7 to about 700 mg per day or from about 10 to about 100 mg per day. The amount of active chemical entity administered will, of course, be dependent on the subject and disease state being treated, the severity of the affliction, the manner and schedule of administration and the judgment of the prescribing physician; for example, a dose range for oral administration may be from about 70 to about 700 mg per day, whereas for intravenous administration the dose range may be from about 700 to about 7000 mg per day. The active agents may be selected for longer or shorter plasma half-lives, respectively.

Administration of the chemical entities described herein including pharmaceutically acceptable salts thereof can be via any of the accepted modes of administration for agents that serve similar utilities including, but not limited to, orally, subcutaneously, intravenously, intranasally, topically, transdermally, sublingually, intramucosally, intraperitoneally, intramuscularly, intrapulmonarilly, vaginally, rectally, and intraocularly (including intraocular injection). Oral, topical, parenteral, and intraocular administration are customary in treating many of the indications recited herein.

Pharmaceutically acceptable compositions include solid, semi-solid, liquid and aerosol dosage forms, such as, e.g. tablets, capsules, powders, liquids, suspensions, suppositories, aerosols, and the like. The chemical entities can also be administered in sustained- or controlled-release dosage forms, including depot injections, osmotic pumps, pills, transdermal (including electrotransport) patches, drops and the like, for prolonged and/or timed, pulsed administration at a predetermined rate. The compositions may be provided in unit dosage forms suitable for single administration of a precise dose.

The chemical entities may be administered either alone or in combination with a conventional pharmaceutical carrier or the like (e.g. mannitol, lactose, starch, magnesium stearate, sodium saccharine, talcum, cellulose, sodium crosscarmellose, glucose, gelatin, sucrose, magnesium carbonate, and the like). If desired, the pharmaceutical composition may also contain minor amounts of nontoxic auxiliary substances such as wetting agents, emulsifying agents, solubilizing agents, pH buffering agents and the like (e.g. sodium acetate, sodium citrate, cyclodextrine derivatives, sorbitan monolaurate, triethanolamine acetate, triethanolamine oleate. Generally, depending on the intended mode of administration, the pharmaceutical composition may contain from about 0.005% to about 95%, for example, from about 0.5% to about 50%, by weight of at least one chemical entity described herein. Actual methods of preparing such dosage forms are known or will be apparent, to those skilled in this art; for example, see *Remington's Pharmaceutical Sciences*, Mack Publishing Company, Easton, Pa. Pharmaceutical compositions are also referred to as pharmaceutical formulations.

In addition, the chemical entities may be co-administered with, and the pharmaceutical compositions can include, other medicinal agents, pharmaceutical agents, adjuvants, and the like.

In certain embodiments, the compositions are in the form of a pill or tablet and contain, along with the active ingredient, one or more of a diluent such as lactose, sucrose, dicalcium phosphate, and the like; a lubricant such as magnesium stearate or the like; and a binder such as starch, gum acacia, polyvinylpyrrolidine, gelatin, cellulose, cellulose derivatives and the like. In another solid dosage form, a powder, marume, solution or suspension (e.g. in propylene carbonate, vegetable oils or triglycerides) may be encapsulated in a gelatin capsule.

Liquid pharmaceutical compositions may, for example, be prepared by dissolving, dispersing, etc. at least one chemical entity and one or more optional pharmaceutical adjuvants in a carrier (e.g. water, saline, aqueous dextrose, glycerol, glycols, ethanol and the like) to form a solution or suspension. Injectables may be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient ranging from about 0.01% to about 10% in solution may be used, and may be higher if the composition is a solid which will be subsequently diluted to the above percentages. In certain embodiments, the composition has from about 0.2% to about 2% of the active agent in solution.

Compositions comprising at least one chemical entity may be administered intraocularly (including intraocular, periocular, and retrobulbar injection and perfusion). When administered intraocularly the sterile composition is typically aqueous. An appropriate buffer system may be added to prevent pH drift under storage conditions. When administered during intraocular surgical procedures, such as retrobulbar or periocular injection and intraocular perfusion or injection, the use of balanced salt irrigating solutions may be necessary. When used in a multidose form, preservatives may be required to prevent microbial contamination during use.

Compositions comprising at least one chemical entity may also be administered topically as eye drops, eye wash, creams, ointments, gels, and sprays. When administered as eye drops or eye wash, the active ingredients are typically dissolved or suspended in suitable carrier, typically a sterile aqueous solvent. An appropriate buffer system may be added to prevent pH drift under storage conditions. When used in a multidose form, preservatives may be required to prevent microbial contamination during use.

Compositions comprising at least one chemical entity may also be administered to the respiratory tract as an aerosol or in a solution for a nebulizer, or as a microfine powder for insufflation, alone or in combination with an inert carrier such as lactose. The particles of the composition typically have diameters of less than 50 microns, for example, less than 10 microns.

Packaged pharmaceutical compositions comprising a pharmaceutical composition described herein and instructions for using the composition to treat a patient suffering from a disease associated with smooth muscle myosin or non-muscle myosin. The packaged pharmaceutical compositions described herein are also used to treat a patients suffering from a disease associated with smooth muscle myosin selected from hypertension, asthma, chronic obstructive pulmonary disease, bronchoconstrictive disease, glaucoma and other ocular indications, incontinence and other bladder disfunctions, irritable bowel syndrome, pre-term labor, esophogial dysmotility, strokes, subarachnoid hemmorhages, pre-menstrual cramps, erectile dysfunction and other acute and chronic diseases and conditions associated with smooth muscle myosin and/or non-muscle myosin.

Also provided is a method of treating or ameliorating a disease associated with smooth muscle myosin or non-muscle myosin in a mammal which method comprises administering to a mammal in need thereof a therapeutically effective amount of at least one chemical entity described herein.

In some embodiments, the method of treating or ameliorating a disease associated with smooth muscle myosin or non-muscle myosin described herein is used to treat diseases selected from hypertension, asthma, chronic obstructive pulmonary disease (COPD), bronchoconstrictive disease, glaucoma and other ocular indications, incontinence and other bladder disfunctions, irritable bowel syndrome, pre-term labor, esophogial dysmotility, strokes, subarachnoid hemmorhages, pre-menstrual cramps, erectile dysfunction and other acute and chronic diseases and conditions associated with smooth muscle myosin and/or non-muscle myosin.

Also provided is a method of treating or ameliorating a disease associated with airway wall remodeling in a mammal which method comprises administering to a mammal in need thereof a therapeutically effective amount of at least one chemical entity described herein.

Generally, to employ the chemical entities described herein in methods of screening for smooth muscle myosin binding, smooth muscle myosin is bound to a support and at least one chemical entity is added to the assay. Alternatively, the chemical entity may be bound to the support and the smooth muscle myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.), and the like. See, e.g. U.S. Pat. No. 6,495,337.

I. EXAMPLES

The following examples serve to more fully describe the manner of using the invention. These examples are presented for illustrative purposes and should not serve to limit the true scope of the invention.

Example 1

Preparation of 6-fluoro-isoquinoline-3-carbonyl azide

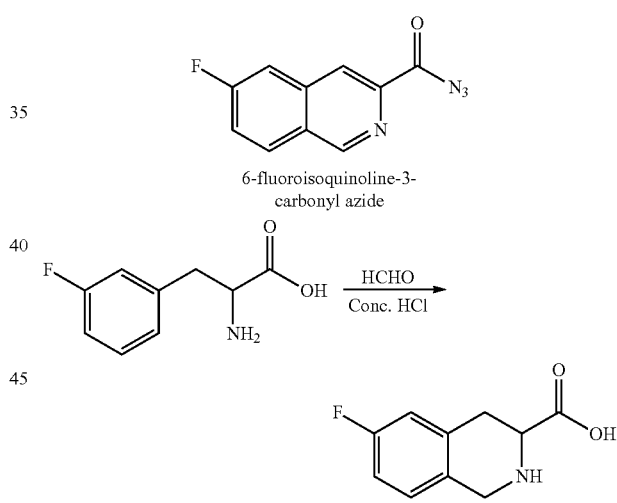

To a suspension of 3-fluoro-DL-phenylalanine (100 g) in conc. HCl (1.0 L) was added aq. formaldehyde solution (37% wt.; 400 mL). The reaction mixture was heated to 90° C. and stirred for 3.5 h, then cooled to RT and stirred overnight and filtered. The filtrate was concentrated and the residue was combined with the precipitate to give 6-fluoro-1,2,3,4-tetrahydroisoquinoline-3-carboxylic acid, which was used without further purification. LRMS (M+H$^+$) m/z 196.1.

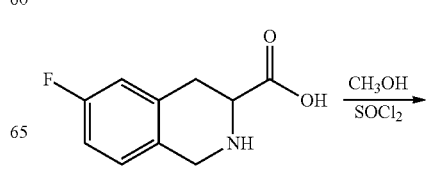

-continued

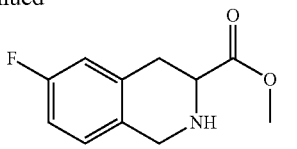

To a suspension of 6-fluoro-1,2,3,4-tetrahydroisoquinoline-3-carboxylic acid in methanol (500 mL) was added SOCl$_2$ (50 mL). The reaction mixture was then refluxed for 1 h until LC-MS indicated the completion of the reaction. The mixture was concentrated, and the resulting residue was dissolved in a mixture of EtOAc (1 L) and sat. sodium bicarbonate solution (500 mL). The organic layer was separated, washed with water and brine, dried over Na$_2$SO$_4$, and concentrated under reduced pressure to give 6-fluoro-1,2,3,4-tetrahydro-isoquinoline-3-carboxylic acid methyl ester as an oil (92 g). LRMS (M+H$^+$) m/z 210.1.

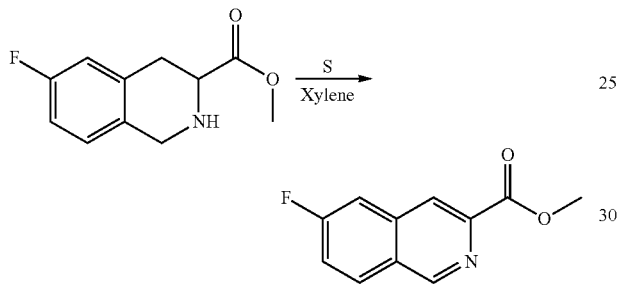

A mixture of 6-fluoro-1,2,3,4-tetrahydro-isoquinoline-3-carboxylic acid methyl ester (92 g) and sulfur (42 g, 3 equiv.) in xylene (5 L) was stirred at 150° C. for 16 h. The reaction mixture was concentrated, and the resulting residue was dissolved in EtOAc, which was washed with water and brine, dried over Na$_2$SO$_4$, and concentrated under reduced pressure to give a crude mixture. Purification by flash column chromatography (hexanes/EtOAc, gradient 50%-100%) gave 6-fluoro-isoquinoline-3-carboxylic acid methyl ester as a light yellow solid (27 g, 24% for 3 steps). LRMS (M+H$^+$) m/z 206.1.

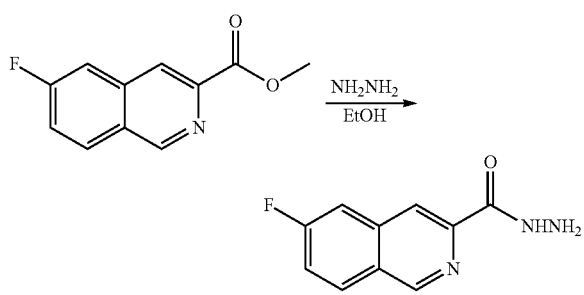

A solution of 6-fluoro-isoquinoline-3-carboxylic acid methyl ester (27 g) and hydrazine (42 g, 10 equiv.) in ethanol (500 mL) was refluxed for 2 h. The reaction mixture was concentrated under high vacuum to remove hydrazine, and the resulting residue was triturated with ethanol (100 mL) to give 6-fluoro-isoquinoline-3-carboxylic acid hydrazide as a light yellow solid (22.8 g, 84%). LRMS (M+H$^+$) m/z 206.1.

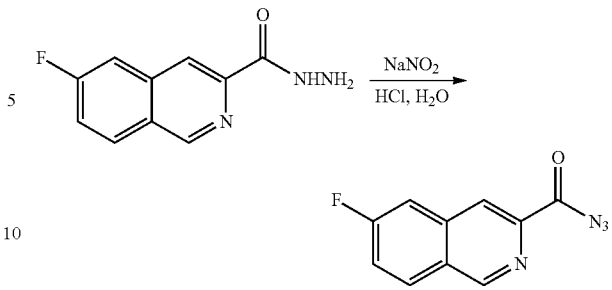

To a suspension of 6-fluoro-isoquinoline-3-carboxylic acid hydrazide in HCl (1 N, 50 mL) and water (1 L) was added a solution of NaNO$_2$ (11.4 g, 170 mmol, 1.5 eq) in water (100 mL) dropwise at 0-5° C. The mixture was stirred at 0-5° C. for 1 h. Another solution of NaNO$_2$ (5.7 g, 85 mmol, 0.5 equiv.) in water (30 mL) was added and the reaction was stirred at 0-5° C. for 3 h until LC-MS indicated the completion of the reaction. The precipitate was filtered, washed with cold water, and dried under high vacuum to give 6-fluoro-isoquinoline-3-carbonyl azide as a light yellow solid (21.3 g, 89%). LRMS (M+H$^+$) m/z 217.1.

Example 2

Preparation of benzo[d]thiazole-2-carbonyl azide

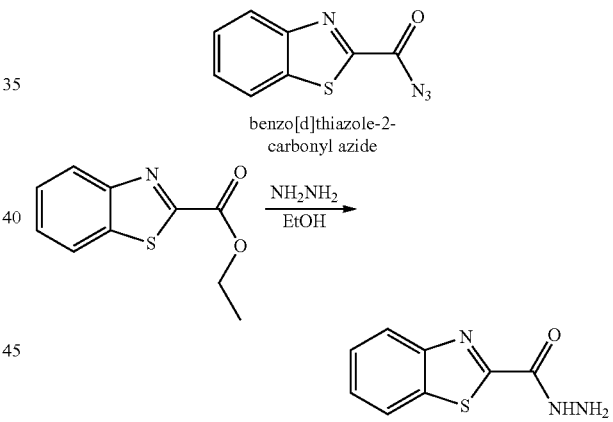

To a solution of ethyl benzo[d]thiazole-2-carboxylate (10 g, 48.25 mmol) in ethanol (200 mL) was added hydrazine (15.5 g, 482.5 mmol). The reaction mixture was stirred at RT for 30 min and concentrated under high vacuum to remove hydrazine. The resulting residue was triturated with ethanol (40 mL) to give benzo[d]thiazole-2-carbohydrazide (9.3 g, quant.) LRMS (M+H$^+$) m/z 194.0.

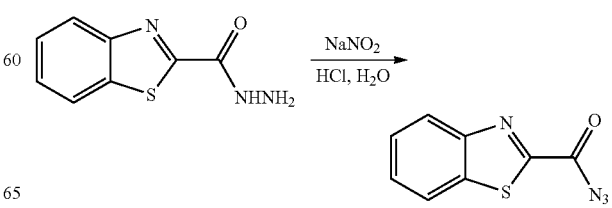

To a suspension of benzo[d]thiazole-2-carbohydrazide (9.3 g, 48.2 mmol) in aqueous HCl (1 N, 75 mL, 75 mmol) and water (200 mL) was added a solution of NaNO$_2$ (6.9 g, 100 mmol) in water (50 mL) dropwise at 0-5° C. The mixture was stirred at 0-5° C. for 2 h and RT for 2 h. The precipitate was filtered, washed with cold water, and dried under high vacuum to give benzo[d]thiazole-2-carbonyl azide (9.0 g, 92%). LRMS (M+H$^+$) m/z 205.1.

Example 3

Preparation of isoquinoline-3-carbonyl azide

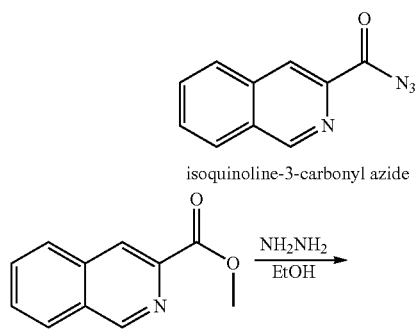

isoquinoline-3-carbonyl azide

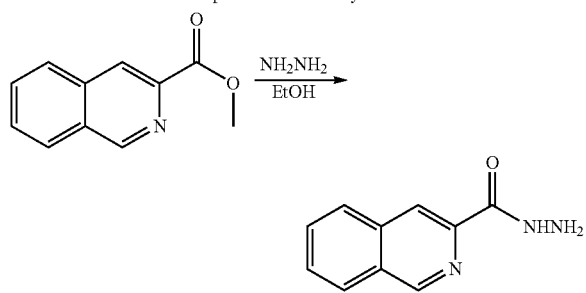

To a solution of methyl isoquinoline-3-carboxylate (10 g, 53.42 mmol) in ethanol (100 mL) was added hydrazine (17.1 g). The reaction mixture was refluxed for 30 min and concentrated under high vacuum to remove hydrazine. The resulting residue was triturated with ethanol (20 mL) to give isoquinoline-3-carbohydrazide (8.6 g, 86%). LRMS (M+H$^+$) m/z 188.1.

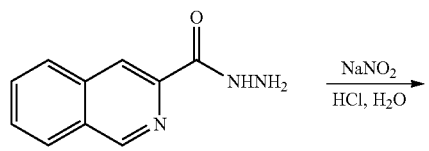

To a suspension of isoquinoline-3-carbohydrazide (43 g, 0.23 mol) in aqueous HCl (1 N, 230 mL) and water (1 L) was added a solution of NaNO$_2$ (23.8 g, 0.34 mol) in water (200 mL) dropwise at 0-5° C. The mixture was stirred at 0-5° C. for 4 h. LC-MS indicated the reaction was not completed. Another solution of NaNO$_2$ (11.9 g, 0.115 mol) in water (60 mL) was added and the reaction mixture was stirred at 0-5° C. until LC-MS indicated the completion of the reaction. The precipitate was filtered, washed with cold water, and dried under high vacuum to give isoquinoline-3-carbonyl azide (42.7 g, 93.8%) as a white solid. LRMS (M+H$^+$) m/z 199.2.

Example 4

Preparation of 5-(3-fluorophenyl)isoxazole-3-carbonyl azide

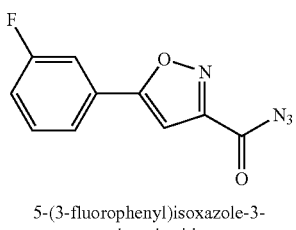

5-(3-fluorophenyl)isoxazole-3-carbonyl azide

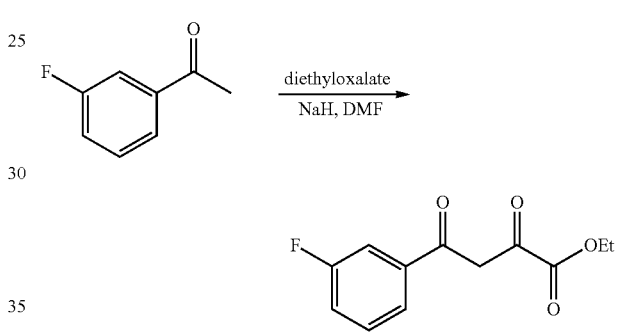

To a solution of 3-fluoro-acetophenone (27.6 g, 200 mmol, 1.0 equiv.) in DMF (400 mL) at 0° C. was added NaH (8.8 g, 220 mmol, 1.1 equiv.) in two portions over 10 min, followed by diethyloxalate (29.8 mL, 220 mmol, 1.1 equiv.) in 20 min. The mixture was stirred for 15 min, then poured to a mixture of ice and saturated NH$_4$Cl solution (500 mL). The mixture was extracted with EtOAc (400 mL×3). The organic layers were combined, dried over MgSO$_4$, and concentrated. The residue was purified by flash column chromatography (hexane/EtOAc, gradient 0% to 40%) to give ethyl 4-(3-fluorophenyl)-2,4-dioxobutanoate as a brownish solid (30 g, 63%). LRMS (M+H$^+$) m/z 239.0.

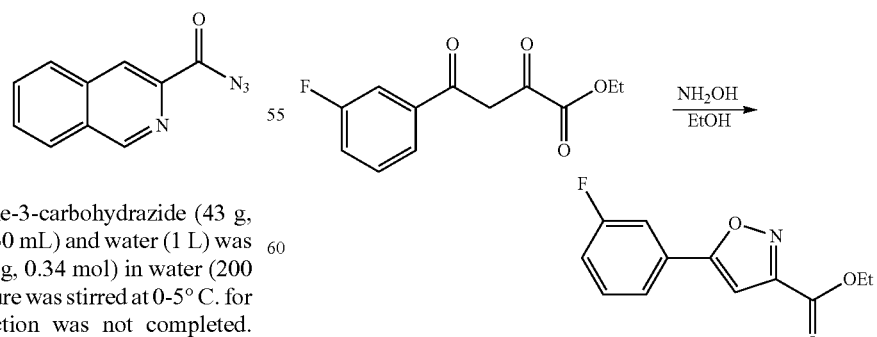

To a solution of ethyl 4-(3-fluorophenyl)-2,4-dioxobutanoate (30.0 g, 126 mmol) in EtOH (300 mL) was added hydroxylamine hydrogen chloride (17 g, 252 mmol). The mixture was stirred at 80° C. for 1 h. The mixture was concentrated to 80 mL and diluted with H₂O (100 mL). The precipitate was filtered and washed with H₂O to give ethyl 5-(3-fluorophenyl)isoxazole-3-carboxylate (25.8 g, 87%). LRMS (M+H⁺) m/z 236.0.

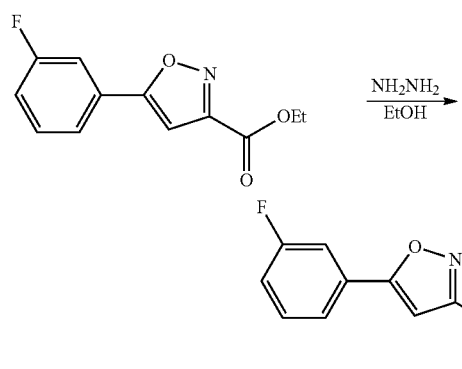

To a solution of ethyl 5-(3-fluorophenyl)isoxazole-3-carboxylate (25.8 g, 110 mmol, 1.0 equiv.) in EtOH (300 mL), was added hydrazine (10.5 mL, 330 mmol, 3.0 equiv.). The mixture was stirred at 80° C. for 1 h and then cooled to RT The precipitate was filtered, washed with H₂O, and dried in vacuum to give 5-(3-fluorophenyl)isoxazole-3-carbohydrazide (20 g). The filtrate was concentrated and the resulting residue was purified on RP-HPLC using a mixture of acetonitrile and H₂O to give desired product (2.5 g). LRMS (M+H⁺) m/z 222.0.

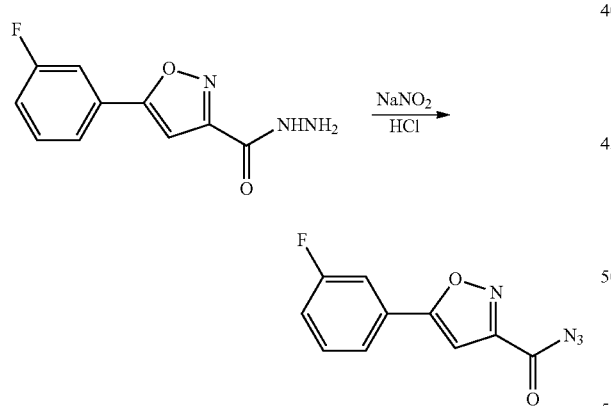

To a suspension of 5-(3-fluorophenyl)isoxazole-3-carbohydrazide (22.5 g, 101 mmol) in H₂O (2000 mL) and HCl (2 N, 101 mL, 2.0 equiv.) at 0° C. was added a solution of sodium nitrite (13.9 g, 202 mmol, 2.0 equiv.) in H₂O (100 mL). The suspension was stirred at RT for 16 h. The precipitate was filtered and washed with H₂O. The solid was dried under high vacuum to give 5-(3-fluorophenyl)isoxazole-3-carbonyl azide as a yellow solid (20 g, 85%). LRMS (M+H⁺) m/z 179.0.

Example 5

Preparation of 3-(3-fluorophenyl)isoxazole-5-carbonyl azide

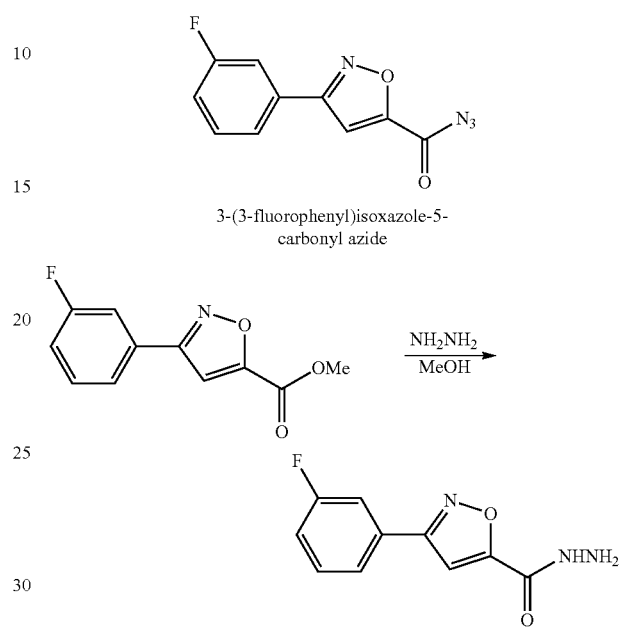

3-(3-fluorophenyl)isoxazole-5-carbonyl azide

A mixture of methyl 3-(3-fluorophenyl)isoxazole-5-carboxylate (prepared according to the literature method: T. T. Dang, U. Albrecht and P. Langer, *Preparation* 2006, No. 15, 2515-252; or treatment of 3-(3-fluorophenyl)isoxazole-5-carboxylic acid with thionyl chloride and methanol) (5.55 g, 25 mmol, 1.0 equiv.), hydrazine (960 mg, 30 mmol) and MeOH (100 mL) was refluxed for 1 h and concentrated. The residue was washed with dichloromethane and dried in vacuum to give 3-(3-fluorophenyl)isoxazole-5-carbohydrazide (5.6 g, quant.). LRMS (M+H⁺) m/z 222.0

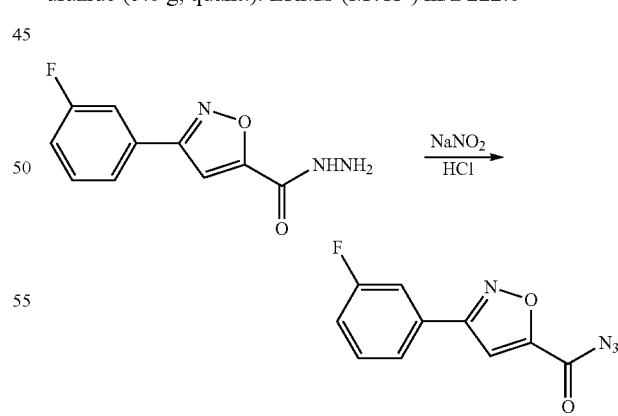

To a suspension of hydrazide (4.33 g, 19.6 mmol, 1.0 equiv.) in H₂O (80 mL) and HCl (1 N, 39.2 mL, 2.0 equiv.) at 0° C. was added a solution of sodium nitrite (2.03 g, 29.4 mmol, 1.5 equiv.) in H₂O (10 mL). The suspension was stirred at RT for 16 h. Then the precipitate was filtered and washed with H₂O until PH=7. The precipitate was dried under high vacuum, which afforded 3-(3-fluorophenyl)isoxazole-5-carbonyl azide as an off white solid (4.0 g, 88%).

Example 6

Preparation of 3-phenylisoxazole-5-carbonyl azide

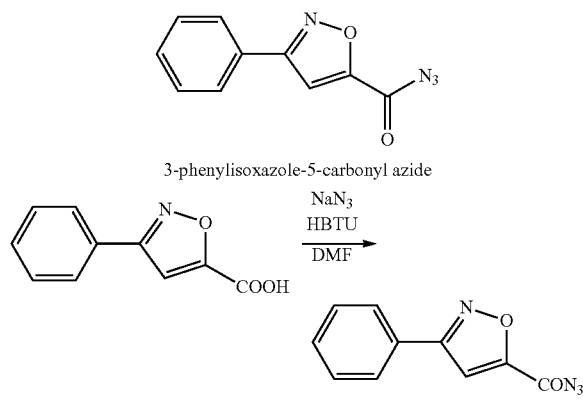

To a solution of 3-phenylisoxazole-5-carboxylic acid (1.0 g, 5 mmol, 1.0 equiv.) in DMF (20 mL) and THF (20 mL), was added HBTU (2.28 g, 6 mmol, 1.2 equiv.), followed by sodium azide (0.65 g, 10 mmol, 2.0 equiv.) and DIEA (2.6 mL, 15 mmol, 3.0 equiv.). The mixture was stirred at RT for 30 min, concentrated, followed by adding of $H_2O$ (40 mL). The precipitate was filtered, washed with $H_2O$, and dried in vacuo to give 3-phenylisoxazole-5-carbonyl azide (0.65 g, 60%). LRMS (M−18+H$^+$) m/z 187.1.

Example 7

Preparation of (2-chloro-3-fluorophenyl)methanamine hydrochloride

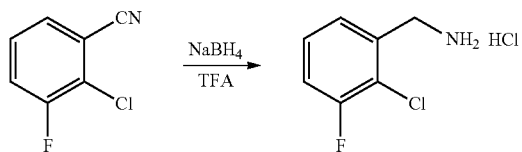 [SMILES: N#Cc1cccc(F)c1Cl ; "NaBH4" ; NCc1cccc(F)c1Cl ; Cl]

To a solution of NaBH$_4$ (24.3 g, 0.643 mol) in THF (400 mL) was added TFA (48 mL, 0.643 mol) slowly at 0° C. After the addition was completed, the mixture was stirred at 0° C. for about 20 min. 2-Chloro-3-fluorobenzonitrile (20 g, 0.128 mol) in THF (100 mL) was then added slowly into the mixture at 0° C. The mixture was stirred from 0° C. to RT until no starting material was observed by LCMS. Half of the solvent was removed, then 10% HCl (250 mL) was added slowly into the residue at 0° C. The mixture was warmed up and heated to reflux until no boron complex was observed by LCMS. The mixture was extracted by diethyl ether. The aqueous solution was basified to pH 8-10 using NaOH (3 N), extracted with EtOAc. The organic layers were combined and concentrated to about 300 mL. HCl (4 N, 50 mL) was added slowly into the resulting solution. The white solid was precipitated and collected by filtration to give (2-chloro-3-fluorophenyl)methanamine hydrochloride (21 g, 84%). LRMS (M+H$^+$) m/z 160.1.

Example 8

Preparation of 4-nitrophenyl 2-chloro-3-fluorobenzylcarbamate

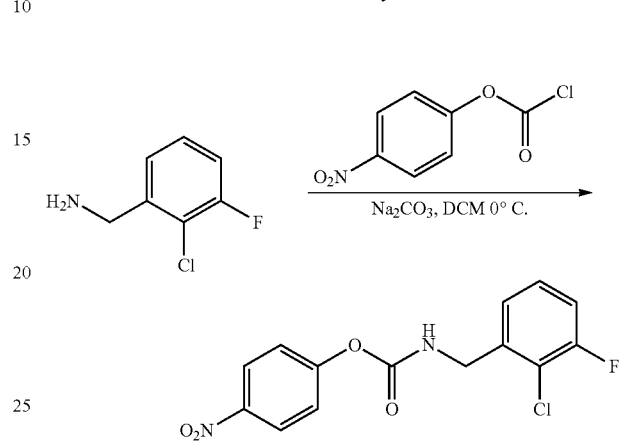

A 5 liter 3-neck RBF was charged with 4-nitrophenylchloroformate (126.3 g, 627 mmol), DCM (3000 mL), under $N_2$ atm and chilled in a 0° C. ice bath. A solution of 2-chloro,3-fluorobenzylamine (100.0 g, 627 mmol) followed by solid Sodium Carbonate (155.0 g, 1460 mmol) was quickly added in one portion into the reaction solution. The reaction mixture was stirred at 0° C. for 1 h and an LC/MS was taken to confirm consumption of the starting material and presence of the nitrophenyl intermediate. The reaction mixture was allowed to warm to room temperature and stirred for approximately 2 h. The mixture was filtered, and the filtrate was concentrated to give a white solid. The solid was redissolved with 600 ml of DCM and heated to 40° C. until all of the material went into solution. The solution was chilled in a 0° C. ice bath to form crystals. The crystals were collected and dried under vacuum to give 4-nitrophenyl 2-chloro-3-fluorobenzylcarbamate. (150 g, 75%).

Example 9

Preparation of (2S)-2-((2-chloro-3-fluorobenzyl)(methyl)amino)-4,5-dihydroxypentyl 6-fluoroisoquinolin-3-ylcarbamate

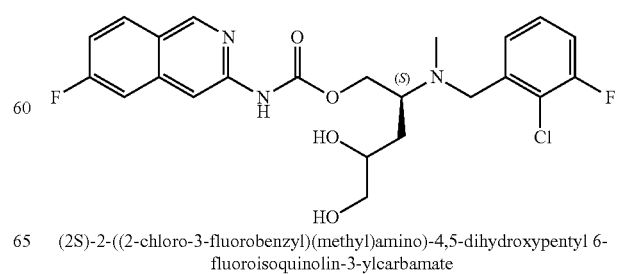

(2S)-2-((2-chloro-3-fluorobenzyl)(methyl)amino)-4,5-dihydroxypentyl 6-fluoroisoquinolin-3-ylcarbamate

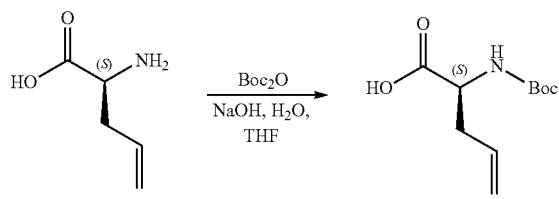

To a solution of (S)-2-aminopent-4-enoic acid (100 g, 0.87 mol), NaOH (2 N, 455 mL) and water (225 mL) in THF (910 mL) was added Boc₂O (199 g, 0.91 mol). The reaction mixture was stirred at RT for 30 h. The reaction mixture was concentrated to remove most of THF. The aqueous solution was washed with 250 mL of EtOAc and acidified to pH3-4 at 0° C. using HCl (2 N, ~260 mL). The mixture was extracted with EtOAc (350 mL×3), washed with water and brine, dried with Na₂SO₄, and concentrated to give (S)-2-(tert-butoxycarbonylamino)pent-4-enoic acid (185 g), which was used without further purification. LRMS (M+Na⁺) m/z 238.2.

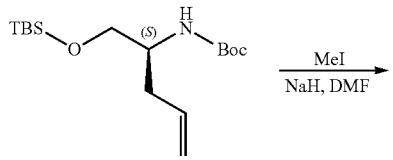

To a solution of (S)-2-(tert-butoxycarbonylamino)pent-4-enoic acid (166 g, 0.77 mol) and Et₃N (214 mL) in THF (2.5 L) was added methyl chloroformate (71.2 mL, 0.93 mol) at 0-5° C. The reaction mixture was stirred for 15 min and filtered to remove TEA salt. To the filtrate was added a solution of NaBH₄ (60 g, 1.54 mol) in a small amount of water at 0-5° C. The reaction was stirred at RT for 1 h and quenched with saturated NH₄Cl solution. The reaction mixture was concentrated to remove most of THF and extracted with EtOAc (700 mL×3). The organic layers were washed with water, NaOH (1 N) and brine, dried over Na₂SO₄, and concentrated to give (S)-tert-butyl 1-hydroxypent-4-en-2-ylcarbamate (165 g), which was used without further purification. LRMS (M+H⁺) m/z 202.1.

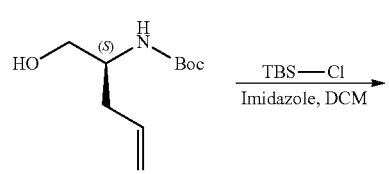

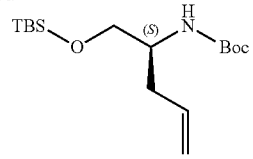

To a solution of (S)-tert-butyl 1-hydroxypent-4-en-2-ylcarbamate (165 g, 0.82 mol) and imidazole (72.5 g, 1.07 mol) in DCM (3 L) was added TBS-Cl (135.4 g, 0.9 mol). The reaction was stirred at RT overnight and filtered. The filtrate was concentrates. The resulting residue was dissolved in EtOAc (L) and washed with water and brine. The organic layer was dried over Na₂SO₄ and concentrated to give (S)-tert-butyl 1-(tert-butyldimethylsilyloxy)pent-4-en-2-ylcarbamate (222.0 g), which was used in the next step without further purification. LRMS (M+H⁺) m/z 316.2.

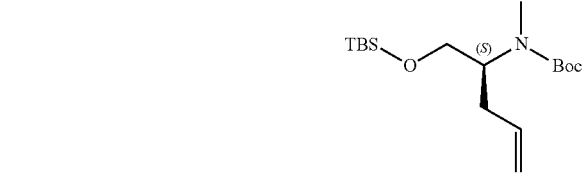

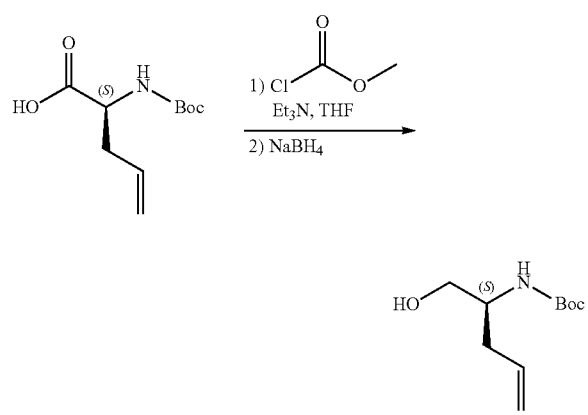

To a solution of (S)-tert-butyl 1-(tert-butyldimethylsilyloxy)pent-4-en-2-ylcarbamate (95 g, 0.3 mol) and MeI (46.7 mL, 0.75 mol) in DMF (500 mL) was added sodium hydride (60%, 18 g, 0.45 mol) at 0° C. The reaction was stirred at 0° C. for 3 h and LC-MS showed the reaction was complete. The reaction was quenched with saturated NH₄Cl solution and filtered. The filtrate was concentrated to remove most of DMF and the residue was dissolved in EtOAc (1.5 L). The organic layer was washed with water and brine, dried over Na₂SO₄. The above steps were repeated with another 127 g of (S)-tert-butyl 1-(tert-butyldimethylsilyloxy)pent-4-en-2-ylcarbamate. The organic layers were combined and concentrated. The resulting residue was purified on silica gel column using a mixture of hexanes and EtOAc to give (S)-tert-butyl 1-(tert-butyldimethylsilyloxy)pent-4-en-2-yl(methyl)carbamate (120 g, 40% for 4 steps). LRMS (M+H⁺) m/z 230.2.

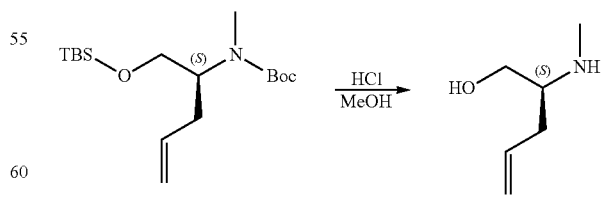

To a solution of (S)-tert-butyl 1-(tert-butyldimethylsilyloxy)pent-4-en-2-yl(methyl)carbamate (3.4 g, 10.3 mmol) in methanol (10 mL) was added HCl (4.0 M in 1,4-dioxane, 25 mL, 0.10 mol). The resulting solution was stirred for 2 h. The solvent was removed, and the remaining residue was dried under vacuum to give (S)-2-(methylamino)pent-4-en-1-ol as a HCl salt, which was used without further purification. LRMS (M+H⁺) m/z 116.2.

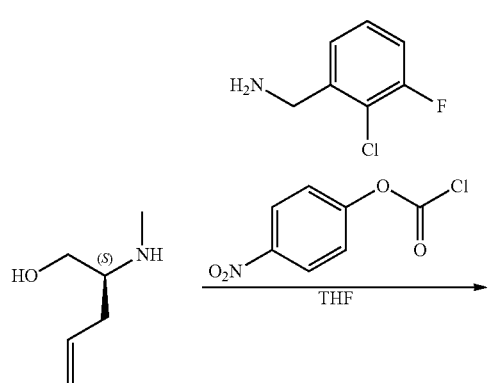

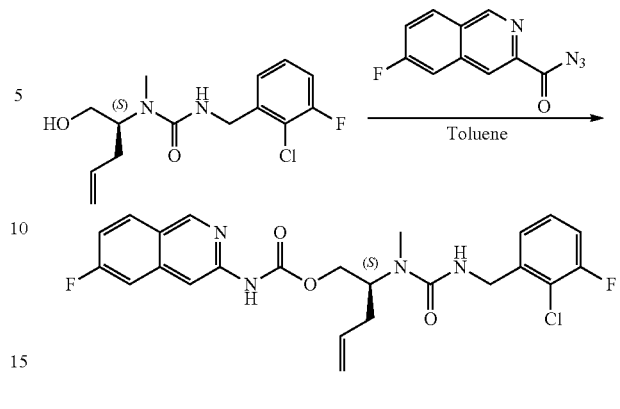

To a solution of (S)-3-(2-chloro-3-fluorobenzyl)-1-(1-hydroxypent-4-en-2-yl)-1-methylurea (2.0 g, 6.65 mmol) and toluene (50 mL) was added 6-fluoro-isoquinoline-3-carbonyl azide (1.58 g, 7.32 mmol). The resulting solution was stirred at 100° C. for 1 h. The solvent was removed, and the remaining residue was purified on silica gel column using a mixture of DCM and MeOH to give (S)-2-(3-(2-chloro-3-fluorobenzyl)-1-methylureido)pent-4-enyl 6-fluoroisoquinolin-3-ylcarbamate (2.50 g, 77%). LRMS (M+H⁺) m/z 489.1.

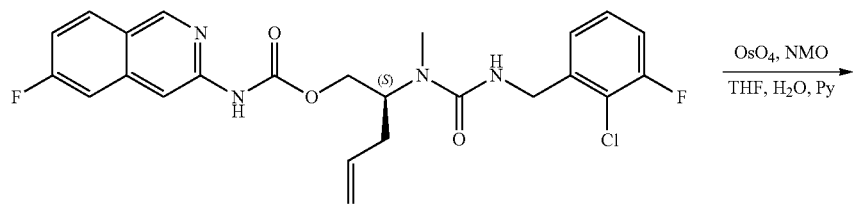

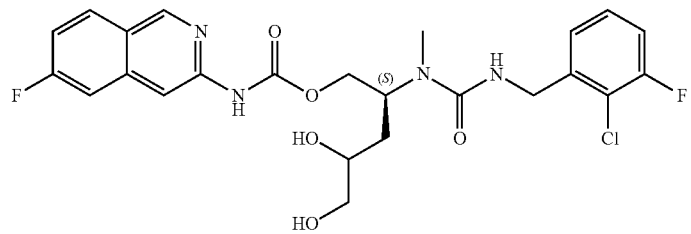

To a solution of 4-nitrophenylchloroformate 8 (2.28 g, 11.3 mmol) in THF (10 mL) was added a solution of 2-chloro-3-fluorobenzylamine hydrochloride (2.22 g, 11.3 mmol) and DIEA (5.38 mL, 30.9 mmol) in THF (10 mL). The resulting solution was stirred at RT for 20 min. The reaction solution was added into a solution of (S)-2-(methylamino)pent-4-en-1-ol hydrochloride (10.3 mmol), DIEA (5.38 mL, 30.9 mmol) in THF (100 mL). The resulting solution was stirred at RT for 1 h. The solvent was removed, and the resulting residue was purified on silica gel column using a mixture of DCM and MeOH to give (S)-3-(2-chloro-3-fluorobenzyl)-1-(1-hydroxypent-4-en-2-yl)-1-methylurea (2.56 g, 82%) as a white solid. LRMS (M+H⁺) m/z 301.2.

To a solution of (S)-2-(3-(2-chloro-3-fluorobenzyl)-1-methylureido)pent-4-enyl 6-fluoroisoquinolin-3-ylcarbamate (0.9 g, 1.84 mmol) in THF (24 mL) and water (6 mL) were added 4-methylmorpholine N-oxide (1.08 g, 9.2 mmol), osmium tetroxide (46.8 mg, 0.184 mmol) and pyridine (15 uL, 0.184 mmol). The resulting solution was stirred for 1 h. The reaction was monitored with LC/MS and additional osmium tetroxide (46.8 mg, 0.184 mmol) was added. The resulting solution was stirred for 1 h. Sodium sulfite (5 g) and sodium bicarbonate (5 g) were added into the reaction. The resulting mixture was stirred for 1 h. The solid was then removed by filtration. The filtrate was diluted with ethyl acetate (100 mL) and washed with saturated sodium bicarbonate. The organic layer was concentrated, and the resulting residue was purified on silica gel column using a mixture of DCM and MeOH to give (2S)-2-(3-(2-chloro-3-fluorobenzyl)-1-methylureido)-4,5-dihydroxypentyl 6-fluoroisoquinolin-3-ylcarbamate (0.9 g, 93%). LRMS (M+H⁺) m/z 523.2.

Example 10

Preparation of (2S)-2-((2-chloro-3-fluorobenzyl)(methyl)amino)-4-hydroxy-5-(phosphonooxy)pentyl 6-fluoroisoquinolin-3-ylcarbamate 2.0 equiv.) in anhydrous DCM (10 mL) was added dimethyl chlorophorophosphate (0.103 mL, 0.956 mmol, 2.0 equiv.) at RT. After the reaction mixture was stirred at RT for 30 min, an additional portion of dimethyl chlorophorophosphate (0.103 mL, 0.956 mmol, 2.0 equiv.) and DIEA (0.167 mL, 0.956 mmol, 2 equiv.) were added. The reaction was quenched with MeOH (5 mL). The solvent was removed and the resulting residue was dissolved in EtOAc (100 mL). The organic layer was washed with saturated NaHCO₃, water and brine, concentrated, and the resulting residue was purified on RP-HPLC

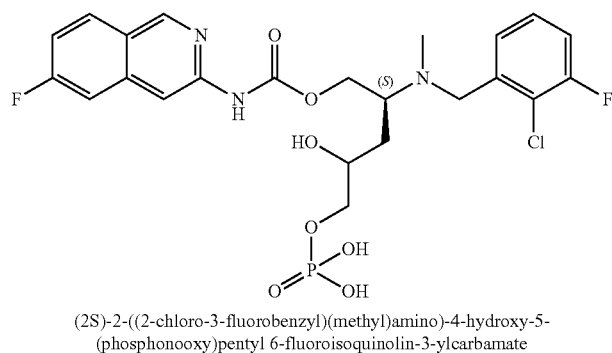

(2S)-2-((2-chloro-3-fluorobenzyl)(methyl)amino)-4-hydroxy-5-(phosphonooxy)pentyl 6-fluoroisoquinolin-3-ylcarbamate

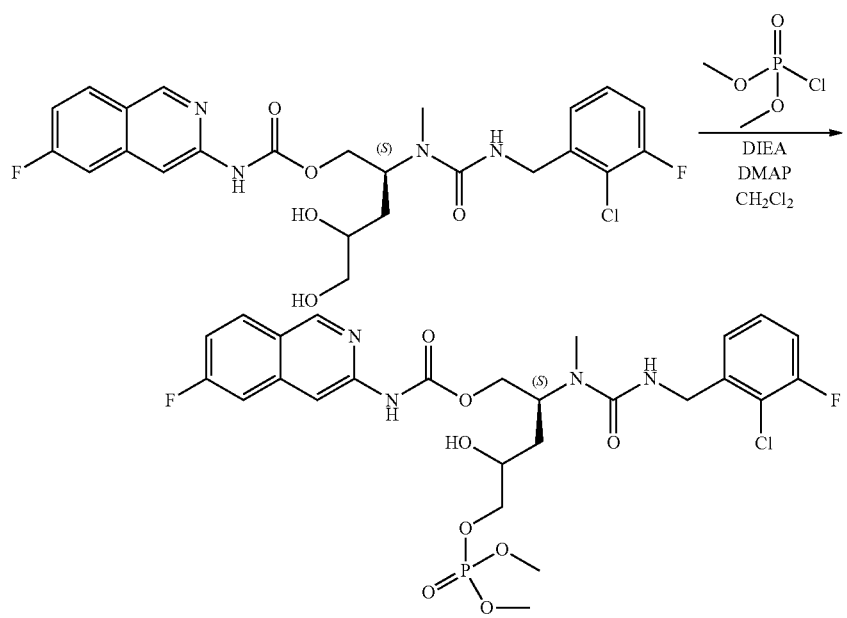

To a solution of (2S)-2-(3-(2-chloro-3-fluorobenzyl)-1-methylureido)-4,5-dihydroxypentyl 6-fluoroisoquinolin-3-ylcarbamate (0.25 g, 0.478 mmol, 1.0 equiv.), DIEA (0.416 mL, 2.39 mmol, 5 equiv.) and DMAP (0.117 g, 0.956 mmol, using a mixture of acetonitrile and H₂O to give (2S)-2-(3-(2-chloro-3-fluorobenzyl)-1-methylureido)-5-(dimethoxyphosphoryloxy)-4-hydroxypentyl 6-fluoroisoquinolin-3-ylcarbamate (150 mg, 50%). LRMS (M+H⁺) m/z 631.2.

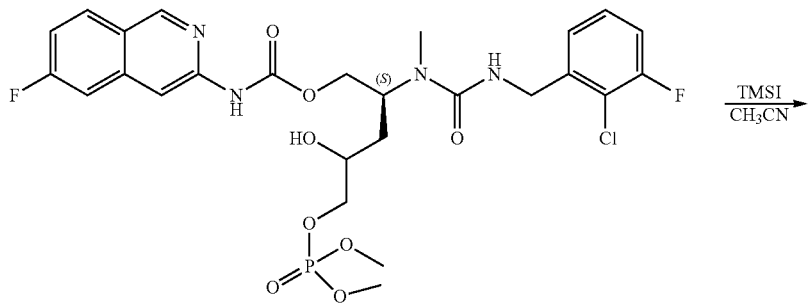

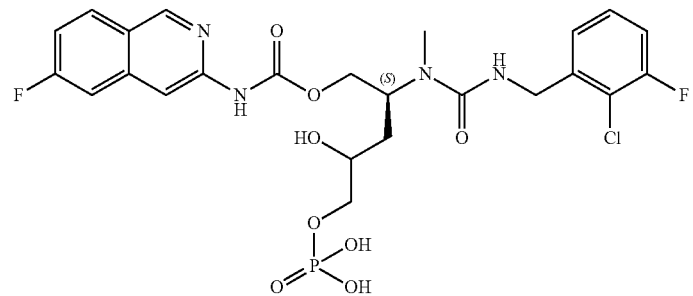

To a solution of (2S)-2-(3-(2-chloro-3-fluorobenzyl)-1-methylureido)-5-(dimethoxyphosphoryloxy)-4-hydroxypentyl 6-fluoroisoquinolin-3-ylcarbamate (0.15 g, 0.238 mmol, 1.0 equiv.) in acetonitrile (2 mL) was added TMSI (0.162 mL, 1.19 mmol, 5.0 equiv.) at RT After stirred at RT for 10 min, the reaction was quenched with MeOH. The solvent was removed, and the resulting residue was purified on RP-HPLC using a mixture of acetonitrile and H₂O (0.1% TFA buffer) to give the desired product. The product was dissolved in a mixture of methanol and water (2:1), and HCl (4 M in 1,4-dioxane, 2 mL) was added. The solvent was removed.

This procedure was repeated to give (2S)-2-(3-(2-chloro-3-fluorobenzyl)-1-methylureido)-4-hydroxy-5-(phosphonooxy)pentyl 6-fluoroisoquinolin-3-ylcarbamate (98 mg, 64%) as a HCl salt. LRMS (M+H⁺) m/z 603.0.

Example 11

Preparation of (S)-2-(3-(2-chloro-3-fluorobenzyl)-1-methylureido)-5-oxo-5-(piperazin-1-yl)pentyl 6-fluoroisoquinolin-3-ylcarbamate

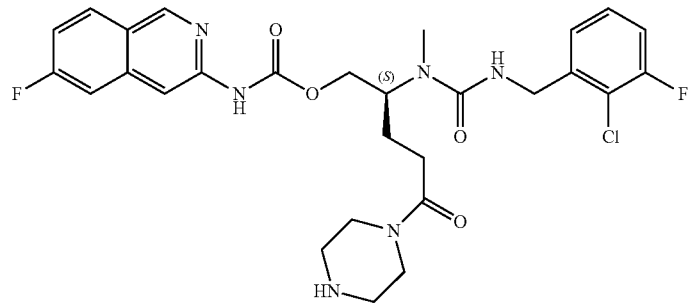

(S)-2-(3-(2-chloro-3-fluorobenzyl)-1-methylureido)-5-oxo-5-(piperazin-1-yl)pentyl 6-fluoroisoquinolin-3-ylcarbamate

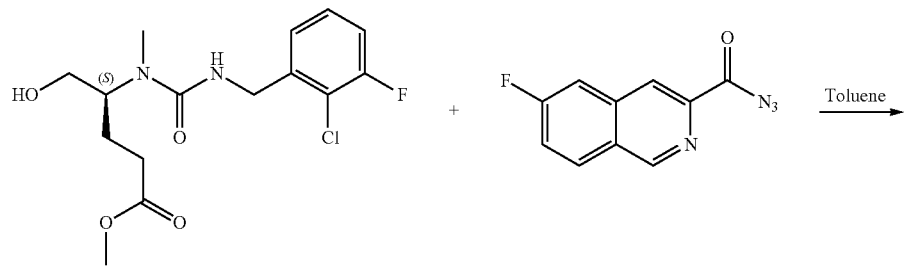

-continued

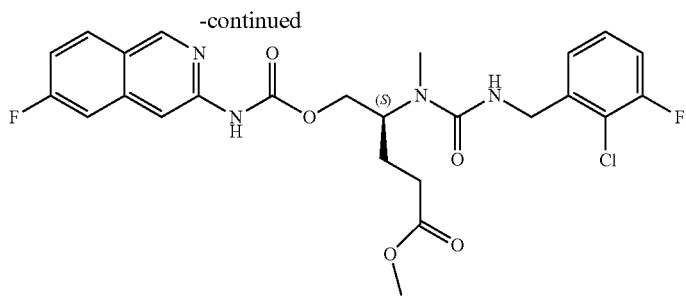

To a solution of (S)-methyl 4-(3-(2-chloro-3-fluorobenzyl)-1-methylureido)-5-hydroxypentanoate (1.06 g, 3.06 mmol, 1.0 equiv) in toluene (12 mL) were added 6-fluoroisoquinoline-3-carbonyl azide (661 mg, 3.06 mmol, 1.0 equiv). The reaction mixture was heated under 100° C. for 1 h and purified on RP-HPLC using a mixture of acetonitrile and H$_2$O to give (S)-methyl 4-(3-(2-chloro-3-fluorobenzyl)-1-methylureido)-5-(6-fluoroisoquinolin-3-ylcarbamoyloxy)pentanoate (400 mg). LRMS (M+H$^+$) m/z 535.2.

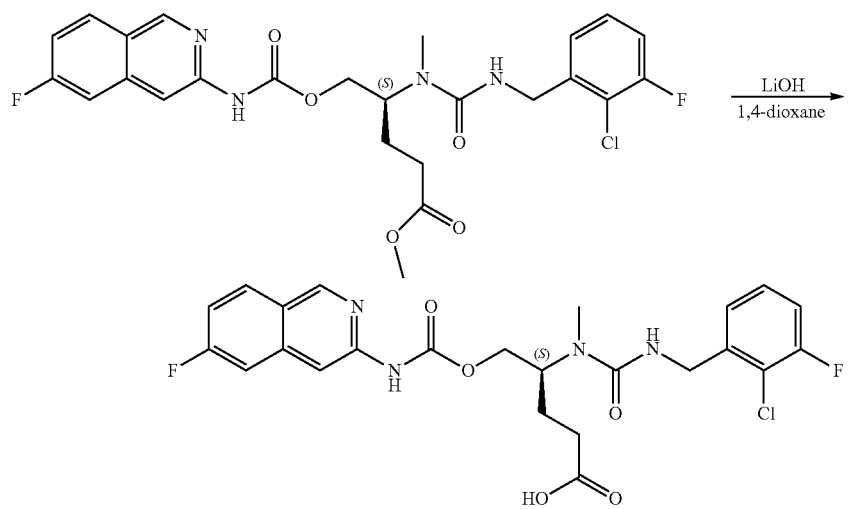

To a solution of (S)-methyl 4-(3-(2-chloro-3-fluorobenzyl)-1-methylureido)-5-(6-fluoroisoquinolin-3-ylcarbamoyloxy)pentanoate (400 mg, 0.748 mmol, 1.0 equiv.) in 1,4-dioxane (1 mL) was added LiOH (2 N, 1.5 mL, 2.99 mmol, 4.0 equiv.). The reaction mixture was stirred at RT for 1 h., then was acidified to pH 1-3 with HCl (1 N). The mixture was diluted in EtOAc. The organic layer was washed by H$_2$O and brine, and concentrated. The resulting residue was purified on RP-HPLC using a mixture of acetonitrile and H$_2$O to give (S)-4-(3-(2-chloro-3-fluorobenzyl)-1-methylureido)-5-(6-fluoroisoquinolin-3-ylcarbamoyloxy)pentanoic acid (340 mg, 87%). LRMS (M+H$^+$) m/z 521.2.

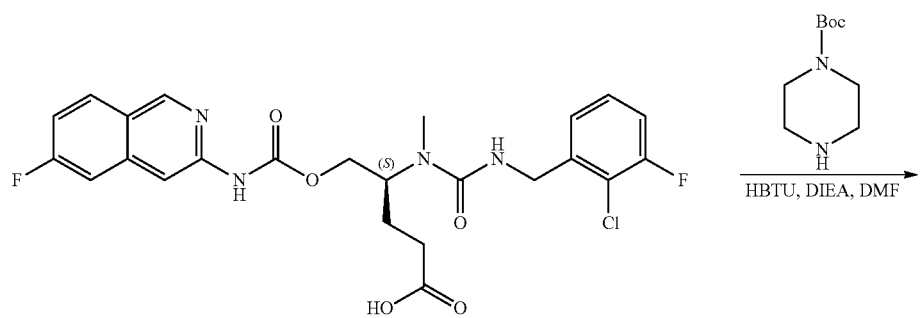

-continued

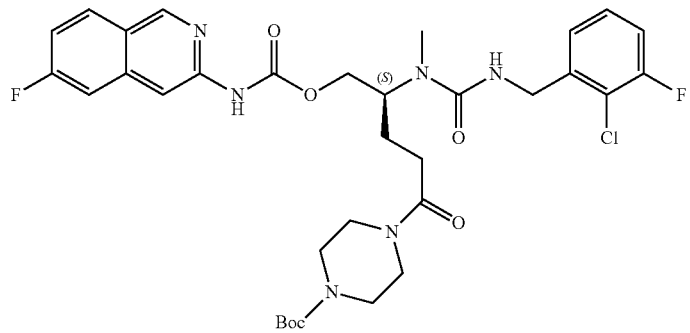

To a solution of (S)-4-(3-(2-chloro-3-fluorobenzyl)-1-methylureido)-5-(6-fluoroisoquinolin-3-ylcarbamoyloxy)pentanoic acid (83 mg, 0.160 mmol, 1.0 equiv) in DMF (1 mL) were added HBTU (72 mg, 0.191 mmol, 1.2 equiv.), tert-butyl-1-piperazine carboxylate (59 mg, 0.320 mmol, 2.0 equiv.) and DIEA (83 µL, 0.480 mmol, 3.0 equiv.). The reaction mixture was stirred 1 h at RT and purified on RP-HPLC using a mixture of acetonitrile and H$_2$O to give (S)-tert-butyl 4-(4-(3-(2-chloro-3-fluorobenzyl)-1-methylureido)-5-(6-fluoroisoquinolin-3-ylcarbamoyloxy)pentanoyl)piperazine-1-carboxylate (61 mg, 55%). LRMS (M+H$^+$) m/z 689.3.

To a solution of (S)-tert-butyl 4-(4-(3-(2-chloro-3-fluorobenzyl)-1-methylureido)-5-(6-fluoroisoquinolin-3-ylcarbamoyloxy)pentanoyl)piperazine-1-carboxylate (56 mg, 0.081 mmol, 1.0 equiv.) in MeOH (1 mL) was added HCl (4 M in 1,4-dioxane, 1 mL). The mixture was stirred overnight and concentrated. The resulting residue was purified on RP-HPLC using a mixture of acetonitrile and H$_2$O. The fractions containing the product were combined and concentrated. The resulting solid was dissolved in EtOAc. The organic solution was washed with saturated NaHCO$_3$. HCl (4 N) was added into the organic solution. The solution was then concentrated to give (S)-2-(3-(2-chloro-3-fluorobenzyl)-1-methylureido)-5-oxo-5-(piperazin-1-yl)pentyl 6-fluoroisoquinolin-3-ylcarbamate (35 mg, 65%) as a HCl salt. LRMS (M+H$^+$) m/z 589.2.

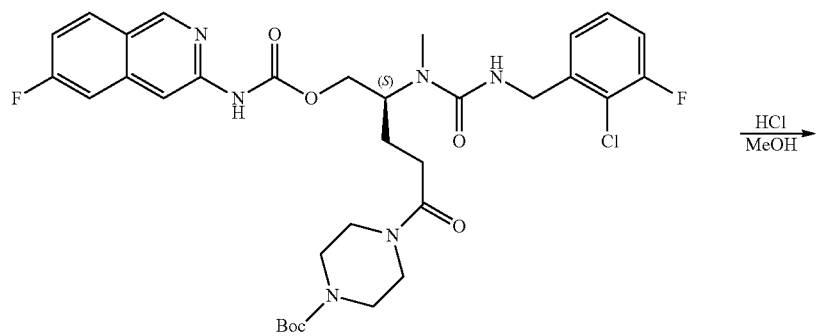

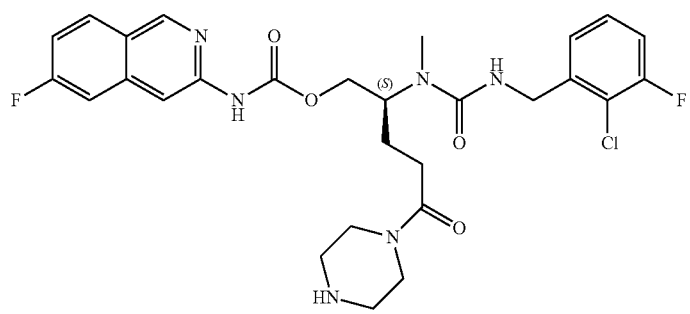

Example 12

Preparation of (S)-2-(3-(2-chloro-4-fluorobenzyl)-1-methylureido)-6-hydroxyhexyl isoquinolin-3-ylcarbamate

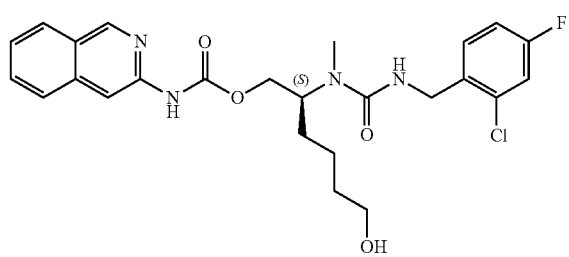

(S)-2-(3-(2-chloro-4-fluorobenzyl)-1-methylureido)-6-hydroxyhexyl isoquinolin-3-ylcarbamate

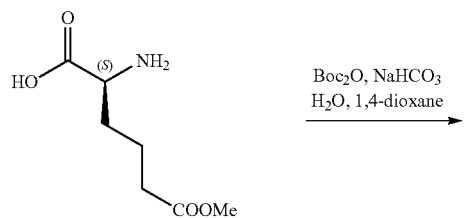

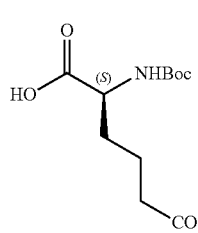

To a solution of (S)-2-amino-6-methoxy-6-oxohexanoic acid (20 g, 95 mmol) in $H_2O$ (50 mL) and 1,4-dioxane (150 mL) was added a solution of $NaHCO_3$ (20 g, 238 mmol, 2.5 equiv.) in $H_2O$ (50 mL) dropwise at 0° C. $Boc_2O$ (25 g, 114 mmol, 1.2 equiv.) was added in 3 portions. The mixture was warmed up to RT and stirred for 1 h. The organic solvent was removed. The aqueous solution was washed with ether (200 mL). The solution was cooled down to 0° C., adjusted to pH 3-4 with HCl (1 N). The solution was extracted with EtOAc (300 mL×2). The organic layers were combined, dried over $MgSO_4$, and concentrated to give (S)-2-(tert-butoxycarbonylamino)-6-methoxy-6-oxohexanoic acid (23.5 g, 90%). LRMS (M-Boc+$H^+$) m/z 176.1.

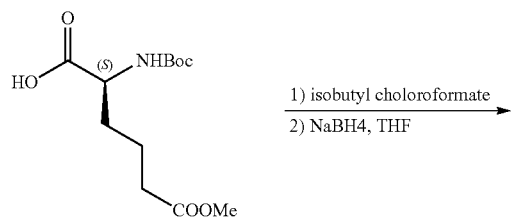

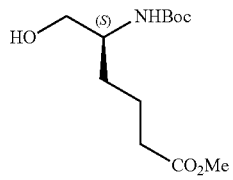

To a solution of (S)-2-(tert-butoxycarbonylamino)-6-methoxy-6-oxohexanoic acid (23.5 g, 85 mmol) in anhydrous THF (100 mL) was added $Et_3N$ (14.2 mL, 102 mmol, 1.2 equiv.). The solution was cooled down to 0° C. and isobutyl chloroformate (12.2 mL, 93.5 mmol, 1.1 equiv.) was added dropwise. The solution was stirred for 30 min. The precipitate was filtered off. The filtrate was cooled down to 0° C. and a suspension of sodium borohydride (6.5 g, 170 mmol, 2 equiv.) in $H_2O$ (3 mL) was added in one portion. The reaction was stirred for 1 h, and quenched with saturated $NH_4Cl$. THF was removed. The residue was dissolved into EtOAc (400 mL) and extracted with saturated $NH_4Cl$ twice. The organic layers were combined, dried and concentrated. The residue was purified on silica gel column (hexanes/EtOAc 1:1) to give (S)-methyl 5-(tert-butoxycarbonylamino)-6-hydroxyhexanoate (20 g, 90%) as a colorless oil. LRMS (M-Boc+$H^+$) m/z 162.1.

To a solution of (S)-methyl 5-(tert-butoxycarbonylamino)-6-hydroxyhexanoate (12 g, 46 mmol) in DMF (100 mL) was added imidazole (7.8 g, 115 mmol, 2.5 equiv.). TBS-Cl (8.25 g, 55 mmol, 1.2 equiv.) was then added in 3 portions. The reaction was complete in 30 min. Diethyl ether (200 mL) and brine (300 mL) were added to the reaction solution. The organic layer was further washed with brine (300 mL), dried, and concentrated to give (S)-methyl 5-(tert-butoxycarbonylamino)-6-(tert-butyldimethylsilyloxy)hexanoate (15.9 g, 92%) as a colorless oil. LRMS (M-Boc+$H^+$) m/z 276.1.

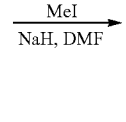

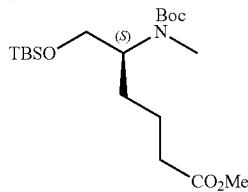

To a solution of (S)-methyl 5-(tert-butoxycarbonylamino)-6-(tert-butyldimethylsilyloxy)hexanoate (15 g, 40 mmol) in DMF (100 mL) was added iodomethane (17 g, 120 mmol, 3 equiv.) at 0° C. NaH (60%, 2.4 g, 60 mmol, 1.5 equiv.) was added in 3 portions. The reaction was stirred at RT for 2 h. EtOAc (150 mL) and brine (200 mL) were added to the reaction mixture. The organic layer was washed with brine (200 mL), dried, and concentrated to give (S)-methyl 5-(tert-butoxycarbonyl(methyl)amino)-6-(tert-butyldimethylsilyloxy)hexanoate (15.5 g, quant.) as a colorless oil. LRMS (M-Boc+H$^+$) m/z 290.1.

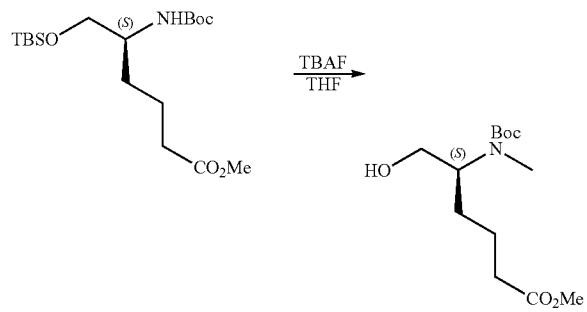

To a solution of (S)-methyl 5-(tert-butoxycarbonyl(methyl)amino)-6-(tert-butyldimethylsilyloxy)hexanoate (6.2 g, 16 mmol) in THF (50 mL) was slowly added TBAF (1 M in THF, 48 mL, 3 equiv.). The reaction was stirred at RT for 1 h. THF was removed. The residue was extracted with EtOAc (100 mL) and brine (100 mL) twice. The organic layers were combined and concentrated. The resulting residue was purified on silica gel column (hexanes/EtOAc 1:1) (S)-methyl 5-(tert-butoxycarbonyl(methyl)amino)-6-hydroxyhexanoate (4.4 g, quant.) as a colorless oil. LRMS (M-Boc+H$^+$) m/z 176.2.

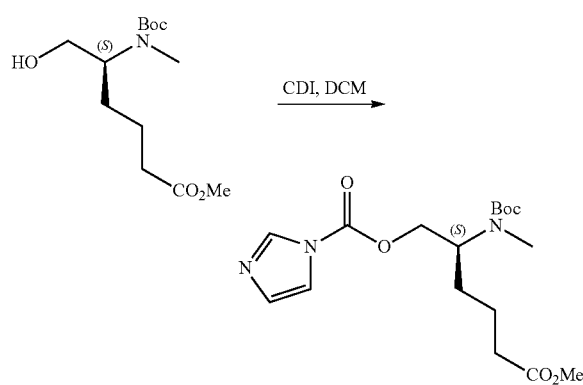

To a solution of (S)-methyl 5-(tert-butoxycarbonyl(methyl)amino)-6-hydroxyhexanoate (4.4 g, 16 mmol) in DCM (50 mL) was added CDI (3.1 g, 19 mmol). The reaction was complete in 30 min. DCM was removed. The residue was purified on silica gel column (hexanes/EtOAc 1:1) to give (S)-2-(tert-butoxycarbonyl(methyl)amino)-6-methoxy-6-oxohexyl 1H-imidazole-1-carboxylate (5.1 g, 85%) as a colorless oil. LRMS (M+Na$^+$) m/z 392.1

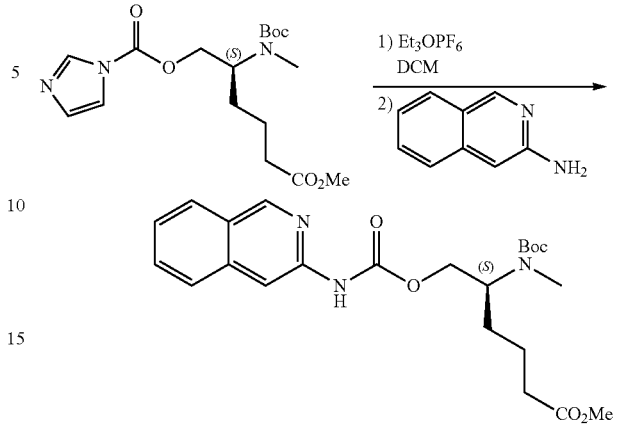

To a solution of (S)-2-(tert-butoxycarbonyl(methyl) amino)-6-methoxy-6-oxohexyl 1H-imidazole-1-carboxylate (2 g, 5.4 mmol) in DCM (10 mL) was added a solution of triethyloxonium hexafluorophosphate (1.61 g, 6.5 mmol, 1.2 equiv.) in DCM (5 mL) dropwise at 0° C. The solution was warmed up to RT and stirred for 15 min. A solution of isoquinolin-3-amine (0.94 g, 6.5 mmol, 1.2 equiv.) in DCM (5 mL) was added. The solution was stirred for overnight. DCM was removed and the residue was purified on RP-HPLC using a mixture of acetonitrile and H$_2$O to give (S)-methyl 5-(tert-butoxycarbonyl(methyl)amino)-6-(isoquinolin-3-ylcarbamoyloxy)hexanoate (1.4 g, 58%). LRMS (M+H$^+$) m/z 446.2.

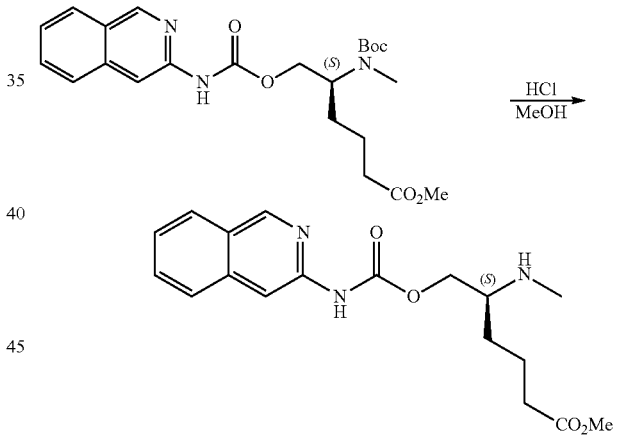

To s solution of (S)-methyl 5-(tert-butoxycarbonyl(methyl)amino)-6-(isoquinolin-3-ylcarbamoyloxy)hexanoate (2.0 g, 4.5 mmol) in MeOH (10 mL) at 0° C. was added HCl (4 M in 1,4-dioxane, 10 mL) dropwise. The solution was stirred at RT for 2 h. The solvents were removed under high vacuum to give (S)-methyl 6-(isoquinolin-3-ylcarbamoyloxy)-5-(methylamino)hexanoate (1.8 g, 94%) as a yellow solid. LRMS (M+H$^+$) m/z 346.2.

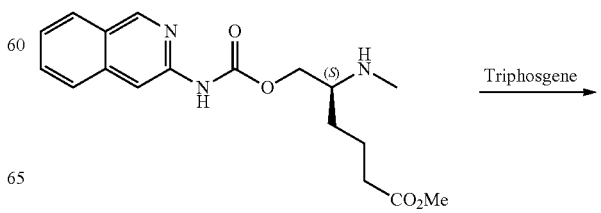

353

-continued

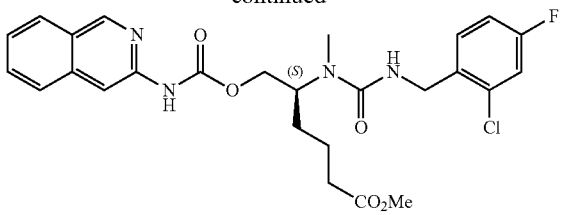

To a solution of triphosgene (71 mg, 0.24 mmol, 0.4 equiv.) in THF (5 mL) were added a solution of 2-chloro-4-fluorobenzylamine (95 mg, 0.6 mmol) and DIEA (0.22 mL, 1.26 mmol, 2.2 equiv.) in THF (5 mL) dropwise at 0° C. under $N_2$. The mixture was stirred at 0° C. for 30 min. A solution of (S)-methyl 6-(isoquinolin-3-ylcarbamoyloxy)-5-(methylamino)hexanoate (0.23, 0.6 mmol) and DIEA (0.11 mL, 0.66 mmol, 1.1 equiv.) in THF (5 mL) was added. The mixture was stirred at RT for 1 h. THF was removed. The residue was purified on RP-HPLC using a mixture of acetonitrile and $H_2O$ to give (S)-methyl 5-(3-(2-chloro-4-fluorobenzyl)-1-methylureido)-6-(isoquinolin-3-ylcarbamoyloxy)hexanoate (0.18 g, 56%) as a white solid. LRMS (M+H$^+$) m/z 531.2.

354

To a solution of (S)-methyl 5-(3-(2-chloro-4-fluorobenzyl)-1-methylureido)-6-(isoquinolin-3-ylcarbamoyloxy)hexanoate (80 mg, 0.15 mmol) in MeOH (1 mL) and THF (1 mL) was added LiBH$_4$ (2 M in THF, 0.3 mL, 4 equiv.) dropwise. The reaction was stirred at RT for 2 h. The reaction was quenched with saturated NH$_4$Cl (5 mL). The mixture was extracted with EtOAc (10 mL). The organic layer was concentrated. The resulting residue was purified on RP-HPLC using a mixture of acetonitrile and H$_2$O to give (S)-2-(3-(2-chloro-4-fluorobenzyl)-1-methylureido)-6-hydroxyhexyl isoquinolin-3-ylcarbamate as a white solid 10 (40 mg, 53%). LRMS (M+H$^+$) m/z 503.5.

Example 13

Preparation of (S)-2-(3-(2,3-difluorobenzyl)-1-methylureido)-6-(phosphonooxy)hexyl isoquinolin-3-ylcarbamate

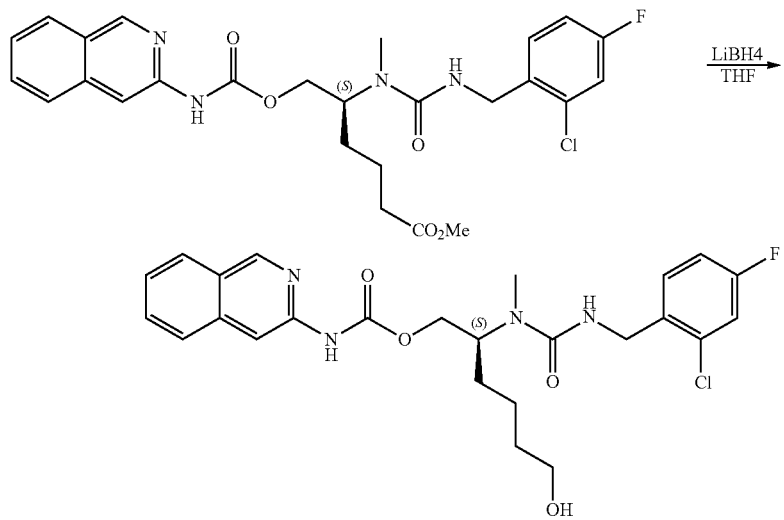

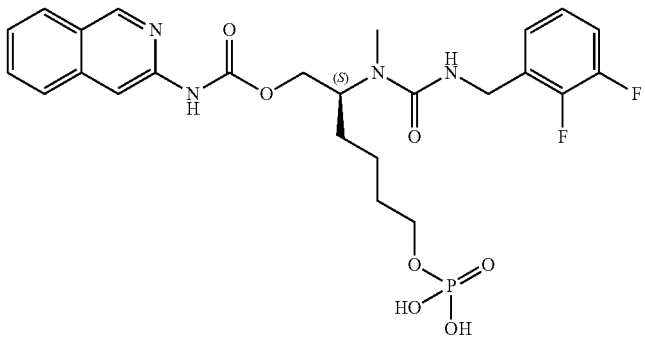

(S)-2-(3-(2,3-difluorobenzyl)-1-methylureido)-6-(phosphonooxy)hexyl isoquinolin-3-ylcarbamate

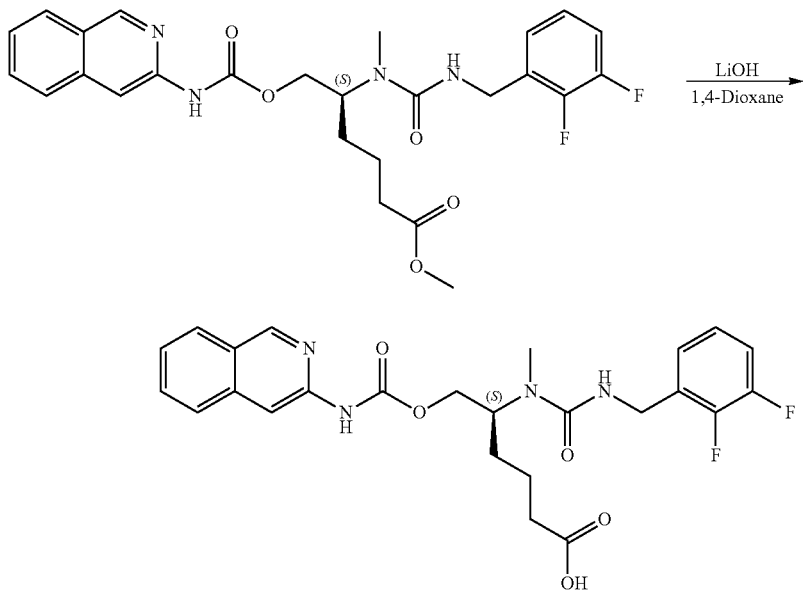

To a solution of (S)-methyl 5-(3-(2,3-difluorobenzyl)-1-methylureido)-6-(isoquinolin-3-ylcarbamoyloxy)hexanoate (1.45 g, 2.04 mmol, 1.0 equiv.) in 1,4-dioxane (18 mL) was added aqueous LiOH (6.12 mL, 6.12 mmol, 3.0 equiv.) at RT After stirred at RT for 1 h, the reaction mixture was acidified with HCl (1.0 N) to pH ~3. The mixture was extracted with EtOAc twice. The combined EtOAc solution was washed with brine, dried over Na$_2$SO$_4$, and concentrated under vacuum to give (S)-5-(3-(2,3-difluorobenzyl)-1-methylureido)-6-(isoquinolin-3-ylcarbamoyloxy)hexanoic acid, which was used without further purification. LRMS (M+H$^+$) m/z 501.3.

mmol, 1.2 equiv.) in anhydrous THF (7 mL) was added isopropyl chloroformate (2.80 mL, 2.80 mmol, 1.2 equiv.) dropwise at 0° C. After stirred at RT for 20 min, the mixture was filtered and transferred to a solution of NaBH$_4$ (0.18 g, 4.76 mmol, 2.0 equiv.) in water (2.0 mL). The resulting mixture was stirred at RT for 1 h, and quenched with saturated NH$_4$Cl. The solution was extracted with EtOAC twice. The organic layers were washed with brine, dried over Na$_2$SO$_4$, and concentrated. The resulting residue was purified on silica gel column (50-100% EtOAc in hexanes followed by 10% MeOH in dichloromethane) to give (S)-2-(3-(2,3-difluo-

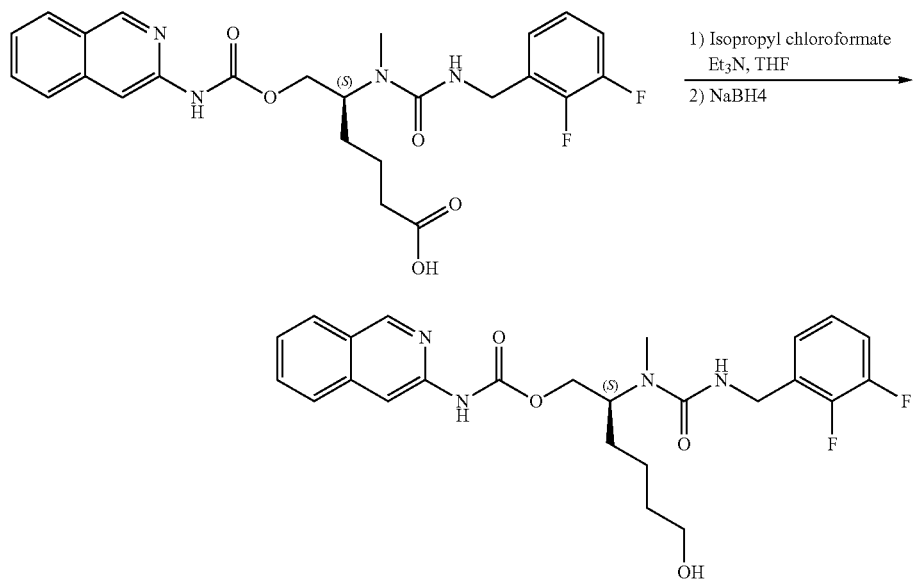

To a solution of (S)-5-(3-(2,3-difluorobenzyl)-1-methylureido)-6-(isoquinolin-3-ylcarbamoyloxy)hexanoic acid (~2.04 mmol, 1.0 equiv.) and triethylamine (0.38 mL, 2.78 robenzyl)-1-methylureido)-6-hydroxyhexyl isoquinolin-3-ylcarbamate (0.58 g, 52% for two steps). LRMS (M+H$^+$) m/z 487.3.

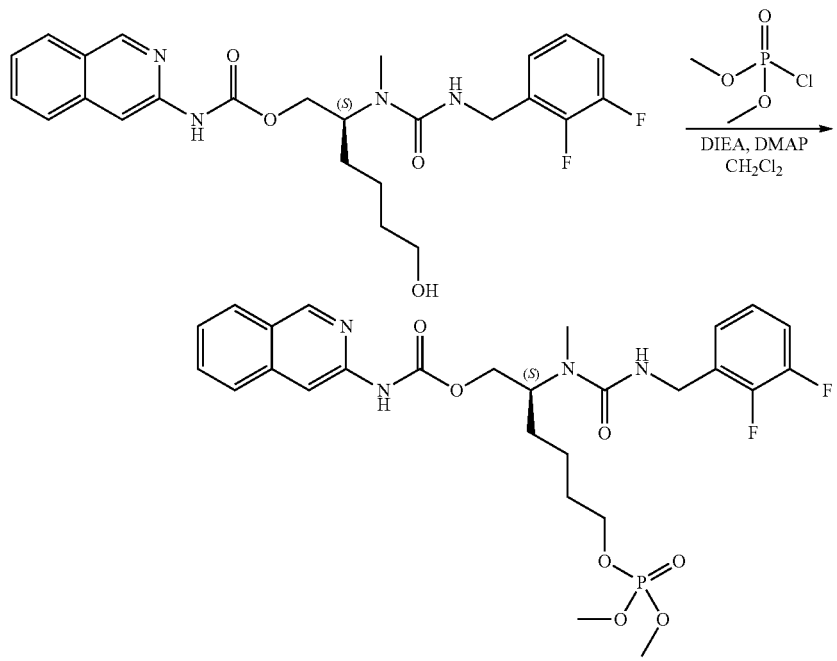

To a solution of (S)-2-(3-(2,3-difluorobenzyl)-1-methylureido)-6-hydroxyhexyl isoquinolin-3-ylcarbamate (0.25 g, 0.51 mmol, 1.0 equiv.), DIEA (0.45 mL, 2.57 mmol, 5 equiv.) and DMAP (0.12 g, 1.53 mmol, 3.0 equiv.) in anhydrous dichloromethane (2.0 mL) was added dimethylphosphoryl chloride (0.18 mL, 1.53 mmol, 3.0 equiv.) at RT After stirred at RT for 45 min, the reaction mixture was extracted with EtOAc. The organic layer was washed with saturated NaHCO$_3$, water and brine, dried over Na$_2$SO$_4$, and concentrated to give (S)-2-(3-(2,3-difluorobenzyl)-1-methylureido)-6-(dimethoxyphosphoryloxy)hexyl isoquinolin-3-ylcarbamate (0.28 g, 93%), which was used without further purification. LRMS (M+H$^+$) m/z 595.3.

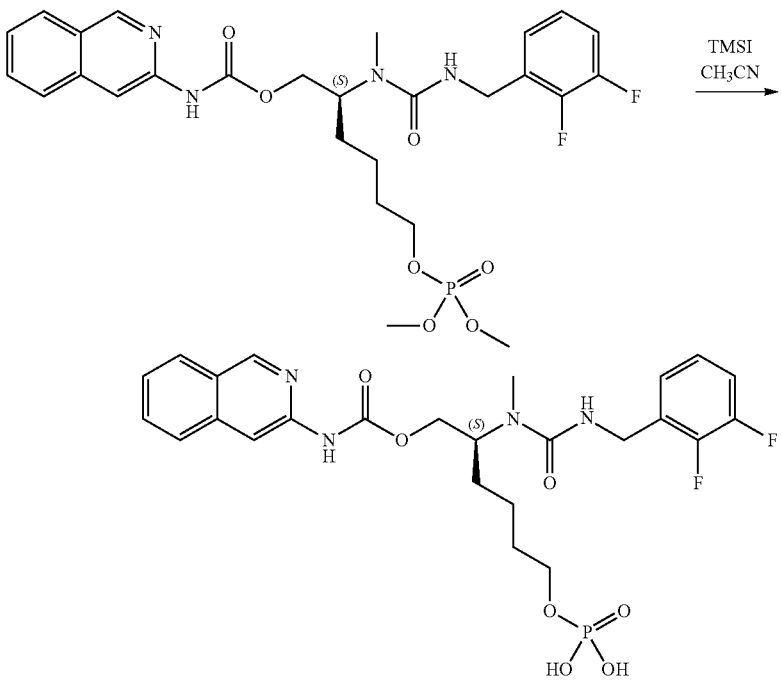

To a solution of (S)-2-(3-(2,3-difluorobenzyl)-1-methylureido)-6-(dimethoxyphosphoryloxy)hexyl isoquinolin-3-ylcarbamate (0.28 g, 0.47 mmol, 1.0 equiv.) in acetonitrile (25 mL) was added TMSI (0.28 mL, 1.88 mmol, 4.0 equiv.) at RT After stirred at RT for 15 min, the reaction was quenched with MeOH. The solvent was concentrated. The resulting residue was purified on RP-HPLC using a mixture of acetonitrile and H₂O with 0.1% TFA. The fractions containing the product were combined and concentrated. The resulting residue was suspended in EtOAc, 5 drops of HCl (4 M in 1,4-dioxane) were added, and the organic solvent was removed. This procedure was repeated to give (S)-2-(3-(2,3-difluorobenzyl)-1-methylureido)-6-(phosphonooxy)hexyl isoquinolin-3-ylcarbamate (0.16 g, 57%) as a HCl salt. LRMS (M+H⁺) m/z 567.2.

Example 14

Preparation of (S)-3-(2-aminoacetamido)-2-(3-(2-chloro-3-fluorobenzyl)-1-methylureido)propyl 6-fluoroisoquinolin-3-ylcarbamate

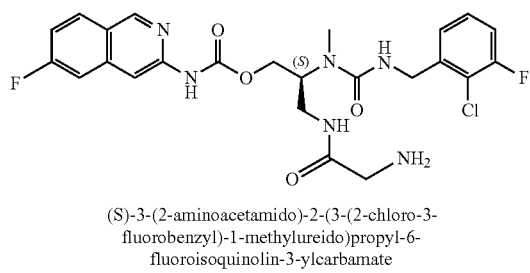

(S)-3-(2-aminoacetamido)-2-(3-(2-chloro-3-fluorobenzyl)-1-methylureido)propyl-6-fluoroisoquinolin-3-ylcarbamate

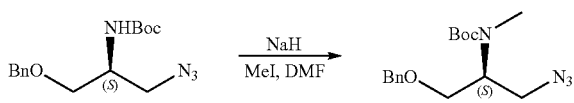

To a solution of (S)-tert-butyl 1-(benzyloxy)-3-hydroxypropan-2-ylcarbamate (1.89 g, 6.4 mmol) in DCM (50 mL) was added MSCl (0.55 mL, 7.04 mmol) and DIEA (1.27 mL, 7.68 mmol). The mixture was stirred at RT for 30 min. The mixture was diluted with DCM (300 mL), washed with NaHCO₃ and brine, dried over Na₂SO₄, filtered, and concentrated under reduced pressure. The crude product was dissolved in DMF (20 mL). To this DMF solution was added NaN₃ (1.25 g, 19.2 mmol) and the mixture was heated to 80° C. for 6 h. LCMS indicated the completion of the reaction. The mixture was cooled to RT, water (20 mL) and EtOAc (200 mL) were added. The organic layer was separated, washed with NaHCO₃, brine, dried over Na₂SO₄, filtered, and concentrated under reduced pressure. The rude was purified on silica gel column to give (S)-tert-butyl 1-azido-3-(benzyloxy) propan-2-ylcarbamate (1.5 g, 73% for 2 steps).

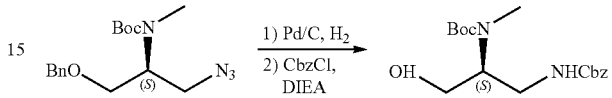

To a solution NaH (0.29 g, 7.35 mmol) in DMF (10 mL) was added a solution of (S)-tert-butyl 1-azido-3-(benzyloxy) propan-2-ylcarbamate (1.5 g, 4.9 mmol) in DMF (10.0 mL). The mixture was stirred for 30 min. MeI (1.0 mL, 9.8 mmol) was then added. The mixture was stirred for another 2 h. LCMS indicated the completion of the reaction. The mixture was quenched with saturated NH₄Cl solution and extracted with EtOAc (200 mL×2). The organic layers were combined, washed with brine, dried over Na₂SO₄, filtered, and concentrated under reduced pressure to give (S)-tert-butyl 1-azido-3-(benzyloxy)propan-2-yl(methyl)carbamate (1.8 g), which was used without purification.

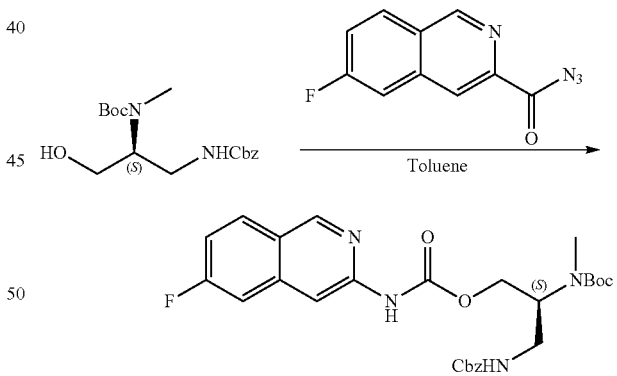

To a solution of (S)-tert-butyl 1-azido-3-(benzyloxy)propan-2-yl(methyl)carbamate (1.8 g of crude, 4.90 mmol) in MeOH (20 mL) was added Pd/C (300 mg). The mixture was transferred to an autoclave reactor, charged with 45 psi of hydrogen, and stirred overnight. The solid was filtered off and the filtrate was added CbzCl (0.83 mL, 5.88 mmol) and DIEA (1.22 mL, 7.35 mmol) and stirred for 30 min. LCMS indicated the completion of the reaction. The reaction mixture was concentrated under reduced pressure, dissolved in EtOAc, washed with NaHCO₃, brine, dried over Na₂SO₄, filtered, and concentrated under reduced pressure to give (S)-tert-butyl 1-(benzyloxycarbonylamino)-3-hydroxypropan-2-yl(methyl)carbamate (2.2 g), which was used without purification. LRMS (M+H⁺-Boc) m/z 239.1.

To a solution of (S)-tert-butyl 1-(benzyloxycarbonylamino)-3-hydroxypropan-2-yl(methyl)carbamate (2.2 g, ~4.90 mmol) in toluene (20 mL) was added 6-fluoro-isoquinoline-3-carbonyl azide (1.16 g, 5.39 mmol) in portions and the mixture was heated to 100° C. for 1 h. The mixture was concentrated to one forth of the amount and purified on silica gel column to give (S)-3-benzyloxycarbonylamino-2-((1-tert-butoxycarbonyl)(methyl)amino)propyl 6-fluoroisoquinolin-3-ylcarbamate (1.5 g, 58% for 4 steps). LRMS (M+H⁺) m/z 527.3.

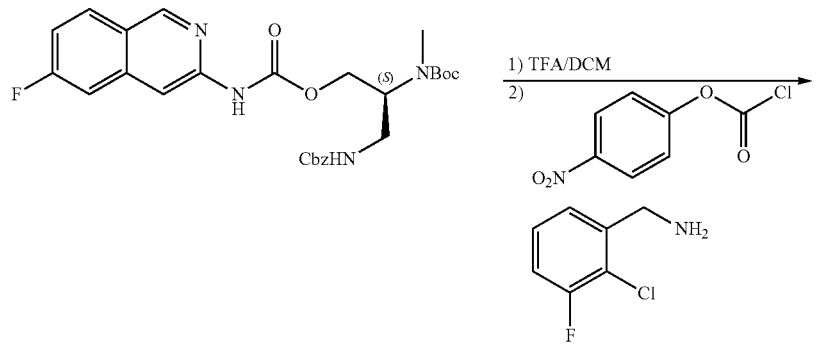

To a solution of (S)-3-benzyloxycarbonylamino-2-((1-tert-butoxycarbonyl)(methyl)amino)propyl 6-fluoroisoquinolin-3-ylcarbamate (1.5 g, 2.85 mmol) in DCM (10.0 mL) was added TFA (1.0 mL). The mixture was stirred for 1 h, concentrated, and re-dissolved in THF (5 mL). To this THF solution was added pre-stirred solution of 4-nitrophenylchloroformate and 2-chloro-3-fluorobenzylamine in THF (15 mL). The reaction mixture was stirred overnight. The mixture was concentrated under reduced pressure, re-dissolved in MeOH, filtered, and purified by RP-HPLC using a mixture of acetonitrile and H$_2$O to give (S)-3-benzyloxycarbonylamino-2-(3-(2-chloro-3-fluorobenzyl)-1-methylureido)propyl 6-fluoroisoquinolin-3-ylcarbamate (1.3 g, 75%). LRMS (M+H$^+$) m/z 612.2.

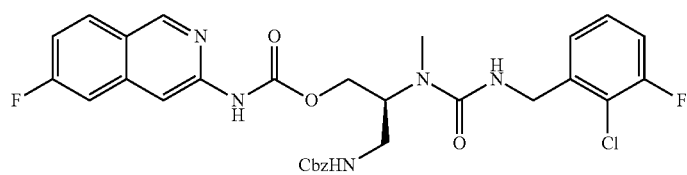

mL) was added TMSI (0.35 mL, 2.56 mmol). The mixture was stirred for 15 min. MeOH (20.0 mL) was added and stirring continued another 15 min. The mixture was concentrated and partitioned between diethyl ether (30 mL) and HCl (2 N, 20 mL). The aqueous layer was separated, adjusted to pH 9, extracted with EtOAc (200 mL×2). The combined organic layers were washed brine, dried over Na$_2$SO$_4$, filtered, and concentrated under reduced pressure to give an crude oil, which was dissolved in DMF (6.0 mL). To this DMF solution were added Boc-Gly-OH (0.36 g, 2.03 mmol) and HBTU (0.77 g, 2.03 mmol). The mixture was stirred for 1 h. The crude was filtered and purified on RP-HPLC using a mixture of acetonitrile and H$_2$O to give (S)-3-(2-tert-butoxy-

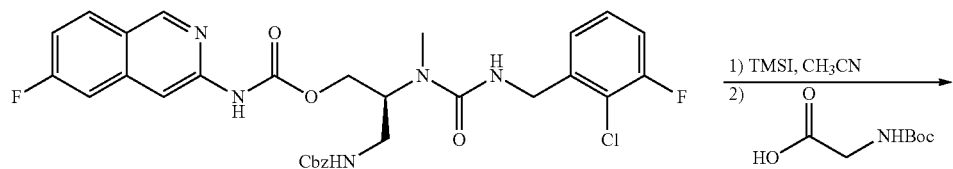

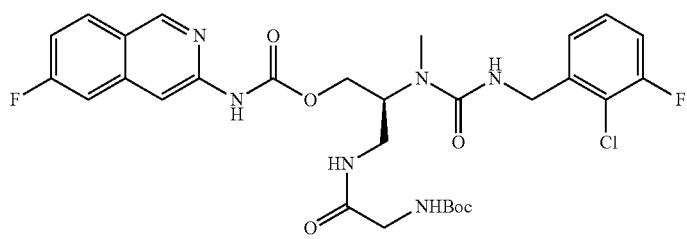

To a solution of (S)-3-benzyloxycarbonylamino-2-(3-(2-chloro-3-fluorobenzyl)-1-methylureido)propyl 6-fluoroisoquinolin-3-ylcarbamate (1.3 g, 2.13 mmol) in CH$_3$CN (20.0 carbonylaminoacetamido)-2-(3-(2-chloro-3-fluorobenzyl)-1-methylureido)propyl 6-fluoroisoquinolin-3-ylcarbamate (0.91 g, 78%). LRMS (M+H$^+$) m/z 635.2.

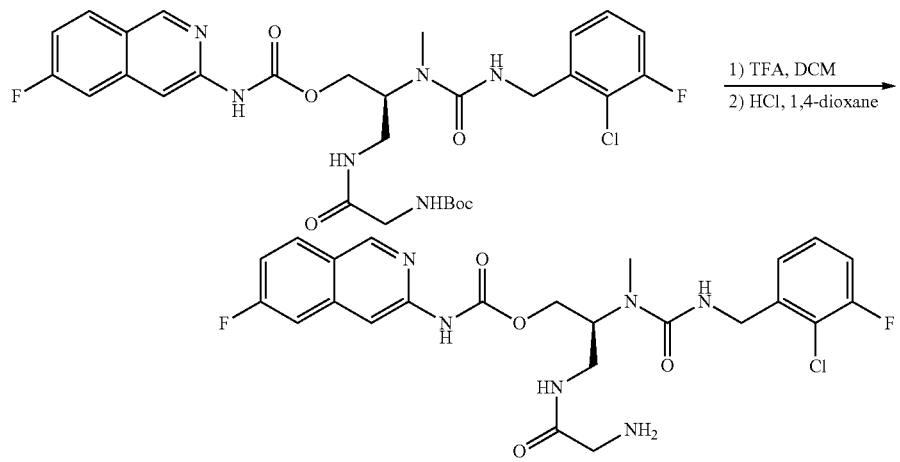

To a solution of (S)-3-(2-tert-butoxycarbonylaminoacetamido)-2-(3-(2-chloro-3-fluorobenzyl)-1-methylureido)propyl 6-fluoroisoquinolin-3-ylcarbamate (0.87 g, 1.37 mmol) in DCM (30.0 mL) was added TFA (3.0 mL). The mixture was stirred for 1 h. The mixture was concentrated and dissolved in EtOAc. The EtOAc solution was washed with $Na_2CO_3$, brine, dried over $Na_2SO_4$, and filtered. To the filtrate was added HCl (4 M in dioxane, 0.7 mL, 2.8 mmol,). The organic solvent was removed under reduced pressure to give (S)-3-(2-aminoacetamido)-2-(3-(2-chloro-3-fluorobenzyl)-1-methylureido) propyl 6-fluoroisoquinolin-3-ylcarbamate (730 mg, 93%) as a HCl salt. LRMS (M+H$^+$) m/z 535.2.

Example 15

Preparation of (S)-5-amino-2-(3-(2-chloro-3-fluorobenzyl)-1-methylureido)pentyl 5-(trifluoromethyl)pyridin-2-ylcarbamate

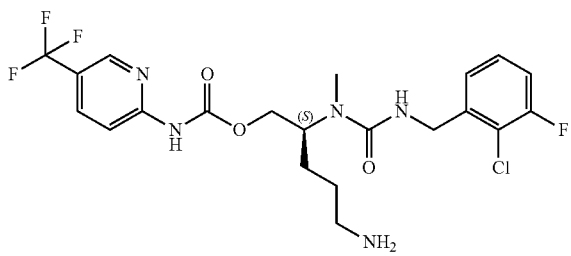

(S)-5-amino-2-(3-(2-chloro-3-fluorobenzyl)-1-methylureido)pentyl 5-(trifluoromethyl)pyridin-2-ylcarbamate

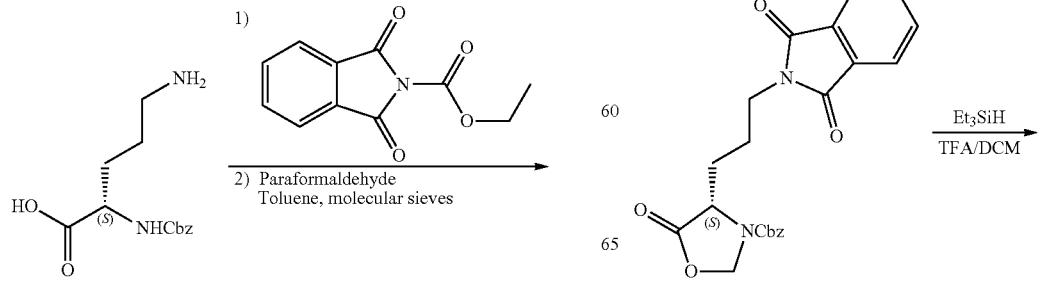

-continued

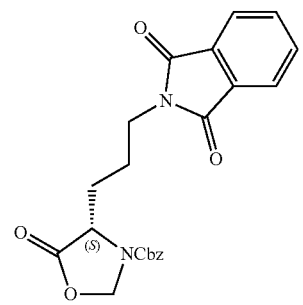

A mixture of (S)-5-amino-2-(benzyloxycarbonylamino)pentanoic acid (10.0 g, 37.56 mmol), ethyl 1,3-dioxoisoindoline-2-carboxylate (9.04 g, 41.28 mmol) in NMP (40.0 mL) was heated to 150° C. for 30 min in 4 microwave reaction tubes. The mixture was diluted with EtOAc (500 mL). The organic layer washed with water (100 mL×2), brine, dried over $Na_2SO_4$, filtered, and concentrated under reduced pressure to give an oil, which was dissolved in toluene. To this toluene solution was added paraformaldehyde, PTSA and molecular sieves (3 Å) and the mixture was heated to 150° C. for 20 min. The mixture was diluted with ether (800 mL), washed with $NaHCO_3$, brine, dried over $Na_2SO_4$, filtered, and concentrated under reduced pressure. The crude was purified on silica gel column using a mixture of EtOAc and hexanes to give (S)-benzyl 4-(3-(1,3-dioxoisoindolin-2-yl)propyl)-5-oxooxazolidine-3-carboxylate (11.6 g, 76% for 2 steps).

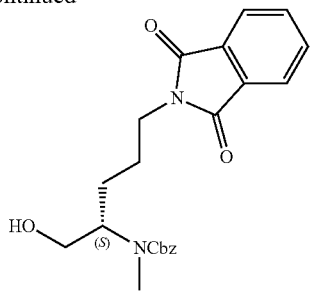

To a solution of (S)-benzyl 4-(3-(1,3-dioxoisoindolin-2-yl)propyl)-5-oxooxazolidine-3-carboxylate (11.6 g, 28.40 mmol) in DCM (30.0 mL) was added Et₃SiH (13.6 mL, 85.3 mmol). The reaction mixture was stirred overnight. The mixture was concentrated under reduced pressure and dissolved in THF (100 mL). To this THY solution was added tert-butyl chloroformate (4.4 mL, 34.08 mmol) at 0° C. followed by TEA (12.0 mL, 85.2 mmol) and stirred at RT for 30 min. The precipitate was filtered off and the filtrate was added into a NaBH₄ suspension in water (1.0 mL) at 0° C., and the mixture was stirred at RT for 30 min. LC/MS indicated the completion of the reaction. The mixture was acidified to pH 3 using HCl (1 N). The aqueous layer was extracted with EtOAc (300 mL×2). The combined organic layer was washed with NaHCO₃, brine, dried over Na₂SO₄, filtered, and concentrated under reduced pressure. The crude was purified on silica gel column using a mixture of EtOAc and hexanes to give (S)-benzyl 5-(1,3-dioxoisoindolin-2-yl)-1-hydroxypentan-2-yl(methyl)carbamate (5.01 g, 45%). LRMS (M+H⁺) m/z 397.3.

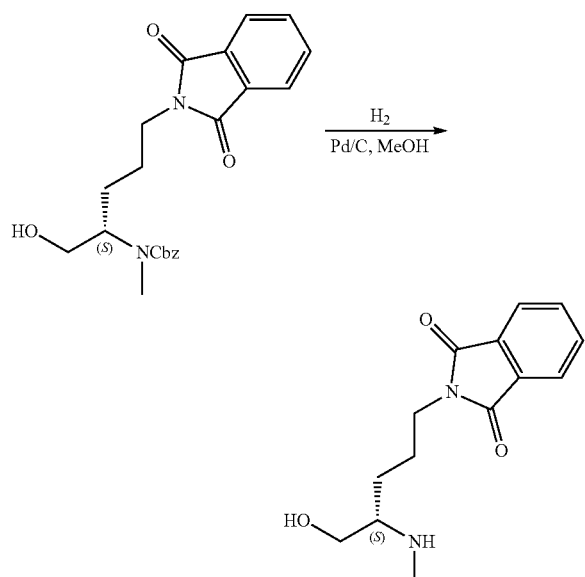

To a solution of (S)-benzyl 5-(1,3-dioxoisoindolin-2-yl)-1-hydroxypentan-2-yl(methyl)carbamate (5.01 g, 12.65 mmol) in MeOH (100 mL) was added Pd/C (1.0 g). The mixture was transferred to an autoclave reactor, charged with 50 psi of hydrogen, and stirred overnight. The mixture was filtered, and the filtrate was concentrated under reduced pressure to give (S)-2-(5-hydroxy-4-(methylamino)pentyl)isoindoline-1,3-dione (3.2 g, 97%). LRMS (M+H⁺) m/z 263.1

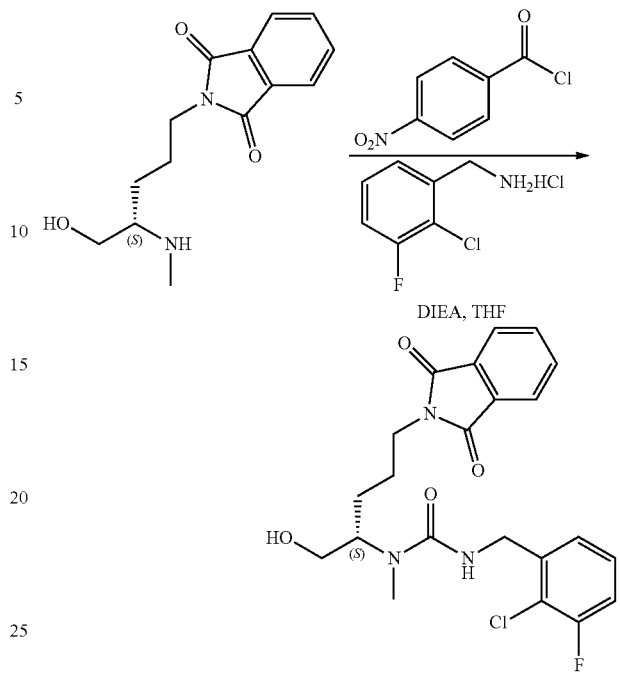

To a solution of 4-nitrophenylchloroformate (460 mg, 2.29 mmol) in THF (20 mL) was added 2-chloro-3-fluorobenzylamine hydrochloride (626 mg, 2.29 mmol) and DIEA (0.76 mL, 4.58 mmol) and the mixture was stirred at RT until TLC showed complete consumption of 2-chloro-3-fluorobenzylamine. The mixture was then added into a solution of (S)-2-(5-hydroxy-4-(methylamino)pentyl)isoindoline-1,3-dione (500 mg, 1.91 mmol) in THF (10 mL). The mixture was stirred overnight, concentrated and purified on RP-HPLC using a mixture of acetonitrile and H₂O to give (S)-3-(2-chloro-3-fluorobenzyl)-1-(5-(1,3-dioxoisoindolin-2-yl)-1-hydroxypentan-2-yl)-1-methylurea (401 mg, 47%). LRMS (M+H⁺) m/z 448.3.

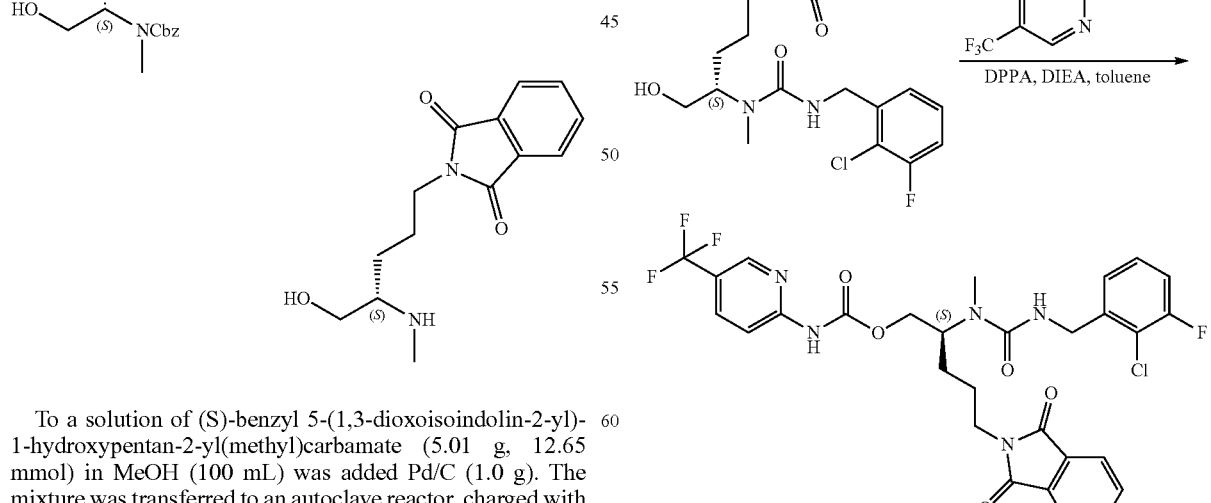

To a solution of (S)-3-(2-chloro-3-fluorobenzyl)-1-(5-(1,3-dioxoisoindolin-2-yl)-1-hydroxypentan-2-yl)-1-methylurea (200 mg, 0.45 mmol), 5-(trifluoromethyl)picolinic acid (256 mg, 1.35 mmol) and DMA (0.3 mL, 1.35 mmol) in toluene (5 mL) was added DPPA (0.27 mL, 1.35 mmol). The mixture was heated to 100° C. for 2 h, and concentrated. The resulting residue was purified on RP-HPLC using a mixture of acetonitrile and $H_2O$ to give (S)-2-(3-(2-chloro-3-fluorobenzyl)-1-methylureido)-5-(1,3-dioxoisoindolin-2-yl) pentyl 5-(trifluoromethyl)pyridin-2-ylcarbamate (150 mg, 80%). LRMS (M+Na$^+$) m/z 658.2.

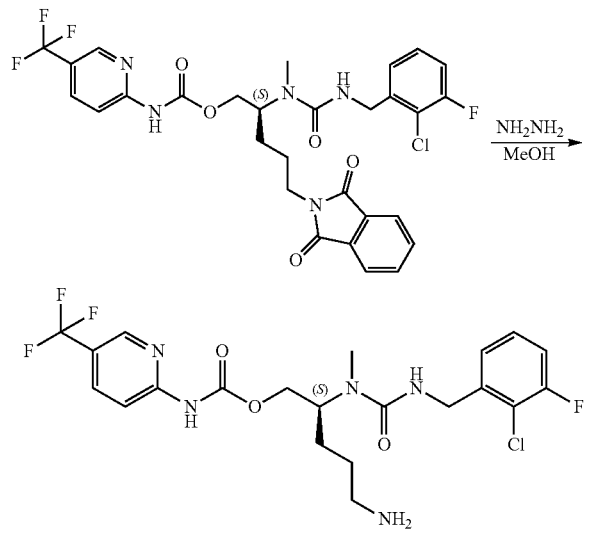

To a solution of (S)-2-(3-(2-chloro-3-fluorobenzyl)-1-methylureido)-5-(1,3-dioxoisoindolin-2-yl)pentyl 5-(trifluoromethyl)pyridin-2-ylcarbamate (150 mg, 0.24 mmol) in MeOH (5.0 mL) was added $NH_2NH_2$ (0.2 mL). The reaction mixture was stirred at RT for 2 h. The mixture was concentrated, dissolved in MeOH, filtered, and purified on RP-HPLC using a mixture of acetonitrile and $H_2O$ to give (S)-5-amino-2-(3-(2-chloro-3-fluorobenzyl)-1-methylureido)pentyl 5-(trifluoromethyl)pyridin-2-ylcarbamate (91 mg, 76%). LRMS (M+H$^+$) m/z 506.1.

Example 16

Preparation of (S)-5-amino-2-(3-(2-chloro-3-fluorobenzyl)-1-methylureido)pentyl 2,7-naphthyridin-3-ylcarbamate

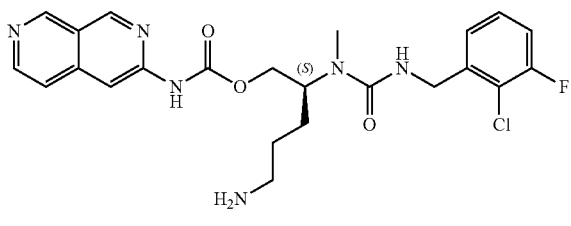

(S)-5-amino-2-(3-(2-chloro-3-fluorobenzyl)-1-methylureido)pentyl 2,7-naphthyridin-3-ylcarbamate

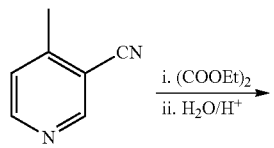

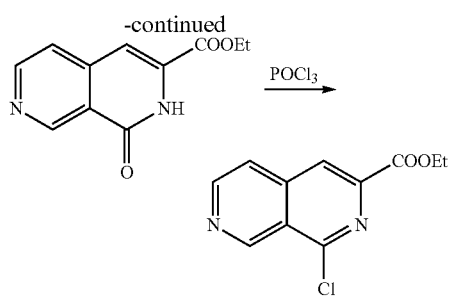

Ethyl 1-chloro-2,7-naphthyridine-3-carboxylate was prepared from 3-cyano-4-picoline according to the published procedures (E. Barbu et. al. *Heterocyclic Communications*, Vol. 6, No. 1, 2000, 25-28) with some modifications.

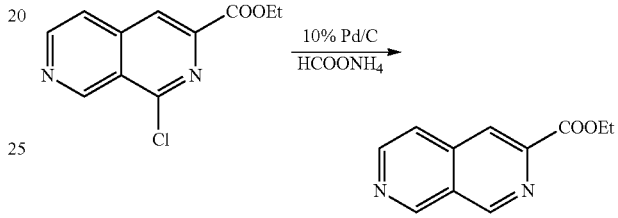

A mixture of 1-chloro-2,7-naphthyridine-3-carboxylate (320 mg, 1.352 mmol), ammonium formate (128 mg, 2.0 mmol), 10% Pd/C (33 mg), EtOAc (5 mL) and MeOH (5 mL) was refluxed for 10 min. The mixture was filtered and concentrated. The resulting residue was purified by RP-HPLC using a mixture of acetonitrile and $H_2O$ to give 2,7-naphthyridine-3-carboxylate (265 mg, 72%). LRMS (M+H$^+$) m/z 203.0.

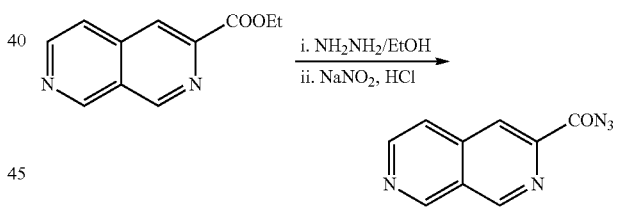

A mixture of 2,7-naphthyridine-3-carboxylate (260 mg, 1.29 mmol), hydrazine (0.20 mL, 6.44 mmol) and ethanol was refluxed for 2 h and concentrated to dryness. The resulting residue was mixed with 2N HCl (1.3 mL, 2.60 mmol) and $H_2O$ (5 mL) and cooled with an ice bath. To the mixture was added a solution of $NaNO_2$ (178 mg, 2.6 mmol in 1 mL $H_2O$) dropwise, the mixture was stirred at 0° C. for 1 h. The mixture was then neutralized with saturated $NaHCO_3$ and extracted with DCM. The DCM solution was washed with water, brine, dried and concentrated to give 2,7-naphthyridine-3-carbonyl azide as a pale yellow solid (244 mg, 95%). LRMS (M−$N_2$+H$^+$) m/z 172.1.

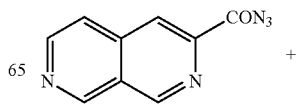

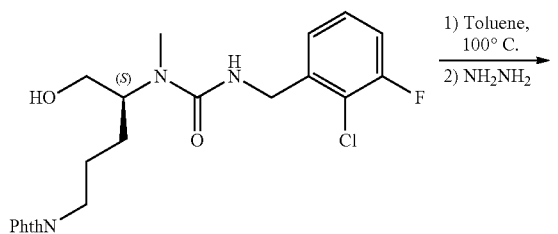

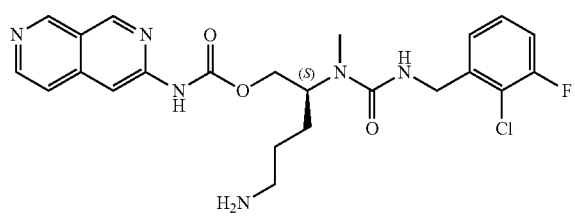

A mixture of 2,7-naphthyridine-3-carbonyl azide (14 mg, 0.07 mmol), (S)-3-(2-chloro-3-fluorobenzyl)-1-(5-(1,3-dioxoisoindolin-2-yl)-1-hydroxypentan-2-yl)-1-methylurea (33 mg, 0.07 mmol) and toluene (2 mL) was stirred at 100° C. for 1 h and concentrated. The resulting residue was treated with hydrazine (0.2 mL) and methanol (1 mL) at RT for 1 h. Concentration followed by purification on RP-HPLC using a mixture of acetonitrile, H$_2$O and 0.1% TFA gave (S)-5-amino-2-(3-(2-chloro-3-fluorobenzyl)-1-methylureido)pentyl 2,7-naphthyridin-3-ylcarbamate as a TFA salt (28 mg, 53%). LRMS (M+H$^+$) m/z 489.1.

Example 17

Preparation of (S)-2-(3-(2-chloro-3-fluorobenzyl)-1-methylureido)-5-oxo-5-(piperazin-1-yl)pentyl benzo[d]thiazol-2-ylcarbamate

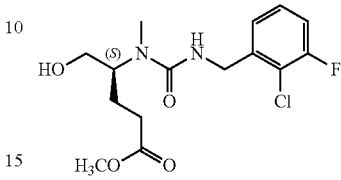

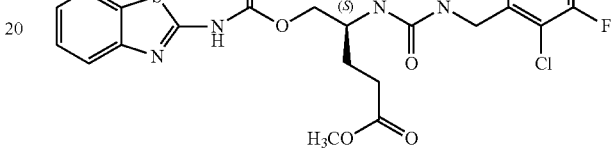

A solution of (S)-methyl 4-(3-(2-chloro-3-fluorobenzyl)-1-methylureido)-5-hydroxypentanoate (4.34 mmol) in toluene (43 mL) under nitrogen was heated to 100° C. in an oil bath. A slurry of benzo[d]thiazole-2-carbonyl azide (973 mg, 1.0 equiv.) in toluene (15 mL) was added in portions over 30 min. The reaction was maintained at 100° C. for 30 min. The solvent was removed in vacuo and the residue subjected to flash chromatography using a mixture of hexanes and EtOAc to give (S)-methyl 5-(benzo[d]thiazol-2-ylcarbamoyloxy)-4-(3-(2-chloro-3-fluorobenzyl)-1-methylureido)pentanoate as a yellow solid (2.35 g, quant.). LRMS (M+H$^+$)=523.5.

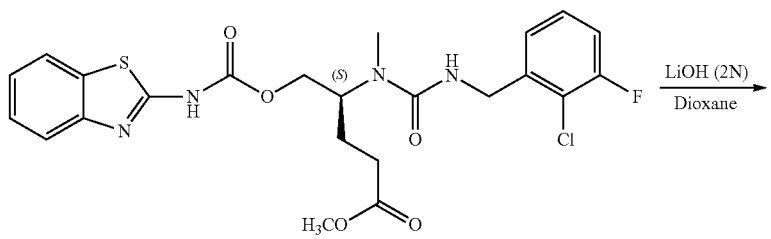

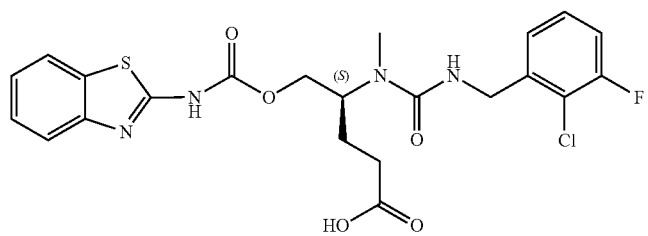

To a solution of (S)-methyl 5-(benzo[d]thiazol-2-ylcarbamoyloxy)-4-(3-(2-chloro-3-fluorobenzyl)-1-methylureido)pentanoate (2.3 g, 4.4 mmol) in 1,4-dioxane (15 mL) was added LiOH (2 N, 4.4 mL, 2 equiv.). The reaction mixture was stirred at RT for 2 h. The mixture was acidified to pH ~3 with HCl (1 N, ~10 mL), and ethyl acetate (50 mL) was added. The organic layer was extracted with EtOAc (3×20 mL), dried over $Na_2SO_4$ and concentrated. A small sample (30 mg) was purified by RP-HPLC (20-100% ACN in $H_2O$) to give (S)-5-(benzo[d]thiazol-2-ylcarbamoyloxy)-4-(3-(2-chloro-3-fluorobenzyl)-1-methylureido)pentanoic acid as a white solid (8 mg). The remainder was used without further purification. LRMS $(M-H^+)$=507.4.

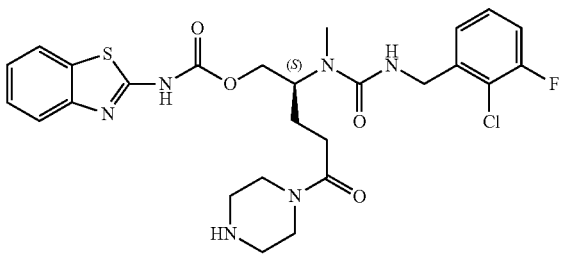

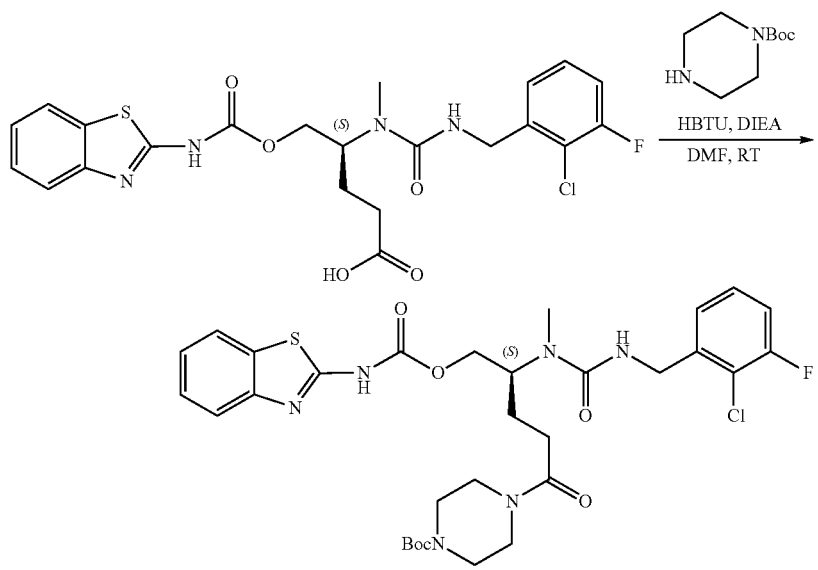

To a solution of (S)-5-(benzo[d]thiazol-2-ylcarbamoyloxy)-4-(3-(2-chloro-3-fluorobenzyl)-1-methylureido)pentanoic acid (~4.41 mmol) in DMF (8 mL) at RT were added N-Boc-piperazine (820 mg, 1 equiv.), DIEA (1.2 mL, 1.5 equiv.), and HBTU (2.00 g, 1.2 equiv.) The reaction was allowed to stir overnight, and the crude was purified by RP-HPLC (5-100% ACN in $H_2O$) to give (S)-tert-butyl 4-(5-(benzo[d]thiazol-2-ylcarbamoyloxy)-4-(3-(2-chloro-3-fluorobenzyl)-1-methylureido)pentanoyl)piperazine-1-carboxylate as a white solid (801 mg, 27% over 2 steps). LRMS $(M+Na^+)$=699.4.

To a solution of (S)-tert-butyl 4-(5-(benzo[d]thiazol-2-ylcarbamoyloxy)-4-(3-(2-chloro-3-fluorobenzyl)-1-methylureido)pentanoyl)piperazine-1-carboxylate (713 mg, 1.05 mmol) in DCM (5 mL) was added TFA (1 mL) and allowed to stir for 30 min. The reaction mixture was concentrated, and the residue purified by RP-HPLC (20-100% ACN in $H_2O$) and concentrated to give (S)-2-(3-(2-chloro-3-fluorobenzyl)-1-methylureido)-5-oxo-5-(piperazin-1-yl)pentyl benzo[d]thiazol-2-ylcarbamate as an off-white solid (430 mg, 71%). LRMS $(M+H^+)$=577.1

Example 18

Preparation of (S)-2-(3-(2-chloro-3-fluorobenzyl)-1-methylureido)-5-oxo-5-(piperazin-1-yl)pentyl isoquinolin-3-ylcarbamate

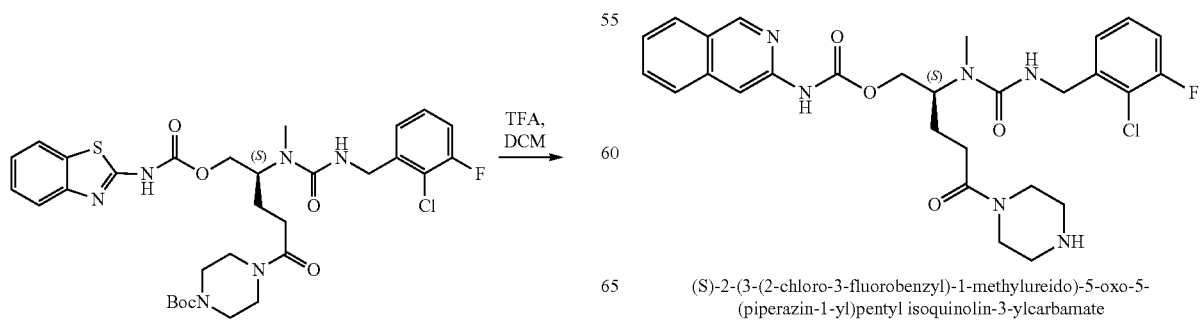

(S)-2-(3-(2-chloro-3-fluorobenzyl)-1-methylureido)-5-oxo-5-(piperazin-1-yl)pentyl isoquinolin-3-ylcarbamate

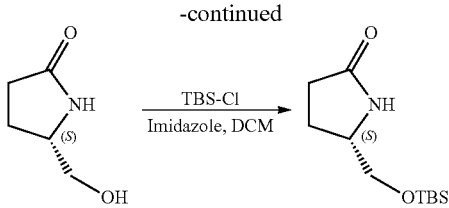

To a solution of (S)-5-(hydroxymethyl)pyrrolidin-2-one (30.0 g, 261 mmol) and imidazole (23.1 g, 340 mmol) in DCM (900 mL) was added TBS-Cl (42.9 g, 288 mmol). The reaction mixture was stirred at RT for 30 min and filtered. The filtrate was washed with water and brine, dried over Na₂SO₄, filtered, and concentrated under reduced pressure. The residue was purified on silica gel column using a mixture of EtOAc and hexanes to give (S)-5-((tert-butyldimethylsilyloxy)methyl)pyrrolidin-2-one (50 g, 83.7%). LRMS (M+H⁺) m/z 230.2.

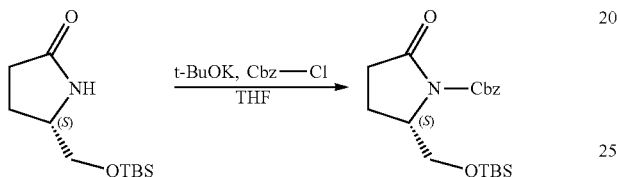

To a solution of (S)-5-((tert-butyldimethylsilyloxy)methyl)pyrrolidin-2-one (48.5 g, 0.21 mol) in THF (100 mL) was added t-BuOK (30.8 g, 0.27 mol) at 0° C. The mixture was stirred at 0° C. for 30 min followed by addition of Cbz-Cl (40.4 mL, 0.27 mol) dropwise at 0° C. The resulting mixture was stirred at RT overnight, quenched with saturated NH₄Cl, concentrated to a small amount, and diluted with EtOAc. The organic layer was washed with water and brine, dried over Na₂SO₄, filtered, and concentrated under reduced pressure. The residue was purified on silica gel column using a mixture of EtOAc and hexanes to give (S)-benzyl 2-((tert-butyldimethylsilyloxy)methyl)-5-oxopyrrolidine-1-carboxylate (70 g, 91%). LRMS (M+H−44) m/z 320.2.

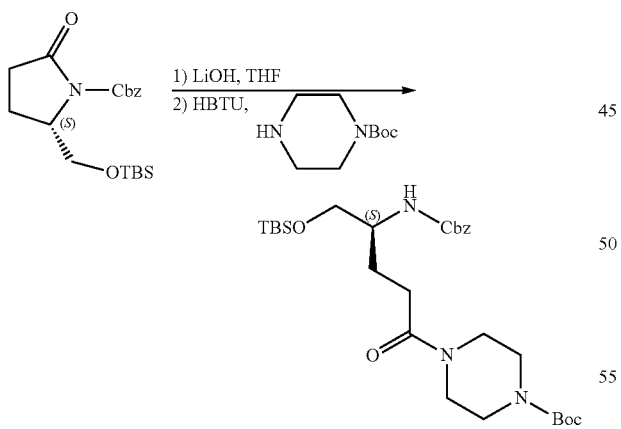

To a solution of (S)-benzyl 2-((tert-butyldimethylsilyloxy)methyl)-5-oxopyrrolidine-1-carboxylate (39 g, 0.107 mol) in THF (214 mL) was added LiOH (2 N, 107.4 mL). The reaction mixture was stirred at RT overnight, concentrated to dryness, and dissolved in DMF (100 mL). To the resulting solution were added HBTU (48.9 g, 0.13 mmol) and Boc-piperazine (24 g, 0.13 mol). The reaction mixture was stirred at RT for 1 h and diluted with water (200 mL) and EtOAc (500 mL). The organic layer was washed with water, dried over Na₂SO₄, filtered and concentrated. The residue was purified on silica gel column using a mixture of EtOAc and hexanes to give (S)-tert-butyl 4-(4-(benzyloxycarbonylamino)-5-(tert-butyldimethylsilyloxy)pentanoyl)piperazine-1-carboxylate (33.3 g, 56.5%). LRMS (M+H) m/z 550.3.

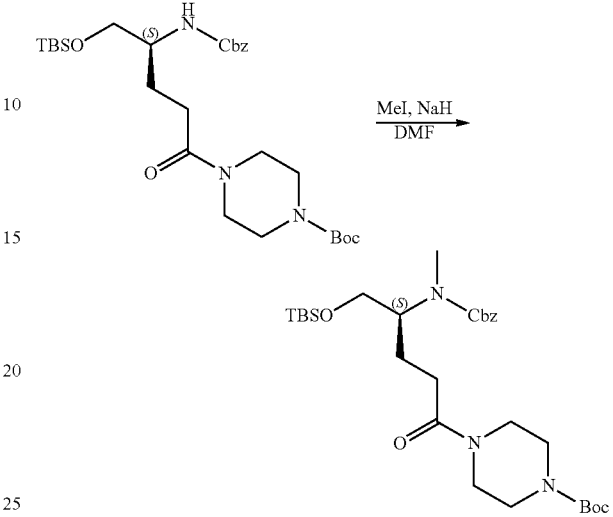

To a solution of (S)-tert-butyl 4-(4-(benzyloxycarbonylamino)-5-(tert-butyldimethylsilyloxy)pentanoyl)piperazine-1-carboxylate (32.3 g, 58.8 mmol) and iodomethane (7.3 mL, 117.6 mmol) in DMF (450 mL) was added solid sodium hydride (60%, 3.5 g, 88.2 mmol) at 0-5° C. The mixture was stirred at 0-5° C. for 30 min and quenched with saturated NH₄Cl solution. The mixture was concentrated to remove most of DMF under high vacuum. The residue was dissolved in EtOAc (700 mL). The organic mixture was washed with water and brine, dried over Na₂SO₄, filtered, and concentrated to give (S)-tert-butyl 4-(4-((benzyloxycarbonyl)(methyl)amino)-5-(tert-butyldimethylsilyloxy)pentanoyl)piperazine-1-carboxylate (34 g, crude), which was used without further purification. LRMS (M+H) m/z 564.3.

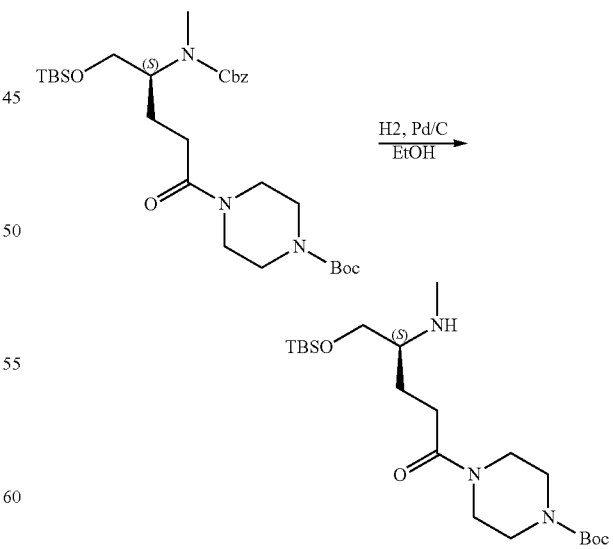

(S)-tert-butyl 4-(4-((benzyloxycarbonyl)(methyl)amino)-5-(tert-butyldimethylsilyloxy)pentanoyl)piperazine-1-carboxylate (21.5 g) and 10% Pd/C (2.2 g) in ethanol (100 mL) was charged with H₂ (50 psi). The resulting mixture was stirred at RT overnight and filtered. The filtrate was concentrated to give (S)-tert-butyl 4-(5-(tert-butyldimethylsilyloxy)-4-(methylamino)pentanoyl)piperazine-1-carboxylate (16 g, crude), which was sued without further purification. LRMS (M+H) m/z 430.3.

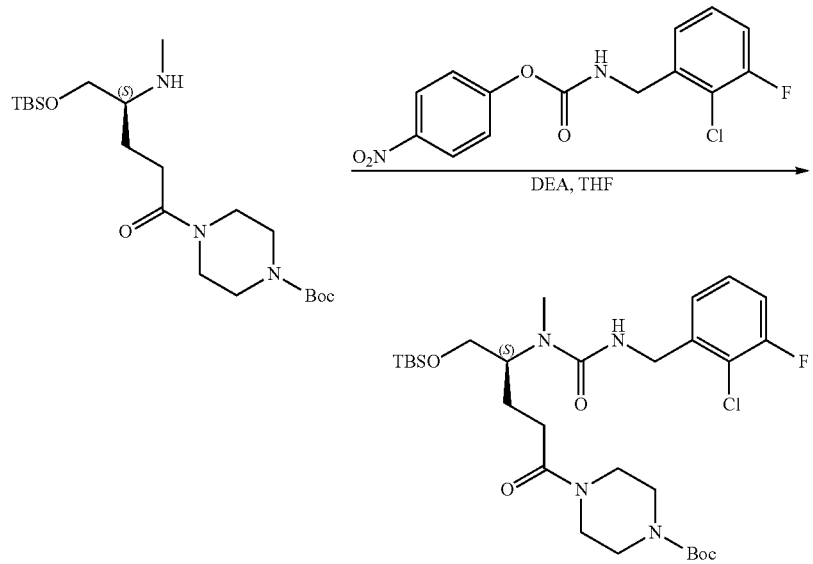

To a solution of (S)-tert-butyl 4-(5-(tert-butyldimethylsilyloxy)-4-(methylamino)pentanoyl)piperazine-1-carboxylate (16 g, 37.3 mmol) and DIEA (1.3 mL, 7.46 mmol) in THF (180 mL) was added 4-nitrophenyl 2-chloro-3-fluorobenzylcarbamate (12 g, 37.3 mmol). The reaction mixture was stirred at RT for 2 h and concentrated. The residue was purified on silica gel using a mixture of EtOAc and hexanes to give (S)-tert-butyl 4-(5-(tert-butyldimethylsilyloxy)-4-(3-(2-chloro-3-fluorobenzyl)-1-methylureido)pentanoyl)piperazine-1-carboxylate (14.3 g, 62.4% for three steps). LRMS (M+H) m/z 615.3.

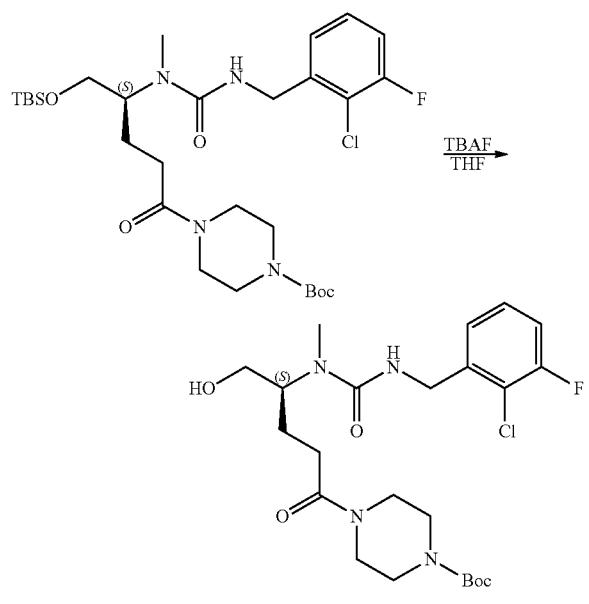

To a solution of (S)-tert-butyl 4-(5-(tert-butyldimethylsilyloxy)-4-(3-(2-chloro-3-fluorobenzyl)-1-methylureido)

pentanoyl)piperazine-1-carboxylate (14 g, 22.8 mmol) in THF (70 mL) was added TBAF (1M, 34.2 mL, 34.2 mmol). The reaction mixture was stirred at RT for 1 h and concentrated. The residue was dissolved in EtOAc (500 mL). The organic mixture was washed with 2% citric acid, NaOH (0.2 N), and brine, dried over $Na_2SO_4$, filtered, and concentrated to give (S)-tert-butyl 4-(4-(3-(2-chloro-3-fluorobenzyl)-1-methylureido)-5-hydroxypentanoyl)piperazine-1-carboxylate (12.1 g, crude), which was used without further purification. LRMS (M+H) m/z 501.2.

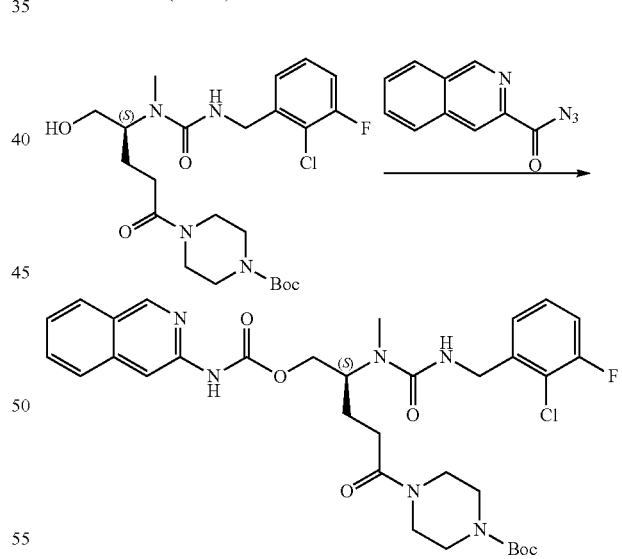

To a solution of (S)-tert-butyl 4-(4-(3-(2-chloro-3-fluorobenzyl)-1-methylureido)-5-hydroxypentanoyl)piperazine-1-carboxylate (11.2 g, 22.4 mmol) in toluene (110 mL) was added isoquinoline-3-carbonyl azide (4.7 g, 23.5 mmol). The reaction mixture was stirred at 100° C. for 30 min and concentrated. The residue was purified on silica gel column using a mixture of EtOAc and hexanes to give (S)-tert-butyl 4-(4-(3-(2-chloro-3-fluorobenzyl)-1-methylureido)-5-(isoquinolin-3-ylcarbamoyloxy)pentanoyl)piperazine-1-carboxylate (10.8 g, 72%). LRMS (M+H) m/z 671.3.

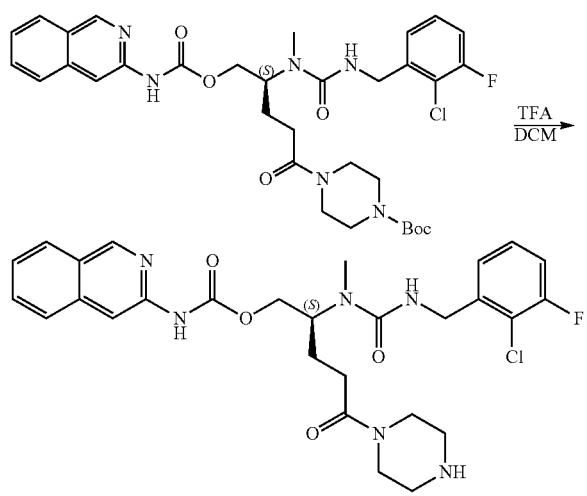

in DCM (200 mL) was added TFA (100 mL). The reaction mixture was stirred at RT for 3 h and concentrated. The residue was purified on silica gel column using a mixture of MeOH and DCM. The fractions were concentrated, dissolved in water (200 mL), neutralized to pH 8-9 with 1N NaOH, and extracted with EtOAc (300 mL×3). The organic layer was dried over $Na_2SO_4$, filtered, and concentrated to give (S)-2-(3-(2-chloro-3-fluorobenzyl)-1-methylureido)-5-oxo-5-(piperazin-1-yl)pentyl isoquinolin-3-ylcarbamate (14 g, 75%). LRMS (M+H) m/z 571.1.

Example 19

Preparation of (S)-2-((2-chloro-3-fluorobenzyl)(methyl)amino)-5-(4-isopropylpiperazin-1-yl)-5-oxopentyl isoquinolin-3-ylcarbamate

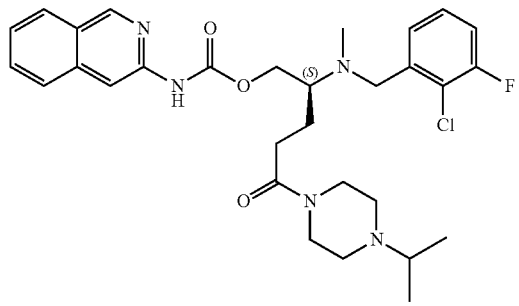

(S)-2-((2-chloro-3-fluorobenzyl)(methyl)amino)-5-(4-isopropylpiperazin-1-yl)-5-oxopentyl isoquinolin-3-ylcarbamate

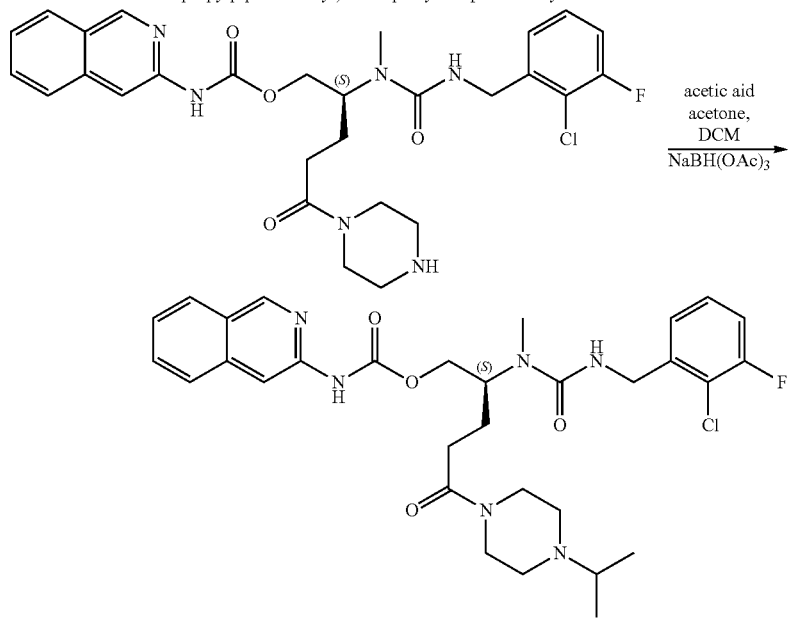

To a solution of (S)-tert-butyl 4-(4-(3-(2-chloro-3-fluorobenzyl)-1-methylureido)-5-(isoquinolin-3-ylcarbamoyloxy)pentanoyl)piperazine-1-carboxylate (22 g, 32.8 mmol)

To a solution of (S)-2-(3-(2-chloro-3-fluorobenzyl)-1-methylureido)-5-oxo-5-(piperazin-1-yl)pentyl isoquinolin-3-ylcarbamate (610 mg, 1.07 mmol) in acetone (1 mL) and DCM (1 mL) was added acetic acid (4 drops, ~0.2 mL). The reaction mixture was stirred at RT for 30 min. To this mixture was added solid NaBH(OAc)$_3$ and the resulting mixture was stirred at RT for 1 h and concentrated. The residue was purified on RP-HPLC using a mixture of acetonitrle and water (0.1% HCOOH buffer). The fractions was collected, concentrated to dryness, and re-dissolved in EtOAc. The organic mixture was washed with Na$_2$CO$_3$, dried over Na$_2$SO$_4$, filtered, and concentrated to give (S)-2-((2-chloro-3-fluorobenzyl)(methyl)amino)-5-(4-isopropylpiperazin-1-yl)-5-oxopentyl isoquinolin-3-ylcarbamate (540 mg, 82%) as white solid. LRMS (M+H$^+$) m/z 613.3.

Example 20

Preparation of Isoquinolin-3-yl-carbamic acid 2-[3-(2-chloro-3-fluoro-benzyl)-1-methyl-ureido]-3-(2,3-dihydroxy-propoxy)-propyl ester

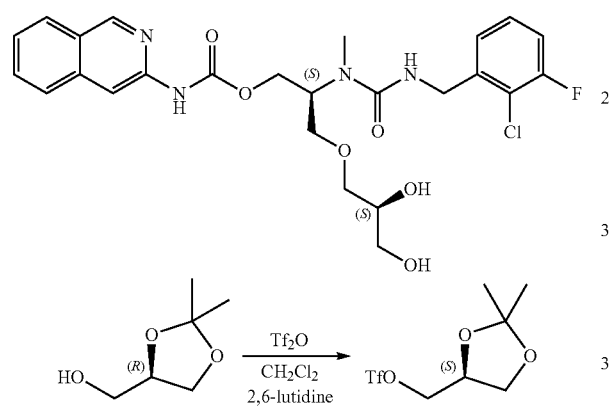

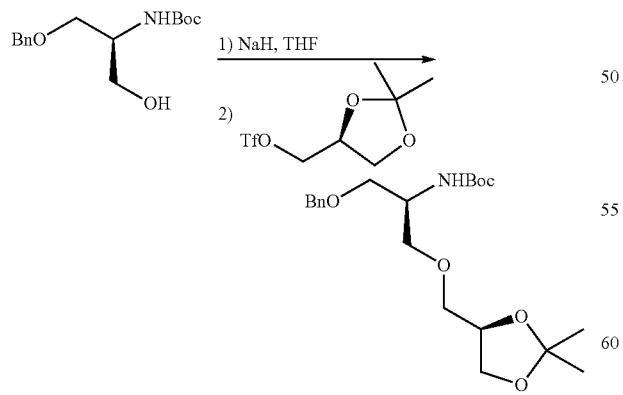

To a mixture of (R)-Solketal (1.85 g, 14.0 mmol), and 2,6-lutidine (2.47 mL, 14.7 mmol) in dichloromethane (45 mL) cooled to 0° C. was added triflic anhydride (4.14 g, 14.7 mmol). The resulting solution was stirred for 2 h at 0° C. then concentrated to give trifluoromethanesulfonic acid 2,2-dimethyl-[1,3]dioxolan-4-ylmethyl ester which was used without further purification.

To a solution of boc-D-serinol (1.33 g, 4.73 mmol) in THF was added sodium hydride (60%, 0.378 g, 9.46 mmol) at 0° C. The reaction mixture was stirred at 0° C. for 0.5 h then trifluoromethanesulfonic acid 2,2-dimethyl-[1,3]dioxolan-4-ylmethyl ester was slowly added over 5 min at 0° C. Once addition was complete reaction was warmed to room temperature and allowed to stir for 2 h. After 2 h, the reaction mixture was cooled to 0° C. and 4 mL of H$_2$O were added. Reaction mixture was then concentrated and the resulting residue was dissolved in EtOAc (200 mL). The organic layer was then washed with 1 M KHSO$_4$, saturated aq. NaHCO$_3$, brine, and dried over Na$_2$SO$_4$. Concentration of the organic layer afforded a yellow oil which was purified on silica gel column using a mixture of hexanes and EtOAc to give [2-benzyloxy-1-(2,2-dimethyl-[1,3]dioxolan-4-ylmethoxymethyl)-ethyl]-carbamic acid tert-butyl ester as a colorless oil (1.39 g, 72%). LRMS (M-Boc+H$^+$) m/z 296.1.

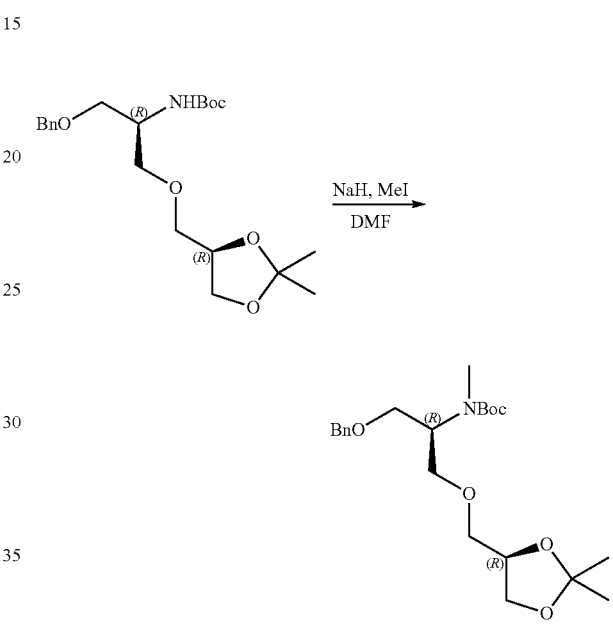

To a solution of [2-Benzyloxy-1-(2,2-dimethyl-[1,3]dioxolan-4-ylmethoxymethyl)-ethyl]-carbamic acid tert-butyl ester (1.26 g, 3.18 mmol) in DMF (10 mL) was added sodium hydride (60%, 0.19 g, 4.78 mmol) at 0° C. in one portion. The reaction was stirred at 0° C. for 0.5 h then MeI (1.36 g, 9.56 mmol) was added. The reaction mixture was then stirred at 0° C. for 3 h at which time the LC-MS showed the reaction was complete. The reaction was quenched with saturated aq. NH$_4$Cl solution and extracted with EtOAc (2×100 mL). The organic layer was then washed with water, brine and dried over Na$_2$SO$_4$. The organic layers were concentrated to give [2-benzyloxy-1-(2,2-dimethyl-[1,3]dioxolan-4-yl-methoxymethyl)-ethyl]-methyl-carbamic acid tert-butyl ester (1.25 g, 96%). LRMS (M-Boc+H$^+$) m/z 310.1.

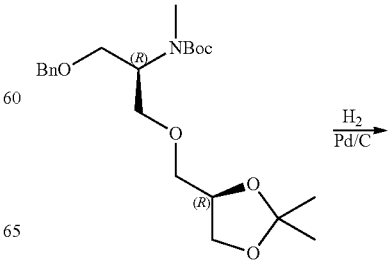

381
-continued

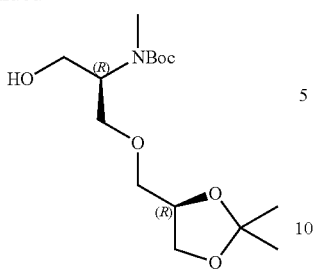

To a solution of crude [2-Benzyloxy-1-(2,2-dimethyl-[1,3]dioxolan-4-ylmethoxymethyl)-ethyl]-methyl-carbamic acid tert-butyl ester (1.25 g, 3.06 mmol) in MeOH (10 mL) was added Pd/C (300 mg). The mixture was transferred to an autoclave reactor, charged with 55 psi of hydrogen, and stirred. After 1.5 h, LCMS analysis indicated the completion of the reaction. The reaction mixture was then filtered through celite and concentrated under reduced pressure to give [1-(2,2-dimethyl-[1,3]dioxolan-4-ylmethoxymethyl)-2-hydroxy-ethyl]-methyl-carbamic acid tert-butyl ester (0.875 g, 95%), which was used without purification. LRMS (M-Boc+H$^+$) m/z 220.2.

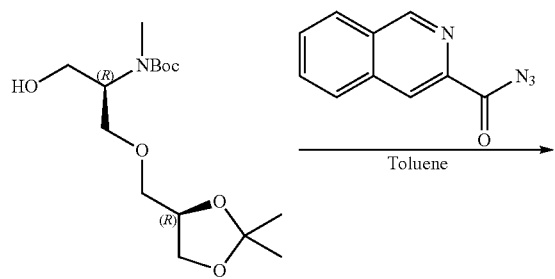

382
-continued

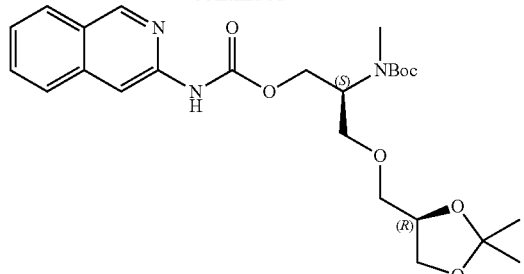

Isoquinoline-3-carbonyl azide (2.36 g, 11.9 mmol) was added to a solution of [1-(2,2-Dimethyl-[1,3]dioxolan-4-ylmethoxymethyl)-2-hydroxy-ethyl]methyl-carbamic acid tert-butyl ester (3.80 g, 11.9 mmol) in toluene (200 mL) were added isoquinoline-3-carbonyl azide (2.36 g, 11.9 mmol, 1.0 equiv). The reaction mixture was heated to 100° C. for 1 h and then concentrated. Purification on silica gel column using a mixture of hexanes and EtOAc to give isoquinolin-3-yl-carbamic acid 2-(tert-butoxycarbonyl-methyl-amino)-3-(2,2-dimethyl-[1,3]dioxolan-4-ylmethoxy)-propyl ester (2.9 g, 50%). LRMS (M-Boc+H$^+$) m/z 390.2.

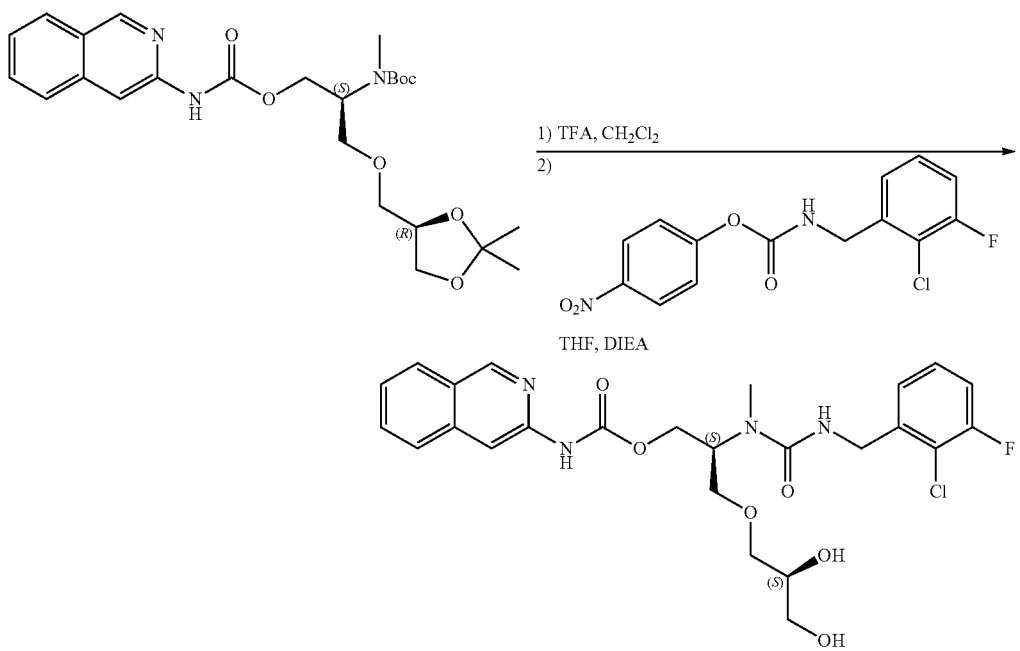

To a solution of Isoquinolin-3-yl-carbamic acid 2-(tert-butoxycarbonyl-methyl-amino)-3-(2,2-dimethyl-[1,3]-dioxolan-4-ylmethoxy)-propyl ester (2.9 g, 5.93 mmol) in DCM (200 mL) was added TFA (12 mL) at 0° C. The mixture was stirred for 2 h, concentrated under reduced pressure, and re-dissolved in THF (10 mL) and DIEA (6.6 mL, 37.8 mmol). To this THF solution was added pre-stirred solution of 4-nitrophenylchloroformate (1.33 g, 6.62 mmol), 2-chloro-3-fluorobenzylamine (1.0 g, 6.3 mmol), and DIEA (1.2 mL, 6.9 mmol) in THF (85 mL) at 0° C. The reaction mixture was stirred for 2 h allowing the reaction to gradually warm to 24° C. The mixture was concentrated under reduced pressure, re-dissolved in MeOH, filtered, and purified by RP-HPLC using a mixture of acetonitrile and H$_2$O to give isoquinolin-3-yl-carbamic acid 2-[3-(2-chloro-3-fluoro-benzyl)-1-methyl-ureido]-3-(2,3-dihydroxy-propoxy)-propyl ester (1.1 g, 45% over two steps). LRMS (M+H$^+$) m/z 535.1.

Example 21

Preparation of Isoquinolin-3-yl-carbamic acid 2-[3-(2-chloro-3-fluoro-benzyl)-1-methyl-ureido]-3-(2-hydroxy-3-phosphonooxy-propoxy)-propyl ester

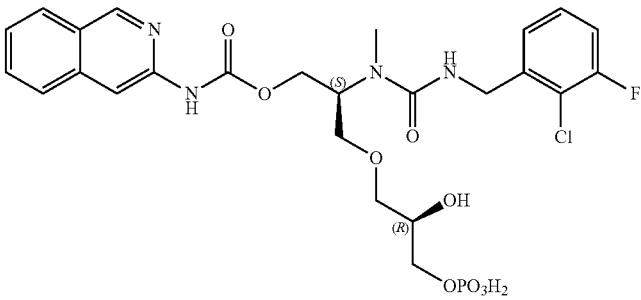

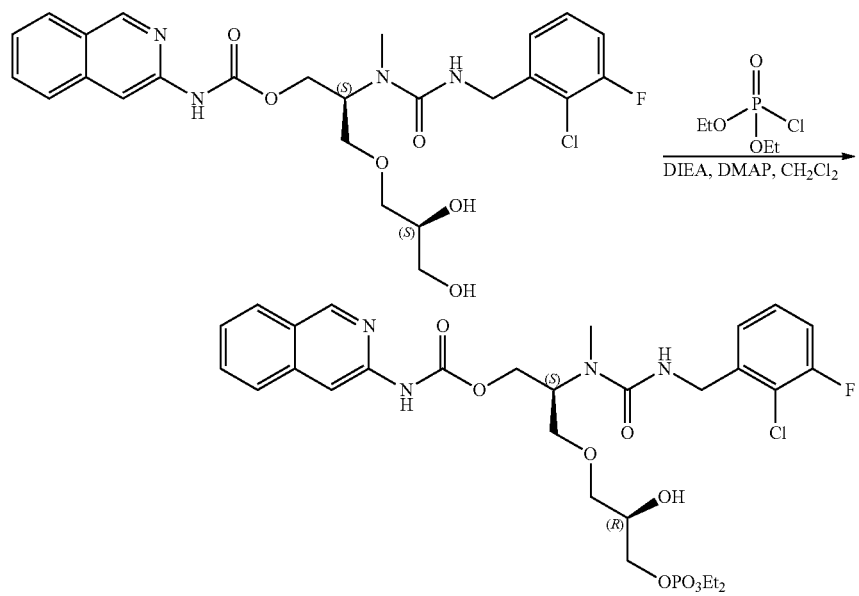

To a mixture of isoquinolin-3-yl-carbamic acid 2-[3-(2-chloro-3-fluoro-benzyl)-1-methyl-ureido]-3-(2,3-dihydroxy-propoxy)-propyl ester (1.2 g, 2.25 mmol), DIEA (1.56 mL, 9.0 mmol) and DMAP (1.11 g, 9.0 mmol.) in anhydrous DCM (250 mL) was added diethyl chlorophorophosphate (1.3 mL, 9.0 mmol) at 0° C. After stirring the reaction at 0° C. for 10 min, LC/MS analysis revealed the reaction was complete. The reaction was quenched with MeOH (80 mL). The mixture was then concentrated and the resulting residue was dissolved in EtOAc (200 mL). The organic layer was washed with saturated aq. $NaHCO_3$, water, brine and concentrated. The resulting residue was purified on RP-HPLC using a mixture of acetonitrile and $H_2O$ to give isoquinolin-3-yl-carbamic acid 2-[3-(2-chloro-3-fluoro-benzyl)-1-methyl-ureido]-3-[3-(diethoxy-phosphoryloxy)-2-hydroxy-propoxy]-propyl ester (601 mg, 47%). LRMS (M+H$^+$) m/z 671.2.

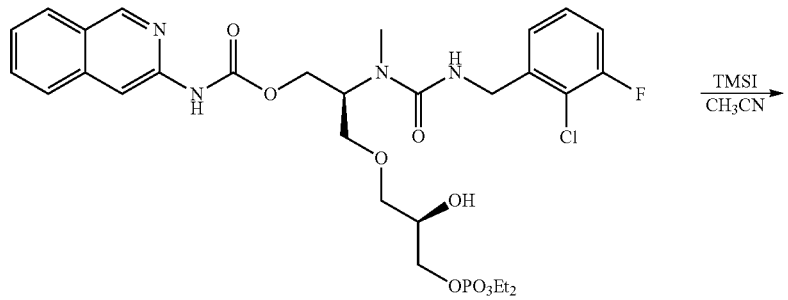

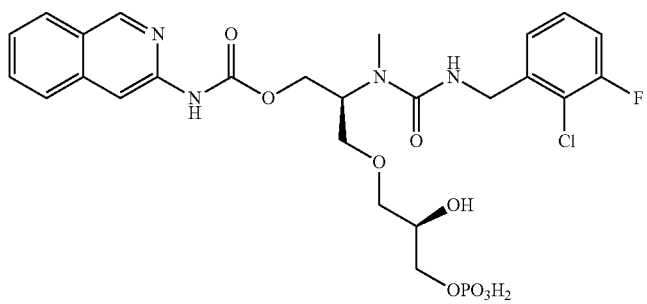

To a solution of Isoquinolin-3-yl-carbamic acid 2-[3-(2-chloro-3-fluoro-benzyl)-1-methyl-ureido]-3-[3-(diethoxy-phosphoryloxy)-2-hydroxy-propoxy]-propyl ester (0.60 g, 0.895 mmol) in acetonitrile (30 mL) was added TMSI (1.43 g, 7.16 mmol) dropwise at 0° C. After stirring at 0° C. for 4.5 h, the reaction was quenched with EtOH. The solvent was removed, and the resulting residue was purified on RP-HPLC using a mixture of acetonitrile and $H_2O$ (0.1% TFA buffer) to give isoquinolin-3-yl-carbamic acid 2-[3-(2-chloro-3-fluoro-benzyl)-1-methyl-ureido]-3-(2-hydroxy-3-phosphonooxy-propoxy)-propyl ester (396 mg, 73%). LRMS [M−H]$^+$ m/z 613.5

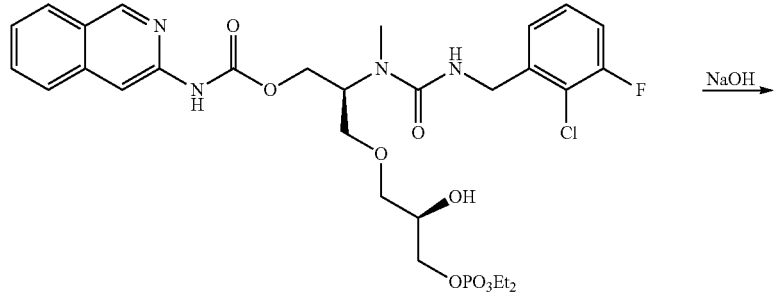

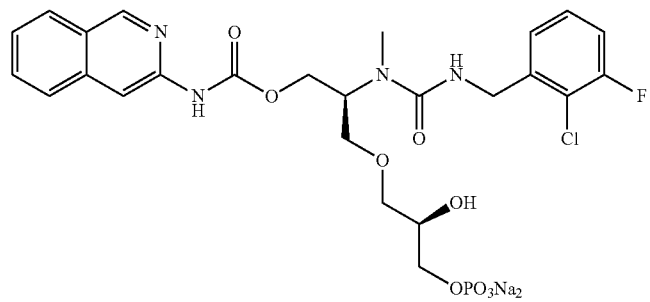

To a solution of Isoquinolin-3-yl-carbamic acid 2-[3-(2-chloro-3-fluoro-benzyl)-1-methyl-ureido]-3-(2-hydroxy-3-phosphonooxy-propoxy)-propyl ester (0.15 g, 0.238 mmol) in MeOH (50 mL) was added 0.1 M NaOH (12.8 mL, 1.28 mmol, at 0° C. (Note: pH was monitored closely making sure not to raise pH above 8). After stirring at 0° C. for 1 h, the solvent was removed and the resulting residue was dissolved in 4 mL of $H_2O$. The solution was then frozen in a dry-ice bath and placed under high vacuum until all the $H_2O$ is removed to give isoquinolin-3-yl-carbamic acid 2-[3-(2-chloro-3-fluoro-benzyl)-1-methyl-ureido]-3-(2-hydroxy-3-phosphonooxy-propoxy)-propyl ester disodium salt (410 mg). LRMS (M−2Na+3H$^+$) m/z 613.5.

Example 22

Preparation of Isoquinolin-3-yl-carbamic acid 2-[3-(2-chloro-3-fluoro-benzyl)-1-methyl-ureido]-5-(4-methyl-piperazin-1-yl)-pentyl ester

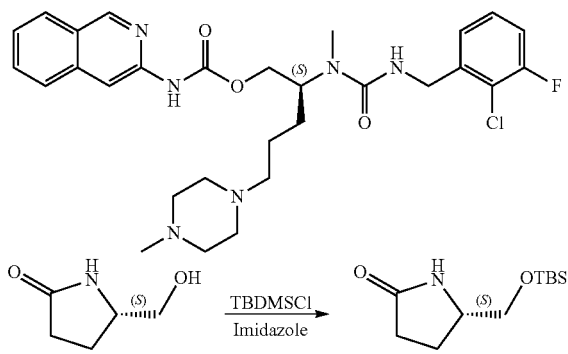

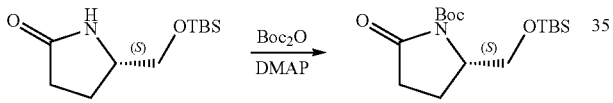

To a solution of 5-hydroxymethyl-pyrrolidin-2-one (20 g, 0.174 mol) in DMF (100 mL) was added imidazole (17.7 g, 0.260 mol) followed by TBDMSCl (27.5 g, 0.182 mol). After 2.5 h, LCMS analysis revealed reaction was complete. EtOAc (600 mL) and brine (300 mL) were added to the reaction solution. The aqueous layer was further extracted with EtOAc (2×350 mL). The combined organic layers were washed with brine, dried, and concentrated to give 5-(tert-butyl-dimethyl-silanyloxymethyl)-pyrrolidin-2-one (39.5 g) as a light yellow oil which was used in the next step without further purification. LRMS (M+H$^+$) m/z 230.1.

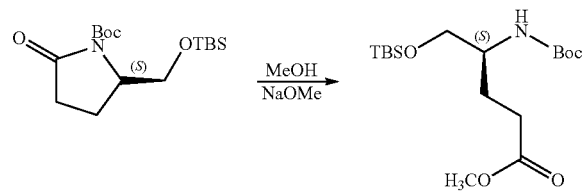

To a solution of 5-(tert-butyl-dimethyl-silanyloxymethyl)-pyrrolidin-2-one (39.5 g of crude material, 173.7 mmol) in CH$_3$CN (570 mL) was added Boc$_2$O (41.7 g, 0.238 mol) and DMAP (2.11 g, 17.4 mmol). The mixture was stirred for 14 h at 24° C. The organic solvent was removed affording an oil which was purified on silica gel column using a mixture of hexanes and EtOAc to give 2-(tert-butyl-dimethyl-silanyloxymethyl)-5-oxo-pyrrolidine-1-carboxylic acid tert-butyl ester (50.9 g, 89% over two steps). LRMS (M-Boc+H$^+$) m/z 230.1.

To a solution of 2-(tert-butyl-dimethyl-silanyloxymethyl)-5-oxo-pyrrolidine-1-carboxylic acid tert-butyl ester (50.2, 0.152 mmol in MeOH (500 mL) was added NaOMe (30% in MeOH, 12 mL) and stirred at 24° C. After 1 h, LCMS analysis indicated reaction was complete. The reaction mixture was then treated with saturated aq. NH$_4$Cl (15 mL) and concentrated. The resulting residue was purified on silica gel column using a mixture of hexanes and EtOAc to give 4-tert-butoxycarbonylamino-5-(tert-butyl-dimethyl-silanyloxy)-pentanoic acid methyl ester (46.8 g, 85%). LRMS (M-Boc+H$^+$) m/z 262.2.

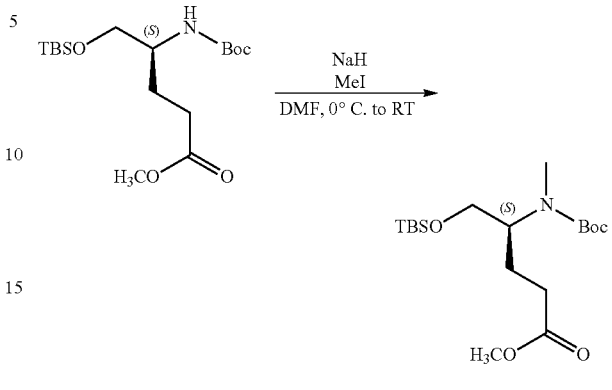

To a solution of (S)-tert-butyl 1-(tert-butyldimethylsilyloxy)pent-4-en-2-ylcarbamate (20 g, 55.0 mmol) and MeI (6.22 mL, 99.7 mmol) in DMF (700 mL) was added sodium hydride (60%, 3.1 g, 77.6 mmol) at 0° C. The reaction was stirred at 0° C. for 2 h then warmed to 10° C. for an additional 2 h at which point LC-MS analysis showed the reaction was complete. The reaction was quenched with saturated aq. NH$_4$Cl solution (800 mL) and EtOAc (2 L). Water was then added to dissolve the solids. The organic layer was washed with water, brine, and dried over Na$_2$SO$_4$. The resulting residue was purified on silica gel column using a mixture of hexanes and EtOAc to give (S)-tert-butyl 1-(tert-butyldimethylsilyloxy)pent-4-en-2-yl(methyl)carbamate (16.9 g, 81%). LRMS (M+H$^+$) m/z 230.2.

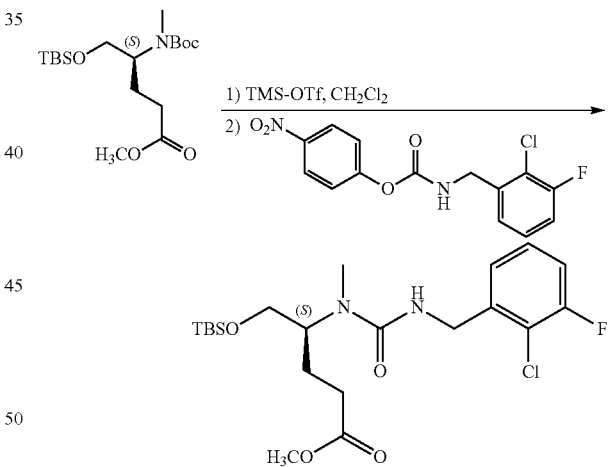

To a solution of (S)-tert-butyl 1-(tert-butyldimethylsilyloxy)pent-4-en-2-yl(methyl)carbamate (91.0 g, 242.6 mmol) in DCM (750 mL) was added TMSOTf (87.8 mL, 485.2 mmol) at 0° C. The mixture was stirred for 1 h, and then poured into saturated aq. NH$_4$Cl (1 L) and CH$_2$Cl$_2$ (1 L) (Note: water (700 mL) was added to dissolve salts). The organic layer was then washed with brine, dried over Na$_2$SO$_4$ and concentrated under reduced pressure. The resulting residue was re-dissolved in THF (300 mL) and DIEA (84.5 mL, 485.2 mmol). To this THF solution was added a pre-stirred solution of 4-nitrophenylchloroformate (56.3 g, 279.0 mmol), 2-chloro-3-fluorobenzylamine (46.5 g, 291.1 mmol), and DIEA (50.7 mL, 291.1 mmol) in THF (1.1 L) at 0° C. The reaction mixture was stirred for 2 h allowing the reaction to gradually warm to 24° C. at which point the LCMS analysis revealed reaction completion. The mixture was concentrated under reduced pressure and purified on silica gel column using a mixture of hexanes and EtOAc to give 5-(tert-butyl-dimethyl-silanyloxy)-4-[3-(2-chloro-3-fluoro-benzyl)-1-methyl-ureido]-pentanoic acid methyl ester (73.1 g, 65% over two steps). LRMS (M+H$^+$) m/z 461.1.

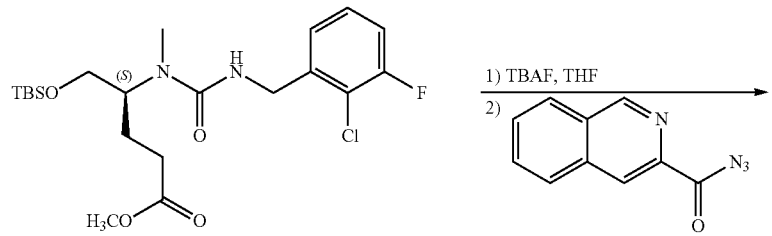

To a solution of 5-(tert-Butyl-dimethyl-silanyloxy)-4-[3-(2-chloro-3-fluoro-benzyl)-1-methyl-ureido]-pentanoic acid methyl ester (21.0 g, 45.6 mmol) in THF (450 mL) was slowly added TBAF (1 M in THF, 68.4 mL, 68.4 mmol). The reaction was stirred at 24° C. for 1 h. THF was removed. The residue was diluted with EtOAc (600 mL) and washed with saturated aq. NH$_4$Cl and brine. The organic layers were dried over Na$_2$SO$_4$ and concentrated. The resulting residue was dissolved in toluene and added into a toluene solution of isoquinoline-3-carbonyl azide (9.07 g, 45.6 mmol) at 100° C. The reaction mixture was heated to 100° C. for 1 h and then concentrated. Resulting residue was purified on silica gel column using hexanes and EtOAc to give 4-[3-(2-chloro-3-fluoro-benzyl)-1-methyl-ureido]-5-(isoquinolin-3-ylcarbamoyloxy)-pentanoic acid methyl ester (16.8 g, 71%) as a colorless oil. LRMS (M+H$^+$) m/z 517.1.

To a solution of 4-[3-(2-chloro-3-fluoro-benzyl)-1-methyl-ureido]-5-(isoquinolin-3-ylcarbamoyloxy)-pentanoic acid methyl ester (80 mg, 0.15 mmol) in THF (100 mL) was added DiBAL-H (1 M in heptanes, 12.2 mL, 12.2 mmol) dropwise at −78° C. The reaction was stirred at −78° C. for 2 h at which point another DiBAL-H aliquot (1 M in heptanes, 12.2 mL, 12.2 mmol) was added again. The reaction was stirred at −78° C. for 2 h and then NaBH$_4$ (0.33 g. 8.72 mmol) was added at −78° C. The reaction was stirred for an additional 2 h allowing the reaction to slowly warm to −20° C. then MeOH (20 mL) was added. The reaction mixture was then concentrated, re-dissolved in EtOAc, and washed with 0.5 N aq. HCl and brine. The organic layer was then dried over Na$_2$SO$_4$ and concentrated. The resulting residue was purified on silica gel column using CH$_2$Cl$_2$ and MeOH to give Isoquinolin-3-yl-carbamic acid 2-[3-(2-chloro-3-fluoro-benzyl)-1-methyl-ureido]-5-hydroxy-pentyl ester as a colorless oil (2.1 g, 74%). LRMS [M+H]$^+$ m/z 489.1.

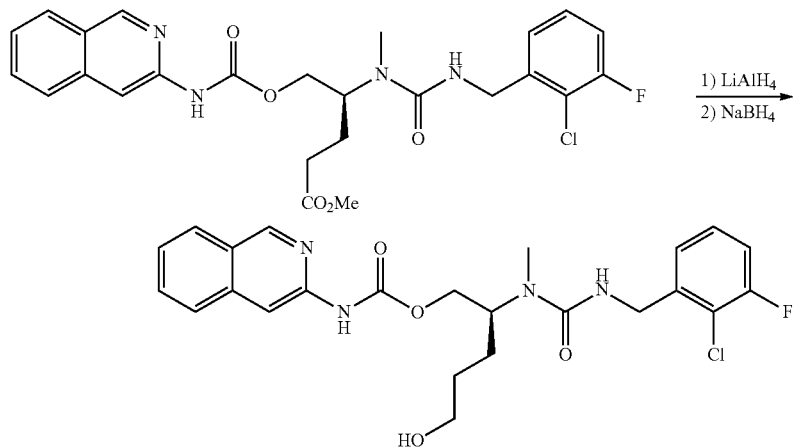

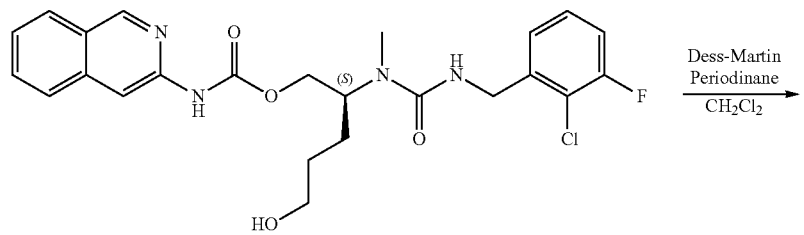

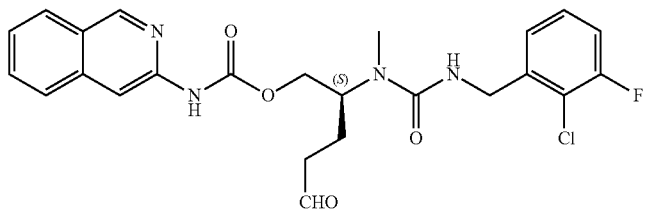

To a solution of Dess-Martin periodinane (2.40 g, 5.65 mmol) in anhydrous CH$_2$Cl$_2$ (100 mL) was added isoquinolin-3-yl-carbamic acid 2-[3-(2-chloro-3-fluoro-benzyl)-1-methyl-ureido]-5-hydroxy-pentyl ester (2.40 g, 4.92 mmol) at RT After 20 min at 24° C., the reaction was analyzed by LC/MS revealing reaction completion. The reaction was quenched with saturated aq. NaHCO$_3$ and 1N aq. Na$_2$S$_2$O$_3$ (40 mL each) and stirred for 0.5 h. The organic layer was separated washed brine, dried over Na$_2$SO$_4$ and then concentrated. The resulting residue was isoquinolin-3-yl-carbamic acid 2-[3-(2-chloro-3-fluoro-benzyl)-1-methyl-ureido]-5-oxo-pentyl ester which was used without further purification (2.37 g crude). LRMS (M+H$^+$) m/z 487.1.

ester (2.37 g crude mixture, 4.92 mmol) in anhydrous DCE (5 mL) and AcOH 1 (1 mL) was added N-methyl piperazine (0.573 mL, 5.16 mmol) at RT After 3 h of stirring at RT, sodium triacetoxyborohydride (4.17 g, 19.7 mmol) was added in one portion followed by 10 mL DCE. The mixture was stirred for 2 h at RT, the diluted in CH$_2$Cl$_2$ and washed with aq. NaHCO$_3$ and brine. After drying the solution over Na$_2$SO$_4$, the reaction mixture was concentrated and the resulting residue was purified on RP-HPLC using a mixture of acetonitrile and H$_2$O with a TFA Buffer. The purified fractions were concentrated, redissolved in EtOAc and washed with saturated aq. NaHCO$_3$. Removal of the solvent afforded isoquinolin-3-yl-carbamic acid 2-[3-(2-chloro-3-fluoro-benzyl)-1-methyl-ureido]-5-(4-methyl-piperazin-1-

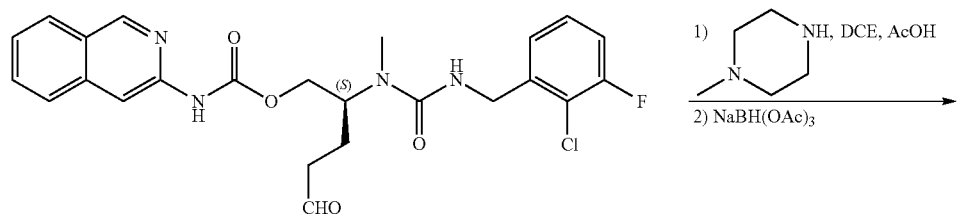

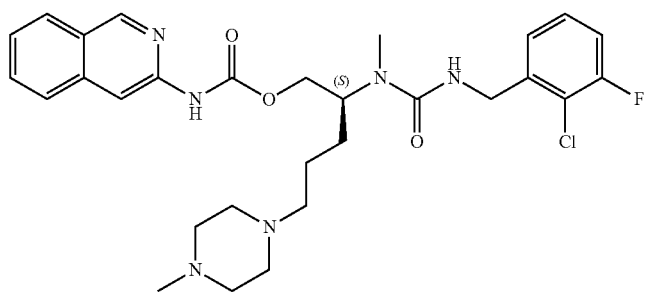

To a solution of isoquinolin-3-yl-carbamic acid 2-[3-(2-chloro-3-fluoro-benzyl)-1-methyl-ureido]-5-oxo-pentyl yl)-pentyl ester as the free base (1.43 g, 51%) LRMS (M+H$^+$) m/z 571.3.

Example 23

Preparation of Isoquinolin-3-yl-carbamic acid 2-[3-(2-chloro-3-fluoro-benzyl)-1-methyl-ureido]-5-(5,6-dihydro-8H-[1,2,4]triazolo[4,3-a]pyrazin-7-yl)-pentyl ester

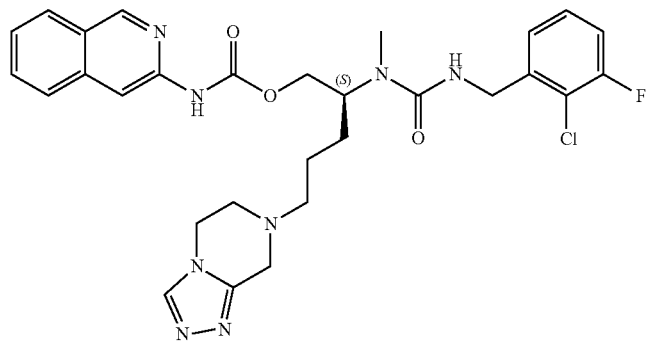

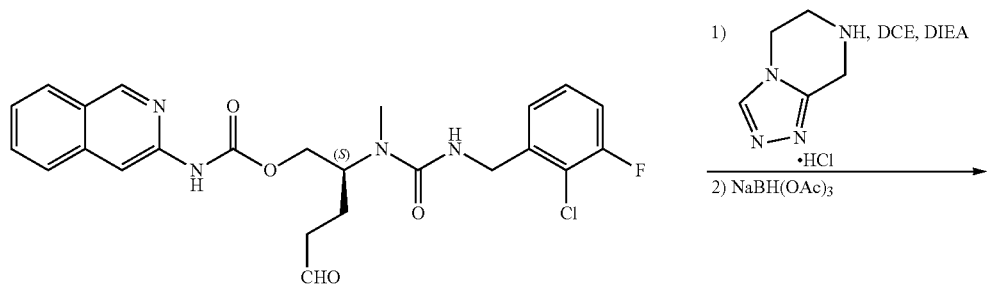

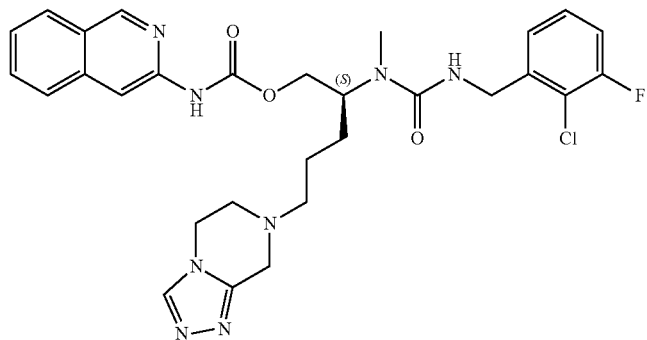

To a solution of isoquinolin-3-yl-carbamic acid 2-[3-(2-chloro-3-fluoro-benzyl)-1-methyl-ureido]-5-oxo-pentyl ester (75 mg crude mixture, 0.15 mmol) in anhydrous DCE (2 mL) and DIEA (56 uL, 0.32 mmol) was added the triazolopiperazine HCl salt (27 mg, 0.17 mmol) at RT. After 5 min of stirring at RT, sodium triacetoxyborohydride (98 mg, 0.45 mmol) was added in one portion. The slurry was stirred for 16 h at RT, the diluted in $CH_2Cl_2$ and washed with saturated aq. $NaHCO_3$ and brine. After drying the solution over $Na_2SO_4$, the reaction mixture was concentrated and the resulting residue was purified on RP-HPLC using a mixture of acetonitrile and $H_2O$ to give isoquinolin-3-yl-carbamic acid 2-[3-(2-chloro-3-fluoro-benzyl)-1-methyl-ureido]-5-(5,6-dihydro-8H-[1,2,4]triazolo[4,3-a]pyrazin-7-yl)-pentyl ester (30 mg, 30%) LRMS (M+H$^+$) m/z 595.2.

Example 24

Preparation of Isoquinolin-3-yl-carbamic acid 2-[3-(2-chloro-3-fluoro-benzyl)-1-methyl-ureido]-5-(2-oxo-piperazin-1-yl-pentyl ester

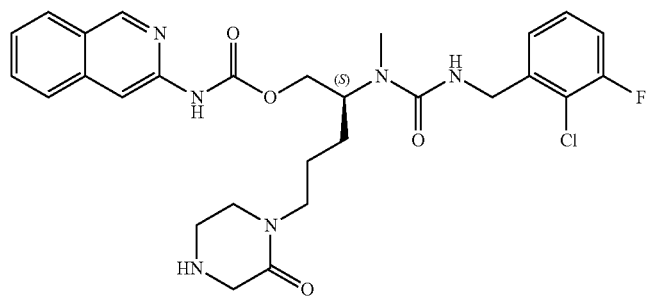

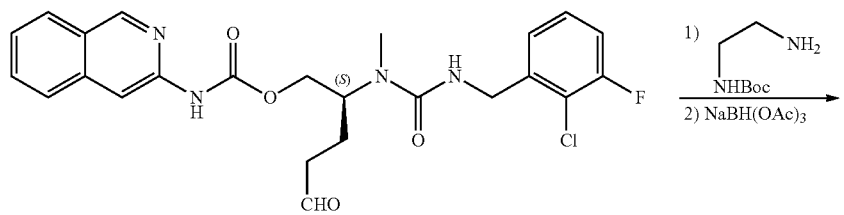

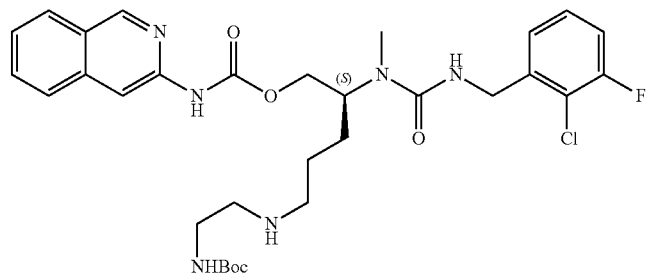

To a solution of isoquinolin-3-yl-carbamic acid 2-[3-(2-chloro-3-fluoro-benzyl)-1-methyl-ureido]-5-oxo-pentyl ester (0.8 g crude mixture, 1.64 mmol) in anhydrous DCE (3 mL) and AcOH (0.1 mL) was added (2-Amino-ethyl)-carbamic acid tert-butyl ester at 24° C. After 10 h of stirring at 24° C., sodium triacetoxyborohydride (1.05 g, 4.92 mmol) was added in one portion. The slurry was stirred for 2 h at 24° C., quenched with methanol and concentrated. The resulting residue was purified on RP-HPLC using a mixture of acetonitrile and $H_2O$ to give isoquinolin-3-yl-carbamic acid 5-(2-tert-butoxycarbonylamino-ethylamino)-2-[3-(2-chloro-3-fluoro-benzyl)-1-methyl-ureido]-pentyl ester (0.25 g, 25%) LRMS (M+H$^+$) m/z 631.2.

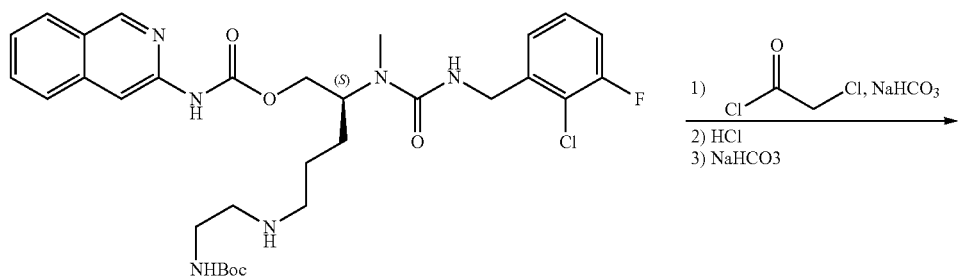

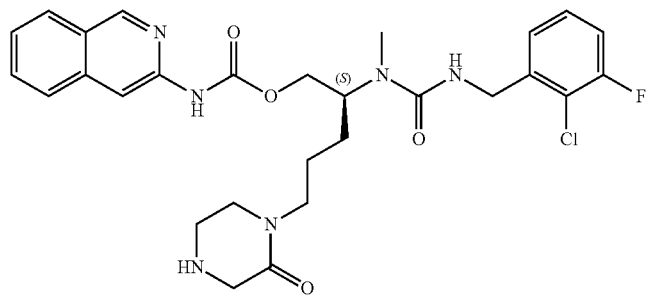

To a solution of isoquinolin-3-yl-carbamic acid 5-(2-tert-butoxycarbonylamino-ethylamino)-2-[3-(2-chloro-3-fluoro-benzyl)-1-methyl-ureido]-pentyl ester (0.25 g, 0.40 mmol) in EtOAc (5 mL) and saturated aq. NaHCO$_3$ (4 mL) was added chloroacetyl chloride (49 mg, 0.43 mmol) at 0° C. After 2 h of stirring at 0° C., phases were separated and organic layers were washed with brine and concentrated, and the resulting residue was re-dissolved in 3 mL of MeOH and treated with 4 M HCl in MeOH (0.105 mL, 0.42 mmol) at 0° C. The mixture was stirred for 2 h at 0° C., and then solid NaHCO$_3$ (150 mg) was added. After stiffing at 0° C. for another 2 h, the reaction mixture was concentrated and taken up in EtOAc. The resulting organic mixture was washed with brine and dried over Na$_2$SO$_4$, and concentrated. The resulting residue was purified on RP-HPLC using a mixture of acetonitrile and H$_2$O (0.1% TFA buffer). The purified fractions were concentrated, redissolved in EtOAc and washed with saturated aq. NaHCO$_3$. Removal of the solvent afforded isoquinolin-3-yl-carbamic acid 2-[3-(2-chloro-3-fluoro-benzyl)-1-methyl-ureido]-5-(2-oxo-piperazin-1-yl)-pentyl ester as the free base (37 mg, 17%) LRMS (M+H$^+$) m/z 571.2.

Example 25

Preparation of (S)-2-(3-(2-chloro-3-fluorobenzyl)-1-methylureido)-3-(1H-imidazol-4-yl)propyl 6-fluoroisoquinolin-3-ylcarbamate

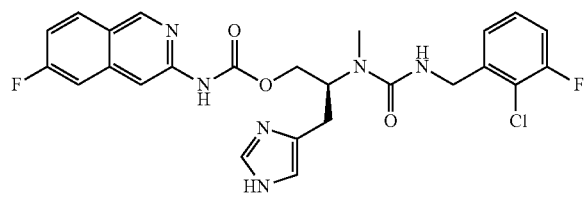

(S)-2-(3-(2-chloro-3-fluorobenzyl)-1-methylureido)-3-(1H-imidazol-4-yl)propyl 6-fluoroisoquinolin-3-ylcarbamate

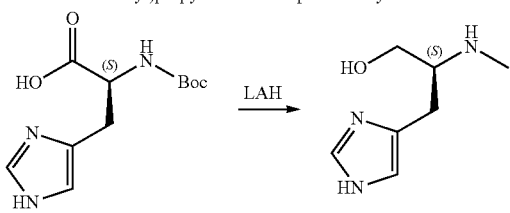

To a solution of (S)-2-(tert-butoxycarbonylamino)-3-(1H-imidazol-4-yl)propanoic acid (1.0 g, 3.92 mmol) in THF (20 mL) was added LAH (2 M, 10 mL, 20 mmol) at 0-5° C. The reaction mixture was stirred at 0-5° C. for 30 min and heat to reflux for 2 h. The reaction mixture was cooled to 0-5° C. and quenched with water (0.8 mL), NaOH (0.8 mL), and water (2.4 mL). The resulting suspension was stirred RT for 30 min and filtered. The filtrate was concentrated to give (S)-3-(1H-imidazol-4-yl)-2-(methylamino)propan-1-ol (400 mg, crude), which was used without further purification. LRMS (M-Boc+H$^+$) m/z 156.1.

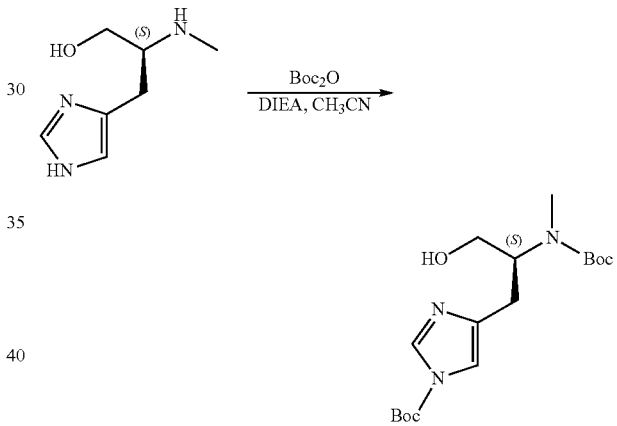

To a solution of (S)-3-(1H-imidazol-4-yl)-2-(methylamino)propan-1-ol (3.92 mmol) in acetonitrile (10 mL) were added Boc$_2$O (1.6 g, 7.34 mmol) and DIEA (1.5 mL, 9.06 mmol). The reaction mixture was stirred at RT for 1 h and concentrated to dryness. The residue was purified on silica gel column using a mixture of EtOAc and hexanes to give (S)-tert-butyl 4-(2-(tert-butoxycarbonyl(methyl)amino)-3-hydroxypropyl)-1H-imidazole-1-carboxylate (260 mg, 19% for two steps). LRMS (M+H$^+$) m/z 356.5.

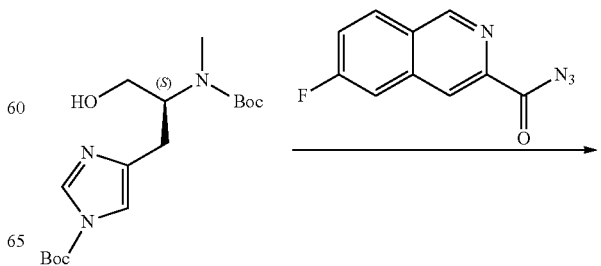

-continued

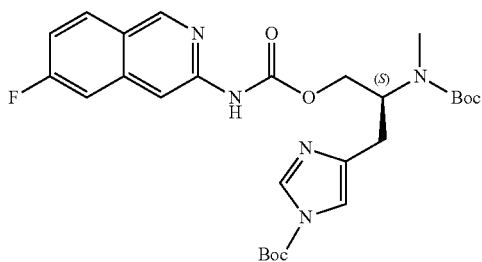

To a solution of (S)-tert-butyl 4-(2-(tert-butoxycarbonyl(methyl)amino)-3-hydroxypropyl)-1H-imidazole-1-carboxylate (260 mg, 0.73 mmol) in toluene (10 mL) was added 6-fluoro-isoquinoline-3-carbonyl azide (174 mg, 0.81 mmol). The reaction mixture was stirred at 100° C. for 30 min, cooled to RT, and concentrated under reduced pressure. The residue was purified on silica gel column using a mixture of EtOAc and hexanes to give (S)-tert-butyl 4-(2-(tert-butoxycarbonyl(methyl)amino)-3-(6-fluoroisoquinolin-3-ylcarbamoyloxy)propyl)-1H-imidazole-1-carboxylate (280 mg, 71%). LRMS (M+H$^+$) m/z 544.2.

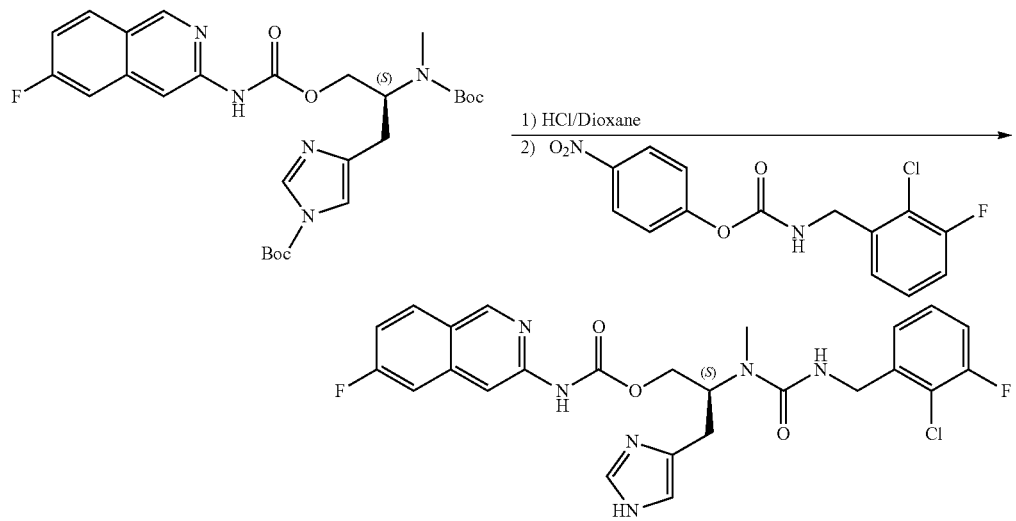

To a solution of (S)-tert-butyl 4-(2-(tert-butoxycarbonyl(methyl)amino)-3-(6-fluoroisoquinolin-3-ylcarbamoyloxy)propyl)-1H-imidazole-1-carboxylate (280 mg, 0.51 mmol) in THF (10 mL) was added HCl (4 N in 1,4-dioxane, 2.55 mL, 10.2 mmol). The reaction mixture was stirred at RT for 1 h and concentrated to dryness. The residue was suspended in THF (20 mL). To the suspension were added DIEA (0.27 mL, 1.53 mmol) and 4-nitrophenyl 2-chloro-3-fluorobenzylcarbamate (166 mg, 0.51 mmol). The reaction mixture was stirred at RT for 2 h and concentrated to dryness. The residue was purified on RP-HPLC using a mixture of acetonitrile and water to give (S)-2-(3-(2-chloro-3-fluorobenzyl)-1-methylureido)-3-(1H-imidazol-4-yl)propyl 6-fluoroisoquinolin-3-ylcarbamate (35 mg, 13%). LRMS (M+H$^+$) m/z 529.5.

Example 26

Preparation of (S)-2-((2-chloro-3-fluorobenzyl)(methyl)amino)-3-(pyridin-2-yl)propyl isoquinolin-3-ylcarbamate

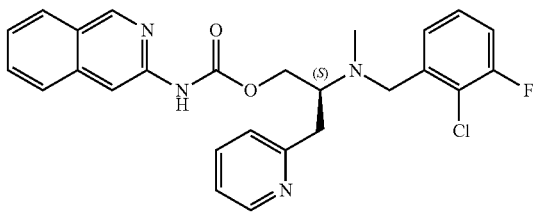

(S)-2-((2-chloro-3-fluorobenzyl)(methyl)amino)-3-(pyridin-2-yl)propyl isoquinolin-3-ylcarbamate -continued

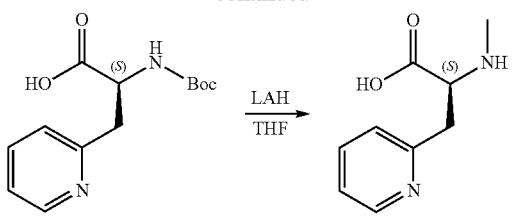

To a solution of (S)-2-(tert-butoxycarbonylamino)-3-(pyridin-2-yl)propanoate (1.05 g, 3.96 mmol) in THF (20 mL) was added LAH (2 M in THF, 4.0 mL, 8.0 mmol) at 0° C. The resulting solution was stirred at 0° C. for 30 min and heated to reflux for 2 h. The reaction mixture was cooled and quenched with water (0.32 mL), NaOH (3 N, 0.32 mL), and water (0.96 mL). The resulting suspension was stirred at RT for 30 min. The mixture was filtered and the filtrate was concentrate to give (S)-2-(methylamino)-3-(pyridin-2-yl)propan-1-ol (510 mg, crude), which was used without further purification.

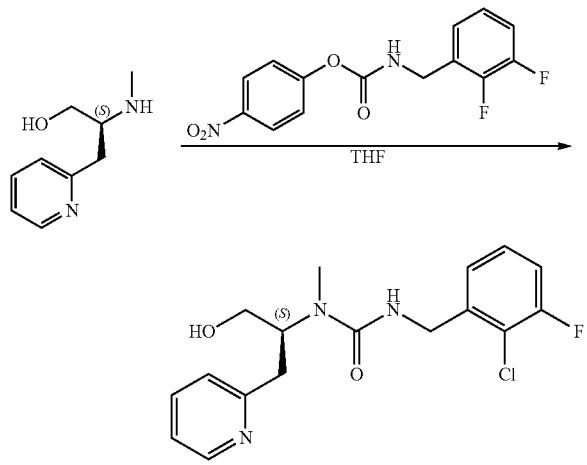

To a solution of (S)-2-(methylamino)-3-(pyridin-2-yl)propan-1-ol (3.93 mmol) in THF (20 mL) was added 4-nitrophenyl 2-chloride-3-fluorobenzylcarbamate (1.29 g, 3.93 mmol). The resulting solution was stirred at RT for 1 h. The solvent was removed and the resulting residue was dissolved in EtOAc (800 mL). The organic mixture was washed with NaOH (1 N, 100 mL×3), HCl (0.5 N, 100 mL), NaHCO$_3$ (sat.), and brine, dried over Na$_2$SO$_4$, filtered, and concentrated under reduced pressure. The residue was purified on RP-HPLC using a mixture of acetonitrile and water to give (S)-3-(2-chloro-3-fluorobenzyl)-1-(1-hydroxy-3-(pyridin-2-yl)propan-2-yl)-1-methylurea (250 mg, 18% for two steps). LRMS (M+H$^+$) m/z 352.2.

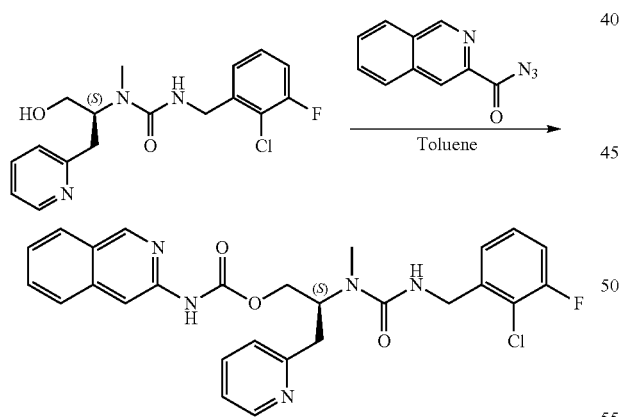

To a solution of (S)-3-(2-chloro-3-fluorobenzyl)-1-(1-hydroxy-3-(pyridin-2-yl)propan-2-yl)-1-methylurea (250 mg, 0.71 mmol) in toluene (10 mL) was added isoquinoline-3-carbonyl azide (142 mg, 0.71 mmol). The resulting solution was stirred at 100° C. for 1 h. The mixture was cooled and concentrated. The residue was purified on RP-HPLC using a mixture of acetonitrile and water to give (S)-2-(3-(2-chloro-3-fluorobenzyl)-1-methylureido)pent-4-enyl isoquinolin-3-ylcarbamate (277.4 mg, 75%) as white solid. LRMS (M+H$^+$) m/z 522.1.

Example 27

Preparation of (S)-5-(2-aminoacetamido)-2-(3-(2-chloro-3-fluorobenzyl)-1-methylureido)pentyl 6-fluoroisoquinolin-3-ylcarbamate

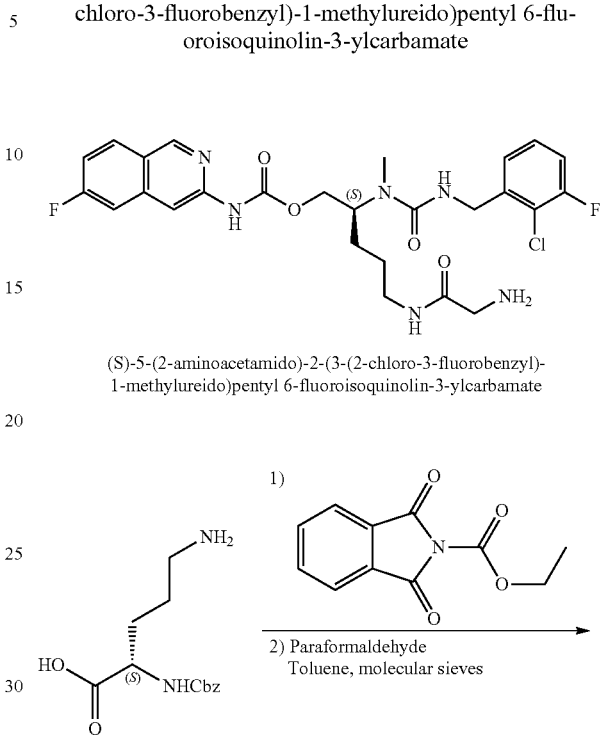

(S)-5-(2-aminoacetamido)-2-(3-(2-chloro-3-fluorobenzyl)-1-methylureido)pentyl 6-fluoroisoquinolin-3-ylcarbamate (S)-5-amino-2-(benzyloxycarbonylamino)pentanoic acid (10.0 g, 37.56 mmol) and ethyl 1,3-dioxoisoindoline-2-carboxylate (9.04 g, 41.28 mmol) in NMP (40.0 mL) were heated to 150° C. for 30 min in 4 microwave reaction tubes. The mixture was diluted with EtOAc (500 mL). The organic mixture was washed with water (100 mL×2) and brine, dried over Na$_2$SO$_4$, filtered, and concentrated under reduced pressure to give an oil, which was redissolved in toluene. To the resulting solution were added paraformaldehyde, PTSA and molecular sieves (3 A) and the mixture was heated to 150° C. for 20 min in a microwave reactor. The reaction mixture was diluted with ether (800 mL), washed with NaHCO$_3$ and brine, dried over Na$_2$SO$_4$, filtered, and concentrated under reduced pressure. The residue was purified on silica gel using a mixture of EtOAc and hexanes to give (S)-benzyl 4-(3-(1,3-dioxoisoindolin-2-yl)propyl)-5-oxooxazolidine-3-carboxylate (11.6 g, 76% for 2 steps).

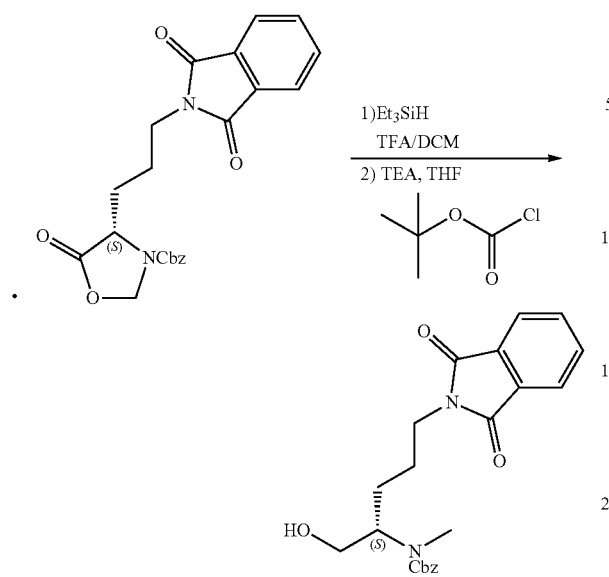

To a solution of (S)-benzyl 4-(3-(1,3-dioxoisoindolin-2-yl)propyl)-5-oxooxazolidine-3-carboxylate (11.6 g, 28.40 mmol) in DCM (30.0 mL) was added Et$_3$SiH (13.6 mL, 85.3 mmol). The reaction mixture was stirred overnight, concentrated under reduced pressure, and dissolved in THF (100 mL). To the resulting solution was added tert-butyl chloroformate (4.4 mL, 34.08 mmol) and TEA (12.0 mL, 85.2 mmol) at 0° C. The reaction mixture was stirred at RT for 30 min. The precipitate was filtered off and the filtrate was added into a suspension of NaBH$_4$ in water (1.0 mL) at 0° C. The reaction mixture was stirred at RT for 30 min. LCMS indicated the completion of the reaction. The reaction mixture was acidified to pH 3 by HCl (1N) and extracted with EtOAc (300 mL×2). The combined organic layers were washed with saturated NaHCO$_3$ and brine, dried over Na$_2$SO$_4$, filtered, and concentrated under reduced pressure. The residue was purified on silica gel using a mixture of EtOAc and hexanes to give (S)-benzyl 5-(1,3-dioxoisoindolin-2-yl)-1-hydroxypentan-2-yl(methyl)carbamate (5.01 g, 45%). LRMS (M+H$^+$) m/z 397.3.

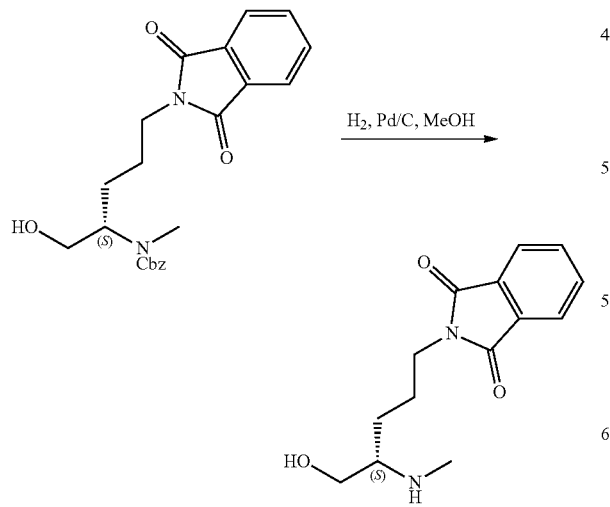

To a solution of (S)-benzyl 5-(1,3-dioxoisoindolin-2-yl)-1-hydroxypentan-2-yl(methyl)carbamate (5.01 g, 12.65 mmol) in MeOH (100 mL) was added Pd/C (1.0 g). The mixture was transferred to an autoclave reactor, charged with hydrogen (50 psi), and stirred at RT overnight. The mixture was filtered and the filtrate was concentrated under reduced pressure to give (S)-2-(5-hydroxy-4-(methylamino)pentyl)isoindolin (3.2 g, 97%) which was used without purification. LRMS (M+H$^+$) m/z 263.1.

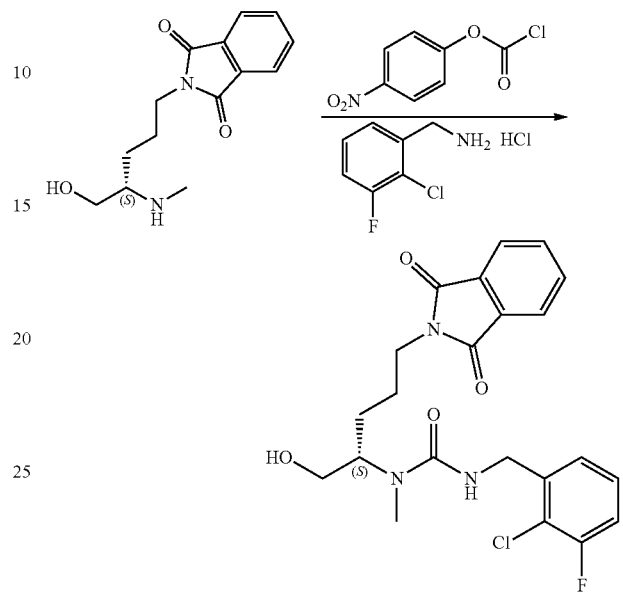

To a solution of 4-nitrophenylchloroformate (1.89 g, 9.39 mmol) in THF (20 mL) was added a solution of 2-chloro-3-fluorobenzylamine hydrochloride (1.24 g, 9.39 mmol) and DIEA (3.9 mL, 23.46 mmol). The resulting solution was stirred at RT for 20 min. The reaction mixture was added into a solution of (S)-2-(5-hydroxy-4-(methylamino)pentyl)isoindolin (2.05 g, 7.82 mmol) in THF (10 mL). The resulting solution was stirred at RT overnight. The mixture was concentrated and purified on RP-HPLC using a mixture of acetonitrile and water to give (S)-3-(2-chloro-3-fluorobenzyl)-1-(5-(1,3-dioxoisoindolin-2-yl)-1-hydroxypentan-2-yl)-1-methylurea (401 mg, 47%). LRMS (M+H$^+$) m/z 448.3.

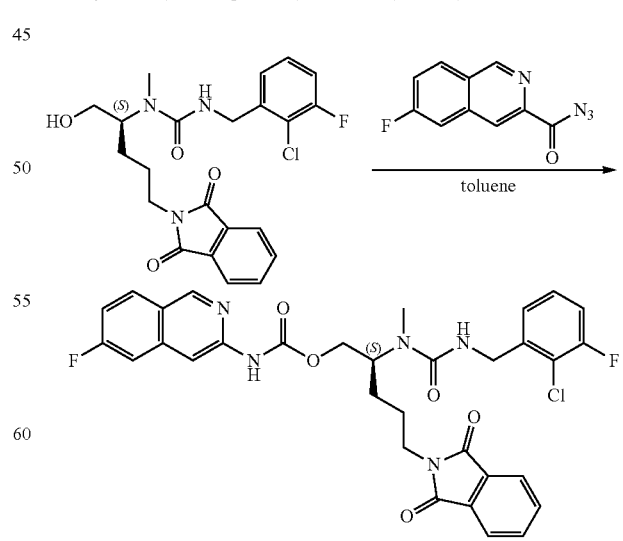

To a solution of (S)-3-(2-chloro-3-fluorobenzyl)-1-(5-(1,3-dioxoisoindolin-2-yl)-1-hydroxypentan-2-yl)-1-methylurea (286 mg, 0.64 mmol) and 6-fluoroisoquinoline-3-carbonyl azide (152 mg, 0.70 mmol) in toluene (5 mL) was heated to 100° C. for 1 h. The reaction mixture was concentrated to dryness. The residue was purified on silica gel column using a mixture of EtOAc and hexanes to give (S)-2-(3-(2-chloro-3-fluorobenzyl)-1-methylureido)-5-(1,3-dioxoisoindolin-2-yl)pentyl 6-fluoroisoquinolin-3-ylcarbamate (400 mg, quant.). LRMS (M+H$^+$) m/z 618.2.

To a solution of (S)-5-amino-2-(3-(2-chloro-3-fluorobenzyl)-1-methylureido)pentyl 6-fluoroisoquinolin-3-ylcarbamate (96 mg, 0.19 mmol), 2-(tert-butoxycarbonylamino)acetic acid (51 mg, 0.29 mmol) and HBTU (110 mg, 0.29 mmol) in DMF (1.0 mL) was added DIEA (63 µL, 0.38 mmol). The mixture was stirred at RT for 30 min. The mixture

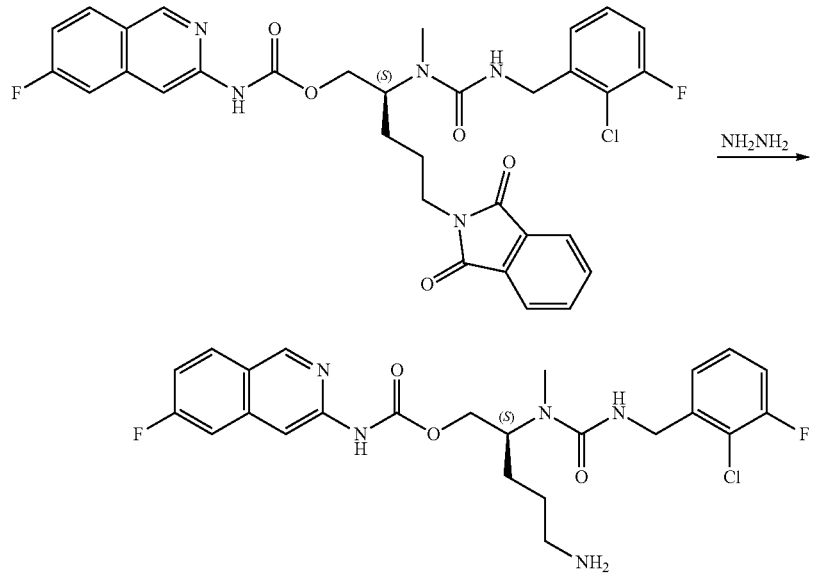

To a solution of (S)-2-(3-(2-chloro-3-fluorobenzyl)-1-methylureido)-5-(1,3-dioxoisoindolin-2-yl)pentyl 6-fluoroisoquinolin-3-ylcarbamate (400 mg, 0.64 mmol) in MeOH (10.0 mL) was added NH$_2$NH$_2$ (1.0 mL). The reaction mixture was stirred at RT for 2 h. The mixture was concentrated and re-dissolved in MeOH. The resulting solution was filtered and purified on RP-HPLC using a mixture of acetonitrile and water to give (S)-5-amino-2-(3-(2-chloro-3-fluorobenzyl)-1-methylureido)pentyl 6-fluoroisoquinolin-3-ylcarbamate (305 mg, quant.). LRMS (M+H$^+$) m/z 506.2.

was filtered and the filtrate was purified by RP-HPLC using a mixture of acetonitrile and water to give (6-Fluoro-isoquinolin-3-yl)-carbamic acid (S)-5-(2-tert-butoxycarbonylamino-acetylamino)-2-[3-(2-chloro-3-fluoro-benzyl)-1-methyl-ureido]-pentyl ester (105 mg, 83%). LRMS (M+Na$^+$) m/z 663.2.

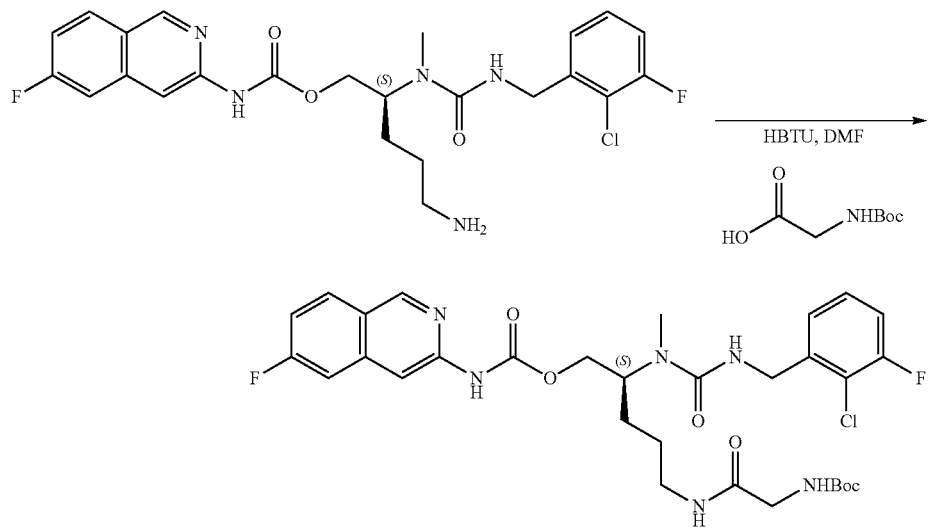

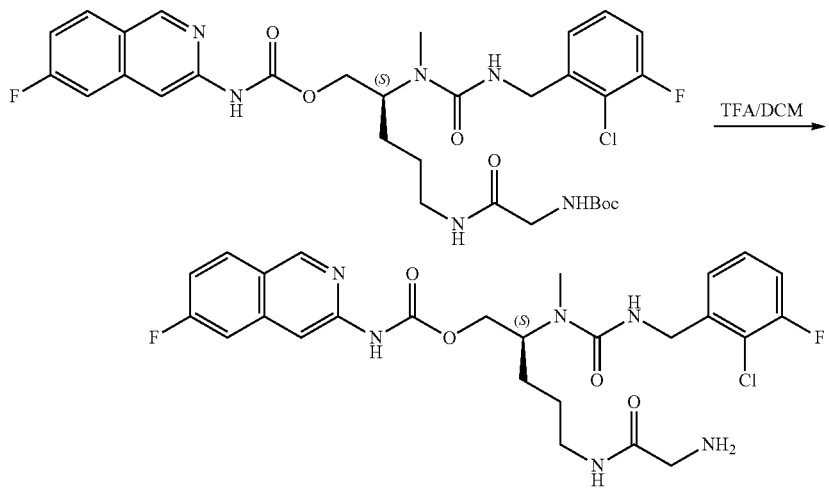

To a solution of (6-Fluoro-isoquinolin-3-yl)-carbamic acid (S)-5-(2-tert-butoxycarbonylamino-acetylamino)-2-[3-(2-chloro-3-fluoro-benzyl)-1-methyl-ureido]-pentyl ester (105 mg, 0.16 mmol) in DCM (10.0 mL) was added TFA (1.0 mL). The mixture was stirred at RT for 2 h. The mixture was concentrated and re-dissolved DCM. The DCM layer was washed with $K_2CO_3$ (2 N), saturated $NaHCO_3$, and brine, dried over $Na_2SO_4$, filtered, and concentrated. The residue was purified on silica gel column using a mixture of DCM and MeOH to give (S)-5-(2-aminoacetamido)-2-(3-(2-chloro-3-fluorobenzyl)-1-methylureido)pentyl 6-fluoroisoquinolin-3-ylcarbamate (71 mg, 79%). LRMS (M+H$^+$) m/z 563.2.

Example 28

Preparation of (S,E)-5-(2-carbamoylguanidino)-2-(3-(2-chloro-3-fluorobenzyl)-1-methylureido)pentyl 6-fluoroisoquinolin-3-ylcarbamate

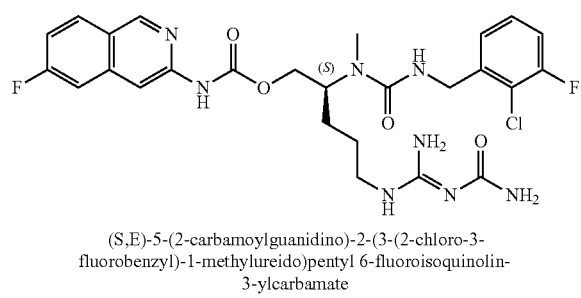

(S,E)-5-(2-carbamoylguanidino)-2-(3-(2-chloro-3-fluorobenzyl)-1-methylureido)pentyl 6-fluoroisoquinolin-3-ylcarbamate

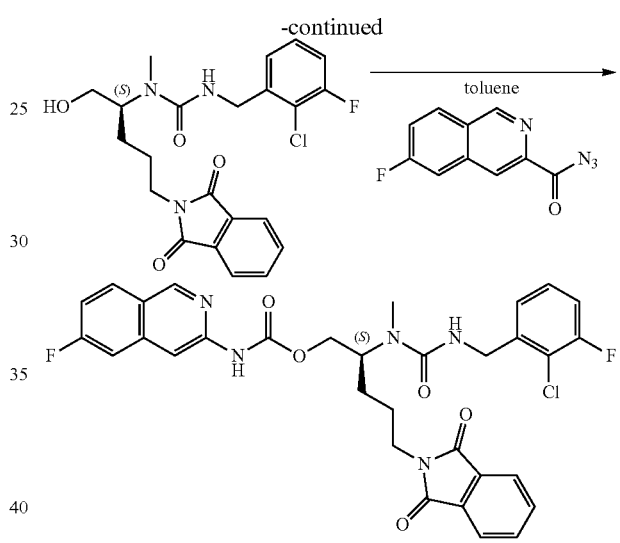

To a solution of (S)-3-(2-chloro-3-fluorobenzyl)-1-(5-(1,3-dioxoisoindolin-2-yl)-1-hydroxypentan-2-yl)-1-methylurea (286 mg, 0.64 mmol) and 6-fluoroisoquinoline-3-carbonyl azide (152 mg, 0.70 mmol) in toluene (5 mL) was heated to 100° C. for 1 h. The reaction mixture was concentrated to dryness. The residue was purified on silica gel column using a mixture of EtOAc and hexanes to give (S)-2-(3-(2-chloro-3-fluorobenzyl)-1-methylureido)-5-(1,3-dioxoisoindolin-2-yl)pentyl 6-fluoroisoquinolin-3-ylcarbamate (400 mg, quant.). LRMS (M+H$^+$) m/z 618.2.

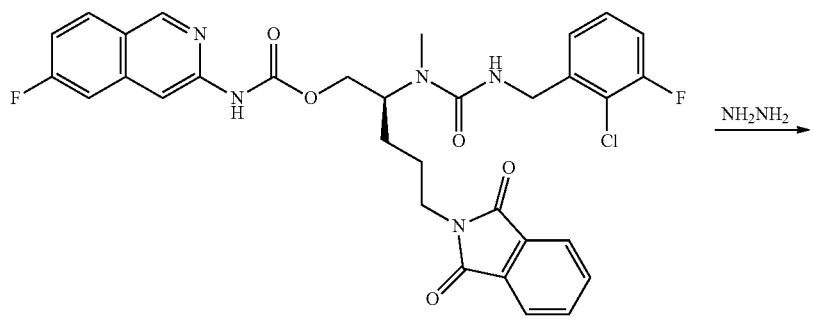

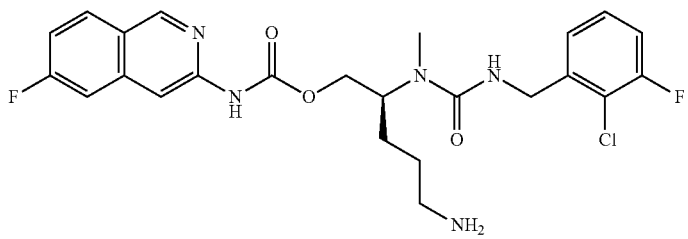

To a solution of (S)-2-(3-(2-chloro-3-fluorobenzyl)-1-methylureido)-5-(1,3-dioxoisoindolin-2-yl)pentyl 6-fluoroisoquinolin-3-ylcarbamate (400 mg, 0.64 mmol) in MeOH (10.0 mL) was added $NH_2NH_2$ (1.0 mL). The reaction mixture was stirred at RT for 2 h. The mixture was concentrated and re-dissolved in MeOH. The mixture was filtered and purified on RP-HPLC using a mixture of acetonitrile and water to give (S)-5-amino-2-(3-(2-chloro-3-fluorobenzyl)-1-methylureido)pentyl 6-fluoroisoquinolin-3-ylcarbamate (305 mg, quant.). LRMS (M+H$^+$) m/z 506.2.

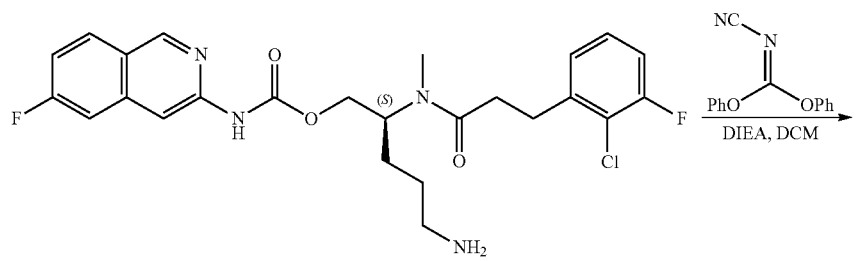

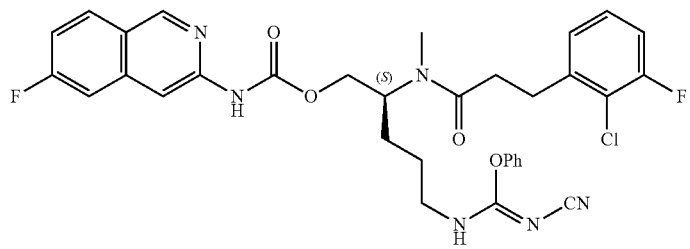

To a solution of (S)-5-(2-aminoacetamido)-2-(3-(2-chloro-3-fluorobenzyl)-1-methylureido)pentyl 6-fluoroisoquinolin-3-ylcarbamate (190 mg, 0.35 mmol) and diphenyl cyanocarbonimidate (83 mg, 0.35 mmol) in DCM (10.0 mL) was added DIEA (0.12 mL, 0.70 mmol). The reaction mixture was stirred at RT for 4 h. The mixture was concentrated under reduced pressure to give (S,Z)-2-(3-(2-chloro-3-fluorophenyl)-N-methylpropanamido)-5-((cyanoimino)(phenoxy)methylamino)pentyl 6-fluoroisoquinolin-3-ylcarbamate, which was used without further purification. LRMS (M+H$^+$) m/z 650.2.

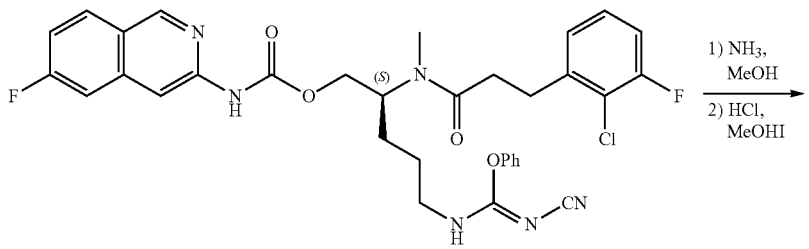

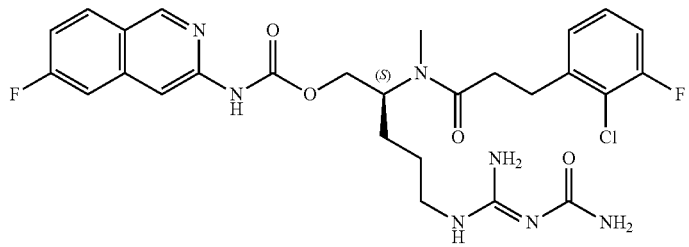

To a solution of (S,Z)-2-(3-(2-chloro-3-fluorophenyl)-N-methylpropanamido)-5-((cyanoimino)(phenoxy)methylamino)pentyl 6-fluoroisoquinolin-3-ylcarbamate (100 mg, crude, 0.12 mmol) in MeOH (7 N ammonia, 1.0 mL) was heated at microwave reactor at 110° C. for 20 min. The mixture was filtered and the filtrate was purified by RP-HPLC using a mixture of acetonitrile and water (0.1% TFA buffer). Upon concentration of the mixture. The mixture was purified again with RP-HPLC using a mixture of acetonitrile and water to give (S,E)-5-(2-carbamoylguanidino)-2-(3-(2-chloro-3-fluorophenyl)-N-methylpropanamido)pentyl 6-fluoroisoquinolin-3-ylcarbamate (18 mg, 25%). LRMS (M+H$^+$) m/z 591.2.

Example 29

Preparation of (S)-5-amino-2-(3-(2-chloro-3-fluorobenzyl)-1-methylureido)pentyl 5-chloropyridin-2-ylcarbamate

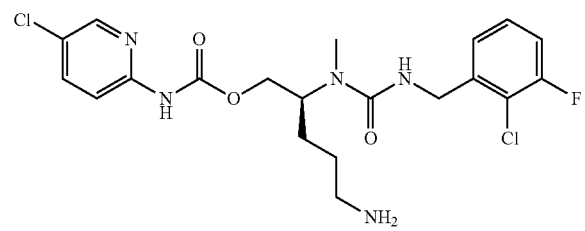

(S)-5-amino-2-(3-(2-chloro-3-fluorobenzyl)-1-methylureido)pentyl 5-chloropyridin-2-ylcarbamate

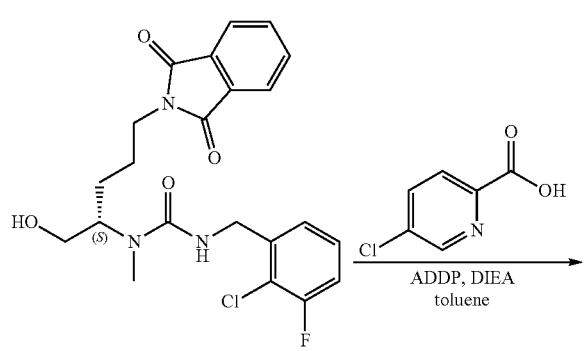

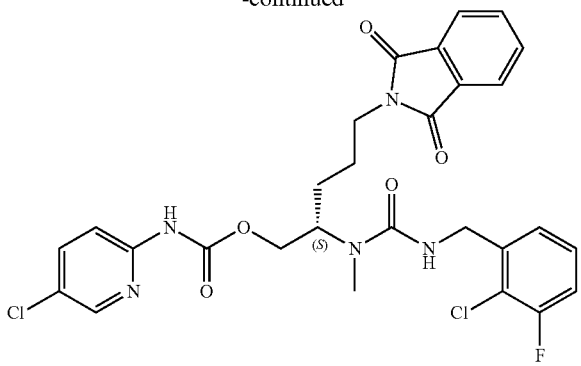

To a solution of (S)-3-(2-chloro-3-fluorobenzyl)-1-(5-(1,3-dioxoisoindolin-2-yl)-1-hydroxypentan-2-yl)-1-methylurea (480 mg, 1.07 mmol), 5-chloropicolinic acid (339 mg, 2.15 mmol), and DIEA (0.36 mL, 2.15 mmol) in toluene (10 mL) was added DPPA (0.46 mL, 2.15 mmol). The reaction mixture was heated to 100° C. for 2 h and concentrated to dryness. The residue was purified on RP-HPLC using a mixture of acetonitrile and water to give (S)-2-(3-(2-chloro-3-fluorobenzyl)-1-methylureido)-5-(1,3-dioxoisoindolin-2-yl)pentyl 5-chloropyridin-2-ylcarbamate (280 mg, 80% pure). LRMS (M+H$^+$) m/z 602.2.

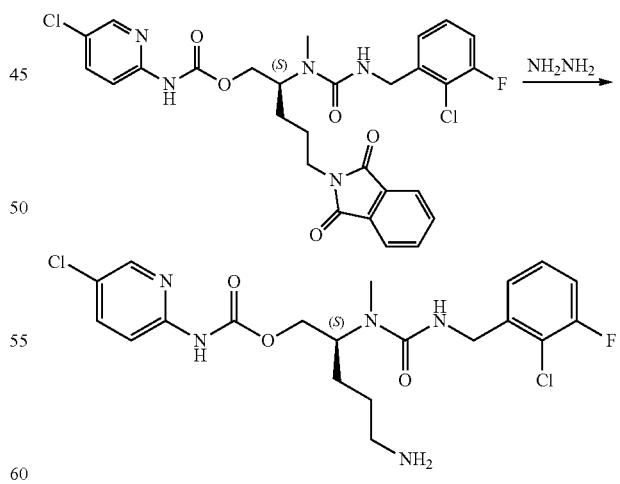

To a solution of (S)-2-(3-(2-chloro-3-fluorobenzyl)-1-methylureido)-5-(1,3-dioxoisoindolin-2-yl)pentyl 5-chloropyridin-2-ylcarbamate (280 mg, 0.47 mmol) in MeOH (5.0 mL) was added NH$_2$NH$_2$ (0.13 mL, 4.7 mmol). The reaction mixture was stirred at RT for 2 h. The mixture was concentrated and re-dissolved in MeOH. The resulting solution was filtered and purified on RP-HPLC using a mixture of acetonitrile and water to give (S)-5-amino-2-(3-(2-chloro-3-fluorobenzyl)-1-methylureido)pentyl 5-chloropyridin-2-ylcarbamate (162 mg, 73%). LRMS (M+H⁺) m/z 472.2.

Example 30

Preparation of (2S,4R)-2-((2-chloro-3-fluorobenzyl)(methyl)amino)-4,5-dihydroxypentyl isoquinolin-3-ylcarbamate and (2S,4S)-2-((2-chloro-3-fluorobenzyl)(methyl)amino)-4,5-dihydroxypentyl isoquinolin-3-ylcarbamate

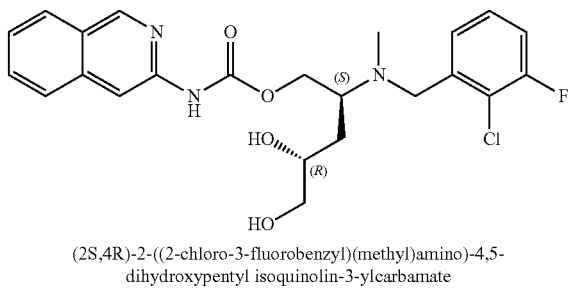

(2S,4R)-2-((2-chloro-3-fluorobenzyl)(methyl)amino)-4,5-dihydroxypentyl isoquinolin-3-ylcarbamate

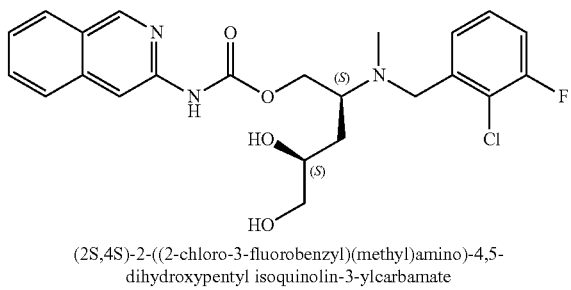

(2S,4S)-2-((2-chloro-3-fluorobenzyl)(methyl)amino)-4,5-dihydroxypentyl isoquinolin-3-ylcarbamate

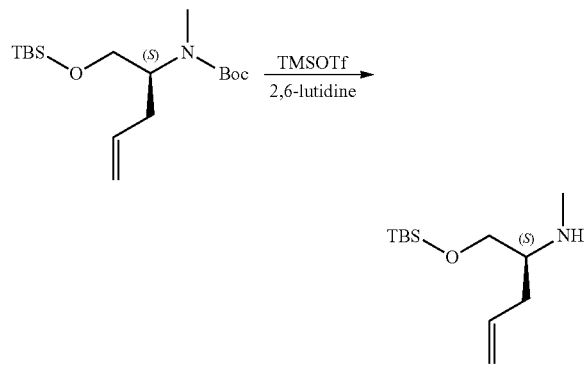

To a solution of (S)-tert-butyl 1-(tert-butyldimethylsilyloxy)pent-4-en-2-yl(methyl)carbamate (10.5 g, 31.9 mmol) in DCM (100 mL) was added 2,6-lutidine (4.8 mL, 41.4 mmol) followed by TMSOTf (7.5 mL, 41.4 mmol). The resulting solution was stirred at RT for 30 min. The solvent was removed and the remaining residue was dried under vacuum to give (S)-1-(tert-butyldimethylsilyloxy)-N-methylpent-4-en-2-amine, which was used without further purification. LRMS (M+H⁺) m/z 230.2.

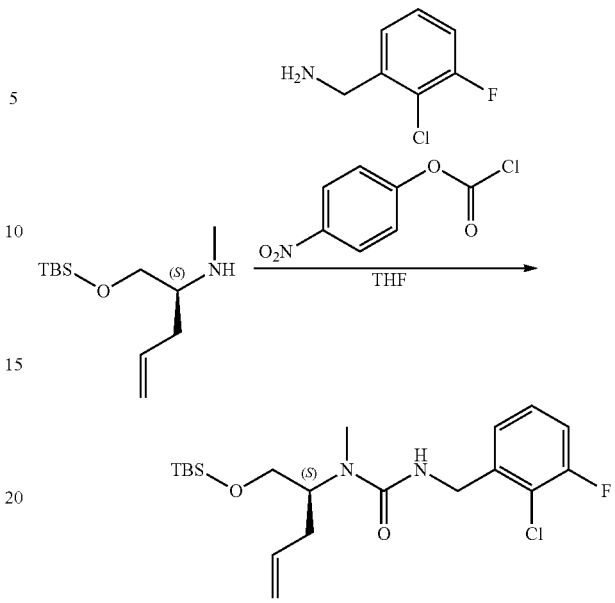

To a solution of 4-nitrophenylchloroformate (7.69 g, 38.3 mmol) in THF (20 mL) was added a solution of 2-chloro-3-fluorobenzylamine hydrochloride (6.09 g, 38.3 mmol) and DIEA (7.9 mL, 47.9 mmol) in THF (20 mL). The resulting solution was stirred at RT for 20 min. The reaction mixture was added into a solution of (S)-1-(tert-butyldimethylsilyloxy)-N-methylpent-4-en-2-amine (31.9 mmol) in THF (100 mL). The resulting solution was stirred at RT overnight. The solvent was removed and the resulting residue was re-dissolved in EtOAc (500 mL). The organic mixture was washed with NaOH (1 N, 100 mL×3), HCl (0.5 N, 100 mL), saturated NaHCO₃, and brine, dried over Na₂SO₄, filtered, and concentrated under reduced pressure. The residue was purified on silica gel column using a mixture of DCM and MeOH to give (S)-1-(1-(tert-butyldimethylsilyloxy)pent-4-en-2-yl)-3-(2-chloro-3-fluorobenzyl)-1-methylurea (10.08 g, 76%) as a white solid. LRMS (M+H⁺) m/z 415.2.

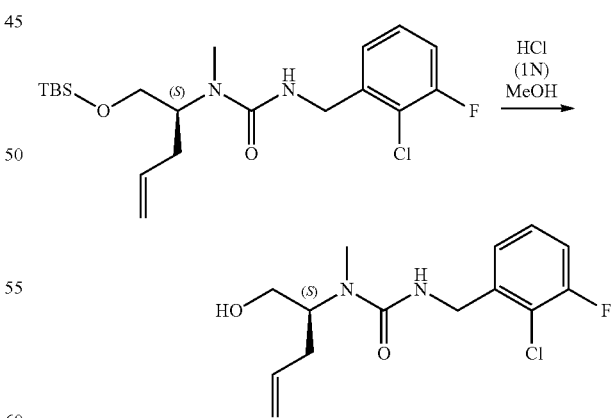

To a solution of (S)-1-(1-(tert-butyldimethylsilyloxy)pent-4-en-2-yl)-3-(2-chloro-3-fluorobenzyl)-1-methylurea (5.80 g, 10.8 mmol) in MeOH (50 mL) was added HCl (1N, 32.0 mL). The resulting solution was stirred at RT for 30 min. The mixture was partially concentrated and filtered. The filtrate was purified on RP-HPLC using a mixture of acetonitrile and water to give (S)-3-(2-chloro-3-fluorobenzyl)-1-(1-hydroxypent-4-en-2-yl)-1-methylurea (2.0 g, 77%) as a white solid, which was used without further purification. LRMS (M+H⁺) m/z 301.2.

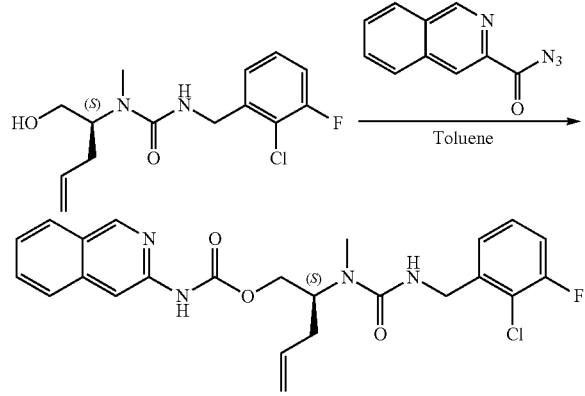

To a solution of (S)-3-(2-chloro-3-fluorobenzyl)-1-(1-hydroxypent-4-en-2-yl)-1-methylurea (1.7 g, 5.65 mmol) in toluene (20 mL) was added isoquinoline-3-carbonyl azide (1.24 g, 6.22 mmol). The resulting solution was stirred at 100° C. for 1 h. The mixture was cooled and the solid was filtered out. The solid was washed with toluene and dry under high vacuum to give (S)-2-(3-(2-chloro-3-fluorobenzyl)-1-methylureido)pent-4-enyl isoquinolin-3-ylcarbamate (2.50 g, 77%). LRMS (M+H⁺) m/z 471.1.

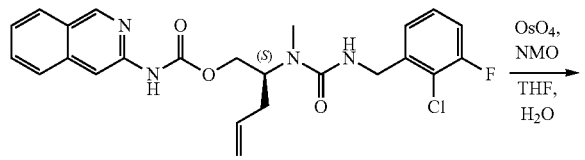

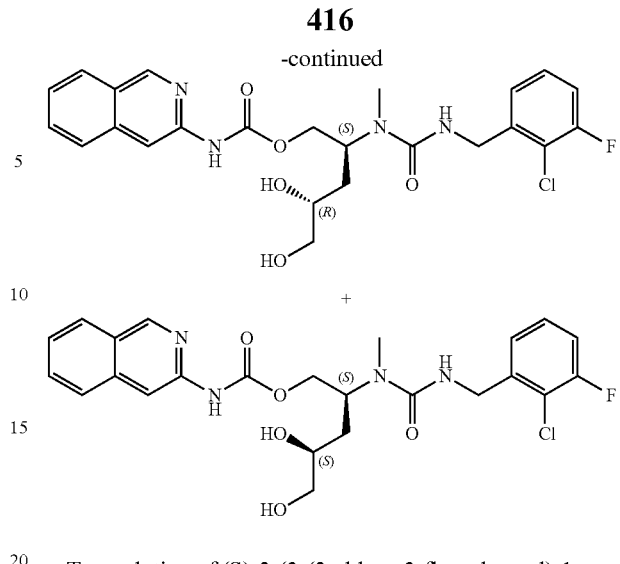

To a solution of (S)-2-(3-(2-chloro-3-fluorobenzyl)-1-methylureido)pent-4-enyl isoquinolin-3-ylcarbamate (1.9 g, 4.03 mmol) in THF (48 mL) and water (12.0 mL) were added 4-methylmorpholine N-oxide (2.36 g, 20.15 mmol) and osmium tetroxide (103.0 mg, 0.4 mmol). The resulting solution was stirred at RT for 2 h. To this mixture was added sodium sulfite (3 g) and the resulting mixture was stirred for 2 h. The solid was then removed by filtration. The filtrate was diluted with ethyl acetate (100 mL). The organic layer was washed with HCl (0.5 N), saturated NaHCO₃, and brine, filtered, and concentrated. The residue was purified by RP-HPLC using a mixture of acetonitrile and water to give (2S,4R)-2-(3-(2-chloro-3-fluorobenzyl)-1-methylureido)-4,5-dihydroxypentyl isoquinolin-3-ylcarbamate (296 mg, 15%), (2S,4S)-2-(3-(2-chloro-3-fluorobenzyl)-1-methylureido)-4,5-dihydroxypentyl isoquinolin-3-ylcarbamate (18.3 mg, 9%), and 1 g of mixture. LRMS (M+H⁺) m/z 505.2.

Example 31

Preparation of sodium (2R,4S)-4-(2-chloro-3-fluorobenzyl)(methyl)amino)-2-hydroxy-5-(isoquinolin-3-ylcarbamoyloxy)pentyl phosphate

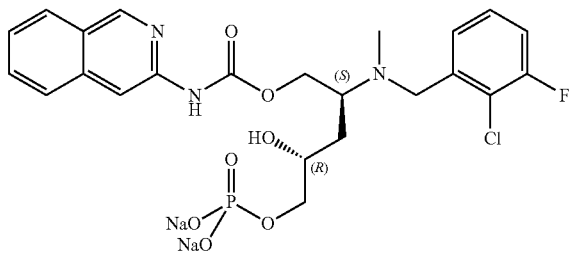

sodium (2R,4S)-4-((2-chloro-3-fluorobenzyl)(methyl)amino)-2-hydroxy-5-(isoquinolin-3-ylcarbamoyloxy)pentyl phosphate

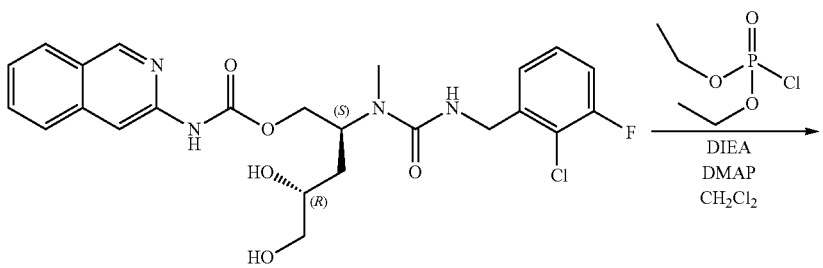

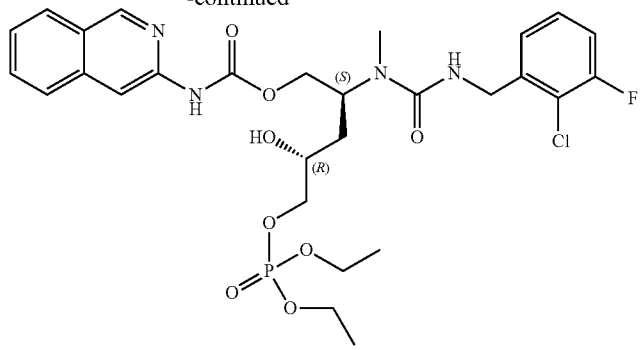

To a solution of (2S,4R)-2-(3-(2-chloro-3-fluorobenzyl)-1-methylureido)-4,5-dihydroxypentyl isoquinolin-3-ylcarbamate (0.26 g, 0.51 mmol), DIEA (0.51 mL, 3.06 mmol) and DMAP (0.251 g, 2.06 mmol) in anhydrous THF (20 mL) and DCM (30 mL) was added diethyl chlorophorophosphate (0.3 mL, 2.06 mmol) at 0° C. After stirred at RT for 10 min, the mixture was quenched with EtOH. The resulting mixture was diluted with DCM (100 mL). The organic mixture was washed with saturated NaHCO$_3$, HCL (1 N), saturated NaHCO$_3$, and brine, dried over Na$_2$SO$_4$, filtered, and concentrated. The residue was purified on RP-HPLC using a mixture of acetonitrile and H$_2$O to give (2S,4R)-2-(3-(2-chloro-3-fluorobenzyl)-1-methylureido)-5-(diethoxyphosphoryloxy)-4-hydroxypentyl isoquinolin-3-ylcarbamate (310 mg, 95%). LRMS (M+H$^+$) m/z 641.2.

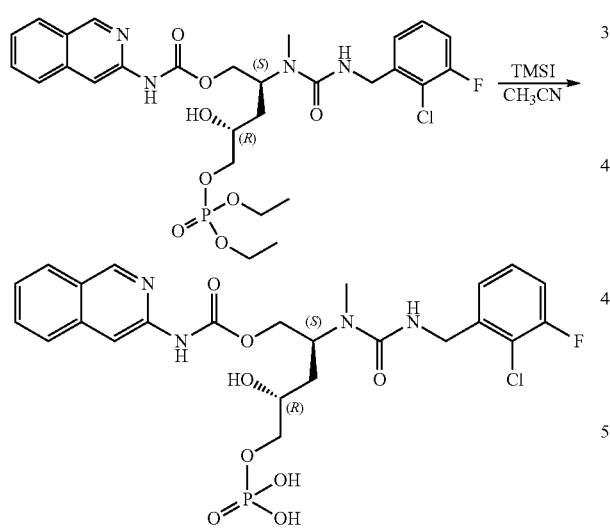

To a solution of (2S,4R)-2-(3-(2-chloro-3-fluorobenzyl)-1-methylureido)-5-(diethoxyphosphoryloxy)-4-hydroxypentyl isoquinolin-3-ylcarbamate (310 mg, 0.64 mmol) in acetonitrile (10 mL) was added TMSI (0.87 mL, 6.4 mmol) at RT. After stirred at RT for 1 h, the reaction was quenched with H$_2$O and DIEA (0.1 mL, 0.64 mmol). The solvent was removed and the resulting residue was purified on RP-HPLC using a mixture of acetonitrile and H$_2$O (0.1% HCOOH buffer) to give (2S,4R)-2-(2-chloro-3-fluorobenzyl)(methyl)amino)-4-hydroxy-5-(phosphonooxy)pentyl 6-fluoroisoquinolin-3-ylcarbamate (212 mg, 57%). LRMS (M+H$^+$) m/z 585.5.

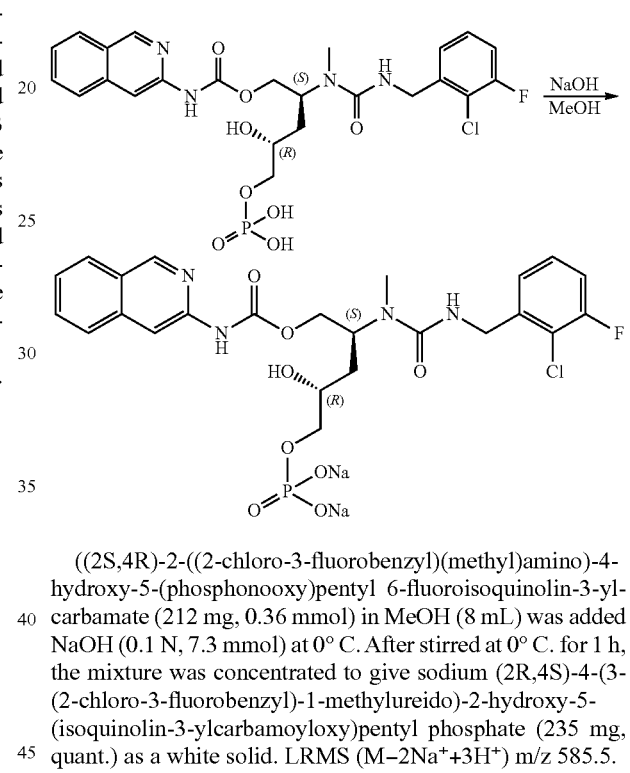

((2S,4R)-2-((2-chloro-3-fluorobenzyl)(methyl)amino)-4-hydroxy-5-(phosphonooxy)pentyl 6-fluoroisoquinolin-3-yl-carbamate (212 mg, 0.36 mmol) in MeOH (8 mL) was added NaOH (0.1 N, 7.3 mmol) at 0° C. After stirred at 0° C. for 1 h, the mixture was concentrated to give sodium (2R,4S)-4-(3-(2-chloro-3-fluorobenzyl)-1-methylureido)-2-hydroxy-5-(isoquinolin-3-ylcarbamoyloxy)pentyl phosphate (235 mg, quant.) as a white solid. LRMS (M−2Na$^+$+3H$^+$) m/z 585.5.

Example 32

Preparation of (2S,4R)-2-((2,3-difluorobenzyl)(methyl)amino)-4,5-dihydroxypentyl isoquinolin-3-yl-carbamate and (2S,4S)-2-((2,3-difluorobenzyl)(methyl)amino)-4,5-dihydroxypentyl isoquinolin-3-ylcarbamate

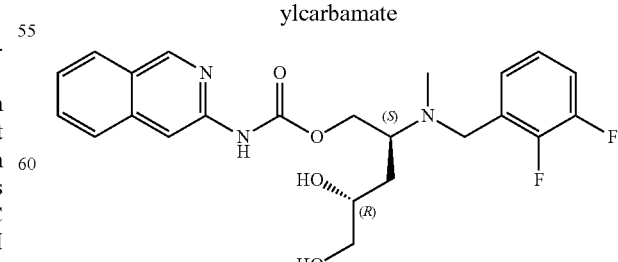

(2S,4R)-2-((2,3-difluorobenzyl)(methyl)amino)-4,5-dihydroxypentyl isoquinolin-3-ylcarbamate -continued

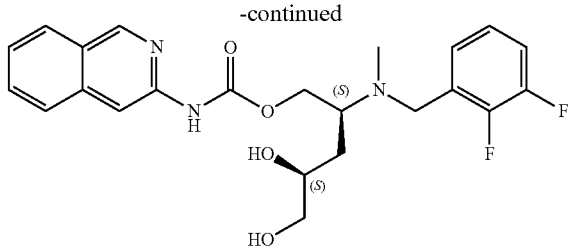

(2S,4S)-2-((2,3-difluorobenzyl)(methyl)amino)-4,5-dihydroxypentyl isoquinolin-3-ylcarbamate

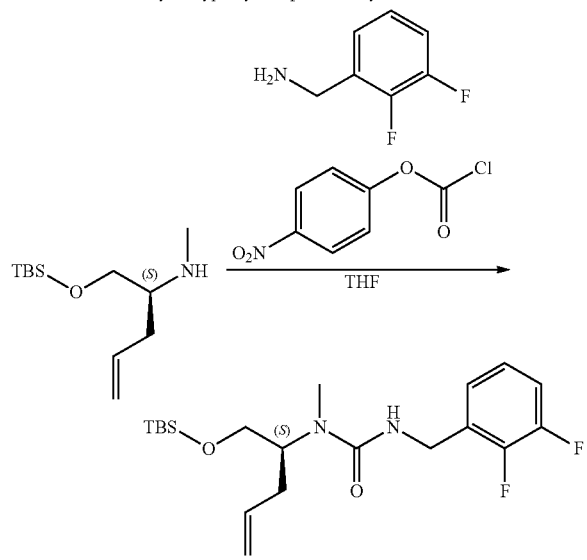

To a solution of 4-nitrophenylchloroformate (7.04 g, 34.9 mmol) in THF (100 mL) was added a solution of 2,3-difluorobenzylamine (4.26 mL, 36.4 mmol) and DIEA (13.2 mL, 75.9 mmol) in THF (20 mL). The resulting solution was stirred at RT for 20 min. The reaction solution was added into a solution of (S)-1-(tert-butyldimethylsilyloxy)-N-methylpent-4-en-2-amine (31.9 mmol) in THF (50 mL). The resulting solution was stirred at RT overnight. The solvent was removed and the resulting residue was re-dissolved in EtOAc (500 mL). The organic mixture was washed with NaOH (1 N, 100 mL×3), HCl (0.5 N, 100 mL), saturated NaHCO$_3$, and brine, dried over Na$_2$SO$_4$, filtered, and concentrated under reduced pressure. The residue was purified on silica gel column using a mixture of DCM and MeOH to give (S)-1-(1-(tert-butyldimethylsilyloxy)pent-4-en-2-yl)-3-(2,3-difluorobenzyl)-1-methylurea (6.8 g, 49%) as a white solid. LRMS (M+H$^+$) m/z 399.2.

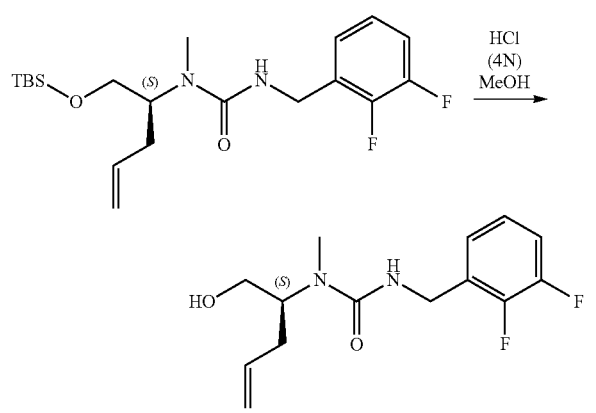

To a solution of (S)-1-(1-(tert-butyldimethylsilyloxy)pent-4-en-2-yl)-3-(2,3-difluorobenzyl)-1-methylurea (3.45 g, 8.65 mmol) in MeOH (60 mL) was added HCl (4 N in dioxane, 11.0 mL). The resulting solution was stirred at RT for 30 min. The mixture was concentrated and re-dissolved in EtOAc. The organic mixture was washed with saturated NaHCO$_3$ and brine, dried over Na$_2$SO$_4$, filtered, and concentrated under reduced pressure to give (S)-3-(2,3-difluorobenzyl)-1-(1-hydroxypent-4-en-2-yl)-1-methylurea (2.5 g, quant.) as a white solid, which was used without further purification. LRMS (M+H$^+$) m/z 285.2.

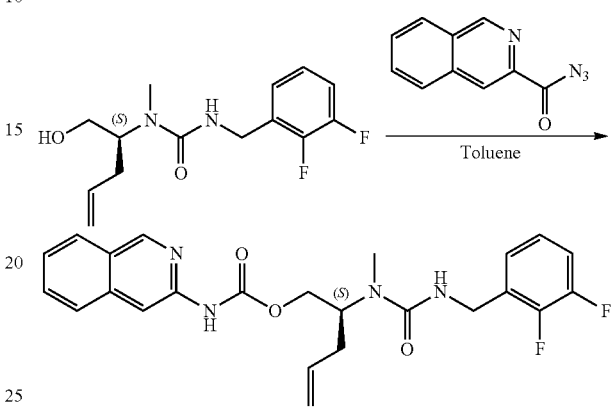

To a solution of (S)-3-(2,3-difluorobenzyl)-1-(1-hydroxypent-4-en-2-yl)-1-methylurea (2.5 g, 8.65 mmol) in toluene (20 mL) was added isoquinoline-3-carbonyl azide (2.46 g, 8.65 mmol). The resulting solution was stirred at 100° C. for 1 h. The mixture was cooled and concentrated to half volume followed by addition of hexanes and DCM to give precipitate. The mixture was filtered and the solid was washed with hexanes to give (S)-2-(3-(2,3-difluorobenzyl)-1-methylureido)pent-4-enyl isoquinolin-3-ylcarbamate (3.42 g, quant.). LRMS (M+H$^+$) m/z 455.2.

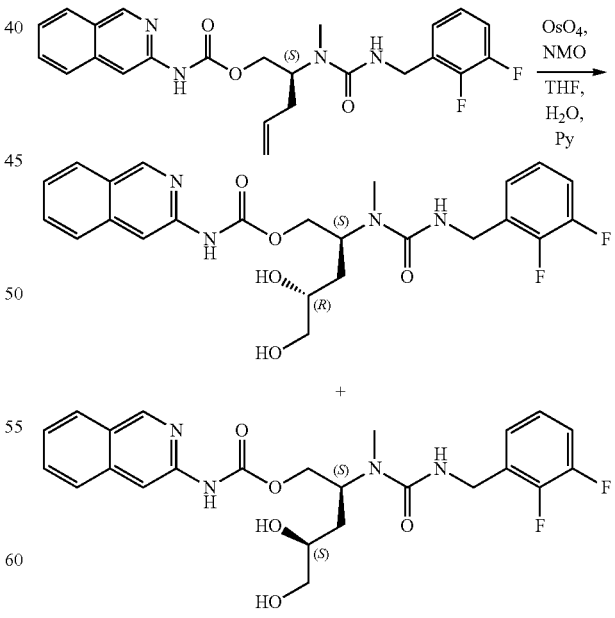

To a solution of (S)-2-(3-(2,3-difluorobenzyl)-1-methylureido)pent-4-enyl isoquinolin-3-ylcarbamate (3.42 g, 7.52 mmol) in THF (100 mL) and water (25.0 mL) were added 4-methylmorpholine N-oxide (4.4 g, 37.6 mmol) and osmium tetroxide (254.2 mg, 0.75 mmol). The resulting solution was stirred overnight. To this mixture was added sodium sulfite (3 g) and the mixture was stirred for 2 h. The solid was then removed by filtration. The filtrate was diluted with ethyl acetate (200 mL). The organic layer was washed with HCl (0.5 N), saturated NaHCO$_3$, and brine, filtered, and partially concentrated. The mixture was filtered and the solid was collected and dried to give a mixture of (2S,4R)-2-(3-(2-chloro-3-fluorobenzyl)-1-methylureido)-4,5-dihydroxypentyl isoquinolin-3-ylcarbamate and (2S,4S)-2-(3-(2-chloro-3-fluorobenzyl)-1-methylureido)-4,5-dihydroxypentyl isoquinolin-3-ylcarbamate (1 g) as 1:2 ratio. The filtrate was concentrated and purified by RP-HPLC using a mixture of acetonitrile and water to give (2S,4R)-2-(3-(2,3-difluorobenzyl)-1-methylureido)-4,5-dihydroxypentyl isoquinolin-3-ylcarbamate (14 mg), (2S,4S)-2-(3-(2,3-difluorobenzyl)-1-methylureido)-4,5-dihydroxypentyl isoquinolin-3-ylcarbamate (10 mg), and a mixture of both (300 mg). LRMS (M+H$^+$) m/z 489.2.

Example 33

Preparation of Sodium (2R,4S)-4-((2,3-difluorobenzyl)(methyl)amino)-2-hydroxy-5-(isoquinolin-3-ylcarbamoyloxy)pentyl phosphate

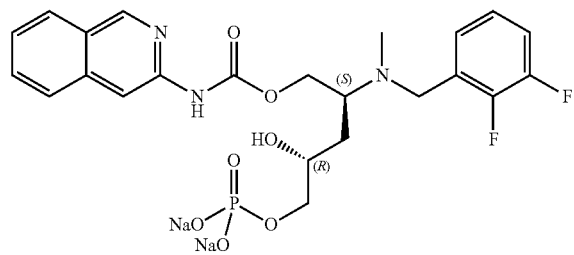

sodium (2R,4S)-4-((2,3-difluorobenzyl)(methyl)amino)-2-hydroxy-5-(isoquinolin-3-ylcarbamoyloxy)pentyl phosphate

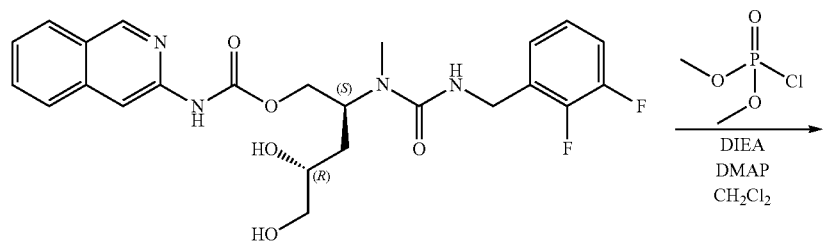

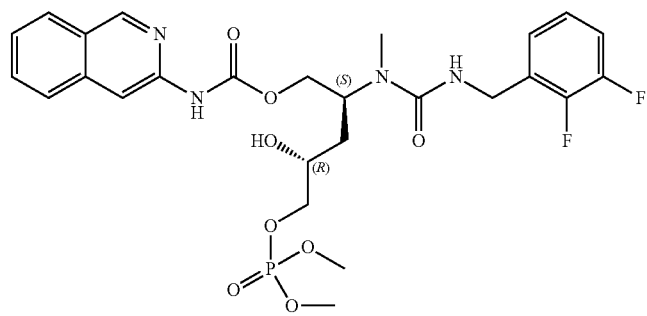

To a solution of (2S,4R)-2-(3-(2,3-difluorobenzyl)-1-methylureido)-4,5-dihydroxypentyl isoquinolin-3-ylcarbamate (0.245 g, 0.50 mmol), DIEA (0.17 mL, 1.0 mmol), and DMAP (0.122 g, 1.0 mmol) in anhydrous THF (12 mL) was added dimethyl chlorophorophosphate (0.11 mL, 1.0 mmol) at 0° C. After stirred at RT for 1 h, an additional dimethyl chlorophorophosphate (0.27 mL, 2.51 mmol) was added at 0° C. The reaction mixture was stirred for 30 min and quenched with MeOH. The resulting mixture was diluted with EtOAc (100 mL). The organic mixture was washed with saturated NaHCO$_3$, HCL (1 N), saturated NaHCO$_3$, and brine, dried over Na$_2$SO$_4$, filtered, and concentrated. The residue was purified on RP-HPLC using a mixture of acetonitrile and H$_2$O to give (2S,4R)-2-(3-(2,3-difluorobenzyl)-1-methylureido)-5-(dimethoxyphosphoryloxy)-4-hydroxypentyl isoquinolin-3-ylcarbamate (150 mg, 50%). LRMS (M+H$^+$) m/z 597.2.

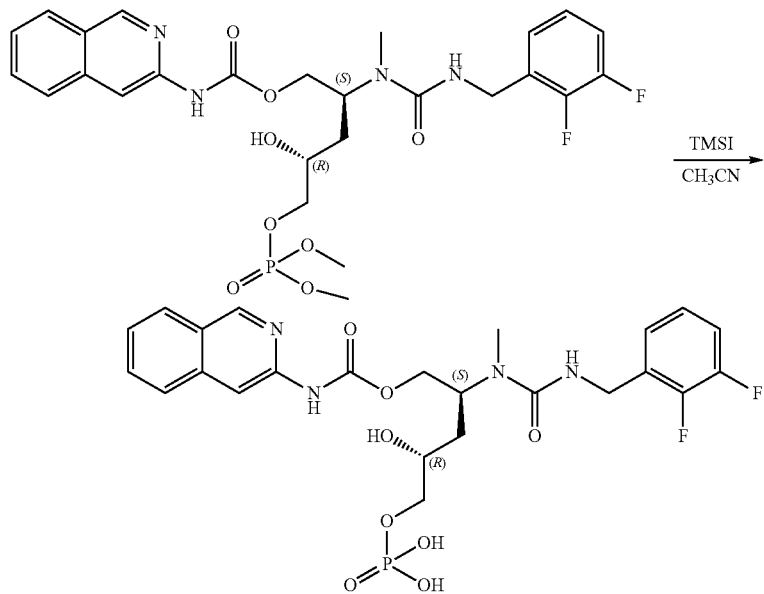

(2S,4R)-2-(3-(2,3-difluorobenzyl)-1-methylureido)-5-(dimethoxyphosphoryloxy)-4-hydroxypentyl isoquinolin-3-ylcarbamate (150 mg, 0.25 mmol) in acetonitrile (10 mL) was added TMSI (0.14 mL, 1.0 mmol) at 0° C. After stirred at RT for 10 min, the reaction was quenched with MeOH. The solvent was removed and the resulting residue was purified on RP-HPLC using a mixture of acetonitrile and H$_2$O (0.1% HCOOH buffer) to give (2S,4R)-2-((2-chloro-3-fluorobenzyl)(methyl)amino)-4-hydroxy-5-(phosphonooxy)pentyl isoquinolin-3-ylcarbamate (100 mg, 70%). LRMS (M+H$^+$) m/z 569.2.

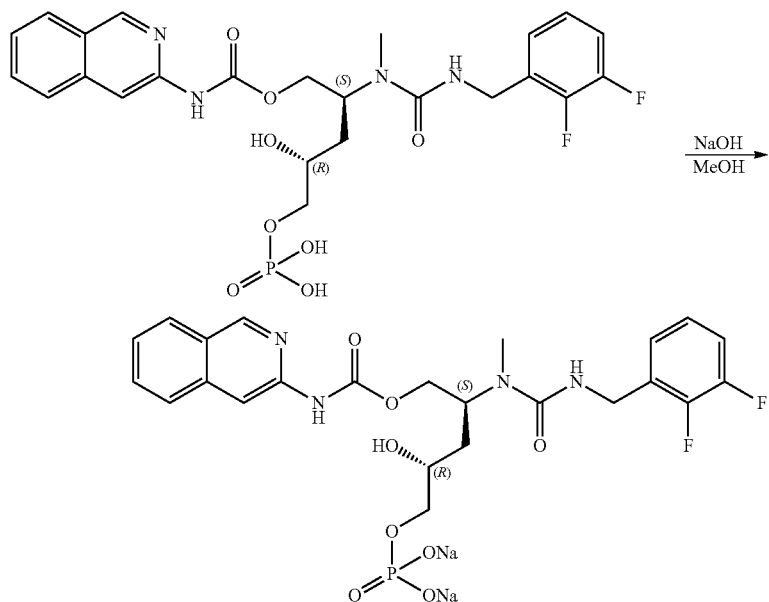

((2S,4R)-2-(2,3-fluorobenzyl)(methyl)amino)-4-hydroxy-5-(phosphonooxy)pentyl isoquinolin-3-ylcarbamate (100 mg, 0.176 mmol) in MeOH (4 mL) was added NaOH (0.1 N, 3.6 mL, 0.36 mmol) at 0° C. After stirred at 0° C. for 1 h, the mixture was concentrated to give sodium (2R,4S)-4-(3-(2,3-difluorobenzyl)-1-methylureido)-2-hydroxy-5-(isoquinolin-3-ylcarbamoyloxy)pentyl phosphate (100.1 mg, 93%) as a white solid. LRMS (M−2Na+3H$^+$) m/z 569.5.

Example 34

Preparation of Sodium (2S,4S)-4-((2,3-difluorobenzyl)(methyl)amino)-2-hydroxy-5-(isoquinolin-3-ylcarbamoyloxy)pentyl phosphate

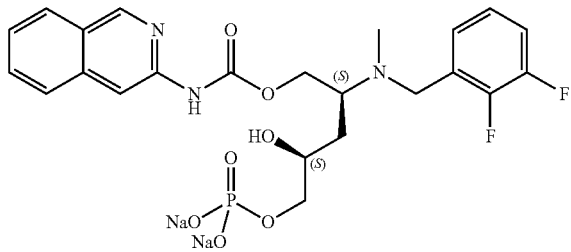

sodium (2S,4S)-4-((2,3-difluorobenzyl)(methyl)amino)-2-hydroxy-5-(isoquinolin-3-ylcarbamoyloxy)pentyl phosphate

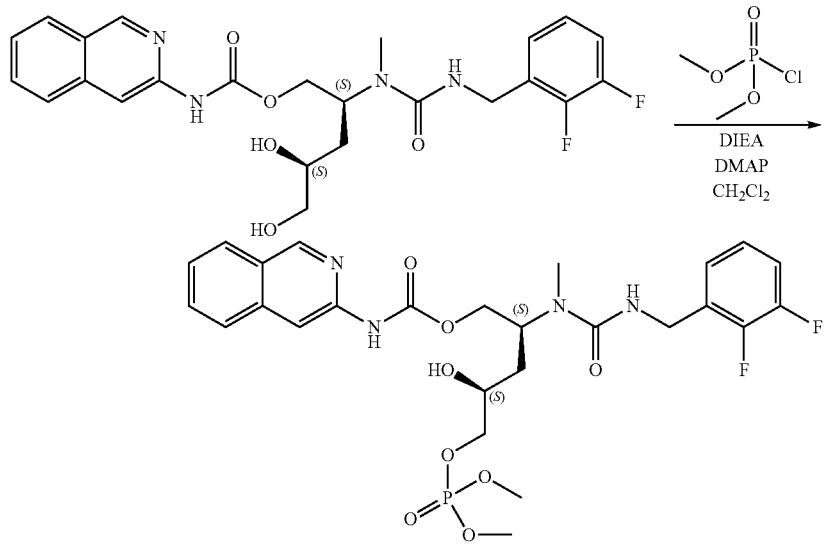

To a solution of (2S,4S)-2-(3-(2,3-difluorobenzyl)-1-methylureido)-4,5-dihydroxypentyl isoquinolin-3-ylcarbamate (0.61 g, 1.23 mmol), DIEA (0.41 mL, 2.45 mmol), and DMAP (0.30 g, 2.46 mmol) in anhydrous THF (20 mL) was added dimethyl chlorophorophosphate (0.13 mL, 1.23 mmol) at 0° C. After stirred at RT for 1 h, an additional dimethyl chlorophorophosphate (0.66 mL, 6.15 mmol) was added at 0° C. The reaction mixture was stirred for 30 min and quenched with MeOH. The mixture was diluted with EtOAc (100 mL). The organic mixture was washed with saturated NaHCO$_3$, HCL (1 N), saturated NaHCO$_3$, water and brine, dried over Na$_2$SO$_4$, filtered, and concentrated. The residue was purified on RP-HPLC using a mixture of acetonitrile and H$_2$O to give (2S,4S)-2-(3-(2,3-difluorobenzyl)-1-methylureido)-5-(dimethoxyphosphoryloxy)-4-hydroxypentyl isoquinolin-3-ylcarbamate (161 mg, 22%). LRMS (M+H$^+$) m/z 597.2.

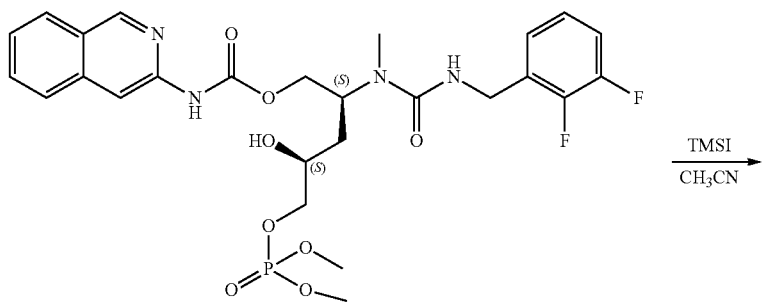

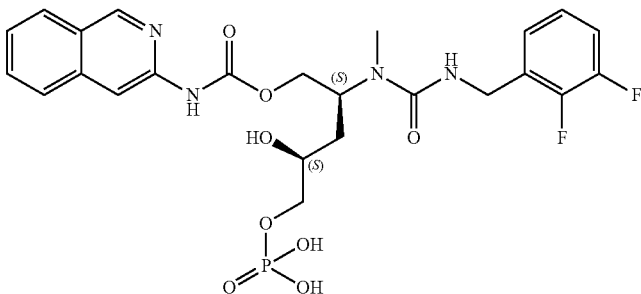

(2S,4S)-2-(3-(2,3-difluorobenzyl)-1-methylureido)-5-(dimethoxyphosphoryloxy)-4-hydroxypentyl isoquinolin-3-ylcarbamate (161 mg, 0.27 mmol) in acetonitrile (5 mL) was added TMSI (0.15 mL, 1.08 mmol) at 0° C. After stirred at RT for 10 min, the reaction was quenched with MeOH. The solvent was removed and the resulting residue was purified on RP-HPLC using a mixture of acetonitrile and H₂O (0.1% HCOOH buffer) to give (2S,4S)-2-((2-chloro-3-fluorobenzyl)(methyl)amino)-4-hydroxy-5-(phosphonooxy)pentyl isoquinolin-3-ylcarbamate (70 mg, 46%). LRMS (M+H⁺) m/z 569.2.

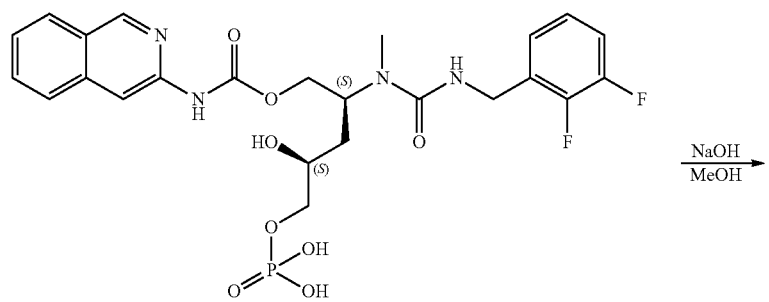

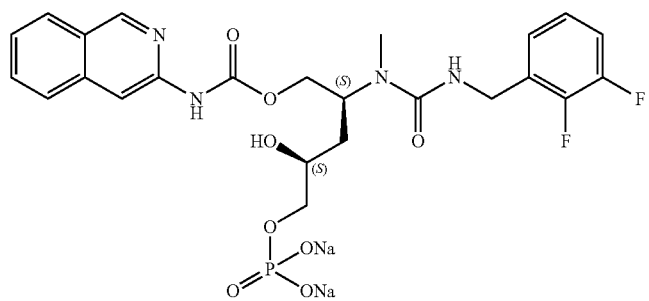

((2S,4S)-2-(2,3-fluorobenzyl)(methyl)amino)-4-hydroxy-5-(phosphonooxy)pentyl isoquinolin-3-ylcarbamate (100 mg, 0.176 mmol) in MeOH (4 mL) was added NaOH (0.1 N, 3.6 mL, 0.36 mmol) at 0° C. After stirred at 0° C. for 1 h, the mixture was concentrated to give sodium (2S,4S)-4-(3-(2,3-difluorobenzyl)-1-methylureido)-2-hydroxy-5-(isoquinolin-3-ylcarbamoyloxy)pentyl phosphate (80 mg, quant.) as a white solid. LRMS (M−2Na⁺+3H⁺) m/z 569.5.

Example 35

Preparation of (2S,4S)-2-(3-(2-chloro-3-fluorobenzyl)-1-methylureido)-4,5-dihydroxypentyl 6-fluoroisoquinolin-3-ylcarbamate and (2S,4R)-2-(3-(2-chloro-3-fluorobenzyl)-1-methylureido)-4,5-dihydroxypentyl 6-fluoroisoquinolin-3-ylcarbamate

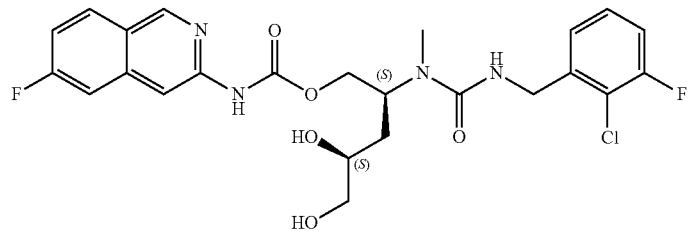

(2S,4S)-2-(3-(2-chloro-3-fluorobenzyl)-1-methylureido)-4,5-dihydroxypentyl 6-fluoroisoquinolin-3-ylcarbamate

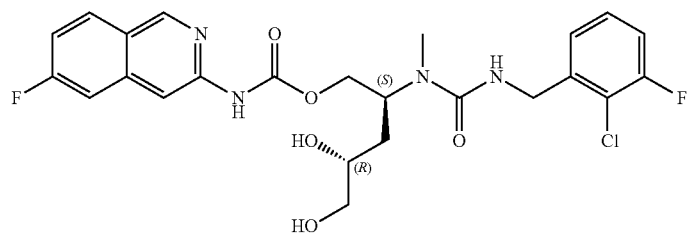

(2S,4R)-2-(3-(2-chloro-3-fluorobenzyl)-1-methylureido)-4,5-dihydroxypentyl 6-fluoroisoquinolin-3-ylcarbamate

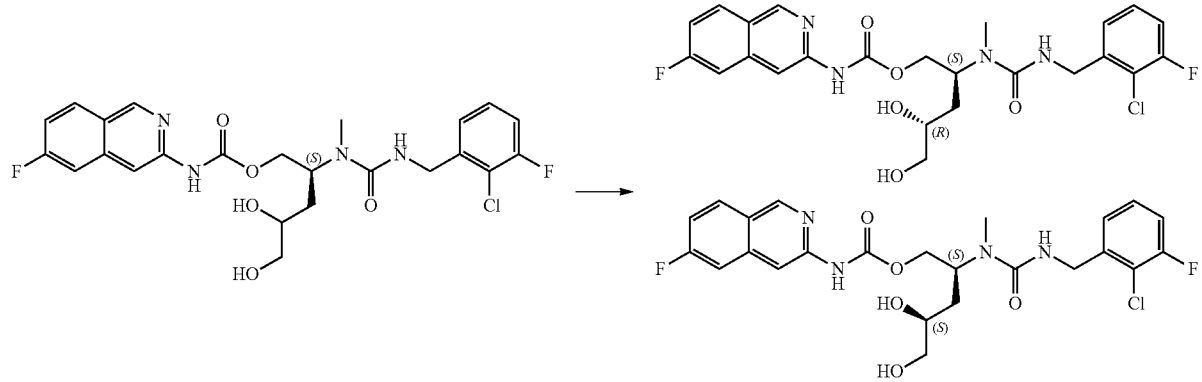

A solution of crude (2S)-2-(3-(2-chloro-3-fluorobenzyl)-1-methylureido)-4,5-dihydroxypentyl 6-fluoroisoquinolin-3-ylcarbamate (0.07 g) in DCM (1 mL) was loaded onto a TLC Silica gel 60 F254 (20×20 cm) plate and developed with a mixture of DCM and methanol (20:1). The top layer was collected and stirred in methanol (50 mL) for 10 min. After filtration, the filtrate was concentrated to give (2S,4S)-2-(3-(2-chloro-3-fluorobenzyl)-1-methylureido)-4,5-dihydroxypentyl 6-fluoroisoquinolin-3-ylcarbamate (0.01 g, 14.3%). LRMS (M+H$^+$) m/z 523.2. The same process was applied to the bottom layer to give (2S,4R)-2-(3-(2-chloro-3-fluorobenzyl)-1-methylureido)-4,5-dihydroxypentyl 6-fluoroisoquinolin-3-ylcarbamate (27 mg, 38.6%). LRMS (M+H$^+$) m/z 523.2.

Example 36

Preparation of (2S)-2-((2,3-difluorobenzyl)(methyl)amino)-5-dihydroxypentyl isoquinolin-3-ylcarbamate

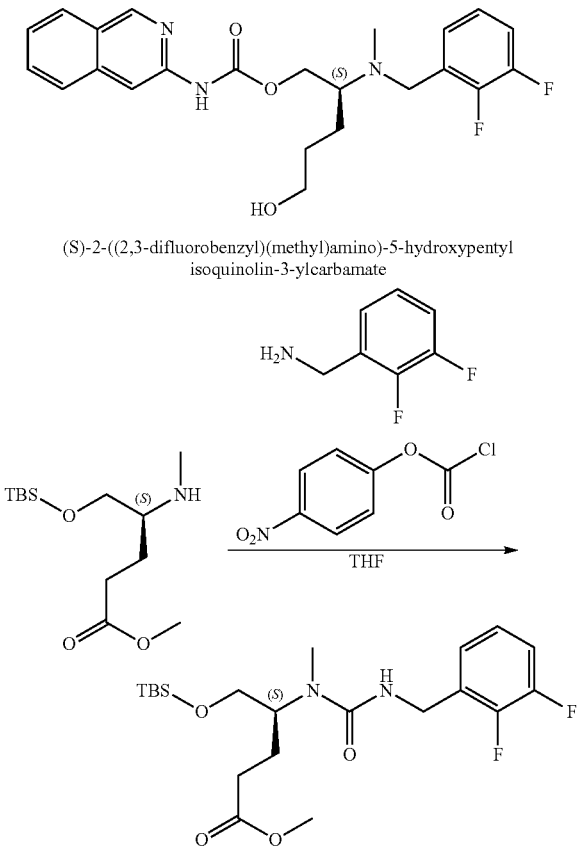

(S)-2-((2,3-difluorobenzyl)(methyl)amino)-5-hydroxypentyl isoquinolin-3-ylcarbamate To a solution of 4-nitrophenylchloroformate (6.66 g, 33.0 mmol) in THF (100 mL) was added a solution of 2,3-difluorobenzylamine (4.04 mL, 34.5 mmol) and DIEA (17.5 mL, 100.5 mmol) in THF (20 mL). The resulting solution was stirred at RT for 20 min. The reaction solution was added into a solution of (S)-methyl 5-(tert-butyldimethylsilyloxy)-4-(methylamino)pentanoate (28.8 mmol) in THF (30 mL). The resulting solution was stirred at RT for 1 h. The solvent was removed and the resulting residue was re-dissolved in EtOAc (500 mL). The organic mixture was washed with NaOH (1 N, 100 mL×3), HCl (0.5 N, 100 mL), saturated NaHCO₃, and brine, dried over Na₂SO₄, filtered, and concentrated under reduced pressure. The residue was purified on silica gel column using a mixture of DCM and MeOH to give (S)-methyl 5-(tert-butyldimethylsilyloxy)-4-(3-(2,3-difluorobenzyl)-1-methylureido)pentanoate (9.7 g, 76% for three steps) as an oil. LRMS (M+H⁺) m/z 445.2.

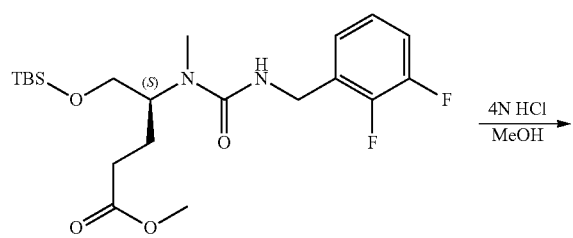

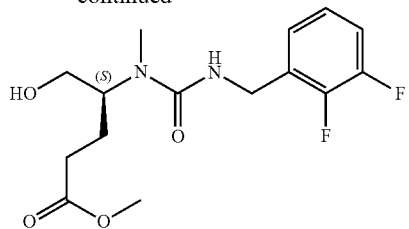

To a solution of (S)-methyl 5-(tert-butyldimethylsilyloxy)-4-(3-(2,3-difluorobenzyl)-1-methylureido)pentanoate (9.7 g, 21.6 mmol) in MeOH (40 mL) was added HCl (4 N in dioxane, 5.40 mL, 21.6 mmol). The resulting solution was stirred at RT for 1 h. The mixture was concentrated and re-dissolved in EtOAc. The organic mixture was washed with saturated NaHCO₃ and brine, dried over Na₂SO₄, filtered, and concentrated under reduced pressure to give (S)-methyl 4-(3-(2,3-difluorobenzyl)-1-methylureido)pentanoate (6.84 g, crude) as a white solid, which was used without further purification. LRMS (M+H⁺) m/z 331.2.

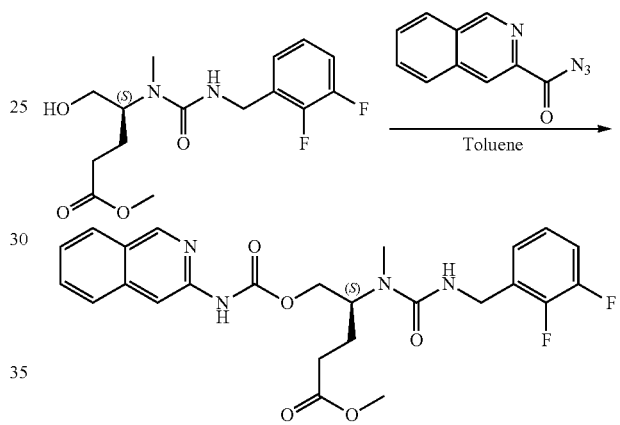

To a solution of (S)-methyl 4-(3-(2,3-difluorobenzyl)-1-methylureido)pentanoate (2.23 g, 6.75 mmol) in toluene (20 mL) was added isoquinoline-3-carbonyl azide (1.33 g, 6.75 mmol). The resulting solution was stirred at 100° C. for 1 h. The mixture was cooled and concentrated. The residue was purified on silica gel to give (S)-methyl 4-(3-(2,3-difluorobenzyl)-1-methylureido)-5-(isoquinolin-3-ylcarbamoyloxy)pentanoate (2.48 g, 73% for two steps). LRMS (M+H⁺) m/z 501.2.

To a solution of (S)-methyl 4-(3-(2,3-difluorobenzyl)-1-methylureido)-5-(isoquinolin-3-ylcarbamoyloxy)pentanoate (1.0 g, 2.0 mmol) in THF (10 mL) was added LAH (2.0 M in THF, 1.5 mL, 3.0 mmol) at 0° C. and stirred at 0° C. for 20 min. The mixture was quenched with H₂O (0.12 mL), NaOH (3 N, 0.12 mL), and H₂O (0.36 mL) and the resulting suspension was stirred at RT for 30 min and filtered. The filtrate was concentrated and the residue was purified on silica gel column using a mixture of EtOAc and hexanes to give (S)-2-(3-(2,3-difluorobenzyl)-1-methylureido)-5-hydroxypentyl isoquinolin-3-ylcarbamate (0.52 g, 55%). LRMS (M+H$^+$) m/z 473.2.

Example 37

Preparation of sodium (S)-4-((2,3-difluorobenzyl)(methyl)amino)-5-(isoquinolin-3-ylcarbamoyloxy)pentyl phosphate

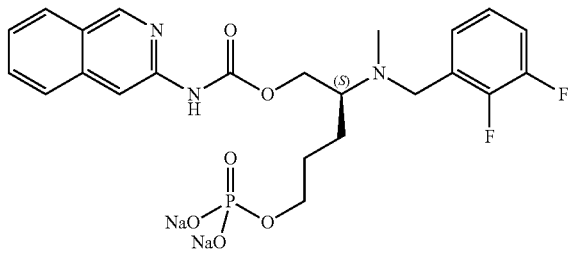

sodium (S)-4-((2,3-difluorobenzyl)(methyl)amino)-5-(isoquinolin-3-ylcarbamoyloxy)pentyl phosphate Method A:

To a solution of (S)-2-(3-(2,3-difluorobenzyl)-1-methylureido)-5-hydroxypentyl isoquinolin-3-ylcarbamate (0.52 g, 1.11 mmol), DIEA (0.96 mL, 5.52 mmol), and DMAP (0.27 g, 2.21 mmol) in anhydrous DCM (10 mL) was added dimethyl chlorophorophosphate (0.36 mL, 3.36 mmol) at RT After stirred at RT for 15 min, the reaction mixture was quenched with MeOH. The mixture was diluted with EtOAc (100 mL). The organic mixture was washed with saturated NaHCO$_3$, HCl (1 N), saturated NaHCO$_3$, and brine, dried over Na$_2$SO$_4$, filtered, and concentrated to give (S)-2-(3-(2,3-difluorobenzyl)-1-methylureido)-5-(dimethoxyphosphoryloxy)pentyl isoquinolin-3-ylcarbamate (626 mg, 98%), which was used without purification. LRMS (M+H$^+$) m/z 581.2.

Method A:

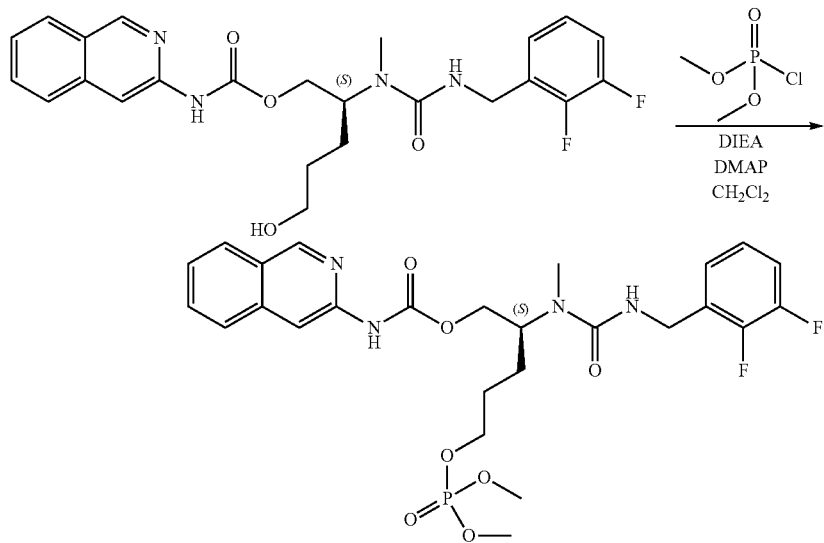

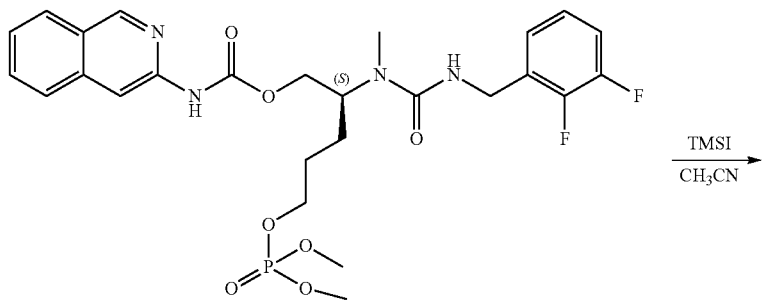

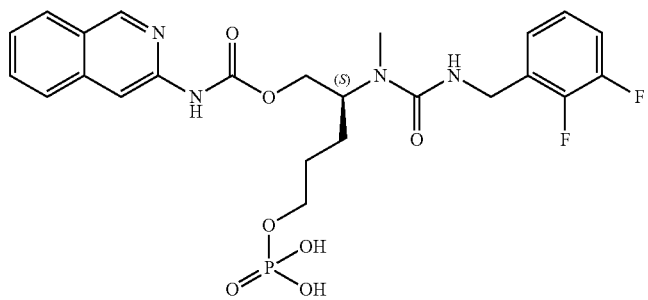

(S)-2-(3-(2,3-difluorobenzyl)-1-methylureido)-5-(dimethoxyphosphoryloxy)pentyl isoquinolin-3-ylcarbamate (531 mg, 0.91 mmol) in acetonitrile (18 mL) was added TMSI (0.50 mL, 3.66 mmol) at 0° C. After stirred at RT for 10 min, the reaction was quenched with MeOH. The solvent was removed and the resulting residue was purified on RP-HPLC using a mixture of acetonitrile and H$_2$O (0.1% HCOOH buffer) to give (S)-2-(3-(2,3-difluorobenzyl)-1-methylureido)-5-(phosphonooxy)pentyl isoquinolin-3-ylcarbamate (261 mg, 52%). LRMS (M+H$^+$) m/z 553.5.

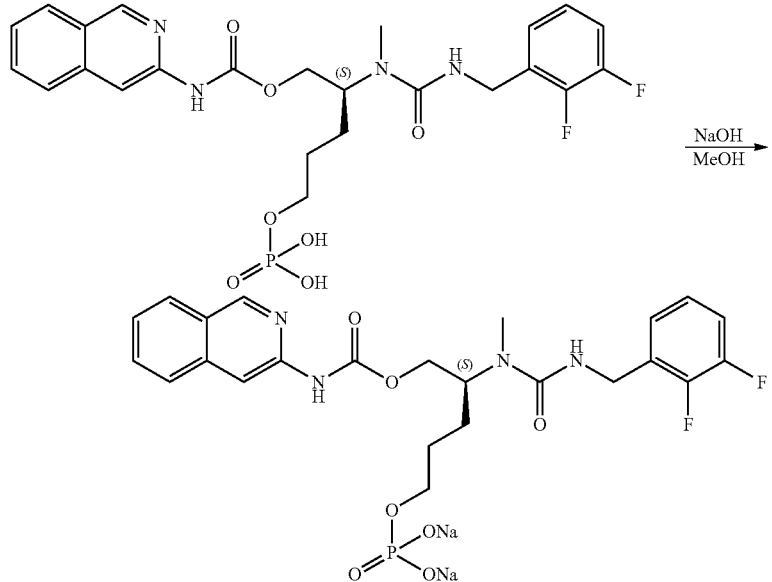

(S)-2-(3-(2,3-difluorobenzyl)-1-methylureido)-5-(phosphonooxy)pentyl isoquinolin-3-ylcarbamate (261 mg, 0.472 mmol) in MeOH (10 mL) was added NaOH (0.1 N, 9.2 mL, 0.92 mmol) at 0° C. After stirred at 0° C. for 1 h, the mixture was concentrated to give sodium (S)-4-((2,3-difluorobenzyl)(methyl)amino)-5-(isoquinolin-3-ylcarbamoyloxy)pentyl phosphate (260 mg, 88%) as a white solid. LRMS (M+H$^+$) m/z 585.5.

Method B:

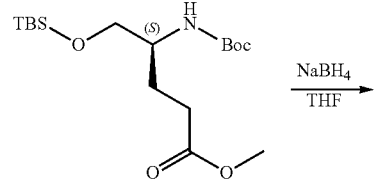

To a solution of (S)-methyl 4-(tert-butoxycarbonylamino)-5-(tert-butyldimethylsilyloxy)pentanoate (40 g, 0.111 mol)

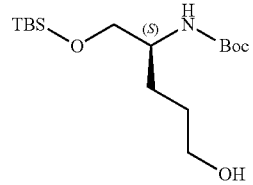

in THF (100 mL) and MeOH (5.0 mL) was added LiBH$_4$ (2M in THF, 56.0 mL, 0.112 mol) at 0° C. The reaction mixture was stirred at RT for 2 h. The reaction mixture was cooled to 0° C. and slowly quenched with saturated NaHCO$_3$ solution. The resulting mixture was stirred RT overnight and filtered. The solid was washed with EtOAc. The combined filtrate was diluted with an additional EtOAc (200 mL). The organic layer was washed with water and brine, dried over Na$_2$SO$_4$, filtered, and concentrated to give (S)-tert-butyl 1-(tert-butyldimethylsilyloxy)-5-hydroxypentan-2-ylcarbamate (39.5 g), which was used without further purification. LRMS (M+Na$^+$) m/z 356.4.2.

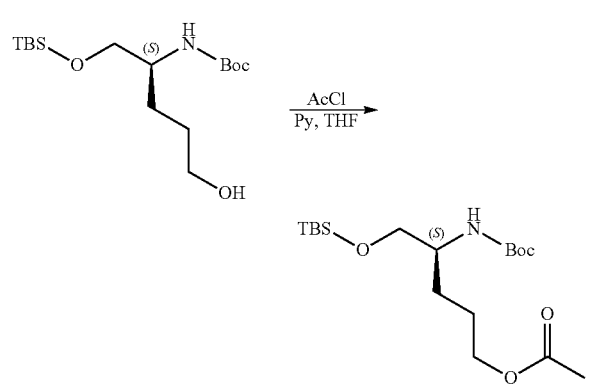

To a solution of (S)-methyl 4-(tert-butoxycarbonyl(methyl)amino)-5-(tert-butyldimethylsilyloxy)pentanoate (111 mmol) and pyridine (150 mL, 1.662 mol) in THF (500 mL) was added acetyl chloride (150 mL, 333.2 mmol) at 0° C. The resulting mixture was stirred at RT for 1 h. The solvent was removed and the remaining residue was diluted with EtOAc. The organic mixture was washed with water and brine, dried over Na$_2$SO$_4$, filtered, and concentrated. The residue was purified on silica gel column to give (S)-4-(tert-butoxycarbonylamino)-5-(tert-butyldimethylsilyloxy)pentyl acetate (39.6 g, 95%). LRMS (M+H$^+$-Boc) m/z 276.2.

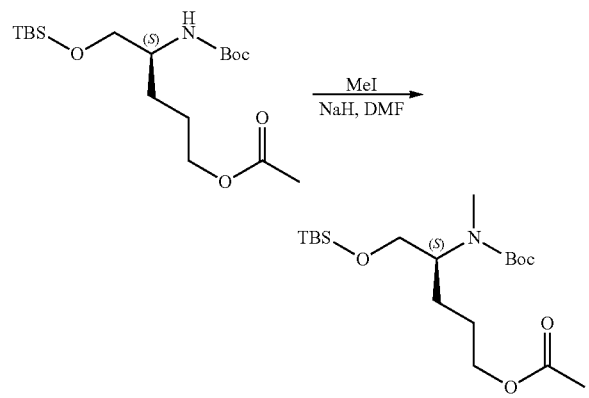

To a solution of (S)-4-(tert-butoxycarbonylamino)-5-(tert-butyldimethylsilyloxy)pentyl acetate (48.2 g, 0.124 mol) and MeI (23.2 mL, 0.372 mol) in DMF (500 mL) was added sodium hydride (60%, 9.9 g, 0.248 mol) at 0° C. The resulting mixture was stirred at 0° C. for 2½ h and LC-MS indicated the reaction was completed. The reaction was quenched with saturated NH$_4$Cl solution and diluted with EtOAc. The organic layer was washed with water and brine, dried over Na$_2$SO$_4$, filtered, and concentrated to give (S)-4-(tert-butoxycarbonyl(methyl)amino)-5-(tert-butyldimethylsilyloxy)pentyl acetate (51 g, crude). LRMS (M+H$^+$-Boc) m/z 290.2.

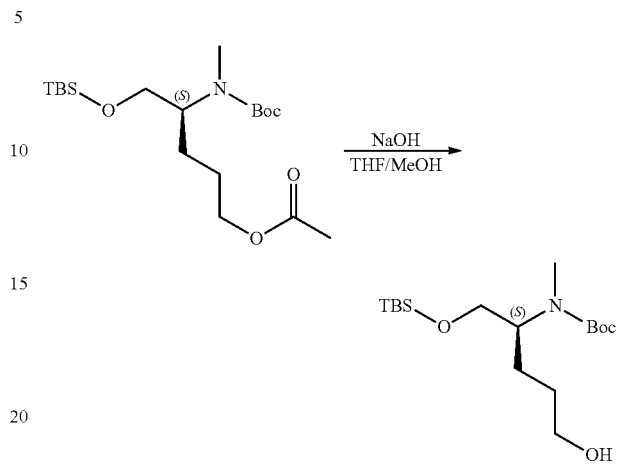

To a solution of (S)-4-(tert-butoxycarbonyl(methyl)amino)-5-(tert-butyldimethylsilyloxy)pentyl acetate (0.124 mol) in THF (200 mL) and MeOH (50 mL) was added sodium hydroxide (2 N, 93 mL, 0.186 mol) at RT The reaction was stirred at RT for 2 h and LC-MS indicated the reaction was completed. The reaction mixture was diluted with EtOAc and the organic layer was washed with water and brine, dried over Na$_2$SO$_4$, filtered, and concentrated. The resulting residue was purified on silica gel column using a mixture of hexanes and EtOAc to give (S)-tert-butyl 1-(tert-butyldimethylsilyloxy)-5-hydroxypentan-2-yl(methyl)carbamate (37.9 g, 88%). LRMS (M+H$^+$-Boc) m/z 248.2.

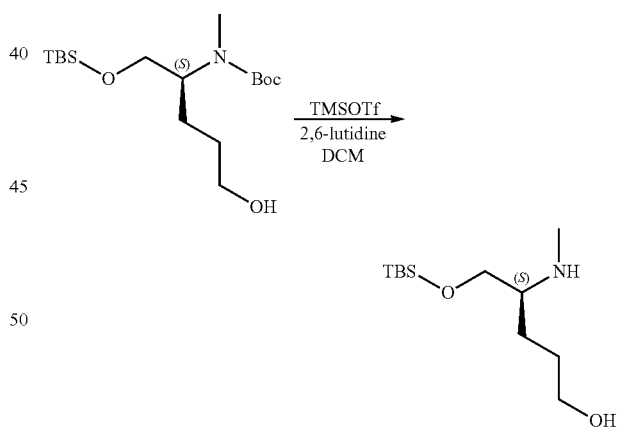

To a solution of (S)-methyl 4-(tert-butoxycarbonyl(methyl)amino)-5-(tert-butyldimethylsilyloxy)pentanoate (37.9 g, 109.2 mmol) in DCM (200 mL) was added 2,6-lutidine (25.3 mL, 218.4 mmol) followed by TMSOTf (29.6 mL, 163.8 mmol). The resulting solution was stirred at RT for 1 h. The solvent was removed and the remaining residue was diluted with EtOAc. The organic mixture was washed with water and brine, dried over Na$_2$SO$_4$, filtered, and concentrated to give (S)-5-(tert-butyldimethylsilyloxy)-4-(methylamino)pentan-1-ol, which was used without further purification. LRMS (M+H$^+$) m/z 248.2.

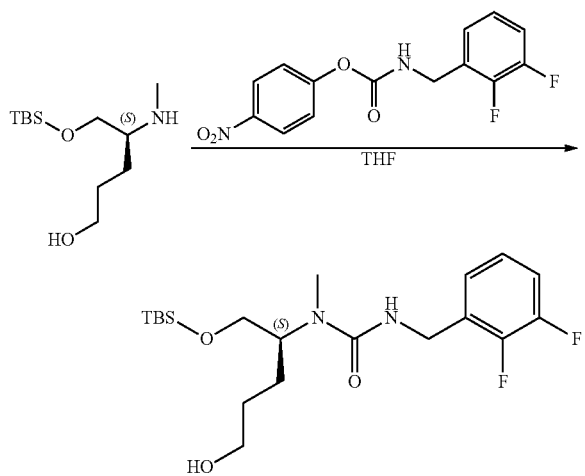

To a solution of (S)-5-(tert-butyldimethylsilyloxy)-4-(methylamino)pentan-1-ol (109.2 mmol) in THF (200 mL) was added 4-nitrophenyl 2,3-difluorobenzylcarbamate (43.72 g, 142.0 mmol). The resulting solution was stirred at RT for 1 h. The solvent was removed and the resulting residue was dissolved in EtOAc (800 mL). The organic mixture was washed with NaOH (1 N, 100 mL×3), HCl (0.5 N, 100 mL), NaHCO$_3$ (sat.), and brine, dried over Na$_2$SO$_4$, filtered, and concentrated under reduced pressure. The residue was purified on silica gel column using a mixture of EtOAC and hexanes to give (S)-1-(1-(tert-butyldimethylsilyloxy)-5-hydroxypentan-2-yl)-3-(2,3-difluorobenzyl)-1-methylurea (35.1 g, 76%) as a pale yellow oil. LRMS (M+H$^+$) m/z 417.2.

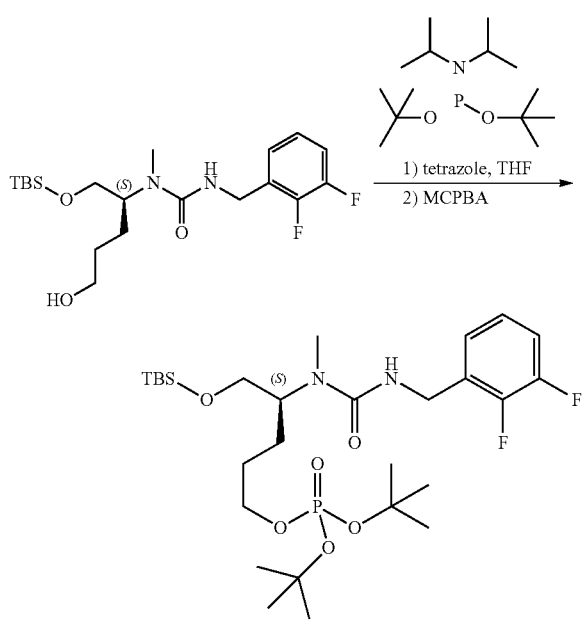

To a solution of (S)-1-(1-(tert-butyldimethylsilyloxy)-5-hydroxypentan-2-yl)-3-(2,3-difluorobenzyl)-1-methylurea-(tert-butyldimethylsilyloxy)-4-(3-(2,3-difluorobenzyl)-1-methylureido)pentanoate (6.1 g, 14.66 mmol) in THF (20 mL) was added tetrazole (0.34 M in acetonitrile, 172.0 mL, 58.64 mmol) followed by addition of di-tert-butyl diisopropylphosphoramidite (9.3 mL, 29.32 mmol) at RT The resulting solution was stirred at RT for 2 h. To this mixture was added MCPBA (70%, 7.3 g, 29.32 mmol) at RT. The reaction mixture was stirred at RT overnight and quenched with Na$_2$SO$_3$. The mixture was filtered and the filtrate was concentrated and dissolved in EtOAc. The organic mixture was washed with NaOH (1 N×2), NaHCO$_3$ (sat.), and brine, dried over Na$_2$SO$_4$, filtered, and concentrated under reduced pressure. The residue was purified on silica gel column using a mixture of EtOAc and hexanes to give (S)-di-tert-butyl 5-(tert-butyldimethylsilyloxy)-4-(3-(2,3-difluorobenzyl)-1-methylureido)pentyl phosphate (4.1 g, 54%). LRMS (M+H$^{+-}$2 $^t$Bu) m/z 491.2.

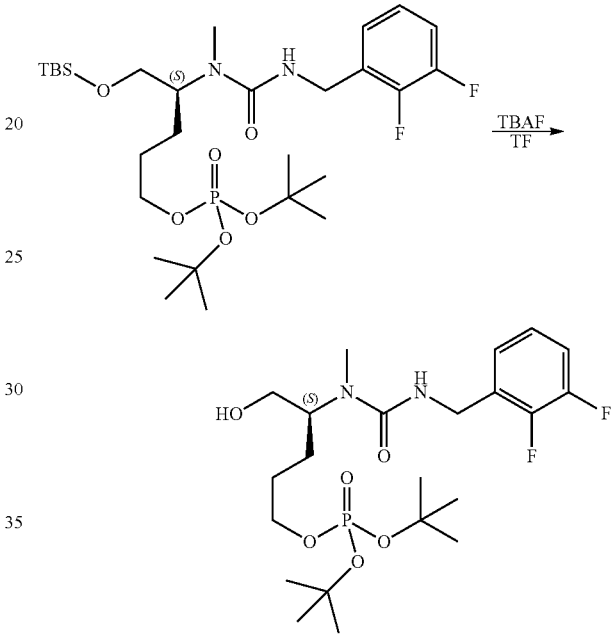

To a solution of (S)-di-tert-butyl 5-(tert-butyldimethylsilyloxy)-4-(3-(2,3-difluorobenzyl)-1-methylureido)pentyl phosphate (4.1 g, 7.95 mmol) in THF (40 mL) was added TBAF (1.0 M in THF, 8.0 mL, 8.0 mmol). The resulting solution was stirred at RT for 1 h. The mixture was quenched with sat. NH$_4$Cl and diluted with EtOAc. The organic layer was washed with sat. NH$_4$Cl (×2) and brine, dried over Na$_2$SO$_4$, filtered, and concentrated under reduced pressure. The residue was purified on silica gel column using a mixture of EtOAc and hexanes to give (S)-di-tert-butyl 4-(3-(2,3-difluorobenzyl)-1-methylureido)-5-hydroxypentyl phosphate (2.52 g, 61%) as a colorless oil. LRMS (M+H$^{+-}$2 $^t$Bu) m/z 383.0.

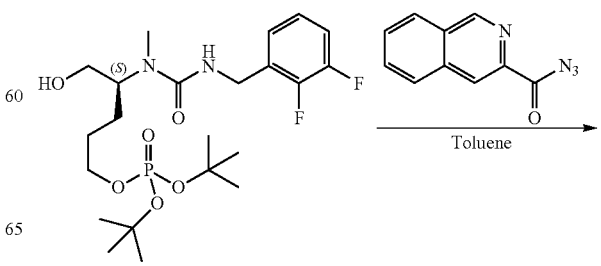

441

-continued

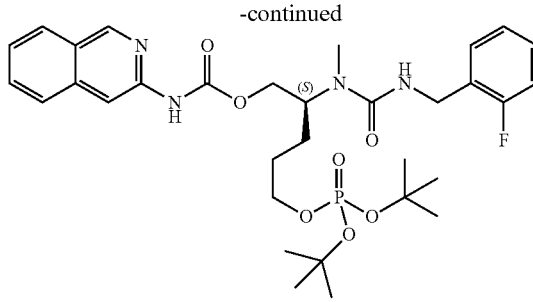

To a solution of (S)-di-tert-butyl 4-(3-(2,3-difluorobenzyl)-1-methylureido)-5-hydroxypentyl phosphate (2.52 g, 4.88 mmol) in toluene (100 mL) were added isoquinoline-3-carbonyl azide (1.2 g, 5.86 mmol) and DIEA (1.2 mL, 7.32 mmol). The resulting solution was stirred at 100° C. for 1 h. The mixture was cooled and concentrated. The residue was purified on silica gel column using a mixture of EtOAc and hexanes (0.1% TEA buffer) to give (S)-methyl 4-(3-(2,3-difluorobenzyl)-1-methylureido)-5-(isoquinolin-3-ylcarbamoyloxy)pentanoate (1.95 g, 60%). LRMS (M+H$^+$) m/z 665.2.

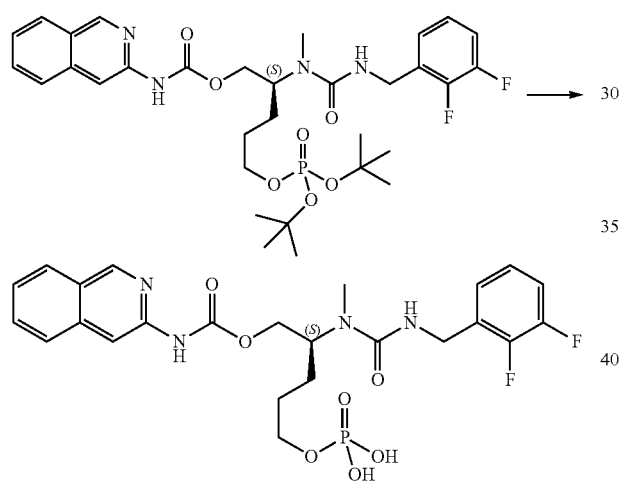

To a solution of (S)-methyl 4-(3-(2,3-difluorobenzyl)-1-methylureido)-5-(isoquinolin-3-ylcarbamoyloxy)pentanoate (1.65 g, 2.48 mmol) in MeOH was added HCl (6 N in MeOH/water, 8 mL, 48 mmol) at RT and stirred at RT for 30 min. The mixture was concentrated to almost dryness, cooled to 0° C., and adjusted pH to 2 using NaOH (1 N). The resulting precipitate was collected and dried to give (S)-2-(3-(2,3-difluorobenzyl)-1-methylureido)-5-(phosphonooxy)pentyl (1.37 g, 99.8%). LRMS (M+H$^+$) m/z 553.5.

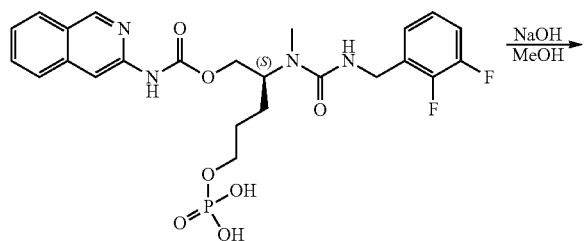

442

-continued

To a solution of (S)-2-(3-(2,3-difluorobenzyl)-1-methylureido)-5-(phosphonooxy)pentyl isoquinolin-3-ylcarbamate (2.50 g, 4.54 mmol) in MeOH (100 mL) was added NaOH (0.1 N, 90.7 mL, 9.07 mmol) at 0° C. After stirred at 0° C. for 1 h, the mixture was concentrated to give sodium (S)-4-((2,3-difluorobenzyl)(methyl)amino)-5-(isoquinolin-3-ylcarbamoyloxy)pentyl phosphate (2.15 g, 79%) as a white solid. LRMS (M−2Na$^+$+3H$^+$) m/z 553.5.

Example 38

Preparation of sodium (S)-4-(3-(2-chloro-3-fluorobenzyl)-1-methylureido)-5-(6-fluoroisoquinolin-3-ylcarbamoyloxy)-2,2-dimethylpentyl phosphate

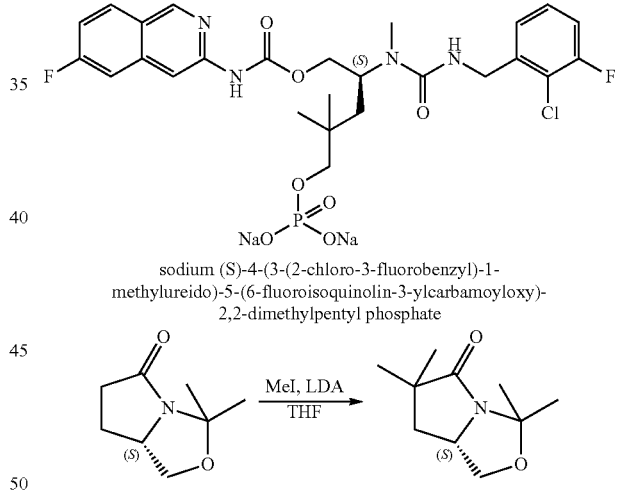

sodium (S)-4-(3-(2-chloro-3-fluorobenzyl)-1-methylureido)-5-(6-fluoroisoquinolin-3-ylcarbamoyloxy)-2,2-dimethylpentyl phosphate To a solution of (S)-3,3-dimethyl-dihydropyrrolo[1,2-c]oxazol-5(1H,3H,6H)-one (3.6 g, 23.2 mmol) and iodomethane (1.74 mL, 27.9 mmol) in THF (100 mL) was added LDA (2 M in THF, 14 mL, 28 mmol) at −76° C. After stirring at −76° C. for 4 h, the reaction mixture was added an additional iodomethane (1.86 mL, 30 mmol) in THF (100 mL) and LDA (2 M in THF, 15 mL, 30 mmol). The resulting mixture was stirred at −76° C. for 4 h, warmed to RT, stirred at RT for 4 days, and quenched with saturated NH$_4$Cl solution. The resulting mixture was diluted with EtOAc. The organic layer was washed with water and brine, dried over Na$_2$SO$_4$, filtered, and concentrated. The residue was purified on silica gel column using a mixture of EtOAc and hexanes to give (S)-3,3,6,6-tetramethyl-dihydropyrrolo[1,2-c]oxazol-5(1H,3H,6H)-one (3.1 g, 73%). LRMS (M+H$^+$) m/z 184.1.

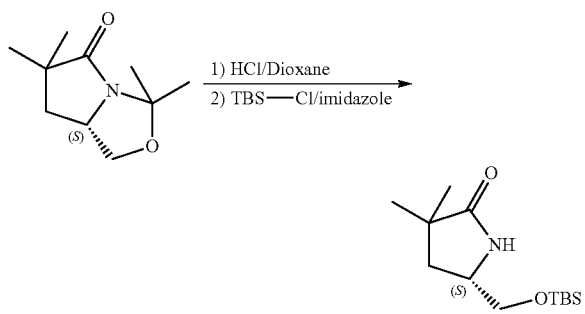

To a solution of (S)-3,3,6,6-tetramethyl-dihydropyrrolo[1,2-c]oxazol-5(1H,3H,6H)-one in methanol (20 mL) was added HCl (4 N in 1,4-dioxane, 10 mL, 40 mmol). The reaction mixture was stirred at RT for 30 min, concentrated to dryness, and re-dissolved in DCM (50 mL). To the resulting solution were added imidazole (1.5 g, 22 mmol) and TBS-Cl (2.8 g, 18.6 mmol) respectively. The mixture was stirred at RT overnight and filtered. The filtrate was concentrated and the residue was purified on silica gel column using a mixture of EtOAc and hexanes to give (S)-5-((tert-butyldimethylsilyloxy)methyl)-3,3-dimethylpyrrolidin-2-one (3.1 g, 71.2%). LRMS (M+H$^+$) m/z 258.3.

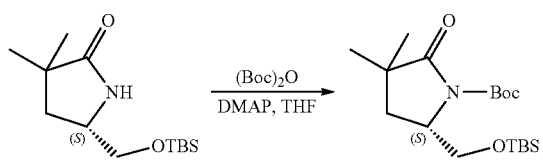

To a solution of (S)-5-((tert-butyldimethylsilyloxy)methyl)-3,3-dimethylpyrrolidin-2-one (3.1 g, 12.1 mmol) and DMAP (2.7 g, 21.8 mmol) in THF (50 mL) was added Boc$_2$O (4.4 g, 20 mmol). The reaction mixture was stirred at RT for 3 h and concentrated. The residue was purified on silica gel column using a mixture of EtOAc and hexanes to give (S)-tert-butyl 5-((tert-butyldimethylsilyloxy)methyl)-3,3-dimethyl-2-oxopyrrolidine-1-carboxylate (4.3 g, quant.). LRMS (M-Boc+H$^+$) m/z 258.2.

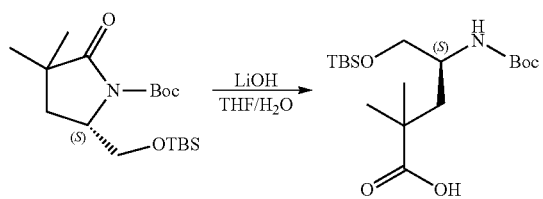

To a solution (S)-tert-butyl 5-((tert-butyldimethylsilyloxy)methyl)-3,3-dimethyl-2-oxopyrrolidine-1-carboxylate (2.7 g, 7.56 mmol) in THF (27 mL) and water (3 mL) was added LiOH (1 N, 15.2 mL, 15.2 mmol). The reaction mixture was stirred at RT overnight and concentrated. The residue was dissolved in water (20 mL), acidified with 10% citric acid to pH 6-7, and extracted with EtOAc. The organic layer was dried over Na$_2$SO$_4$, filtered, and concentrated to give (S)-4-(tert-butoxycarbonylamino)-5-(tert-butyldimethylsilyloxy)-2,2-dimethylpentanoic acid (2.6 g, 91.7%), which was used without further purification. LRMS (M-Boc+H$^+$) m/z 276.2.

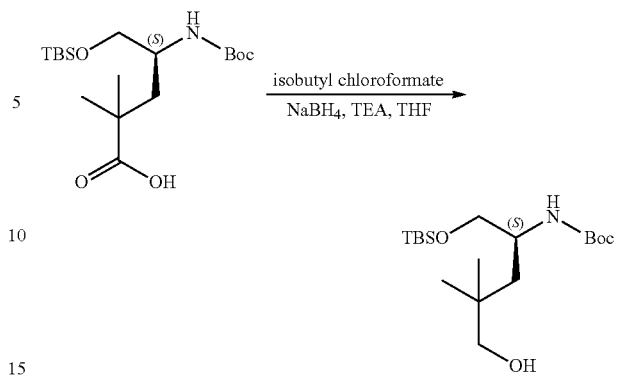

To a solution of (S)-4-(tert-butoxycarbonylamino)-5-(tert-butyldimethylsilyloxy)-2,2-dimethylpentanoic acid (2.5 g, 6.7 mmol) and TEA (1.9 mL, 13.4 mmol) in THF (50 mL) was added isobutyl chloroformate (1.1 mL, 8.04 mmol) at 0-5° C. The reaction mixture was stirred at 0-5° C. for 15 min and filtered. To the filtrate was added a suspension of NaBH$_4$ (0.5 g, 13.4 mmol) in water (5 mL) at 0-5° C. The reaction mixture was stirred at 0-5° C. for 30 min, quenched with saturated NH$_4$Cl solution, and extracted with EtOAc (200 mL). The organic layer was washed with water and brine, dried over Na$_2$SO$_4$, filtered, and concentrated. The residue was purified on silica gel column using a mixture of EtOAc and hexanes to give (S)-tert-butyl 1-(tert-butyldimethylsilyloxy)-5-hydroxy-4,4-dimethylpentan-2-ylcarbamate (2.0 g, 83.1%). LRMS (M+H$^+$-Boc) m/z 262.2.

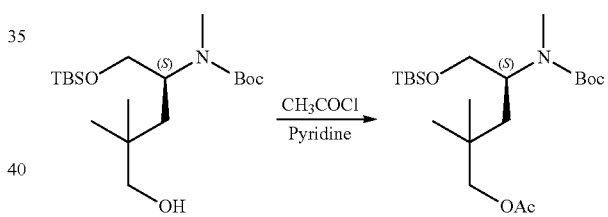

To a solution of (S)-tert-butyl 1-(tert-butyldimethylsilyloxy)-5-hydroxy-4,4-dimethylpentan-2-yl(methyl)carbamate (1.23 g, 3.27 mmol) in THF (20 mL) were added pyridine (0.79 mL) and acetyl chloride (0.386 g, 4.91 mmol). The reaction mixture was stirred at RT overnight and filtered. The filtrate was concentrated to give (S)-4-(tert-butoxycarbonyl(methyl)amino)-5-(tert-butyldimethylsilyloxy)-2,2-dimethylpentyl acetate (1.36 g, crude), which was used without further purification. LRMS (M-Boc+H$^+$) m/z 318.2

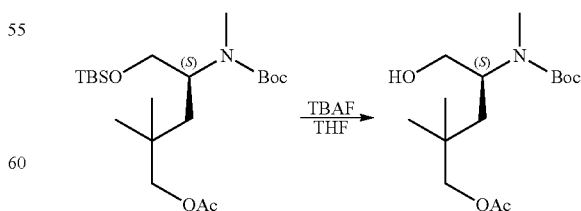

To a solution of (S)-4-(tert-butoxycarbonyl(methyl)amino)-5-(tert-butyldimethylsilyloxy)-2,2-dimethylpentyl acetate (3.27 mmol) in THF (100 mL) was added TBAF (1.0 M, 16.3 mL, 16.3 mmol). The reaction mixture was stirred at RT for 1 h and concentrated to dryness. The residue was dissolved in EtOAc. The organic mixture was washed with 10% citric acid, saturated NaHCO$_3$, and brine, dried over Na$_2$SO$_4$, filtered, and concentrated to give (S)-4-(tert-butoxycarbonyl(methyl)amino)-5-hydroxy-2,2-dimethylpentyl (0.95 g, crude), which was sued without further purification. LRMS (M-Boc+H$^+$) m/z 204.1

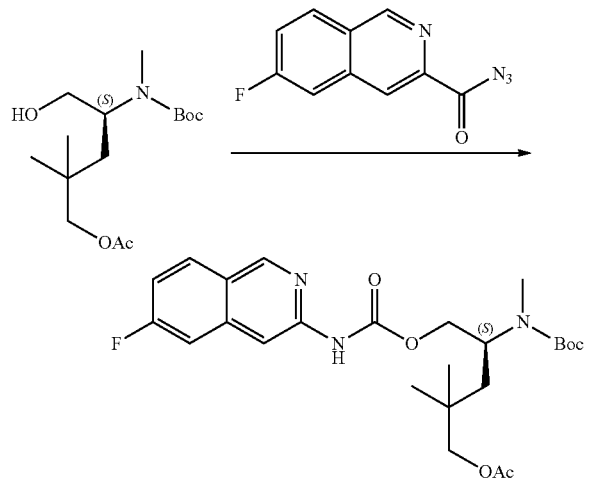

To a solution of (S)-4-(tert-butoxycarbonyl(methyl)amino)-5-hydroxy-2,2-dimethylpentyl (3.27 mmol) in toluene (20 mL) was added 6-fluoroisoquinoline-3-carbonyl azide (0.83 g, 3.84 mmol). The reaction mixture was stirred at 100° C. for 30 min, cooled, and concentrated. The residue was purified on silica gel column using a mixture of EtOAc and hexanes to give (S)-4-(tert-butoxycarbonyl(methyl)amino)-5-(6-fluoroisoquinolin-3-ylcarbamoyloxy)-2,2-dimethylpentyl acetate (1.5 g, 93% for three steps). LRMS (M+H$^+$) m/z 492.5

To a solution of (S)-4-(tert-butoxycarbonyl(methyl)amino)-5-(6-fluoroisoquinolin-3-ylcarbamoyloxy)-2,2-dimethylpentyl acetate (1.9 g, 3.8 mmol) in THF (50 mL) was added HCl (4 N in 1,4-dioxane, 19 mL, 76 mmol). The reaction mixture was stirred at RT for 1 h and concentrated to dryness. The residue was suspended in THF (100 mL). To the suspension were added DIEA (2.0 mL, 11.4 mmol) and 4-nitrophenyl 2-chloro-3-fluorobenzylcarbamate (1.2 g, 3.8 mmol). The reaction mixture was stirred at RT for 2 h and concentrated. The residue was purified on RP-HPLC using a mixture of acetonitrile and water to give (S)-2-(3-(2-chloro-3-fluorobenzyl)-1-methylureido)-5-hydroxy-4,4-dimethylpentyl 6-fluoroisoquinolin-3-ylcarbamate (1.1 g, 53%). LRMS (M+H$^+$) m/z 535.5

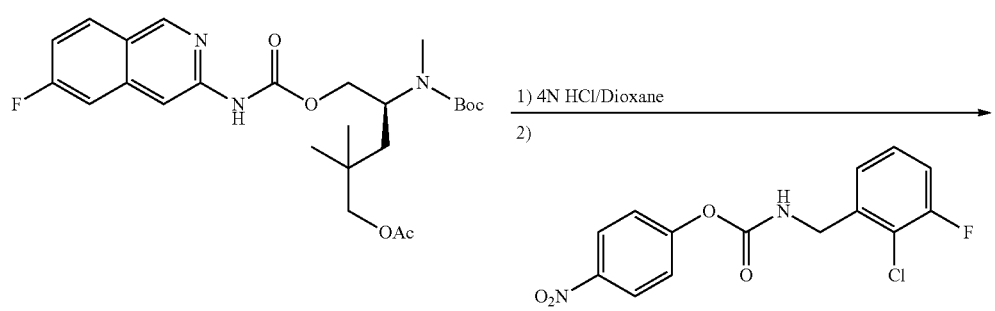

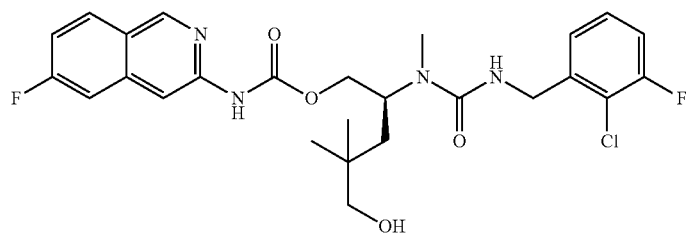

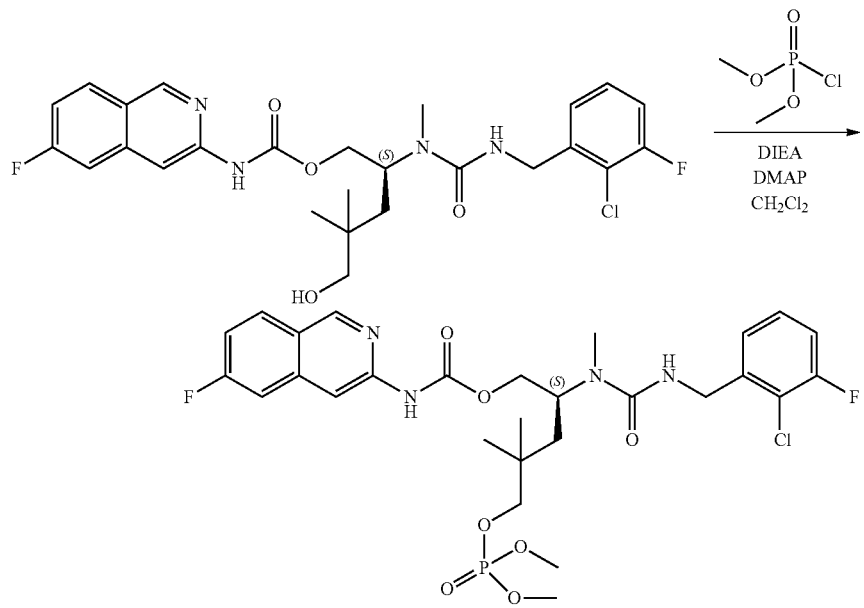

To a solution of (S)-2-(3-(2-chloro-3-fluorobenzyl)-1-methylureido)-5-hydroxy-4,4-dimethylpentyl 6-fluoroisoquinolin-3-ylcarbamate (0.45 g, 0.84 mmol), DIEA (0.73 mL, 4.2 mmol), and DMAP (1.02 g, 8.4 mmol) in anhydrous DCM (20 mL) was added dimethyl chlorophorophosphate (0.72 mL, 6.72 mmol) at RT After stirring at RT for 30 min, the reaction mixture was added an additional portion of dimethyl chlorophorophosphate (0.103 mL, 0.956 mmol) and DIEA (0.167 mL, 0.956 mmol). The reaction mixture was monitored by LC/MS. Upon the completion of the reaction, the mixture was quenched with MeOH (10 mL). The solvent was removed and the resulting residue was dissolved in EtOAc (100 mL). The organic mixture was washed with saturated NaHCO$_3$, water, and brine, dried over Na$_2$SO$_4$, filtered, and concentrated. The resulting residue was purified on RP-HPLC using a mixture of acetonitrile and water to give (S)-2-(3-(2-chloro-3-fluorobenzyl)-1-methylureido)-5-(dimethoxyphosphoryloxy)-4,4-dimethylpentyl 6-fluoroisoquinolin-3-ylcarbamate (280 mg, 52%). LRMS (M+H$^+$) m/z 643.6.

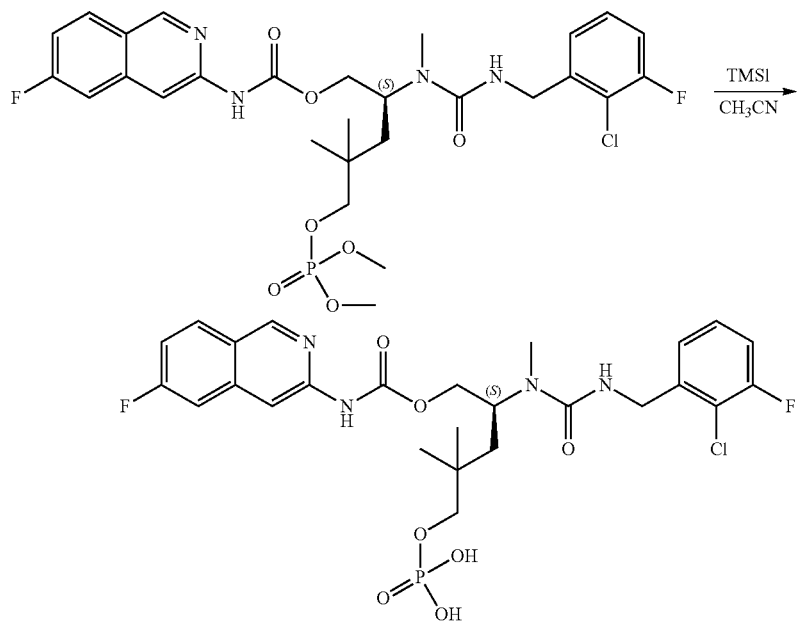

To a solution of (S)-2-(3-(2-chloro-3-fluorobenzyl)-1-methylureido)-5-(dimethoxyphosphoryloxy)-4,4-dimethylpentyl 6-fluoroisoquinolin-3-ylcarbamate (0.5 g, 0.79 mmol) in acetonitrile (50 mL) was added TMSI (0.848 mL, 6.23 mmol) at 0° C. After stirred at 0° C. for 30 min, the reaction was quenched with MeOH. The solvent was removed and the resulting residue was purified on RP-HPLC using a mixture of acetonitrile and water (0.1% HCOOH buffer) to give (S)-2-(3-(2-chloro-3-fluorobenzyl)-1-methylureido)-4,4-dimethyl-5-(phosphonooxy)pentyl 6-fluoroisoquinolin-3-ylcarbamate (340 mg, 71.1%). LRMS (M+H$^+$) m/z 615.5.

solution (50 mL) was added with vigorous stirring, followed by dropwise addition of a solution of di-tert-butylphosphite (20 g, 100 mmol) in dichloromethane (20 mL), the rate of addition was controlled to keep the temperature of reaction mixture not to exceed to 25° C. After addition of phosphite,

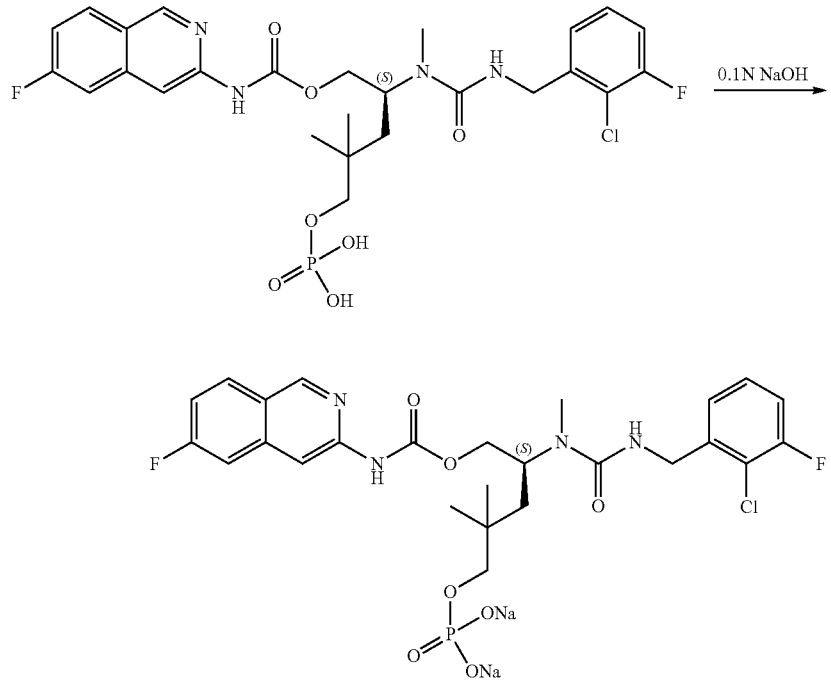

To a solution of S)-2-(3-(2-chloro-3-fluorobenzyl)-1-methylureido)-4,4-dimethyl-5-(phosphonooxy)pentyl 6-fluoroisoquinolin-3-ylcarbamate (340 mg, 0.55 mmol) in MeOH (30 mL) was added NaOH (0.1 N, 10.8 mL, 1.08 mmol) at 0° C. The reaction mixture was stirred at 0° C. for 10 min and concentrated. The residue was dissolved in small amount of water and lyophilized to give sodium (S)-4-(3-(2-chloro-3-fluorobenzyl)-1-methylureido)-5-(6-fluoroisoquinolin-3-ylcarbamoyloxy)-2,2-dimethylpentyl phosphate (343 mg, 94.1%) as white solid. LRMS (M−2Na$^+$+3H$^+$) m/z 615.5.

the mixture was further stirred at room temperature for 3 h, diluted with dichloromethane (20 mL) and separated. The organic phase was washed with saturated sodium bisulfite, water, brine, dried (Na$_2$SO$_4$), filtered and concentrated at RT. After removing the solvent, the residue was further pumped in vacuo for 1 h to give di-tert-butyl phosphorobromidate as a colorless oil (23.5 g, 86%).

Example 39

Preparation of di-tert-butyl phosphorobromidate

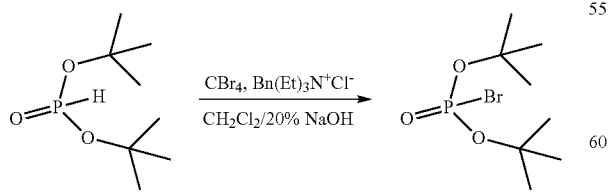

A 500 mL 3-neck flask equipped with dropping funnel and thermometer was charged with carbon tetrabromide (16.58 g, 50 mmol), benzyltriethylammonium chloride (1.14 g, 5.0 mmol) and dichloromethane (50 mL). A 20% w/w NaOH Example 40

Preparation of 1-((2S,4R)-1-(tert-butyldimethylsilyloxy)-4,5-dihydroxypentan-2-yl)-3-(2-chloro-3-fluorobenzyl)-1-methylurea

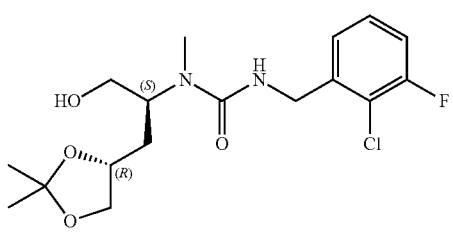

3-(2-chloro-3-fluorobenzyl)-1-((S)-1-((R)-2,2-dimethyl-1,3-dioxolan-4-yl)-3-hydroxypropan-2-yl)-1-methylurea

Method A

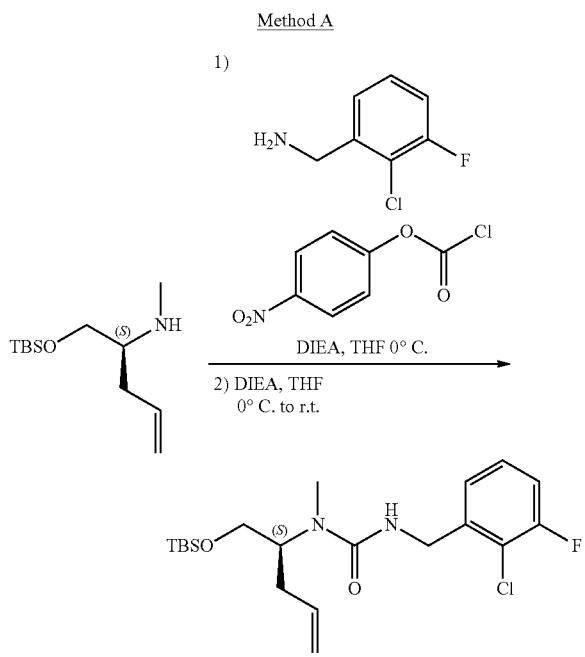

A 2 L 3-neck RBF was charged with 4-nitrophenylchloroformate (19.3 g, 96 mmol) and THF (400 mL) under $N_2$ and chilled to 0° C. in ice bath. To this mixture was added a solution of 2,3-difluorobenzylamine (14.2 g, 92 mmol) and DIEA (17.4 mL, 100 mmol) in one portion. The reaction mixture was stirred at 0° C. for 5 min and then an LC/MS or TLC was taken to confirm consumption of the starting material and presence of the nitrophenyl intermediate. A solution of [(S)-1-(tert-Butyl-dimethyl-silanyloxymethyl)-but-3-enyl]-methyl-amine (76 mmol) in THF (150 mL) was quickly added in one portion to the reaction mixture followed by DIEA (31.7 mL, 182 mmol). The reaction mixture was allowed to warm up to RT for approximately 2 h. The solvent was removed. The crude was diluted with ethyl acetate (1 L), washed with NaOH (1N, 500 mL×4) and brine, dried over sodium sulfate, filtered, and concentrated under reduced pressure. The crude oil was purified on silica gel using a gradient of 0 to 30% ethyl acetate in hexanes to obtain (S)-1-(1-(tert-butyldimethylsilyloxy)pent-4-en-2-yl)-3-(2,3-difluorobenzyl)-1-methylurea (26.1 g, 70%) as a white solid.

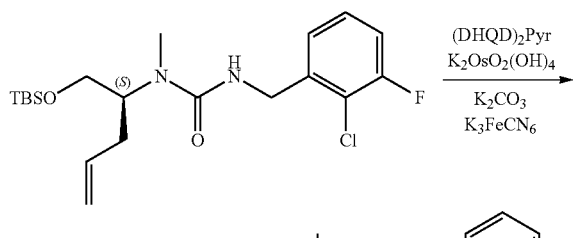

To a mixture of t-BuOH (300 mL) and water (300 mL) were added $K_2CO_3$ (17.0 g, 123 mmol,), (DHQD)$_2$Pyr (361 mg, 0.41 mmol), $K_2OsO_2(OH)_4$ (151 mg, 0.41 mmol), $K_3FeCN_6$ (40.5 g, 123 mmol) at RT The mixture was stirred at RT for 2 h and then cooled to 0° C. To the mixture was added a suspension of (S)-1-(1-(tert-butyldimethylsilyloxy)pent-4-en-2-yl)-3-(2-chloro-3-fluorobenzyl)-1-methylurea (17.0 g, 41 mmol) in 100 mL of t-BuOH/water (1:1), and the reaction was stirred at 0° C. overnight. LC-MS indicted the reaction was completed, $Na_2S_2O_3 \cdot 5H_2O$ (30.6 g, 123 mmol) was added to the reaction, and the reaction was stirred at RT for 30 min. The mixture was diluted with ethyl acetate (1 L), washed with water (250 mL×2) and brine (250 mL), dried over $Na_2SO_4$, and filtered. The filtrate was concentrated and purified on silica gel to give 1-((2S,4R)-1-(tert-butyldimethylsilyloxy)-4,5-dihydroxypentan-2-yl)-3-(2-chloro-3-fluorobenzyl)-1-methylurea (10.1 g, 55%) as a colorless oil.

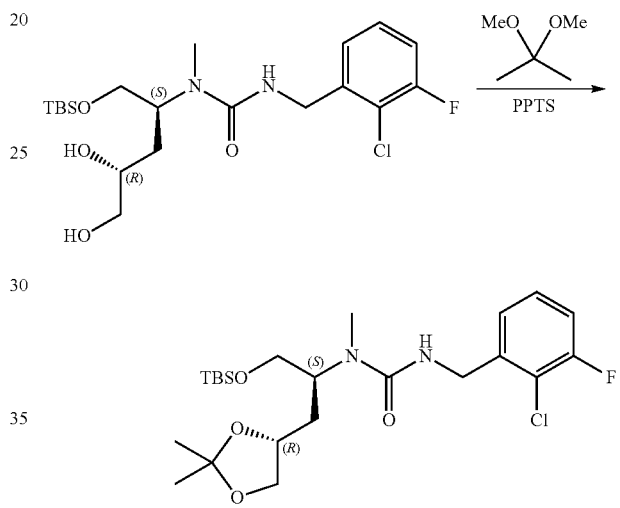

To a solution of the 1-((2S,4R)-1-(tert-butyldimethylsilyloxy)-4,5-dihydroxypentan-2-yl)-3-(2-chloro-3-fluorobenzyl)-1-methylurea 1 (4.5 g, 10.0 mmol) in DMF (170 mL) were added 2,2-dimethoxypropane (12.45 mL, 100.0 mmol) and PPTS (0.050 g, 0.02 mmol) at 0° C. After 1 h the reaction was warmed up to RT and stirred for an additional 2.5 h. The crude reaction mixture was then added into a saturated aqueous solution of $NaHCO_3$ (350 mL) and extracted with EtOAc (3×300 mL). Combined organic layers were washed with Brine (2×400 mL) and dried over $MgSO_4$. The solution was then concentrated to give 1-((S)-1-(tert-butyldimethylsilyloxy)-3-((R)-2,2-dimethyl-1,3-dioxolan-4-yl)propan-2-yl)-3-(2-chloro-3-fluorobenzyl)-1-methylurea, which was used without further purification. LRMS (M+H$^+$) m/z 490.1.

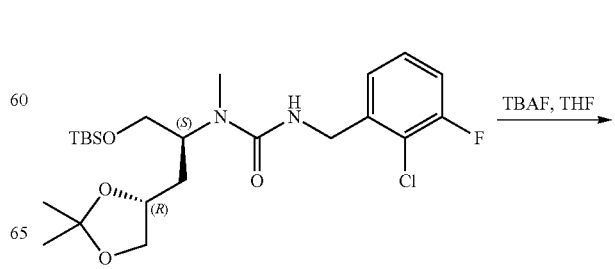

-continued

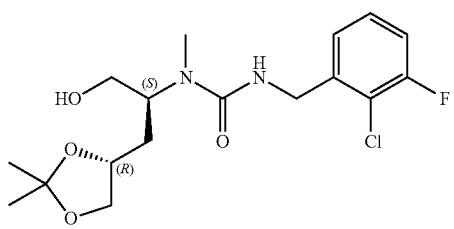

To a solution of the above crude 1-((S)-1-(tert-butyldimethylsilyloxy)-3-((R)-2,2-dimethyl-1,3-dioxolan-4-yl)propan-2-yl)-3-(2-chloro-3-fluorobenzyl)-1-methylurea in THF (300 mL) was added tetrabutylammonium fluoride (10.0 mL, 1 M in THF, 10.0 mmol). The resulting solution was then stirred at RT for 1 h. The reaction mixture was added into a saturated aqueous solution of NH₄Cl (350 mL) and extracted with EtOAc (2×350 mL). Combined organic layers were washed with Brine (2×400 mL) and dried over MgSO₄. The solution was then concentrated. The resulting residue was purified on a silica gel column using a mixture of DCM and MeOH to give 3-(2-chloro-3-fluorobenzyl)-1-(S)-1-((R)-2,2-dimethyl-1,3-dioxolan-4-yl)-3-hydroxypropan-2-yl)-1-methylurea (2.3 g, 61% over two steps). LRMS (M+H⁺) m/z 375.1.

Method B

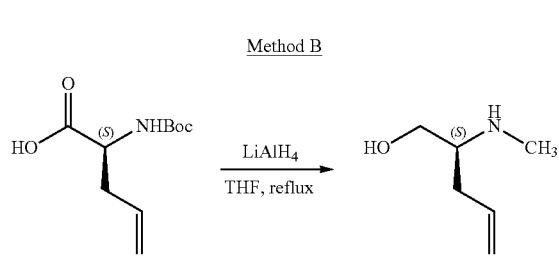

To a solution of (S)-2-(tert-butoxycarbonylamino) pent-4-enoic acid (20 g, 93 mmol) in anhydrous THF (3 mL) was added LiAlH₄ (2M in THF, 186 mmol). The mixture was heated to 65° C. The reaction was allowed to stir for 3 h until complete by LC/MS. The reaction was cooled to 0° C., and H₂O (7.6 mL) was added and stirred for 4 min, followed by NaOH (3N, 7.6 mL), and a second portion of H₂O (23 mL). The white precipitate was removed by filtration (EtOAc wash) and the filtrate was concentrated to give (S)-2-(methylamino)pent-4-en-1-ol as a clear viscous oil, which was used without further purification.

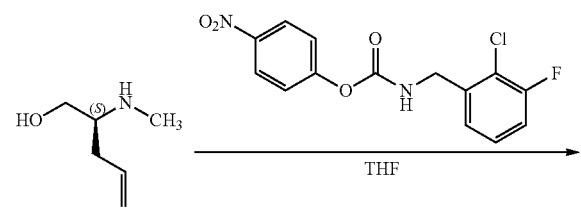

-continued

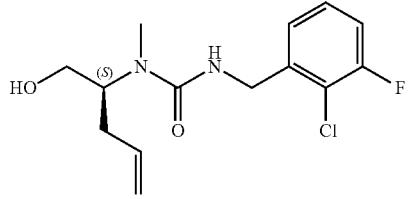

To a solution of crude (S)-2-(methylamino)pent-4-en-1-ol (~93 mmol) and DIEA (17.8 mL) in THF (310 mL) was stirred at ambient temperature and the nitrophenol carbamate (18.8 g, 93 mmol) was added in one portion, followed by additional DIEA (32.4 mL). The reaction was stirred for 40 min until deemed complete by LC/MS and diluted with EtOAc (200 mL), washed with saturated Na₂CO₃ (3×50 mL), dried over anhydrous Na₂SO₄ and concentrated. The residue was subjected to flash chromatography (0 to 100% EtOAc in hexanes) to give (S)-3-(2-chloro-3-fluorobenzyl)-1-(1-hydroxypent-4-en-2-yl)-1-methylurea (16.9 g, 52% over 2 steps) as a white solid. LRMS (M+H⁺) m/z 301.0.

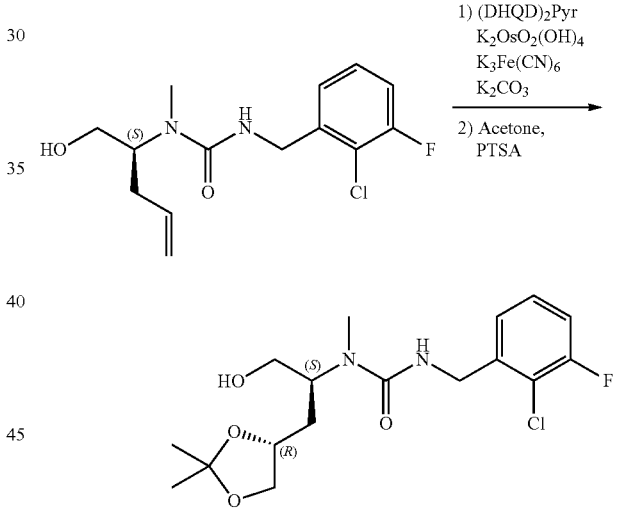

A dry 500 mL round-bottom flask was charged with a solution of K₂CO₃ (8.5 g) in water (100 mL). tert-Butanol (100 mL) was added, followed by K₂OsO₂(OH)₄(136 mg, 0.02 equiv.), (DHQD)₂Pyr (363 mg, 0.02 equiv.), and K₃Fe(CN)₆ (20.3 g, 3 equiv.). The mixture was stirred at ambient temperature until most of the solids had dissolved (~30 min.). The mixture was cooled to 0° C. and the substrate was added (6.2 g, 1 equiv) as a single portion. The reaction was stirred at 4° C. for 24 h. The mixture was allowed to warm to RT, and diluted with water (300 mL). The organic layer was extracted with EtOAc (3×200 mL), dried over anhydrous Na₂SO₄ and concentrated. The resulting crude material was dissolved in acetone (100 mL) and PTSA (400 mg) was added. The reaction was allowed to stir for 3 h, and diluted with EtOAc (100 mL) solid Na₂CO₃ (5 g) was added, and the mixture was stirred for 1 hr. The mixture was filtered and concentrated. The residue was subjected to flash chromatography (0 to 100% EtOAc in hexanes) to give a mixture of diastereomers, which was recrystallized in BuOAc to give 3-(2-chloro-3-fluorobenzyl)-1-(S)-1-((R)-2,2-dimethyl-1,3-dioxolan-4-yl)-3-hydroxypropan-2-yl)-1-methylurea (1.3 g, 17%) as a white solid. LRMS (M+H) m/z 375.1

Example 41

Preparation of (S)-2-(3-(2-chloro-3-fluorobenzyl)-1-methylureido)-3-((R)-2,2-dimethyl-1,3-dioxolan-4-yl)propyl isoquinolin-3-ylcarbamate

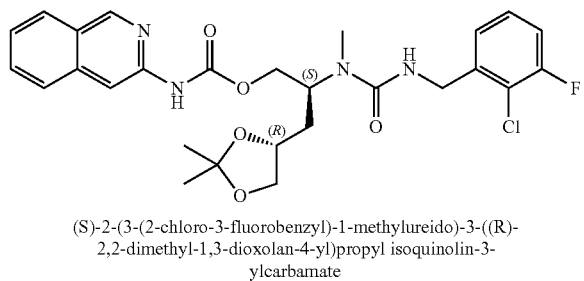

(S)-2-(3-(2-chloro-3-fluorobenzyl)-1-methylureido)-3-((R)-2,2-dimethyl-1,3-dioxolan-4-yl)propyl isoquinolin-3-ylcarbamate Method A

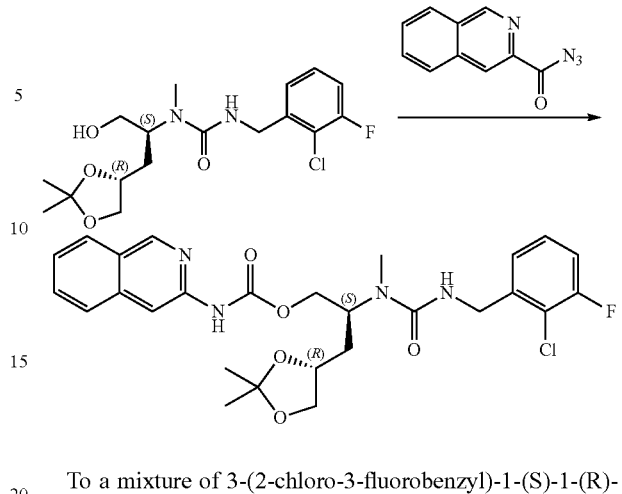

To a mixture of 3-(2-chloro-3-fluorobenzyl)-1-(S)-1-(R)-2,2-dimethyl-1,3-dioxolan-4-yl)-3-hydroxypropan-2-yl)-1-methylurea (8.4 g, 22 mmol) in toluene (200 mL) at 100° C. was added acyl azide (4.35 g, 22 mmol, 1 equiv.) in portions. The mixture was stirred at 100° C. for 30 min and concentrated to dryness. The residue was purified on silica gel using a mixture of EtOAc and hexanes to give (S)-2-(3-(2-chloro-3-fluorobenzyl)-1-methylureido)-3-((R)-2,2-dimethyl-1,3-dioxolan-4-yl)propyl isoquinolin-3-ylcarbamate (7.6 g, 64%) as a light yellow solid. LRMS (M+H⁺) m/z 545.1.

Method B

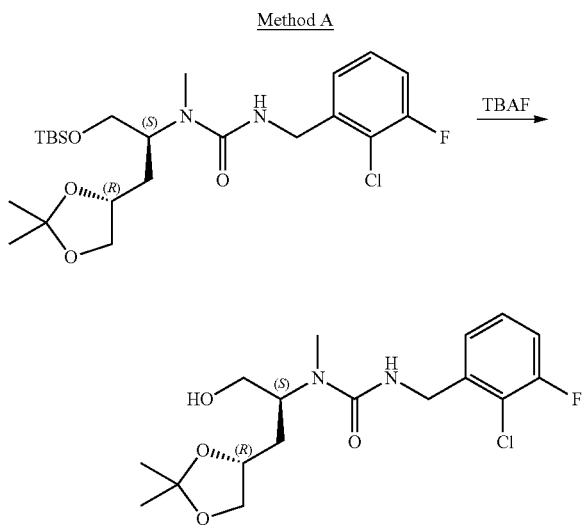

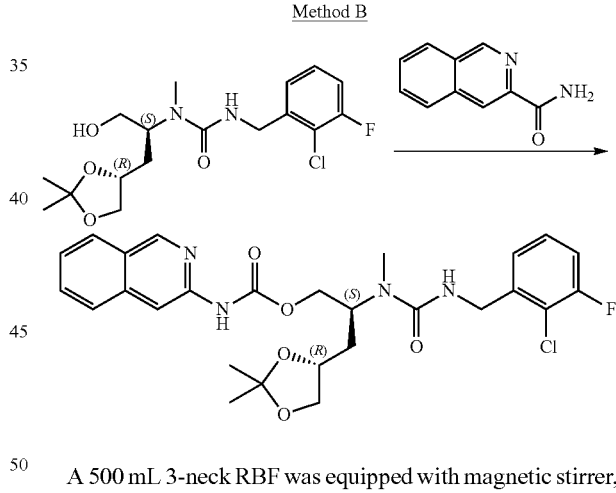

To a solution of 1-((S)-1-(tert-butyldimethylsilyloxy)-3-(R)-2,2-dimethyl-1,3-dioxolan-4-yl)propan-2-yl)-3-(2-chloro-3-fluorobenzyl)-1-methylurea (11.4 g, 23 mmol) in THF at 0° C., was added TBAF (23 mmol, 1 equiv.) dropwise. The reaction was completed in 30 min. The solvents were removed. The residue was dissolved in EtOAc (150 mL) and washed with 3% citric acid (150 mL) twice, followed by saturated NaHCO₃ (100 mL) and brine (100 mL). The organic layer was concentrated to give 3-(2-chloro-3-fluorobenzyl)-1-((S)-1-(R)-2,2-dimethyl-1,3-dioxolan-4-yl)-3-hydroxypropan-2-yl)-1-methylurea, which was used without further purification. LRMS (M+H⁺) m/z 375.4.

A 500 mL 3-neck RBF was equipped with magnetic stirrer, heating mantle, set-point controller, thermowell, thermocouple and nitrogen bubbler. The flask was charged with 3-(2-chloro-3-fluorobenzyl)-1-(S)-1-((R)-2,2-dimethyl-1,3-dioxolan-4-yl)-3-hydroxypropan-2-yl)-1-methylurea (15.7 g, 41.9 mmol), iodobenzene diacetate (27 g, 2.0 equiv.) and methyl tert-butyl ether (141 mL). The mixture was warmed to ~55° C. and the amide (7.6 g, 1.05 equiv.) was added in small portions. The reaction was stirred for 1 h. The reaction was cooled to ambient temperature and quenched by addition of saturated aq. NaHCO₃ (150 mL). The organic phase was extracted with ethyl acetate, and the combined organics were washed with water and brine. The organic phase was dried over MgSO₄ and concentrated. Residual solvents were removed by azeotrope from DCM and hexanes (3×) to give (S)-2-(3-(2-chloro-3-fluorobenzyl)-1-methylureido)-3-(R)-2,2-dimethyl-1,3-dioxolan-4-yl)propyl isoquinolin-3-ylcarbamate as a solid (25.3 g), which was used without further purification. LRMS (M+H⁺) m/z 545.1.

Example 42

Preparation of sodium (2R,4S)-4-(3-(2-chloro-3-fluorobenzyl)-1-methylureido)-2-hydroxy-5-(isoquinolin-3-ylcarbamoyloxy)pentyl phosphate and potassium (2R,4S)-4-(3-(2-chloro-3-fluorobenzyl)-1-methylureido)-2-hydroxy-5-(isoquinolin-3-ylcarbamoyloxy)pentyl phosphate

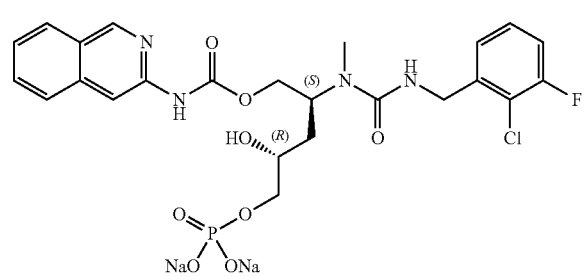

sodium (2R,4S)-4-(3-(2-chloro-3-fluorobenzyl)-1-methylureido)-2-hydroxy-5-(isoquinolin-3-ylcarbamoyloxy)pentyl phosphate

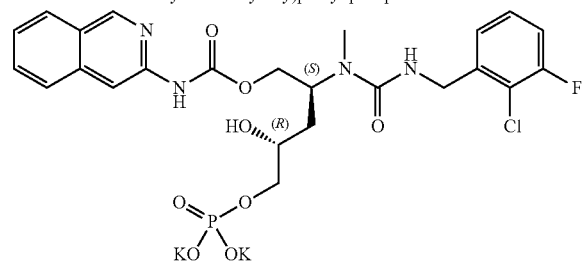

potassium (2R,4S)-4-(3-(2-chloro-3-fluorobenzyl)-1-methylureido)-2-hydroxy-5-(isoquinolin-3-ylcarbamoyloxy)pentyl phosphate

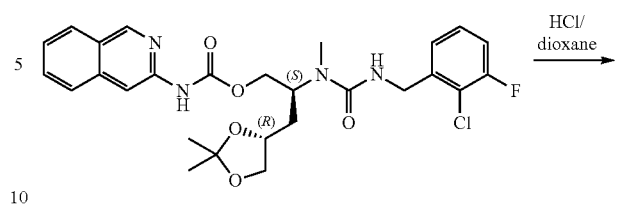

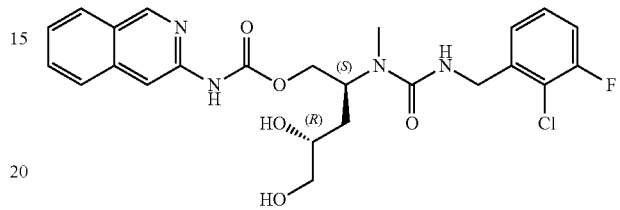

To a solution of (S)-2-(3-(2-chloro-3-fluorobenzyl)-1-methylureido)-3-(R)-2,2-dimethyl-1,3-dioxolan-4-yl)propyl isoquinolin-3-ylcarbamate (7.6 g, 14 mmol) in MeOH (35 mL) at 0° C., was added HCl/dioxane (4 N, 35 mL) dropwise. The solution was warmed up to RT and stirred for 2 h. The solvents were removed. DCM (100 mL) was then added. The pH was adjusted by Et₃N to pH 8. The precipitate was filtered and washed with DCM. 6.1 g of desired product was obtained as a white solid. The filtrate was concentrated and purified by HPLC to give 0.4 g of desired product. Combination of products afforded (2S,4R)-2-(3-(2-chloro-3-fluorobenzyl)-1-methylureido)-4,5-dihydroxypentyl isoquinolin-3-ylcarbamate (6.5 g, 92%). LRMS (M+H⁺) m/z 505.1.

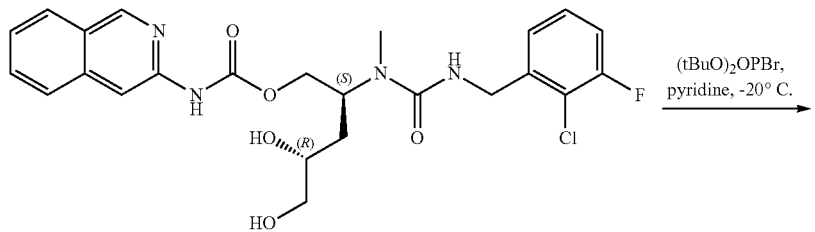

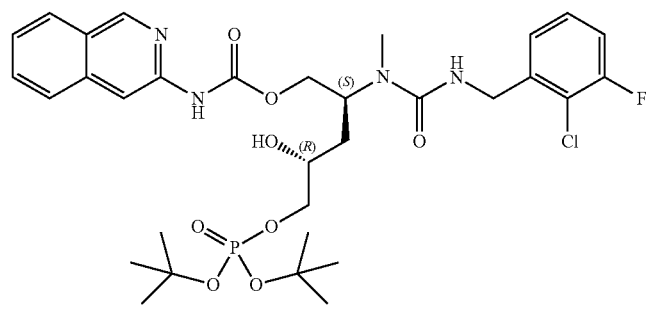

To a solution of (2S,4R)-2-(3-(2-chloro-3-fluorobenzyl)-1-methylureido)-4,5-dihydroxypentyl isoquinolin-3-ylcarbamate (2.5 g, 5 mmol) in anhydrous pyridine (20 mL) at −20° C. was added di-tert-butylphosphoryl bromide (5.46 g, 20 mmol, 4 equiv.) dropwise under $N_2$. The reaction was completed in 5 min. EtOH (1 mL) was added to quench the reaction. The solvents were removed. The residue was dissolved into EtOAc. The pyridine HBr salt was filtered off and the filtrate was concentrated to give (2S,4R)-2-(3-(2-chloro-3-fluorobenzyl)-1-methylureido)-5-(di-tert-butoxyphosphoryloxy)-4-hydroxypentyl isoquinolin-3-ylcarbamate, which was used without further purification. LRMS (M+H$^+$) m/z 697.2.

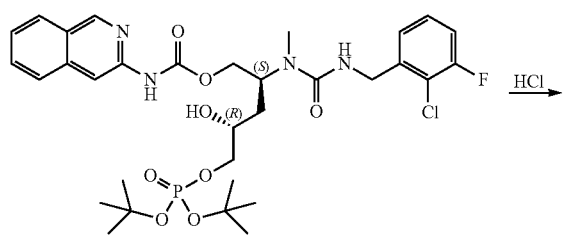

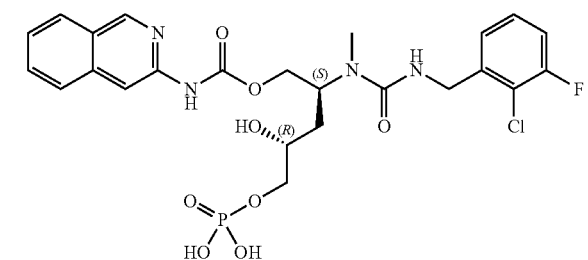

To a solution of the above crude (2S,4R)-2-(3-(2-chloro-3-fluorobenzyl)-1-methylureido)-5-(di-tert-butoxyphosphoryloxy)-4-hydroxypentyl isoquinolin-3-ylcarbamate in MeOH (8 mL) at 0° C. was added conc. HCl (12 N, 8 mL, 20 equiv.) dropwise. The mixture was stirred for 30 min and concentrated. The residue was dissolved in 50 mL H2O. Aqueous NaOH solution (1 N) was added to adjusted the PH to 3~4. EtOAc (50 mL) was then added. The mixture was stirred at RT for 1 h. The white solid was then filtered and washed with $H_2O$ and EtOAc, followed by drying in vacuo to give (2S,4R)-2-(3-(2-chloro-3-fluorobenzyl)-1-methylureido)-4-hydroxy-5-(phosphonooxy)pentyl isoquinolin-3-ylcarbamate as a white powder (2.4 g, 86% for 2 steps). LRMS (M+H) m/z 585.5.

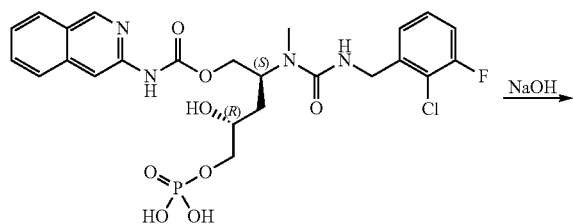

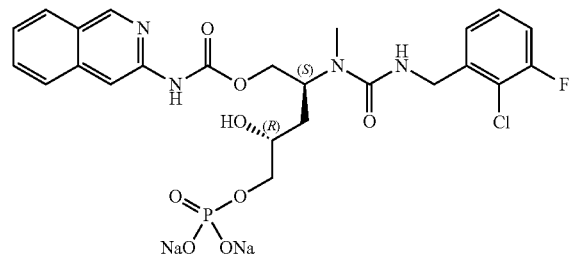

To a solution of (2S,4R)-2-(3-(2-chloro-3-fluorobenzyl)-1-methylureido)-4-hydroxy-5-(phosphonooxy)pentyl isoquinolin-3-ylcarbamate in MeOH (50 mL) at 0° C. was added NaOH solution (0.5 N, 16 mL, 2 equiv.) dropwise. The solution was stirred at 0° C. for 1 h and concentrated to give sodium (2R,4S)-4-(3-(2-chloro-3-fluorobenzyl)-1-methylureido)-2-hydroxy-5-(isoquinolin-3-ylcarbamoyloxy)pentyl phosphate as a white solid (quant.). The solid could be further crystallized by trituration with EtOH, followed by re-crystallization from EtOH—$H_2O$ (6:1) to give the crystalline form. LRMS (M−2Na+3H$^+$) m/z 585.5.

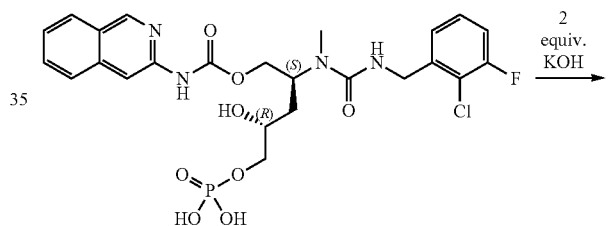

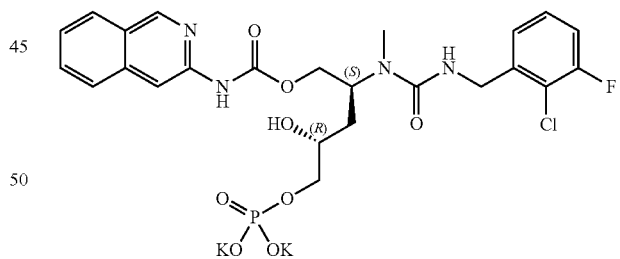

To a solution of the above phosphonic acid (2.0 g, 3.4 mmol) in MeOH (20 mL) at 0° C. was added KOH solution (0.5 N, 13.6 mL, 2 equiv.) dropwise. The solution was stirred for 1 h. The solvents were removed. The residue was triturated with EtOH, followed by re-crystallization from EtOH—$H_2O$ (6:1) at 60° C. to give potassium (2R,4S)-4-(3-(2-chloro-3-fluorobenzyl)-1-methylureido)-2-hydroxy-5-(isoquinolin-3-ylcarbamoyloxy)pentyl phosphate as a crystalline form. LRMS (M−2K+3H$^+$) m/z 585.5.

Example 43

Preparation of sodium (2R,4S)-4-(3-(2,3-difluorobenzyl)-1-methylureido)-2-hydroxy-5-(isoquinolin-3-ylcarbamoyloxy)pentyl phosphate

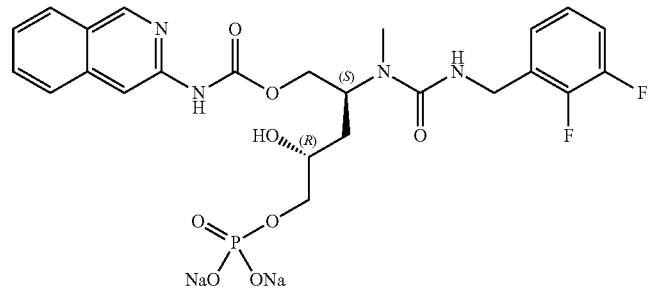

sodium (2R,4S)-4-(3-(2,3-difluorobenzyl)-1-methylureido)-2-hydroxy-5-isoquinolin-3-ylcarbamoyloxy)pentyl phosphate

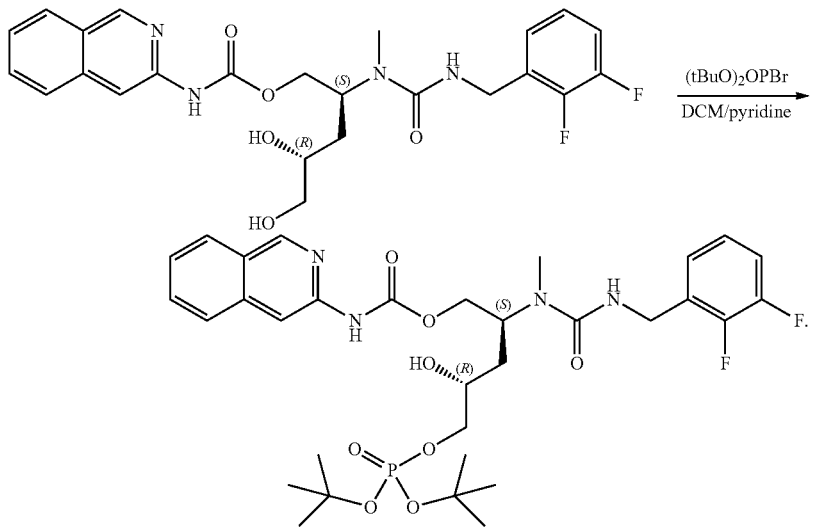

To a solution of (2S,4R)-2-(3-(2,3-difluorobenzyl)-1-methylureido)-4,5-dihydroxypentyl isoquinolin-3-ylcarbamate (4.7 g, 9.62 mmol) in anhydrous pyridine (12 mL) and dichloromethane (36 mL) at −30° C. was added di-tert-butylphosphoryl bromide (7.88 g, 28.87 mmol) dropwise under atmosphere of $N_2$. The reaction mixture was stirred vigorously at −30° C. for 75 min until the reaction completed. EtOH (2 mL) was then added to quench the reaction. The solvents were removed. The residue was triturated with EtOAc (200 mL). The pyridine HBr salt was filtered off and the filtrate was concentrated to give (2S,4R)-5-(di-tert-butoxyphosphoryloxy)-2-(3-(2,3-difluorobenzyl)-1-methylureido)-4-hydroxypentyl isoquinolin-3-ylcarbamate, which was used without further purification.

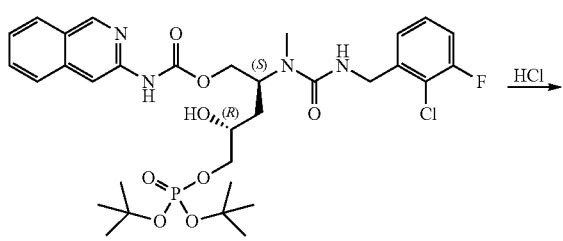

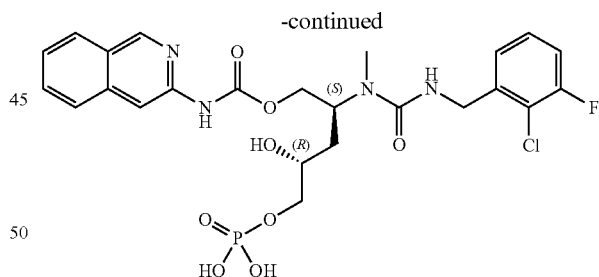

To a solution of the crude (2S,4R)-5-(di-tert-butoxyphosphoryloxy)-2-(3-(2,3-difluorobenzyl)-1-methylureido)-4-hydroxypentyl isoquinolin-3-ylcarbamate in MeOH (15 mL) at 0° C. was added conc. HCl (12 N, 16 mL, 192.4 mmol) dropwise. The mixture was stirred for 30 min and concentrated. The residue was dissolved in 50 mL H2O. Aqueous NaOH solution (1 N) was added to adjusted the PH to 3~4. EtOAc (50 mL) was then added. The mixture was stirred at RT for 1 h. The white solid was then filtered and washed with $H_2O$ and EtOAc and dried under high vacuum to give (2S,4R)-2-(3-(2-chloro-3-fluorobenzyl)-1-methylureido)-4-hydroxy-5-(phosphonooxy)pentyl isoquinolin-3-ylcarbamate (2.85 g) as a white powder (4.95 g, 89% for 2 steps). LRMS (M−H⁺) m/z 567.5

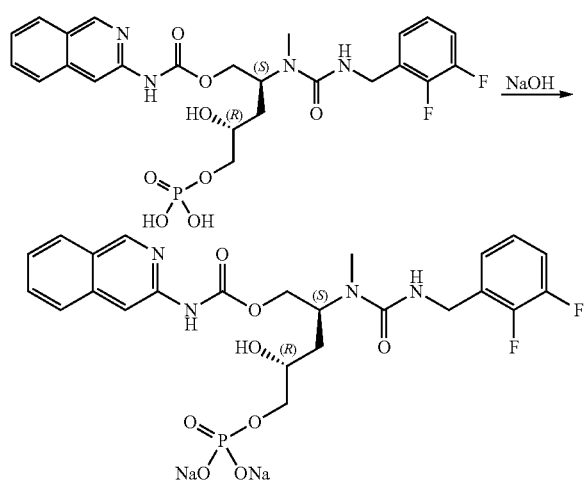

To a solution of the crude (2.85 g) (2S,4R)-2-(3-(2-chloro-3-fluorobenzyl)-1-methylureido)-4-hydroxy-5-(phosphonooxy)pentyl isoquinolin-3-ylcarbamate in MeOH (10 mL) at 0° C. was added NaOH solution (0.5 N, 20.07 mL, 2 equiv.) dropwise. The solution was stirred at 0° C. for 1 h and concentrated to give sodium (2R,4S)-4-(3-(2,3-difluorobenzyl)-1-methylureido)-2-hydroxy-5-(isoquinolin-3-ylcarbamoyloxy)pentyl phosphate as a white solid (3.08 g, quant.). LRMS (M−H⁺) m/z 567.5. The solid could be further crystallized by trituration with EtOH, followed by re-crystallization from EtOH—H₂O (6:1) to give the crystalline form.

Example 44

Preparation of (S)-2-(2-chloro-3-fluorobenzyl)(methyl)amino)-3-(2,2-difluoroethylamino)propyl isoquinolin-3-ylcarbamate

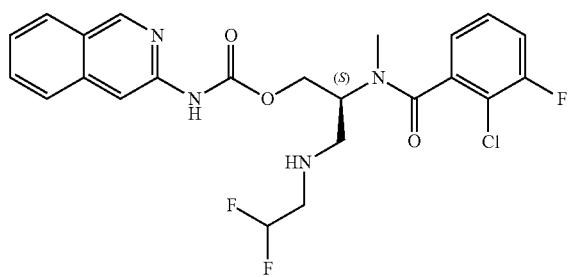

(S)-2-((2-chloro-3-fluorobenzyl)(methyl)amino)-3-(2,2-difluoroethylamino)propyl isoquinolin-3-ylcarbamate

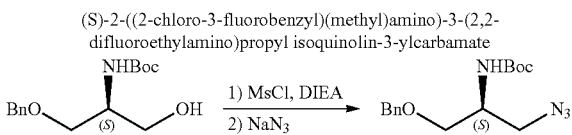

To a solution of (S)-tert-butyl 1-(benzyloxy)-3-hydroxypropan-2-ylcarbamate (1.89 g, 6.4 mmol) in DCM (50 mL) was added MsCl (0.55 mL, 7.04 mmol) followed by DIEA (1.27 mL, 7.68 mmol). The mixture was stirred at RT for 30 min and diluted with DCM (300 mL). The organic mixture washed with NaHCO₃, brine, dried over Na₂SO₄, filtered, and concentrated under reduced pressure. The residue was then dissolved in DMF (20.0 mL). To the resulting solution was added NaN₃ (1.25 g, 19.2 mmol) and the mixture was heated at 80° C. for 6 h. LCMS indicated the completion of the reaction. The mixture was cooled to RT and added water (20 mL) and EtOAc (200 mL). The organic layer was separated, washed with NaHCO₃ and brine, dried over Na₂SO₄, filtered, and concentrated under reduced pressure. The residue was purified on silica gel column using a mixture of EtOAc and hexanes to give (S)-tert-butyl 1-azido-3-(benzyloxy)propan-2-ylcarbamate (1.5 g, 73% for 2 steps).

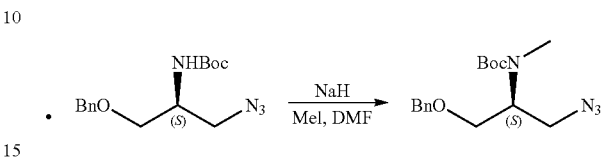

To a solution NaH (0.29 g, 7.35 mmol) in DMF (10 mL) was added a solution of (S)-tert-butyl 1-azido-3-(benzyloxy)propan-2-ylcarbamate (1.5 g, 4.9 mmol) in DMF (10.0 mL). The mixture was stirred at RT for 30 min followed by addition of MeI (1.0 mL, 9.8 mmol). The resulting mixture was stirred for another 2 h. LCMS indicated the completion of the reaction. The mixture was quenched with saturated NH₄Cl solution and extracted with EtOAc (200 mL×2). The combined organic layers were washed with brine, dried over Na₂SO₄, filtered, and concentrated under reduced pressure to give (S)-tert-butyl 1-azido-3-(benzyloxy)propan-2-yl(methyl)carbamate (1.8 g, crude), which was used without purification.

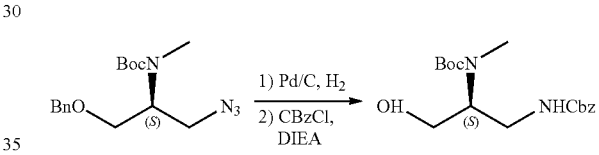

To a solution of the crude (S)-tert-butyl 1-azido-3-(benzyloxy)propan-2-yl(methyl)carbamate (1.8 g, ~4.90 mmol) in MeOH (20 mL) was added Pd/C (300 mg). The mixture was transferred to an autoclave reactor, charged with hydrogen (45 psi), and stirred at RT overnight. The solid was filtered off. To the filtrate were added CbzCl (0.83 mL, 5.88 mmol) and DIEA (1.22 mL, 7.35 mmol) and the resulting mixture was stirred at RT for 30 min. The reaction mixture was concentrated under reduced pressure and dissolved in EtOAc. The organic mixture was washed with NaHCO₃ and brine, dried over Na₂SO₄, filtered, and concentrated under reduced pressure to give [(S)-2-(tert-Butoxycarbonyl-methyl-amino)-3-hydroxy-propyl]carbamic acid benzyl ester (2.2 g of crude), which was used without purification (2.2 g, crude). LRMS (M+H⁺-Boc) m/z 239.1.

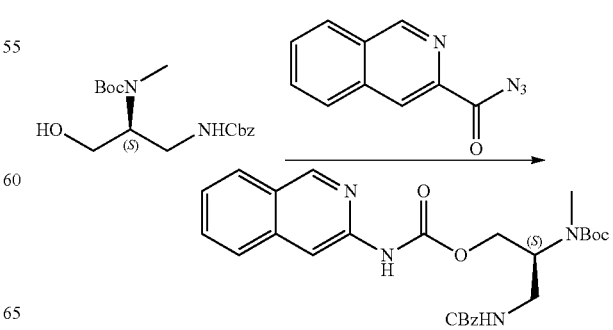

To a solution of [(S)-2-(tert-Butoxycarbonyl-methyl-amino)-3-hydroxy-propyl]carbamic acid benzyl ester (2.2 g of crude mixture, 4.90 mmol) in toluene (20 mL) was added isoquinoline-3-carbonyl azide (1.16 g, 5.39 mmol) in portions and the mixture was heated to 100° C. for 1 h. The mixture was concentrated to one forth of the amount and the remaining residue was purified on silica gel column using a mixture of EtOAc and hexanes to give [(S)-2-(tert-Butoxycarbonyl-methyl-amino)-3-(isoquinolin-3-ylcarbamoyloxy)-propyl]-carbamic acid benzyl ester (1.5 g, 58% for 4 steps). LRMS (M+H$^+$) m/z 527.3.

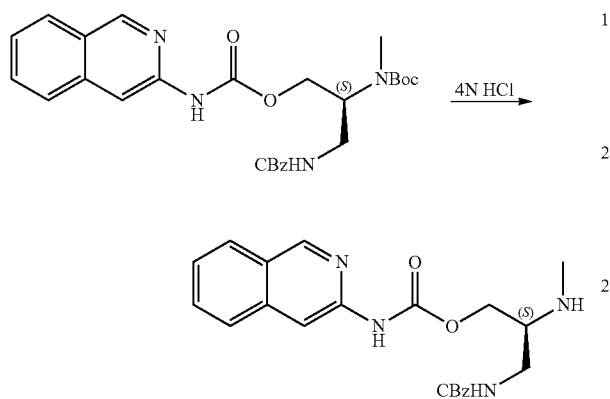

To a solution of [(S)-2-(tert-Butoxycarbonyl-methyl-amino)-3-(isoquinolin-3-ylcarbamoyloxy)-propyl]-carbamic acid benzyl ester (4.58 g, 9.0 mmol) in MeOH (7.5 mL) was added HCl (4 N in 1,4-dioxane, 22.5 mL, 90.0 mmol). The mixture was stirred at RT for 2 h, concentrated, and re-dissolved in EtOAc. The organic mixture was washed with sat. NaHCO$_3$, water, and brine, dried over Na$_2$SO$_4$, filtered, and concentrated to give Isoquinolin-3-yl-carbamic acid (S)-3-benzyloxycarbonylamino-2-methylamino-propyl ester (3.59 g), which was used without further purification. LRMS (M+H$^+$) m/z 409.2.

To a solution of the crude isoquinolin-3-yl-carbamic acid (S)-3-benzyloxycarbonylamino-2-methylamino-propyl ester (9.0 mmol) in THF (35 mL) were added 4-nitrophenyl 2-chloro-3-fluorobenzylcarbamate (2.85 g, 8.79 mmol) and DIEA (2.3 mL, 13.2 mmol) at RT. The reaction mixture was stirred at RT for 30 min. The solvent was removed and the residue was dissolved in EtOAc (400 mL). The organic mixture was washed with NaOH (1 N, 50 mL×3), HCl (0.5 N, 50 mL), saturated NaHCO$_3$, and brine, dried over Na$_2$SO$_4$, filtered, and concentrated under reduced pressure. The residue was purified on silica gel column using a mixture of EtOAC and hexanes to give Isoquinolin-3-yl-carbamic acid (S)-3-benzyloxycarbonylamino-2-[3-(2-chloro-3-fluoro-benzyl)-1-methyl-ureido]-propyl ester (3.8 g, 71% for two steps) as white foam. LRMS (M+H$^+$) m/z 594.2.

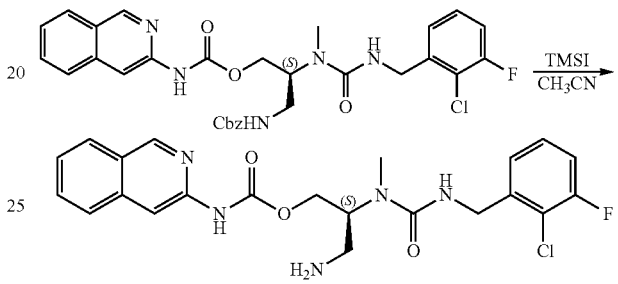

To a solution of isoquinolin-3-yl-carbamic acid (S)-3-benzyloxycarbonylamino-2-[3-(2-chloro-3-fluoro-benzyl)-1-methyl-ureido]-propyl ester (1.3 g, 2.13 mmol) in CH$_3$CN (20.0 mL) was added TMSI (0.35 mL, 2.56 mmol). The mixture was stirred at RT for 15 min and quenched with MeOH (20.0 mL). The resulting mixture was stirred for another 15 min, concentrated to dryness, and partitioned in between ether (30 mL) and HCl (2 N, 20 mL). The aqueous layer was separated, basified to pH 9, and extracted with EtOAc (200 mL×2). The combined organic layers were washed brine, dried over Na$_2$SO$_4$, filtered, and concentrated under reduced pressure to give (S)-3-amino-2-(3-(2-chloro-3-fluorobenzyl)-1-methylureido)propyl isoquinolin-3-ylcarbamate (2.7 g) as a light yellow foam solid, which was used without further purification. LRMS (M+H$^+$) m/z 460.1.

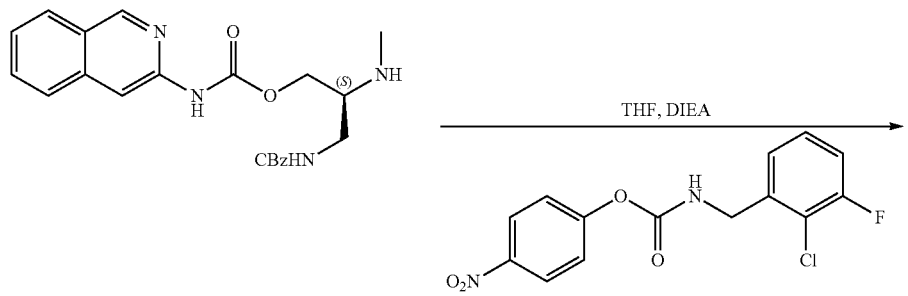

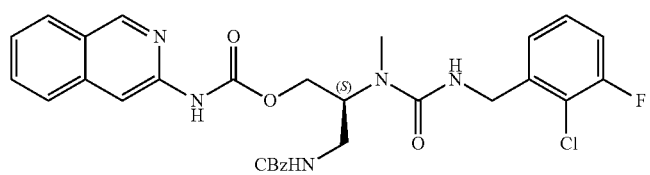

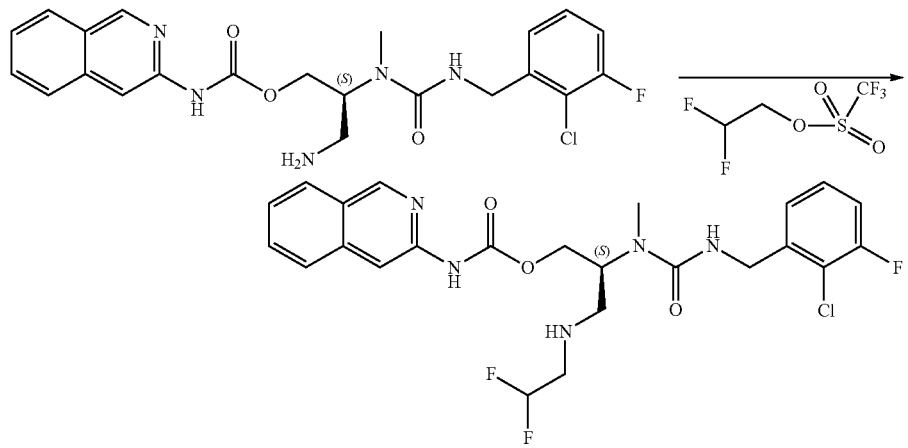

To a solution of (S)-3-amino-2-(3-(2-chloro-3-fluorobenzyl)-1-methylureido)propyl isoquinolin-3-ylcarbamate (200 mg, 0.44 mmol) in THF (2.0 mL) were added 2,2-difluoroethyl trifluoromethanesulfonate (94 mg, 0.44 mmol) and DIEA (0.15 mL, 0.88 mmol) at RT The reaction mixture was stirred at RT for 30 min. The solvent was removed. The resulting residue was dissolved in MeOH and mixture was purified on RP-HPLC using a mixture of acetonitrile and water to give (S)-2-(3-(2-chloro-3-fluorobenzyl)-1-methylureido)-3-(2,2-difluoroethylamino)propyl isoquinolin-3-ylcarbamate (130 mg, 56% for two steps). LRMS (M+H$^+$) m/z 524.2.

Example 45

Preparation of (S)-2-((2-chloro-3-fluorobenzyl)(methyl)amino)-3-(2,2-difluoroethylamino)propyl 3-(3-fluorophenyl)isoxazol-5-ylcarbamate

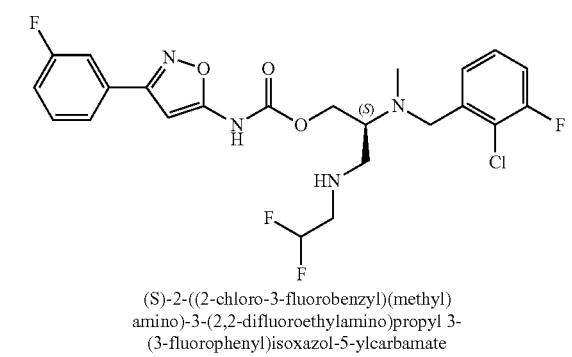

(S)-2-((2-chloro-3-fluorobenzyl)(methyl)amino)-3-(2,2-difluoroethylamino)propyl 3-(3-fluorophenyl)isoxazol-5-ylcarbamate

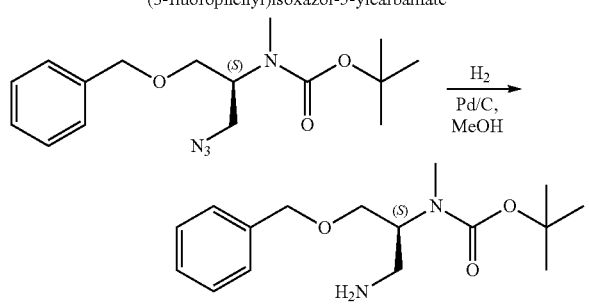

To a solution of (S)-tert-butyl 1-azido-3-(benzyloxy)propan-2-yl(methyl)carbamate (4 g, 11.66 mmol) in EtOH (100 mL) and AcOH (10 mL) was added Pd/C (10%, 1.0 g). The resulting mixture was transferred to an autoclave and charged with hydrogen (45 psi). The reaction mixture was stirred at RT for 1 h and filtered. The filtrate was concentrated to give (S)-tert-butyl 1-amino-3-(benzyloxy)propan-2-yl(methyl)carbamate, which was used without further purification. LRMS (M+Na$^+$) m/z 317.2.

To a solution of (S)-tert-butyl 1-amino-3-(benzyloxy)propan-2-yl(methyl)carbamate (5.1 mmol) in MeOH (50 mL) were added 2,2-difluoroethyl trifluoromethanesulfonate (1.09 g, 5.1 mmol) and DIEA (1.68 mL, 10.2 mmol). The resulting mixture was stirred at RT for 1 h followed by addition of Boc$_2$O (1.67 g, 7.65 mmol). The mixture was concentrated and the residue was purified on silica gel column using a mixture of EtOAc and hexanes to give [(S)-3-Benzyloxy-2-(tert-butoxycarbonyl-methyl-amino)-propyl]-(2,2-difluoro-ethyl)-carbamic acid tert-butyl ester (2.42 g, quant.). LRMS (M+Na$^+$) m/z 481.2.

469

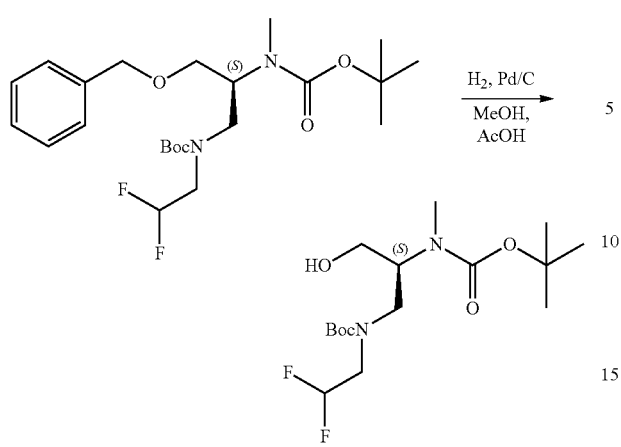

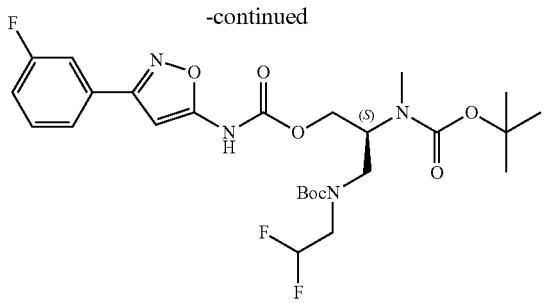

To a solution of [(S)-3-Benzyloxy-2-(tert-butoxycarbonyl-methyl-amino)-propyl]-(2,2-difluoro-ethyl)-carbamic acid tert-butyl ester (2.42 g, 5.28 mmol) in MeOH (20 mL) and AcOH (2.0 mL) was added Pd/C (10%, 1.0 g). The reaction

470

-continued

To a solution of [(S)-2-(tert-Butoxycarbonyl-methyl-amino)-3-hydroxy-propyl]-(2,2-difluoro-ethyl)-carbamic acid tert-butylester (200 mg, 0.86 mmol) in toluene (8.0 mL) was added 3-(3-fluorophenyl)isoxazole-5-carbonyl azide (317 mg, 0.86 mmol). The resulting solution was stirred at 100° C. for 1 h. The mixture was cooled and concentrated. The residue was purified on RP-HPLC using a mixture of acetonitrile and water to give {(S)-2-(tert-Butoxycarbonyl-methyl-amino)-3-[3-(3-fluoro-phenyl)-isoxazol-5-ylcarbamoyloxy]-propyl}-(2,2-difluoro-ethyl)-carbamic acid tert-butyl ester (291 mg, 60%). LRMS (M+Na$^+$) m/z 595.2.

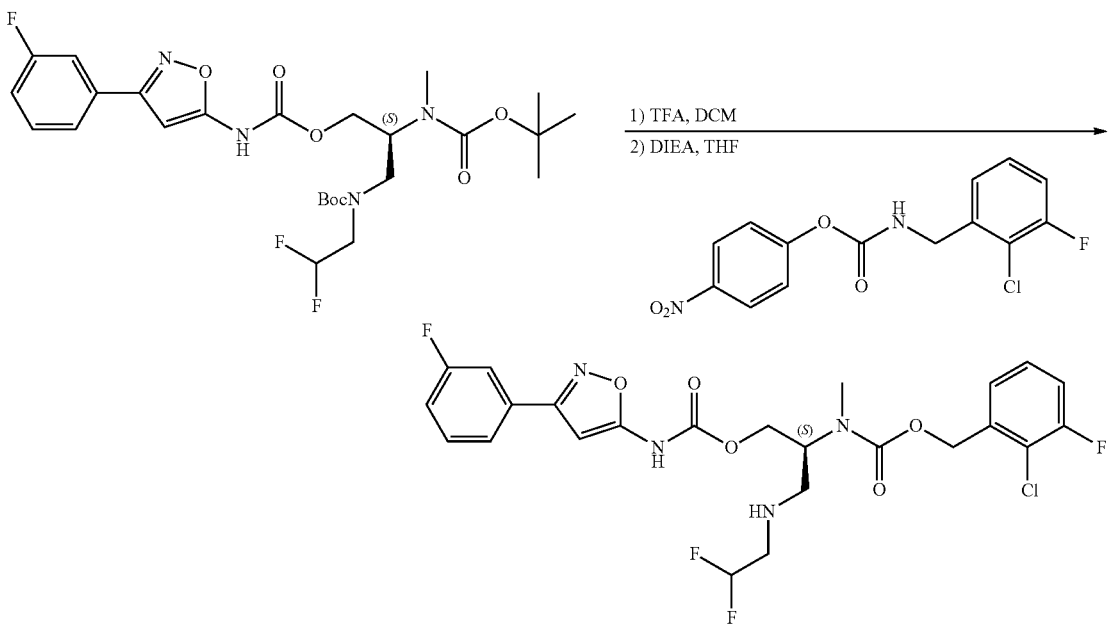

mixture was transferred to an autoclave and charged with hydrogen (50 psi). The mixture was stirred RT for 20 h and filtered. The filtrated was concentrated and the residue was purified on silica gel using a mixture of EtOAc and hexanes to give [(S)-2-(tert-Butoxycarbonyl-methyl-amino)-3-hydroxy-propyl]-(2,2-difluoro-ethyl)-carbamic acid tert-butylester (1.81 g, 93%). LRMS (M+Na$^+$) m/z 391.2.

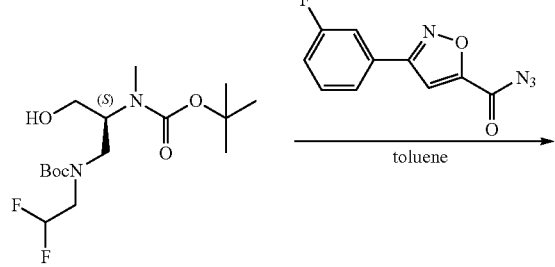

To a solution of {(S)-2-(tert-Butoxycarbonyl-methyl-amino)-3-[3-(3-fluoro-phenyl)-isoxazol-5-ylcarbamoyloxy]-propyl}-(2,2-difluoro-ethyl)-carbamic acid tert-butyl ester (291 mg, 0.62 mmol) in DCM (5 mL) was added TFA (1.0 mL). The mixture was stirred at RT for 1 h, concentrated, and dissolved in THF (10 mL). To the resulting solution were added 4-nitrophenyl 2-chloro-3-fluorobenzylcarbamate (220 mg, 0.68 mmol) and TEA (0.3 mL, 1.24 mmol) at 0° C. The resulting mixture was stirred at 0° C. for 1 h. The solvent was removed and the resulting residue was purified on RP-HPLC using a mixture of acetonitrile and water to give (S)-2-(2,3-difluorobenzyl)(methyl)amino)-5-(2-methyl-6,7-dihydro-1H-imidazo[4,5-c]pyridin-5(4H)-yl)-5-oxopentyl isoquinolin-3-ylcarbamate (135 mg, 39% for two steps) as white solid. LRMS (M+H$^+$) m/z 559.2.

Example 46

Preparation of (S)-2-((2-chloro-3-fluorobenzyl)(methyl)amino)-5-(2-methyl-6,7-dihydro-1H-imidazo[4,5-c]pyridin-5(4H)-yl)-5-oxopentyl isoquinolin-3-ylcarbamate

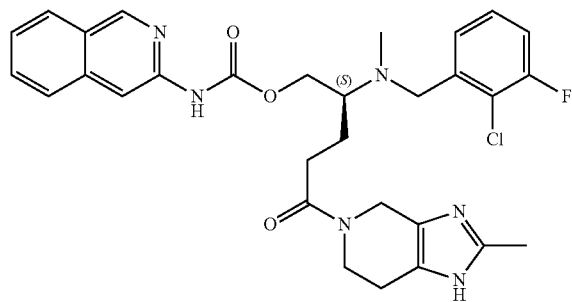

(S)-2-((2-chloro-3-fluorobenzyl)(methyl)amino)-5-(2-methyl-6,7-dihydro-1H-imidazo[4,5-c]pyridin-5(4H)-yl)-5-oxopentyl isoquinolin-3-ylcarbamate

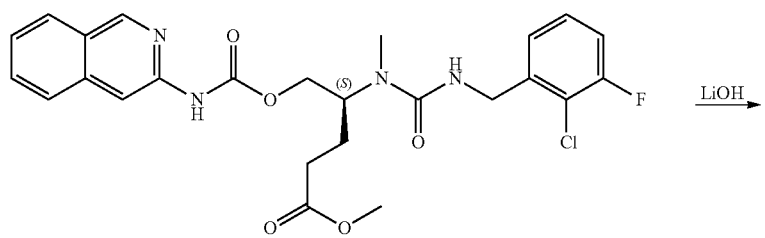

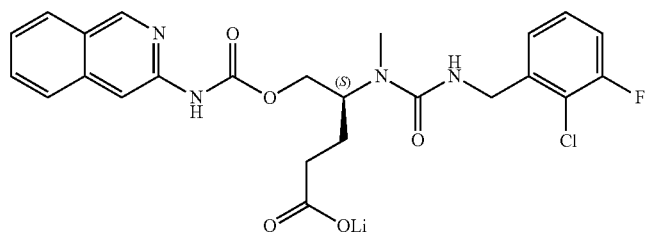

To a solution of (S)-methyl 4-(3-(2-chloro-3-fluorobenzyl)-1-methylureido)-5-(isoquinolin-3-ylcarbamoyloxy)pentanoate (220 mg, 0.43 mmol) in 1,4-dioxane (5 mL) was added LiOH (2N, 1.3 mL, 2.6 mmol). The reaction mixture was stirred at RT for 1 h and concentrated to give lithium (S)-4-(3-(2-chloro-3-fluorobenzyl)-1-methylureido)-5-(isoquinolin-3-ylcarbamoyloxy)pentanoate, which was used without further purification. LRMS (M+H$^+$) m/z 503.2.

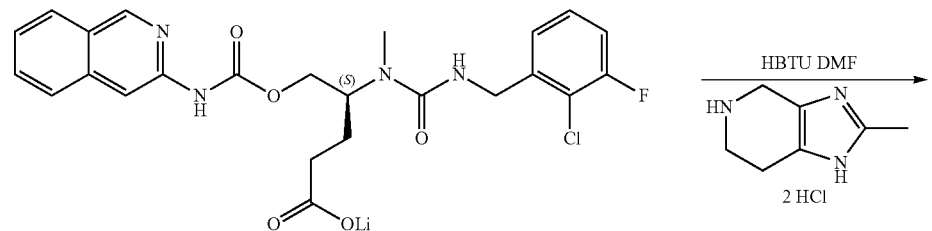

-continued

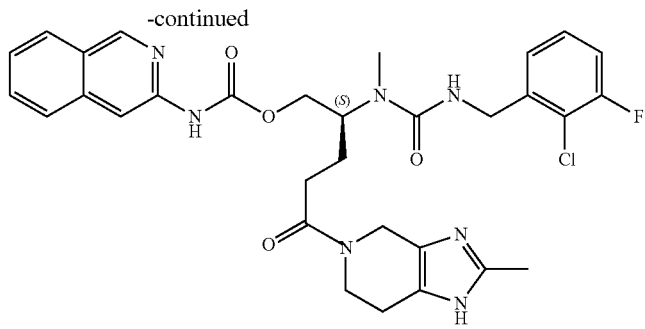

To a suspension of lithium (S)-4-(3-(2-chloro-3-fluorobenzyl)-1-methylureido)-5-(isoquinolin-3-ylcarbamoyloxy)pentanoate (0.43 mmol) and HBTU (244 mg, 0.64 mmol) in DMF (5 mL) was added 2-methyl-4,5,6,7-tetrahydro-1H-imidazo[4,5-c]pyridine dihydrochloride. The resulting mixture was stirred at RT for 1 h, filtered, and purified on RP-HPLC using a mixture of acetonitrile and water to give (S)-2-((2-chloro-3-fluorobenzyl)(methyl)amino)-5-(2-methyl-6,7-dihydro-1H-imidazo[4,5-c]pyridin-5(4H)-yl)-5-oxopentyl isoquinolin-3-ylcarbamate (182.1 mg, 68% for two steps). LRMS (M+H$^+$) m/z 622.2.

Example 47

Preparation of (S)-5-amino-2-(3-(2-chloro-3-fluorobenzyl)-1-methylureido)-4,4-difluoropentyl 6-fluoroisoquinolin-3-ylcarbamate

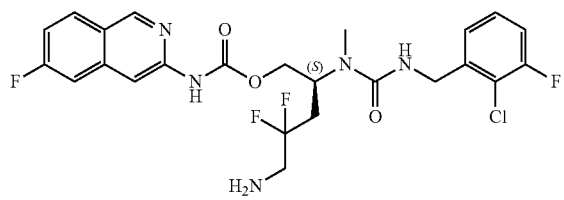

(S)-5-amino-2-(3-(2-chloro-3-fluorobenzyl)-1-methylureido)-4,4-difluoropentyl
6-fluoroisoquinolin-3-ylcarbamate

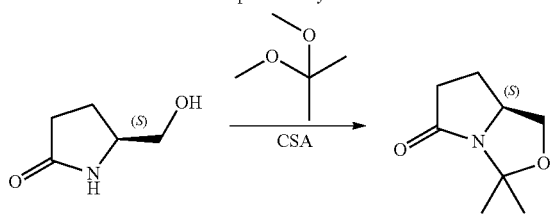

To a mixture of S-(+)-5-hydroxymethyl-2-pyrrolidinone (7.5 g, 65.1 mmol) and 2,2-dimethoxypropane (DMP) (50 mL) was added camphorsulfonic acid (CSA) (753 mg, cat.). The mixture was refluxed for 2 h, and concentrated in vacuo. Fresh DMP (50 mL) was then added, and the mixture was refluxed overnight. After concentrated, the remaining residue was purified on pre-silica gel column (hexane and ethyl acetate) to give (S)-3,3-dimethyl-dihydropyrrolo[1,2-c]oxazol-5(1H,3H,6H)-one as a pale yellow oil (4.0 g, 40%). LRMS (M+H$^+$) m/z 156.2.

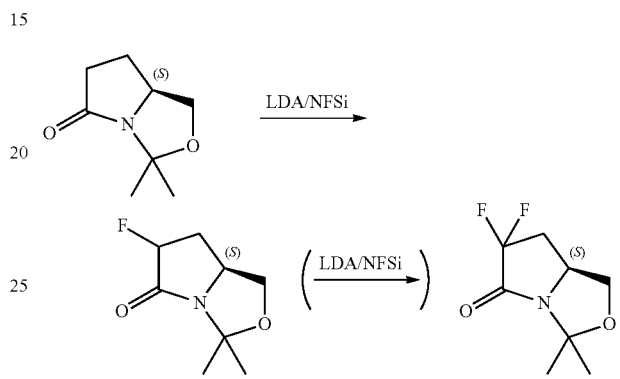

To a mixture of diisopropylamine (58.2 mL, 0.412 mol, 2.0 equiv), and THF (600 mL) at −78° C. was added a solution of $^n$BuLi (39.1 mL, 0.391 mmol, 1.9 equiv) (10M) slowly, and the resulting solution was stirred for 40 min. A solution of (S)-3,3-dimethyl-dihydropyrrolo[1,2-c]oxazol-5(1H,3H,6H)-one (32 g, 0.206 mmol) in THF (50 mL) was added slowly. The resulting light yellow mixture was stirred at −78° C. for 1 h. After addition of a solution of NFSi (84.4 g, 0.268 mmol, 1.3 equiv) in THF (100 mL), the reaction was allowed to stir below −55° C. for 1 h. The reaction was quenched with saturated aqueous NH$_4$Cl, and the mixture was warmed to RT. The THF was removed in vacuo, and the resulting residue was partitioned between EtOAc and H$_2$O. After separating layers, the aqueous layer was extracted further with EtOAc. The combined organic layers were dried (Na$_2$SO$_4$), filtered, and concentrated to leave an orange residue that was purified by silica gel column (hexanes/EtOAc) to give (S)-6,6-difluoro-3,3-dimethyl-dihydropyrrolo[1,2-c]oxazol-5(1H,3H,6H)-one and (5S)-2,2-(7aS)-6-fluoro-3,3-dimethyl-dihydropyrrolo[1,2-c]oxazol-5(1H,3H,6H)-one as an oil-like solid (20.0 g, 55.8%). LRMS (M+H$^+$) m/z 174.2.

(5S)-2,2-(7aS)-6-fluoro-3,3-dimethyl-dihydropyrrolo[1,2-c]oxazol-5(1H,3H,6H)-one (20.0 g, 0.115 mol) was subjected to the same fluorination procedure second time to give ((S)-6,6-difluoro-3,3-dimethyl-dihydropyrrolo[1,2-c]oxazol-5(1H,3H,6H)-one (15.0 g, 68.2%) LRMS (M+H$^+$) m/z 192.2.

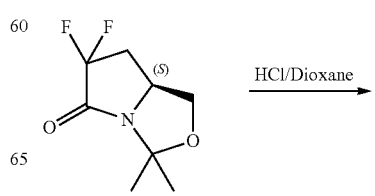

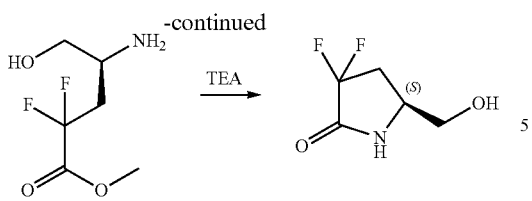

To a solution of (S)-6,6-difluoro-3,3-dimethyl-dihydropyrrolo[1,2-c]oxazol-5(1H,3H,6H)-one (1.35 g, 0.706 mmol) in methanol (10 mL) was added HCl in dioxane (2.65 mL, 4N) under ice-water bath and then stirred at RT overnight. The reaction mixture was concentrated. The resulting residue was dissolved in THF (10 mL) and TEA (5 mL) was added. The resulting solution was stirred for 1 h. The reaction mixture was concentrated to give a crude mixture. Purification by flash column chromatography (hexanes/EtOAc) gave (S)-3,3-difluoro-5-(hydroxymethyl)pyrrolidin-2-one (0.80 g 75%). LRMS (M+H$^+$) m/z 152.2.

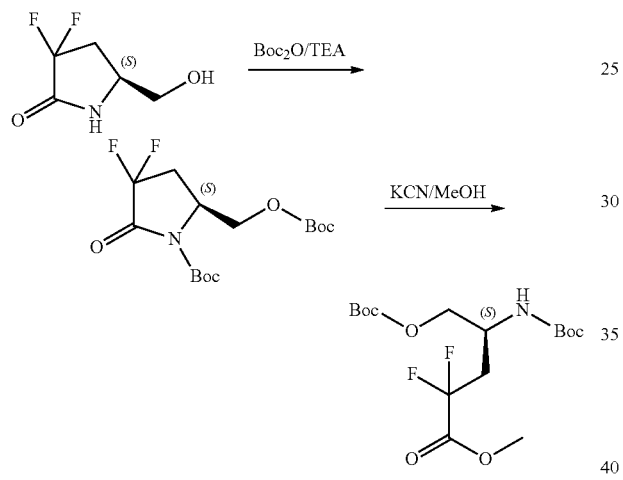

To a mixture of (S)-3,3-difluoro-5-(hydroxymethyl)pyrrolidin-2-one (28.9 g, 0.191 mol), triethyl amine (53.2 mL, 0.382 mol) and DMAP (11.7 g, 0.0955 mol) in THF (200 mL) was added Di-t-butyl-dicarbonate (83.4 g, 0.382 mol). The reaction mixture was stirred for 2 h and concentrated. The resulting residue was diluted with methanol (200 mL) and potassium cyanide (3.6 g, 0.0955 mol) was added. The resulting mixture was stirred for 1 h. The solvents were removed in vacuo, and the resulting residue was partitioned between DCM and H$_2$O. After separating layers, the aqueous layer was extracted further with DCM. The combined organic layers were dried (Na$_2$SO$_4$), filtered, and concentrated, and the resulting residue was purified by silica gel column (hexanes/EtOAc) to give (S)-methyl 4-(tert-butoxycarbonylamino)-5-(tert-butoxycarbonyloxy)-2,2-difluoropentanoate (44.1 g, 60%). LRMS (M+Na$^+$) m/z 406.4

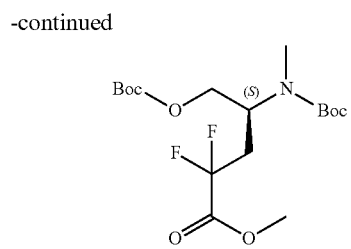

To a mixture of (S)-methyl 4-(tert-butoxycarbonylamino)-5-(tert-butoxycarbonyloxy)-2,2-difluoropentanoate (46.0 g, 0.12 mol) and MeI (15.0 mL, 0.24 mol) in DMF (300 mL) was added sodium hydride (60%, 7.2 g, 0.18 mol) at 0° C. The reaction mixture was stirred at 0° C. for 3 h and LC-MS showed the reaction was completed. The reaction was quenched with saturated NH$_4$Cl solution and filtered. The filtrate was concentrated to remove most of DMF and the residue was dissolved in EtOAc (1.5 L). The organic layer was washed with water and brine, dried over Na$_2$SO$_4$. The organic layers were combined and concentrated. The resulting residue was purified on silica gel column (hexanes/EtOAc) to give (S)-methyl 4-(tert-butoxycarbonyl(methyl)amino)-5-(tert-butoxycarbonyloxy)-2,2-difluoropentanoate (42 g, 88%). LRMS (M+Na$^+$) m/z 420.4.

To a solution of (S)-methyl 4-(tert-butoxycarbonyl(methyl)amino)-5-(tert-butoxycarbonyloxy)-2,2-difluoropentanoate (42.0 g, 0.106 mol) in THF (300 mL) was added Lithium borohydride (79.3 mL, 2 M, 0.159 mol) in THF at 0° C. The reaction mixture was stirred at 0° C. for 1 h and at RT for 2 h. LC-MS showed the reaction was complete. The reaction mixture was concentrated and partitioned between EtOAc and H$_2$O. After separating layers, the aqueous layer was extracted further with EtOAc. The combined organic layers were dried (Na$_2$SO$_4$), filtered, and concentrated, and the resulting residue was purified by silica gel column (hexanes/EtOAc) to give (S)-tert-butyl 1-(tert-butoxycarbonyloxy)-4,4-difluoro-5-hydroxypentan-2-yl(methyl)carbamate (35.3 g, 90%). LRMS (M+Na$^+$) m/z 392.4.

477
-continued

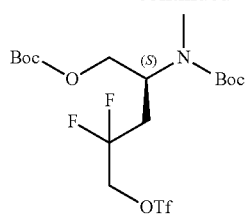

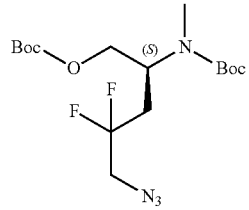

To a mixture of (S)-tert-butyl 1-(tert-butoxycarbonyloxy)-4,4-difluoro-5-hydroxypentan-2-yl(methyl)carbamate (35.3 g, 0.0956 mol) and lutidine (22.2 mL, 0.191 mol) in DCM (300 mL) was added trifluoromethanesulfonic anhydride (19.3 mL, 0.115 mol) at 0° C. The reaction mixture was stirred at 0° C. for 1 h. LC-MS showed the reaction was complete. The reaction mixture was concentrated down. The resulting residue was dissolved in DMF (100 mL) and sodium azide (62.1 g, 0.956 mol) was added. The reaction mixture was stirred at RT overnight. The reaction solution was partitioned between EtOAc and saturated sodium bicarbonate solution. After separating layers, the aqueous layer was extracted further with EtOAc. The combined organic layers were dried ($Na_2SO_4$), filtered, and concentrated, and the resulting residue was purified by silica gel column (hexanes/EtOAc) to give (S)-tert-butyl 5-azido-1-(tert-butoxycarbonyloxy)-4,4-difluoropentan-2-yl(methyl)carbamate (0.0956 mol, 100%). LRMS (M+Na$^+$) m/z 417.4.

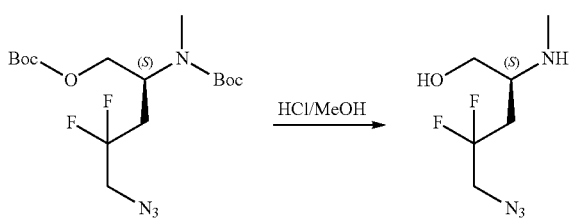

To a solution of (S)-tert-butyl 5-azido-1-(tert-butoxycarbonyloxy)-4,4-difluoropentan-2-yl(methyl)carbamate (95.6 mmol) in methanol (10 mL) was added Hydrogen chloride (4.0 M in 1,4-dioxane, 240 mL, 0.596 mol). The resulting solution was stirred for overnight. The solvent was removed, and the remaining residue was dried under reduced pressure to give (S)-5-azido-4,4-difluoro-2-(methylamino)pentan-1-ol as a HCl salt, which was used without further purification. LRMS (M+H$^+$) m/z 195.3.

478

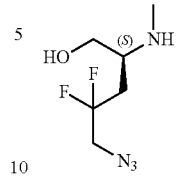

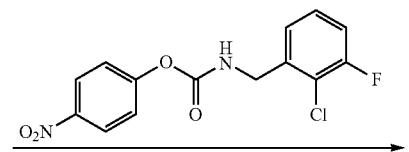

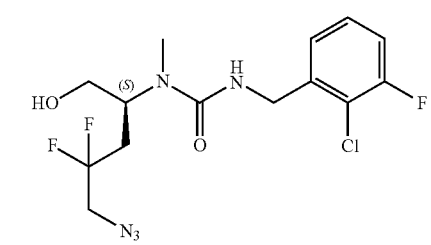

To a solution of (S)-5-azido-4,4-difluoro-2-(methylamino)pentan-1-ol HCl salt (95.6 mmol) and DIEA (33.3 mL, 0.191 mol) in THF (300 mL) was added O-(4-nitrophenyl)-N-(2-chloro-3-fluorobenzyl) carbamate (34.1 g, 0.105 mol). The resulting mixture was stirred at RT for 1 h. The solvent was removed, and the resulting residue was purified on silica gel column (DCM/MeOH) to give (S)-1-(5-azido-4,4-difluoro-1-hydroxypentan-2-yl)-3-(2-chloro-3-fluorobenzyl)-1-methylurea (25.4 g, 70%). LRMS (M+H$^+$) m/z 380.4.

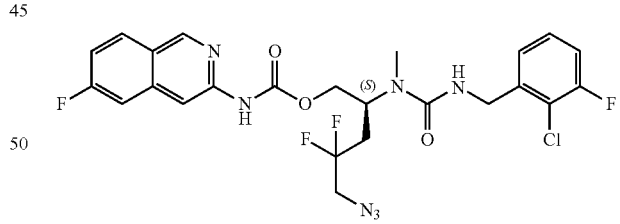

To a solution of (S)-1-(5-azido-4,4-difluoro-1-hydroxypentan-2-yl)-3-(2-chloro-3-fluorobenzyl)-1-methylurea (25.4 g, 0.0669 mol) and toluene (500 mL) was added 6-fluoroisoquinoline-3-carbonyl azide (17.4 g, 0.0803 mol). The resulting solution was stirred at 100 C for 2 h and concentrated, and the remaining residue was purified on silica gel column (DCM/MeOH) to give (S)-5-azido-2-(3-(2-chloro-3-fluorobenzyl)-1-methylureido)-4,4-difluoropentyl 6-fluoroisoquinolin-3-ylcarbamate (25.0 g, 84.7%). LRMS (M+H$^+$) m/z 568.5.

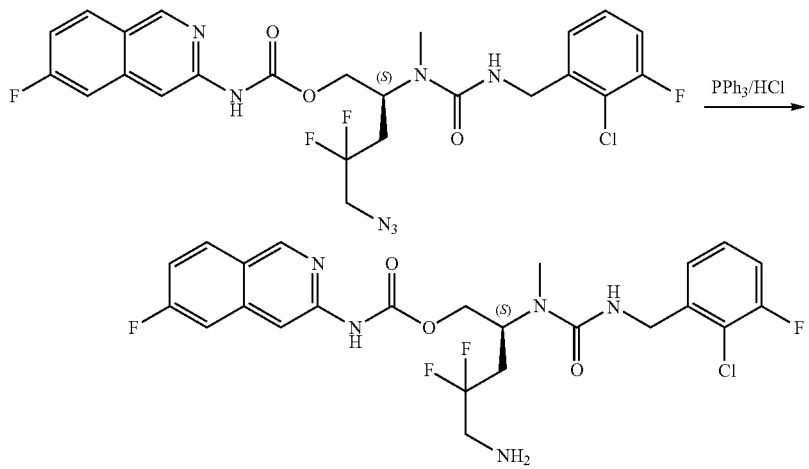

To a mixture of (S)-5-azido-2-(3-(2-chloro-3-fluorobenzyl)-1-methylureido)-4,4-difluoropentyl 6-fluoroisoquinolin-3-ylcarbamate (25.0 g, 0.0441 mol), THF (300 mL) and water (100 mL) was added triphenylphosphine (13.9 g, 0.0529 mol) and aq. HCl solution (53 mL, 2N, 0.106 mol). The resulting mixture was stirred at RT for 1 h and concentrated down to about 200 mL. Water (200 mL) was then added. The resulting mixture (pH<4) was extracted with EtOAc (300 mL) and the EtOAc solution was discarded. The remaining aq. solution was adjusted to pH>8 by adding NaOH (2N) and extracted with DCM (200 mL×3). The organic layer was washed with water and brine, dried over $Na_2SO_4$. The organic layers were combined and concentrated. The resulting residue was purified on silica gel column (DCM/MeOH) to give (S)-5-amino-2-(3-(2-chloro-3-fluorobenzyl)-1-methylureido)-4,4-difluoropentyl 6-fluoroisoquinolin-3-ylcarbamate (12.1 g, 50.7%). LRMS (M+H$^+$) m/z 542.5.

Example 48

Preparation of (S)-2-(3-(2-chloro-3-fluorobenzyl)-1-methylureido)-3-(5,6,7,8-tetrahydroimidazo[1,5-a]pyrazin-3-yl)propyl isoquinolin-3-ylcarbamate

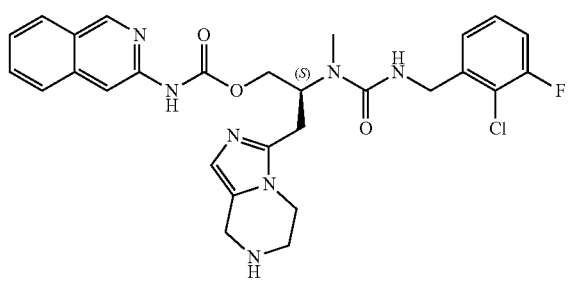

(S)-2-(3-(2-chloro-3-fluorobenzyl)-1-methylureido)-3-(5,6,7,8-tetrahydroimidazo[1,5-a]pyrazin-3-yl)propyl isoquinolin-3-ylcarbamate

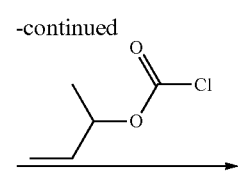

To a mixture of (S)-2-((benzyloxycarbonyl)(methyl)amino)-4-tert-butoxy-4-oxobutanoic acid dicyclohexylaminomonium salt (20 g, 0.0386 mol) and Et$_3$N (7.90 mL, 0.0579 mol) in THF (500 mL) was added isobutyl chloroformate (6.05 mL, 0.0463 mol) at 0° C. The reaction mixture was stirred for 1 h, and filtered to remove TEA salt. To the filtrate was added a solution of NaBH$_4$ (2.19 g, 0.0579 mol) in THF (50 mL) and water (100 mL) at 0-5° C. The reaction mixture was stirred at RT for 1 h and quenched with saturated NH$_4$Cl solution. The reaction mixture was concentrated to remove most of THF and extracted with EtOAc (700 mL×3). The organic layers were washed with water, NaHCO3 and brine, dried over Na$_2$SO$_4$, and concentrated to give (S)-tert-butyl 3-((benzyloxycarbonyl)(methyl)amino)-4-hydroxybutanoate (10 g), which was used without further purification. LRMS (M+Na$^+$) m/z 346.1.

481

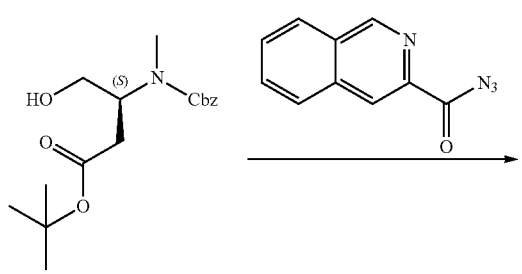

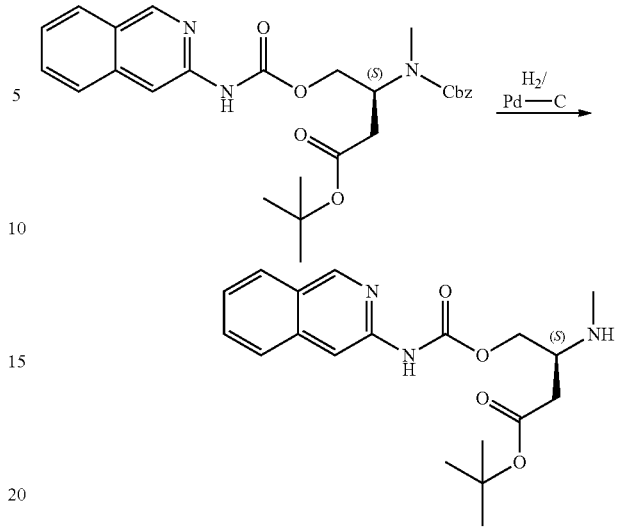

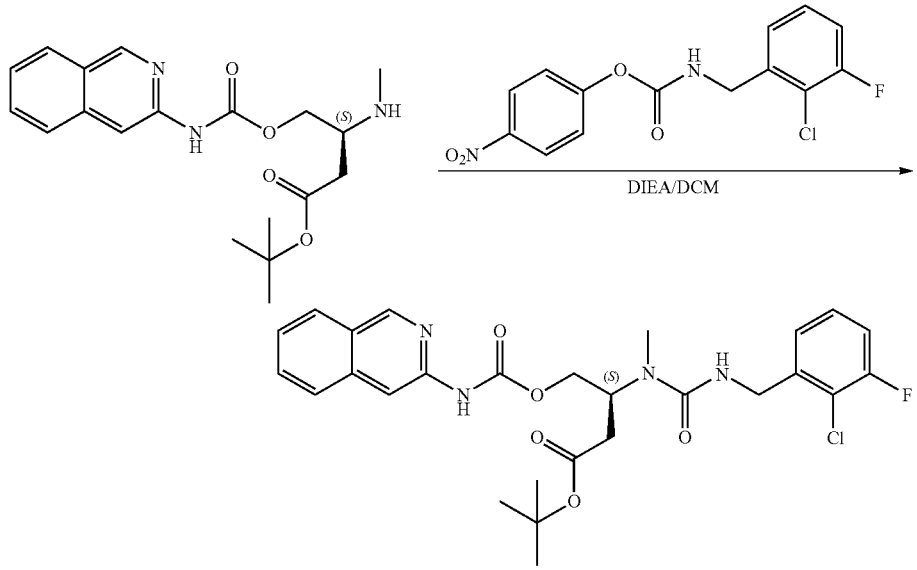

To a mixture of (S)-tert-butyl 3-((benzyloxycarbonyl)(methyl)amino)-4-hydroxybutanoate (4.0 g, 12.4 mmol) and toluene (100 mL) was added isoquinoline-3-carbonyl azide (2.94 g, 14.9 mmol). The resulting mixture was stirred at 100° C. for 2 h. The solvent was removed, and the remaining residue was purified on silica gel column (hexanes/EtOAc) to give (S)-tert-butyl 3-((benzyloxycarbonyl)(methyl)amino)-4-(isoquinolin-3-ylcarbamoyloxy)butanoate (3.6 g, 58.9%). LRMS (M+H⁺) m/z 494.1.

482

To a solution of (S)-tert-butyl 3-((benzyloxycarbonyl)(methyl)amino)-4-(isoquinolin-3-ylcarbamoyloxy)butanoate (1.8 g, 3.65 mmol) and MeOH (5 mL) was added 10% Pd—C (500 mg). The resulting mixture was stirred under 12 psi of hydrogen for 1 h. The mixture was filtered and concentrated, and the remaining residue was dried in vacuo to give (S)-tert-butyl 4-(isoquinolin-3-ylcarbamoyloxy)-3-(methylamino)butanoate (1.3 g), which was used without further purification. LRMS (M+H⁺) m/z 360.1

To a mixture of (S)-tert-butyl 4-(isoquinolin-3-ylcarbamoyloxy)-3-(methylamino)butanoate (1.3 g, 3.65 mmol) and DIEA (1.27 mL, 7.3 mmol) in THF (50 mL) was added O-(4-nitrophenyl)-N-(2-chloro-3-fluorobenzyl) carbamate (1.78 g, 0.00547 mol). The resulting mixture was stirred at RT for 2 h and diluted with EtOAc (100 mL). The organic layer was washed by NaHCO₃ solution and concentrated. The resulting residue was purified on silica gel column (hexanes/EtOAc) to give (S)-tert-butyl 3-(3-(2-chloro-3-fluorobenzyl)-1-methylureido)-4-(isoquinolin-3-ylcarbamoyloxy)butanoate (1.1 g, 55.3%). LRMS (M+H⁺) m/z 545.1.

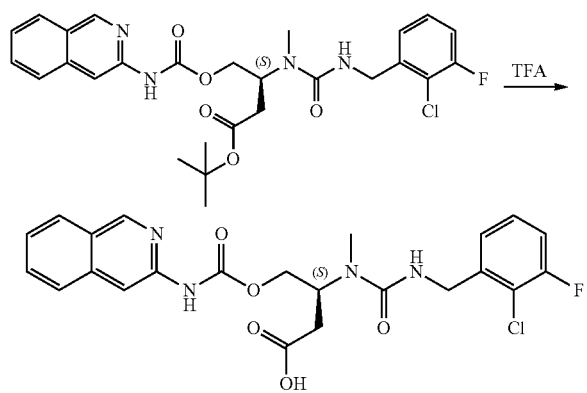

To a mixture of (S)-tert-butyl 3-(3-(2-chloro-3-fluorobenzyl)-1-methylureido)-4-(isoquinolin-3-ylcarbamoyloxy)butanoate (0.8 g, 1.47 mmol) and DCM (10 mL) was added TFA (10 mL). The resulting solution was stirred at RT for 1 h. The mixture was concentrated, and the remaining residue was dried in vacuo to give (S)-3-(3-(2-chloro-3-fluorobenzyl)-1-methylureido)-4-(isoquinolin-3-ylcarbamoyloxy)butanoic acid (1.3 g), which was used without further purification. LRMS (M+H⁺) m/z 489.1.

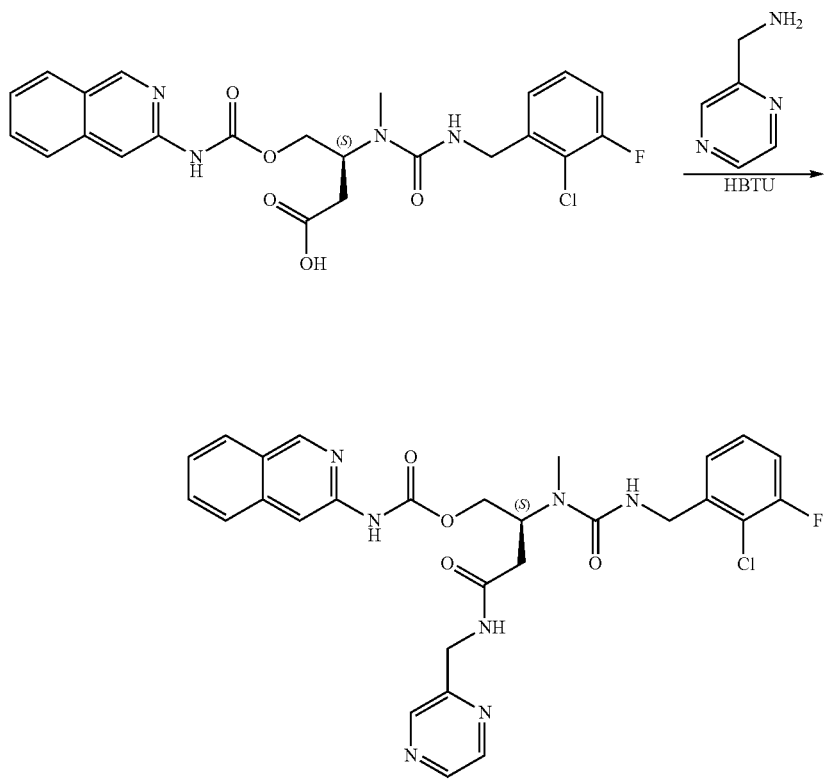

To a mixture of the crude (S)-3-(3-(2-chloro-3-fluorobenzyl)-1-methylureido)-4-(isoquinolin-3-ylcarbamoyloxy)butanoic acid (1.47 mmol) and DMF (5 mL) were added DIEA (0.512 mL, 2.94 mmol) and HBTU (0.667 g, 1.76 m mol). The resulting mixture was stirred at RT for 10 min and 2-aminomethylpyrazine (0.192 g, 1.76 mmol) was added. The resulting mixture was stirred at RT for 30 min. The mixture was diluted with EtOAc (100 mL). The organic layer was washed by NaHCO₃ solution and concentrated. The resulting residue was purified on silica gel column (DCM/MeOH) to give (S)-2-(3-(2-chloro-3-fluorobenzyl)-1-methylureido)-4-oxo-4-(pyrazin-2-ylmethylamino)butyl isoquinolin-3-ylcarbamate (0.65 g, 76.2%). LRMS (M+H⁺) m/z 580.1

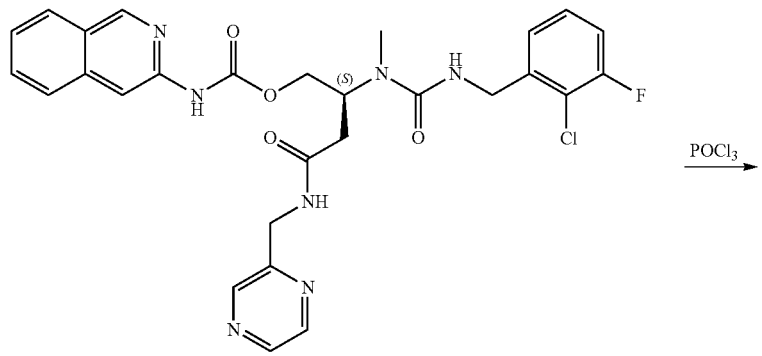

POCl₃ →

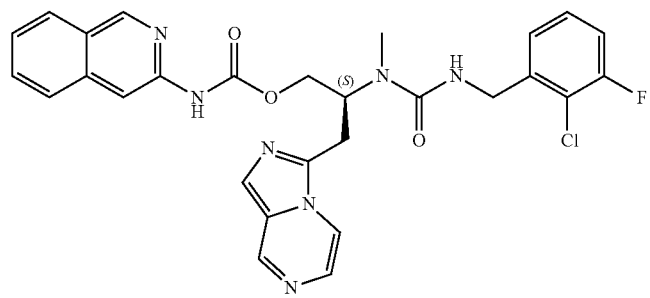

To a mixture of (S)-2-(3-(2-chloro-3-fluorobenzyl)-1-methylureido)-4-oxo-4-(pyrazin-2-ylmethylamino)butyl isoquinolin-3-ylcarbamate (650 mg, 1.12 mmol) and DCM (50 mL) were added phosphoryl chloride (0.514 mL, 0.00561 mol). The resulting mixture was stirred at RT for overnight. The resulting solution was concentrated. The resulting residue was purified on prep-HPLC (ACN/H₂O with 0.1% HCOOH) to give (S)-2-(3-(2-chloro-3-fluorobenzyl)-1-methylureido)-3-(imidazo[1,5-a]pyrazin-3-yl)propyl isoquinolin-3-ylcarbamate (0.27 g, 43%). LRMS (M+H⁺) m/z 562.1

To a solution of (S)-2-(3-(2-chloro-3-fluorobenzyl)-1-methylureido)-3-(imidazo[1,5-a]pyrazin-3-yl)propyl isoquinolin-3-ylcarbamate (100 mg, 0.178 mmol) and MeOH (5 mL) were added 10% Pd—C (100 mg). The resulting mixture was stirred under 12 psi of hydrogen for h. The mixture was filtered and concentrated. The resulting residue was purified on prep-HPLC (ACN/H2O with 0.1% HCOOH) to give (S)-2-(3-(2-chloro-3-fluorobenzyl)-1-methylureido)-3-(5,6,7,8-tetrahydroimidazo[1,5-a]pyrazin-3-yl)propyl isoquinolin-3-ylcarbamate (35 mg, 35%). LRMS (M+H⁺) m/z 566.1.

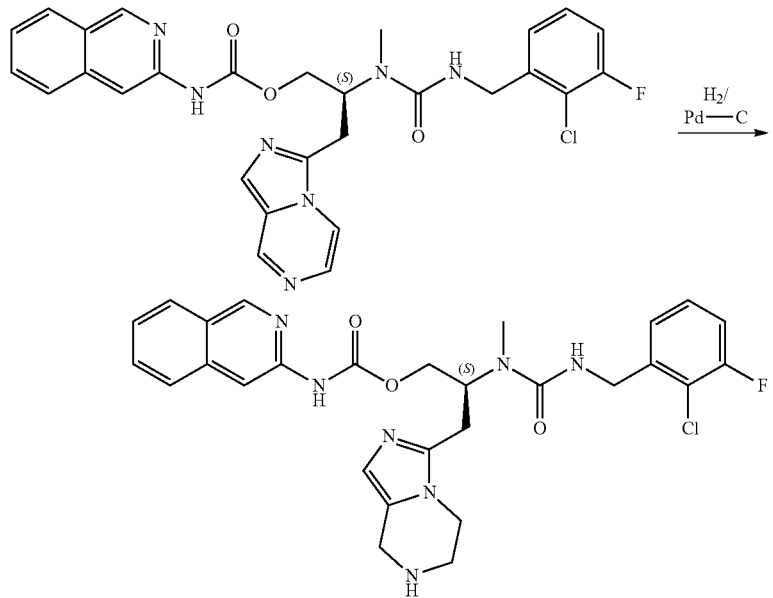

Example 49

Preparation of (S)-2-(3-(2-chloro-3-fluorobenzyl)-1-methylureido)-5-(3-(2-hydroxyethyl)ureido)pentyl 6-fluoroisoquinolin-3-ylcarbamate

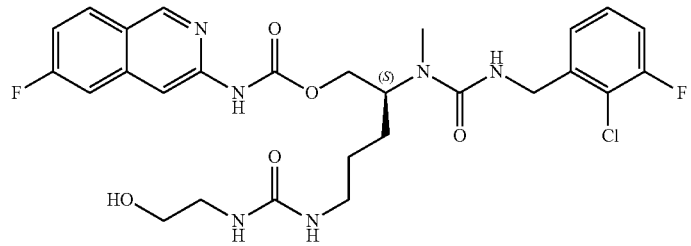

(S)-2-(3-(2-chloro-3-fluorobenzyl)-1-methylureido)-5-(3-(2-hydroxyethyl)ureido)pentyl 6-fluoroisoquinolin-3-ylcarbamate

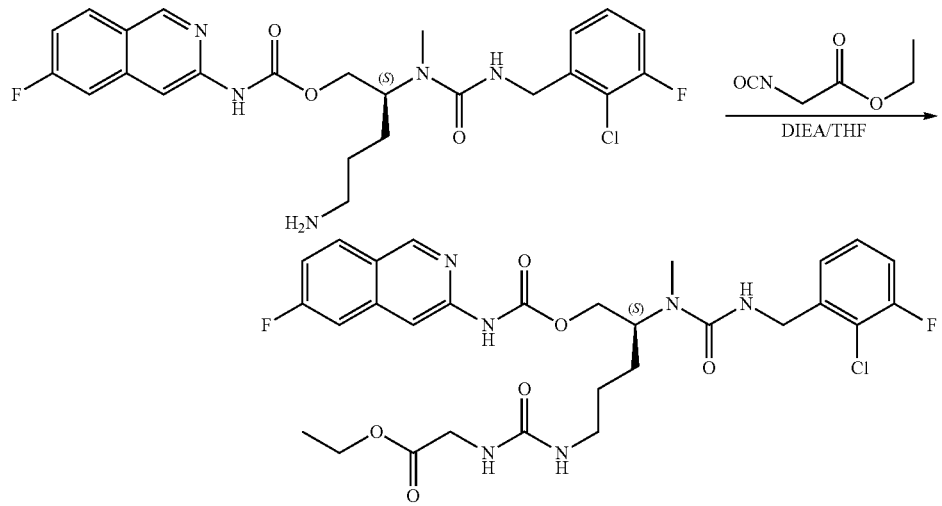

To a mixture of (S)-5-amino-2-(3-(2-chloro-3-fluorobenzyl)-1-methylureido)pentyl 6-fluoroisoquinolin-3-ylcarbamate (0.40 g, 0.792 mmol), DIEA (0.276 mL, 1.58 mmol) and THF (2 mL), ethyl isocyanatoacetate (0.108 mL, 0.950 mmol) was added. The mixture was refluxed for 30 min, and concentrated. The remaining residue was purified on silica gel column (DCM/MeOH) to give (S)-ethyl 1-(2-chloro-3-fluorophenyl)-5-((6-fluoroisoquinolin-3-ylcarbamoyloxy)methyl)-4-methyl-3,10-dioxo-2,4,9,11-tetraazatridecan-13-oate (0.40 g, 80%). LRMS (M+H⁺) m/z 635.6.

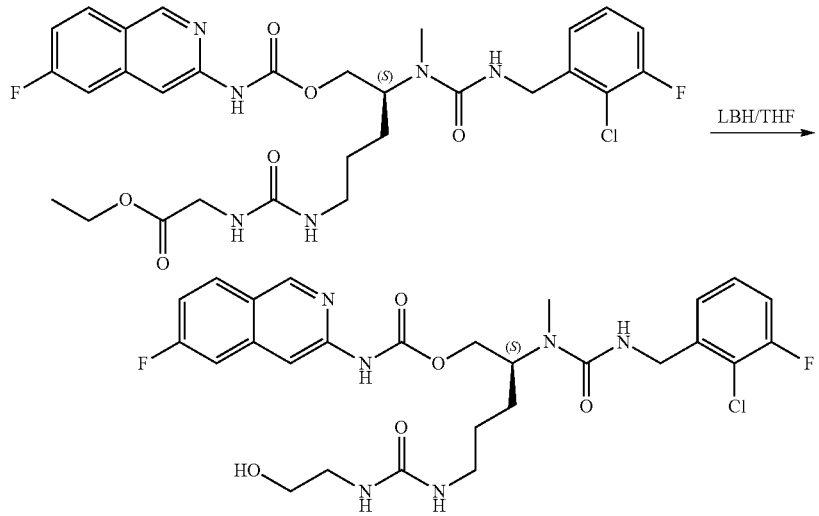

To a solution of (S)-ethyl 1-(2-chloro-3-fluorophenyl)-5-(6-fluoroisoquinolin-3-ylcarbamoyloxy)methyl)-4-methyl-3,10-dioxo-2,4,9,11-tetraazatridecan-13-oate (0.40 g, 0.63 mmol) in THF (20 mL) was added Lithium borohydride (1.57 mL, 2 M, 3.15 mmol) in THF at 0° C. The reaction was stirred at 0° C. for 10 min. MeOH (1 mL) was added to the reaction solution and the resulting solution was stirred at RT for 2 h. The reaction was quenched with saturated NH$_4$Cl solution. The resulting residue was partitioned between EtOAc and H$_2$O. The aqueous layer was extracted further with EtOAc. The combined organic layers were dried (Na$_2$SO$_4$), filtered, and concentrated, and the resulting residue was purified by silica gel column (hexanes/EtOAc) to give (S)-2-(3-(2-chloro-3-fluorobenzyl)-1-methylureido)-5-(3-(2-hydroxyethyl)ureido)pentyl 6-fluoroisoquinolin-3-ylcarbamate (0.34 g, 91%). LRMS (M+Na$^+$) m/z 593.6.

Example 50

Preparation of (2S,4R)-2-(3-(2-chloro-3-fluorobenzyl)-1-methylureido)-4,5-dihydroxypentyl 3-phenylisoxazol-5-ylcarbamate

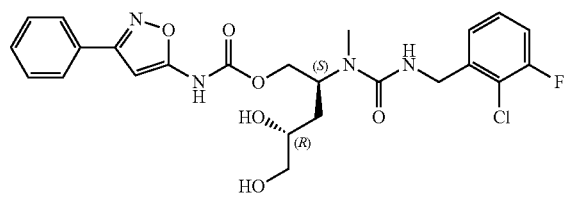

(2S,4R)-2-(3-(2-chloro-3-fluorobenzyl)-1-methylureido)-4,5-dihydroxypentyl 3-phenylisoxazol-5-ylcarbamate

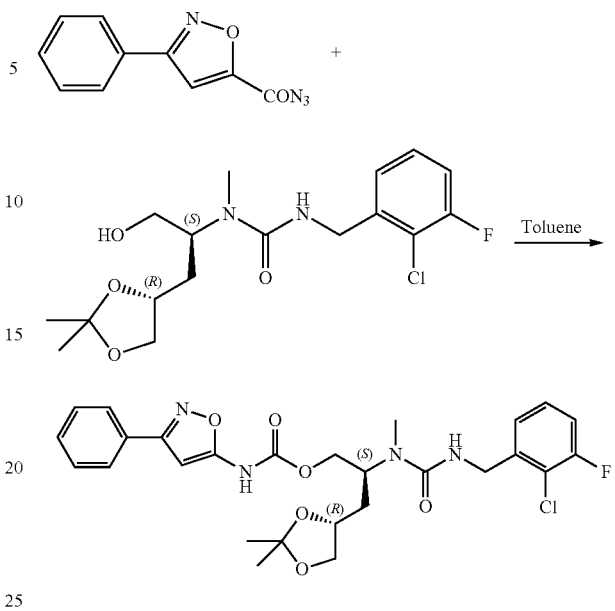

To a solution of 3-(2-chloro-3-fluorobenzyl)-1-((S)-1-((R)-2,2-dimethyl-1,3-dioxolan-4-yl)-3-hydroxypropan-2-yl)-1-methylurea (0.52 g, 1.4 mmol, 1.0 equiv.) in toluene (20 mL) at 100° C., was added 3-phenylisoxazole-5-carbonyl azide (0.3 g, 1.4 mmol, 1.0 equiv.). The solution was stirred for 1 h. The solvent was removed, and the remaining residue was purified on silica gel column using a mixture of hexane and EtOAc to give (S)-2-(3-(2-chloro-3-fluorobenzyl)-1-methylureido)-3-((R)-2,2-dimethyl-1,3-dioxolan-4-yl)propyl 3-phenylisoxazol-5-ylcarbamate (0.42 g, 60%). LRMS (M+H$^+$) m/z 561.1.

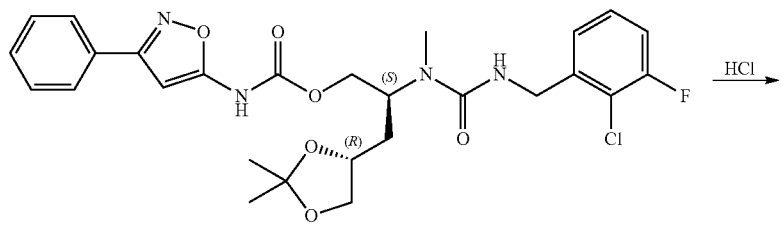

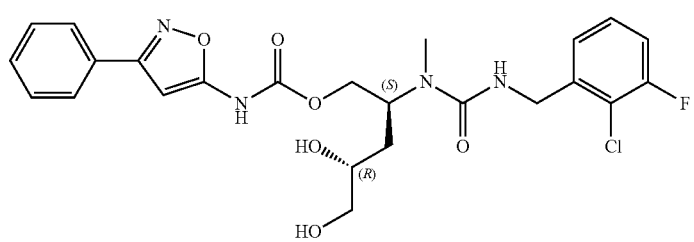

To a solution of (S)-2-(3-(2-chloro-3-fluorobenzyl)-1-methylureido)-3-(R)-2,2-dimethyl-1,3-dioxolan-4-yl)propyl 3-phenylisoxazol-5-ylcarbamate (0.4 g, 0.7 mmol, 1.0 equiv.) in MeOH (5 mL) at 0° C., was added HCl/Dioxane (4 N, 3 mL). The mixture was warmed up to RT, stirred for 1 h, concentrated and purified on silica gel column using a mixture of DCM and MeOH to give (2S,4R)-2-(3-(2-chloro-3-fluorobenzyl)-1-methylureido)-4,5-dihydroxypentyl 3-phenylisoxazol-5-ylcarbamate (0.35 g, 96%, white solid). LRMS (M+H$^+$) m/z 521.1.

Example 51

Preparation of Sodium (2R,4S)-4-(3-(2-chloro-3-fluorobenzyl)-1-methylureido)-2-hydroxy-5-(3-phenylisoxazol-5-ylcarbamoyloxy)pentyl phosphate To a mixture of (2S,4R)-2-(3-(2-chloro-3-fluorobenzyl)-1-methylureido)-4,5-dihydroxypentyl 3-phenylisoxazol-5-ylcarbamate (0.25 g, 0.48 mmol, 1.0 equiv.), DMAP (0.23 g, 1.92 mmol, 4.0 equiv.), and DIEA (0.33 mL, 1.92 mmol, 4.0 equiv.) in DCM (50 mL) at ° C., was added diethyl chlorophosphate (0.20 mL, 1.44 mmol, 3.0 equiv.) dropwise. The reaction was quenched with EtOH in 5 min, followed by treatment with saturated NaHCO$_3$. The organic layer was concentrated, and the resulting residue was purified on RP-HPLC using a mixture of acetonitrile and H$_2$O to give (2S,4R)-2-(3-(2-chloro-3-fluorobenzyl)-1-methylureido)-5-(diethoxyphosphoryloxy)-4-hydroxypentyl 3-phenylisoxazol-5-ylcarbamate (56 mg, 20%). LRMS (M+H$^+$) m/z 657.1.

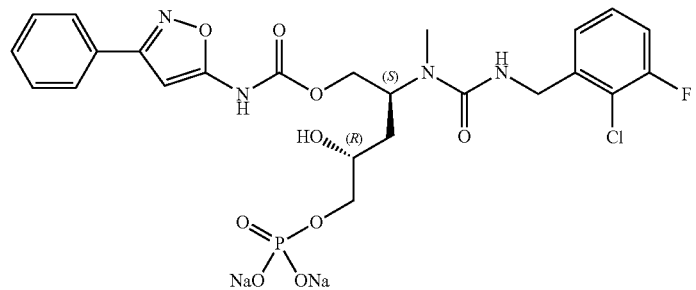

sodium (2R,4S)-4-(3-(2-chloro-3-fluorobenzyl)-1-methylureido)-2-hydroxy-5-(3-phenylisoxazol-5-ylcarbamoyloxy)pentyl phosphate

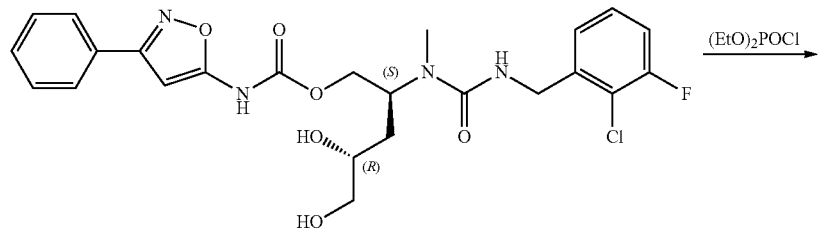

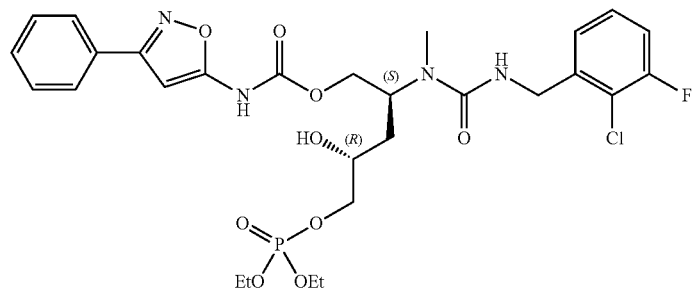

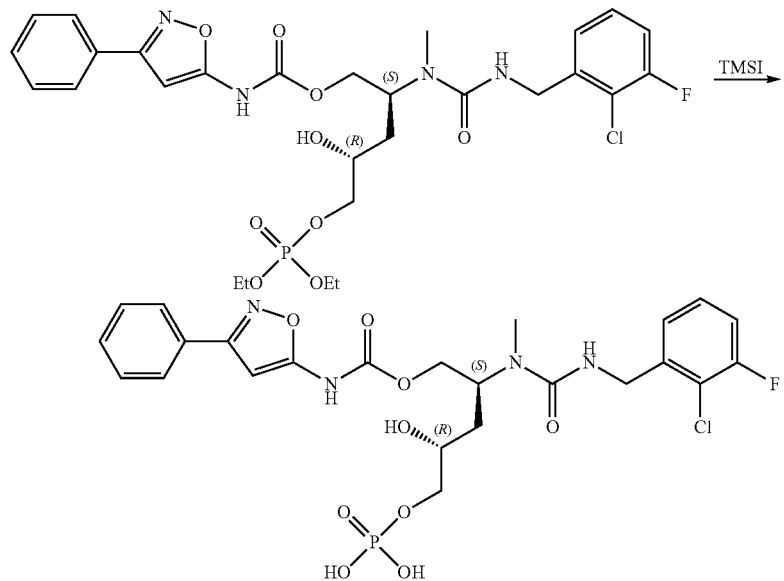

To a mixture of (2S,4R)-2-(3-(2-chloro-3-fluorobenzyl)-1-methylureido)-5-(diethoxyphosphoryloxy)-4-hydroxypentyl 3-phenylisoxazol-5-ylcarbamate (56 mg, 0.085 mmol, 1.0 equiv.) in acetonitrile (5 mL) was added TMSI (0.115 mL, 0.85 mmol, 10.0 equiv.) at 0° C. After stirring at RT for 10 min, the reaction wag quenched with MeOH. The solvent was removed, and the resulting residue was purified on RP-HPLC using a mixture of acetonitrile and H$_2$O (with 0.1% TFA buffer). The fractions of product was concentrated, dissolved in a mixture of methanol and water (2:1), followed by addition of HCl (4 N in 1,4-dioxane, 2 mL). The mixture was concentrated to give (2S,4R)-2-(3-(2-chloro-3-fluorobenzyl)-1-methylureido)-4-hydroxy-5-(phosphonooxy)pentyl 3-phenylisoxazol-5-ylcarbamate (48 mg, 94%) as a white solid. LRMS (M+H$^+$) m/z 601.5.

To a mixture of (2S,4R)-2-(3-(2-chloro-3-fluorobenzyl)-1-methylureido)-4-hydroxy-5-(phosphonooxy)pentyl 3-phenylisoxazol-5-ylcarbamate (48 mg, 0.08 mmol, 1.0 equiv.) at 0° C., was added NaOH (0.1 N, 1.6 mL, 2.0 equiv.) dropwise. The mixture was stirred at RT for 1 h followed by concentration to give sodium (2R,4S)-4-(3-(2-chloro-3-fluorobenzyl)-1-methylureido)-2-hydroxy-5-(3-phenylisoxazol-5-ylcarbamoyloxy)pentyl phosphate (55 mg, quant.) as a white solid. LRMS (M−2Na$^+$ 3H$^+$) m/z 601.5.

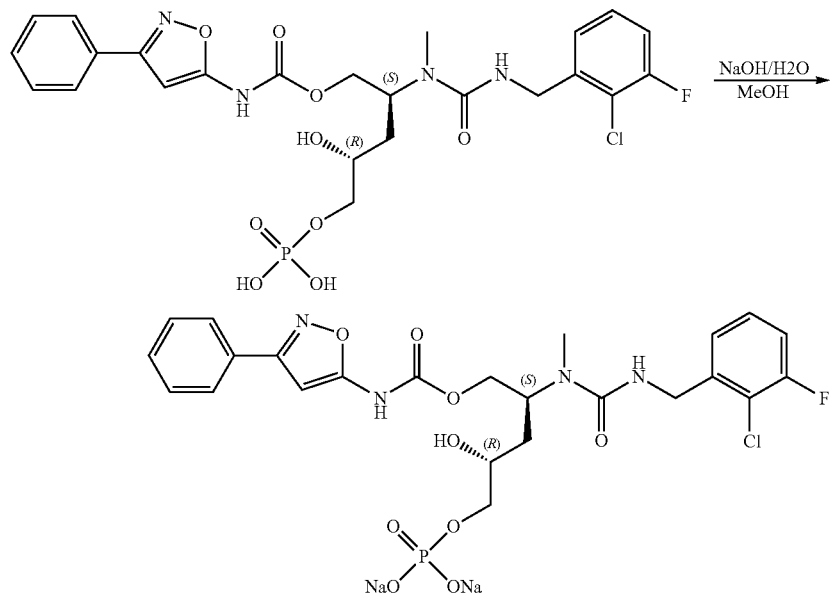

Example 52

Preparation of (S)-2-(3-(2-chloro-3-fluorobenzyl)-1-methylureido)-5-oxo-5-(piperazin-1-yl)pentyl 3-(3-fluorophenyl)isoxazol-5-ylcarbamate

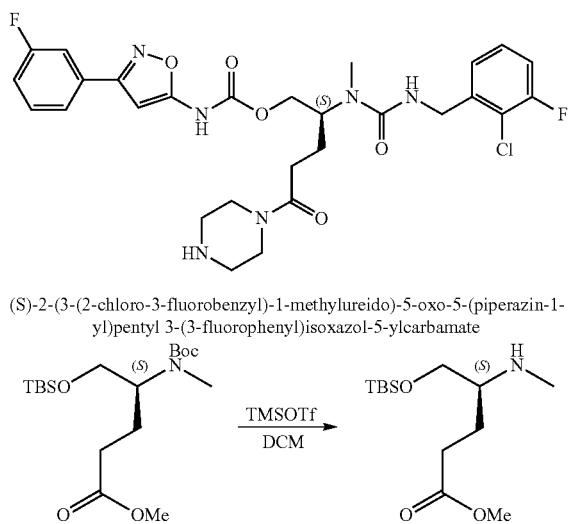

(S)-2-(3-(2-chloro-3-fluorobenzyl)-1-methylureido)-5-oxo-5-(piperazin-1-yl)pentyl 3-(3-fluorophenyl)isoxazol-5-ylcarbamate To a mixture of (S)-methyl 4-(tert-butoxycarbonyl(methyl)amino)-5-(tert-butyldimethylsilyloxy)pentanoate (41 g, 109 mmol, 1.0 equiv.), lutidine (19 mL, 163 mmol, 1.5 equiv.) in DCM (400 mL) at 0° C., was added TMSOTf (23.7 mL, 131 mmol, 1.2 equiv.) dropwise. The solution was stirred at RT for 1 h. The solvents were removed and the residue was used without further purification.

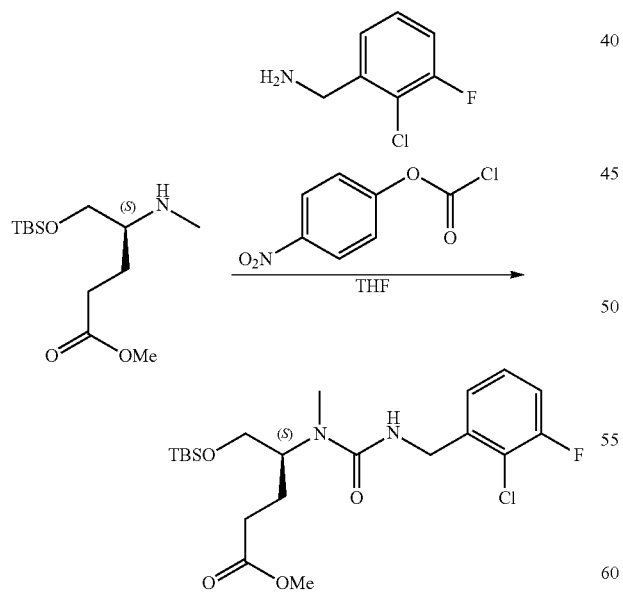

To a solution of 4-nitrophenylchloroformate (24.22 g, 120 mmol, 1.1 equiv.) in THF (100 mL) was added a solution of 2-chloro-3-fluorobenzylamine (19.1 g, 120 mmol, 1.1 equiv.) and DIEA (46 mL, 264 mmol, 2.2 equiv.) in THF (100 mL). The resulting solution was stirred at RT for 20 min. The reaction mixture was added into a solution of (S)-methyl 5-(tert-butyldimethylsilyloxy)-4-(methylamino)pentanoate (30 g, 109 mmol, 1.0 equiv.), DIEA (23 mL, 132 mmol, 1.1 equiv.) in THF (100 mL). The resulting mixture was stirred at RT for 1 h. The solvent was removed, and the resulting residue was dissolved into EtOAc (300 mL) and washed with brine (400 mL), saturated Na$_2$CO$_3$ (400 mL), and brine (400 mL). The organic layer was concentrated and the residue was purified on silica gel column using a mixture of Hexane and EtOAc to give (S)-methyl 5-(tert-butyldimethylsilyloxy)-4-(3-(2-chloro-3-fluorobenzyl)-1-methylureido)pentanoate (32.6 g, 65%) as a yellowish solid. LRMS (M+H$^+$) m/z 461.1.

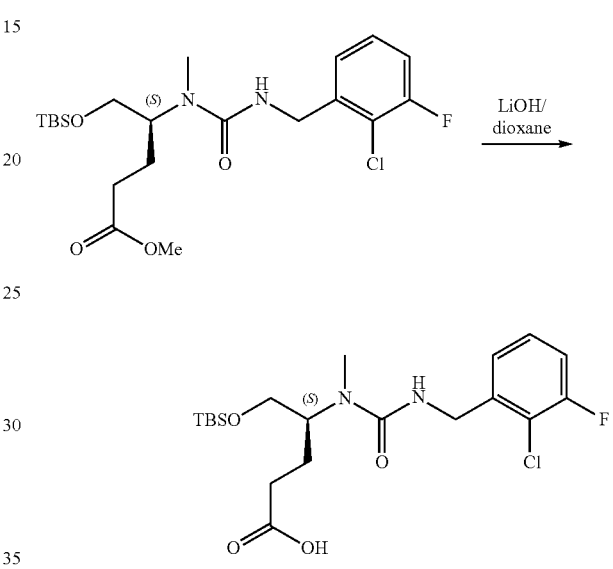

To a solution of (S)-methyl 5-(tert-butyldimethylsilyloxy)-4-(3-(2-chloro-3-fluorobenzyl)-1-methylureido)pentanoate (5.3 g, 11.5 mmol, 1.0 equiv.) in dioxane (60 mL), was added LiOH (1 N, 34.5 mL, 3 equiv.) dropwise. The solution was stirred at RT for 1 h. The solvents were removed and the residue was used without further purification.

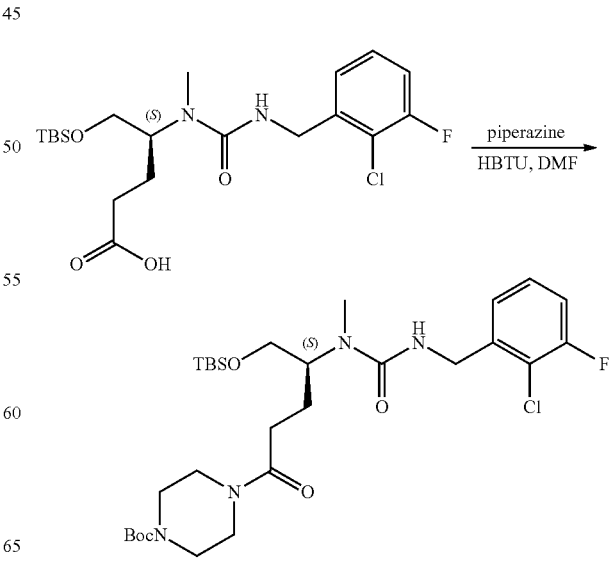

To a solution of (S)-5-(tert-butyldimethylsilyloxy)-4-(3-(2-chloro-3-fluorobenzyl)-1-methylureido)pentanoic acid (4.46 g, 10 mmol, 1.0 equiv.) in DMF (50 mL), was added HBTU (5.69 g, 15 mmol, 1.5 equiv.), 1-N-Boc-piperazine (2.79 g, 15 mmol, 1.5 equiv.) and DIEA (5.21 mL, 30 mmol, 3.0 equiv.) in sequence. The reaction was completed in 15 min. Ether (100 mL) and brine (100 mL) were added to the reaction mixture. The organic layer was dried and concentrated. The residue was purified on silica gel column using a mixture of hexane and EtOAc to give (S)-tert-butyl 4-(5-(tert-butyldimethylsilyloxy)-4-(3-(2-chloro-3-fluorobenzyl)-1-methylureido)pentanoyl)piperazine-1-carboxylate (4.2 g, 68%). LRMS (M+H$^+$) m/z 615.2.

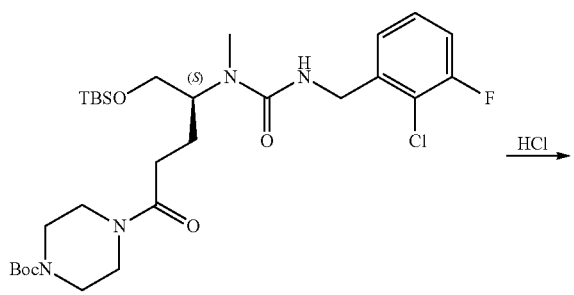

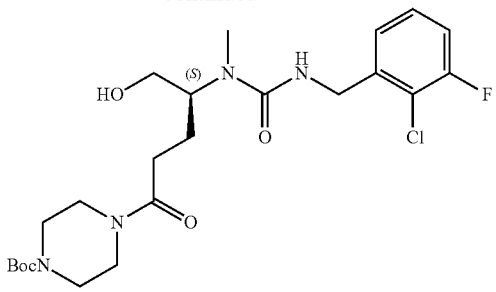

To a solution of (S)-tert-butyl 4-(5-(tert-butyldimethylsilyloxy)-4-(3-(2-chloro-3-fluorobenzyl)-1-methylureido)pentanoyl)piperazine-1-carboxylate (4.2 g, 6.8 mmol, 1.0 equiv.) in MeOH (35 mL), was added HCl (2N, 0.68 mL, 1.36 mmol, 0.2 equiv.). The reaction was stirred at RT for 1 h. NaHCO$_3$ (1.1 g, 13.6 mmol, 2.0 equiv) was added to quench the reaction. The solvents were removed. The residue was dissolved in EtOAc (100 mL). The salt was filtered off and the filtrate was concentrated to give (S)-tert-butyl 4-(4-(3-(2-chloro-3-fluorobenzyl)-1-methylureido)-5-hydroxypentanoyl)piperazine-1-carboxylate (3.4 g, quant.). LRMS (M+H$^+$) m/z 501.2.

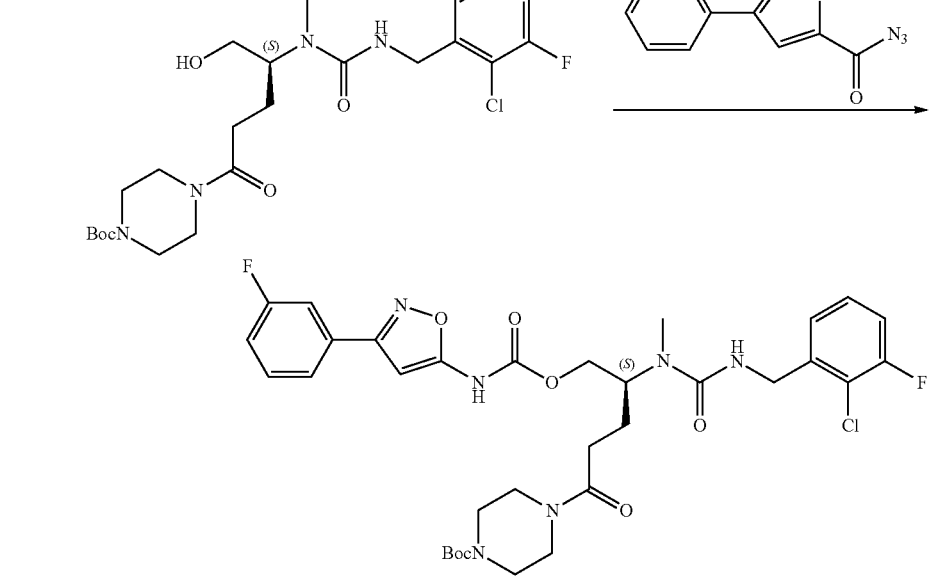

To a solution of (S)-tert-butyl 4-(4-(3-(2-chloro-3-fluorobenzyl)-1-methylureido)-5-hydroxypentanoyl)piperazine-1-carboxylate (0.30 g, 0.6 mmol, 1.0 equiv.) in toluene (10 mL) at 100° C., was added 3-(3-fluorophenyl)isoxazole-5-carbonyl azide (0.13 g, 0.6 mmol, 1.0 equiv.). The solution was stirred for 1 h. The solvent was removed and the residue was purified on RP-HPLC using a mixture of acetonitrile and H$_2$O to give (S)-tert-butyl 4-(4-(3-(2-chloro-3-fluorobenzyl)-1-methylureido)-5-(3-(3-fluorophenyl)isoxazol-5-ylcarbamoyloxy)pentanoyl)piperazine-1-carboxylate (0.3 g, 60%). LRMS (M+H$^+$) m/z 705.1.

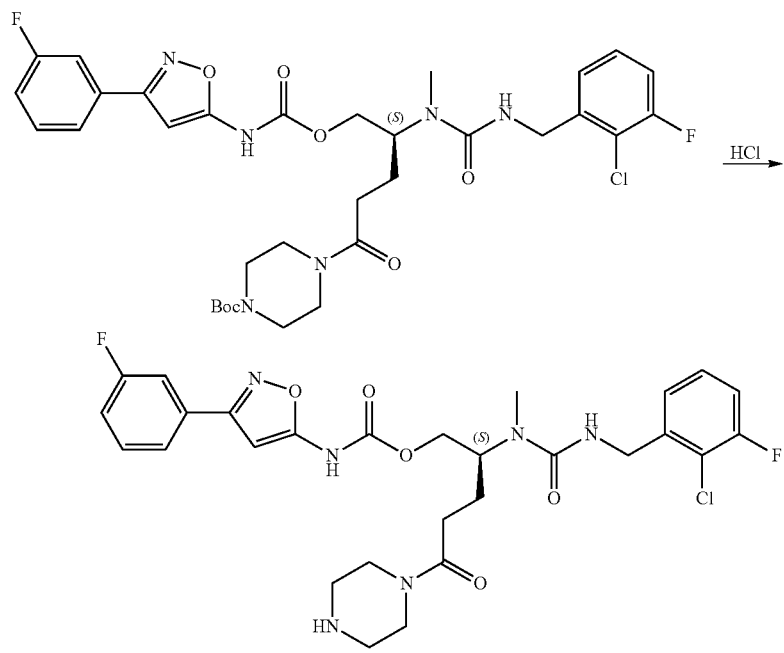

To a solution of (S)-tert-butyl 4-(4-(3-(2-chloro-3-fluorobenzyl)-1-methylureido)-5-(3-(3-fluorophenyl)isoxazol-5-ylcarbamoyloxy)pentanoyl)piperazine-1-carboxylate (0.3 g, 0.36 mmol, 1.0 equiv.) in MeOH (2 mL) at 0° C., was added HCl/dioxane (4 N, 0.9 mL, 3.6 mmol, 10 equiv.). The solution was stirred at RT for 1 h. The solvents were removed and the residue was purified on RP-HPLC using a mixture of acetonitrile and H$_2$O with 0.1% TFA. The elute was diluted with EtOAc (10 mL) and then basified with saturated NaHCO$_3$. The organic layer was dried and concentrated to give (S)-2-(3-(2-chloro-3-fluorobenzyl)-1-methylureido)-5-oxo-5-(piperazin-1-yl)pentyl 3-(3-fluorophenyl)isoxazol-5-ylcarbamate (0.2 g, 92%). LRMS (M+H$^+$) m/z 605.1.

Example 53

Preparation of (S)-2-(3-(2-chloro-3-fluorobenzyl)-1-methylureido)-5-oxo-5-(piperazin-1-yl)pentyl 5-(3-fluorophenyl)isoxazol-3-ylcarbamate

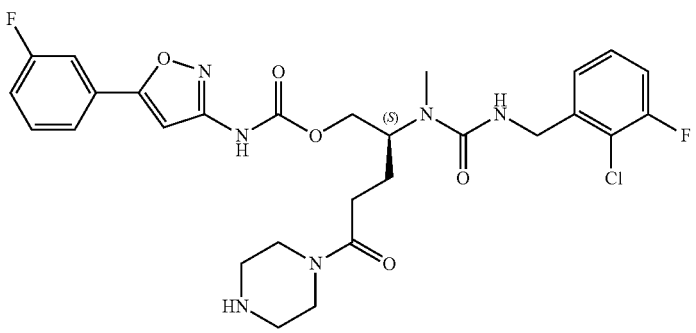

(S)-2-(3-(2-chloro-3-fluorobenzyl)-1-methylureido)-5-oxo-5-(piperazin-1-yl)pentyl 5-(3-fluorophenyl)isoxazol-3-ylcarbamate

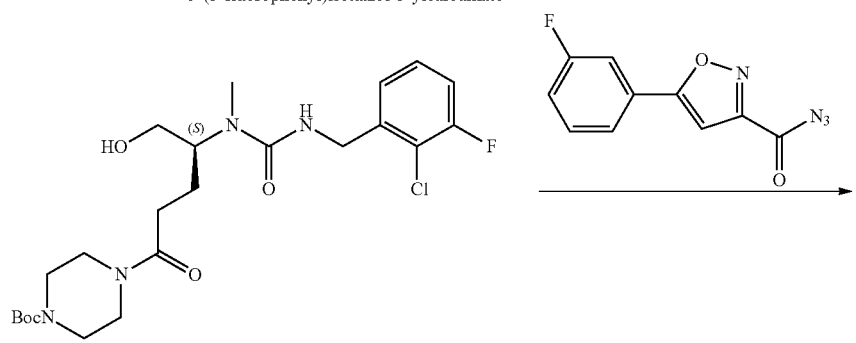

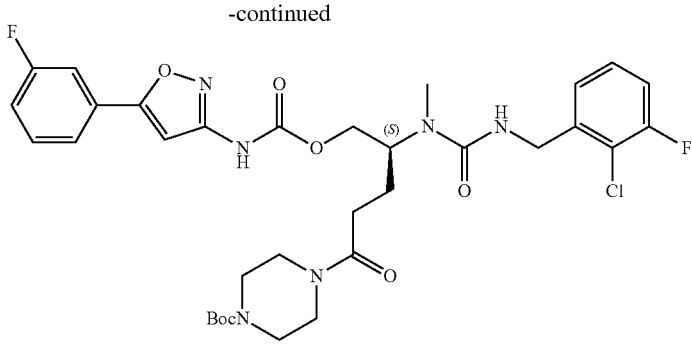

To a solution of (S)-tert-butyl 4-(4-(3-(2-chloro-3-fluorobenzyl)-1-methylureido)-5-hydroxypentanoyl)piperazine-1-carboxylate (0.30 g, 0.6 mmol, 1.0 equiv.) in toluene (10 mL) at 100° C., was added 5-(3-fluorophenyl)isoxazole-3-carbonyl azide (0.13 g, 0.6 mmol, 1.0 equiv.). The mixture was stirred for 1 h. The solvent was removed and the residue was purified on RP-HPLC using a mixture of acetonitrile and H$_2$O to give (S)-tert-butyl 4-(4-(3-(2-chloro-3-fluorobenzyl)-1-methylureido)-5-(5-(3-fluorophenyl)isoxazol-3-ylcarbamoyloxy)pentanoyl)piperazine-1-carboxylate (0.3 g, 60%). LRMS (M+H$^+$) m/z 705.1.

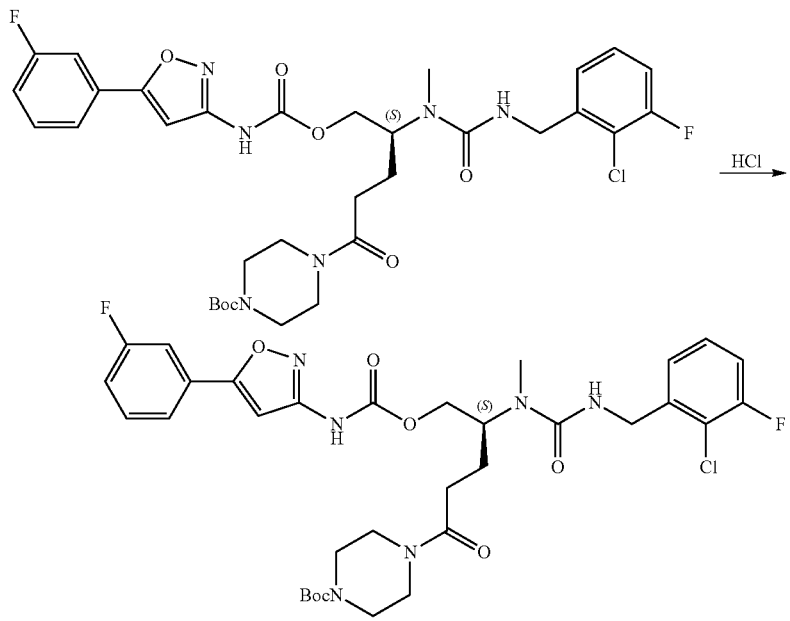

To a solution of (S)-tert-butyl 4-(4-(3-(2-chloro-3-fluorobenzyl)-1-methylureido)-5-(5-(3-fluorophenyl)isoxazol-3-ylcarbamoyloxy)pentanoyl)piperazine-1-carboxylate (0.3 g, 0.36 mmol, 1.0 equiv.) in MeOH (2 mL) at 0° C., was added HCl/dioxane (4 N, 0.9 mL, 3.6 mmol, 10 equiv.). The solution was stirred at RT for 1 h. The solvents were removed and the residue was purified on RP-HPLC using a mixture of acetonitrile and H$_2$O with 0.1% TFA. The elute was diluted with EtOAc (10 mL) and then basified with saturated NaHCO$_3$. The organic layer was dried and concentrated to give (S)-2-(3-(2-chloro-3-fluorobenzyl)-1-methylureido)-5-oxo-5-(piperazin-1-yl)pentyl 5-(3-fluorophenyl)isoxazol-3-ylcarbamate (0.18 g, 90%). LRMS (M+H$^+$) m/z 605.1.

Example 54
Preparation of (S)-5-amino-2-(3-(2-chloro-3-fluorobenzyl)-1-methylureido)-4,4-difluoropentyl 3-(3-fluorophenyl)isoxazol-5-ylcarbamate

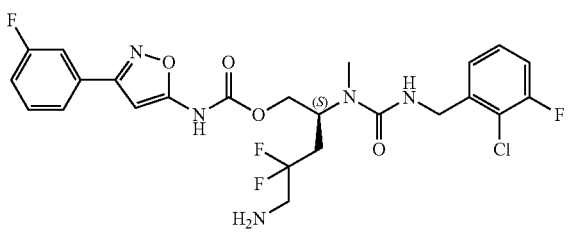

(S)-5-amino-2-(3-(2-chloro-3-fluorobenzyl)-1-methylureido)-4,4-difluoropentyl 3-(3-fluorophenyl)isoxazol-5-ylcarbamate

504 luoro-1-hydroxypentan-2-yl)-3-(2-chloro-3-fluorobenzyl)-1-methylurea (2.6 g, 86%) as a white solid. LRMS (M+H$^+$) m/z 380.1.

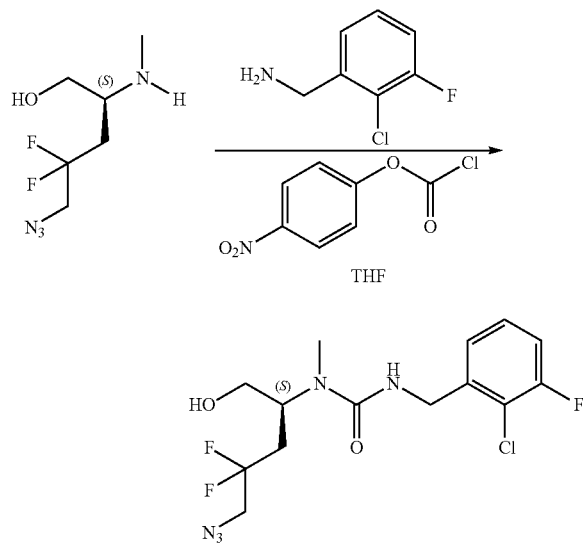

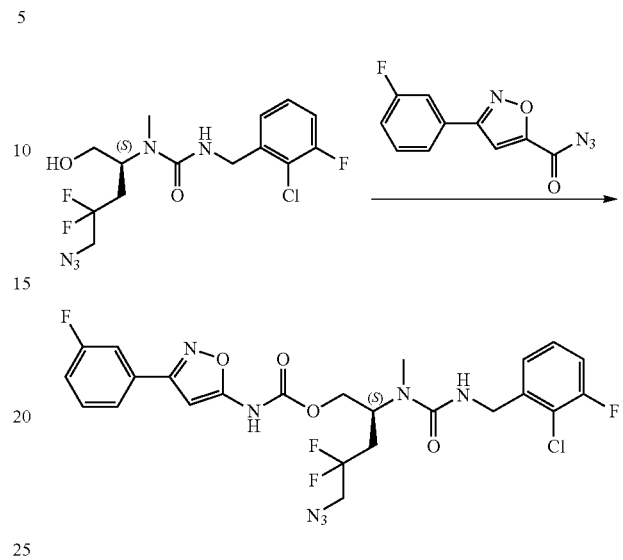

To a solution of 4-nitrophenylchloroformate (1.62 g, 8 mmol) in THF (10 mL) was added a solution of 2-chloro-3-fluorobenzylamine (1.27 g, 8 mmol) and DIEA (2.78 mL, 16 mmol, 2.0 equiv.) in THF (10 mL). The resulting mixture was stirred at RT for 20 min and added into a mixture of (S)-5-azido-4,4-difluoro-2-(methylamino)pentan-1-ol (1.5 g, 8.0 mmol, 1.0 equiv.), DIEA (2.78 mL, 16 mmol) and THF (10 mL). The resulting mixture was stirred at RT for 1 h. The solvent was removed and purified on RP-HPLC using a mixture of acetonitrile and H$_2$O to give (S)-1-(5-azido-4,4-dif- To a solution of (S)-1-(5-azido-4,4-difluoro-1-hydroxypentan-2-yl)-3-(2-chloro-3-fluorobenzyl)-1-methylurea (0.30 g, 0.8 mmol, 1.0 equiv.) in toluene (20 mL) at 100° C., was added 3-(3-fluorophenyl)isoxazole-5-carbonyl azide (0.19 g, 0.8 mmol, 1.0 equiv.). The mixture was stirred at 100° C. for 1 h. The mixture was concentrated and purified on RP-HPLC using a mixture of acetonitrile and H$_2$O to give (S)-5-azido-2-(3-(2-chloro-3-fluorobenzyl)-1-methylureido)-4,4-difluoropentyl 3-(3-fluorophenyl)isoxazol-5-ylcarbamate (0.33 g, 71%) as a white solid. LRMS (M+H$^+$) m/z 584.1.

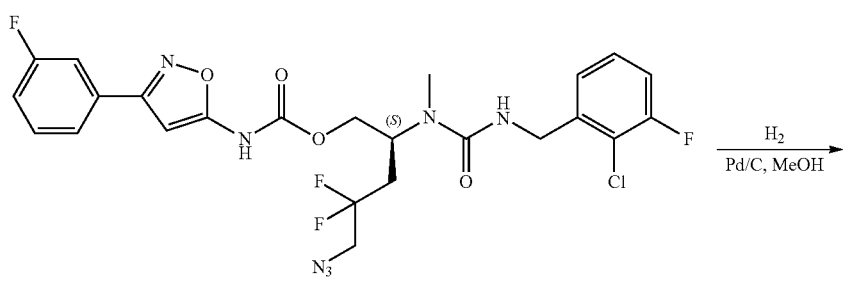

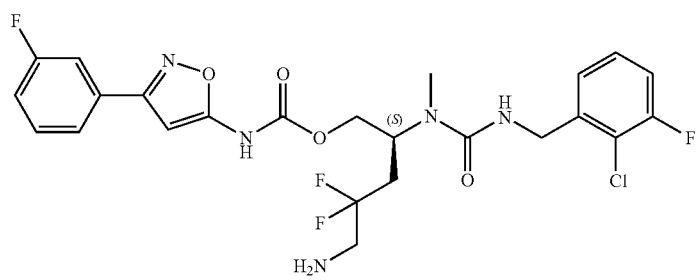

To a mixture of (S)-5-azido-2-(3-(2-chloro-3-fluorobenzyl)-1-methylureido)-4,4-difluoropentyl 3-(3-fluorophenyl)isoxazol-5-ylcarbamate (0.35 g, 0.6 mmol) in MeOH (2 mL), was added 10% Pd/C (0.1 g). The mixture was transferred to an autoclave reactor, charged with 10 psi of hydrogen, and stirred for 10 mM. The catalyst was filtered off and the filtrate was concentrated. The residue was purified on RP-HPLC using a mixture of acetonitrile and $H_2O$ with 0.1% TFA. The elute was washed with saturated $NaHCO_3$. The organic layer was concentrated to give (S)-5-amino-2-(3-(2-chloro-3-fluorobenzyl)-1-methylureido)-4,4-difluoropentyl 3-(3-fluorophenyl)isoxazol-5-ylcarbamate (0.18 g, 54%) as a white solid. LRMS (M+H$^+$) m/z 558.1.

Example 55

Screening assays were performed using a pyruvate kinase and lactate dehydrogenase-coupled ATPase assay containing the following reagents: Potassium PIPES (50 mM), $MgCl_2$ (3 mM), KCl (100 mM), ATP (0.15 mM), DTT (1 mM), BSA (0.1 mg/ml), NADH (0.5 mM), PEP (1.5 mM), pyruvate kinase (4 U/ml), lactate dehydrogenase (8 U/ml), and antifoam (50 ppm) (concentrations expressed are final assay concentrations). The pH was adjusted to 6.80 at 22° C. by addition of potassium hydroxide. Lead optimization assays were performed with a more sensitive pyruvate kinase/horseradish peroxidase/pyruvate oxidase-coupled ATPase assay containing the following reagents: Potassium PIPES (12 mM), $MgCl_2$ (2 mM), KCl (100 mM), ATP (0.15 mM), BSA (0.05 mg/ml), potassium phosphate (2 mM), amplex red (0.1 mM), PEP (0.1 mM), pyruvate kinase (4 U/ml), horseradish peroxidase (0.5 U/ml), pyruvate oxidase (0.5 U/ml), and antifoam (50 ppm) (concentrations expressed are final assay concentrations). The pH was adjusted to 7.00 at 22° C. by addition of potassium hydroxide.

The protein components specific to this assay are chicken gizzard smooth muscle myosin subfragment-1 that has been chemically crosslinked to either cardiac or skeletal actin using an excess of 1-Ethyl-3-[3-dimethylaminopropyl]carbodiimide hydrochloride and N-hydroxysuccinimide. The exact concentration of the crosslinked smooth muscle myosin in the assay is determined empirically, by titration to achieve a desired rate of ATP hydrolysis. The concentration varies between protein preparations due to variations in the fraction of active molecules in each preparation.

Compound dose response assays are performed by first preparing a dilution series of test compound, each with an assay mixture containing potassium PIPES, $MgCl_2$, KCl, ATP, BSA, potassium phosphate, amplex red, PEP, crosslinked smooth muscle actomyosin (subfragment-1), antifoam, and water. The assay is started by adding an equal volume of solution containing potassium Pipes, $MgCl_2$, KCl, BSA, potassium phosphate, pyruvate kinase, horseradish peroxidase, pyruvate oxidase, antifoam, and water. ATP hydrolysis is monitored by measuring the fluorescence of amplex red (excitation at 480 nm, emission at 615 nm). The resulting dose response curve is fit by the 4 parameter equation y=Bottom+((Top-Bottom)/(1+(($IC_{50}$/X)^Hill))). The $IC_{50}$ is defined as the concentration at which ATPase activity is midway between the top and bottom of the dose response curve.

Certain chemical entities described herein have an $IC_{50}$ less than 10 μM; for example, less than 1 μM.

Example 56

Using procedures similar to those described herein, the compounds in the following table were synthesized and tested.

| m/z M + H | ChemicalName |
|---|---|
| 438.1 | N-[(2-chlorophenyl)methyl](4-{[N-(1-ethyl(4-piperidyl))carbamoyloxy]methyl}(2H-3,4,5,6-tetrahydropyran-4-yl))carboxamide |
| 500.1 | N-[(2-chlorophenyl)methyl](4-{[N-(4-methyl-2-phenyl(1,3-thiazol-5-yl))carbamoyloxy]methyl}(2H-3,4,5,6-tetrahydropyran-4-yl))carboxamide |
| 465.1 | {1-(2-aminoacetyl)-4-[(N-(2-thienyl)carbamoyloxy)methyl](4-piperidyl)}-N-[(2-chlorophenyl)methyl]carboxamide |
| 479.0 M + H$^+$ − Boc | (tert-butoxy)-N-[2-(4-{N-[(2-chlorophenyl)methyl]carbamoyl}-4-{[N-(4-methyl(2-thienyl))carbamoyloxy]methyl}piperidyl)-2-oxoethyl]carboxamide |
| 377.0 | {[(2-chlorophenyl)methyl]amino}-N-methyl-N-{2-[N-(6-methyl(3-pyridyl))carbamoyloxy]ethyl}carboxamide |
| 397.0 | N-(4,5-dimethyl(1,3-thiazol-2-yl))[2-({[(2-chlorophenyl)methyl]amino}-N-methylcarbonylamino)ethoxy]carboxamide |
| 383.0 | [2-({[(2-chlorophenyl)methyl]amino}-N-methylcarbonylamino)ethoxy]-N-(5-methyl(1,3-thiazol-2-yl))carboxamide |
| 376.9 | [2-({[(2-chlorophenyl)methyl]amino}-N-methylcarbonylamino)ethoxy]-N-(5-methyl(2-pyridyl))carboxamide |
| 431.1 | {[(2-chlorophenyl)methyl]amino}-N-methyl-N-(2-{N-[6-(trifluoromethyl)(3-pyridyl)]carbamoyloxy}ethyl)carboxamide |
| 378.0 | {[(2-chlorophenyl)methyl]amino}-N-methyl-N-{2-[N-(5-methylpyrazin-2-yl)carbamoyloxy]ethyl}carboxamide |
| 433.0 | {[(2-chlorophenyl)methyl]amino}-N-methyl-N-{2-[N-(4-methylbenzothiazol-2-yl)carbamoyloxy]ethyl}carboxamide |
| 384.1 | {[(2-chlorophenyl)methyl]amino}-N-methyl-N-{2-[N-(5-methyl(1,3,4-thiadiazol-2-yl))carbamoyloxy]ethyl}carboxamide |
| 446.1 | {[(2-chlorophenyl)methyl]amino}-N-methyl-N-{2-[N-(5-phenyl(1,3,4-thiadiazol-2-yl))carbamoyloxy]ethyl}carboxamide |
| 398.1 | {[(2-chlorophenyl)methyl]amino}-N-{2-[N-(5-ethyl(1,3,4-thiadiazol-2-yl))carbamoyloxy]ethyl}-N-methylcarboxamide |
| 437.9 | {[(2-chlorophenyl)methyl]amino}-N-methyl-N-(2-{N-[5-(trifluoromethyl)(1,3,4-thiadiazol-2-yl)]carbamoyloxy}ethyl)carboxamide |
| 366.9 | {[(2-chlorophenyl)methyl]amino}-N-methyl-N-{2-[N-(5-methylisoxazol-3-yl)carbamoyloxy]ethyl}carboxamide |

-continued

| m/z M + H | ChemicalName |
|---|---|
| 367.2 | {[(2-chlorophenyl)methyl]amino}-N-methyl-N-{2-[N-(3-methylisoxazol-5-yl)carbamoyloxy]ethyl}carboxamide |
| 444.1 | N-{2-[N-(5-bromopyrimidin-2-yl)carbamoyloxy]ethyl}{[(2-chlorophenyl)methyl]amino}-N-methylcarboxamide |
| 443.9 | N-{2-[N-(5-bromopyrazin-2-yl)carbamoyloxy]ethyl}{[(2-chlorophenyl)methyl]amino}-N-methylcarboxamide |
| 388.2 | [2-({[(2-chlorophenyl)methyl]amino}-N-methylcarbonylamino)ethoxy]-N-(5-cyano(2-pyridyl))carboxamide |
| 431.2 | [2-({[(2-chlorophenyl)methyl]amino}-N-methylcarbonylamino)ethoxy]-N-[5-(trifluoromethyl)(2-pyridyl)]carboxamide |
| 381.0 | [2-({[(2-chlorophenyl)methyl]amino}-N-methylcarbonylamino)ethoxy]-N-(5-fluoro(2-pyridyl))carboxamide |
| 442.9 | N-(5-bromo(2-pyridyl))[2-({[(2-chlorophenyl)methyl]amino}-N-methylcarbonylamino)ethoxy]carboxamide |
| 377.1 | [2-({[(2-chlorophenyl)methyl]amino}-N-methylcarbonylamino)ethoxy]-N-(4-methyl(2-pyridyl))carboxamide |
| 363.1 | [2-({[(2-chlorophenyl)methyl]amino}-N-methylcarbonylamino)ethoxy]-N-(2-pyridyl)carboxamide |
| 439.0 | [2-({[(2-chlorophenyl)methyl]amino}-N-methylcarbonylamino)ethoxy]-N-(5-phenyl(2-pyridyl))carboxamide |
| 389.1 | [2-({[(2-chlorophenyl)methyl]amino}-N-methylcarbonylamino)ethoxy]-N-(5-vinyl(2-pyridyl))carboxamide |
| 391.0 | [2-({[(2-chlorophenyl)methyl]amino}-N-methylcarbonylamino)ethoxy]-N-(5-ethyl(2-pyridyl))carboxamide |
| 357.1 | N-(5-ethyl(2-pyridyl))(2-{N-methyl[benzylamino]carbonylamino}ethoxy)carboxamide |
| 419.1 | N-[2-(N-benzothiazol-2-ylcarbamoyloxy)ethyl]{[(2-chlorophenyl)methyl]amino}-N-methylcarboxamide |
| 433.1 | {[(2-chlorophenyl)methyl]amino}-N-methyl-N-{2-[N-(6-methylbenzothiazol-2-yl)carbamoyloxy]ethyl}carboxamide |
| 421.0 | methyl 6-{[2-({[(2-chlorophenyl)methyl]amino}-N-methylcarbonylamino)ethoxy]carbonylamino}pyridine-3-carboxylate |
| 428.2 | {[(2-chlorophenyl)methyl]amino}-N-methyl-N-{2-[N-(1-phenylpyrazol-3-yl)carbamoyloxy]ethyl}carboxamide |
| 430.1 | [2-({[(2-chlorophenyl)methyl]amino}-N-methylcarbonylamino)ethoxy]-N-(5-phenyl(1,3,4-oxadiazol-2-yl))carboxamide |
| 409.1 | N-[5-(tert-butyl)isoxazol-3-yl][2-({[(2-chlorophenyl)methyl]amino}-N-methylcarbonylamino)ethoxy]carboxamide |
| 403.1 | N-benzo[d]isoxazol-3-yl[2-({[(2-chlorophenyl)methyl]amino}-N-methylcarbonylamino)ethoxy]carboxamide |
| 402.1 | N-benzimidazol-2-yl[2-({[(2-chlorophenyl)methyl]amino}-N-methylcarbonylamino)ethoxy]carboxamide |
| 406.1 | 6-{[2-({[(2-chlorophenyl)methyl]amino}-N-methylcarbonylamino)ethoxy]carbonylamino}pyridine-3-carboxamide |
| 393.0 | {[(2-chlorophenyl)methyl]amino}-N-(2-{N-[5-(hydroxymethyl)(2-pyridyl)]carbamoyloxy}ethyl)-N-methylcarboxamide |
| 405.1 | N-{2-[N-(5-acetyl(2-pyridyl))carbamoyloxy]ethyl}{[(2-chlorophenyl)methyl]amino}-N-methylcarboxamide |
| 407.1 | {[(2-chlorophenyl)methyl]amino}-N-(2-{N-[5-(hydroxyethyl)(2-pyridyl)]carbamoyloxy}ethyl)-N-methylcarboxamide |
| 421.1 | {[(2-chlorophenyl)methyl]amino}-N-(2-{N-[5-(1-hydroxy-isopropyl)(2-pyridyl)]carbamoyloxy}ethyl)-N-methylcarboxamide |
| 413.0 | [2-({[(2-chlorophenyl)methyl]amino}-N-methylcarbonylamino)ethoxy]-N-(3-isoquinolyl)carboxamide |
| 413.2 | [2-({[(2-chlorophenyl)methyl]amino}-N-methylcarbonylamino)ethoxy]-N-(2-quinolyl)carboxamide |
| 575.0 | (1-(2-aminoacetyl)-4-{[N-(5-bromo(2-pyridyl))carbamoyloxy]methyl}(4-piperidyl))-N-[(2,3-dichlorophenyl)methyl]carboxamide |
| 413.1 | {[(2-chlorophenyl)methyl]amino}-N-methyl-N-[2-(N-(6-quinolyl)carbamoyloxy)ethyl]carboxamide |
| 419.2 | N-[2-(N-benzothiazol-6-ylcarbamoyloxy)ethyl]{[(2-chlorophenyl)methyl]amino}-N-methylcarboxamide |
| 510.2 | {1-(2-aminoacetyl)-4-[(N-(2-quinolyl)carbamoyloxy)methyl](4-piperidyl)}-N-[(2-chlorophenyl)methyl]carboxamide |
| 530.1 | (1-(2-aminoacetyl)-4-{[N-(4-methylbenzothiazol-2-yl)carbamoyloxy]methyl}(4-piperidyl))-N-[(2-chlorophenyl)methyl]carboxamide |
| 536.2 | (1-(2-aminoacetyl)-4-{[N-(5-phenyl(2-pyridyl))carbamoyloxy]methyl}(4-piperidyl))-N-[(2-chlorophenyl)methyl]carboxamide |
| 474.1 | (1-(2-aminoacetyl)-4-{[N-(5-methyl(2-pyridyl))carbamoyloxy]methyl}(4-piperidyl))-N-[(2-chlorophenyl)methyl]carboxamide |
| 543.1 | (1-(2-aminoacetyl)-4-{[N-(5-phenyl(1,3,4-thiadiazol-2-yl))carbamoyloxy]methyl}(4-piperidyl))-N-[(2-chlorophenyl)methyl]carboxamide |
| 510.1 | {1-(2-aminoacetyl)-4-[(N-(3-isoquinolyl)carbamoyloxy)methyl](4-piperidyl)}-N-[(2-chlorophenyl)methyl]carboxamide |

| m/z M + H | ChemicalName |
|---|---|
| 530.1 | (1-(2-aminoacetyl)-4-{[N-(6-methylbenzothiazol-2-yl)carbamoyloxy]methyl}(4-piperidyl))-N-[(2-chlorophenyl)methyl]carboxamide |
| 584.1 | [1-(2-aminoacetyl)-4-({N-[6-(trifluoromethyl)benzothiazol-2-yl]carbamoyloxy}methyl)(4-piperidyl)]-N-[(2-chlorophenyl)methyl]carboxamide |
| 449.0 | N-[2-(N-benzothiazol-2-ylcarbamoyloxy)ethyl]{[(2-chlorophenyl)methyl]amino}-N-(2-hydroxyethyl)carboxamide |
| 441.1 | [(2S)-2-({[(2-chlorophenyl)methyl]amino}-N-methylcarbonylamino)butoxy]-N-(3-isoquinolyl)carboxamide |
| 461.1 | [(2S)-2-({[(2-chlorophenyl)methyl]amino}-N-methylcarbonylamino)butoxy]-N-(6-methylbenzothiazol-2-yl)carboxamide |
| 414.1 | [2-({[(2-chlorophenyl)methyl]amino}-N-methylcarbonylamino)ethoxy]-N-quinoxalin-2-ylcarboxamide |
| 447.0 | N-(5,6-dimethylbenzothiazol-2-yl)[2-({[(2-chlorophenyl)methyl]amino}-N-methylcarbonylamino)ethoxy]carboxamide |
| 497.0 | [2-({[(2-chlorophenyl)methyl]amino}-N-methylcarbonylamino)ethoxy]-N-[6-(methylsulfonyl)benzothiazol-2-yl]carboxamide |
| 503.0 | [2-({[(2-chlorophenyl)methyl]amino}-N-methylcarbonylamino)ethoxy]-N-[6-(trifluoromethoxy)benzothiazol-2-yl]carboxamide |
| 486.9 | [2-({[(2-chlorophenyl)methyl]amino}-N-methylcarbonylamino)ethoxy]-N-[6-(trifluoromethyl)benzothiazol-2-yl]carboxamide |
| 491.0 | ethyl 2-{[2-({[(2-chlorophenyl)methyl]amino}-N-methylcarbonylamino)ethoxy]carbonylamino}benzothiazole-6-carboxylate |
| 449.0 | [2-({[(2-chlorophenyl)methyl]amino}-N-methylcarbonylamino)ethoxy]-N-(6-methoxybenzothiazol-2-yl)carboxamide |
| 449.0 | [2-({[(2-chlorophenyl)methyl]amino}-N-methylcarbonylamino)ethoxy]-N-(4-methoxybenzothiazol-2-yl)carboxamide |
| 487.9 | N-(5,6-dichlorobenzothiazol-2-yl)[2-({[(2-chlorophenyl)methyl]amino}-N-methylcarbonylamino)ethoxy]carboxamide |
| 420.1 | [2-({[(2-chlorophenyl)methyl]amino}-N-methylcarbonylamino)ethoxy]-N-(1,3-thiazolo[5,4-b]pyridin-2-yl)carboxamide |
| 462.1 | 2-{[2-({[(2-chlorophenyl)methyl]amino}-N-methylcarbonylamino)ethoxy]carbonylamino}benzothiazole-6-carboxamide |
| 447.1 | [2-({[(2-chlorophenyl)methyl]amino}-N-methylcarbonylamino)ethoxy]-N-(5-(3-pyridyl)(1,3,4-thiadiazol-2-yl))carboxamide |
| 447.1 | [2-({[(2-chlorophenyl)methyl]amino}-N-methylcarbonylamino)ethoxy]-N-(5-(4-pyridyl)(1,3,4-thiadiazol-2-yl))carboxamide |
| 455.1 | [(2S)-2-({[(2-chlorophenyl)methyl]amino}-N-methylcarbonylamino)-3-methylbutoxy]-N-(3-isoquinolyl)carboxamide |
| 475.1 | [(2S)-2-({[(2-chlorophenyl)methyl]amino}-N-methylcarbonylamino)-3-methylbutoxy]-N-(6-methylbenzothiazol-2-yl)carboxamide |
| 469.1 | [(2S)-2-({[(2-chlorophenyl)methyl]amino}-N-methylcarbonylamino)-4-methylpentyloxy]-N-(3-isoquinolyl)carboxamide |
| 489 | [(2S)-2-({[(2-chlorophenyl)methyl]amino}-N-methylcarbonylamino)-4-methylpentyloxy]-N-(6-methylbenzothiazol-2-yl)carboxamide |
| 512.1 | {[(2-chlorophenyl)methyl]amino}-N-[2-(3-diazo-3-azaprop-3-enyloxy)ethyl]-N-[2-(N-(3-isoquinolyl)carbamoyloxy)ethyl]carboxamide |
| 486.2 | N-[2-(2-aminoethoxy)ethyl]{[(2-chlorophenyl)methyl]amino}-N-[2-(N-(3-isoquinolyl)carbamoyloxy)ethyl]carboxamide |
| 528.2 | {[(2-chlorophenyl)methyl]amino}-N-[2-(N-(3-isoquinolyl)carbamoyloxy)ethyl]-N-{2-[2-(trimethylamino)ethoxy]ethyl}carboxamide |
| 423.1 | [2-({[(2-chlorophenyl)methyl]amino}-N-methylcarbonylamino)ethoxy]-N-(4,5,6,7-tetrahydrobenzothiazol-2-yl)carboxamide |
| 429.1 | [2-({[(2-chlorophenyl)methyl]amino}-N-methylcarbonylamino)ethoxy]-N-(4-hydroxy(2-quinolyl))carboxamide |
| 413.1 | [2-({[(2-chlorophenyl)methyl]amino}-N-methylcarbonylamino)ethoxy]-N-(3-quinolyl)carboxamide |
| 444.1 | [2-({[(2-chlorophenyl)methyl]amino}-N-methylcarbonylamino)ethoxy]-N-(6-methyl-4-oxo(3-hydroquinazolin-2-yl))carboxamide |
| 561.2 | phenylmethyl (3S)-3-({[(2-chlorophenyl)methyl]amino}-N-methylcarbonylamino)-4-(N-(3-isoquinolyl)carbamoyloxy)butanoate |
| 581.1 | phenylmethyl (3S)-3-({[(2-chlorophenyl)methyl]amino}-N-methylcarbonylamino)-4-[N-(6-methylbenzothiazol-2-yl)carbamoyloxy]butanoate |
| 457.1 | [(2S)-2-({[(2-chlorophenyl)methyl]amino}-N-methylcarbonylamino)-4-hydroxybutoxy]-N-(3-isoquinolyl)carboxamide |
| 485.1 | methyl (3S)-3-({[(2-chlorophenyl)methyl]amino}-N-methylcarbonylamino)-4-(N-(3-isoquinolyl)carbamoyloxy)butanoate |
| 488.2 | {[(2-chlorophenyl)methyl]amino}-N-[2-(2-hydroxyethoxy)ethyl]-N-[2-(N-(3-isoquinolyl)carbamoyloxy)ethyl]carboxamide |

| m/z M + H | ChemicalName |
|---|---|
| 514.2 | N-{2-[2-(dimethylamino)ethoxy]ethyl}{[(2-chlorophenyl)methyl]amino}-N-[2-(N-(3-isoquinolyl)carbamoyloxy)ethyl]carboxamide |
| 500.2 | {[(2-chlorophenyl)methyl]amino}-N-[2-(N-(3-isoquinolyl)carbamoyloxy)ethyl]-N-{2-[2-(methylamino)ethoxy]ethyl}carboxamide |
| 411.2 | 4-({[(2-chlorophenyl)methyl]amino}-N-methylcarbonylamino)-N-(3-isoquinolyl)butanamide |
| 397.1 | 3-({[(2-chlorophenyl)methyl]amino}-N-methylcarbonylamino)-N-(3-isoquinolyl)propanamide |
| 575.2 | phenylmethyl (4S)-4-({[(2-chlorophenyl)methyl]amino}-N-methylcarbonylamino)-5-(N-(3-isoquinolyl)carbamoyloxy)pentanoate |
| 499.1 | methyl (4S)-4-({[(2-chlorophenyl)methyl]amino}-N-methylcarbonylamino)-5-(N-(3-isoquinolyl)carbamoyloxy)pentanoate |
| 427.1 | [(2R)-2-({[(2-chlorophenyl)methyl]amino}-N-methylcarbonylamino)propoxy]-N-(3-isoquinolyl)carboxamide |
| 427.1 | {[(2-chlorophenyl)methyl]methylamino}-N-[2-(N-(3-isoquinolyl)carbamoyloxy)ethyl]-N-methylcarboxamide |
| 472.2 | [2-(N-((2R)-2-amino-3-hydroxypropyl){[(2-chlorophenyl)methyl]amino}carbonylamino)ethoxy]-N-(3-isoquinolyl)carboxamide |
| 427.1 | [(2S)-2-({[(2-chlorophenyl)methyl]amino}-N-methylcarbonylamino)propoxy]-N-(3-isoquinolyl)carboxamide |
| 471.0 | [(2S)-2-({[(2-chlorophenyl)methyl]amino}-N-methylcarbonylamino)-5-hydroxypentyloxy]-N-(3-isoquinolyl)carboxamide |
| 433.1 | N-{(1S)-2-hydroxy-1-[(N-(3-isoquinolyl)carbamoyloxy)methyl]ethyl}{[(2-chlorophenyl)methyl]amino}-N-methylcarboxamide |
| 421.0 | N-{(1S)-1-[(N-(3-isoquinolyl)carbamoyloxy)methyl]propyl}-N-methyl{[(2-methylphenyl)methyl]amino}carboxamide |
| 403.0 | N-benzoxazol-2-yl[2-({[(2-chlorophenyl)methyl]amino}-N-methylcarbonylamino)ethoxy]carboxamide |
| 455.0 | N-(5,6-difluorobenzothiazol-2-yl)[2-({[(2-chlorophenyl)methyl]amino}-N-methylcarbonylamino)ethoxy]carboxamide |
| 513.1 | methyl (5S)-5-({[(2-chlorophenyl)methyl]amino}-N-methylcarbonylamino)-6-(N-(3-isoquinolyl)carbamoyloxy)hexanoate |
| 499.1 | (5S)-5-({[(2-chlorophenyl)methyl]amino}-N-methylcarbonylamino)-6-(N-(3-isoquinolyl)carbamoyloxy)hexanoic acid |
| 485.2 | N-{(1S)-5-hydroxy-1-[(N-(3-isoquinolyl)carbamoyloxy)methyl]pentyl}{[(2-chlorophenyl)methyl]amino}-N-methylcarboxamide |
| 510.2 | N-{(1S)-6-diazo-1-[(N-(3-isoquinolyl)carbamoyloxy)methyl]-6-azahex-6-enyl}{[(2-chlorophenyl)methyl]amino}-N-methylcarboxamide |
| 484.2 | N-{(1S)-5-amino-1-[(N-(3-isoquinolyl)carbamoyloxy)methyl]pentyl}{[(2-chlorophenyl)methyl]amino}-N-methylcarboxamide |
| 533.2 | N-{(1S)-2-(N-(3-isoquinolyl)carbamoyloxy)-1-[(phenylmethoxy)methyl]ethyl}{[(2-chlorophenyl)methyl]amino}-N-methylcarboxamide |
| 499.2 | N-{(1S)-2-(N-(3-isoquinolyl)carbamoyloxy)-1-[(phenylmethoxy)methyl]ethyl}-N-methyl[benzylamino]carboxamide |
| 471.2 | (3S)-3-({[(2-chlorophenyl)methyl]amino}-N-methylcarbonylamino)-4-(N-(3-isoquinolyl)carbamoyloxy)butanoic acid |
| 485.2 | [(2R)-2-({[(2-chlorophenyl)methyl]amino}-N-methylcarbonylamino)-6-hydroxyhexyloxy]-N-(3-isoquinolyl)carboxamide |
| 485.2 | N-{(1S)-3-hydroxy-1-[(N-(3-isoquinolyl)carbamoyloxy)methyl]-3-methylbutyl}{[(2-chlorophenyl)methyl]amino}-N-methylcarboxamide |
| 514.1 | (3S)-3-({[(2-chlorophenyl)methyl]amino}-N-methylcarbonylamino)-4-(N-(3-isoquinolyl)carbamoyloxy)-N-methoxy-N-methylbutanamide |
| 526.2 | N-{(1S)-1-[(N-(3-isoquinolyl)carbamoyloxy)methyl]-3-morpholin-4-ylpropyl}{[(2-chlorophenyl)methyl]amino}-N-methylcarboxamide |
| 513.2 | N-{(1S)-5-hydroxy-1-[(N-(3-isoquinolyl)carbamoyloxy)methyl]-5-methylhexyl}{[(2-chlorophenyl)methyl]amino}-N-methylcarboxamide |
| 497.2 | N-{(1S)-5-hydroxy-1-[(N-(3-isoquinolyl)carbamoyloxy)methyl]-5-methylhexyl}{[(2-fluorophenyl)methyl]amino}-N-methylcarboxamide |
| 539.2 | N-{(1S)-1-[(N-(3-isoquinolyl)carbamoyloxy)methyl]-3-(4-methylpiperazinyl)propyl}{[(2-chlorophenyl)methyl]amino}-N-methylcarboxamide |
| 567.3 | N-{(1S)-3-(4-acetylpiperazinyl)-1-[(N-(3-isoquinolyl)carbamoyloxy)methyl]propyl}{[(2-chlorophenyl)methyl]amino}-N-methylcarboxamide |
| 597.3 | ethyl 4-[(3S)-3-({[(2-chlorophenyl)methyl]amino}-N-methylcarbonylamino)-4-(N-(3-isoquinolyl)carbamoyloxy)butyl]piperazinecarboxylate |
| 603.3 | N-{(1S)-1-[(N-(3-isoquinolyl)carbamoyloxy)methyl]-3-[4-(methylsulfonyl)piperazinyl]propyl}{[(2-chlorophenyl)methyl]amino}-N-methylcarboxamide |

-continued

| m/z M + H | ChemicalName |
|---|---|
| 531.2 | methyl (5S)-5-({[(2-chloro-4-fluorophenyl)methyl]amino}-N-methylcarbonylamino)-6-(N-(3-isoquinolyl)carbamoyloxy)hexanoate |
| 531.2 | methyl (5S)-5-({[(2-chloro-3-fluorophenyl)methyl]amino}-N-methylcarbonylamino)-6-(N-(3-isoquinolyl)carbamoyloxy)hexanoate |
| 471.2 | N-{(1S,3S)-3-hydroxy-1-[(N-(3-isoquinolyl)carbamoyloxy)methyl]butyl}{[(2-chlorophenyl)methyl]amino}-N-methylcarboxamide |
| 471.2 | N-{(1S,3R)-3-hydroxy-1-[(N-(3-isoquinolyl)carbamoyloxy)methyl]butyl}{[(2-chlorophenyl)methyl]amino}-N-methylcarboxamide |
| 499.3 | N-{(1S)-4-hydroxy-1-[(N-(3-isoquinolyl)carbamoyloxy)methyl]-4-methylpentyl}{[(2-chlorophenyl)methyl]amino}-N-methylcarboxamide |
| 503.5 | N-{(1S)-5-hydroxy-1-[(N-(3-isoquinolyl)carbamoyloxy)methyl]pentyl}{[(2-chloro-4-fluorophenyl)methyl]amino}-N-methylcarboxamide |
| 531.3 | N-{(1S)-5-hydroxy-1-[(N-(3-isoquinolyl)carbamoyloxy)methyl]-5-methylhexyl}{[(2-chloro-4-fluorophenyl)methyl]amino}-N-methylcarboxamide |
| 503.2 | N-{(1S)-5-hydroxy-1-[(N-(3-isoquinolyl)carbamoyloxy)methyl]pentyl}{[(2-chloro-3-fluorophenyl)methyl]amino}-N-methylcarboxamide |
| 470.2 | [(2S)-5-amino-2-({[(2-chlorophenyl)methyl]amino}-N-methylcarbonylamino)pentyloxy]-N-(3-isoquinolyl)carboxamide |
| 515.2 | methyl (5S)-5-({[(2,3-difluorophenyl)methyl]amino}-N-methylcarbonylamino)-6-(N-(3-isoquinolyl)carbamoyloxy)hexanoate |
| 547.2 | methyl (5S)-5-({[(2,3-dichlorophenyl)methyl]amino}-N-methylcarbonylamino)-6-(N-(3-isoquinolyl)carbamoyloxy)hexanoate |
| 531.2 | methyl (5S)-5-({[(3-chloro-2-fluorophenyl)methyl]amino}-N-methylcarbonylamino)-6-(N-(3-isoquinolyl)carbamoyloxy)hexanoate |
| 487.2 | N-{(1S)-5-hydroxy-1-[(N-(3-isoquinolyl)carbamoyloxy)methyl]pentyl}{[(2,3-difluorophenyl)methyl]amino}-N-methylcarboxamide |
| 485.2 | N-{(1S)-4-hydroxy-1-[(N-(3-isoquinolyl)carbamoyloxy)methyl]pentyl}{[(2-chlorophenyl)methyl]amino}-N-methylcarboxamide |
| 542.3 | (5S)-5-({[(2-chlorophenyl)methyl]amino}-N-methylcarbonylamino)-6-(N-(3-isoquinolyl)carbamoyloxy)-N-methoxy-N-methylhexanamide |
| 497.2 | N-{(1S)-1-[(N-(3-isoquinolyl)carbamoyloxy)methyl]-5-oxohexyl}{[(2-chlorophenyl)methyl]amino}-N-methylcarboxamide |
| 499.2 | N-{(1S)-5-hydroxy-1-[(N-(3-isoquinolyl)carbamoyloxy)methyl]hexyl}{[(2-chlorophenyl)methyl]amino}-N-methylcarboxamide |
| 519.2 | N-{(1S)-5-hydroxy-1-[(N-(3-isoquinolyl)carbamoyloxy)methyl]pentyl}{[(2,3-dichlorophenyl)methyl]amino}-N-methylcarboxamide |
| 531.2 | N-{(1S)-5-hydroxy-1-[(N-(3-isoquinolyl)carbamoyloxy)methyl]-5-methylhexyl}{[(2-chloro-3-fluorophenyl)methyl]amino}-N-methylcarboxamide |
| 547.2 | N-{(1S)-5-hydroxy-1-[(N-(3-isoquinolyl)carbamoyloxy)methyl]-5-methylhexyl}{[(2,3-dichlorophenyl)methyl]amino}-N-methylcarboxamide |
| 515.2 | N-{(1S)-5-hydroxy-1-[(N-(3-isoquinolyl)carbamoyloxy)methyl]-5-methylhexyl}{[(2,3-difluorophenyl)methyl]amino}-N-methylcarboxamide |
| 531.2 | N-{(1S)-5-hydroxy-1-[(N-(3-isoquinolyl)carbamoyloxy)methyl]-5-methylhexyl}{[(3-chloro-2-fluorophenyl)methyl]amino}-N-methylcarboxamide |
| 515.2 | N-{(1S)-5-hydroxy-1-[(N-(3-isoquinolyl)carbamoyloxy)methyl]-5-methylhexyl}{[(2,4-difluorophenyl)methyl]amino}-N-methylcarboxamide |
| 547.2 | N-{(1S)-5-hydroxy-1-[(N-(3-isoquinolyl)carbamoyloxy)methyl]-5-methylhexyl}{[(2,4-dichlorophenyl)methyl]amino}-N-methylcarboxamide |
| 527.2 | [(2S)-2-({[(2-chlorophenyl)methyl]amino}-N-methylcarbonylamino)-4-hydroxy-4-methylpentyloxy]-N-(5,6-difluorobenzothiazol-2-yl)carboxamide |
| 503.2 | N-{(1S)-3-hydroxy-1-[(N-(3-isoquinolyl)carbamoyloxy)methyl]-3-methylbutyl}{[(2-chloro-4-fluorophenyl)methyl]amino}-N-methylcarboxamide |
| 513.1 | (3S)-4-[N-(5,6-difluorobenzothiazol-2-yl)carbamoyloxy]-3-({[(2-chlorophenyl)methyl]amino}-N-methylcarbonylamino)butanoic acid |
| 527.2 | methyl (3S)-4-[N-(5,6-difluorobenzothiazol-2-yl)carbamoyloxy]-3-({[(2-chlorophenyl)methyl]amino}-N-methylcarbonylamino)butanoate |
| 526.2 | N-[(5S)-5-({[(2-chlorophenyl)methyl]amino}-N-methylcarbonylamino)-6-(N-(3-isoquinolyl)carbamoyloxy)hexyl]acetamide |

-continued

| m/z M + H | ChemicalName |
|---|---|
| 402.0 | {[(2-chlorophenyl)methyl]amino}-N-[2-(N-(4-hydroimidazo[1,2-a]pyridin-2-yl)carbamoyloxy)ethyl]-N-methylcarboxamide |
| 545.2 | N-((1S)-1-{[N-(5,6-difluorobenzothiazol-2-yl)carbamoyloxy]methyl}-3-hydroxy-3-methylbutyl){[(2-chloro-4-fluorophenyl)methyl]amino}-N-methylcarboxamide |
| 402.0 | [2-({[(2-chlorophenyl)methyl]amino}-N-methylcarbonylamino)ethoxy]-N-(8-hydropyrazolo[1,5-a]pyridin-2-yl)carboxamide |
| 620.2 | N-[(5S)-5-({[(2-chlorophenyl)methyl]amino}-N-methylcarbonylamino)-6-(N-(3-isoquinolyl)carbamoyloxy)hexyl]-2-diazo-3,3,3-trifluoropropanamide |
| 545.2 | N-((1S)-1-{[N-(5,6-difluorobenzothiazol-2-yl)carbamoyloxy]methyl}-3-hydroxy-3-methylbutyl){[(2-chloro-3-fluorophenyl)methyl]amino}-N-methylcarboxamide |
| 545.2 | N-((1S)-1-{[N-(5,6-difluorobenzothiazol-2-yl)carbamoyloxy]methyl}-3-hydroxy-3-methylbutyl){[(3-chloro-2-fluorophenyl)methyl]amino}-N-methylcarboxamide |
| 471.2 | N-{(1R)-2-hydroxy-1-[(N-(3-isoquinolyl)carbamoyloxy)methyl]-2-methylpropyl}{[(2-chlorophenyl)methyl]amino}-N-methylcarboxamide |
| 471.2 | methyl (2R)-2-({[(2-chlorophenyl)methyl]amino}-N-methylcarbonylamino)-3-(N-(3-isoquinolyl)carbamoyloxy)propanoate |
| 522.1 | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-methylcarboxamide |
| 522.1 | N-((1S)-1-{[N-(6-fluoro(3-isoquinolyl))carbamoyloxy]methyl}-3-hydroxy-3-methylbutyl){[(2-chloro-3-fluorophenyl)methyl]amino}-N-methylcarboxamide |
| 503.2 | N-((1S)-1-{[N-(6-fluoro(3-isoquinolyl))carbamoyloxy]methyl}-3-hydroxy-3-methylbutyl){[(2-chlorophenyl)methyl]amino}-N-methylcarboxamide |
| 503.1 | N-{(1S)-3-hydroxy-1-[(N-(3-isoquinolyl)carbamoyloxy)methyl]-3-methylbutyl}{[(2-chloro-3-fluorophenyl)methyl]amino}-N-methylcarboxamide |
| 402.1 | [2-({[(2-chlorophenyl)methyl]amino}-N-methylcarbonylamino)ethoxy]-N-(8-hydropyrrolo[1,2-e]pyrimidin-3-yl)carboxamide |
| 543.1 | N-{(1S)-2-[N-(6-fluoro(3-isoquinolyl))carbamoyloxy]-1-[(3-oxopiperazinyl)methyl]ethyl}{[(2-chlorophenyl)methyl]amino}-N-methylcarboxamide |
| 543.2 | N-{(1S)-2-[N-(6-fluoro(3-isoquinolyl))carbamoyloxy]-1-[(4-methylpiperazinyl)methyl]ethyl}{[(2-chlorophenyl)methyl]amino}-N-methylcarboxamide |
| 512.2 | N-[(1S)-2-(N-(3-isoquinolyl)carbamoyloxy)-1-(morpholin-4-ylmethyl)ethyl]{[(2-chlorophenyl)methyl]amino}-N-methylcarboxamide |
| 557.2 | [(2S)-2-({[(2-chlorophenyl)methyl]amino}-N-methylcarbonylamino)-3-(4-methyl-3-oxopiperazinyl)propoxy]-N-(6-fluoro(3-isoquinolyl))carboxamide |
| 517.2 | [(2S)-2-({[(2-chlorophenyl)methyl]amino}-N-methylcarbonylamino)-4-hydroxy-3,4-dimethylpentyloxy]-N-(6-fluoro(3-isoquinolyl))carboxamide |
| 517.2 | [(2S)-2-({[(2-chlorophenyl)methyl]amino}-N-methylcarbonylamino)-4-hydroxy-3,4-dimethylpentyloxy]-N-(6-fluoro(3-isoquinolyl))carboxamide |
| 506.2 | N-{(1S)-1-[(dimethylamino)methyl]-2-[N-(6-fluoro(3-isoquinolyl))carbamoyloxy]ethyl}{[(2-chloro-3-fluorophenyl)methyl]amino}-N-methylcarboxamide |
| 475.0 | [((2S)-1-{N-[(2-chloro-4-fluorophenyl)methyl]carbamoyl}pyrrolidin-2-yl)methoxy]-N-(6-fluoro(3-isoquinolyl))carboxamide |
| 521.2 | [(2S)-2-({[(2-chloro-3-fluorophenyl)methyl]amino}-N-methylcarbonylamino)-4-hydroxy-4-methylpentyloxy]-N-(5-fluoro(3-isoquinolyl))carboxamide |
| 521.2 | [(2S)-2-({[(2-chloro-4-fluorophenyl)methyl]amino}-N-methylcarbonylamino)-4-hydroxy-4-methylpentyloxy]-N-(5-fluoro(3-isoquinolyl))carboxamide |
| 503.2 | [(2S)-2-({[(2-chlorophenyl)methyl]amino}-N-methylcarbonylamino)-4-hydroxy-4-methylpentyloxy]-N-(5-fluoro(3-isoquinolyl))carboxamide |
| 553.2 | N-{(1S)-1-[(N-(3-isoquinolyl)carbamoyloxy)methyl]-3-(4-methyl-3-oxopiperazinyl)propyl}{[(2-chlorophenyl)methyl]amino}-N-methylcarboxamide |
| 539.2 | N-{(1S)-1-[(N-(3-isoquinolyl)carbamoyloxy)methyl]-3-(3-oxopiperazinyl)propyl}{[(2-chlorophenyl)methyl]amino}-N-methylcarboxamide |
| 521.2 | [(2S)-2-({[(2-chloro-3-fluorophenyl)methyl]amino}-N-methylcarbonylamino)-4-hydroxy-4-methylpentyloxy]-N-(7-fluoro(3-isoquinolyl))carboxamide |
| 521.2 | [(2S)-2-({[(2-chloro-4-fluorophenyl)methyl]amino}-N-methylcarbonylamino)-4-hydroxy-4-methylpentyloxy]-N-(7-fluoro(3-isoquinolyl))carboxamide |
| 503.2 | [(2S)-2-({[(2-chlorophenyl)methyl]amino}-N-methylcarbonylamino)-4-hydroxy-4-methylpentyloxy]-N-(7-fluoro(3-isoquinolyl))carboxamide |

-continued

| m/z M + H | ChemicalName |
|---|---|
| 463.2 | {[(2-chloro-3-fluorophenyl)methyl]amino}-N-ethyl-N-{2-[N-(6-fluoro(3-isoquinolyl))carbamoyloxy]ethyl}carboxamide |
| 477.0 | {[(2-chloro-3-fluorophenyl)methyl]amino}-N-{2-[N-(6-fluoro(3-isoquinolyl))carbamoyloxy]ethyl}-N-(methylethyl)carboxamide |
| 463.2 | {[(2-chloro-4-fluorophenyl)methyl]amino}-N-ethyl-N-{2-[N-(6-fluoro(3-isoquinolyl))carbamoyloxy]ethyl}carboxamide |
| 477.0 | {[(2-chloro-4-fluorophenyl)methyl]amino}-N-{2-[N-(6-fluoro(3-isoquinolyl))carbamoyloxy]ethyl}-N-(methylethyl)carboxamide |
| 549.2 | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-(methylethyl)carboxamide |
| 531.2 | N-((1S)-1-{[N-(6-fluoro(3-isoquinolyl))carbamoyloxy]methyl}-3-hydroxy-3-methylbutyl){[(2-chlorophenyl)methyl]amino}-N-(methylethyl)carboxamide |
| 475.0 | [((2S)-1-{N-[(2-chloro-4-fluorophenyl)methyl]carbamoyl}pyrrolidin-2-yl)methoxy]-N-(8-hydroxypyrrolo[1,2-e]pyrimidin-3-yl)carboxamide |
| 416.0 | [2-({[(2-chlorophenyl)methyl]amino}-N-methylcarbonylamino)ethoxy]-N-pyridino[4,3-d]pyridin-3-ylcarboxamide |
| 475.0 | [((2S)-1-{N-[(2-chloro-3-fluorophenyl)methyl]carbamoyl}pyrrolidin-2-yl)methoxy]-N-(6-fluoro(3-isoquinolyl))carboxamide |
| 507.1 | {[(2-chloro-3-fluorophenyl)methyl]amino}-N-{2-[N-(6-fluoro(3-isoquinolyl))carbamoyloxy]ethyl}-N-(2-hydroxy-2-methylpropyl)carboxamide |
| 517.1 | {[(2-chloro-3-fluorophenyl)methyl]amino}-N-{2-[N-(6-fluoro(3-isoquinolyl))carbamoyloxy]ethyl}-N-(2,2,2-trifluoroethyl)carboxamide |
| 461.0 | {[(2-chloro-3-methoxyphenyl)methyl]amino}-N-{2-[N-(6-fluoro(3-isoquinolyl))carbamoyloxy]ethyl}-N-methylcarboxamide |
| 517.1 | N-((1S)-1-{[N-(6-fluoro(3-isoquinolyl))carbamoyloxy]methyl}-3-hydroxy-3-methylbutyl){[(2-chlorophenyl)methyl]amino}-N-ethylcarboxamide |
| 535.2 | N-((1S)-1-{[N-(6-fluoro(3-isoquinolyl))carbamoyloxy]methyl}-3-hydroxy-3-methylbutyl){[(2-chloro-4-fluorophenyl)methyl]amino}-N-ethylcarboxamide |
| 596.2 | N-((1S)-4-amino-1-{[N-(6-fluoro(3-isoquinolyl))carbamoyloxy]methyl}butyl){[(2-chloro-4-fluorophenyl)methyl]amino}-N-methylcarboxamide |
| 533.2 | N-((1S)-4-amino-1-{[N-(6-fluoro(3-isoquinolyl))carbamoyloxy]methyl}butyl){[(2-bromophenyl)methyl]amino}-N-methylcarboxamide |
| 557.2 | N-(2-aminoethyl)(4-{N-[(2-chlorophenyl)methyl]carbamoyl}-4-{[N-(6-fluoro(3-isoquinolyl))carbamoyloxy]methyl}piperidyl)carboxamide |
| 645.3 | (tert-butoxy)-N-[2-(4-{N-[(2-bromophenyl)methyl]carbamoyl}-4-{[N-(4-ethylphenyl)carbamoyloxy]methyl}piperidyl)-2-oxoethyl]-N-methylcarboxamide |
| 545.2 | [(4-{N-[(2-bromophenyl)methyl]carbamoyl}-1-[2-(methylamino)acetyl](4-piperidyl))methoxy]-N-(4-ethylphenyl)carboxamide |
| 499.0 | N-(2,2-difluoroethyl){[(2-chloro-3-fluorophenyl)methyl]amino}-N-{2-[N-(6-fluoro(3-isoquinolyl))carbamoyloxy]ethyl}carboxamide |
| 531.0 | {[(2-chloro-3-fluorophenyl)methyl]amino}-N-{2-[N-(6-fluoro(3-isoquinolyl))carbamoyloxy]ethyl}-N-(3,3,3-trifluoropropyl)carboxamide |
| MS: 491.0 (M + 1) | [((2S,4R)-1-{N-[(2-chloro-3-fluorophenyl)methyl]carbamoyl}-4-hydroxypyrrolidin-2-yl)methoxy]-N-(6-fluoro(3-isoquinolyl))carboxamide |
| 458.0 | [((2S)-1-{N-[(2-chloro-3-fluorophenyl)methyl]carbamoyl}pyrrolidin-2-yl)methoxy]-N-pyridino[4,3-d]pyridin-3-ylcarboxamide |
| 447.1 | {[(2-chloro-3-hydroxyphenyl)methyl]amino}-N-{2-[N-(6-fluoro(3-isoquinolyl))carbamoyloxy]ethyl}-N-methylcarboxamide |
| 474.0 | (2-{1-[(2-chloro-4-fluorophenyl)methyl]-3-methyl-2-oxopyrrolidin-3-yl}ethoxy)-N-(6-fluoro(3-isoquinolyl))carboxamide |
| 506.1 | N-((1S)-4-amino-1-{[N-(6-fluoro(3-isoquinolyl))carbamoyloxy]methyl}butyl){[(2-chloro-3-fluorophenyl)methyl]amino}-N-methylcarboxamide |
| 491.1 | ((5S,3R)-1-{N-[(2-chloro-3-fluorophenyl)methyl]carbamoyl}-5-(hydroxymethyl)pyrrolidin-3-yloxy)-N-(6-fluoro(3-isoquinolyl))carboxamide |
| 474.1 | {[((2S)-1-{N-[(2-chloro-3-fluorophenyl)methyl]carbamoyl}pyrrolidin-2-yl)methyl]amino}-N-(6-fluoro(3-isoquinolyl))carboxamide |
| 489.0 | methyl 2-chloro-3-{[(N-{2-[N-(6-fluoro(3-isoquinolyl))carbamoyloxy]ethyl}-N-methylcarbamoyl)amino]methyl}benzoate |
| 491.2 | 4-amino-N-[(2-chloro-4-fluorophenyl)methyl]-2-{2-[N-(6-fluoro(3-isoquinolyl))carbamoyloxy]ethyl}-2-methylbutanamide |
| 488.2 | N-((1S)-4-amino-1-{[N-(6-fluoro(3-isoquinolyl))carbamoyloxy]methyl}butyl){[(2-chlorophenyl)methyl]amino}-N-methylcarboxamide |

| m/z M + H | ChemicalName |
|---|---|
| 552.2 | N-((1S)-4-[(2,2-difluoroethyl)amino]-1-{[N-(6-fluoro(3-isoquinolyl))carbamoyloxy]methyl}butyl){[(2-chlorophenyl)methyl]amino}-N-methylcarboxamide |
| 490.0 | [((2S,4R)-4-amino-1-{N-[(2-chloro-3-fluorophenyl)methyl]carbamoyl}pyrrolidin-2-yl)methoxy]-N-(6-fluoro(3-isoquinolyl))carboxamide |
| 647.1 | N-((5S,3R)-1-{N-[(2-chloro-3-fluorophenyl)methyl]carbamoyl}-5-{[N-(6-fluoro(3-isoquinolyl))carbamoyloxy]methyl}pyrrolidin-3-yl)-2-[(tert-butoxy)carbonylamino]acetamide |
| 547.0 | N-((5S,3R)-1-{N-[(2-chloro-3-fluorophenyl)methyl]carbamoyl}-5-{[N-(6-fluoro(3-isoquinolyl))carbamoyloxy]methyl}pyrrolidin-3-yl)-2-aminoacetamide |
| 461.0 | [((2S)-1-{N-[(2-chloro-3-fluorophenyl)methyl]carbamoyl}azetidin-2-yl)methoxy]-N-(6-fluoro(3-isoquinolyl))carboxamide |
| 489.2 | N-((1S)-1-{[N-(6-fluoro(3-isoquinolyl))carbamoyloxy]methyl}but-3-enyl){[(2-chloro-3-fluorophenyl)methyl]amino}-N-methylcarboxamide |
| 523.2 | N-((1S)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 606.2 | N-((1S)-4-[(tert-butoxy)carbonylamino]-1-{[N-(6-fluoro(3-isoquinolyl))carbamoyloxy]methyl}butyl){[(2-chloro-3-fluorophenyl)methyl]amino}-N-methylcarboxamide |
| 488.1 | N-{(1S)-4-amino-1-[(N-(3-isoquinolyl)carbamoyloxy)methyl]butyl}{[(2-chloro-3-fluorophenyl)methyl]amino}-N-methylcarboxamide |
| 488.2 | N-{(1S)-4-amino-1-[(N-(3-isoquinolyl)carbamoyloxy)methyl]butyl}{[(2-chloro-4-fluorophenyl)methyl]amino}-N-methylcarboxamide |
| 504.2 | N-{(1S)-4-amino-1-[(N-(3-isoquinolyl)carbamoyloxy)methyl]butyl}{[(2,3-dichlorophenyl)methyl]amino}-N-methylcarboxamide |
| 461.2 | ({[2-chloro-3-(hydroxymethyl)phenyl]methyl}amino)-N-{2-[N-(6-fluoro(3-isoquinolyl))carbamoyloxy]ethyl}-N-methylcarboxamide |
| 462.2 | N-[(2-chloro-3-fluorophenyl)methyl]-4-[N-(6-fluoro(3-isoquinolyl))carbamoyloxy]-2,2-dimethylbutanamide |
| 488.2 | N-[(2-chloro-3-fluorophenyl)methyl]-2-{2-[N-(6-fluoro(3-isoquinolyl))carbamoyloxy]ethyl}-2-methylpent-4-enamide |
| 522.2 | N-[(2-chloro-3-fluorophenyl)methyl]-2-{2-[N-(6-fluoro(3-isoquinolyl))carbamoyloxy]ethyl}-4,5-dihydroxy-2-methylpentanamide |
| 506.2 | N-[(2-chloro-3-fluorophenyl)methyl]-2-{2-[N-(6-fluoro(3-isoquinolyl))carbamoyloxy]ethyl}-5-hydroxy-2-methylpentanamide |
| 465.1 | {[(2,5-dichlorophenyl)methyl]amino}-N-{2-[N-(6-fluoro(3-isoquinolyl))carbamoyloxy]ethyl}-N-methylcarboxamide |
| 449.2 | {[(5-chloro-2-fluorophenyl)methyl]amino}-N-{2-[N-(6-fluoro(3-isoquinolyl))carbamoyloxy]ethyl}-N-methylcarboxamide |
| 535.2 | methyl (4S)-4-({[(2-chloro-3-fluorophenyl)methyl]amino}-N-methylcarbonylamino)-5-[N-(6-fluoro(3-isoquinolyl))carbamoyloxy]pentanoate |
| 549.2 | ethyl (4S)-4-({[(2-chloro-3-fluorophenyl)methyl]amino}-N-methylcarbonylamino)-5-[N-(6-fluoro(3-isoquinolyl))carbamoyloxy]pentanoate |
| 564.2 | (4S)-4-({[(2-chloro-3-fluorophenyl)methyl]amino}-N-methylcarbonylamino)-5-[N-(6-fluoro(3-isoquinolyl))carbamoyloxy]-N-methoxy-N-methylpentanamide |
| 552.2 | N-((1S)-1-{[N-(6-fluoro(3-isoquinolyl))carbamoyloxy]methyl}-4-[(2-fluoroethyl)amino]butyl){[(2-chloro-3-fluorophenyl)methyl]amino}-N-methylcarboxamide |
| 570.2 | N-((1S)-4-[(2,2-difluoroethyl)amino]-1-{[N-(6-fluoro(3-isoquinolyl))carbamoyloxy]methyl}butyl){[(2-chloro-3-fluorophenyl)methyl]amino}-N-methylcarboxamide |
| 588.2 | N-((1S)-1-{[N-(6-fluoro(3-isoquinolyl))carbamoyloxy]methyl}-4-[(2,2,2-trifluoroethyl)amino]butyl){[(2-chloro-3-fluorophenyl)methyl]amino}-N-methylcarboxamide |
| 582.2 | N-((1S)-4-(3,3-difluoroazetidinyl)-1-{[N-(6-fluoro(3-isoquinolyl))carbamoyloxy]methyl}butyl){[(2-chloro-3-fluorophenyl)methyl]amino}-N-methylcarboxamide |
| 596.2 | N-((1S)-4-(3,3-difluoropyrrolidinyl)-1-{[N-(6-fluoro(3-isoquinolyl))carbamoyloxy]methyl}butyl){[(2-chloro-3-fluorophenyl)methyl]amino}-N-methylcarboxamide |
| 507.2 | N-((1S)-1-{[N-(6-fluoro(3-isoquinolyl))carbamoyloxy]methyl}-4-hydroxybutyl){[(2-chloro-3-fluorophenyl)methyl]amino}-N-methylcarboxamide |
| 448.2 | N-[(2-chloro-3-fluorophenyl)methyl]-4-[N-(6-fluoro(3-isoquinolyl))carbamoyloxy]-2-methylbutanamide |
| 503.2 | N-((1S)-1-{[N-(6-fluoro(3-isoquinolyl))carbamoyloxy]methyl}-5-hydroxypentyl){[(2-chlorophenyl)methyl]amino}-N-methylcarboxamide |

-continued

| m/z M + H | ChemicalName |
|---|---|
| 521.2 | N-((1S)-1-{[N-(6-fluoro(3-isoquinolyl))carbamoyloxy]methyl}-5-hydroxypentyl){[(2-chloro-3-fluorophenyl)methyl]amino}-N-methylcarboxamide |
| 523.2 | N-((1S,3S)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 523.2 | N-((1S,3R)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 648.1 | 4-{2-[(tert-butoxy)carbonylamino]acetylamino}-N-[(2-chloro-3-fluorophenyl)methyl]-2-{2-[N-(6-fluoro(3-isoquinolyl))carbamoyloxy]ethyl}-2-methylbutanamide |
| 548.1 | 4-(2-aminoacetylamino)-N-[(2-chloro-3-fluorophenyl)methyl]-2-{2-[N-(6-fluoro(3-isoquinolyl))carbamoyloxy]ethyl}-2-methylbutanamide |
| 505.2 | 5-amino-N-[(2-chloro-3-fluorophenyl)methyl]-2-{2-[N-(6-fluoro(3-isoquinolyl))carbamoyloxy]ethyl}-2-methylpentanamide |
| 520.2 | N-[(2-chloro-3-fluorophenyl)methyl]-2-{2-[N-(6-fluoro(3-isoquinolyl))carbamoyloxy]ethyl}-6-hydroxy-2-methylhexanamide |
| 562.2 | 5-(2-aminoacetylamino)-N-[(2-chloro-3-fluorophenyl)methyl]-2-{2-[N-(6-fluoro(3-isoquinolyl))carbamoyloxy]ethyl}-2-methylpentanamide |
| 522.2 | N-((1S)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 474.2 | N-{2-[N-(5-bromo-4-methyl(2-pyridyl))carbamoyloxy]ethyl}{[(2-chloro-3-fluorophenyl)methyl]amino}-N-methylcarboxamide |
| 413.2 | {[(2-chloro-3-fluorophenyl)methyl]amino}-N-{2-[N-(5-fluoro-4-methyl(2-pyridyl))carbamoyloxy]ethyl}-N-methylcarboxamide |
| 395.2 | {[(2-chlorophenyl)methyl]amino}-N-{2-[N-(5-fluoro-4-methyl(2-pyridyl))carbamoyloxy]ethyl}-N-methylcarboxamide |
| 520.2 | N-((1S)-4-amino-1-{[N-(6-fluoro(3-isoquinolyl))carbamoyloxy]methyl}pentyl){[(2-chloro-3-fluorophenyl)methyl]amino}-N-methylcarboxamide |
| 490.2 | N-[(2-chloro-3-fluorophenyl)methyl]-2-{2-[N-(6-fluoro(3-isoquinolyl))carbamoyloxy]ethyl}-2-methylpentanamide |
| 593.2 | (2S)-N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-amino-3-hydroxypropanamide |
| 593.2 | (2R)-N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-amino-3-hydroxypropanamide |
| 563.2 | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-aminoacetamide |
| 538.2 | N-((1S)-4-amino-5,5-difluoro-1-{[N-(6-fluoro(3-isoquinolyl))carbamoyloxy]methyl}pentyl){[(2-chlorophenyl)methyl]amino}-N-methylcarboxamide |
| 492.2 | N-[(2-chloro-3-fluorophenyl)methyl]-2-{2-[N-(6-fluoro(3-isoquinolyl))carbamoyloxy]ethyl}-4-hydroxy-2-methylbutanamide |
| 634.3 | 2-({2-[(tert-butoxy)carbonylamino]acetylamino}methyl)-N-[(2-chloro-3-fluorophenyl)methyl]-4-[N-(6-fluoro(3-isoquinolyl))carbamoyloxy]-2-methylbutanamide |
| 534.2 | 2-[(2-aminoacetylamino)methyl]-N-[(2-chloro-3-fluorophenyl)methyl]-4-[N-(6-fluoro(3-isoquinolyl))carbamoyloxy]-2-methylbutanamide |
| 449.2 | {[(2-chloro-5-fluorophenyl)methyl]amino}-N-{2-[N-(6-fluoro(3-isoquinolyl))carbamoyloxy]ethyl}-N-methylcarboxamide |
| 591.1 | 2-{2-[(tert-butoxy)carbonylamino]ethyl}-N-[(2-chloro-3-fluorophenyl)methyl]-4-[N-(6-fluoro(3-isoquinolyl))carbamoyloxy]-2-methylbutanamide |
| 491.1 | 4-amino-N-[(2-chloro-3-fluorophenyl)methyl]-2-{2-[N-(6-fluoro(3-isoquinolyl))carbamoyloxy]ethyl}-2-methylbutanamide |
| 549.0 | N-[(2-chloro-3-fluorophenyl)methyl]-2-{2-[N-(6-fluoro(3-isoquinolyl))carbamoyloxy]ethyl}-4-(2-hydroxyacetylamino)-2-methylbutanamide |
| 678.1 | 4-{(2S)-2-[(tert-butoxy)carbonylamino]-3-hydroxypropanoylamino}-N-[(2-chloro-3-fluorophenyl)methyl]-2-{2-[N-(6-fluoro(3-isoquinolyl))carbamoyloxy]ethyl}-2-methylbutanamide |
| 578.1 | 4-((2S)-2-amino-3-hydroxypropanoylamino)-N-[(2-chloro-3-fluorophenyl)methyl]-2-{2-[N-(6-fluoro(3-isoquinolyl))carbamoyloxy]ethyl}-2-methylbutanamide |
| 579.1 | 4-(2,3-dihydroxypropanoylamino)-N-[(2-chloro-3-fluorophenyl)methyl]-2-{2-[N-(6-fluoro(3-isoquinolyl))carbamoyloxy]ethyl}-2-methylbutanamide |
| 519.2 | 6-amino-N-[(2-chloro-3-fluorophenyl)methyl]-2-{2-[N-(6-fluoro(3-isoquinolyl))carbamoyloxy]ethyl}-2-methylhexanamide |

-continued

| m/z M + H | ChemicalName |
|---|---|
| 491.2 | [((2R,3R)-1-{N-[(2-chloro-3-fluorophenyl)methyl]carbamoyl}-3-hydroxypyrrolidin-2-yl)methoxy]-N-(6-fluoro(3-isoquinolyl))carboxamide |
| 631.2 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dimethyl phosphate |
| 539.2 | N-((1S,3S)-1-{[N-(6-fluoro-2-hydroxy(3-isoquinolyl))carbamoyloxy]methyl}-3,4-dihydroxybutyl){[(2-chloro-3-fluorophenyl)methyl]amino}-N-methylcarboxamide |
| 539.2 | N-((1S,3R)-1-{[N-(6-fluoro-2-hydroxy(3-isoquinolyl))carbamoyloxy]methyl}-3,4-dihydroxybutyl){[(2-chloro-3-fluorophenyl)methyl]amino}-N-methylcarboxamide |
| 397.2 | N-{2-[N-(5-chloro(2-pyridyl))carbamoyloxy]ethyl}{[(2-chlorophenyl)methyl]amino}-N-methylcarboxamide |
| 522.2 | ({(4S)-6-(aminomethyl)-1-[(2-chloro-3-fluorophenyl)methyl]-6-fluoro-3-methyl-2-oxo(1,3-diazaperhydroin-4-yl)}methoxy)-N-(6-fluoro(3-isoquinolyl))carboxamide |
| 556.2 | N-((1S)-4-amino-5,5-difluoro-1-{[N-(6-fluoro(3-isoquinolyl))carbamoyloxy]methyl}pentyl){[(2-chloro-3-fluorophenyl)methyl]amino}-N-methylcarboxamide |
| 690.2 | N-((1S)-5,5-difluoro-1-{[N-(6-fluoro(3-isoquinolyl))carbamoyloxy]methyl}-4-[(phenylmethoxy)carbonylamino]pentyl){[(2-chloro-3-fluorophenyl)methyl]amino}-N-methylcarboxamide |
| 616.0 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl hydrogen methyl phosphate |
| 521.2 | N-((1S)-3,4-diamino-1-{[N-(6-fluoro(3-isoquinolyl))carbamoyloxy]methyl}butyl){[(2-chloro-3-fluorophenyl)methyl]amino}-N-methylcarboxamide |
| 576.1 | 6-(2-aminoacetylamino)-N-[(2-chloro-3-fluorophenyl)methyl]-2-{2-[N-(6-fluoro(3-isoquinolyl))carbamoyloxy]ethyl}-2-methylhexanamide |
| 536.1 | N-[(2-chloro-3-fluorophenyl)methyl]-2-{2-[N-(6-fluoro(3-isoquinolyl))carbamoyloxy]ethyl}-5,6-dihydroxy-2-methylhexanamide |
| 522.2 | N-((1S,3R)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 522.2 | N-((1S,3S)-4-amino-1-{[N-(6-fluoro(3-isoquinolyl))carbamoyloxy]methyl}-3-hydroxybutyl){[(2-chloro-3-fluorophenyl)methyl]amino}-N-methylcarboxamide |
| 601.0 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 555.2 | 2-{2-[(2,2-difluoroethyl)amino]ethyl}-N-[(2-chloro-3-fluorophenyl)methyl]-4-[N-(6-fluoro(3-isoquinolyl))carbamoyloxy]-2-methylbutanamide |
| 420.2 | {[(2-chloro-3-fluorophenyl)methyl]amino}-N-{2-[N-(5-cyano-4-methyl(2-pyridyl))carbamoyloxy]ethyl}-N-methylcarboxamide |
| 409.2 | N-{2-[N-(4,5-dimethyl(2-pyridyl))carbamoyloxy]ethyl}{[(2-chloro-3-fluorophenyl)methyl]amino}-N-methylcarboxamide |
| 391.2 | N-{2-[N-(4,5-dimethyl(2-pyridyl))carbamoyloxy]ethyl}{[(2-chlorophenyl)methyl]amino}-N-methylcarboxamide |
| 608.3 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl 2-(dimethylamino)acetate |
| 580.1 | (3S)-N-(2,3-dihydroxypropyl)-3-({[(2-chloro-3-fluorophenyl)methyl]amino}-N-methylcarbonylamino)-4-[N-(6-fluoro(3-isoquinolyl))carbamoyloxy]butanamide |
| 649.2 | (3S)-N-{2-[(tert-butoxy)carbonylamino]ethyl}-3-({[(2-chloro-3-fluorophenyl)methyl]amino}-N-methylcarbonylamino)-4-[N-(6-fluoro(3-isoquinolyl))carbamoyloxy]butanamide |
| 689.2 | tert-butyl 4-[(3S)-3-({[(2-chloro-3-fluorophenyl)methyl]amino}-N-methylcarbonylamino)-4-[N-(6-fluoro(3-isoquinolyl))carbamoyloxy]butanoylamino]piperidinecarboxylate |
| 675.2 | tert-butyl 4-[(3S)-3-({[(2-chloro-3-fluorophenyl)methyl]amino}-N-methylcarbonylamino)-4-[N-(6-fluoro(3-isoquinolyl))carbamoyloxy]butanoyl]piperazinecarboxylate |
| 549.1 | (3S)-N-(2-aminoethyl)-3-({[(2-chloro-3-fluorophenyl)methyl]amino}-N-methylcarbonylamino)-4-[N-(6-fluoro(3-isoquinolyl))carbamoyloxy]butanamide |
| 589.2 | (3S)-3-({[(2-chloro-3-fluorophenyl)methyl]amino}-N-methylcarbonylamino)-4-[N-(6-fluoro(3-isoquinolyl))carbamoyloxy]-N-(4-piperidyl)butanamide |
| 575.1 | [(2S)-2-({[(2-chloro-3-fluorophenyl)methyl]amino}-N-methylcarbonylamino)-4-oxo-4-piperazinylbutoxy]-N-(6-fluoro(3-isoquinolyl))carboxamide |

-continued

| m/z M + H | ChemicalName |
|---|---|
| 490.2 | [((2S,3S)-3-amino-1-{N-[(2-chloro-3-fluorophenyl)methyl]carbamoyl}pyrrolidin-2-yl)methoxy]-N-(6-fluoro(3-isoquinolyl))carboxamide |
| 516.0 | [((2S,3S)-1-{N-[(2-chloro-3-fluorophenyl)methyl]carbamoyl}-3-(diazoazamvinyl)pyrrolidin-2-yl)methoxy]-N-(6-fluoro(3-isoquinolyl))carboxamide |
| 509.1 | N-{2-[N-(5-bromo(3-isoquinolyl))carbamoyloxy]ethyl}{[(2-chloro-3-fluorophenyl)methyl]amino}-N-methylcarboxamide |
| 489.1 | methyl 3-{[2-({[(2-chloro-3-fluorophenyl)methyl]amino}-N-methylcarbonylamino)ethoxy]carbonylamino}isoquinoline-5-carboxylate |
| 432.1 | {[(2-chloro-3-fluorophenyl)methyl]amino}-N-methyl-N-[2-(N-pyridino[3,4-d]pyridin-3-ylcarbamoyloxy)ethyl]carboxamide |
| 507.1 | (3S)-3-({[(2-chloro-3-fluorophenyl)methyl]amino}-N-methylcarbonylamino)-4-[N-(6-fluoro(3-isoquinolyl))carbamoyloxy]butanoic acid |
| 679.2 | N-{(2R)-2-[(tert-butoxy)carbonylamino]-3-hydroxypropyl}(3S)-3-({[(2-chloro-3-fluorophenyl)methyl]amino}-N-methylcarbonylamino)-4-[N-(6-fluoro(3-isoquinolyl))carbamoyloxy]butanamide |
| 579.1 | N-((2R)-2-amino-3-hydroxypropyl)(3S)-3-({[(2-chloro-3-fluorophenyl)methyl]amino}-N-methylcarbonylamino)-4-[N-(6-fluoro(3-isoquinolyl))carbamoyloxy]butanamide |
| 576.2 | [(2S)-2-({[(2-chloro-3-fluorophenyl)methyl]amino}-N-methylcarbonylamino)-4-morpholin-4-yl-4-oxobutoxy]-N-(6-fluoro(3-isoquinolyl))carboxamide |
| 491.2 | [((3S,2R)-1-{N-[(2-chloro-3-fluorophenyl)methyl]carbamoyl}-3-hydroxypyrrolidin-2-yl)methoxy]-N-(6-fluoro(3-isoquinolyl))carboxamide |
| 535.2 | N-[(2S)-2-({[(2-chloro-3-fluorophenyl)methyl]amino}-N-methylcarbonylamino)-3-[N-(6-fluoro(3-isoquinolyl))carbamoyloxy]propyl]-2-aminoacetamide |
| 565.2 | (2S)-N-[(2S)-2-({[(2-chloro-3-fluorophenyl)methyl]amino}-N-methylcarbonylamino)-3-[N-(6-fluoro(3-isoquinolyl))carbamoyloxy]propyl]-2-amino-3-hydroxypropanamide |
| 565.2 | (2R)-N-[(2S)-2-({[(2-chloro-3-fluorophenyl)methyl]amino}-N-methylcarbonylamino)-3-[N-(6-fluoro(3-isoquinolyl))carbamoyloxy]propyl]-2-amino-3-hydroxypropanamide |
| 578.2 | [(2S)-3-[(tert-butoxy)carbonylamino]-2-({[(2-chloro-3-fluorophenyl)methyl]amino}-N-methylcarbonylamino)propoxy]-N-(6-fluoro(3-isoquinolyl))carboxamide |
| 478.1 | [(2S)-3-amino-2-({[(2-chloro-3-fluorophenyl)methyl]amino}-N-methylcarbonylamino)propoxy]-N-(6-fluoro(3-isoquinolyl))carboxamide |
| 606.2 | (5S)-5-({[(2-chloro-3-fluorophenyl)methyl]amino}-N-methylcarbonylamino)-6-[N-(6-fluoro(3-isoquinolyl))carbamoyloxy]hexyl 2-(dimethylamino)acetate |
| 550.2 | N-((1S)-5-diazo-3-fluoro-1-{[N-(6-fluoro(3-isoquinolyl))carbamoyloxy]methyl}-5-azapent-5-enyl){[(2-chloro-3-fluorophenyl)methyl]amino}-N-methylcarboxamide |
| 432.1 | {[(2-chloro-3-fluorophenyl)methyl]amino}-N-methyl-N-[2-(N-pyridino[2,3-d]pyridin-7-ylcarbamoyloxy)ethyl]carboxamide |
| 461.2 | {[(2-chloro-3-fluorophenyl)methyl]amino}-N-(2-{N-[5-(hydroxymethyl)(3-isoquinolyl)]carbamoyloxy}ethyl)-N-methylcarboxamide |
| 509.1 | N-{2-[N-(8-bromo(3-isoquinolyl))carbamoyloxy]ethyl}{[(2-chloro-3-fluorophenyl)methyl]amino}-N-methylcarboxamide |
| 473.2 | N-{2-[N-(5-acetyl(3-isoquinolyl))carbamoyloxy]ethyl}{[(2-chloro-3-fluorophenyl)methyl]amino}-N-methylcarboxamide |
| 474.2 | 3-{[2-({[(2-chloro-3-fluorophenyl)methyl]amino}-N-methylcarbonylamino)ethoxy]carbonylamino}isoquinoline-5-carboxamide |
| 524.2 | N-((1S)-4-amino-3-fluoro-1-{[N-(6-fluoro(3-isoquinolyl))carbamoyloxy]methyl}butyl){[(2-chloro-3-fluorophenyl)methyl]amino}-N-methylcarboxamide |
| 629.2 | (5S)-5-({[(2-chloro-3-fluorophenyl)methyl]amino}-N-methylcarbonylamino)-6-[N-(6-fluoro(3-isoquinolyl))carbamoyloxy]hexyl dimethyl phosphate |
| 619.2 | N-{(1S)-4-(1,3-dioxobenzo[c]azolin-2-yl)-1-[(N-(3-isoquinolyl)carbamoyloxy)methyl]butyl}{[(2-chloro-3-fluorophenyl)methyl]amino}-N-methylcarboxamide |
| 545.2 | N-[(4S)-4-({[(2-chloro-3-fluorophenyl)methyl]amino}-N-methylcarbonylamino)-5-(N-(3-isoquinolyl)carbamoyloxy)pentyl]-2-aminoacetamide |
| 575.2 | (2S)-N-[(4S)-4-({[(2-chloro-3-fluorophenyl)methyl]amino}-N-methylcarbonylamino)-5-(N-(3-isoquinolyl)carbamoyloxy)pentyl]-2-amino-3-hydroxypropanamide |

-continued

| m/z M + H | ChemicalName |
|---|---|
| 575.2 | (2R)-N-[(4S)-4-({[(2-chloro-3-fluorophenyl)methyl]amino}-N-methylcarbonylamino)-5-(N-(3-isoquinolyl)carbamoyloxy)pentyl]-2-amino-3-hydroxypropanamide |
| 592.2 | (4S)-4-({[(2-chloro-3-fluorophenyl)methyl]amino}-N-methylcarbonylamino)-5-[N-(6-fluoro(3-isoquinolyl))carbamoyloxy]pentyl 2-(dimethylamino)acetate |
| 587.1 | (4S)-4-({[(2-chloro-3-fluorophenyl)methyl]amino}-N-methylcarbonylamino)-5-[N-(6-fluoro(3-isoquinolyl))carbamoyloxy]pentyl dihydrogen phosphate |
| 492.1 | [(2S)-4-amino-2-({[(2-chloro-3-fluorophenyl)methyl]amino}-N-methylcarbonylamino)butoxy]-N-(6-fluoro(3-isoquinolyl))carboxamide |
| 549.2 | N-[(3S)-3-({[(2-chloro-3-fluorophenyl)methyl]amino}-N-methylcarbonylamino)-4-[N-(6-fluoro(3-isoquinolyl))carbamoyloxy]butyl]-2-aminoacetamide |
| 720.1 | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-[(tert-butoxy)carbonylamino]-3-methylbutanoate |
| 720.1 | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-[(tert-butoxy)carbonylamino]-3-methylbutanoate |
| 620.1 | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-amino-3-methylbutanoate |
| 620.1 | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-amino-3-methylbutanoate |
| 599.0 | (5S)-5-({[(2-chloro-3-fluorophenyl)methyl]amino}-N-methylcarbonylamino)-6-[N-(6-fluoro(3-isoquinolyl))carbamoyloxy]hexyl dihydrogen phosphate |
| 548.1 | N-((1S)-4-(amidinoamino)-1-{[N-(6-fluoro(3-isoquinolyl))carbamoyloxy]methyl}butyl){[(2-chloro-3-fluorophenyl)methyl]amino}-N-methylcarboxamide |
| 549.1 | N-[(4S)-4-({[(2-chloro-3-fluorophenyl)methyl]amino}-N-methylcarbonylamino)-5-[N-(6-fluoro(3-isoquinolyl))carbamoyloxy]pentyl]aminoamide |
| 587.2 | N-(4-{[(1E)-2-cyano-1-(methylamino)-2-azavinyl]amino}(1S)-1-{[N-(6-fluoro(3-isoquinolyl))carbamoyloxy]methyl}butyl){[(2-chloro-3-fluorophenyl)methyl]amino}-N-methylcarboxamide |
| 594.2 | (4S)-4-({[(2-chloro-3-fluorophenyl)methyl]amino}-N-methylcarbonylamino)-5-[N-(6-fluoro(3-isoquinolyl))carbamoyloxy]pentyl (2S)-2-amino-3-hydroxypropanoate |
| 594.1 | (4S)-4-({[(2-chloro-3-fluorophenyl)methyl]amino}-N-methylcarbonylamino)-5-[N-(6-fluoro(3-isoquinolyl))carbamoyloxy]pentyl (2R)-2-amino-3-hydroxypropanoate |
| 606.2 | (4S)-4-({[(2-chloro-3-fluorophenyl)methyl]amino}-N-methylcarbonylamino)-5-[N-(6-fluoro(3-isoquinolyl))carbamoyloxy]pentyl (2S)-2-amino-3-methylbutanoate |
| 606.2 | (4S)-4-({[(2-chloro-3-fluorophenyl)methyl]amino}-N-methylcarbonylamino)-5-[N-(6-fluoro(3-isoquinolyl))carbamoyloxy]pentyl (2R)-2-amino-3-methylbutanoate |
| 432.2 | {[(2-chloro-3-fluorophenyl)methyl]amino}-N-methyl-N-[2-(N-pyridino[3,2-d]pyridin-6-ylcarbamoyloxy)ethyl]carboxamide |
| 489.1 | N-{(1S)-4-amino-1-[(N-pyridino[4,3-d]pyridin-3-ylcarbamoyloxy)methyl]butyl}{[(2-chloro-3-fluorophenyl)methyl]amino}-N-methylcarboxamide |
| 489.1 | N-{(1S)-4-amino-1-[(N-pyridino[3,2-d]pyridin-6-ylcarbamoyloxy)methyl]butyl}{[(2-chloro-3-fluorophenyl)methyl]amino}-N-methylcarboxamide |
| 689.3 | tert-butyl 4-[(4S)-4-({[(2-chloro-3-fluorophenyl)methyl]amino}-N-methylcarbonylamino)-5-[N-(6-fluoro(3-isoquinolyl))carbamoyloxy]pentanoyl]piperazinecarboxylate |
| 663.3 | (4S)-N-{2-[(tert-butoxy)carbonylamino]ethyl}-4-({[(2-chloro-3-fluorophenyl)methyl]amino}-N-methylcarbonylamino)-5-[N-(6-fluoro(3-isoquinolyl))carbamoyloxy]pentanamide |
| 693.3 | N-{(2R)-2-[(tert-butoxy)carbonylamino]-3-hydroxypropyl}(4S)-4-({[(2-chloro-3-fluorophenyl)methyl]amino}-N-methylcarbonylamino)-5-[N-(6-fluoro(3-isoquinolyl))carbamoyloxy]pentanamide |
| 689.3 | tert-butyl 3-[(4S)-4-({[(2-chloro-3-fluorophenyl)methyl]amino}-N-methylcarbonylamino)-5-[N-(6-fluoro(3-isoquinolyl))carbamoyloxy]pentanoylamino]pyrrolidinecarboxylate |
| 456.1 | {[(2-chloro-3-fluorophenyl)methyl]amino}-N-{2-[N-(8-cyano(3-isoquinolyl))carbamoyloxy]ethyl}-N-methylcarboxamide |

| m/z M + H | ChemicalName |
|---|---|
| 563.2 | (4S)-N-(2-aminoethyl)-4-({[(2-chloro-3-fluorophenyl)methyl]amino}-N-methylcarbonylamino)-5-[N-(6-fluoro(3-isoquinolyl))carbamoyloxy]pentanamide |
| 589.2 | N-((1S)-1-{[N-(6-fluoro(3-isoquinolyl))carbamoyloxy]methyl}-4-oxo-4-piperazinylbutyl){[(2-chloro-3-fluorophenyl)methyl]amino}-N-methylcarboxamide |
| 593.2 | N-((2R)-2-amino-3-hydroxypropyl)(4S)-4-({[(2-chloro-3-fluorophenyl)methyl]amino}-N-methylcarbonylamino)-5-[N-(6-fluoro(3-isoquinolyl))carbamoyloxy]pentanamide |
| 589.2 | (4S)-4-({[(2-chloro-3-fluorophenyl)methyl]amino}-N-methylcarbonylamino)-5-[N-(6-fluoro(3-isoquinolyl))carbamoyloxy]-N-pyrrolidin-3-ylpentanamide |
| 579.1 | (2S)-N-[(3S)-3-({[(2-chloro-3-fluorophenyl)methyl]amino}-N-methylcarbonylamino)-4-[N-(6-fluoro(3-isoquinolyl))carbamoyloxy]butyl]-2-amino-3-hydroxypropanamide |
| 579.2 | (2R)-N-[(3S)-3-({[(2-chloro-3-fluorophenyl)methyl]amino}-N-methylcarbonylamino)-4-[N-(6-fluoro(3-isoquinolyl))carbamoyloxy]butyl]-2-amino-3-hydroxypropanamide |
| 573.2 | N-(4-[((1E)-1-amino-2-cyano-2-azavinyl)amino](1S)-1-{[N-(6-fluoro(3-isoquinolyl))carbamoyloxy]methyl}butyl){[(2-chloro-3-fluorophenyl)methyl]amino}-N-methylcarboxamide |
| 591.2 | N-(4-[((1E)-1-amino-2-carbamoyl-2-azavinyl)amino](1S)-1-{[N-(6-fluoro(3-isoquinolyl))carbamoyloxy]methyl}butyl){[(2-chloro-3-fluorophenyl)methyl]amino}-N-methylcarboxamide |
| 601.2 | N-((1S)-4-{[(1Z)-1-(dimethylamino)-2-cyano-2-azavinyl]amino}-1-{[N-(6-fluoro(3-isoquinolyl))carbamoyloxy]methyl}butyl){[(2-chloro-3-fluorophenyl)methyl]amino}-N-methylcarboxamide |
| 511.0 | N-(6-bromo(3-isoquinolyl))[2-({[(2-chloro-3-fluorophenyl)methyl]amino}-N-methylcarbonylamino)ethoxy]carboxamide |
| 636.2 | N-((1S)-4-(1,3-dioxobenzo[c]azolin-2-yl)-1-{[N-(6-fluoro(3-isoquinolyl))carbamoyloxy]methyl}butyl){[(2-chloro-3-fluorophenyl)methyl]amino}-N-methylcarboxamide |
| 676.2 | (2S)-N-[(4S)-4-({[(2-chloro-3-fluorophenyl)methyl]amino}-N-methylcarbonylamino)-5-(N-pyridino[4,3-d]pyridin-3-ylcarbamoyloxy)pentyl]-2-[(tert-butoxy)carbonylamino]-3-hydroxypropanamide |
| 576.2 | (2S)-N-[(4S)-4-({[(2-chloro-3-fluorophenyl)methyl]amino}-N-methylcarbonylamino)-5-(N-pyridino[4,3-d]pyridin-3-ylcarbamoyloxy)pentyl]-2-amino-3-hydroxypropanamide |
| 676.2 | (2S)-N-[(4S)-4-({[(2-chloro-3-fluorophenyl)methyl]amino}-N-methylcarbonylamino)-5-(N-pyridino[3,2-d]pyridin-6-ylcarbamoyloxy)pentyl]-2-[(tert-butoxy)carbonylamino]-3-hydroxypropanamide |
| 576.2 | (2S)-N-[(4S)-4-({[(2-chloro-3-fluorophenyl)methyl]amino}-N-methylcarbonylamino)-5-(N-pyridino[3,2-d]pyridin-6-ylcarbamoyloxy)pentyl]-2-amino-3-hydroxypropanamide |
| 739.2 | (3S)-3-({[(2-chloro-3-fluorophenyl)methyl]amino}-N-methylcarbonylamino)-4-[N-(6-fluoro(3-isoquinolyl))carbamoyloxy]-1-[(methoxyphosphinyl)methyl]butyl dimethyl phosphate |
| 489.0 | methyl 3-{[2-({[(2-chloro-3-fluorophenyl)methyl]amino}-N-methylcarbonylamino)ethoxy]carbonylamino}isoquinoline-6-carboxylate |
| 520.1 | N-((1S)-3-carbamoyl-1-{[N-(6-fluoro(3-isoquinolyl))carbamoyloxy]methyl}propyl){[(2-chloro-3-fluorophenyl)methyl]amino}-N-methylcarboxamide |
| 521.1 | (4S)-4-({[(2-chloro-3-fluorophenyl)methyl]amino}-N-methylcarbonylamino)-5-[N-(6-fluoro(3-isoquinolyl))carbamoyloxy]pentanoic acid |
| 517.2 | methyl (4S)-4-({[(2-chloro-3-fluorophenyl)methyl]amino}-N-methylcarbonylamino)-5-(N-(3-isoquinolyl)carbamoyloxy)pentanoate |
| 506.1 | N-[(1S)-4-amino-1-({N-[5-(trifluoromethyl)(2-pyridyl)]carbamoyloxy}methyl)butyl]{[(2-chloro-3-fluorophenyl)methyl]amino}-N-methylcarboxamide |
| 519.1 | N-((1S)-3-amidino-1-{[N-(6-fluoro(3-isoquinolyl))carbamoyloxy]methyl}propyl){[(2-chloro-3-fluorophenyl)methyl]amino}-N-methylcarboxamide |
| 547.1 | N-((1S)-4-(ethylamino)-1-{[N-(6-fluoro(3-isoquinolyl))carbamoyloxy]methyl}-4-iminobutyl){[(2-chloro-3-fluorophenyl)methyl]amino}-N-methylcarboxamide |
| 503.2 | (4S)-4-({[(2-chloro-3-fluorophenyl)methyl]amino}-N-methylcarbonylamino)-5-(N-(3-isoquinolyl)carbamoyloxy)pentanoic acid |
| 509.0 | N-(7-bromo(3-isoquinolyl))[2-({[(2-chloro-3-fluorophenyl)methyl]amino}-N-methylcarbonylamino)ethoxy]carboxamide |
| 572.3 | (5S)-5-({[(2,3-difluorophenyl)methyl]amino}-N-methylcarbonylamino)-6-(N-(3-isoquinolyl)carbamoyloxy)hexyl 2-(dimethylamino)acetate |

| m/z M + H | ChemicalName |
|---|---|
| 567.2 | (5S)-5-({[(2,3-difluorophenyl)methyl]amino}-N-methylcarbonylamino)-6-(N-(3-isoquinolyl)carbamoyloxy)hexyl dihydrogen phosphate |
| 586.3 | (5S)-5-({[(2,3-difluorophenyl)methyl]amino}-N-methylcarbonylamino)-6-(N-(3-isoquinolyl)carbamoyloxy)hexyl (2S)-2-amino-3-methylbutanoate |
| 586.3 | (5S)-5-({[(2,3-difluorophenyl)methyl]amino}-N-methylcarbonylamino)-6-(N-(3-isoquinolyl)carbamoyloxy)hexyl (2R)-2-amino-3-methylbutanoate |
| 764.1 | (5S)-5-({[(2-chloro-3-fluorophenyl)methyl]amino}-N-methylcarbonylamino)-6-[N-(6-fluoro(3-isoquinolyl))carbamoyloxy]hexyl (2S)-3-(tert-butoxy)-2-[(tert-butoxy)carbonylamino]propanoate |
| 608.1 | (5S)-5-({[(2-chloro-3-fluorophenyl)methyl]amino}-N-methylcarbonylamino)-6-[N-(6-fluoro(3-isoquinolyl))carbamoyloxy]hexyl (2S)-2-amino-3-hydroxypropanoate |
| 764.1 | (5S)-5-({[(2-chloro-3-fluorophenyl)methyl]amino}-N-methylcarbonylamino)-6-[N-(6-fluoro(3-isoquinolyl))carbamoyloxy]hexyl (2R)-3-(tert-butoxy)-2-[(tert-butoxy)carbonylamino]propanoate |
| 608.1 | (5S)-5-({[(2-chloro-3-fluorophenyl)methyl]amino}-N-methylcarbonylamino)-6-[N-(6-fluoro(3-isoquinolyl))carbamoyloxy]hexyl (2R)-2-amino-3-hydroxypropanoate |
| 532.1 | methyl (5S)-5-({[(2-chloro-3-fluorophenyl)methyl]amino}-N-methylcarbonylamino)-6-(N-pyridino[4,3-d]pyridin-3-ylcarbamoyloxy)hexanoate |
| 518.1 | (5S)-5-({[(2-chloro-3-fluorophenyl)methyl]amino}-N-methylcarbonylamino)-6-(N-pyridino[4,3-d]pyridin-3-ylcarbamoyloxy)hexanoic acid |
| 504.1 | N-{(1S)-5-hydroxy-1-[(N-pyridino[4,3-d]pyridin-3-ylcarbamoyloxy)methyl]pentyl}{[(2-chloro-3-fluorophenyl)methyl]amino}-N-methylcarboxamide |
| 532.1 | methyl (5S)-5-({[(2-chloro-3-fluorophenyl)methyl]amino}-N-methylcarbonylamino)-6-(N-pyridino[3,4-d]pyridin-3-ylcarbamoyloxy)hexanoate |
| 518.1 | (5S)-5-({[(2-chloro-3-fluorophenyl)methyl]amino}-N-methylcarbonylamino)-6-(N-pyridino[3,4-d]pyridin-3-ylcarbamoyloxy)hexanoic acid |
| 489.2 | N-((1S)-1-{[N-(6-fluoro(3-isoquinolyl))carbamoyloxy]methyl}-3,4-dihydroxybutyl){[(3-fluorophenyl)methyl]amino}-N-methylcarboxamide |
| 489.1 | methyl 3-{[2-({[(2-chloro-3-fluorophenyl)methyl]amino}-N-methylcarbonylamino)ethoxy]carbonylamino}isoquinoline-7-carboxylate |
| 568.2 | N-((1S)-5-diazo-3,3-difluoro-1-{[N-(6-fluoro(3-isoquinolyl))carbamoyloxy]methyl}-5-azapent-5-enyl){[(2-chloro-3-fluorophenyl)methyl]amino}-N-methylcarboxamide |
| 472.2 | [(2S)-5-amino-2-({[(2-chloro-3-fluorophenyl)methyl]amino}-N-methylcarbonylamino)pentyloxy]-N-(5-chloro(2-pyridyl))carboxamide |
| 444.2 | [(2S)-3-amino-2-({[(3-fluorophenyl)methyl]amino}-N-methylcarbonylamino)propoxy]-N-(6-fluoro(3-isoquinolyl))carboxamide |
| 472.1 | N-{(1S)-1-[(N-pyridino[3,4-d]pyridin-3-ylcarbamoyloxy)methyl]but-3-enyl}{[(2-chloro-3-fluorophenyl)methyl]amino}-N-methylcarboxamide |
| 506.1 | N-{(1S)-3,4-dihydroxy-1-[(N-pyridino[3,4-d]pyridin-3-ylcarbamoyloxy)methyl]butyl}{[(2-chloro-3-fluorophenyl)methyl]amino}-N-methylcarboxamide |
| 542.2 | N-((1S)-4-amino-3,3-difluoro-1-{[N-(6-fluoro(3-isoquinolyl))carbamoyloxy]methyl}butyl){[(2-chloro-3-fluorophenyl)methyl]amino}-N-methylcarboxamide |
| 622.2 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2S)-2-amino-3-methylbutanoate |
| 622.2 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2R)-2-amino-3-methylbutanoate |
| 610.1 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2S)-2-amino-3-hydroxypropanoate |
| 610.1 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl (2R)-2-amino-3-hydroxypropanoate |
| 686.2 | N-[(2S)-2-({[(2-chloro-3-fluorophenyl)methyl]amino}-N-methylcarbonylamino)-3-[N-(6-fluoro(3-isoquinolyl))carbamoyloxy]propyl][4-(phenylcarbonyl)phenyl]carboxamide |
| 686.2 | N-[(2S)-2-({[(2-chloro-3-fluorophenyl)methyl]amino}-N-methylcarbonylamino)-3-[N-(6-fluoro(3-isoquinolyl))carbamoyloxy]propyl][3-(phenylcarbonyl)phenyl]carboxamide |

-continued

| m/z M + H | ChemicalName |
|---|---|
| 696.1 | N-[(4S)-4-({[(2-chloro-3-fluorophenyl)methyl]amino}-N-methylcarbonylamino)-5-(N-(3-isoquinolyl)carbamoyloxy)pentyl][4-(phenylcarbonyl)phenyl]carboxamide |
| 696.2 | N-[(4S)-4-({[(2-chloro-3-fluorophenyl)methyl]amino}-N-methylcarbonylamino)-5-(N-(3-isoquinolyl)carbamoyloxy)pentyl][3-(phenylcarbonyl)phenyl]carboxamide |
| 612.2 | [(2S)-2-({[(2-chloro-3-fluorophenyl)methyl]amino}-N-methylcarbonylamino)-3-[(phenylmethoxy)carbonylamino]propoxy]-N-(6-fluoro(3-isoquinolyl))carboxamide |
| 635.2 | N-[(2S)-2-({[(2-chloro-3-fluorophenyl)methyl]amino}-N-methylcarbonylamino)-3-[N-(6-fluoro(3-isoquinolyl))carbamoyloxy]propyl]-2-[(tert-butoxy)carbonylamino]acetamide |
| 461.0 | {[(2-chloro-3-fluorophenyl)methyl]amino}-N-(2-{N-[7-(hydroxymethyl)(3-isoquinolyl)]carbamoyloxy}ethyl)-N-methylcarboxamide |
| 461.1 | {[(2-chloro-3-fluorophenyl)methyl]amino}-N-(2-{N-[6-(hydroxymethyl)(3-isoquinolyl)]carbamoyloxy}ethyl)-N-methylcarboxamide |
| 471.1 | [(2S)-2-({[(2-chloro-3-fluorophenyl)methyl]amino}-N-methylcarbonylamino)pent-4-enyloxy]-N-(3-isoquinolyl)carboxamide |
| 509.1 | {[(5-bromo-2-chlorophenyl)methyl]amino}-N-{2-[N-(6-fluoro(3-isoquinolyl))carbamoyloxy]ethyl}-N-methylcarboxamide |
| 457.1 | [(2S)-2-({[(2-chloro-3-fluorophenyl)methyl]amino}-N-methylcarbonylamino)pent-4-enyloxy]-N-(5-chloro(2-pyridyl))carboxamide |
| 505.2 | [(2S)-2-({[(2-chloro-3-fluorophenyl)methyl]amino}-N-methylcarbonylamino)-4,5-dihydroxypentyloxy]-N-(3-isoquinolyl)carboxamide |
| 489.2 | methyl 4-chloro-3-{[(N-{2-[N-(6-fluoro(3-isoquinolyl))carbamoyloxy]ethyl}-N-methylcarbamoyl)amino]methyl}benzoate |
| 505.2 | [(2S,4R)-2-({[(2-chloro-3-fluorophenyl)methyl]amino}-N-methylcarbonylamino)-4,5-dihydroxypentyloxy]-N-(3-isoquinolyl)carboxamide |
| 505.2 | [(2S,4S)-2-({[(2-chloro-3-fluorophenyl)methyl]amino}-N-methylcarbonylamino)-4,5-dihydroxypentyloxy]-N-(3-isoquinolyl)carboxamide |
| 489.1 | [(2S)-2-({[(2-chloro-3-fluorophenyl)methyl]amino}-N-methylcarbonylamino)-4,5-dihydroxypentyloxy]-N-(5-chloro(2-pyridyl))carboxamide |
| 585.2 | (4S)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate |
| 490.2 | [(2S)-2-({[(3-fluorophenyl)methyl]amino}-N-methylcarbonylamino)-4,5-dihydroxypentyloxy]-N-(3-isoquinolyl)carboxamide |
| 565.2 | (5S)-5-({[(2-chlorophenyl)methyl]amino}-N-methylcarbonylamino)-6-(N-(3-isoquinolyl)carbamoyloxy)hexyl dihydrogen phosphate |
| 590.2 | (4S)-4-({[(2-chloro-3-fluorophenyl)methyl]amino}-N-methylcarbonylamino)-2-hydroxy-5-(N-(3-isoquinolyl)carbamoyloxy)pentyl 2-(dimethylamino)acetate |
| 619.1 | N-{(1S)-4-(1,3-dioxobenzo[c]azolin-2-yl)-1-[(N-pyridino[3,4-d]pyridin-3-ylcarbamoyloxy)methyl]butyl}{[(2-chloro-3-fluorophenyl)methyl]amino}-N-methylcarboxamide |
| 489.1 | N-{(1S)-4-amino-1-[(N-pyridino[3,4-d]pyridin-3-ylcarbamoyloxy)methyl]butyl}{[(2-chloro-3-fluorophenyl)methyl]amino}-N-methylcarboxamide |
| 489.2 | [(2S)-2-({[(2-chloro-3-fluorophenyl)methyl]amino}-N-methylcarbonylamino)-5-hydroxypentyloxy]-N-(3-isoquinolyl)carboxamide |
| 569.2 | (4S)-4-({[(2-chloro-3-fluorophenyl)methyl]amino}-N-methylcarbonylamino)-5-(N-(3-isoquinolyl)carbamoyloxy)pentyl dihydrogen phosphate |
| 571.2 | [(2S)-2-({[(2-chloro-3-fluorophenyl)methyl]amino}-N-methylcarbonylamino)-5-oxo-5-piperazinylpentyloxy]-N-(3-isoquinolyl)carboxamide |
| 672.2 | tert-butyl 4-[(4S)-4-({[(2-chloro-3-fluorophenyl)methyl]amino}-N-methylcarbonylamino)-5-(N-(3-isoquinolyl)carbamoyloxy)pentanoyl]piperazinecarboxylate |
| 455.2 | N-{(1S)-1-[(N-(3-isoquinolyl)carbamoyloxy)methyl]but-3-enyl}{[(2,3-difluorophenyl)methyl]amino}-N-methylcarboxamide |
| 489.2 | N-{(1S)-3,4-dihydroxy-1-[(N-(3-isoquinolyl)carbamoyloxy)methyl]butyl}{[(2,3-difluorophenyl)methyl]amino}-N-methylcarboxamide |

-continued

| m/z M + H | ChemicalName |
|---|---|
| 489.2 | N-{(1S,3S)-3,4-dihydroxy-1-[(N-(3-isoquinolyl)carbamoyloxy)methyl]butyl}{[(2,3-difluorophenyl)methyl]amino}-N-methylcarboxamide |
| 489.2 | N-{(1S,3R)-3,4-dihydroxy-1-[(N-(3-isoquinolyl)carbamoyloxy)methyl]butyl}{[(2,3-difluorophenyl)methyl]amino}-N-methylcarboxamide |
| 461.2 | ({[2-chloro-5-(hydroxymethyl)phenyl]methyl}amino)-N-{2-[N-(6-fluoro(3-isoquinolyl))carbamoyloxy]ethyl}-N-methylcarboxamide |
| 569.2 | (4S)-4-({[(2,3-difluorophenyl)methyl]amino}-N-methylcarbonylamino)-2-hydroxy-5-(N-(3-isoquinolyl)carbamoyloxy)pentyl dihydrogen phosphate |
| 501.2 | N-[(2S)-2-({[(2,3-difluorophenyl)methyl]amino}-N-methylcarbonylamino)-3-(N-(3-isoquinolyl)carbamoyloxy)propyl]-2-aminoacetamide |
| 508.1 | N-{(1S)-4-amino-3,3-difluoro-1-[(N-(3-isoquinolyl)carbamoyloxy)methyl]butyl}{[(2,3-difluorophenyl)methyl]amino}-N-methylcarboxamide |
| 524.2 | N-{(1S)-4-amino-3,3-difluoro-1-[(N-(3-isoquinolyl)carbamoyloxy)methyl]butyl}{[(2-chloro-3-fluorophenyl)methyl]amino}-N-methylcarboxamide |
| 603.2 | (4S,2R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 603.2 | (2S,4S)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 639.1 | (5S)-5-({[(2-chloro-3-fluorophenyl)methyl]amino}-N-methylcarbonylamino)-6-(N-(3-isoquinolyl)carbamoyloxy)hexyl diethyl phosphate |
| 472.2 | N-{(1S)-1-[(N-pyridino[4,3-d]pyridin-3-ylcarbamoyloxy)methyl]but-3-enyl}{[(2-chloro-3-fluorophenyl)methyl]amino}-N-methylcarboxamide |
| 506.2 | N-{(1S)-3,4-dihydroxy-1-[(N-pyridino[4,3-d]pyridin-3-ylcarbamoyloxy)methyl]butyl}{[(2-chloro-3-fluorophenyl)methyl]amino}-N-methylcarboxamide |
| 517.1 | N-[(2S)-2-({[(2-chloro-3-fluorophenyl)methyl]amino}-N-methylcarbonylamino)-3-(N-(3-isoquinolyl)carbamoyloxy)propyl]-2-aminoacetamide |
| 611.2 | (5S)-5-({[(2-chloro-3-fluorophenyl)methyl]amino}-N-methylcarbonylamino)-6-(N-(3-isoquinolyl)carbamoyloxy)hexyl dimethyl phosphate |
| 583.2 | (5S)-5-({[(2-chloro-3-fluorophenyl)methyl]amino}-N-methylcarbonylamino)-6-(N-(3-isoquinolyl)carbamoyloxy)hexyl dihydrogen phosphate |
| 533.2 | methyl (5S)-5-({[(2,3-difluorophenyl)methyl]amino}-N-methylcarbonylamino)-6-[N-(6-fluoro(3-isoquinolyl))carbamoyloxy]hexanoate |
| 569.2 | (4S,2R)-4-({[(2,3-difluorophenyl)methyl]amino}-N-methylcarbonylamino)-2-hydroxy-5-(N-(3-isoquinolyl)carbamoyloxy)pentyl dihydrogen phosphate |
| 569.2 | (2S,4S)-4-({[(2,3-difluorophenyl)methyl]amino}-N-methylcarbonylamino)-2-hydroxy-5-(N-(3-isoquinolyl)carbamoyloxy)pentyl dihydrogen phosphate |
| 505.2 | [(2S)-2-({[(2,3-difluorophenyl)methyl]amino}-N-methylcarbonylamino)-6-hydroxyhexyloxy]-N-(6-fluoro(3-isoquinolyl))carboxamide |
| 613.1 | (5S)-5-({[(2,3-difluorophenyl)methyl]amino}-N-methylcarbonylamino)-6-[N-(6-fluoro(3-isoquinolyl))carbamoyloxy]hexyl dimethyl phosphate |
| 585.1 | (5S)-5-({[(2,3-difluorophenyl)methyl]amino}-N-methylcarbonylamino)-6-[N-(6-fluoro(3-isoquinolyl))carbamoyloxy]hexyl dihydrogen phosphate |
| 541.2 | [(2S)-2-({[(2,3-difluorophenyl)methyl]amino}-N-methylcarbonylamino)-4-oxo-4-piperazinylbutoxy]-N-(3-isoquinolyl)carboxamide |
| 557.2 | [(2S)-2-({[(2-chloro-3-fluorophenyl)methyl]amino}-N-methylcarbonylamino)-4-oxo-4-piperazinylbutoxy]-N-(3-isoquinolyl)carboxamide |
| 507.2 | [(2S,4S)-2-({[(2,3-difluorophenyl)methyl]amino}-N-methylcarbonylamino)-4,5-dihydroxypentyloxy]-N-(6-fluoro(3-isoquinolyl))carboxamide |
| 507.2 | [(2S,4R)-2-({[(2,3-difluorophenyl)methyl]amino}-N-methylcarbonylamino)-4,5-dihydroxypentyloxy]-N-(6-fluoro(3-isoquinolyl))carboxamide |
| 531.1 | methyl (5S)-5-({[(2,3-difluorophenyl)methyl]amino}-N-methylcarbonylamino)-6-[N-(5-phenylisoxazol-3-yl)carbamoyloxy]hexanoate |
| 515.2 | methyl (5R)-5-({[(2,3-difluorophenyl)methyl]amino}-N-methylcarbonylamino)-6-(N-(3-isoquinolyl)carbamoyloxy)hexanoate |

| m/z M + H | ChemicalName |
|---|---|
| 499.1 | methyl (5S)-5-({[(2,3-difluorophenyl)methyl]amino}-N-methylcarbonylamino)-6-[N-(5-chloro(2-pyridyl))carbamoyloxy]hexanoate |
| 490.5 | N-{(1S)-3,4-dihydroxy-1-[(N-quinazolin-2-ylcarbamoyloxy)methyl]butyl}{[(2,3-difluorophenyl)methyl]amino}-N-methylcarboxamide |
| 511.1 | [(2S,4R)-2-({[(2-chloro-3-fluorophenyl)methyl]amino}-N-methylcarbonylamino)-4,5-dihydroxypentyloxy]-N-benzothiazol-2-ylcarboxamide |
| 501.2 | methyl (4S)-4-({[(2,3-difluorophenyl)methyl]amino}-N-methylcarbonylamino)-5-(N-(3-isoquinolyl)carbamoyloxy)pentanoate |
| 519.2 | methyl (4S)-4-({[(2,3-difluorophenyl)methyl]amino}-N-methylcarbonylamino)-5-[N-(6-fluoro(3-isoquinolyl))carbamoyloxy]pentanoate |
| 473.2 | N-{(1S)-4-hydroxy-1-[(N-(3-isoquinolyl)carbamoyloxy)methyl]butyl}{[(2,3-difluorophenyl)methyl]amino}-N-methylcarboxamide |
| 491.2 | N-((1S)-1-{[N-(6-fluoro(3-isoquinolyl))carbamoyloxy]methyl}-4-hydroxybutyl){[(2,3-difluorophenyl)methyl]amino}-N-methylcarboxamide |
| 548.5 | methyl (5S)-5-({[(2,3-difluorophenyl)methyl]amino}-N-methylcarbonylamino)-6-[N-(5-phenyl(1,3,4-thiadiazol-2-yl))carbamoyloxy]hexanoate |
| 566.5 | methyl (5S)-5-({[(2,3-difluorophenyl)methyl]amino}-N-methylcarbonylamino)-6-{N-[5-(4-fluorophenyl)(1,3,4-thiadiazol-2-yl)]carbamoyloxy}hexanoate |
| 582.5 | methyl (5S)-5-({[(2,3-difluorophenyl)methyl]amino}-N-methylcarbonylamino)-6-{N-[5-(4-chlorophenyl)(1,3,4-thiadiazol-2-yl)]carbamoyloxy}hexanoate |
| 562.5 | methyl (5S)-5-({[(2,3-difluorophenyl)methyl]amino}-N-methylcarbonylamino)-6-{N-[5-(4-methylphenyl)(1,3,4-thiadiazol-2-yl)]carbamoyloxy}hexanoate |
| 578.5 | methyl (5S)-5-({[(2,3-difluorophenyl)methyl]amino}-N-methylcarbonylamino)-6-{N-[5-(4-methoxyphenyl)(1,3,4-thiadiazol-2-yl)]carbamoyloxy}hexanoate |
| 582.5 | methyl (5S)-5-({[(2,3-difluorophenyl)methyl]amino}-N-methylcarbonylamino)-6-{N-[5-(2-chlorophenyl)(1,3,4-thiadiazol-2-yl)]carbamoyloxy}hexanoate |
| 487.2 | [(2R)-2-({[(2,3-difluorophenyl)methyl]amino}-N-methylcarbonylamino)-6-hydroxyhexyloxy]-N-(3-isoquinolyl)carboxamide |
| 595.2 | (5R)-5-({[(2,3-difluorophenyl)methyl]amino}-N-methylcarbonylamino)-6-(N-3-isoquinolyl)carbamoyloxy)hexyl dimethyl phosphate |
| 567.5 | (5R)-5-({[(2,3-difluorophenyl)methyl]amino}-N-methylcarbonylamino)-6-(N-(3-isoquinolyl)carbamoyloxy)hexyl dihydrogen phosphate |
| 583.5 | (5S)-5-({[(2,3-difluorophenyl)methyl]amino}-N-methylcarbonylamino)-6-[N-(6-fluoro(3-isoquinolyl))carbamoyloxy]hexyl hydroxysulfonate |
| 523.5 | [(2R,4R)-2-({[(2-chloro-3-fluorophenyl)methyl]amino}-N-methylcarbonylamino)-4,5-dihydroxypentyloxy]-N-(6-fluoro(3-isoquinolyl))carboxamide |
| 549.4 | [(2R)-3-((4R)-2-oxo(1,3-dioxolan-4-yl))-2-({[(2-chloro-3-fluorophenyl)methyl]amino}-N-methylcarbonylamino)propoxy]-N-(6-fluoro(3-isoquinolyl))carboxamide |
| 559.2 | [(2S)-2-({[(2,3-difluorophenyl)methyl]amino}-N-methylcarbonylamino)-4-oxo-4-piperazinylbutoxy]-N-(6-fluoro(3-isoquinolyl))carboxamide |
| 571.5 | (4S)-4-({[(2,3-difluorophenyl)methyl]amino}-N-methylcarbonylamino)-5-[N-(6-fluoro(3-isoquinolyl))carbamoyloxy]pentyl dihydrogen phosphate |
| 487.4 | (4S)-4-({[(2,3-difluorophenyl)methyl]amino}-N-methylcarbonylamino)-5-(N-(3-isoquinolyl)carbamoyloxy)pentanoic acid |
| 505.5 | (4S)-4-({[(2,3-difluorophenyl)methyl]amino}-N-methylcarbonylamino)-5-[N-(6-fluoro(3-isoquinolyl))carbamoyloxy]pentanoic acid |
| 655.7 | tert-butyl 4-[(4S)-4-({[(2,3-difluorophenyl)methyl]amino}-N-methylcarbonylamino)-5-(N-(3-isoquinolyl)carbamoyloxy)pentanoyl]piperazinecarboxylate |
| 673.7 | tert-butyl 4-[(4S)-4-({[(2,3-difluorophenyl)methyl]amino}-N-methylcarbonylamino)-5-[N-(6-fluoro(3-isoquinolyl))carbamoyloxy]pentanoyl]piperazinecarboxylate |
| 533.1 | methyl (5S)-5-({[(2,3-difluorophenyl)methyl]amino}-N-methylcarbonylamino)-6-{N-[5-(trifluoromethyl)(2-pyridyl)]carbamoyloxy}hexanoate |
| 627.5 | methyl (5S)-5-({[(2,3-difluorophenyl)methyl]amino}-N-methylcarbonylamino)-6-{N-[5-(4-bromophenyl)(1,3,4-thiadiazol-2-yl)]carbamoyloxy}hexanoate |
| 573.5 | methyl (5S)-5-({[(2,3-difluorophenyl)methyl]amino}-N-methylcarbonylamino)-6-{N-[5-(4-cyanophenyl)(1,3,4-thiadiazol-2-yl)]carbamoyloxy}hexanoate |

| m/z M + H | ChemicalName |
|---|---|
| 566.5 | methyl (5S)-5-({[(2,3-difluorophenyl)methyl]amino}-N-methylcarbonylamino)-6-{N-[5-(2-fluorophenyl)(1,3,4-thiadiazol-2-yl)]carbamoyloxy}hexanoate |
| 553.4 | (4S)-4-({[(2,3-difluorophenyl)methyl]amino}-N-methylcarbonylamino)-5-(N-(3-isoquinolyl)carbamoyloxy)pentyl dihydrogen phosphate |
| 601.5 | (4S)-4-({[(2-chloro-3-fluorophenyl)methyl]amino}-N-methylcarbonylamino)-5-[N-(6-fluoro(3-isoquinolyl))carbamoyloxy]-2-hydroxypentyl hydroxysulfonate |
| 503.1 | N-((1S)-5-hydroxy-1-{[N-(5-phenylisoxazol-3-yl)carbamoyloxy]methyl}pentyl){[(2,3-difluorophenyl)methyl]amino}-N-methylcarboxamide |
| 603.1 | (2S,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 603.1 | (2R,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl dihydrogen phosphate |
| 523.2 | N-((3S,1R)-1-{[N-(6-fluoro(3-isoquinolyl))carbamoyloxy]methyl}-3,4-dihydroxybutyl){[(2-chloro-3-fluorophenyl)methyl]amino}-N-methylcarboxamide |
| 549.2 | N-{(1R)-1-[((4S)-2-oxo(1,3-dioxolan-4-yl)]methyl]-2-[N-(6-fluoro(3-isoquinolyl))carbamoyloxy]ethyl}{[(2-chloro-3-fluorophenyl)methyl]amino}-N-methylcarboxamide |
| 555.4 | N-{(1S)-1-[(N-(3-isoquinolyl)carbamoyloxy)methyl]-4-oxo-4-piperazinylbutyl}{[(2,3-difluorophenyl)methyl]amino}-N-methylcarboxamide |
| 573.4 | N-((1S)-1-{[N-(6-fluoro(3-isoquinolyl))carbamoyloxy]methyl}-4-oxo-4-piperazinylbutyl){[(2,3-difluorophenyl)methyl]amino}-N-methylcarboxamide |
| 511.2 | methyl (5S)-5-({[(2,3-difluorophenyl)methyl]amino}-N-methylcarbonylamino)-6-{N-[5-(tert-butyl)isoxazol-3-yl]carbamoyloxy}hexanoate |
| 587.2 | (4S,2R)-4-({[(2,3-difluorophenyl)methyl]amino}-N-methylcarbonylamino)-5-[N-(6-fluoro(3-isoquinolyl))carbamoyloxy]-2-hydroxypentyl dihydrogen phosphate |
| 495.1 | ({(1S,3R)-1-[(N-benzoxazol-2-ylcarbamoyloxy)methyl]-3,4-dihydroxybutyl}methylamino)-N-[(2-chloro-3-fluorophenyl)methyl]carboxamide |
| 529.1 | [((1S,3R)-1-{[N-(5-chlorobenzoxazol-2-yl)carbamoyloxy]methyl}-3,4-dihydroxybutyl)methylamino]-N-[(2-chloro-3-fluorophenyl)methyl]carboxamide |
| 545.1 | methyl (5S)-5-({N-[(2,3-difluorophenyl)methyl]carbamoyl}methylamino)-6-{N-[5-(4-methylphenyl)isoxazol-3-yl]carbamoyloxy}hexanoate |
| 561.1 | N-{1-[((4R)-2,2-dimethyl(1,3-dioxolan-4-yl))methyl](1S)-2-[N-(5-phenylisoxazol-3-yl)carbamoyloxy]ethyl}{[(2-chloro-3-fluorophenyl)methyl]amino}-N-methylcarboxamide |
| 521.1 | N-((1S,3R)-3,4-dihydroxy-1-{[N-(5-phenylisoxazol-3-yl)carbamoyloxy]methyl}butyl){[(2-chloro-3-fluorophenyl)methyl]amino}-N-methylcarboxamide |
| 523.1 | methyl (5S)-5-({[(2,3-difluorophenyl)methyl]amino}-N-methylcarbonylamino)-6-{N-[5-(trifluoromethyl)isoxazol-3-yl]carbamoyloxy}hexanoate |
| 625.2 | (2S,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl diethyl phosphate |
| 625.2 | (2R,4R)-4-({[(2-chloro-3-fluorophenyl)methyl]amino}-N-methylcarbonylamino)-5-[N-(6-fluoro(3-isoquinolyl))carbamoyloxy]-2-hydroxypentyl diethyl phosphate |
| 761.7 | (3S,1R)-3-({[(2,3-difluorophenyl)methyl]amino}-N-methylcarbonylamino)-1-[(ethoxyphosphinyl)methyl]-4-(N-(3-isoquinolyl)carbamoyloxy)butyl diethyl phosphate |
| 625.6 | (4S,2R)-4-({[(2,3-difluorophenyl)methyl]amino}-N-methylcarbonylamino)-2-hydroxy-5-(N-(3-isoquinolyl)carbamoyloxy)pentyl diethyl phosphate |
| 537.1 | N-((1S)-1-{[N-(6-fluoro(3-isoquinolyl))carbamoyloxy]methyl}-4-hydroxy-3-(hydroxymethyl)butyl){[(2-chloro-3-fluorophenyl)methyl]amino}-N-methylcarboxamide |
| 549.1 | methyl (5S)-5-({[(2,3-difluorophenyl)methyl]amino}-N-methylcarbonylamino)-6-{N-[5-(4-fluorophenyl)isoxazol-3-yl]carbamoyloxy}hexanoate |
| 609.1 | methyl (5S)-5-({[(2,3-difluorophenyl)methyl]amino}-N-methylcarbonylamino)-6-{N-[5-(4-bromophenyl)isoxazol-3-yl]carbamoyloxy}hexanoate |

| m/z M + H | ChemicalName |
| --- | --- |
| 521.1 | N-[(1S)-1-({N-[5-(4-fluorophenyl)isoxazol-3-yl]carbamoyloxy}methyl)-5-hydroxypentyl]{[(2,3-difluorophenyl)methyl]amino}-N-methylcarboxamide |
| 581.1 | N-[(1S)-1-({N-[3-(4-bromophenyl)isoxazol-5-yl]carbamoyloxy}methyl)-5-hydroxypentyl]{[(2,3-difluorophenyl)methyl]amino}-N-methylcarboxamide |
| 528.1 | N-[(1S)-1-({N-[3-(4-cyanophenyl)isoxazol-5-yl]carbamoyloxy}methyl)-5-hydroxypentyl]{[(2,3-difluorophenyl)methyl]amino}-N-methylcarboxamide |
| 531.1 | methyl (5S)-5-({[(2,3-difluorophenyl)methyl]amino}-N-methylcarbonylamino)-6-[N-(3-phenylisoxazol-5-yl)carbamoyloxy]hexanoate |
| 503.1 | N-((1S)-5-hydroxy-1-{[N-(3-phenylisoxazol-5-yl)carbamoyloxy]methyl}pentyl){[(2,3-difluorophenyl)methyl]amino}-N-methylcarboxamide |
| 685.6 | [(2S)-5-({[[(tert-butoxy)carbonylamino]sulfonyl}amino)-2-({[(2-chloro-3-fluorophenyl)methyl]amino}-N-methylcarbonylamino)pentyloxy]-N-(6-fluoro(3-isoquinolyl))carboxamide |
| 585.5 | N-((1S)-1-{[N-(6-fluoro(3-isoquinolyl))carbamoyloxy]methyl}-4-(sulfamoylamino)butyl){[(2-chloro-3-fluorophenyl)methyl]amino}-N-methylcarboxamide |
| 564.5 | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2-hydroxyacetamide |
| 594.0 | N-[(4S)-4-({[(2-chloro-3-fluorophenyl)methyl]amino}-N-methylcarbonylamino)-5-[N-(6-fluoro(3-isoquinolyl))carbamoyloxy]pentyl]-2,3-dihydroxypropanamide |
| 613.5 | N-((1S)-4-{[(dimethylamino)sulfonyl]amino}-1-{[N-(6-fluoro(3-isoquinolyl))carbamoyloxy]methyl}butyl){[(2-chloro-3-fluorophenyl)methyl]amino}-N-methylcarboxamide |
| 612.5 | N-((1S)-1-{[N-(6-fluoro(3-isoquinolyl))carbamoyloxy]methyl}-4-[(propylsulfonyl)amino]butyl){[(2-chloro-3-fluorophenyl)methyl]amino}-N-methylcarboxamide |
| 543.5 | N-((1S)-3,3-difluoro-1-{[N-(6-fluoro(3-isoquinolyl))carbamoyloxy]methyl}-4-hydroxybutyl){[(2-chloro-3-fluorophenyl)methyl]amino}-N-methylcarboxamide |
| 583.2 | (5S)-5-({[(2,3-difluorophenyl)methyl]amino}-N-methylcarbonylamino)-6-[N-(5-phenylisoxazol-3-yl)carbamoyloxy]hexyl dihydrogen phosphate |
| 539.5 | [(2S,4R)-2-({[(2-chloro-3-fluorophenyl)methyl]amino}-N-methylcarbonylamino)-4,5-dihydroxypentyloxy]-N-(5,6-dimethylbenzothiazol-2-yl)carboxamide |
| 617.6 | N-[4-({(1E)-2-cyano-1-[(2-hydroxyethyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 591.4 | (4S,2R)-5-(N-benzothiazol-2-ylcarbamoyloxy)-4-({[(2-chloro-3-fluorophenyl)methyl]amino}-N-methylcarbonylamino)-2-hydroxypentyl dihydrogen phosphate |
| 599.6 | N-[4-({(1E)-2-cyano-1-[(2-hydroxyethyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| 613.6 | N-[4-({(1E)-2-cyano-1-[(3-hydroxypropyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| 525.4 | [(2S,4R)-2-({[(2-chloro-3-fluorophenyl)methyl]amino}-N-methylcarbonylamino)-4,5-dihydroxypentyloxy]-N-(6-methylbenzothiazol-2-yl)carboxamide |
| 629.6 | N-{4-[((1E)-2-cyano-1-{[2-hydroxy-1-(hydroxymethyl)ethyl]amino}-2-azavinyl)amino](1S)-1-[(N-(3-isoquinolyl)carbamoyloxy)methyl]butyl}{[(2-chloro-3-fluorophenyl)methyl]amino}-N-methylcarboxamide |
| 651.5 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl dimethyl phosphate |
| 672.6 | {N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}methyl dimethyl phosphate |
| 623.5 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl dihydrogen phosphate |
| 657.6 | (4S,2R)-4-({[(2-chloro-3-fluorophenyl)methyl]amino}-N-methylcarbonylamino)-2-hydroxy-5-[N-(5-phenylisoxazol-3-yl)carbamoyloxy]pentyl diethyl phosphate |
| 599.4 | (4S,2R)-4-({[(2-chloro-3-fluorophenyl)methyl]amino}-N-methylcarbonylamino)-2-hydroxy-5-[N-(5-phenylisoxazol-3-yl)carbamoyloxy]pentyl dihydrogen phosphate |

-continued

| m/z M + H | ChemicalName |
|---|---|
| 546.4 | [(2S,4R)-2-({[(2-chloro-3-fluorophenyl)methyl]amino}-N-methylcarbonylamino)-4,5-dihydroxypentyloxy]-N-(6-chlorobenzothiazol-2-yl)carboxamide |
| 529.4 | [(2S,4R)-2-({[(2-chloro-3-fluorophenyl)methyl]amino}-N-methylcarbonylamino)-4,5-dihydroxypentyloxy]-N-(6-fluorobenzothiazol-2-yl)carboxamide |
| 547.4 | [(2S,4R)-2-({[(2-chloro-3-fluorophenyl)methyl]amino}-N-methylcarbonylamino)-4,5-dihydroxypentyloxy]-N-(5,6-difluorobenzothiazol-2-yl)carboxamide |
| 535.1 | [(2S)-2-({[(2-chloro-3-fluorophenyl)methyl]amino}-N-methylcarbonylamino)-5-hydroxy-4,4-dimethylpentyloxy]-N-(6-fluoro(3-isoquinolyl))carboxamide |
| 615.5 | (4S)-4-({[(2-chloro-3-fluorophenyl)methyl]amino}-N-methylcarbonylamino)-5-[N-(6-fluoro(3-isoquinolyl))carbamoyloxy]-2,2-dimethylpentyl dihydrogen phosphate |
| 537.2 | N-[(1S)-1-({N-[5-(4-chlorophenyl)isoxazol-3-yl]carbamoyloxy}methyl)-5-hydroxypentyl]{[(2,3-difluorophenyl)methyl]amino}-N-methylcarboxamide |
| 537.2 | N-[(1S)-1-({N-[5-(2-chlorophenyl)isoxazol-3-yl]carbamoyloxy}methyl)-5-hydroxypentyl]{[(2,3-difluorophenyl)methyl]amino}-N-methylcarboxamide |
| 521.1 | N-[(1S)-1-({N-[5-(3-fluorophenyl)isoxazol-3-yl]carbamoyloxy}methyl)-5-hydroxypentyl]{[(2,3-difluorophenyl)methyl]amino}-N-methylcarboxamide |
| 561.1 | N-{1-[((4R)-2,2-dimethyl(1,3-dioxolan-4-yl))methyl](1S)-2-[N-(3-phenylisoxazol-5-yl)carbamoyloxy]ethyl}{[(2-chloro-3-fluorophenyl)methyl]amino}-N-methylcarboxamide |
| 521.1 | N-((1S,3R)-3,4-dihydroxy-1-{[N-(3-phenylisoxazol-5-yl)carbamoyloxy]methyl}butyl){[(2-chloro-3-fluorophenyl)methyl]amino}-N-methylcarboxamide |
| 544.2 | methyl (5S)-5-({[(2,3-difluorophenyl)methyl]amino}-N-methylcarbonylamino)-6-[N-(1-methyl-5-phenylpyrazol-3-yl)carbamoyloxy]hexanoate |
| 544.2 | methyl (5S)-5-({[(2,3-difluorophenyl)methyl]amino}-N-methylcarbonylamino)-6-[N-(1-methyl-3-phenylpyrazol-5-yl)carbamoyloxy]hexanoate |
| 516.2 | N-((1S)-5-hydroxy-1-{[N-(1-methyl-5-phenylpyrazol-3-yl)carbamoyloxy]methyl}pentyl){[(2,3-difluorophenyl)methyl]amino}-N-methylcarboxamide |
| 516.2 | N-((1S)-5-hydroxy-1-{[N-(1-methyl-3-phenylpyrazol-5-yl)carbamoyloxy]methyl}pentyl){[(2,3-difluorophenyl)methyl]amino}-N-methylcarboxamide |
| 562.1 | N-{1-[((4R)-2,2-dimethyl(1,3-dioxolan-4-yl))methyl](1S)-2-[N-(5-phenyl(1,2,4-oxadiazol-3-yl))carbamoyloxy]ethyl}{[(2-chloro-3-fluorophenyl)methyl]amino}-N-methylcarboxamide |
| 522.4 | N-((1S,3R)-3,4-dihydroxy-1-{[N-(5-phenyl(1,2,4-oxadiazol-3-yl))carbamoyloxy]methyl}butyl){[(2-chloro-3-fluorophenyl)methyl]amino}-N-methylcarboxamide |
| 635.6 | ethyl 2-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)acetate |
| 537.2 | N-[(1S)-1-({N-[5-(3-chlorophenyl)isoxazol-3-yl]carbamoyloxy}methyl)-5-hydroxypentyl]{[(2,3-difluorophenyl)methyl]amino}-N-methylcarboxamide |
| 545.1 | methyl (5S)-5-({[(2,3-difluorophenyl)methyl]amino}-N-methylcarbonylamino)-6-[N-(4-methyl-3-phenylisoxazol-5-yl)carbamoyloxy]hexanoate |
| 697.6 | 2-[(((1E)-1-{[(4S)-4-({[(2-chloro-3-fluorophenyl)methyl]amino}-N-methylcarbonylamino)-5-(N-(3-isoquinolyl)carbamoyloxy)pentyl]amino}-2-carbamoyl-2-azavinyl)amino]ethyl dihydrogen phosphate |
| 593.6 | [(2S)-2-({[(2-chloro-3-fluorophenyl)methyl]amino}-N-methylcarbonylamino)-5-{[(2-hydroxyethyl)amino]carbonylamino}pentyloxy]-N-(6-fluoro(3-isoquinolyl))carboxamide |
| 545.1 | N-{1-[((4R)-2,2-dimethyl(1,3-dioxolan-4-yl))methyl](1S)-2-[N-(5-phenylisoxazol-3-yl)carbamoyloxy]ethyl}{[(2,3-difluorophenyl)methyl]amino}-N-methylcarboxamide |
| 505.1 | N-((1S,3R)-3,4-dihydroxy-1-{[N-(5-phenylisoxazol-3-yl)carbamoyloxy]methyl}butyl){[(2,3-difluorophenyl)methyl]amino}-N-methylcarboxamide |
| 641.6 | (4S,2R)-4-({[(2,3-difluorophenyl)methyl]amino}-N-methylcarbonylamino)-2-hydroxy-5-[N-(5-phenylisoxazol-3-yl)carbamoyloxy]pentyl diethyl phosphate |

| m/z M + H | ChemicalName |
|---|---|
| 777.2 | (3S,1R)-3-({[(2,3-difluorophenyl)methyl]amino}-N-methylcarbonylamino)-1-[(ethoxyphosphinyl)methyl]-4-[N-(5-phenylisoxazol-3-yl)carbamoyloxy]butyl diethyl phosphate |
| 585.5 | (4S,2R)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate |
| 583.5 | (4S,2R)-4-({[(2,3-difluorophenyl)methyl]amino}-N-methylcarbonylamino)-2-hydroxy-5-[N-(5-phenylisoxazol-3-yl)carbamoyloxy]pentyl dihydrogen phosphate |
| 673.6 | 2-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)ethyl dihydrogen phosphate |
| 539.1 | N-[(1S,3R)-1-({N-[5-(3-fluorophenyl)isoxazol-3-yl]carbamoyloxy}methyl)-3,4-dihydroxybutyl]{[(2-chloro-3-fluorophenyl)methyl]amino}-N-methylcarboxamide |
| 579.1 | N-(1-[((4R)-2,2-dimethyl(1,3-dioxolan-4-yl))methyl](1S)-2-{N-[5-(3-fluorophenyl)isoxazol-3-yl]carbamoyloxy}ethyl){[(2-chloro-3-fluorophenyl)methyl]amino}-N-methylcarboxamide |
| 523.2 | N-{(1S)-2-[N-(6-fluoro(3-isoquinolyl))carbamoyloxy]-1-[(2-hydroxyethoxy)methyl]ethyl}{[(2-chloro-3-fluorophenyl)methyl]amino}-N-methylcarboxamide |
| 603.2 | 2-[(2S)-2-({[(2-chloro-3-fluorophenyl)methyl]amino}-N-methylcarbonylamino)-3-[N-(6-fluoro(3-isoquinolyl))carbamoyloxy]propoxy]ethyl dihydrogen phosphate |
| 607.1 | N-[(4S)-4-({[(2-chloro-3-fluorophenyl)methyl]amino}-N-methylcarbonylamino)-5-[N-(6-fluoro(3-isoquinolyl))carbamoyloxy]pentyl][(3-hydroxypropyl)amino]carboxamide |
| 625.5 | (4S,2R)-5-[N-(6-chlorobenzothiazol-2-yl)carbamoyloxy]-4-({[(2-chloro-3-fluorophenyl)methyl]amino}-N-methylcarbonylamino)-2-hydroxypentyl dihydrogen phosphate |
| 617.6 | N-[4-({(1E)-2-carbamoyl-1-[(2-hydroxyethyl)amino]-2-azavinyl}amino)(1S)-1-[(N-(3-isoquinolyl)carbamoyloxy)methyl]butyl]{[(2-chloro-3-fluorophenyl)methyl]amino}-N-methylcarboxamide |
| 635.6 | N-[4-({(1E)-2-carbamoyl-1-[(2-hydroxyethyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 659.7 | N-[4-({(1E)-2-cyano-1-[(3-hydroxy-2,2-dimethylpropyl)amino]-2-azavinyl}amino)(1S)-1-{[N-(6-fluoro(3-isoquinolyl))carbamoyloxy]methyl}butyl]{[(2-chloro-3-fluorophenyl)methyl]amino}-N-methylcarboxamide |
| 631.5 | 2-[(2S)-2-({[(2-chloro-3-fluorophenyl)methyl]amino}-N-methylcarbonylamino)-3-[N-(6-fluoro(3-isoquinolyl))carbamoyloxy]propoxy]ethyl dimethyl phosphate |
| 675.1 | (4S,2R)-4-({[(2-chloro-3-fluorophenyl)methyl]amino}-N-methylcarbonylamino)-5-{N-[5-(3-fluorophenyl)isoxazol-3-yl]carbamoyloxy}-2-hydroxypentyl diethyl phosphate |
| 617.5 | (4S,2R)-4-({[(2-chloro-3-fluorophenyl)methyl]amino}-N-methylcarbonylamino)-5-{N-[5-(3-fluorophenyl)isoxazol-3-yl]carbamoyloxy}-2-hydroxypentyl dihydrogen phosphate |
| 609.4 | (4S,2R)-4-({[(2-chloro-3-fluorophenyl)methyl]amino}-N-methylcarbonylamino)-5-[N-(6-fluorobenzothiazol-2-yl)carbamoyloxy]-2-hydroxypentyl dihydrogen phosphate |
| 743.7 | 3-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)-2,2-dimethylpropyl dimethyl phosphate |
| 715.7 | 3-({N-[(4S)-4-({[(2-chloro-3-fluorophenyl)methyl]amino}-N-methylcarbonylamino)-5-[N-(6-fluoro(3-isoquinolyl))carbamoyloxy]pentyl]carbamoyl}amino)-2,2-dimethylpropyl dihydrogen phosphate |
| 601.5 | (4S,2R)-4-({[(2-chloro-3-fluorophenyl)methyl]amino}-N-methylcarbonylamino)-2-hydroxy-5-[N-(3-phenylisoxazol-5-yl)carbamoyloxy]pentyl dihydrogen phosphate |
| 565.6 | N-{(1S)-2-[N-(6-fluoro(3-isoquinolyl))carbamoyloxy]-1-[(3-hydroxy-2,2-dimethylpropoxy)methyl]ethyl}{[(2-chloro-3-fluorophenyl)methyl]amino}-N-methylcarboxamide |
| 647.6 | N-[4-({(1E)-cyano-1-[(3-hydroxy-2,2-dimethylpropyl)amino]-2-azavinyl}amino)(1S)-1-[(N-benzothiazol-2-ylcarbamoyloxy)methyl]butyl]{[(2-chloro-3-fluorophenyl)methyl]amino}-N-methylcarboxamide |
| 605.5 | N-[4-({(1E)-2-cyano-1-[(2-hydroxyethyl)amino]-2-azavinyl}amino)(1S)-1-[(N-benzothiazol-2-ylcarbamoyloxy)methyl]butyl]{[(2-chloro-3-fluorophenyl)methyl]amino}-N-methylcarboxamide |

| m/z M + H | ChemicalName |
|---|---|
| 529.5 | N-{1-[((4R)-2,2-dimethyl(1,3-dioxolan-4-yl))methyl](1S)-2-(N-(3-isoquinolyl)carbamoyloxy)ethyl}{[(2,3-difluorophenyl)methyl]amino}-N-methylcarboxamide |
| 595.1 | N-(1-[((4R)-2,2-dimethyl(1,3-dioxolan-4-yl))methyl](1S)-2-{N-[5-(3-chlorophenyl)isoxazol-3-yl]carbamoyloxy}ethyl){[(2-chloro-3-fluorophenyl)methyl]amino}-N-methylcarboxamide |
| 555.5 | N-[(1S,3R)-1-({N-[5-(3-chlorophenyl)isoxazol-3-yl]carbamoyloxy}methyl)-3,4-dihydroxybutyl]{[(2-chloro-3-fluorophenyl)methyl]amino}-N-methylcarboxamide |
| 643.5 | 3-[(2S)-2-({[(2-chloro-3-fluorophenyl)methyl]amino}-N-methylcarbonylamino)-3-[N-(6-fluoro-3-isoquinolyl))carbamoyloxy]propoxy]-2,2-dimethylpropyl dihydrogen phosphate |
| 635.5 | (4S,2R)-4-({[(2-chloro-3-fluorophenyl)methyl]amino}-N-methylcarbonylamino)-5-{N-[5-(3-chlorophenyl)isoxazol-3-yl]carbamoyloxy}-2-hydroxypentyl dihydrogen phosphate |
| 472.5 | N-{(1S)-4-amino-1-[(N-(3-isoquinolyl)carbamoyloxy)methyl]butyl}{[(2,3-difluorophenyl)methyl]amino}-N-methylcarboxamide |
| 490.5 | N-((1S)-4-amino-1-{[N-(6-fluoro(3-isoquinolyl))carbamoyloxy]methyl}butyl){[(2,3-difluorophenyl)methyl]amino}-N-methylcarboxamide |
| 603.6 | N-{1-[({(1E)-2-cyano-1-[(3-hydroxypropyl)amino]-2-azavinyl}amino)methyl](1S)-2-[N-(6-fluoro(3-isoquinolyl))carbamoyloxy]ethyl}{[(2-chloro-3-fluorophenyl)methyl]amino}-N-methylcarboxamide |
| 504.5 | N-{(1S)-1-[(N-benzothiazol-2-ylcarbamoyloxy)methyl]-5-diazo-5-azapent-5-enyl}{[(2,3-difluorophenyl)methyl]amino}-N-methylcarboxamide |
| 478.1 | N-{(1S)-4-amino-1-[(N-benzothiazol-2-ylcarbamoyloxy)methyl]butyl}{[(2,3-difluorophenyl)methyl]amino}-N-methylcarboxamide |
| 516.5 | N-((1S)-5-diazo-1-{[N-(6-fluoro(3-isoquinolyl))carbamoyloxy]methyl}-5-azapent-5-enyl){[(2,3-difluorophenyl)methyl]amino}-N-methylcarboxamide |
| 626.5 | 2-[(4S)-4-({[(2-chloro-3-fluorophenyl)methyl]amino}-N-methylcarbonylamino)-5-(N-(3-isoquinolyl)carbamoyloxy)pentanoylamino]ethyl dihydrogen phosphate |
| 668.6 | 3-[(4S)-4-({[(2-chloro-3-fluorophenyl)methyl]amino}-N-methylcarbonylamino)-5-(N-(3-isoquinolyl)carbamoyloxy)pentanoylamino]-2,2-dimethylpropyl dihydrogen phosphate |
| 587.2 | 3-{[(5S)-5-({[(2,3-difluorophenyl)methyl]amino}-N-methylcarbonylamino)-6-(N-(3-isoquinolyl)carbamoyloxy)hexyl]oxycarbonyl}propanoic acid |
| 546.0 | (4S)-4-({[(2-chloro-3-fluorophenyl)methyl]amino}-N-methylcarbonylamino)-N-(2-hydroxyethyl)-5-(N-(3-isoquinolyl)carbamoyloxy)pentanamide |
| 635.2 | N-[(4S)-4-({[(2-chloro-3-fluorophenyl)methyl]amino}-N-methylcarbonylamino)-5-[N-(6-fluoro(3-isoquinolyl))carbamoyloxy]pentyl][(3-hydroxy-2,2-dimethylpropyl)amino]carboxamide |
| 560.0 | (4S)-4-({[(2-chloro-3-fluorophenyl)methyl]amino}-N-methylcarbonylamino)-N-(3-hydroxypropyl)-5-(N-(3-isoquinolyl)carbamoyloxy)pentanamide |
| 588.0 | (4S)-4-({[(2-chloro-3-fluorophenyl)methyl]amino}-N-methylcarbonylamino)-N-(3-hydroxy-2,2-dimethylpropyl)-5-(N-(3-isoquinolyl)carbamoyloxy)pentanamide |
| 560.0 | (4S)-N-((2S)-2-hydroxypropyl)-4-({[(2-chloro-3-fluorophenyl)methyl]amino}-N-methylcarbonylamino)-5-(N-(3-isoquinolyl)carbamoyloxy)pentanamide |
| 560.0 | N-((2R)-2-hydroxypropyl)(4S)-4-({[(2-chloro-3-fluorophenyl)methyl]amino}-N-methylcarbonylamino)-5-(N-(3-isoquinolyl)carbamoyloxy)pentanamide |
| 553.1 | N-{(1S)-1-[((2S)-2,3-dihydroxypropoxy)methyl]-2-[N-(6-fluoro(3-isoquinolyl))carbamoyloxy]ethyl}{[(2-chloro-3-fluorophenyl)methyl]amino}-N-methylcarboxamide |
| 738.6 | 2-[(4S)-4-({[(2-chloro-3-fluorophenyl)methyl]amino}-N-methylcarbonylamino)-5-(N-(3-isoquinolyl)carbamoyloxy)pentanoylamino]ethyl ditert-butyl phosphate |
| 615.7 | [(2S)-2-({[(2-chloro-3-fluorophenyl)methyl]amino}-N-methylcarbonylamino)-5-[4-(2-hydroxyethyl)piperazinyl]-5-oxopentyloxy]-N-(3-isoquinolyl)carboxamide |
| 504.2 | N-((1S)-3-carbamoyl-1-{[N-(6-fluoro(3-isoquinolyl))carbamoyloxy]methyl}propyl){[(2,3-difluorophenyl)methyl]amino}-N-methylcarboxamide |

| m/z M + H | ChemicalName |
| --- | --- |
| 504.5 | N-((1S)-4-amino-1-{[N-(3-phenylisoxazol-5-yl)carbamoyloxy]methyl}butyl){[(2-chloro-3-fluorophenyl)methyl]amino}-N-methylcarboxamide |
| 523.5 | methyl (4S)-5-(N-benzothiazol-2-ylcarbamoyloxy)-4-({[(2-chloro-3-fluorophenyl)methyl]amino}-N-methylcarbonylamino)pentanoate |
| 699.5 M + Na+ | tert-butyl 4-[(4S)-5-(N-benzothiazol-2-ylcarbamoyloxy)-4-({[(2-chloro-3-fluorophenyl)methyl]amino}-N-methylcarbonylamino)pentanoyl]piperazinecarboxylate |
| 687.2 | tert-butyl 4-[(4S)-4-({[(2-chloro-3-fluorophenyl)methyl]amino}-N-methylcarbonylamino)-5-[N-(3-phenylisoxazol-5-yl)carbamoyloxy]pentanoyl]piperazinecarboxylate |
| 587.2 | N-((1S)-4-oxo-1-{[N-(3-phenylisoxazol-5-yl)carbamoyloxy]methyl}-4-piperazinylbutyl){[(2-chloro-3-fluorophenyl)methyl]amino}-N-methylcarboxamide |
| 577.1 | N-{(1S)-1-[(N-benzothiazol-2-ylcarbamoyloxy)methyl]-4-oxo-4-piperazinylbutyl}{[(2-chloro-3-fluorophenyl)methyl]amino}-N-methylcarboxamide |
| 687.2 | tert-butyl 4-[(4S)-4-({[(2-chloro-3-fluorophenyl)methyl]amino}-N-methylcarbonylamino)-5-[N-(5-phenylisoxazol-3-yl)carbamoyloxy]pentanoyl]piperazinecarboxylate |
| 587.2 | N-((1S)-4-oxo-1-{[N-(5-phenylisoxazol-3-yl)carbamoyloxy]methyl}-4-piperazinylbutyl){[(2-chloro-3-fluorophenyl)methyl]amino}-N-methylcarboxamide |
| 695.7 | 2-{4-[(4S)-4-({[(2-chloro-3-fluorophenyl)methyl]amino}-N-methylcarbonylamino)-5-(N-(3-isoquinolyl)carbamoyloxy)pentanoyl]piperazinyl}ethyl dihydrogen phosphate |
| 723.7 | 2-{4-[(4S)-4-({[(2-chloro-3-fluorophenyl)methyl]amino}-N-methylcarbonylamino)-5-(N-(3-isoquinolyl)carbamoyloxy)pentanoyl]piperazinyl}ethyl dimethyl phosphate |
| 633.6 | ethyl 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)acetate |
| 507.4 | (4S)-5-(N-benzothiazol-2-ylcarbamoyloxy)-4-({[(2-chloro-3-fluorophenyl)methyl]amino}-N-methylcarbonylamino)pentanoic acid |
| 591.6 | N-[(4S)-4-({[(2-chloro-3-fluorophenyl)methyl]amino}-N-methylcarbonylamino)-5-[N-(3-phenylisoxazol-5-yl)carbamoyloxy]pentyl][(2-hydroxyethyl)amino]carboxamide |
| 535.1 | N-{(1S)-1-[((2S)-2,3-dihydroxypropoxy)methyl]-2-(N-(3-isoquinolyl)carbamoyloxy)ethyl}{[(2-chloro-3-fluorophenyl)methyl]amino}-N-methylcarboxamide |
| 517.1 | methyl (4S)-4-({[(2,3-difluorophenyl)methyl]amino}-N-methylcarbonylamino)-5-[N-(5-phenylisoxazol-3-yl)carbamoyloxy]pentanoate |
| 517.1 | methyl (4S)-4-({[(2,3-difluorophenyl)methyl]amino}-N-methylcarbonylamino)-5-[N-(3-phenylisoxazol-5-yl)carbamoyloxy]pentanoate |
| 699.6 | 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)ethyl dimethyl phosphate |
| 669.5 | 2-({N-[(4S)-4-({[(2-chloro-3-fluorophenyl)methyl]amino}-N-methylcarbonylamino)-5-[N-(3-phenylisoxazol-5-yl)carbamoyloxy]pentyl]carbamoyl}amino)ethyl dihydrogen phosphate |
| 617.6 | ethyl 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino)acetate |
| 671.2 | tert-butyl 4-[(4S)-4-({[(2,3-difluorophenyl)methyl]amino}-N-methylcarbonylamino)-5-[N-(5-phenylisoxazol-3-yl)carbamoyloxy]pentanoyl]piperazinecarboxylate |
| 571.2 | [(2S)-2-({[(2,3-difluorophenyl)methyl]amino}-N-methylcarbonylamino)-5-oxo-5-piperazinylpentyloxy]-N-(5-phenylisoxazol-3-yl)carboxamide |
| 671.2 | tert-butyl 4-[(4S)-4-({[(2,3-difluorophenyl)methyl]amino}-N-methylcarbonylamino)-5-[N-(3-phenylisoxazol-5-yl)carbamoyloxy]pentanoyl]piperazinecarboxylate |
| 571.2 | [(2S)-2-({[(2,3-difluorophenyl)methyl]amino}-N-methylcarbonylamino)-5-oxo-5-piperazinylpentyloxy]-N-(3-phenylisoxazol-5-yl)carboxamide |
| 505.2 | N-{(1S)-1-[(2-hydroxyethoxy)methyl]-2-(N-(3-isoquinolyl)carbamoyloxy)ethyl}{[(2-chloro-3-fluorophenyl)methyl]amino}-N-methylcarboxamide |
| 585.2 | 2-[(2S)-2-({[(2-chloro-3-fluorophenyl)methyl]amino}-N-methylcarbonylamino)-3-(N-(3-isoquinolyl)carbamoyloxy)propoxy]ethyl dihydrogen phosphate |
| 597.1 | (4S)-4-({[(2-chloro-3-fluorophenyl)methyl]amino}-N-methylcarbonylamino)-5-(N-(3-isoquinolyl)carbamoyloxy)-2,2-dimethylpentyl dihydrogen phosphate |

| m/z M + H | ChemicalName |
|---|---|
| 517.1 | [(2S)-2-({[(2-chloro-3-fluorophenyl)methyl]amino}-N-methylcarbonylamino)-5-hydroxy-4,4-dimethylpentyloxy]-N-(3-isoquinolyl)carboxamide |
| 613.5 | (2R)-3-[(2S)-2-({[(2-chloro-3-fluorophenyl)methyl]amino}-N-methylcarbonylamino)-3-(N-(3-isoquinolyl)carbamoyloxy)propoxy]-2-hydroxypropyl dihydrogen phosphate |
| 683.7 | 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino)ethyl dimethyl phosphate |
| 575.6 | N-[(4S)-4-({[(2-chloro-3-fluorophenyl)methyl]amino}-N-methylcarbonylamino)-5-(N-(3-isoquinolyl)carbamoyloxy)pentyl][(2-hydroxyethyl)amino]carboxamide |
| 655.5 | 2-({N-[(4S)-4-({[(2-chloro-3-fluorophenyl)methyl]amino}-N-methylcarbonylamino)-5-(N-(3-isoquinolyl)carbamoyloxy)pentyl]carbamoyl}amino)ethyl dihydrogen phosphate |
| 533.1 | methyl (4S)-4-({[(2-chloro-3-fluorophenyl)methyl]amino}-N-methylcarbonylamino)-5-[N-(3-phenylisoxazol-5-yl)carbamoyloxy]pentanoate |
| 701.2 | tert-butyl 4-[(4S)-4-({[(2-chloro-3-fluorophenyl)methyl]amino}-N-methylcarbonylamino)-5-[N-(3-phenylisoxazol-5-yl)carbamoyloxy]pentanoyl]-1,4-diazaperhydroepinecarboxylate |
| 601.2 | [(2S)-2-({[(2-chloro-3-fluorophenyl)methyl]amino}-N-methylcarbonylamino)-5-(1,4-diazaperhydroepinyl)-5-oxopentyloxy]-N-(3-phenylisoxazol-5-yl)carboxamide |
| 601.2 | [(2S)-2-({[(2-chloro-3-fluorophenyl)methyl]amino}-N-methylcarbonylamino)-5-(4-methylpiperazinyl)-5-oxopentyloxy]-N-(3-phenylisoxazol-5-yl)carboxamide |
| 533.1 | N-((1S)-4-hydroxy-3,3-dimethyl-1-{[N-(3-phenylisoxazol-5-yl)carbamoyloxy]methyl}butyl){[(2-chloro-3-fluorophenyl)methyl]amino}-N-methylcarboxamide |
| 629.2 | methyl 4-[(4S)-4-({[(2-chloro-3-fluorophenyl)methyl]amino}-N-methylcarbonylamino)-5-(N-(3-isoquinolyl)carbamoyloxy)pentanoyl]piperazine-2-carboxylate |
| 601.1 | N-{(1S)-4-[3-(hydroxymethyl)piperazinyl]-1-[(N-(3-isoquinolyl)carbamoyloxy)methyl]-4-oxobutyl}{[(2-chloro-3-fluorophenyl)methyl]amino}-N-methylcarboxamide |
| 701.2 | tert-butyl 4-[(4S)-4-({[(2-chloro-3-fluorophenyl)methyl]amino}-N-methylcarbonylamino)-5-(N-(3-isoquinolyl)carbamoyloxy)pentanoyl]-2-(hydroxymethyl)piperazinecarboxylate |
| 641.2 | (4S,2R)-4-({[(2,3-difluorophenyl)methyl]amino}-N-methylcarbonylamino)-2-hydroxy-5-[N-(3-phenylisoxazol-5-yl)carbamoyloxy]pentyl diethyl phosphate |
| 601.2 | N-{(1S)-4-[(3S)-3-(hydroxymethyl)piperazinyl]-1-[(N-(3-isoquinolyl)carbamoyloxy)methyl]-4-oxobutyl}{[(2-chloro-3-fluorophenyl)methyl]amino}-N-methylcarboxamide |
| 665.3 | (4S)-4-({[(2,3-difluorophenyl)methyl]amino}-N-methylcarbonylamino)-5-(N-(3-isoquinolyl)carbamoyloxy)pentyl ditert-butyl phosphate |
| 533.5 | N-((1S)-4-hydroxy-4-methyl-1-{[N-(3-phenylisoxazol-5-yl)carbamoyloxy]methyl}pentyl){[(2-chloro-3-fluorophenyl)methyl]amino}-N-methylcarboxamide |
| 535.5 | N-{1-[((2R)-2,3-dihydroxypropoxy)methyl](1S)-2-(N-(3-isoquinolyl)carbamoyloxy)ethyl}{[(2-chloro-3-fluorophenyl)methyl]amino}-N-methylcarboxamide |
| 595.2 | N-{1-[((2R)-2,3-dihydroxypropoxy)methyl](1S)-2-(N-(3-isoquinolyl)carbamoyloxy)ethyl}-N-((2S)-2,3-dihydroxypropyl){[(2-chloro-3-fluorophenyl)methyl]amino}carboxamide |
| 601.2 | N-{4-[(3R)-3-(hydroxymethyl)piperazinyl](1S)-1-[(N-(3-isoquinolyl)carbamoyloxy)methyl]-4-oxobutyl}{[(2-chloro-3-fluorophenyl)methyl]amino}-N-methylcarboxamide |
| 615.5 | (2S)-3-[(2S)-2-({[(2-chloro-3-fluorophenyl)methyl]amino}-N-methylcarbonylamino)-3-(N-(3-isoquinolyl)carbamoyloxy)propoxy]-2-hydroxypropyl dihydrogen phosphate |
| 599.6 | (2S)-3-[(2S)-2-({[(2,3-difluorophenyl)methyl]amino}-N-methylcarbonylamino)-3-(N-(3-isoquinolyl)carbamoyloxy)propoxy]-2-hydroxypropyl dihydrogen phosphate |
| 519.2 | N-{(1S)-1-[((2S)-2,3-dihydroxypropoxy)methyl]-2-(N-(3-isoquinolyl)carbamoyloxy)ethyl}{[(2,3-difluorophenyl)methyl]amino}-N-methylcarboxamide |
| 505.2 | [(2R,4R)-2-({[(2-chloro-3-fluorophenyl)methyl]amino}-N-methylcarbonylamino)-4,5-dihydroxypentyloxy]-N-(3-isoquinolyl)carboxamide |
| 505.2 | [(4S,2R)-2-({[(2-chloro-3-fluorophenyl)methyl]amino}-N-methylcarbonylamino)-4,5-dihydroxypentyloxy]-N-(3-isoquinolyl)carboxamide |

| m/z M + H | ChemicalName |
|---|---|
| 585.5 | (2S,4R)-4-({[(2-chloro-3-fluorophenyl)methyl]amino}-N-methylcarbonylamino)-2-hydroxy-5-(N-(3-isoquinolyl)carbamoyloxy)pentyl dihydrogen phosphate |
| 608.1 | [(2S)-2-({[(2-chloro-3-fluorophenyl)methyl]amino}-N-methylcarbonylamino)-5-imidazo[2,1-c]piperazin-7-yl-5-oxopentyloxy]-N-(3-isoquinolyl)carboxamide |
| 571.6 | [(2R)-2-({[(2-chloro-3-fluorophenyl)methyl]amino}-N-methylcarbonylamino)-5-oxo-5-piperazinylpentyloxy]-N-(3-isoquinolyl)carboxamide |
| 610.1 | [(2S)-2-({[(2-chloro-3-fluorophenyl)methyl]amino}-N-methylcarbonylamino)-5-oxo-5-(1,2,4-triazolo[3,4-c]piperazin-7-yl)pentyloxy]-N-(3-isoquinolyl)carboxamide |
| 642.6 | N-((1S)-4-[(tert-butoxy)carbonylamino]-3,3-difluoro-1-{[N-(6-fluoro(3-isoquinolyl))carbamoyloxy]methyl}butyl){[(2-chloro-3-fluorophenyl)methyl]amino}-N-methylcarboxamide |
| 570.5 | N-((1S)-4-carbonylamino-3,3-difluoro-1-{[N-(6-fluoro(3-isoquinolyl))carbamoyloxy]methyl}butyl){[(2-chloro-3-fluorophenyl)methyl]amino}-N-methylcarboxamide |
| 527.2 | [(2S)-2-({[(2,3-difluorophenyl)methyl]amino}-N-methylcarbonylamino)-4-imidazol-2-ylbutoxy]-N-(6-fluoro(3-isoquinolyl))carboxamide |
| 618.6 | N-((1S)-1-{[N-(6-fluoro(3-isoquinolyl))carbamoyloxy]methyl}-4-(piperazinylcarbonylamino)butyl){[(2-chloro-3-fluorophenyl)methyl]amino}-N-methylcarboxamide |
| 571.1 | [(2S)-2-({[(2-chloro-3-fluorophenyl)methyl]amino}-N-methylcarbonylamino)-4,4-difluoro-5-hydroxy-5-methylhexyloxy]-N-(6-fluoro(3-isoquinolyl))carboxamide |
| 594.6 | N-{(1S)-4-imidazo[5,1-c]piperazin-7-yl-1-[(N-(3-isoquinolyl)carbamoyloxy)methyl]butyl}{[(2-chloro-3-fluorophenyl)methyl]amino}-N-methylcarboxamide |
| 595.2 | N-{(1S)-1-[(N-(3-isoquinolyl)carbamoyloxy)methyl]-4-(1,2,4-triazolo[3,4-c]piperazin-7-yl)butyl}{[(2-chloro-3-fluorophenyl)methyl]amino}-N-methylcarboxamide |
| 692.1 | (4S)-4-({[(2-chloro-3-fluorophenyl)methyl]amino}-N-methylcarbonylamino)-2,2-difluoro-5-[N-(6-fluoro(3-isoquinolyl))carbamoyloxy]pentyl 4-nitrobenzoate |
| 708.1 | (4S)-4-({[(2-chloro-3-fluorophenyl)methyl]amino}-N-methylcarbonylamino)-2,2-difluoro-5-{N-[5-(3-fluorophenyl)isoxazol-3-yl]carbamoyloxy}pentyl 4-nitrobenzoate |
| 559.1 | N-[(1S)-3,3-difluoro-1-({N-[5-(3-fluorophenyl)isoxazol-3-yl]carbamoyloxy}methyl)-4-hydroxybutyl]{[(2-chloro-3-fluorophenyl)methyl]amino}-N-methylcarboxamide |
| 534.1 | N-((1S)-4-carbonylamino-1-{[N-(6-fluoro(3-isoquinolyl))carbamoyloxy]methyl}butyl){[(2-chloro-3-fluorophenyl)methyl]amino}-N-methylcarboxamide |
| 578.1 | N-((1S)-1-{[N-(6-fluoro(3-isoquinolyl))carbamoyloxy]methyl}-4-[(2-hydroxy-2-methylpropyl)amino]butyl){[(2-chloro-3-fluorophenyl)methyl]amino}-N-methylcarboxamide |
| 650.2 | N-((1S)-4-bis(2-hydroxy-2-methylpropyl)amino}-1-{[N-(6-fluoro(3-isoquinolyl))carbamoyloxy]methyl}butyl){[(2-chloro-3-fluorophenyl)methyl]amino}-N-methylcarboxamide |
| 542.2 | [(2S)-2-({[(2-chloro-3-fluorophenyl)methyl]amino}-N-methylcarbonylamino)-3-[(2,2,2-trifluoroethyl)amino]propoxy]-N-(3-isoquinolyl)carboxamide |
| 524.2 | [(2S)-3-[(2,2-difluoroethyl)amino]-2-({[(2-chloro-3-fluorophenyl)methyl]amino}-N-methylcarbonylamino)propoxy]-N-(3-isoquinolyl)carboxamide |
| 532.2 | methyl 2-{[(2S)-2-({[(2-chloro-3-fluorophenyl)methyl]amino}-N-methylcarbonylamino)-3-(N-(3-isoquinolyl)carbamoyloxy)propyl]amino}acetate |
| 532.3 | [(2S)-2-({[(2-chloro-3-fluorophenyl)methyl]amino}-N-methylcarbonylamino)-3-[(2-hydroxy-2-methylpropyl)amino]propoxy]-N-(3-isoquinolyl)carboxamide |
| 571.5 | N-((1S)-1-{[N-(6-fluoro(3-isoquinolyl))carbamoyloxy]methyl}-3-hydroxy-3-methylbutyl)-N-(2,2-difluoroethyl){[(2-chloro-3-fluorophenyl)methyl]amino}carboxamide |
| 541.1 | N-((1S)-3,3-difluoro-4-hydroxy-1-{[N-(5-phenylisoxazol-3-yl)carbamoyloxy]methyl}butyl){[(2-chloro-3-fluorophenyl)methyl]amino}-N-methylcarboxamide |
| 541.1 | N-((1S)-3,3-difluoro-4-hydroxy-1-{[N-(3-phenylisoxazol-5-yl)carbamoyloxy]methyl}butyl){[(2-chloro-3-fluorophenyl)methyl]amino}-N-methylcarboxamide |
| 525.1 | N-{(1S)-3,3-difluoro-4-hydroxy-1-[(N-(3-isoquinolyl)carbamoyloxy)methyl]butyl}{[(2-chloro-3-fluorophenyl)methyl]amino}-N-methylcarboxamide |

-continued

| m/z M + H | ChemicalName |
|---|---|
| 537.1 | N-[(1S)-1-({N-[5-(3-fluorophenyl)isoxazol-3-yl]carbamoyloxy}methyl)-3-hydroxy-3-methylbutyl]{[(2-chloro-3-fluorophenyl)methyl]amino}-N-methylcarboxamide |
| 519.1 | N-((1S)-3-hydroxy-3-methyl-1-{[N-(5-phenylisoxazol-3-yl)carbamoyloxy]methyl}butyl){[(2-chloro-3-fluorophenyl)methyl]amino}-N-methylcarboxamide |
| 515.2 | (4R)-4-({[(2,3-difluorophenyl)methyl]amino}-N-methylcarbonylamino)-5-(N-(3-isoquinolyl)carbamoyloxy)pentyl acetate |
| 473.5 | N-{(1R)-4-hydroxy-1-[(N-(3-isoquinolyl)carbamoyloxy)methyl]butyl}{[(2,3-difluorophenyl)methyl]amino}-N-methylcarboxamide |
| 553.5 | (4R)-4-({[(2,3-difluorophenyl)methyl]amino}-N-methylcarbonylamino)-5-(N-(3-isoquinolyl)carbamoyloxy)pentyl dihydrogen phosphate |
| 506.2 | [(2S)-2-({[(2-chloro-3-fluorophenyl)methyl]amino}-N-methylcarbonylamino)-3-[(2-fluoroethyl)amino]propoxy]-N-(3-isoquinolyl)carboxamide |
| 553.5 | N-{(1S)-3-hydroxy-1-[(N-(3-isoquinolyl)carbamoyloxy)methyl]-3-methylbutyl}-N-(2,2-difluoroethyl){[(2-chloro-3-fluorophenyl)methyl]amino}carboxamide |
| 587.5 | N-[(1S)-1-({N-[5-(3-fluorophenyl)isoxazol-3-yl]carbamoyloxy}methyl)-3-hydroxy-3-methylbutyl]-N-(2,2-difluoroethyl){[(2-chloro-3-fluorophenyl)methyl]amino}carboxamide |
| 599.1 | N-[(1S)-3,3-difluoro-1-({N-[3-(3-fluorophenyl)isoxazol-5-yl]carbamoyloxy}methyl)-4-hydroxybutyl]{[(2-chloro-3-fluorophenyl)methyl]amino}-N-methylcarboxamide |
| 551.5 | methyl (4S)-4-({[(2-chloro-3-fluorophenyl)methyl]amino}-N-methylcarbonylamino)-5-{N-[3-(3-fluorophenyl)isoxazol-5-yl]carbamoyloxy}pentanoate |
| 543.2 | [(2S)-2-({[(2-chloro-3-fluorophenyl)methyl]amino}-N-methylcarbonylamino)-3-(1-methylimidazol-4-yl)propoxy]-N-(6-fluoro(3-isoquinolyl))carboxamide |
| 538.2 | [(2S)-2-({[(2-chloro-3-fluorophenyl)methyl]amino}-N-methylcarbonylamino)-3-[(methylsulfonyl)amino]propoxy]-N-(3-isoquinolyl)carboxamide |
| 529.5 | [(2S)-2-({[(2-chloro-3-fluorophenyl)methyl]amino}-N-methylcarbonylamino)-3-imidazol-4-ylpropoxy]-N-(6-fluoro(3-isoquinolyl))carboxamide |
| 663.2 | N-{(1S)-1-[(N-(3-isoquinolyl)carbamoyloxy)methyl]-4-[2-(trifluoromethyl)(1,2,4-triazolo[5,1-c]piperazin-7-yl)]butyl}{[(2-chloro-3-fluorophenyl)methyl]amino}-N-methylcarboxamide |
| 522.1 | [(2S)-2-({[(2-chloro-3-fluorophenyl)methyl]amino}-N-methylcarbonylamino)-3-(2-pyridyl)propoxy]-N-(3-isoquinolyl)carboxamide |
| 605.1 | [(2S)-2-({[(2-chloro-3-fluorophenyl)methyl]amino}-N-methylcarbonylamino)-5-oxo-5-piperazinylpentyloxy]-N-[3-(3-fluorophenyl)isoxazol-5-yl]carboxamide |
| 605.1 | [(2S)-2-({[(2-chloro-3-fluorophenyl)methyl]amino}-N-methylcarbonylamino)-5-oxo-5-piperazinylpentyloxy]-N-[5-(3-fluorophenyl)isoxazol-3-yl]carboxamide |
| 705.1 | tert-butyl 4-[(4S)-4-({[(2-chloro-3-fluorophenyl)methyl]amino}-N-methylcarbonylamino)-5-{N-[3-(3-fluorophenyl)isoxazol-5-yl]carbamoyloxy}pentanoyl]piperazinecarboxylate |
| 580.1 | N-{(1S)-3-imidazo[1,5-a]piperazin-3-yl-1-[(N-(3-isoquinolyl)carbamoyloxy)methyl]propyl}{[(2-chloro-3-fluorophenyl)methyl]amino}-N-methylcarboxamide |
| 580.1 | [(2S)-4-(7-{N-[(2-chloro-3-fluorophenyl)methyl]carbamoyl}imidazo[1,5-a]piperazin-3-yl)-2-(methylamino)butoxy]-N-(3-isoquinolyl)carboxamide |
| 765.1 | N-[(1S)-3-(7-{N-[(2-chloro-3-fluorophenyl)methyl]carbamoyl}imidazo[1,5-a]piperazin-3-yl)-1-[(N-(3-isoquinolyl)carbamoyloxy)methyl]propyl]{[(2-chloro-3-fluorophenyl)methyl]amino}-N-methylcarboxamide |
| 680.2 | tert-butyl 3-[(3S)-3-({[(2-chloro-3-fluorophenyl)methyl]amino}-N-methylcarbonylamino)-4-(N-(3-isoquinolyl)carbamoyloxy)butyl]imidazo[5,1-c]piperazine-7-carboxylate |
| 594.1 | (4S)-4-({[(2-chloro-3-fluorophenyl)methyl]amino}-N-methylcarbonylamino)-5-(N-(3-isoquinolyl)carbamoyloxy)-N-(pyrazin-2-ylmethyl)pentanamide |
| 576.1 | N-{(1S)-3-(4-hydroimidazo[1,5-a]pyrazin-3-yl)-1-[(N-(3-isoquinolyl)carbamoyloxy)methyl]propyl}{[(2-chloro-3-fluorophenyl)methyl]amino}-N-methylcarboxamide |
| 613.2 | [(2S)-2-({[(2-chloro-3-fluorophenyl)methyl]amino}-N-methylcarbonylamino)-5-[4-(methylethyl)piperazinyl]-5-oxopentyloxy]-N-(3-isoquinolyl)carboxamide |
| 627.2 | [(2S)-2-({[(2-chloro-3-fluorophenyl)methyl]amino}-N-methylcarbonylamino)-5-(9-oxa-3,6-diazabicyclo[4.4.0]dec-3-yl)-5-oxopentyloxy]-N-(3-isoquinolyl)carboxamide |

-continued

| m/z M + H | ChemicalName |
|---|---|
| 585.2 | [(2S)-2-({[(2-chloro-3-fluorophenyl)methyl]amino}-N-methylcarbonylamino)-5-(4-methylpiperazinyl)-5-oxopentyloxy]-N-(3-isoquinolyl)carboxamide |
| 595.1 | N-{(1S)-1-[(N-(3-isoquinolyl)carbamoyloxy)methyl]-4-(1,2,4-triazolo[5,1-c]piperazin-7-yl)butyl}{[(2-chloro-3-fluorophenyl)methyl]amino}-N-methylcarboxamide |
| 609.1 | N-{(1S)-1-[(N-(3-isoquinolyl)carbamoyloxy)methyl]-4-(3-methyl(1,2,4-triazolo[3,4-c]piperazin-7-yl))butyl}{[(2-chloro-3-fluorophenyl)methyl]amino}-N-methylcarboxamide |
| 606.1 | N-{(1S)-4-(1,1-dioxo(1,4-thiazaperhydroin-4-yl))-1-[(N-(3-isoquinolyl)carbamoyloxy)methyl]butyl}{[(2-chloro-3-fluorophenyl)methyl]amino}-N-methylcarboxamide |
| 571.1 | N-{(1S)-1-[(N-(3-isoquinolyl)carbamoyloxy)methyl]-4-(4-methylpiperazinyl)butyl}{[(2-chloro-3-fluorophenyl)methyl]amino}-N-methylcarboxamide |
| 558.1 | N-{(1S)-1-[(N-(3-isoquinolyl)carbamoyloxy)methyl]-4-morpholin-4-ylbutyl}{[(2-chloro-3-fluorophenyl)methyl]amino}-N-methylcarboxamide |
| 557.1 | N-{(1S)-1-[(N-(3-isoquinolyl)carbamoyloxy)methyl]-4-piperazinylbutyl}{[(2-chloro-3-fluorophenyl)methyl]amino}-N-methylcarboxamide |
| 601.2 | {[(2-chloro-3-fluorophenyl)methyl]amino}-N-(2-(N-(3-isoquinolyl)carbamoyloxy)-1-{[1-benzylimidazol-2-yl]methyl}ethyl)-N-methylcarboxamide |
| 525.2 | {[(2-chloro-3-fluorophenyl)methyl]amino}-N-{2-(N-(3-isoquinolyl)carbamoyloxy)-1-[(1-methylimidazol-2-yl)methyl]ethyl}-N-methylcarboxamide |
| 511.1 | {[(2-chloro-3-fluorophenyl)methyl]amino}-N-[1-(imidazol-2-ylmethyl)-2-(N-(3-isoquinolyl)carbamoyloxy)ethyl]-N-methylcarboxamide |
| 623.1 | N-{(1S)-1-[(N-(3-isoquinolyl)carbamoyloxy)methyl]-4-(2-methyl(4,5,6,7-tetrahydroimidazo[5,4-c]pyridin-5-yl))-4-oxobutyl}{[(2-chloro-3-fluorophenyl)methyl]amino}-N-methylcarboxamide |
| 639.2 | N-{(1S)-1-[(N-(3-isoquinolyl)carbamoyloxy)methyl]-4-[4-(2,2,2-trifluoroethyl)piperazinyl]butyl}{[(2-chloro-3-fluorophenyl)methyl]amino}-N-methylcarboxamide |
| 580.1 | (3S)-3-({[(2-chloro-3-fluorophenyl)methyl]amino}-N-methylcarbonylamino)-4-(N-(3-isoquinolyl)carbamoyloxy)-N-(pyrazin-2-ylmethyl)butanamide |
| 511.1 | [(2S)-2-({[(2-chloro-3-fluorophenyl)methyl]amino}-N-methylcarbonylamino)-3-imidazol-4-ylpropoxy]-N-(3-isoquinolyl)carboxamide |
| 460.1 | N-{(1S)-2-amino-1-[(N-(3-isoquinolyl)carbamoyloxy)methyl]ethyl}{[(2-chloro-3-fluorophenyl)methyl]amino}-N-methylcarboxamide |
| 562.1 | N-[(1S)-1-(4-hydroimidazo[1,5-a]pyrazin-3-ylmethyl)-2-(N-(3-isoquinolyl)carbamoyloxy)ethyl]{[(2-chloro-3-fluorophenyl)methyl]amino}-N-methylcarboxamide |
| 599.3 | N-{(1S)-4-(4-acetylpiperazinyl)-1-[(N-(3-isoquinolyl)carbamoyloxy)methyl]butyl}{[(2-chloro-3-fluorophenyl)methyl]amino}-N-methylcarboxamide |
| 574.2 | N-{(1S)-4-(3-fluoropiperidyl)-1-[(N-(3-isoquinolyl)carbamoyloxy)methyl]butyl}{[(2-chloro-3-fluorophenyl)methyl]amino}-N-methylcarboxamide |
| 590.1 | {N-[(2S)-2-({[(2-chloro-3-fluorophenyl)methyl]amino}-N-methylcarbonylamino)-3-(N-(3-isoquinolyl)carbamoyloxy)propyl]carbamoyloxy}ethyl acetate |
| 571.2 | N-{(1S)-1-[(N-(3-isoquinolyl)carbamoyloxy)methyl]-4-(2-oxopiperazinyl)butyl}{[(2-chloro-3-fluorophenyl)methyl]amino}-N-methylcarboxamide |
| 558.1 | N-[(1S)-4-amino-3,3-difluoro-1-({N-[5-(3-fluorophenyl)isoxazol-3-yl]carbamoyloxy}methyl)butyl]{[(2-chloro-3-fluorophenyl)methyl]amino}-N-methylcarboxamide |
| 584.1 | N-[(1S)-5-diazo-3,3-difluoro-1-({N-[5-(3-fluorophenyl)isoxazol-3-yl]carbamoyloxy}methyl)-5-azapent-5-enyl]{[(2-chloro-3-fluorophenyl)methyl]amino}-N-methylcarboxamide |
| 584.0 | N-[(1S)-5-diazo-3,3-difluoro-1-({N-[3-(3-fluorophenyl)isoxazol-5-yl]carbamoyloxy}methyl)-5-azapent-5-enyl]{[(2-chloro-3-fluorophenyl)methyl]amino}-N-methylcarboxamide |
| 558.1 | N-[(1S)-4-amino-3,3-difluoro-1-({N-[3-(3-fluorophenyl)isoxazol-5-yl]carbamoyloxy}methyl)butyl]{[(2-chloro-3-fluorophenyl)methyl]amino}-N-methylcarboxamide |
| 566.1 | N-[(1S)-1-(imidazo[1,5-a]piperazin-3-ylmethyl)-2-(N-(3-isoquinolyl)carbamoyloxy)ethyl]{[(2-chloro-3-fluorophenyl)methyl]amino}-N-methylcarboxamide |
| 537.1 | N-[(1S)-1-({N-[3-(3-fluorophenyl)isoxazol-5-yl]carbamoyloxy}methyl)-3-hydroxy-3-methylbutyl]{[(2-chloro-3-fluorophenyl)methyl]amino}-N-methylcarboxamide |

-continued

| m/z M + H | ChemicalName |
|---|---|
| 558.0 | [(2S)-3-[(2,2-difluoroethyl)amino]-2-({[(2-chloro-3-fluorophenyl)methyl]amino}-N-methylcarbonylamino)propoxy]-N-[5-(3-fluorophenyl)isoxazol-3-yl]carboxamide |
| 540.1 | [(2S)-3-[(2,2-difluoroethyl)amino]-2-({[(2-chloro-3-fluorophenyl)methyl]amino}-N-methylcarbonylamino)propoxy]-N-(5-phenylisoxazol-3-yl)carboxamide |
| 558.1 | [(2S)-3-[(2,2-difluoroethyl)amino]-2-({[(2-chloro-3-fluorophenyl)methyl]amino}-N-methylcarbonylamino)propoxy]-N-[3-(3-fluorophenyl)isoxazol-5-yl]carboxamide |
| 540.1 | [(2S)-3-[(2,2-difluoroethyl)amino]-2-({[(2-chloro-3-fluorophenyl)methyl]amino}-N-methylcarbonylamino)propoxy]-N-(3-phenylisoxazol-5-yl)carboxamide |
| 743.0 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-[3-(3-fluorophenyl)isoxazol-5-yl]carbo |
| 725.1 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-(3-phenylisoxazol-5-yl)carboxamide |
| 745.0 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-[5-(3-fluorophenyl)isoxazol-3-yl]carbo |
| 725.0 | [(2S)-3-(N-(2,2-difluoroethyl){[(2-chloro-3-fluorophenyl)methyl]amino}carbonylamino)-2-({[(2-chloro-3-fluorophenyl)methyl]amino}-N-methylcarbonylamino)propoxy]-N-(5-phenylisoxazol-3-yl)carboxamide |
| 499.1 | N-[(1R,2R)-2-(N-(3-isoquinolyl)carbamoyloxy)cyclohexyl]{[(2-chloro-3-fluorophenyl)methyl]amino}-N-ethylcarboxamide |
| 494.1 | N-[(1S)-2-amino-1-({N-[5-(3-fluorophenyl)isoxazol-3-yl]carbamoyloxy}methyl)ethyl]{[(2-chloro-3-fluorophenyl)methyl]amino}-N-methylcarboxamide |
| 431.1 | {[(2-chloro-3-fluorophenyl)methyl]amino}-N-[2-(N-(3-isoquinolyl)carbamoyloxy)ethyl]-N-methylcarboxamide |
| 485.1 | N-[(1S,2S)-2-(N-(3-isoquinolyl)carbamoyloxy)cyclohexyl]{[(2-chloro-3-fluorophenyl)methyl]amino}-N-methylcarboxamide |
| 471.1 | N-[(2S,1R)-2-(N-(3-isoquinolyl)carbamoyloxy)cyclopentyl]{[(2-chloro-3-fluorophenyl)methyl]amino}-N-methylcarboxamide |
| 471.1 | N-[(1S,2S)-2-(N-(3-isoquinolyl)carbamoyloxy)cyclopentyl]{[(2-chloro-3-fluorophenyl)methyl]amino}-N-methylcarboxamide |
| 504.1 | [(2S)-2-({[(2-chloro-3-fluorophenyl)methyl]amino}-N-methylcarbonylamino)-3-[(2-hydroxyethyl)amino]propoxy]-N-(3-isoquinolyl)carboxamide |
| 548.1 | [(2S)-3-[bis(2-hydroxyethyl)amino]-2-({[(2-chloro-3-fluorophenyl)methyl]amino}-N-methylcarbonylamino)propoxy]-N-(3-isoquinolyl)carboxamide |
| 499.0 | [2-({[(2-chloro-3-fluorophenyl)methyl]amino}-N-methylcarbonylamino)ethoxy]-N-[1-(trifluoromethyl)(3-isoquinolyl)]carboxamide |
| 499.0 | [2-({[(2-chloro-3-fluorophenyl)methyl]amino}-N-methylcarbonylamino)ethoxy]-N-[4-(trifluoromethyl)(3-isoquinolyl)]carboxamide |
| 476.1 | [(2S)-3-amino-2-({[(2-chloro-3-fluorophenyl)methyl]amino}-N-methylcarbonylamino)propoxy]-N-(5-phenylisoxazol-3-yl)carboxamide |
| 602.0 | [(2S)-3-amino-2-({[(2-chloro-3-fluorophenyl)methyl]amino}-N-methylcarbonylamino)propoxy]-N-(4-iodo-5-phenylisoxazol-3-yl)carboxamide |
| 619.9 | [(2S)-3-amino-2-({[(2-chloro-3-fluorophenyl)methyl]amino}-N-methylcarbonylamino)propoxy]-N-[5-(3-fluorophenyl)-4-iodoisoxazol-3-yl]carboxamide |
| 647.1 | [(2S)-2-({[(2-chloro-3-fluorophenyl)methyl]amino}-N-methylcarbonylamino)-5-[4-(methylethyl)piperazinyl]-5-oxopentyloxy]-N-[5-(3-fluorophenyl)isoxazol-3-yl]carboxamide |
| 629.1 | [(2S)-2-({[(2-chloro-3-fluorophenyl)methyl]amino}-N-methylcarbonylamino)-5-[4-(methylethyl)piperazinyl]-5-oxopentyloxy]-N-(5-phenylisoxazol-3-yl)carboxamide |
| 647.1 | [(2S)-2-({[(2-chloro-3-fluorophenyl)methyl]amino}-N-methylcarbonylamino)-5-[4-(methylethyl)piperazinyl]-5-oxopentyloxy]-N-[3-(3-fluorophenyl)isoxazol-5-yl]carboxamide |
| 619.1 | [(2S)-2-({[(2-chloro-3-fluorophenyl)methyl]amino}-N-methylcarbonylamino)-5-(4-methylpiperazinyl)-5-oxopentyloxy]-N-[3-(3-fluorophenyl)isoxazol-5-yl]carboxamide |
| 459.1 | [3-({[(2-chloro-3-fluorophenyl)methyl]amino}-N-methylcarbonylamino)-2-methylpropoxy]-N-(3-isoquinolyl)carboxamide |

| m/z M + H | ChemicalName |
|---|---|
| 457.0 | N-{(2S,1R)-2-[(N-(3-isoquinolyl)carbamoyloxy)methyl]cyclopropyl}{[(2-chloro-3-fluorophenyl)methyl]amino}-N-methylcarboxamide |
| 491.1 | [((2S)-1-{N-[(2-chloro-3-fluorophenyl)methyl]carbamoyl}pyrrolidin-2-yl)methoxy]-N-[3-(3-fluorophenyl)isoxazol-5-yl]carboxamide |
| 459.1 | {[(2-chloro-3-fluorophenyl)methyl]amino}-N-[2-(N-(3-isoquinolyl)carbamoyloxy)-1-methylpropyl]-N-methylcarboxamide |
| 445.1 | {[(2-chloro-3-fluorophenyl)methyl]amino}-N-[2-(N-(3-isoquinolyl)carbamoyloxy)-1-methylpropyl]carboxamide |
| 584.1 | N-((1S)-3-{3-[(dimethylamino)methyl](1,2,4-oxadiazol-5-yl)}-1-[(N-(3-isoquinolyl)carbamoyloxy)methyl]propyl){[(2-chloro-3-fluorophenyl)methyl]amino}-N-methylcarboxamide |
| 599.1 | N-{(1S)-4-(4-ethylpiperazinyl)-1-[(N-(3-isoquinolyl)carbamoyloxy)methyl]-4-oxobutyl}{[(2-chloro-3-fluorophenyl)methyl]amino}-N-methylcarboxamide |
| 613.1 | N-{(1S)-1-[(N-(3-isoquinolyl)carbamoyloxy)methyl]-4-oxo-4-(4-propylpiperazinyl)butyl}{[(2-chloro-3-fluorophenyl)methyl]amino}-N-methylcarboxamide |
| 627.1 | N-{(1S)-1-[(N-(3-isoquinolyl)carbamoyloxy)methyl]-4-[4-(2-methylpropyl)piperazinyl]-4-oxobutyl}{[(2-chloro-3-fluorophenyl)methyl]amino}-N-methylcarboxamide |
| 541.1 | N-{(1S)-1-[(N-(3-isoquinolyl)carbamoyloxy)methyl]-3-(3-methyl(1,2,4-oxadiazol-5-yl))propyl}{[(2-chloro-3-fluorophenyl)methyl]amino}-N-methylcarboxamide |
| 653.1 | N-{(1S)-1-[(N-(3-isoquinolyl)carbamoyloxy)methyl]-4-[4-(2,2,2-trifluoroethyl)(1,4-diazaperhydroepinyl)]butyl}{[(2-chloro-3-fluorophenyl)methyl]amino}-N-methylcarboxamide |
| 629.2 | [(2S)-2-({[(2-chloro-3-fluorophenyl)methyl]amino}-N-methylcarbonylamino)-5-[4-(methylethyl)piperazinyl]-5-oxopentyloxy]-N-(3-phenylisoxazol-5-yl)carboxamide |
| 619.1 | [(2S)-2-({[(2-chloro-3-fluorophenyl)methyl]amino}-N-methylcarbonylamino)-5-(4-methylpiperazinyl)-5-oxopentyloxy]-N-[5-(3-fluorophenyl)isoxazol-3-yl]carboxamide |
| 601.1 | [(2S)-2-({[(2-chloro-3-fluorophenyl)methyl]amino}-N-methylcarbonylamino)-5-(4-methylpiperazinyl)-5-oxopentyloxy]-N-(5-phenylisoxazol-3-yl)carboxamide |
| 444.0 | N-((1S)-2-amino-1-{[N-(5-chloro(2-pyridyl))carbamoyloxy]methyl}ethyl){[(2-chloro-3-fluorophenyl)methyl]amino}-N-methylcarboxamide |
| 585.2 | [5-((3R)-3-methylpiperazinyl)(2S)-2-({[(2-chloro-3-fluorophenyl)methyl]amino}-N-methylcarbonylamino)-5-oxopentyloxy]-N-(3-isoquinolyl)carboxamide |
| 585.2 | [(2S)-5-((3S)-3-methylpiperazinyl)-2-({[(2-chloro-3-fluorophenyl)methyl]amino}-N-methylcarbonylamino)-5-oxopentyloxy]-N-(3-isoquinolyl)carboxamide |
| 585.2 | [(2S)-5-((2S)-2-methylpiperazinyl)-2-({[(2-chloro-3-fluorophenyl)methyl]amino}-N-methylcarbonylamino)-5-oxopentyloxy]-N-(3-isoquinolyl)carboxamide |
| 585.1 | [5-((2R)-2-methylpiperazinyl)(2S)-2-({[(2-chloro-3-fluorophenyl)methyl]amino}-N-methylcarbonylamino)-5-oxopentyloxy]-N-(3-isoquinolyl)carboxamide |
| 599.1 | [(2S)-5-(3,5-dimethylpiperazinyl)-2-({[(2-chloro-3-fluorophenyl)methyl]amino}-N-methylcarbonylamino)-5-oxopentyloxy]-N-(3-isoquinolyl)carboxamide |
| 599.1 | [(2S)-5-((3S,5R)-3,5-dimethylpiperazinyl)-2-({[(2-chloro-3-fluorophenyl)methyl]amino}-N-methylcarbonylamino)-5-oxopentyloxy]-N-(3-isoquinolyl)carboxamide |
| 611.1 | [(2S)-2-({[(2-chloro-3-fluorophenyl)methyl]amino}-N-methylcarbonylamino)-5-(4-cyclopropylpiperazinyl)-5-oxopentyloxy]-N-(3-isoquinolyl)carboxamide |
| 625.2 | [(2S)-2-({[(2-chloro-3-fluorophenyl)methyl]amino}-N-methylcarbonylamino)-5-(4-cyclobutylpiperazinyl)-5-oxopentyloxy]-N-(3-isoquinolyl)carboxamide |
| 576 | N-[(2S)-2-({[(2-chloro-3-fluorophenyl)methyl]amino}-N-methylcarbonylamino)-3-(N-(3-isoquinolyl)carbamoyloxy)propyl]-3-hydroxy-2-(hydroxymethyl)-2-methylpropanamide |
| 510 | N-[(1S)-2-amino-1-({N-[3-(3-chlorophenyl)isoxazol-5-yl]carbamoyloxy}methyl)ethyl]{[(2-chloro-3-fluorophenyl)methyl]amino}-N-methylcarboxamide |
| 599.2 | [(2S)-5-(3,3-dimethylpiperazinyl)-2-({[(2-chloro-3-fluorophenyl)methyl]amino}-N-methylcarbonylamino)-5-oxopentyloxy]-N-(3-isoquinolyl)carboxamide |
| 639.1 | [(2S)-5-[(2S)-2-(trifluoromethyl)piperazinyl]-2-({[(2-chloro-3-fluorophenyl)methyl]amino}-N-methylcarbonylamino)-5-oxopentyloxy]-N-(3-isoquinolyl)carboxamide |

| m/z M+H | ChemicalName |
|---|---|
| 644.1 | N-((1S)-2-{N-[3-(3-chlorophenyl)isoxazol-5-yl]carbamoyloxy}-1-{[(phenylmethoxy)carbonylamino]methyl}ethyl){[(2-chloro-3-fluorophenyl)methyl]amino}-N-methylcarboxamide |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of Formula I

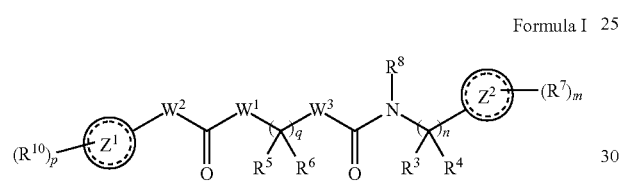

Formula I or a pharmaceutically acceptable salt thereof, wherein
$W^1$ is O;
$W^2$ is $NR^{13}$;
$W^3$ is $NR^{14}$;
$Z^1$ is selected from isoquinolinyl, thiadiazolyl, and isoxazolyl;
$Z^2$ is phenyl;
$R^8$ is selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl;
$R^{13}$ and $R^{14}$ are independently selected from hydrogen, optionally substituted alkyl, optionally substituted alkenyl, optionally substituted alkynyl, optionally substituted aryl, optionally substituted heteroaryl, optionally substituted cycloalkyl, and optionally substituted heterocycloalkyl;
for each occurrence, $R^3$, $R^4$, and $R^5$ are independently selected from hydrogen, hydroxy, carboxy, sulfonyl, sulfinyl, sulfanyl, optionally substituted alkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted cycloalkyl, optionally substituted heterocycloalkyl, optionally substituted aminocarbonyl, and optionally substituted aminosulfonyl;
$R^7$ and $R^{10}$ are independently selected from hydrogen, cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;
m is selected from 0, 1, 2, and 3;
n is selected from 0, 1, 2, 3, and 4;
$-(CR^5R^6)_q-$ is $-CH_2CH(R^5)-$; and
p is selected from 0, 1, 2, and 3.

2. The compound of claim 1 wherein $R^{13}$ is selected from hydrogen and optionally substituted lower alkyl.

3. The compound of claim 2 wherein $R^{13}$ is hydrogen.

4. The compound of claim 1 wherein $R^{14}$ is selected from hydrogen and optionally substituted lower alkyl.

5. The compound of claim 4 wherein $R^{14}$ is selected from hydrogen, lower alkyl, and lower alkyl substituted with one or two groups selected from hydroxy, optionally substituted amino, and optionally substituted alkoxy.

6. The compound of claim 5 wherein $R^{14}$ is selected from hydrogen, methyl, ethyl, propyl, and isopropyl, wherein methyl, ethyl, propyl, and isopropyl are optionally substituted with one or two groups selected from hydroxy, optionally substituted amino, and optionally substituted alkoxy.

7. The compound of claim 6 wherein $R^{14}$ is selected from hydrogen, methyl, ethyl, propyl, and isopropyl, wherein methyl, ethyl, propyl, and isopropyl are optionally substituted with one or two hydroxy groups.

8. The compound of claim 7 wherein $R^{14}$ is selected from methyl, ethyl, hydroxymethyl, 2-hydroxyethyl, and isopropyl.

9. The compound of claim 8 wherein $R^{14}$ is selected from methyl and ethyl.

10. The compound of claim 1 wherein $R^8$ is selected from hydrogen and optionally substituted lower alkyl.

11. The compound of claim 10 wherein $R^8$ is selected from hydrogen and methyl.

12. The compound of claim 11 wherein in $R^8$ is hydrogen.

13. The compound of claim 1 wherein $R^5$ is selected from hydrogen, optionally substituted lower alkyl, and optionally substituted alkenyl.

14. The compound of claim 1 wherein $W^2$ is NH and $R^{14}$ is methyl.

15. The compound of claim 1 wherein m is 0.

16. The compound of claim 1 wherein m is selected from 1 and 2, and each $R^7$ is selected from halo and optionally substituted alkyl.

17. The compound of claim 16 wherein each $R^7$ is selected from chloro, fluoro, and methyl.

18. The compound of claim 17 wherein —(R$^7$)$_m$, together with Z$^2$ to which it is attached, forms a group selected from 2-chlorophenyl, 2-methylphenyl, 2-chloro-4-fluorophenyl, 2-chloro-3-fluorophenyl, 2,3-dichlorophenyl, 2,3-difluorophenyl, 2,4-dichlorophenyl, 2,4-difluorophenyl, and 3-chloro-2-fluorophenyl.

19. The compound of claim 1 wherein n is 1.

20. The compound of claim 19 wherein each R$^3$ and R$^4$ is independently selected from hydrogen and optionally substituted lower alkyl.

21. The compound of claim 20 wherein each R$^3$ and R$^4$ is hydrogen.

22. The compound of claim 1 wherein p is selected from 0, 1, and 2, and R$^{10}$ is selected from halo, optionally substituted alkyl, optionally substituted alkenyl, optionally substituted heterocycloalkyl, and optionally substituted aryl.

23. The compound of claim 1 wherein p is 0 and Z$^1$ is isoquinolin-3-yl.

24. The compound of claim 1 wherein Z$^1$ is isoquinolin-3-yl, p is selected from 1 and 2, and each R$^{10}$ is independently selected from halo.

25. The compound of claim 1 wherein Z$^1$ is isoxazol-5-yl, p is 1, and R$^{10}$ is selected from optionally substituted phenyl.

26. The compound of claim 1 wherein Z$^1$ is isoxazol-3-yl, p is 1, and R$^{10}$ is selected from optionally substituted phenyl.

27. The compound of claim 1 wherein Z$^1$ is 1,3,4-thiadiazol-2-yl, p is 1, and R$^{10}$ is selected from optionally substituted phenyl.

28. A pharmaceutical composition comprising a pharmaceutically acceptable carrier and at least one compound of claim 1.

29. A pharmaceutical composition of claim 28 wherein the composition is formulated in a form selected from a tablet, capsule, powder, liquid, suspension, suppository, and aerosol.

30. The compound of claim 13 wherein R$^5$ is lower alkyl substituted with one, two, or three groups selected from 4-(lower alkyl)piperazin-1-yl, oxopiperazin-1-yl, morpholino, benzyloxy, benzyloxycarbonyl, methoxycarbonyl, hydroxy, amino, dimethylamino, methoxy(methyl)carbamoyl, acetamido, acetyl, azido, phosphato and halo.

31. The compound of claim 30 wherein R$^5$ is lower alkyl substituted with one, two, or three groups selected from hydroxy and phosphato.

32. The compound of claim 31 wherein R$^5$ is lower alkyl substituted with one, two, or three groups selected from hydroxy and —OP(O)(OH)$_2$.

33. The compound of claim 32 wherein R$^5$ is lower alkyl substituted with —OP(O)(OH)$_2$ and optionally further substituted with one or two hydroxy groups.

34. The compound of claim 13 wherein R$^5$ is lower alkyl substituted with optionally substituted heteroaryl.

35. The compound of claim 34 wherein R$^5$ is lower alkyl substituted with imidazol-4-yl, imidazol-2-yl, pyridin-2-yl, 1,2,4-oxadiazol-5-yl, isoxazol-5-yl, imidazo[1,5-a]piperazin-3-yl, or 4-hydroimidazo[1,5-a]pyrazin-3-yl, each of which is optionally substituted.

36. The compound of claim 13 wherein R$^5$ is lower alkyl substituted with optionally substitute aminocarbonyl.

37. A compound of Formula I

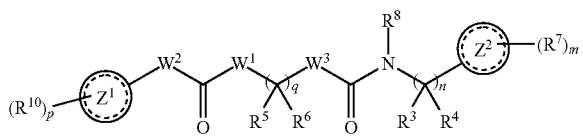

Formula I or a pharmaceutically acceptable salt thereof, wherein
W$^1$ is O;
W$^2$ is NR$^{13}$;
W$^3$ is NR$^{14}$;
Z$^1$ is selected from isoquinolinyl, thiadiazolyl, and isoxazolyl;
Z$^2$ is phenyl;
R$^3$ is hydrogen;
R$^4$ is hydrogen;
—(CR$^5$R$^8$)$_q$— is —CH$_2$CH(R$^5$)—;
R$^5$ is lower alkyl substituted with one, two, or three groups selected from hydroxy and phosphato;
R$^7$ and R$^{10}$ are independently selected from hydrogen, cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;
R$^8$ is selected from hydrogen and alkyl;
R$^{13}$ and R$^{14}$ are independently selected from hydrogen and alkyl;
m is selected from 0, 1, 2, and 3;
n is 1; and
p is selected from 0, 1, 2, and 3.

38. The compound of claim 37, wherein R$^5$ is lower alkyl substituted with one or two groups selected from hydroxy and —OP(O)(OH)$_2$.

39. The compound of claim 38, wherein m is selected from 1 and 2, and each R$^7$ is selected from halo and optionally substituted alkyl.

40. The compound of claim 39 wherein —(R$^7$)$_m$ together with Z$^2$ to which it is attached form a group selected from 2-chlorophenyl, 2-methylphenyl, 2-chloro-4-fluorophenyl, 2-chloro-3-fluorophenyl, 2,3-dichlorophenyl, 2,3-difluorophenyl, 2,4-dichlorophenyl, 2,4-difluorophenyl, and 3-chloro-2-fluorophenyl.

41. The compound of claim 40, wherein p is 0 and Z$^1$ is isoquinolin-3-yl.

42. The compound of claim 40, wherein Z$^1$ is isoquinolin-3-yl, p is selected from 1 and 2, and each R$^{10}$ is independently selected from halo.

43. The compound of claim 40, wherein Z$^1$ is isoxazol-5-yl, p is 1, and R$^{10}$ is selected from optionally substituted phenyl.

44. The compound of claim 40, wherein Z$^1$ is isoxazol-3-yl, p is 1, and R$^{10}$ is selected from optionally substituted phenyl.

45. The compound of claim 40, wherein Z$^1$ is 1,3,4-thiadiazol-2-yl, p is 1, and R$^{10}$ is selected from optionally substituted phenyl.

* * * * *